(12) United States Patent
Zhao et al.

(10) Patent No.: US 12,134,610 B2
(45) Date of Patent: *Nov. 5, 2024

(54) SOMATOSTATIN SUBTYPE-2 RECEPTOR (SST2R) TARGETED THERAPEUTICS AND USES THEREOF

(71) Applicant: Crinetics Pharmaceuticals, Inc., San Diego, CA (US)

(72) Inventors: Jian Zhao, San Diego, CA (US); Yunfei Zhu, San Diego, CA (US); Mi Chen, San Diego, CA (US)

(73) Assignee: CRINETICS PHARMACEUTICALS, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/434,159

(22) Filed: Feb. 6, 2024

(65) Prior Publication Data

US 2024/0254105 A1    Aug. 1, 2024

Related U.S. Application Data

(63) Continuation of application No. 18/535,503, filed on Dec. 11, 2023.

(60) Provisional application No. 63/597,871, filed on Nov. 10, 2023, provisional application No. 63/387,235, filed on Dec. 13, 2022.

(51) Int. Cl.
| C07D 401/14 | (2006.01) |
| A61P 35/00 | (2006.01) |
| C07D 405/14 | (2006.01) |
| C07D 491/22 | (2006.01) |
| C07D 498/04 | (2006.01) |

(52) U.S. Cl.
CPC ............ *C07D 401/14* (2013.01); *A61P 35/00* (2018.01); *C07D 405/14* (2013.01); *C07D 491/22* (2013.01); *C07D 498/04* (2013.01)

(58) Field of Classification Search
None
See application file for complete search history.

(56) References Cited

U.S. PATENT DOCUMENTS

| 5,416,064 | A | 5/1995 | Chari et al. |
| 5,658,920 | A | 8/1997 | Terasawa et al. |
| 6,025,372 | A | 2/2000 | Yang et al. |
| 6,127,343 | A | 10/2000 | Ankersen et al. |
| 6,884,869 | B2 | 4/2005 | Senter et al. |

(Continued)

FOREIGN PATENT DOCUMENTS

| AU | 2014325078 B2 | 10/2018 |
| CA | 2925651 A1 | 4/2015 |

(Continued)

OTHER PUBLICATIONS

Abbott et al. MiRP1 forms IKr potassium channels with HERG and is associated with cardiac arrhythmia. Cell 97:175-187 (1999).

(Continued)

*Primary Examiner* — Jeffrey S Lundgren
*Assistant Examiner* — Anthony Joseph Seitz
(74) *Attorney, Agent, or Firm* — WILSON SONSINI GOODRICH & ROSATI

(57) ABSTRACT

Described herein are somatostatin subtype-2 receptor (SST2R) targeted therapeutics that target tumor cells expressing SST2R and their use in the treatment of cancer.

29 Claims, 1 Drawing Sheet

Biodistribution of $^{111}$In-Compound 1

(56) References Cited

U.S. PATENT DOCUMENTS

| | | |
|---|---|---|
| 7,091,186 B2 | 8/2006 | Senter et al. |
| 7,498,298 B2 | 3/2009 | Doronina et al. |
| 7,553,816 B2 | 6/2009 | Senter et al. |
| 7,659,241 B2 | 2/2010 | Senter et al. |
| 7,754,744 B2 | 7/2010 | Binggeli et al. |
| 8,110,574 B2 | 2/2012 | Thurieau et al. |
| 8,568,728 B2 | 10/2013 | Jeffrey |
| 8,778,925 B2 | 7/2014 | McDonald et al. |
| 9,630,976 B2 | 4/2017 | Ishida et al. |
| 9,643,951 B2 | 5/2017 | Ishida et al. |
| 10,214,540 B2 | 2/2019 | Ishida et al. |
| 10,441,663 B2 | 10/2019 | Bennett et al. |
| 10,624,968 B2 | 4/2020 | Bennett et al. |
| 10,696,689 B2 | 6/2020 | Han et al. |
| 10,898,578 B2 | 1/2021 | Poudel et al. |
| 11,072,598 B2 | 7/2021 | Han et al. |
| 11,186,590 B2 | 11/2021 | Han et al. |
| 11,479,540 B2 | 10/2022 | Zhao et al. |
| 11,608,335 B2 | 3/2023 | Zhao et al. |
| 11,834,462 B2 | 12/2023 | Han et al. |
| 2006/0281764 A1 | 12/2006 | Gaul et al. |
| 2009/0041791 A1 | 2/2009 | Feng |
| 2009/0324620 A1 | 12/2009 | Fuselier et al. |
| 2010/0092496 A1 | 4/2010 | Boyd et al. |
| 2011/0059971 A1 | 3/2011 | Thurieau et al. |
| 2012/0107332 A1 | 5/2012 | Jeffrey |
| 2013/0040978 A1 | 2/2013 | Duffy et al. |
| 2014/0031535 A1 | 1/2014 | Jeffrey |
| 2015/0232478 A1* | 8/2015 | Ishida ............... A61K 31/517 |
| | | 514/249 |
| 2016/0311794 A1 | 10/2016 | Ishida et al. |
| 2020/0000816 A1 | 1/2020 | Ishida et al. |
| 2021/0113706 A1 | 4/2021 | Poudel et al. |
| 2022/0048924 A1 | 2/2022 | Han et al. |
| 2022/0144802 A1 | 5/2022 | Zhao et al. |
| 2022/0249686 A1 | 8/2022 | Chuprakov et al. |
| 2023/0105344 A1* | 4/2023 | Lee ..................... A61P 35/00 |
| | | 424/1.53 |
| 2024/0058456 A1 | 2/2024 | Deutsch et al. |
| 2024/0123080 A1 | 4/2024 | Moquist et al. |
| 2024/0254106 A1* | 8/2024 | Zhao .................. A61P 35/00 |

FOREIGN PATENT DOCUMENTS

| | | |
|---|---|---|
| EP | 2871179 A1 | 5/2015 |
| EP | 3053916 A1 | 8/2016 |
| EP | 3053961 A1 | 8/2016 |
| EP | 3053916 B1 | 1/2019 |
| EP | 3581569 A1 | 12/2019 |
| WO | WO-9845285 A1 | 10/1998 |
| WO | WO-2006135644 A1 | 12/2006 |
| WO | WO-2008051272 A2 | 5/2008 |
| WO | WO-2009051705 A1 | 4/2009 |
| WO | WO-2009158467 A2 | 12/2009 |
| WO | WO-2010041054 A1 | 4/2010 |
| WO | WO-2011027249 A2 | 3/2011 |
| WO | WO-2011144891 A1 | 11/2011 |
| WO | WO-2011146324 A1 | 11/2011 |
| WO | WO-2013088395 A1 | 6/2013 |
| WO | WO-2015188934 A1 | 12/2015 |
| WO | WO-2017075495 A1 | 5/2017 |
| WO | WO-2018013676 A1 | 1/2018 |
| WO | WO-2018081521 A1 | 5/2018 |
| WO | WO-2018170284 A1 | 9/2018 |
| WO | WO-2019023278 A1 | 1/2019 |
| WO | WO-2019157458 A1 | 8/2019 |
| WO | WO-2019231879 A1 | 12/2019 |
| WO | WO-2020061046 A1 | 3/2020 |
| WO | WO-2020117954 A2 | 6/2020 |
| WO | WO-2020154437 A1 | 7/2020 |
| WO | WO-2020190725 A1 | 9/2020 |
| WO | WO-2020190731 A1 | 9/2020 |
| WO | WO-2020190762 A1 | 9/2020 |
| WO | WO-2021030262 A1 | 2/2021 |
| WO | WO-2021046112 A1 | 3/2021 |
| WO | WO-2022155347 A1 | 7/2022 |
| WO | WO-2022155362 A1 | 7/2022 |
| WO | WO-2022261221 A1 * | 12/2022 |
| WO | WO-2022261235 A1 | 12/2022 |
| WO | WO-2024129614 A1 | 6/2024 |

OTHER PUBLICATIONS

Akaiwa et al. Antibody-Drug Conjugate Payloads; Study of Auristatin Derivatives. Chem Pharm Bull (Tokyo) 68(3):201-211 (2020).

Alas et al., Peptide-Drug Conjugates with Different Linkers for Cancer Therapy. Journal of Medicinal Chemistry 64(1):216-232 (2021).

Ammala et al., Targeted delivery of antisense oligonucleotides to pancreatic beta-cells. Science Advances 4(10):eaat3386 [1-11] (2018).

Anami et al., Glutamic acid-valine-citrulline linkers ensure stability and efficacy of antibody-drug conjugates in mice. Nature communications 9(1):2512 (2018).

Attwood et al., Trends in kinase drug discovery: targets, indications and inhibitor design. Nature reviews. Drug discovery 20(11):839-861 (2021).

Baeriswyl et al., Bicyclic Peptides With Optimized Ring Size Inhibit Human Plasma Kallikrein and Its Orthologues While Sparing Paralogous Proteases. ChemMedChem 7(7):1173-1176 (2012).

Bai et al., Small-molecule SMAC mimetics as new cancer therapeutics. Pharmacology & therapeutics 144(1):82-95 (2014).

Beck et al. Strategies and challenges for the next generation of antibody-drug conjugates. Nature Reviews. Drug Discovery 16(5):315-337 (2017).

Beck et al. The next generation of antibody-drug conjugates comes of age. Discov Med 10(53):329-339 (2010).

Bennet et al., MMAE Delivery Using the Bicycle Toxin Conjugate BT5528. Molecular Cancer Therapeutics 19:1385-1394 (2020).

Berge et al. Pharmaceutical Salts. Journal of Pharmaceutical Sciences 66(1):1-19 (Jan. 1977).

Braun et al., Beyond Conventional Immune-checkpoint Inhibition—Novel Immunotherapies for Renal Cell Carcinoma. Nature Reviews Clinical Oncology 18(4):199-214.

Brazeau et al. Hypothalamic polypeptide that inhibits the secretion of immunoreactive pituitary growth hormone. Science 179:77-79 (1973).

Bundgaard. Design and Application of Pro-drugs. A Textbook of Drug Design and Development. pp. 113-191 (1991).

Bundgaard. Means to Enhance Penetration: Prodrugs as a Means to Improve the Delivery of Peptide Drugs. Advanced Drug Delivery Review 8:1-38 (1992).

Burstyn-Cohen et al., TAM receptors, Phosphatidylserine, inflammation, and Cancer. Cell communication and signaling : CCS 17(1):156 (2019).

Cazzamalli et al., Linker Stability Influences the Anti-tumor Activity of Acetazolamide-drug Conjugates for the Therapy of Renal Cell Carcinoma. Journal of Controlled Release 246:39-45 (2017).

Chen et al., Small-Molecule Immuno-Oncology Therapy: Advances, Challenges and New Directions. Current topics in medicinal chemistry 19(3):180-185 (2019).

Chia et al., A Patent Review on FDA-Approved Antibody-Drug Conjugates, Their Linkers and Drug Payloads. ChemMedChem 17(11):e202200032 (2022).

Cho et al., Tumor-Specific Monomethyl Auristatin E (MMAE) Prodrug Nanoparticles for Safe and Effective Chemotherapy. Pharmaceutics 14(10):2131 (2022).

Chuprakov et al., Tandem-Cleavage Linkers Improve the In Vivo Stability and Tolerability of Antibody-Drug Conjugates. Bioconjugate chemistry 32(4):746-754 (2021).

Colville et al., Death-seq identifies regulators of cell death and senolytic therapies. Cell metabolism 35(10):1814-1829 (2023).

Cooper et al. Peptides as a platform for targeted therapeutics for cancer: peptide-drug conjugates (PDCs). Chem Soc Rev 50(3):1480-1494 (2021).

Co-pending U.S. Appl. No. 18/535,503, inventors Zhao; Jian et al., filed Dec. 11, 2023.

(56) References Cited

OTHER PUBLICATIONS

Co-pending U.S. Appl. No. 18/566,887, inventors Struthers; R. Scott et al., filed Dec. 4, 2023.
Corbet et al., Tumour acidosis: from the passenger to the driver's seat. Nature reviews. Cancer 17(10)577-593 (2017).
Corso et al., Innovative Linker Strategies for Tumor-Targeted Drug Conjugates. Chemistry 25:14740-14757 (2019).
Cosin Roger et al., Metabolite Sensing GPCRs: Promising Therapeutic Targets for Cancer Treatment?. Cells 9(2345):1-33 (2020).
Crider. Somatostatin receptor agonists and antagonists. Expert Opinion on Therapeutic Patents 13(9):1427-1441 (2003).
Dias et al., Neutrophil Elastase Promotes Linker Cleavage and Paclitaxel Release from an Integrin-Targeted Conjugate. Chemistry—A European Journal Communication 25:1696-1700 (2019).
Drago et al., Unlocking the potential of antibody-drug conjugates for cancer therapy. Nature reviews. Clinical oncology 18(6):327-344 (2021).
Drake et al., Stable, Site-Specific ADC Conjugation with SMARTag® Technology andInnovative Linker. ADC Review 1-9 (2022).
Eder et al., Bicyclic Peptides as a New Modality for Imaging and Targeting of Proteins Overexpressed by Tumors. Cancer Research 79(4):841-852 (2019).
Erickson et al., Antibody-Maytansinoid Conjugates Are Activated in Targeted Cancer Cells by Lysosomal Degradation and Linker-dependent Intracellular Processing. Cancer Research 66(8):4426-4433 (2006).
Esch et al. Primary structure of ovine hypothalamic somatostatin-28 and somatostatin-25. PNAS USA 77:6827-6831 (1980).
Evans et al., Synthetic Toll-like Receptors 7 and 8 Agonists: Structure-Activity Relationship in the Oxoadenine Series. ACS omega 4(13):15665-15677 (2019).
Feigin et al., G-protein-coupled receptor GPR161 is overexpressed in breast cancer and is a promoter of cell proliferation and invasion. Proceedings of the National Academy of Sciences of the United States of America 111(11):4191-4196 (2014).
Figueras et al., Octreotide Conjugates for Tumor Targeting and Imaging. Pharmaceutics 11(5):220 (2019).
Fu et al., Antibody Drug Conjugate: The "Biological Missile" for Targeted Cancer Therapy. Signal Transduction and Targeted Therapy 7(1):93 (2022).
Gad et al., The Emerging Role of Adhesion GPCRs in Cancer. ACS pharmacology & translational science 3(1):29-42 (2020).
Gallo et al., Enhancing the Pharmacokinetics and Antitumor Activity of an α-Amanitin-Based Small-Molecule Drug Conjugate via Conjugation with an Fc Domain. Journal of medicinal chemistry 64(7):4117-4129 (2021).
Gauthé et al., Potential Targets Other Than PSMA for Prostate Cancer Theranostics: A Systematic Review. Journal of Clinical Medicine 10(4909):4909 (2021).
Gauzy-Lazo et al., Advances in Antibody-Drug Conjugate Design: Current Clinical Landscape and Future Innovations. SLAS Discovery 25(8):843-868 (2020).
Giese et al., Linker Architectures as Steric Auxiliaries for Altering Enzyme-Mediated Payload Release from Bioconjugates. Bioconjugate Chemistry 32:2257-2267 (2021).
Goeij et al., New developments for antibody-drug conjugate-based therapeutic approaches. Current Opinion in Immunology 40:14-23 (2016).
Gogia et al., Antibody-Drug Conjugates: A Review of Approved Drugs and Their Clinical Level of Evidence. Cancers 15(15):3886 (2023).
Gravbrot et al., Therapeutic Monoclonal Antibodies Targeting Immune Checkpoints for the Treatment of Solid Tumors. Antibodies 8(4):51 (2019).
Guinan et al., Recent Advances in the Chemical Synthesis and Evaluation of Anticancer Nucleoside Analogues. Molecules 25(2050):2050 (2020).
Harvey et al., CD73's Potential as an Immunotherapy Target in Gastrointestinal Cancers. Frontiers in Immunology 11:508 (2020).
Hashimoto et al., CD137 as an Attractive T Cell Co-Stimulatory Target in the TNFRSF for Immuno-Oncology Drug Development. Cancers 13(10):2288 (2021).
Hawner et al., Cellular Targeting of Oligonucleotides by Conjugation with Small Molecules. Molecules 25(24):5963 (2020).
He et al., Peptide Conjugates with Small Molecules Designed to Enhance E cacy and Safety. Molecules 24(1855):1855 (2019).
He et al., SSTR2 is a prognostic factor and a promising therapeutic target in glioma. American journal of translational research 13(10):11223-11234 (2021).
He et al., Tumor microenvironment responsive drug delivery systems. Asian journal of pharmaceutical sciences 15(4):416-448 (2020).
Heinis et al., Phage-encoded Combinatorial Chemical Libraries Based on Bicyclic Peptides. Nature Chemical biology 5(7):502-507 (2009).
Hoppenz et al. Peptide-Drug Conjugates and Their Targets in Advanced Cancer Therapies. Front Chem 8:571 (2020).
Hurov et al., BT7480, A Novel Fully Synthetic Bicycle Tumor-targeted Immune Cell Agonist™ (Bicycle TICA™) Induces Tumor Localized Cd137 Agonism. The Journal for Immuno Therapy of Cancer 9(11):e002883 (2021).
Insel et al., GPCRomics: GPCR Expression in Cancer Cells and Tumors Identifies New, Potential Biomarkers and Therapeutic Targets. Frontiers in pharmacology 22(9):431 (2018).
Ishida et al. Discovery and SAR Studies of Orally Active Somatostatin Receptor Subtype-2 (SSTR2) Agonists for the Treatment of Acromegaly. ACS Chem Neurosci 11(10):1482-1494 (2020).
Jain et al. Current ADC Linker Chemistry. Pharm Res. 32(11):3526-40 (2015).
Jeffrey et al.: Development and Properties of Beta-glucuronide Linkers for Monoclonal Antibody-drug Conjugates. Bioconjugate Chemistry 17:831 (2006).
Jonnalagadda et al., Novel N,N-dialkyl Cyanocinnamic Acids as Monocarboxylate Transporter 1 and 4 Inhibitors. Oncotarget 10(24):2355-2368 (2019).
Keam et al., Lutetium Lu 177 Vipivotide Tetraxetan First Approval. Molecular Diagnosis & Therapy 26:467-475 (2022).
Kern et al., Role of mTOR as an Essential Kinase in SCLC. Journal of Thoracic Oncology 15(9):1522-34 (2020).
Kerr et al., The Next Generation of Immunotherapy for Cancer: Small Molecules Could Make Big Waves. Journal of immunology 202(1):11-19 (2019).
Khlebnikov et al. A Novel Strategy for the Synthesis of 3-(N-Heteryl)pyrrole Derivatives. Org Lett 14(14):3768-71 (2012).
Khongorzul et al., Antibody-Drug Conjugates: A Comprehensive Review. Molecular Cancer Research 18(1):3-19 (2019).
Kim et al., Bispecific Small Molecule-Antibody Conjugate Targeting Prostate Cancer. Proceedings of the National Academy of Sciences of the United States of America 110(44):17796-17801 (2013).
Lee et al., A PSMA-Targeted Bispecific Antibody for Prostate Cancer Driven by a Small-Molecule Targeting Ligand. Science Advances 7(33):eabi8193 (2021).
Legigan et al., The first generation of β-galactosidase-responsive prodrugs designed for the selective treatment of solid tumors in prodrug monotherapy. Angewandte Chemie 51(46):11606-11610 (2012).
Lehman et al., Somatostatin receptor 2 signaling promotes growth and tumor survival in small-cell lung cancer. International journal of cancer 144(5):1104-1114 (2019).
Lerchen et al., A Small Molecule-Drug Conjugate (SMDC) Consisting of a Modified Camptothecin Payload Linked to an αVß3 Binder for the Treatment of Multiple Cancer Types. Cancers 14(2):391 (2022).
Li et al., Clinical Pharmacology of vc-MMAE Antibody-drug Conjugates in Cancer Patients: Learning From Eight First-in-human Phase 1 Studies. mAbs 12(1):1699768 (2020).
Li et al., Conjugating MMAE to a novel anti-HER2 antibody for selective targeted delivery. European Review for Medical and Pharmacological Sciences 24(24):12929-12937 (2020).
Li et al., Discovery of a novel, orally active, small molecule gonadotropin-releasing hormone (GnRH) receptor antagonist. J Med Chem. 49(11):3362-3367 (2006).

(56) References Cited

OTHER PUBLICATIONS

Liu et al. Nonpeptide somatostatin agonists with sst4 selectivity: synthesis and structure-activity relationships of thioureas. J Med Chem 41(24):4693-705 (1998).
Lu et al. Linkers Having a Crucial Role in Antibody-Drug Conjugates. Int J Mol Sci 17(4):561 (2016).
Mallinger et al. Discovery of Potent, Orally Bioavailable, Small-Molecule Inhibitors of WNT Signaling from a Cell-Based Pathway Screen. J Med Chem 58(4):1717-35 (2015).
Mandriani et al., Development of anti-somatostatin receptors CAR T cells for treatment of neuroendocrine tumors. Journal for immunotherapy of cancer 10(6):e004854 (2022).
Mansi et al., Distinct In Vitro Binding Profile of the Somatostatin Receptor Subtype 2 Antagonist [177Lu]Lu-OPS201 Compared to the Agonist [177Lu]Lu-DOTA-TATE. Pharmaceuticals 14(12):1265 (2021).
McCombs et al. Antibody Drug Conjugates: Design and Selection of Linker, Payload and Conjugation Chemistry. AAPS J 17(2):339-351 (2015).
Mollaoglu et al., MYC Drives Progression of Small Cell Lung Cancer to a Variant Neuroendocrine Subtype with Vulnerability to Aurora Kinase Inhibition. Cancer Cell 31:270-285 (2017).
Moyano-Galceran et al., Adaptive RSK-EphA2-GPRC5A Signaling Switch Triggers Chemotherapy Resistance in Ovarian Cancer. EMBO Molecular Medicine 12(4):e11177 (2020).
Mudd et al., Discovery of BT8009: A Nectin-4 Targeting Bicycle Toxin Conjugate for the Treatment of Cancer. Journal of Medicinal Chemistry 65(21):14337-14347 (2022).
Mudd et al., Identification and Optimization of EphA2-Selective Bicycles for the Delivery of Cytotoxic Payloads. Journal of medicinal chemistry 63(8):4107-4116 (2020).
Murányi et al., Novel Crizotinib-GnRH Conjugates Revealed the Significance of Lysosomal Trapping in GnRH-Based Drug Delivery Systems. International Journal of Molecular Sciences 20:5590 (2019).
Niaz et al., Prostate-specific Membrane Antigen Based Antibody-drug Conjugates for Metastatic Castration-resistance Prostate Cancer. Cureus 12(2):e7147 (2020).
Nolting. Chapter 5: Linker technologies for antibody-drug conjugates. Methods Mol Biol 1045:71-100 (2013).
Ogitani et al., DS-8201a, A Novel HER2-Targeting ADC with a Novel DNA Topoisomerase I Inhibitor, Demonstrates a Promising Antitumor Efficacy with Differentiation from T-DM1. Clinical cancer research 22(20):5097-5108 (2016).
Ortiz-Marciales et al. Catalytic enantioselective borane reduction of benzyl oximes: preparation of (S)-1-Pyridin-3-yl-Ethylamine Bis Hydrochloride. Organic Synth. 87:36-52 (2010).
Patel et al. Somatostatin receptors. Trends Endocrinol Metab 8:398-405 (1997).
PCT/US2022/032707 International Search Report and Written Opinion dated Sep. 26, 2022.
Pillow et al., Decoupling stability and release in disulfide bonds with antibody-small molecule conjugates. Chemical science 8(1):366-370 (2017).
Pismataro et al., Small Molecules Targeting DNA Polymerase Theta (POLθ) as Promising Synthetic Lethal Agents for Precision Cancer Therapy. Journal of Medicinal Chemistry 66(10):6498-6522 (2023).
Polley et al., Small Cell Lung Cancer Screen of Oncology Drugs, Investigational Agents, and Gene and microRNA Expression. Journal of the National Cancer Institute 108(10):djw122 (2016).
Poreba et al., Fluorescent probes towards selective cathepsin B detection and visualization in cancer cells and patient samples. Chemical science 10(36):8461-8477 (2019).
Poreba et al., Protease-activated Prodrugs: Strategies, Challenges, and Future Directions. The FEBS Journal 287:1936-1969 (2020).
Poudel et al., Chemical Modification of Linkers Provides Stable Linker-Payloads for the Generation of Antibody-Drug Conjugates. ACS Medicinal Chemistry Letters 11(11):2190-2194 (2020).
Pradayrol et al. N-terminally extended somatostatin: the primary structure of somatostatin-28. FEBS Letters 109:55-58 (1980).
Price et al. Matching chelators to radiometals for radiopharmaceuticals. Chem Soc Rev 43(1):260-90 (2014).
Puri et al., Monocarboxylate Transporter 1 and 4 Inhibitors as Potential Therapeutics for Treating Solid Tumours: a Review With Structure-activity Relationship Insights. European Journal of Medicinal Chemistry 199:112393 (2020).
Raimondi et al., Rare, Functional, Somatic Variants in Gene Families Linked to Cancer Genes: GPCR Signaling as a Paradigm. Oncogene 38:6491-6506.
Reisine et al. Molecular biology of somatostatin receptors. Endocr Rev 16:427-442 (1995).
Reubi et al. Approaches to Multireceptor Targeting: Hybrid Radioligands, Radioligand Cocktails, and Sequential Radioligand Applications. J Nucl Med 58(Suppl 2):10S-16S (2017).
Riechelmann et al., Therapy Sequencing in Patients With Advanced Neuroendocrine Neoplasms. American Society of Clinical Oncology educational 43:e389278 (2023).
Rigby et al., BT8009; A Nectin-4 Targeting Bicycle Toxin Conjugate for Treatment of Solid Tumors. Molecular Cancer Therapeutics 21(12):1747-1756.
Rosner et al., Antibody-Drug Conjugates for Lung Cancer: Payloads and Progress. American Society of Clinical Oncology Educational Book 43:e389968 (2023).
Sanaei et al., Recent Advances in Immune Checkpoint Therapy in Non-small Cell Lung Cancer and Opportunities for Nanoparticle-based Therapy. European Journal of Pharmacology 909:174404) (2021).
Sanguinetti et al. hERG potassium channels and cardiac arrhythmia. Nature 440(7083):463-469 (2006).
Schaaf et al., Defining the role of the tumor vasculature in antitumor immunity and immunotherapy. Cell Death Dis. 9(2):115 (2018).
Schulz et al. Comparative Evaluation of the Biodistribution Profiles of a Series of Nonpeptidic Neurotensin Receptor-1 Antagonists Reveals a Promising Candidate for Theranostic Applications. J Nucl Med 57(7):1120-1123 (2016).
Science IP Report. Chemical Structure Search (May 24, 2016) (311 pgs.).
Sheyi et al., Linkers: An Assurance for Controlled Delivery of Antibody-Drug Conjugate. Pharmaceutics 14(369):396 (2022).
Si et al., Anti-SSTR2 Antibody-drug Conjugate for Neuroendocrine Tumor Therapy. Cancer Gene Therapy 28(7-8):799-812 (2021).
Srinivasarao et al., Principles in the Design of Ligand-targeted Cancer Therapeutics and Imaging Agents. Nat Rev Drug Discov 14(3):203-19 (2015).
Sriram et al., GPCRs show widespread differential mRNA expression and frequent mutation and copy number variation in solid tumors. PLoS biology 17(11):e3000434 (2019).
Stella. Prodrugs: Some Thoughts and Current Issues. J Pharm Sci 99(12):4755-4765 (2010).
Su et al., Antibody-Drug Conjugates: Recent Advances in Linker Chemistry. Acta Pharmaceutica Sinica B 11(12):3889-3907.
Sun et al., Effects of camptothecin conjugated to a somatostatin analog vector on growth of tumor cell lines in culture and related tumors in rodents. Drug delivery 11(4):231-238 (2004).
Teufel et al., Stable and Long-Lasting, Novel Bicyclic Peptide Plasma Kallikrein Inhibitors for the Treatment of Diabetic Macular Edema. Journal of medicinal chemistry 61(7):2823-2836 (2018).
Thomas et al., Antibody-Drug Conjugates for Cancer Therapy. The Lancet Oncology 17(6):e254-e262 (2016).
Tong et al., An Insight into FDA Approved Antibody-Drug Conjugates for Cancer Therapy. Molecules 26(19):5847 (2021).
Tran et al., Establishment of Novel Neuroendocrine Carcinoma Patient-Derived Xenograft Models for Receptor Peptide-Targeted Therapy. Cancers 14(8):1-13 (2022).
Tse et al., Abt-263: A Potent and Orally Bioavailable Bcl-2 Family Inhibitor. Cancer Research 68(9):3421-3428 (2008).
Upadhyaya et al., Anticancer Immunity Induced by a Synthetic Tumor-Targeted CD137 Agonist. The Journal for Immuno Therapy of Cancer 9(1):e001762 (2021).
Upadhyaya et al., Discovery and Optimization of a Synthetic Class of Nectin-4-Targeted CD137 Agonists for Immuno-oncology. Journal of medicinal chemistry 64(14):9858-9872 (2022).

(56) References Cited

OTHER PUBLICATIONS

Valko et al., Application of Biomimetic HPLC to Estimate Lipophilicity, Protein and Phospholipid Binding of Potential Peptide Therapeutics. ADMET and DMPK 6(2):162-175 (2018).

Vrettos et al., On the Design Principles of Peptide-drug Conjugates for Targeted Drug Delivery to the Malignant Tumor Site. Beilstein the Journal of Organic Chemistry 14:930-954 (2018).

Wang et al., Antibody-Drug Conjugates: Recent Advances in Payloads. Acta Pharmaceutica Sinica B 13(10):4025-4059 (2023).

Wang et al., Comprehensive Surfaceome Profiling to Identify and Validate Novel Cell-Surface Targets in Osteosarcoma. Molecular Cancer Therapeutics 21(6):903-913 (2022).

Wang et al., Structural basis of human monocarboxylate transporter 1 inhibition by anti-cancer drug candidates. Cell 184(2):370-383 (2021).

Weckbecker et al. Opportunities in somatostatin research: biological, chemical and therapeutic aspects. Nat Rev Drug Discov 2(12):999-1017 (2003).

Whalen et al., Targeting the Somatostatin Receptor 2 with the Miniaturized Drug Conjugate, PEN-221: A Potent and Novel Therapeutic for the Treatment of Small Cell Lung Cancer. Molecular cancer therapeutics 18(11):1926-1936 (2019).

White et al., Discovery of an SSTR2-Targeting Maytansinoid Conjugate (PEN-221) with Potent Activity in Vitro and in Vivo. Journal of medicinal chemistry 62(5):2708-2719 (2019).

Widder et al. Section III: Prodrugs Kinetics. Method in Enzymology. 112:309-396 (1985).

Wiley et al., GPR68: An Emerging Drug Target in Cancer. International journal of molecular sciences 20(3):559 (2019).

Wolf et al. Cytochrome P450 CYP2D6. IARC Sci Publ 148:209-229 (1999).

Wolkenberg et al. Design, synthesis, and evaluation of novel 3,6-diaryl-4-aminoalkoxyquinolines as selective agonists of somatostatin receptor subtype 2. J Med Chem 54:2351-2358 (2011).

Worm et al. Targeting of peptide-binding receptors on cancer cells with peptide-drug conjugates. Peptide Science 112(3):e24171 (2020).

Wu et al. Arming antibodies: prospects and challenges for immunoconjugates. Nat. Biotechnol. 23:1137-1146 (2005).

Wu et al., Illuminating the Onco-GPCRome: Novel G Protein-coupled Receptor-driven Oncocrine Networks and Targets for Cancer Immunotherapy. Journal of Biological Chemistry 294(29):11062-11086 (2019).

Yamato et al., DS-7300a, a DNA Topoisomerase I Inhibitor, DXd-Based Antibody-Drug Conjugate Targeting B7-H3, Exerts Potent Antitumor Activities in Preclinical Models. Molecular cancer therapeutics 21(4):635-646 (2022).

Yang et al., GPRC5A Is a Negative Regulator of the Pro-Survival PI3K/Akt Signaling Pathway in Triple-Negative Breast Cancer. Frontiers in oncology 10:624493 (2021).

Zanden et al., Opportunities for Small Molecules in Cancer Immunotherapy. Trends in Immunology 41(6):493-511 (2020).

Zhao et al. Discovery of nonpeptide 3,4-dihydroquinazoline-4-carboxamides as potent and selective sst2 agonists. Bioorg Med Chem Lett 30(17):127391 (2020).

Zhao et al. Discovery of Paltusotine (CRN00808), a Potent, Selective, and Orally Bioavailable Non-peptide SST2 Agonist. ACS Med Chem Lett 14(1):66-74 (2022).

Zhao et al. Discovery of substituted 3H-pyrido[2,3-d]pyrimidin-4-ones as potent, biased, and orally bioavailable sst2 agonist. Bioorg Med Chem Lett 30(21):127496 (2020).

Zhong et al., Lung Tumor Suppressor GPRC5A Binds EGFR and Restrains Its Effector Signaling. American Association for Cancer Research 75(9):1801-14 (2015).

De Jong, M. et al., Yttrium-90 and indium-111 labelling, receptor binding and biodistribution of [DOTA0,d-Phe1,Tyr3]octreotide, a promising somatostatin analogue for radionuclide therapy. European journal of nuclear medicine 24(4):368-371 (1997).

Lau, Joseph., et al., Insight into the Development of PET Radiopharmaceuticals for Oncology. Cancers 12(5):1-34 (2020).

PCT/US2023/083429 International Search Report and Written Opinion dated Mar. 19, 2024.

\* cited by examiner

SOMATOSTATIN SUBTYPE-2 RECEPTOR (SST2R) TARGETED THERAPEUTICS AND USES THEREOF

CROSS-REFERENCE TO RELATED APPLICATIONS

This application is a continuation of U.S. patent application Ser. No. 18/535,503, filed on Dec. 11, 2023, which claims the benefit of U.S. Provisional Patent Application No. 63/387,235, filed on Dec. 13, 2022; and U.S. Provisional Patent Application No. U.S. 63/597,871, filed on Nov. 10, 2023; each of which is incorporated herein by reference in its entirety.

FIELD OF THE INVENTION

Described herein are somatostatin subtype-2 receptor (SST2R) drug conjugates and methods of using such drug conjugates as cancer therapeutics, diagnostics, or both.

BACKGROUND OF THE INVENTION

Neoplasms are abnormal growth of cells and cause enormous medical burdens, including morbidity and mortality, in humans. Neoplasms include benign or noncancerous neoplasms which do not display malignant features and are generally unlikely to become dangerous (e.g., adenomas); malignant neoplasms display features such as genetic mutations, loss of normal function, rapid division, ability to metastasize (invade) to other tissues, and exhibit neoplasms of uncertain or unknown behavior. Malignant neoplasms (i.e., cancerous solid tumors) are the leading cause of death in industrialized countries. Noncancerous neoplasms, including benign adenomas, can also cause significant morbidity and mortality. Although standard treatments can achieve significant effects in tumor growth inhibition and even tumor elimination, the applied drugs exhibit only minor selectivity for the malignant tissue over healthy tissue and their severe side effects limit their efficacy and use. Specific targeting of neoplastic cells without affecting healthy tissue is a major desire for effective solid tumor therapy. Non-peptide SST2R ligands conjugated to suitable drug cargos or payloads represent a novel class of small molecule drug conjugates (SMDCs) for selective cancer therapeutics or diagnostics.

SUMMARY OF THE INVENTION

Described herein are SST2R modulators that target the delivery of payloads to tumors that express the SSTR2, and their use in the treatment of tumors. The present disclosure provides an alternative and improved method for the treatment of tumors. In some embodiments, the SMDCs disclosed herein provide an improved method for targeting SST2R-expressing tumor cells over traditional therapies, which have narrow therapeutic indexes.

In one aspect, described herein is a compound that has the structure of Formula (I), or a pharmaceutically acceptable salt thereof:

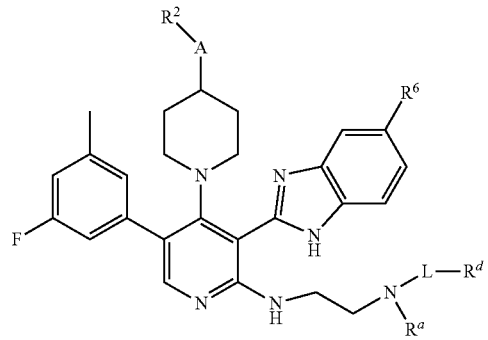

Formula (I)

wherein:
A is —N(H)— or —O—;
$R^a$ is hydrogen or $C_1$-$C_6$alkyl;
$R^2$ is hydrogen or $C_1$-$C_6$alkyl;
$R^6$ is chloro or —C(=O)NH$_2$;
L is -$L^1$-$L^2$-;
  $L^1$ is an optional spacer; and
  $L^2$ is an optional linker;
  wherein at least one of $L^1$ or $L^2$ is present; and
$R^d$ is a payload moiety comprising a chemotherapeutic agent.
In some embodiments, $L^2$ is present and is -($L^{2a}$)$_w$-$L^{2b}$- or -$L^{2c}$-;
  each $L^{2a}$ is independently selected from natural or unnatural amino acids, wherein any free amine of an amino acid is optionally independently substituted with —CH$_3$;
  $L^{2b}$ is absent or —N($R^{10}$)(unsubstituted or substituted benzyl)-OC(=O)—; wherein substituted benzyl is substituted with —C(=O)NHR$^{12}$ or a monosaccharide;
  each $R^{10}$ is independently selected from hydrogen, and $C_1$-$C_6$alkyl;
  each $R^{12}$ is independently selected from hydrogen, $C_4$-$C_{20}$polyethylene glycol, and unsubstituted or substituted $C_1$-$C_6$alkyl, wherein the substituted $C_1$-$C_6$alkyl is substituted with —NHR$^{13}$, —C(=O)NHR$^{13}$, or —NHC(=O)R$^{13}$;
  each $R^{13}$ is independently selected from hydrogen, $C_4$-$C_{20}$polyethylene glycol, and $C_4$-$C_{20}$polyethylene glycol-NH$_2$;
  or when $R^{13}$ is present and at least one free carboxylic group of an amino acid of $L^{2a}$ is present, then $R^{13}$ and the free carboxylic group of the amino acid of $L^{2a}$ are taken together to form a ring;
  w is 1, 2, 3, 4, 5, or 6; and
  each $L^{2c}$ is N-maleimidomethyl-cyclohexane-1-carbonyl (MCC) or —S—.
In some embodiments, $L^1$ is present and is —$X^2$-$L^3$-$L^4$-:
  $X^2$ is —C(=O)(CH$_2$)$_p$—, —(CH$_2$)$_p$—, —C(=O)CH(CH$_2$SO$_3$H)NHC(=O)—, or —($X^{2a}$)$_p$—;
  each $X^{2a}$ is independently selected from natural or unnatural amino acids, wherein any free amine of an amino acid is optionally independently substituted with —CH$_3$;
  p is 0, 1, 2, 3, 4, 5, or 6;
$L^3$ is absent, unsubstituted or substituted $C_1$-$C_{10}$alkylene, unsubstituted or substituted $C_1$-$C_{10}$heteroalkylene, $C_4$-$C_{20}$polyethylene glycol, or —($X^3$CH$_2$CH$_2$)$_t$—;
  each $X^3$ is independently selected from O and NR$^{10}$;

each t is independently 1, 2, 3, 4, 5, 6, 7, 8, 9, 10, 11, or 12;

$L^4$ is absent, or $-L^{4a}-(CH_2)_u-L^{4b}-(CH_2)_u-L^{4c}-$;

$L^{4a}$ is absent, $-O-$, $-NR^{10}-$, $-NR^{10}C(=O)-$, $-C(=O)NR^{10}-$, or $-C(=O)-$;

$L^{4b}$ is absent, or unsubstituted or substituted N-containing 5 to 10 membered heterocycloalkylene; wherein any free amine of the N-containing 5 to 10 membered heterocycloalkylene is optionally independently substituted with $-CH_2CO_2H$;

$L^{4c}$ is absent, $-O-$, $-NR^{10}-$, $-NR^{10}C(=O)-$, $-C(=O)NR^{10}-$, $-C(=O)NR^{10}(CH_2)_uO(CH_2)_uC(=O)-$, $CH(CH_2SO_3H)C(=O)NR^{10}(CH_2)_uO(CH_2)_uC(=O)-$, $-C(=O)-$, $-CH(=N)-$, $-CH(=N-NH)-$, $-CCH_3(=N)-$, $-CCH_3(=N-NH)-$, $-C(=O)-(C_1-C_6\text{alkylene})-$, $-C(=O)NR^{10}-(C_1-C_6\text{alkylene})-$, $-NR^{10}C(=O)-(C_1-C_6\text{alkylene})-$, $-NR^{10}-(C_1-C_6\text{alkylene})-$ or $C_1-C_6\text{alkylene}-$;

each u is independently 0, 1, 2, 3, 4, 5, or 6; and each $R^{10}$ is independently selected from hydrogen, and $C_1-C_6\text{alkyl}$.

In some embodiments, $R^d$ is:

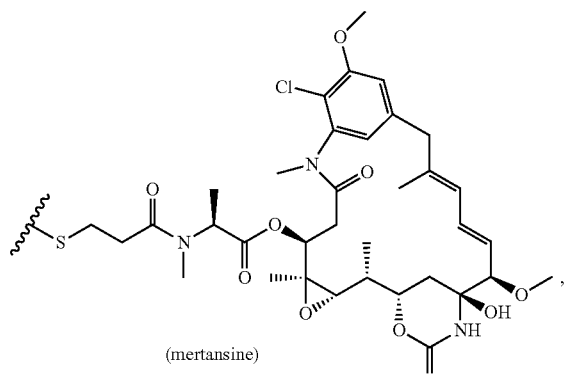

(mertansine)

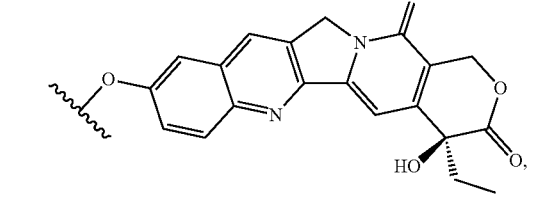

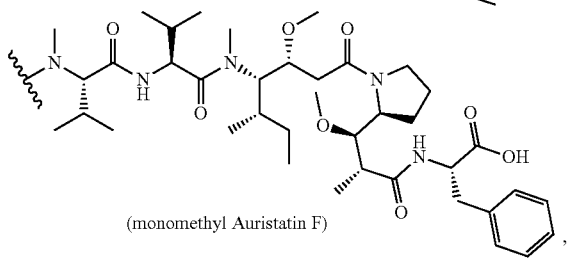

(monomethyl Auristatin F)

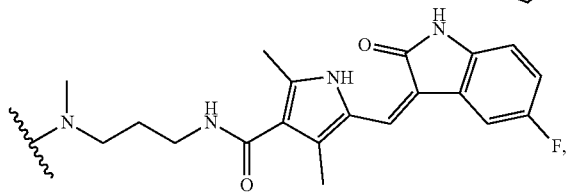

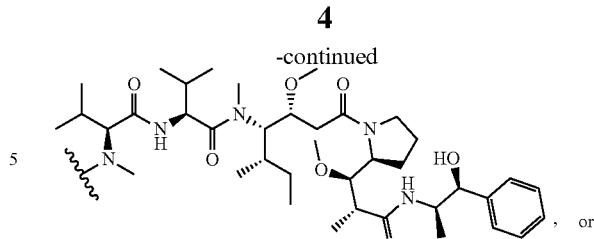

(monomethyl Auristatin E)

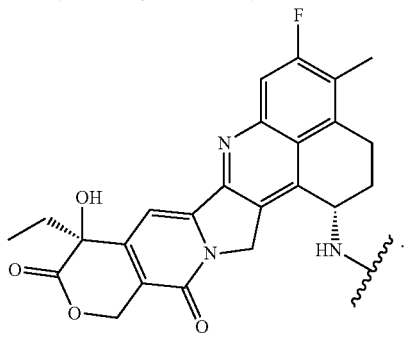

(Exatecan)

In another aspect, described herein is a method for the treatment of cancer comprising administering to a mammal with cancer an effective amount of a compound of Formula (I), or a pharmaceutically acceptable salt thereof.

In another aspect, described herein is a method for treating tumors comprising administering to a mammal with tumors an effective amount of a compound of Formula (I), or a pharmaceutically acceptable salt thereof.

In some embodiments, the mammal has anal cancer, bladder cancer, bowel cancer, brain cancer, breast cancer, colon cancer, colorectal cancer, endometrial cancer, esophageal cancer, gallbladder cancer, gastric cancer, heart cancer, kidney cancer, lung cancer, liver cancer, melanoma, uterine cancer, lymphoma, ovarian cancer, pancreatic cancer, prostate cancer, thymus cancer, pheochromocytoma, medullary thyroid carcinoma, head & neck cancer, or melanoma. In some embodiments, the mammal has an endocrine cancer. In some embodiments, the endocrine cancer comprises adrenal tumors, neuroendocrine tumors, parathyroid tumors, pituitary tumors, or thyroid tumors. In some embodiments, the mammal has neuroendocrine tumors. In some embodiments, the mammal has somatostatin receptor-positive gastroenteropancreatic neuroendocrine tumors (GEP-NETs).

In another aspect, described herein is a method of targeting delivery of a chemotherapeutic to tumors in a mammal comprising administering to a mammal with tumors a compound of Formula (I), or a pharmaceutically acceptable salt thereof.

In another aspect, described herein is a method of killing tumors in a mammal that overexpress the somatostatin subtype-2 receptor (SST2R) comprising administering to the mammal a compound of Formula (I), or a pharmaceutically acceptable salt thereof.

In any of the embodiments disclosed herein, the mammal is a human.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Figure 1:
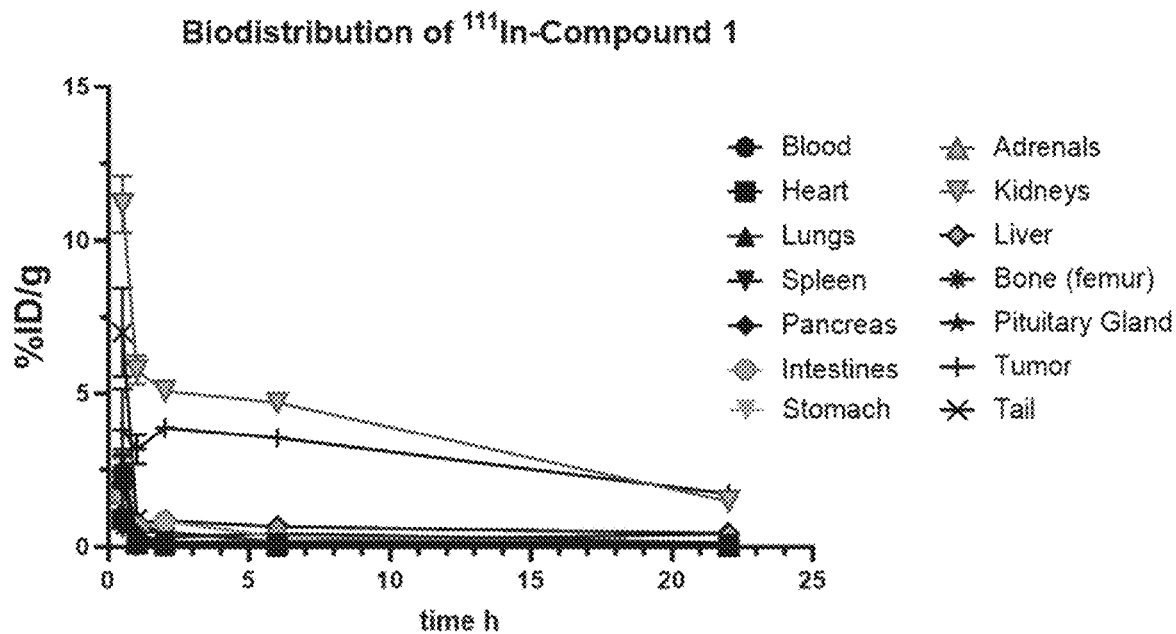
FIG. 1 depicts time-activity curves of selected organ activity of $^{111}$In-Compound 1 in female swiss nude mice with AR4J2 pancreatic tumors; uptake of $^{111}$In-Compound 1 in tumor and normal tissues in tumor bearing animals is shown (Mean±SD).
Figure 2:
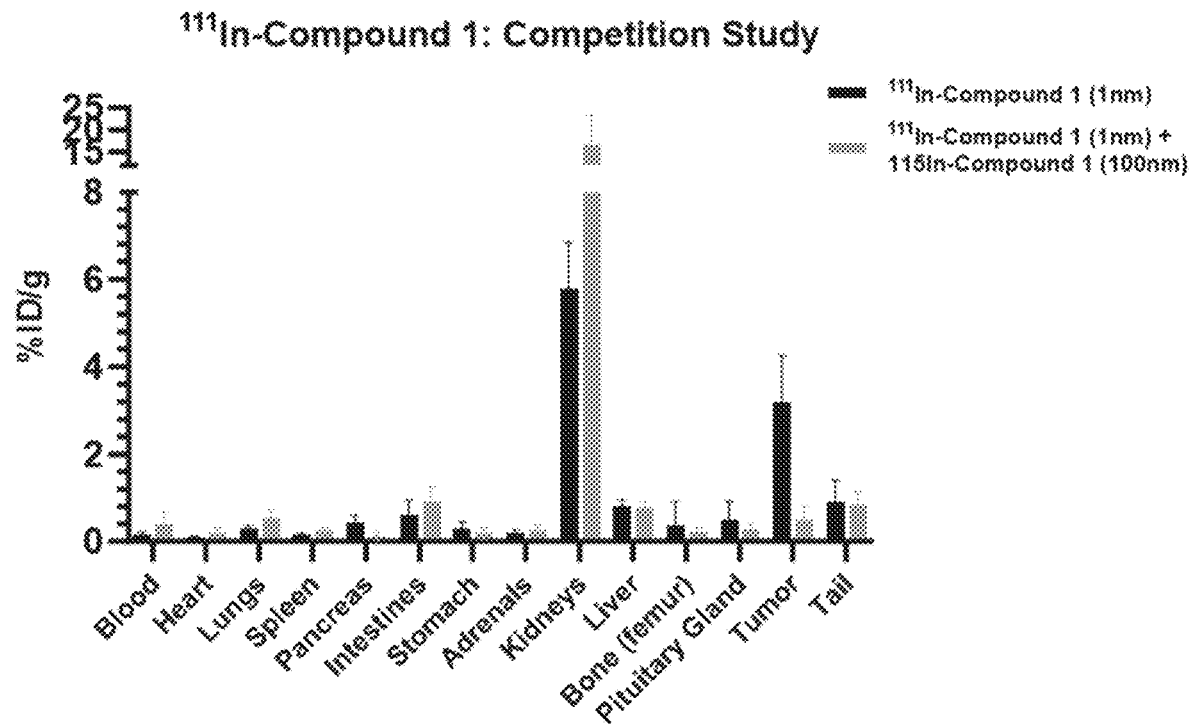
FIG. 2 depicts uptake of $^{111}$In-Compound 1 alone and with excessive $^{115}$In-Compound 1 at 2 h post-dose in the xenograft mouse model with AR42J derived tumors; organ activity in % ID/g of tissue at 2 h post-dose and selective blocking of $^{111}$In-Compound 1 uptake in the presence of excess $^{115}$In-Compound 1 are shown; this study demonstrates specific SST2R-mediated uptake in tumors that is blocked with excessive $^{115}$In-Compound 1 (Mean±SD).

Cancer, a disease in which some cells undergo a genetic change in the control of their growth and replication that results in uncontrolled growth and spreading, is one of the leading causes of death worldwide. General types of cancers include solid tumors (cancers that typically originate in organs), carcinomas (cancers that originate in skin or tissues that line organs), sarcomas (cancers of connective tissues such as bones), leukemias (cancers of bone marrow), and lymphomas and myelomas (cancers of the immune system). Neoplasms are abnormal growth of cells that result in solid tumors which may be benign (i.e., do not display malignant features and are generally unlikely to become dangerous such as adenomas), malignant (i.e., display features such as genetic mutations, loss of normal function, rapid division, and can metastasize (invade) to other tissues), and of uncertain or unknown behavior. State-of-the-art treatment of neoplasms is accomplished by a combination of surgical procedures, chemotherapy, and radiation therapy. Surgical procedures can be curative under some conditions, but often requires multiple interventions as well as combination with radiation and chemotherapy. Chemotherapy proves to be a potent weapon in the fight against cancer in many cases, but further optimization is required. Chemotherapy is typically performed by systemic administration of potent cytotoxic drugs, but these compounds lack tumor selectivity and therefore also kill healthy cells in the body. This non-specific toxicity causes the severe side effects commonly associated with of chemotherapy. Radiotherapy is the use of high-energy radiation to kill cells. The source of radiation may be external-beam radiation (applied using an external source), internal radiation (placement of a radioactive material near the target cells), or radiotherapy from the systemic administration of a radioactive material. Similar to chemotherapy, many radiation therapy options also lack tumor cell identification properties needed to achieve the ultimate goal of targeted tumor therapy with drug molecules or radionuclides.

GPCRs are a large and diverse group of integral membrane receptors and as a consequence are expressed in every cell type in the body. GPCRs are generally poorly antigenic making them difficult targets for antibody-based strategies. For many GPCRs, a large proportion of the protein population resides in intracellular compartments at any given time, which reduces the total number of cell surface binding sites accessible to antibodies or peptides.

Many human tumors overexpress different GPCRs, often times at significantly higher density than other tissues. For example, gastroenteropancreatic (GEP) neuroendocrine tumors (NETs) overexpress somatostatin receptors, namely SSTR2, SSTR3, and SSTR5. Breast cancers also overexpress SSTR2. Due to the complicated GPCR overexpression profiles in neoplasms, targeting multiple receptors simultaneously may address issues such as heterogeneity, resistance, and change of phenotype during disease progression that have hampered many current treatment options.

The class of somatostatin receptors (SSTRs) consists of five members (SSTR1, SSTR2, SSTR2, SSTR4, SSTR5), which are widely expressed in different tissues in the body including nervous, pituitary, kidney, lung, and immune cells. Their natural ligand is the neuropeptide somatostatin (SST), which occurs in two active isoforms, SST-14 and SST-28. In combination with their receptors, both isoforms act as inhibitory hormones. An important physiological function of the SSTR/SST axis is, for example, the inhibition of the release of growth hormones. SSTRs, particularly the SSTR subtype 2, are found highly expressed in many neoplastic cells and in tumoral blood vessels. Overexpression of SSTRs, in particular SSTR2, has been found in various neuroendocrine tumors, as well as other tumors such as breast, ovarian, and lung cancer. Targeting of the SSTR2 for drug delivery has been accomplished by using stabilized, cyclic somatostatin analogs such as octreotate, octreotide, and lanreotide. For example, covalently attaching a DOTA chelator to octreotide (DOTA-TATE, also known as DOTA-(Tyr$^3$)-octreotate) has made it possible to target delivery of radionuclides to tumor cells expressing somatostatin receptors. $^{177}$Lu DOTA-TATE therapy is a form of peptide receptor radionuclide therapy (PRRT) which targets somatostatin receptors and is a form of targeted drug delivery.

Most currently available GPCR-targeting drugs act at receptors for which the native ligands are small molecules, such as histamine, adrenaline, and neurotransmitters. Drugs targeting GPCR for which the native ligands are peptides or proteins, are typically also peptides or proteins.

Peptides are intrinsically sensitive to proteolytic enzymes and peptidases present in most tissues, and are rapidly degraded into multiple fragments which no longer have significant affinity for the intended receptors. There are ways to stabilize peptides (e.g., incorporating peptidomimetic structures or using more stable D amino acids in the peptide backbone) but these modifications can lead to loss of affinity and/or selectivity, and negtively impact physicochemical properties (e.g., poor solubility and tendency to aggregate). In addition, peptides may cause unwanted immunogenic responses complicating later stages of development by masking the therapeutic effect and impacting the safety assessment.

When peptide ligands are linked to cytotoxic payloads, the resulting conjugates often degrade rapidly in blood plasma and produce cytotoxic peptide fragments which may nonspecifically bind to both tumor and normal tissue. This premature breakdown of peptide drug conjugates (PDCs) and antibody drug conjugates (ADCs) reduces the amount of cytotoxic payloads distributed to targeted tumors, lowering treatment efficacy, and possibly increasing toxicity. In addition, peptides are most likely exclusively excreted via the kidneys, which may limit PDC applications. Marked kidney uptake of some peptide-based therapeutics has limited their routine use.

High affinity, small molecule ligands that bind peptide GPCRs and protein GPCRs, such as chemokine GPCRs, have been described and are cell permeable and can access populations of receptors in the endoplasmic reticulum and endosomes. Owing to the low molecular weight of non-peptide small molecules, vascular permeability and tumor penetration should be improved compared to high molecular weight conjugates based on peptides and antibodies. The binding affinity of small molecule nonpeptide ligands in many cases surpasses that of FDA approved antibodies by orders of magnitude.

Provided herein are SMDCs which are SST2R ligand drug conjugates. The conjugated drug cargo or payload moiety is connected to the ligand in a manner that does not affect the binding affinity of the small molecule SST2R ligand to the SST2R. The conjugated drug cargos or payload moieties include chemotherapeutic agents and radionuclides, which are connected to the ligand using a spacer and/or linker moiety.

Solid Tumors: Benign and/or Malignant Neoplasms (Cancer)

In one aspect, compounds of Formula (I) are used to treat benign and/or malignant neoplasms (solid tumors), wherein the neoplasm comprises cells that overexpress cell surface GPCRs.

The term "neoplasm" as used herein, refers to an abnormal growth of cells that may proliferate in an uncontrolled way and may have the ability to metastasize (spread).

Neoplasms include solid tumors, adenomas, carcinomas, sarcomas, leukemias and lymphomas, at any stage of the disease with or without metastases.

A solid tumor is an abnormal mass of tissue that usually does not contain cysts or liquid areas. Solid tumors may be benign (not cancer), or malignant (cancer). Different types of solid tumors are named for the type of cells that form them. Examples of solid tumors are sarcomas, carcinomas, and lymphomas. Leukemias (cancers of the blood) generally do not form solid tumors.

Solid tumors are cancers that typically originate in organs, such as the bladder, bowel, brain, breast, endometrium, heart, kidney, lung, liver, uterus, ovaries, pancreas or other endocrine organs (thyroid), and prostate.

An adenoma is a tumor that is not cancer. It starts in gland-like cells of the epithelial tissue (thin layer of tissue that covers organs, glands, and other structures within the body). An adenoma can grow from many glandular organs, including the adrenal glands, pituitary gland, thyroid, prostate, and others. Over time adenomas may become malignant, at which point they are called adenocarcinomas. While benign, they have the potential to cause serious health complications by compressing other structures (mass effect) and by producing large amounts of hormones in an unregulated, non-feedback-dependent manner (causing paraneoplastic syndromes).

Adenomas typically are found in the colon (e.g. adenomatous polyps, which have a tendency to become malignant and to lead to colon cancer), kidneys (e.g. renal adenomas may be precursor lesions to renal carcinomas), adrenal glands (e.g. adrenal adenomas, such as pheochromocytoma; some secrete hormones such as cortisol, causing Cushing's syndrome, aldosterone causing Conn's syndrome, or androgens causing hyperandrogenism), thyroid (e.g. thyroid adenoma), pituitary (e.g. pituitary adenomas, such as prolactinoma), parathyroid (e.g. an adenoma of a parathyroid gland may secrete inappropriately high amounts of parathyroid hormone and thereby cause primary hyperparathyroidism), liver (e.g. hepatocellular adenoma), breast (e.g. fibroadenomas), appendix (e.g. cystadenoma), bronchial (e.g. bronchial adenomas may cause carcinoid syndrome, a type of paraneoplastic syndrome), prostate (e.g. prostate adenoma), sebaceous gland (e.g. sebaceous adenoma), and salivary glands.

Metastasis is the spread of malignant cells to new areas of the body, often by way of the lymph system or bloodstream. A metastatic tumor is one that has spread from the primary site of origin, or where it started, into different areas of the body. Metastatic tumors comprise malignant cells that express cell surface GPCRs.

Tumors formed from cells that have spread are called secondary tumors. Tumors may have spread to areas near the primary site, called regional metastasis, or to parts of the body that are farther away, called distant metastasis.

In some embodiments, the tumor to be treated comprises tumor cells expressing a GPCR, wherein the tumor is a primary or metastatic tumor. In some embodiments, the tumor to be treated comprises tumor cells expressing a GPCR, wherein the tumor is a primary or metastatic tumor of gastrointestinal origin, such as colorectal cancer, stomach cancer, small intestine cancer, or esophageal cancer. In some embodiments, the tumor to be treated comprises tumor cells expressing a GPCR, wherein the tumor is a primary or metastatic tumor of the pancreas. In some embodiments, the tumor to be treated comprises tumor cells expressing a GPCR, wherein the tumor is a primary or metastatic tumor of the lungs, such as squamous cell carcinoma, adenosquamous carcinoma, or adenocarcinoma. In some embodiments, the tumor to be treated comprises tumor cells expressing a GPCR, wherein the tumor is a primary or metastatic neuroectodermal tumor, such as aphaechromotcytoma or a paraganglioma. In some embodiments, the tumor to be treated comprises tumor cells expressing a GPCR, wherein the tumor is a primary or metastatic bronchopulmonary or gastrointestinal neuroendocrine tumor. In some embodiments, the tumor to be treated comprises tumor cells expressing a GPCR, wherein the tumor is a primary or metastatic tumor of the rectum or colon.

In some embodiments, compounds of Formula (I) are used to treat a sarcoma, such as leiomyosarcoma or rhabdomyosarcoma.

In some embodiments, compounds of Formula (I) are used to treat an adenoma.

In another aspect, provided herein is a method for treating cancer in a mammal comprising administering to the mammal in need thereof, a SMDC disclosed herein. In some embodiments, the cancer comprises tumor cells expressing one or more peptide hormone GPCRs. In some embodiments, the cancer comprises tumor cells that overexpress one or more GPCRs. In some embodiments, the cancer comprises a solid tumor. In some embodiments, the cancer comprises a sarcoma, carcinoma, or lymphoma. In some embodiments, the cancer comprises a neuroendocrine tumor. In some embodiments, the cancer comprises an insulinoma. In some embodiments, the cancer comprises peptide hormone GPCR-positive (e.g., somatostatin receptor-positive) gastroenteropancreatic neuroendocrine tumors (GEP-NETs).

In some embodiments, the compound of Formula (I) is administered to an oncology patient. In some embodiments, the oncology patient has been diagnosed with a carcinoma, sarcoma, primary tumor, metastatic tumor, solid tumor, non-solid tumor, blood tumor, leukemia or lymphoma.

Carcinomas include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma, etc.

Sarcomas include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Solid tumors include, but are not limited to, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma. Benign solid tumors include adenomas.

Leukemias include, but are not limited to, a) chronic myeloproliferative syndromes (neoplastic disorders of multipotential hematopoietic stem cells); b) acute myelogenous leukemias (neoplastic transformation of a multipotential hematopoietic stem cell or a hematopoietic cell of restricted lineage potential; c) chronic lymphocytic leukemias (CLL; clonal proliferation of immunologically immature and functionally incompetent small lymphocytes), including B-cell CLL, T-cell CLL prolymphocyte leukemia, and hairy cell leukemia; and d) acute lymphoblastic leukemias (characterized by accumulation of lymphoblasts). Lymphomas include, but are not limited to, B-cell lymphomas (e.g., Burkitt's lymphoma); Hodgkin's lymphoma; and the like.

Primary and metastatic tumors include, e.g., lung cancer (including, but not limited to, lung adenocarcinoma, squamous cell carcinoma, large cell carcinoma, bronchioloalveolar carcinoma, non-small-cell carcinoma, small cell carcinoma, mesothelioma); breast cancer (including, but not limited to, ductal carcinoma, lobular carcinoma, inflammatory breast cancer, clear cell carcinoma, mucinous carcinoma); colorectal cancer (including, but not limited to, colon cancer, rectal cancer); anal cancer; pancreatic cancer (including, but not limited to, pancreatic adenocarcinoma, islet cell carcinoma, neuroendocrine tumors); prostate cancer; ovarian carcinoma (including, but not limited to, ovarian epithelial carcinoma or surface epithelial-stromal tumor including serous tumor, endometrioid tumor and mucinous cystadenocarcinoma, sex-cord-stromal tumor); liver and bile duct carcinoma (including, but not limited to, hepatocellular carcinoma, cholangiocarcinoma, hemangioma); esophageal carcinoma (including, but not limited to, esophageal adenocarcinoma and squamous cell carcinoma); non-Hodgkin's lymphoma; bladder carcinoma; carcinoma of the uterus (including, but not limited to, endometrial adenocarcinoma, uterine papillary serous carcinoma, uterine clear-cell carcinoma, uterine sarcomas and leiomyosarcomas, mixed mullerian tumors); glioma, glioblastoma, medulloblastoma, and other tumors of the brain; kidney cancers (including, but not limited to, renal cell carcinoma, clear cell carcinoma, Wilm's tumor); cancer of the head and neck (including, but not limited to, squamous cell carcinomas); cancer of the stomach (including, but not limited to, stomach adenocarcinoma, gastrointestinal stromal tumor); thymus cancer, multiple myeloma; testicular cancer; germ cell tumor; neuroendocrine tumor; cervical cancer; carcinoids of the gastrointestinal tract, breast, and other organs; and signet ring cell carcinoma.

Small Molecule SST2R Ligands

In one aspect, described herein is a small molecule SST2R drug conjugate.

In some embodiments, the SMDC is a compound having the structure of Formula (A), or a pharmaceutically acceptable salt thereof.

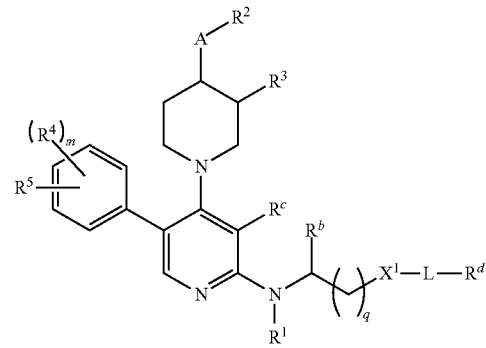

Formula (A)

wherein:

A is —N(H)— or —O—;

$X^1$ is —N($R^a$)—, —O—, —C(=O)—, —C(=O)N($R^a$)—, —S(=O)—, —(CH$_2$)C($R^a$)=N—O—(CH$_2$)—;

$R^a$ is hydrogen or $C_1$-$C_6$alkyl;

$R^b$ is hydrogen or $C_1$-$C_6$alkyl;

or when both $R^a$ and $R^b$ are present then $R^a$ and $R^b$ are taken together with the intervening atoms to which they are attached to form a piperidine or pyrrolidine;

q is 1, 2, or 3;

$R^1$ is hydrogen;

$R^2$ is hydrogen or $C_1$-$C_6$alkyl;

$R^3$ is hydrogen, —OR$^8$, —N(R$^8$)$_2$, —CN, halogen, $C_1$-$C_6$alkyl, or $C_1$-$C_6$fluoroalkyl;

or $R^2$ and $R^3$ are taken together with the intervening atoms to which they are attached to form a morpholine;

each $R^4$ and $R^5$ is independently hydrogen, halogen, $C_1$-$C_6$alkyl, $C_1$-$C_6$fluoroalkyl, substituted or unsubstituted $C_1$-$C_6$heteroalkyl, —CN, —N(R$^8$)$_2$, or —OR$^8$;

m is 1, 2, or 3;

$R^c$ is

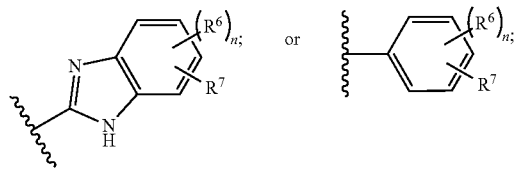

each $R^6$ and $R^7$ is independently hydrogen, halogen, $C_1$-$C_4$alkyl, $C_1$-$C_4$fluoroalkyl, $C_2$-$C_4$alkenyl, $C_2$-$C_4$alkynyl, substituted or unsubstituted C₁-C₆heteroalkyl, substituted or unsubstituted phenyl, substituted or unsubstituted C₃-C₆cycloalkyl, —CN, —OR⁸, —CO₂R⁸, —C(=O)N(R⁸)₂, —N(R⁸)₂, —NR⁸C(=O)R⁹, —NR⁸C(=O)OR⁹, —SR⁸, —S(=O)R⁹, —SO₂R⁹, or —SO₂N(R⁸)₂;

n is 1, 2, or 3;

each R⁸ is independently hydrogen, C₁-C₄alkyl, C₁-C₄fluoroalkyl, substituted or unsubstituted C₁-C₄heteroalkyl;

each R⁹ is independently C₁-C₄alkyl, C₁-C₄fluoroalkyl, substituted or unsubstituted C₁-C₄heteroalkyl;

L is -L¹-L²-;

L¹ is an optional spacer;

L² is an optional linker;

wherein at least one of L¹ or L² is present;

R^d is a payload moiety comprising: (i) a chemotherapeutic agent; or (ii) a chelating moiety or a radionuclide complex thereof.

In some embodiments, the SMDC is a compound having the structure of Formula (A), or a pharmaceutically acceptable salt thereof:

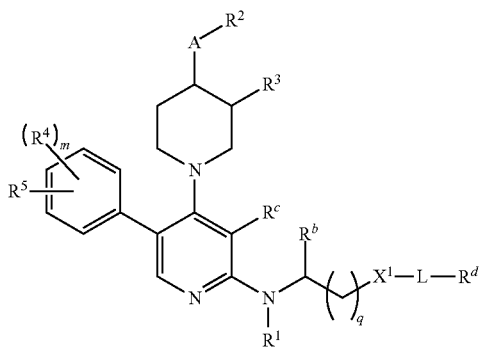

Formula (A)

wherein:

A is —N(H)— or —O—;

X¹ is —N(R^a)—, —O—, —C(=O)—, —C(=O)N(R^a)—, —S(=O)—, —(CH₂)C(R^a)=N—O—(CH₂)—;

R^a is hydrogen or C₁-C₆alkyl;

R^b is hydrogen or C₁-C₆alkyl;

or when both R^a and R^b are present then R^a and R^b are taken together with the intervening atoms to which they are attached to form a piperidine or pyrrolidine;

q is 1, 2, or 3;

R¹ is hydrogen;

R² is hydrogen or C₁-C₆alkyl;

R³ is hydrogen, —OR⁸, —N(R⁸)₂, —CN, halogen, C₁-C₆alkyl, or C₁-C₆fluoroalkyl;

or R² and R³ are taken together with the intervening atoms to which they are attached to form a morpholine;

each R⁴ and R⁵ is independently hydrogen, halogen, C₁-C₆alkyl, C₁-C₆fluoroalkyl, substituted or unsubstituted C₁-C₆heteroalkyl, —CN, —N(R⁸)₂, or —OR⁸;

m is 1, 2, or 3;

R^c is

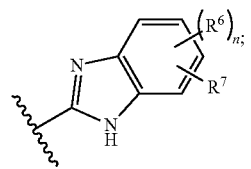 or 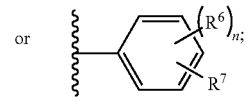

each R⁶ and R⁷ is independently hydrogen, halogen, C₁-C₄alkyl, C₁-C₄fluoroalkyl, C₂-C₄alkenyl, C₂-C₄alkynyl, substituted or unsubstituted C₁-C₆heteroalkyl, substituted or unsubstituted phenyl, substituted or unsubstituted C₃-C₆cycloalkyl, —CN, —OR⁸, —CO₂R⁸, —C(=O)N(R⁸)₂, —N(R⁸)₂, —NR⁸C(=O)R⁹, —NR⁸C(=O)OR⁹, —SR⁸, —S(=O)R⁹, —SO₂R⁹, or —SO₂N(R⁸)₂;

n is 1, 2, or 3;

each R⁸ is independently hydrogen, C₁-C₄alkyl, C₁-C₄fluoroalkyl, substituted or unsubstituted C₁-C₄heteroalkyl;

each R⁹ is independently C₁-C₄alkyl, C₁-C₄fluoroalkyl, substituted or unsubstituted C₁-C₄heteroalkyl;

L is -L¹-L²-;

L¹ is an optional spacer;

L² is an optional linker;

wherein at least one of L¹ or L² is present;

R^d is a payload moiety comprising a chelating moiety or a radionuclide complex thereof.

In some embodiments, R² is hydrogen; R³ is hydrogen —OH, or —OCH₃; or R² and R³ are taken together with the intervening atoms to which they are attached to form a morpholine.

In some embodiments, R² is hydrogen; and R³ is hydrogen.

In some embodiments, each R⁴ and R⁵ is independently hydrogen, F, Cl, Br, C₁-C₄alkyl, C₁-C₄fluoroalkyl, —CN, —N(R⁸)₂, or —OR⁸.

In some embodiments, each R⁴ and R⁵ is independently hydrogen, F, Cl, Br, —CH₃, —CH₂F, —CHF₂, —CF₃, —CN, —NH₂, —NHCH₃, —N(CH₃)₂, —OH, —OCH₃, or —OCF₃.

In some embodiments, A is —N(H)—; R^a is hydrogen, —CH₃, or —CH₂CH₃; R^b is hydrogen, —CH₃, or —CH₂CH₃; or when both R^a and R^b are present then R^a and R^b are taken together with the intervening atoms to which they are attached to form a piperidine; and R¹ is hydrogen, —CH₃, or —CH₂CH₃.

In some embodiments, the compound of Formula (A) has the structure of Formula (I), or a pharmaceutically acceptable salt thereof:

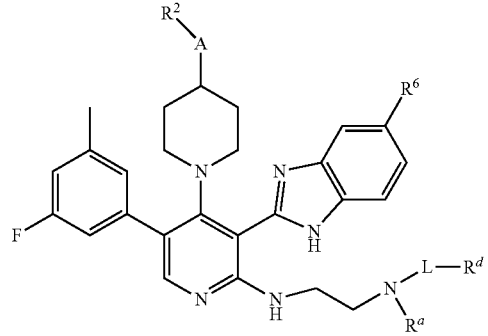

Formula (I)

wherein:

A is —N(H)— or —O—;

$R^a$ is hydrogen or $C_1$-$C_6$alkyl;

$R^2$ is hydrogen or $C_1$-$C_6$alkyl;

$R^6$ is chloro or —C(=O)NH$_2$;

L is -$L^1$-$L^2$-;

$L^1$ is an optional spacer; and $L^2$ is an optional linker;

wherein at least one of $L^1$ or $L^2$ is present; and $R^d$ is a payload moiety comprising a chemotherapeutic agent.

In some embodiments, A is —N(H)—.

In some embodiments $R^2$ is hydrogen.

In some embodiments, $R^a$ is hydrogen or methyl. In some embodiments, $R^a$ is hydrogen.

In some embodiments, $R^6$ is chloro.

In some embodiments, the compound of Formula (A) has the structure of Formula (Ia), or a pharmaceutically acceptable salt thereof:

Formula (Ia)

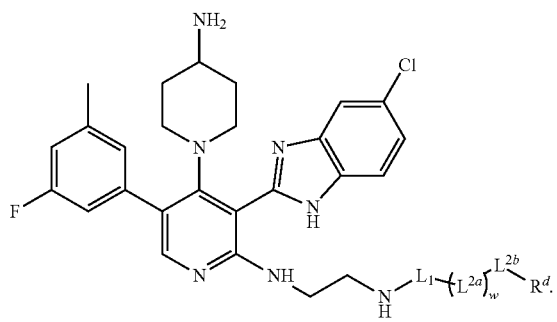

In some embodiments, the compound of Formula (A) has the structure of Formula (Ib), or a pharmaceutically acceptable salt thereof:

Formula (Ib)

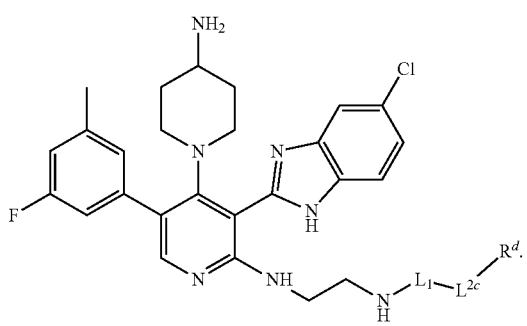

Compounds of the present disclosure also include tautomeric forms. Tautomeric forms result from the swapping of a single bond with an adjacent double bond and the concomitant migration of a proton. Tautomeric forms include prototropic tautomers which are isomeric protonation states having the same empirical formula and total charge. Examples prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, such as, 1H- and 3H-imidazole, 1H-, 2H- and 4H-1,2,4-triazole, 2H- and 2H-isoindole, and 2H- and 2H-pyrazole. Tautomeric forms can be in equilibrium or sterically locked into one form by appropriate substitution.

Payload Moieties ($R^d$) Comprising Cytotoxic Payloads/Drugs

In some embodiments, $R^d$ comprises a chemotherapeutic drug.

In some embodiments, $R^d$ is:

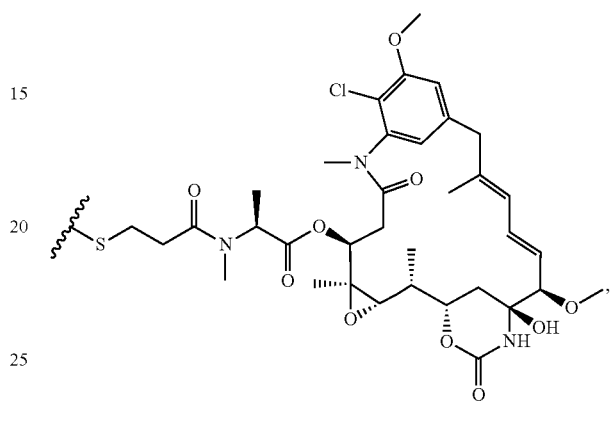

(mertansine)

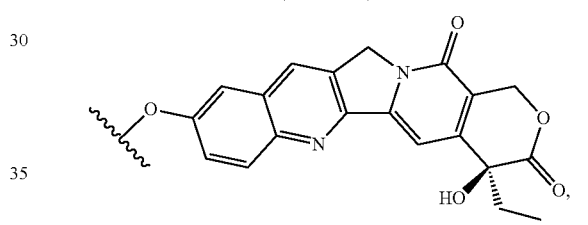

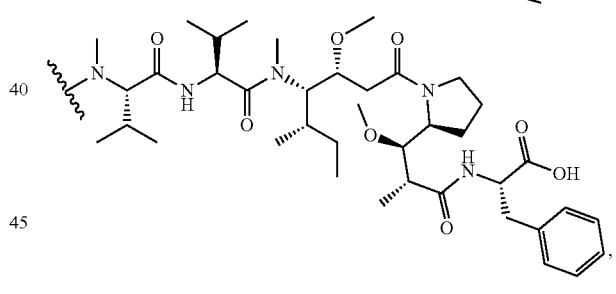

(monomethyl Auristatin F)

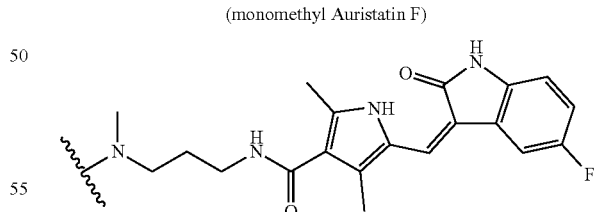

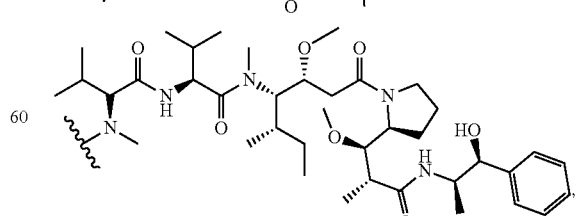

, or (monomethyl Auristatin E)

-continued

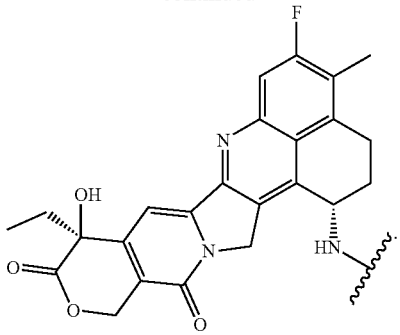

(Exatecan)

In some embodiments, $R^d$ is:

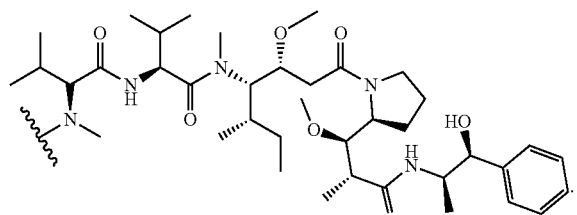

(monomethyl Auristatin E)

Spacer and Linkers

In one embodiment, the SST2R targeting ligand is covalently linked to the payload/drug via a spacer ($L^1$) and/or linker ($L^2$).

In some embodiments, the spacer ($L^1$) has a prescribed length thereby linking the ligand and the payload or linker/payload while allowing an appropriate distance therebetween. The spacer can also modulate the pharmacological activity of the SMDC.

In some embodiments, the spacer comprises a dendritic type spacer for covalent attachment of more than one drug moieties and/or ligands through a branching, multifunctional moiety. A dendritic type spacer can increase the molar ratio of ligand to payload, i.e. loading, which is related to the potency of the conjugate.

In some embodiments, $L^1$ is absent, or $L^1$ is a spacer that is present and is —$X^2$-$L^3$-$L^4$-;

$X^2$ is —C(=O)(CH$_2$)$_p$—, —(CH$_2$)$_p$—, —C(=O)CH(CH$_2$SO$_3$H)NHC(=O)—, or —(X$^{2a}$)$_p$—;

each $X^{2a}$ is independently selected from natural or unnatural amino acids, wherein any free amine of an amino acid is optionally independently substituted with —CH$_3$;

p is 0, 1, 2, 3, 4, 5, or 6;

$L^3$ is absent, unsubstituted or substituted $C_1$-$C_{10}$alkylene, unsubstituted or substituted $C_1$-$C_{10}$heteroalkylene, $C_4$-$C_{20}$polyethylene glycol, or —(X$^3$CH$_2$CH$_2$)$_t$—;

each $X^3$ is independently selected from O and NR$^{10}$;

each t is independently 1, 2, 3, 4, 5, 6, 7, 8, 9, 10, 11, or 12;

$L^4$ is absent, or -$L^{4a}$-(CH$_2$)$_u$-$L^{4b}$-(CH$_2$)$_u$-$L^{4c}$-;

$L^{4a}$ is absent, —O—, —NR$^{10}$—, —NR$^{10}$C(=O)—, —C(=O)NR$^{10}$—, or —C(=O)—;

$L^{4b}$ is absent, or unsubstituted or substituted N-containing 5 to 10 membered heterocycloalkylene; wherein any free amine of the N-containing 5 to 10 membered heterocycloalkylene is optionally independently substituted with —CH$_2$CO$_2$H;

$L^{4c}$ is absent, —O—, —NR$^{10}$—, —NR$^{10}$C(=O)—, —C(=O)NR$^{10}$—, —C(=O)NR$^{10}$ (CH$_2$)$_u$O(CH$_2$)$_u$C(=O)—, CH(CH$_2$SO$_3$H)C(=O)NR$^{10}$ (CH$_2$)$_u$O (CH$_2$)$_u$C(=O)—, —C(=O)—, —CH(=N)—, —CH(=N—NH)—, —CCH$_3$(=N)—, —CCH$_3$ (=N—NH)—, —C(=O)—($C_1$-$C_6$alkylene)-, —C(=O)NR$^{10}$—($C_1$-$C_6$alkylene)-, —NR$^{10}$C (=O)—($C_1$-$C_6$alkylene)-, —NR$^{10}$—($C_1$-$C_6$alkylene)- or $C_1$-$C_6$alkylene-;

each u is independently 0, 1, 2, 3, 4, 5, or 6; and each $R^{10}$ is independently selected from hydrogen, and $C_1$-$C_6$alkyl.

In some embodiments, $L^{4b}$ absent or

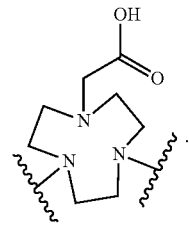 [SMILES: *N1CCN(*)CCN(CC(=O)O)CC1]

In some embodiments, $X^2$ is —C(=O)(CH$_2$)$_p$—; p is 0, 1, 2, 3 or 4; $L^3$ is unsubstituted or substituted $C_1$-$C_{10}$heteroalkylene, $C_4$-$C_{20}$polyethylene glycol, or —(X$^3$CH$_2$CH$_2$)$_t$—; each $X^3$ is independently selected from O and NR$^{10}$; and each t is independently 1, 2, 3, 4, 5, 6, 7, 8, 9, 10, 11, or 12.

In some embodiments, $L^4$ is absent or -$L^{4a}$-; and $L^{4a}$ is —NR$^{10}$—, —NR$^{10}$C(=O)—, —C(=O)NR$^{10}$—, or —C(=O)—.

In some embodiments, $L^1$ is absent, or $L^1$ is a spacer that is present and is:

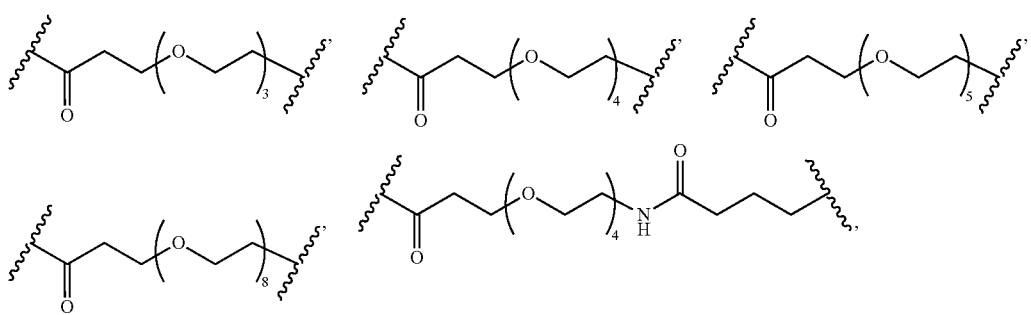

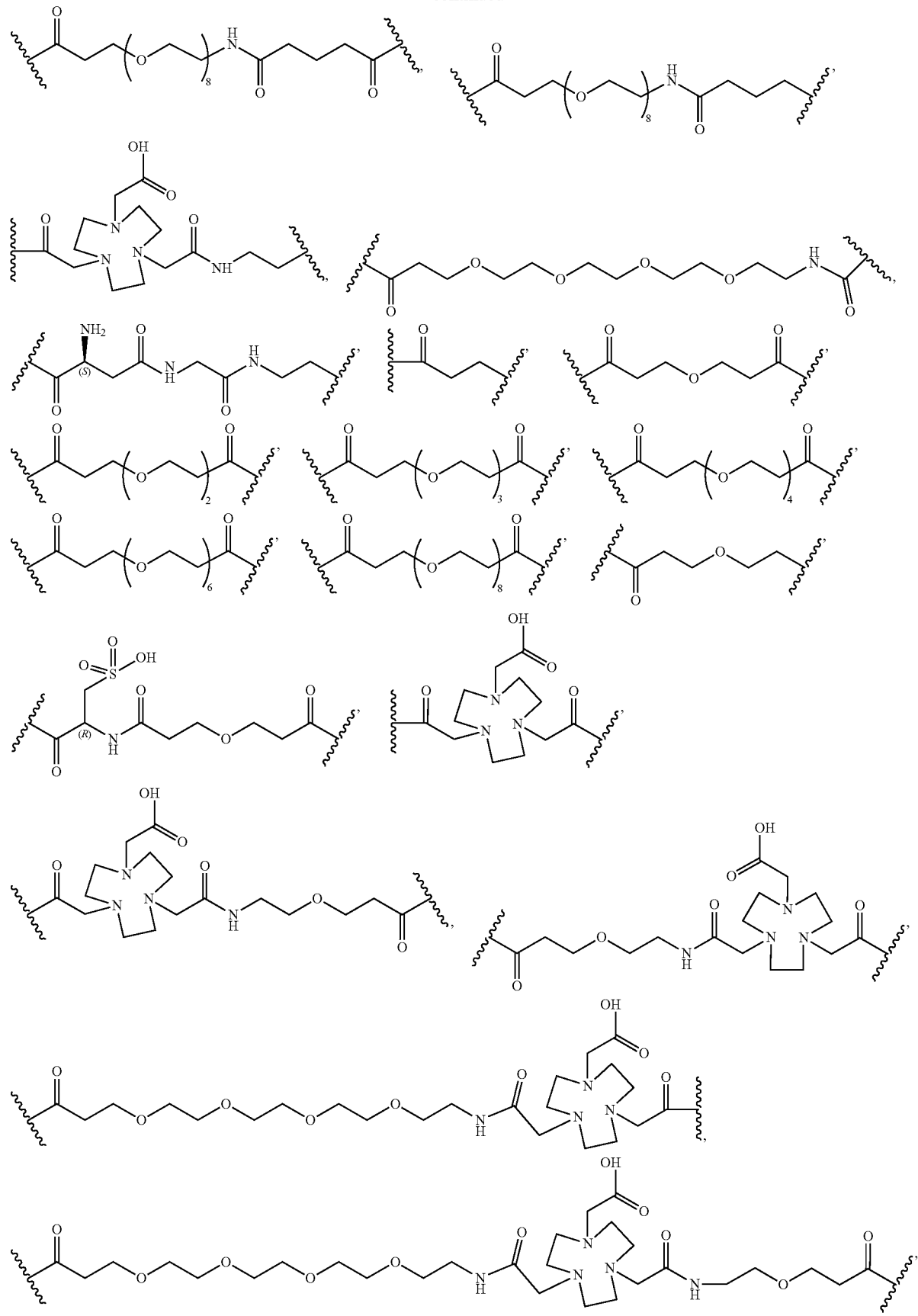

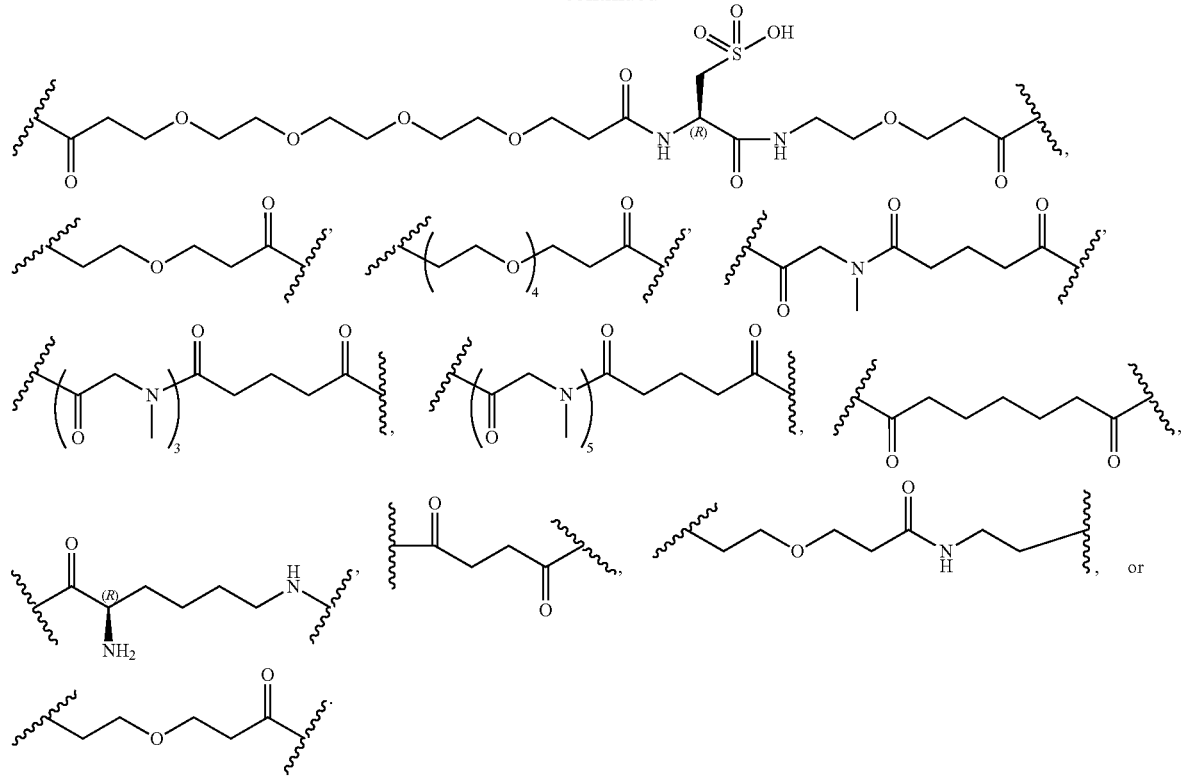

In some embodiments, $L^1$ is a spacer that is present and is:

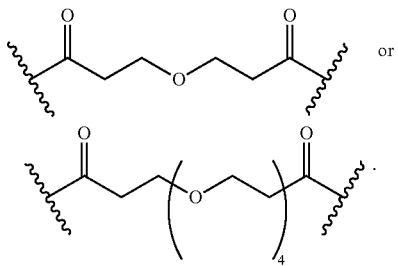

In some embodiments, a linker ($L^2$) is incorporated between the spacer ($L^1$) and the payload ($R^d$) and comprises a peptide linkage. The peptide linkage comprises L-amino acids and/or D-amino acids. In some embodiments, D-amino acids are preferred in order to minimize immunogenicity and nonspecific cleavage by background peptidases or proteases. Cellular uptake of oligo-D-arginine sequences is known to be as good as or better than that of oligo-L-arginines.

A linker unit may be "self-immolative" or a "non-self-immolative." A "non-self-immolative" linker unit is one in which part or all of the linker unit remains bound to the drug moiety upon enzymatic (e.g., proteolytic) cleavage of the conjugate. A "self-immolative" linker unit allows for release of the drug moiety without a separate hydrolysis step.

In certain embodiments, the linker comprises a p-aminobenzyl unit. In one such embodiment, a p-aminobenzyl alcohol is attached to an amino acid unit via an amide bond, and a carbamate, methylcarbamate, or carbonate is made between the benzyl alcohol and a cytotoxic agent. In one embodiment, the linker comprises p-aminobenzyloxycarbonyl (PAB). In certain embodiments, the phenylene portion of a p-amino benzyl unit is substituted with $Q_m$, wherein Q is —$C_1$-$C_8$ alkyl, —O—($C_1$-$C_8$ alkyl), -halogen, -nitro or -cyano; and m is an integer ranging from 0-4.

In some embodiments, a linker is cleavable. In some embodiments, a linker is designed for cleavage in the presence of particular conditions or in a particular environment, such conditions or environments near such targeted cells, tissues, or regions. Cleavable linkers rely on the inherent properties of a cell's cytoplasmic compartments for selective release of the cytotoxic drug. Such linkers mainly include chemically cleavable linkers that respond to low pH (acid-labile linkers) or reducing environment (disulfide linkers), and enzymatically cleavable linkers that are susceptible to the action of certain lysosomal enzymes (peptide linkers or β-glucuronide linkers).

In some embodiments, a linker is cleavable under physiological conditions. In some embodiments, a linker is cleavable under intracellular conditions. In some embodiments, the linker is chemically cleavable. In some embodiments, the linker is enzymatically cleavable. In some embodiments, the linker is pH-sensitive, i.e., sensitive to hydrolysis at certain pH values. For example, the pH-sensitive linker can be hydrolyzable under acidic conditions. For example, a linker can be an acid-labile linker that is hydrolyzable in the lysosome (e.g., a hydrazone, semicarbazone, thiosemicarbazone, cis-aconitic amide, orthoester, acetal, ketal, or the like). Such linkers can be relatively stable under neutral pH conditions, such as those in the blood, but are unstable below pH 7.0, such as pH 6.5 to 4.5, the approximate pH of the lysosome and/or endosome.

In some embodiments, the linker comprises one or more of di-sulfide bonds.

In some embodiments, the linker is cleaved in or near tissues suffering from hypoxia, such as cancer cells and cancerous tissues. In some embodiments, the linker comprises a disulfide bond. In some embodiments, a linker comprising a disulfide bond is preferentially cleaved in hypoxic regions. Hypoxia is thought to cause cancer cells to become more resistant to radiation and chemotherapy, and also to initiate angiogenesis. In a hypoxic environment in the presence of, for example, leaky or necrotic cells, free thiols and other reducing agents become available extracellularly, while the O2 that normally keeps the extracellular environment oxidizing is by definition depleted. In some embodiments, this shift in the redox balance promotes reduction and cleavage of a disulfide bond within a linker.

In some embodiments, the linker is cleaved by an intracellular peptidase or protease enzyme, including, but not limited to, a lysosomal or endosomal protease. In some embodiments, the linker is cleaved by a glycosidase, e.g., glucuronidase. Small peptide sequences such as Val-Cit and Phe-Lys have been developed as linkers for ADCs. These bi-peptide linkers show good stability in serum, yet can be recognized and rapidly hydrolyzed by certain lysosomal proteases, such as cathepsin B, following internalization. β-glucuronide linkers can be readily cleaved by the abundant lysosomal enzyme 0-glucuronidase, facilitating facile and selective release of the active drug. In other embodiments, the linker is not cleavable.

In some embodiments, the linker is cleaved by a protease, a matrix metalloproteinase, a serine protease, or a combination thereof. In some embodiments, the linker is cleaved by a reducing agent. In some embodiments, the linker is cleaved by an oxidizing agent or oxidative stress.

In some embodiments, the linker is cleaved by a matrix metalloproteinases (MMP). The hydrolytic activity of matrix metalloproteinases (MMPs) has been implicated in the invasive migration of metastatic tumor cells.

In some embodiments, the linker is cleaved by proteolytic enzymes or reducing environment, as may be found near cancerous cells. Such an environment, or such enzymes, are typically not found near normal cells.

In some embodiments, the linker is cleaved by serine proteases including but not limited to thrombin and cathepsins. In some embodiments, the linker is cleaved by cathepsin K, cathepsin S, cathepsin D, cathepsin E, cathepsin W, cathepsin F, cathepsin A, cathepsin C, cathepsin H, cathepsin Z, or any combinations thereof. In some embodiments, the linker is cleaved by cathepsin K and/or cathepsin S.

In some embodiments, the linker is cleaved in a necrotic environment. Necrosis often leads to the release of enzymes or other cell contents that may be used to trigger cleavage of a linker. In some embodiments, cleavage of the linker occurs by necrotic enzymes (e.g., by calpains).

In some embodiments, $L^2$ is an optional non-cleavable linker or a cleavable linker.

In some embodiments, $L^2$ is an optional cleavable linker that is an acid-sensitive linker, protease sensitive linker, or glutathione-sensitive linker.

In some embodiments, $L^2$ is absent, or $L^2$ is a linker that is present and is -$(L^{2a})_w$-$L^{2b}$- or -$L^{2c}$-;

each $L^{2a}$ is independently selected from natural or unnatural amino acids, wherein any free amine of an amino acid is optionally independently substituted with —$CH_3$;

$L^{2b}$ is absent or —N($R^{10}$)(unsubstituted or substituted benzyl)-OC(=O)—; wherein substituted benzyl is substituted with —C(=O)NHR$^{12}$ or a monosaccharide;

each $R^{10}$ is independently selected from hydrogen, and $C_1$-$C_6$alkyl;

each $R^{12}$ is independently selected from hydrogen, $C_4$-$C_{20}$polyethylene glycol, and unsubstituted or substituted $C_1$-$C_6$alkyl, wherein the substituted $C_1$-$C_6$alkyl is substituted with —NHR$^{13}$, —C(=O)NHR$^{13}$, or —NHC(=O)R$^{13}$;

each $R^{13}$ is independently selected from hydrogen, $C_4$-$C_{20}$polyethylene glycol, and $C_4$-$C_{20}$polyethylene glycol-NH$_2$;

or when $R^{13}$ is present and at least one free carboxylic group of an amino acid of $L^{2a}$ is present, then $R^{13}$ and the free carboxylic group of the amino acid of $L^{2a}$ are taken together to form a ring;

w is 1, 2, 3, 4, 5, or 6; and each $L^2$, is N-maleimidomethyl-cyclohexane-1-carbonyl (MCC) or —S—.

In some embodiments, $L^{2b}$ is selected from:

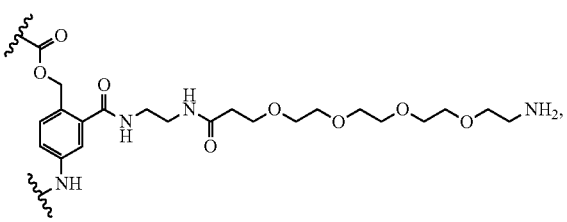

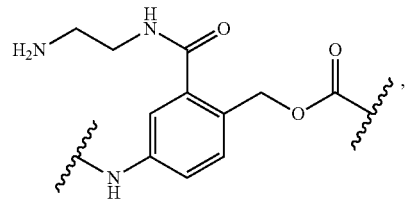

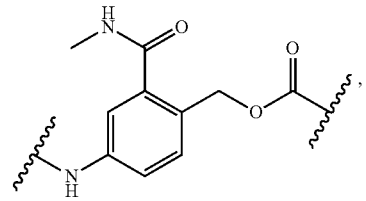

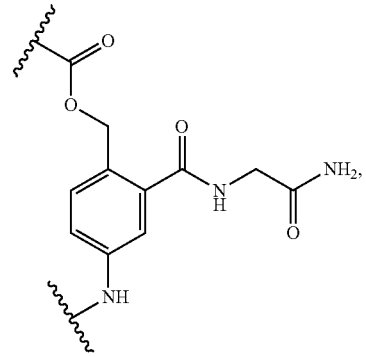

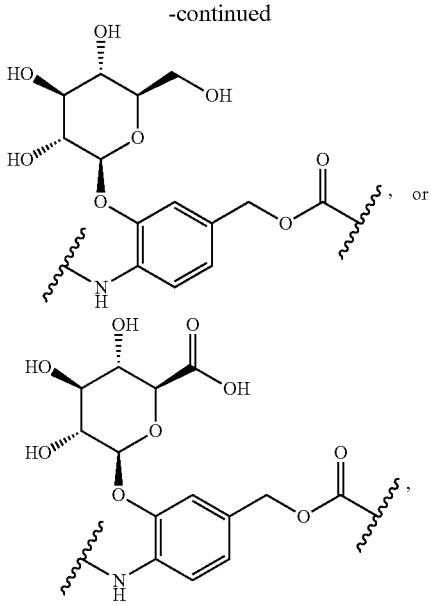

In some embodiments, each $L^{2a}$ is independently select from natural or unnatural amino acids, wherein any free amine of an amino acid is optionally independently substituted with —CH$_3$, wherein the natural or unnatural amino acids are selected from alanine (Ala), Ala(SO$_3$H), 3-(1-piperidinyl)alanine, cyclohexylalanine, arginine (Arg), asparagine (Asn), aspartate (Asp), cysteine (Cys), glutamine (Gln), glutamate (Glu), glycine (Gly), leucine (Leu), lysine (Lys), methionine (Met), phenylalanine (Phe), homophenylalanine, proline (Pro), serine (Ser), 3-homoserine, tyrosine (Tyr), Tyr(SO$_3$H), valine (Val), citrulline, β-alanine, β3-homoserine, β3-homolysine, and β3-homoglutamic acid.

In some embodiments, each $L^{2a}$ is independently select from natural or unnatural amino acids, wherein any free amine of an amino acid is optionally independently substituted with —CH$_3$, wherein the natural or unnatural amino acids are selected from alanine (Ala), Ala(SO$_3$H), arginine (Arg), asparagine (Asn), aspartate (Asp), cysteine (Cys), glutamine (Gln), glutamate (Glu), glycine (Gly), leucine (Leu), lysine (Lys), methionine (Met), phenylalanine (Phe), serine (Ser), valine (Val), and citrulline.

In some embodiments, $L^2$ is -($L^{2a}$)$_w$-$L^{2b}$-; and -($L^{2a}$)$_w$- is valine-citrulline, valine-alanine, methionine-valine-lysine, glycine-phenylalanine-glycine-glycine, tyrosine-arginine-valine, arginine-valine, and phenylalanine-lysine.

In some embodiments $L^2$ is -$L^{2c}$- and $L^{2c}$ is N-maleimidomethyl-cyclohexane-1-carbonyl (MCC) or —S—.

In some embodiments, $L^2$ is absent, or $L^2$ is a linker that is present and is:

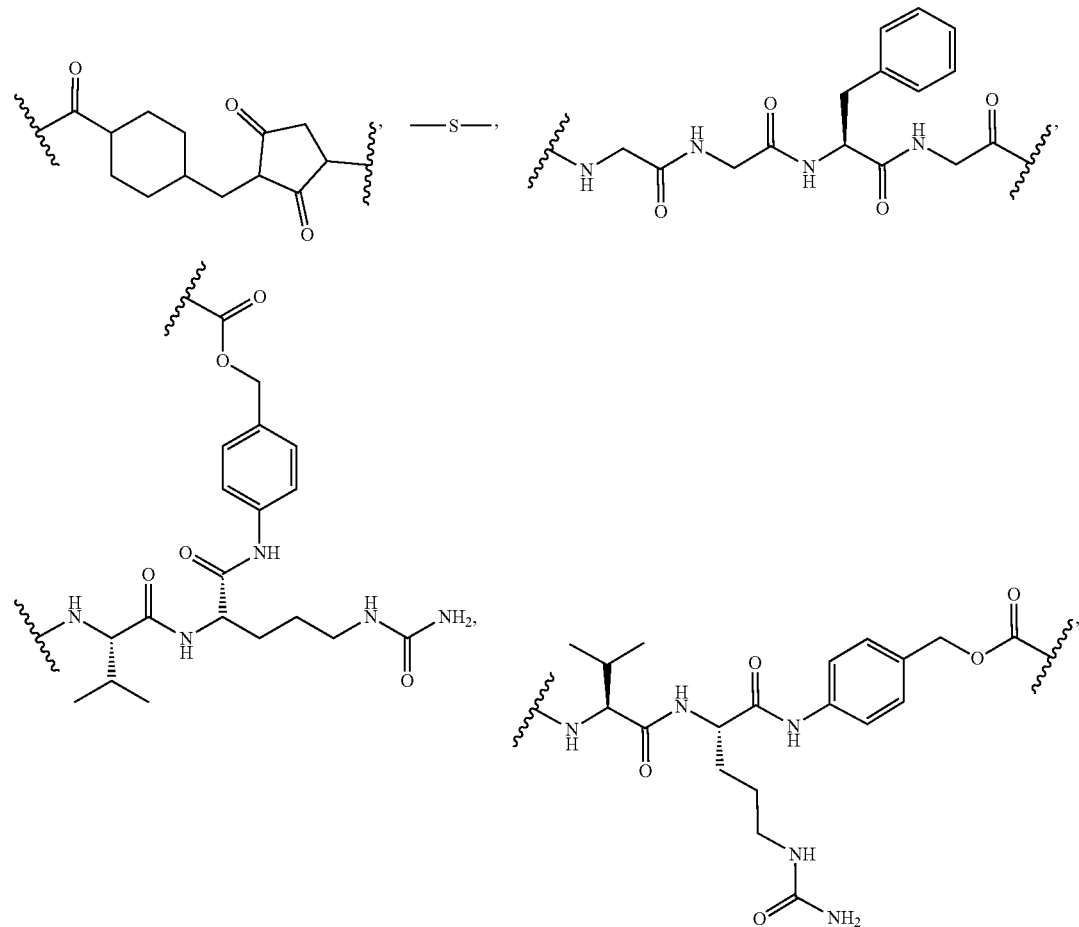

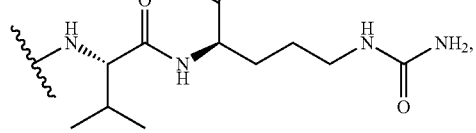
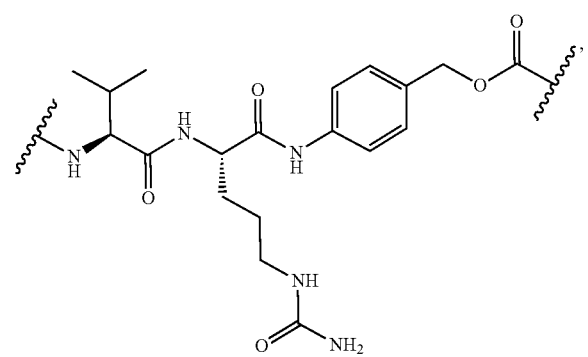
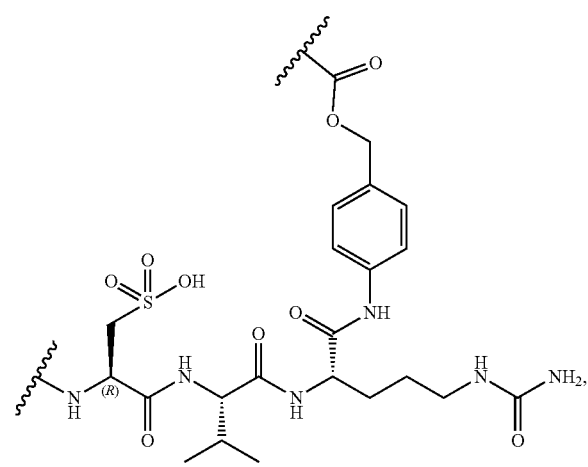
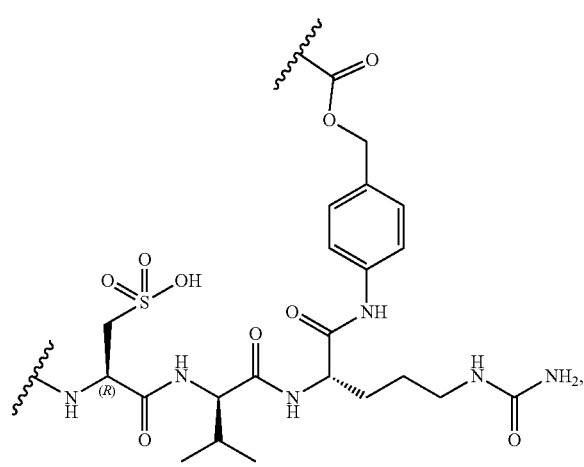
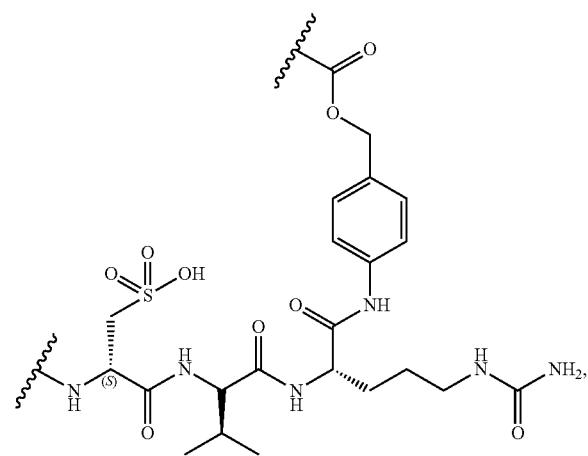

-continued
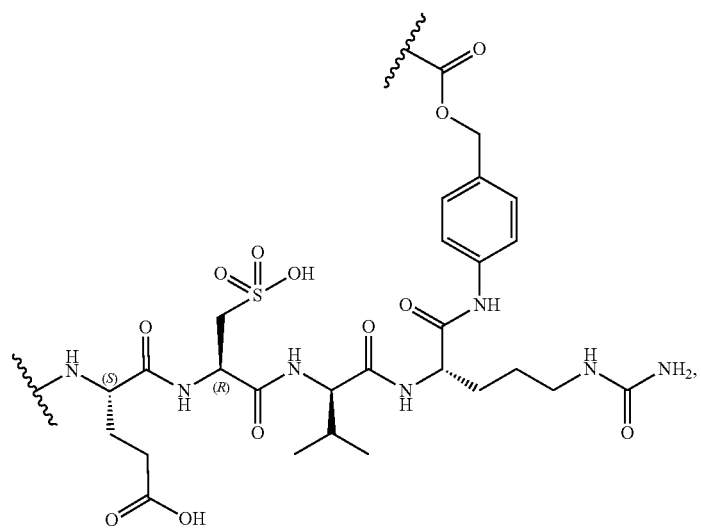
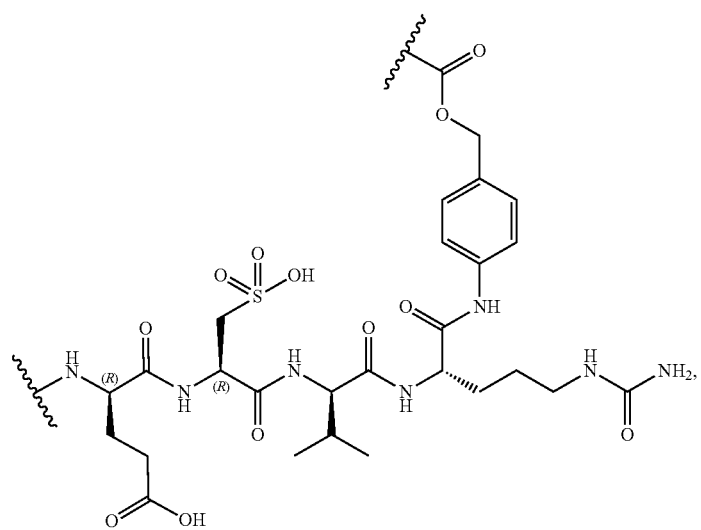
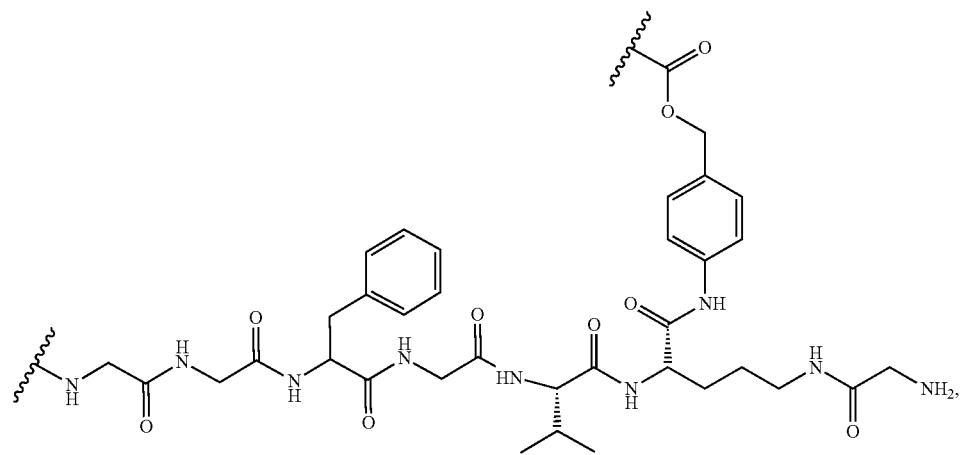

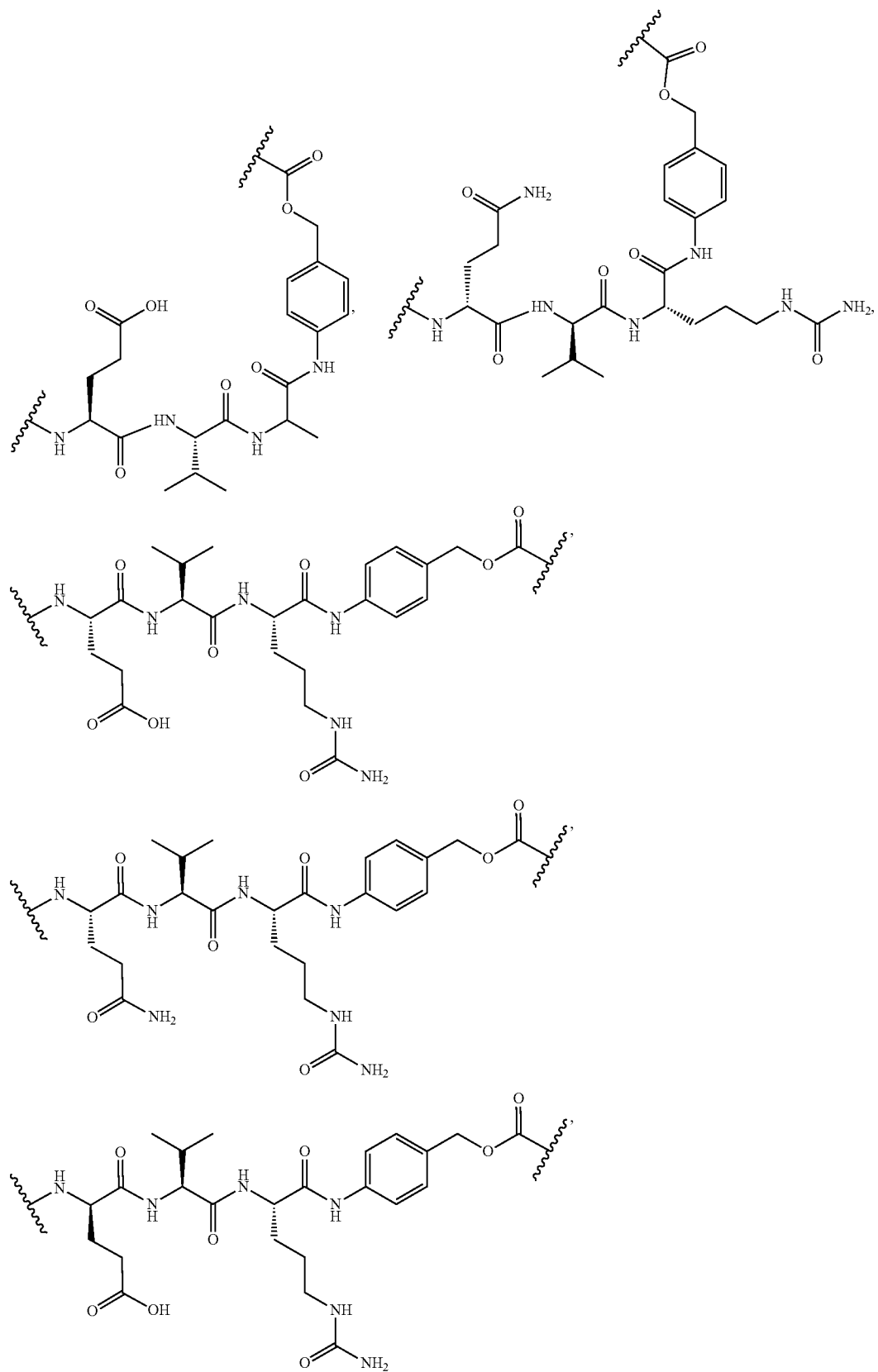

-continued
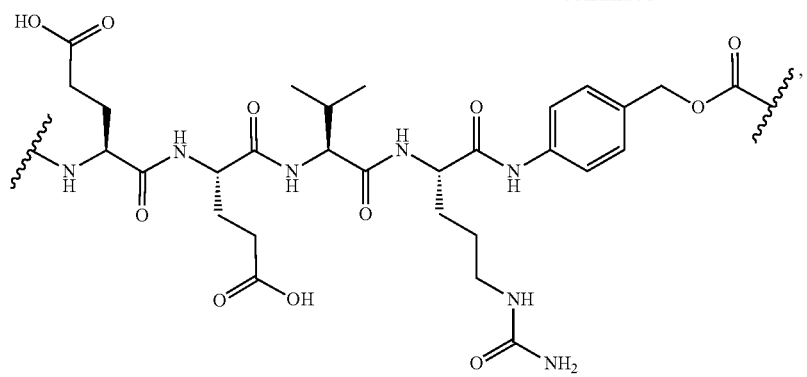
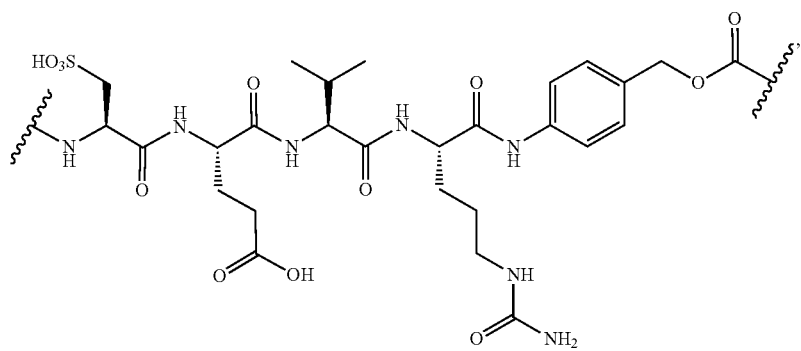
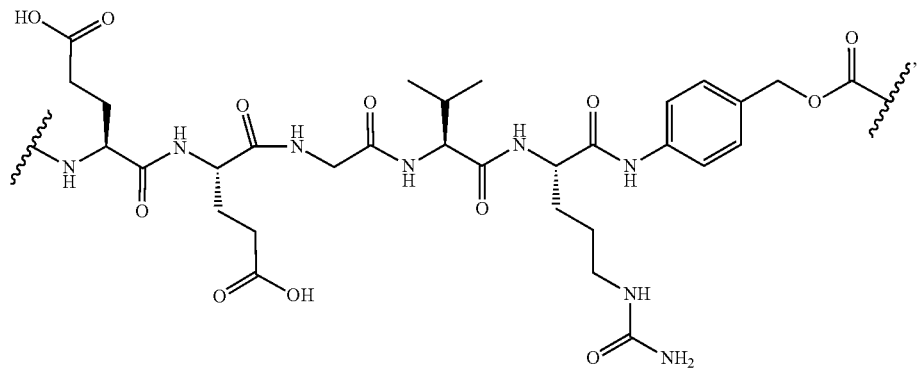
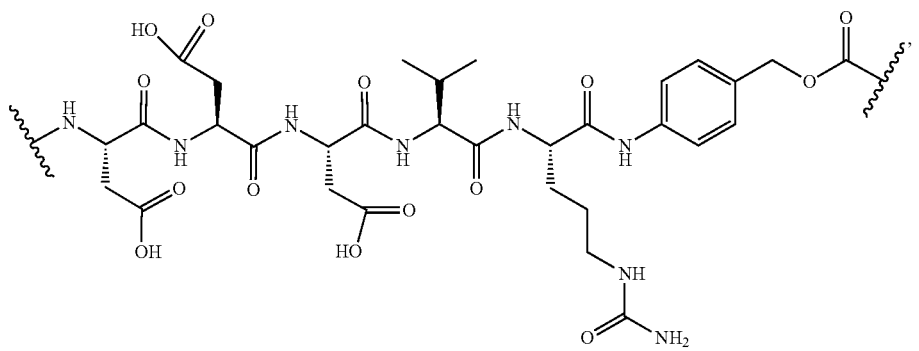

-continued
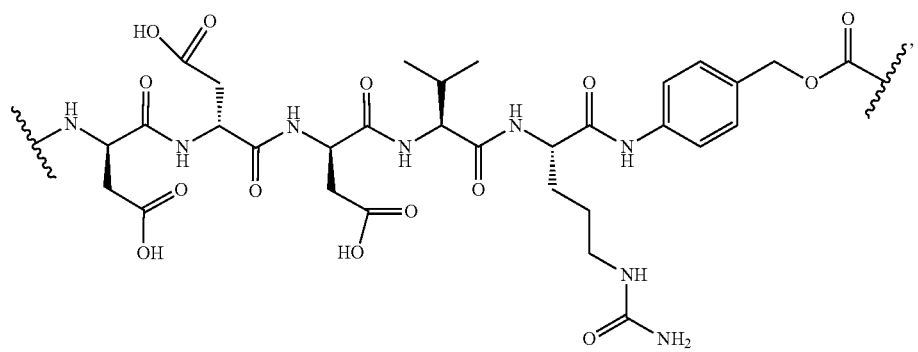
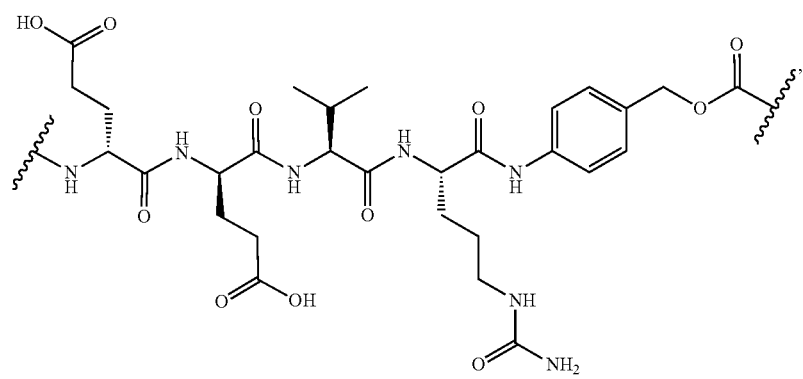
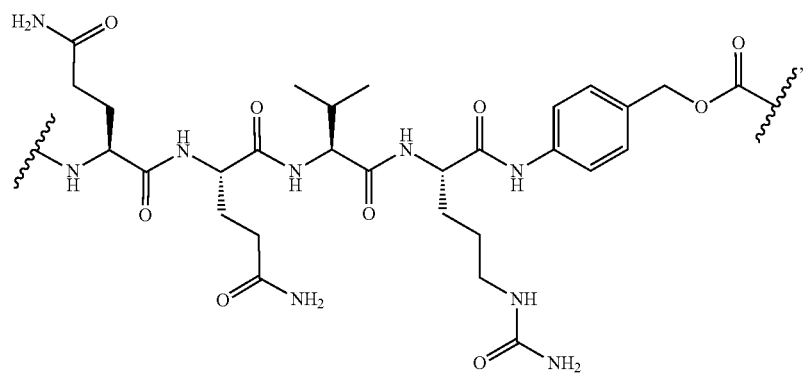
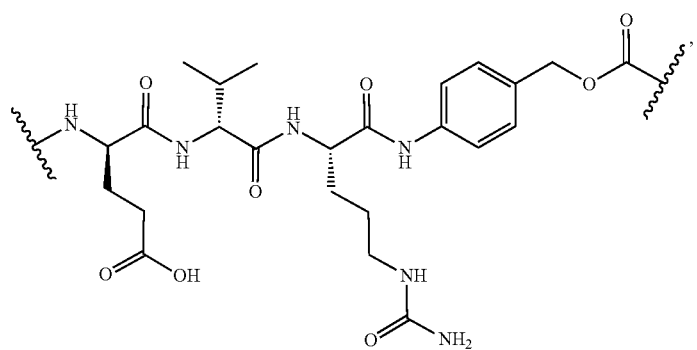

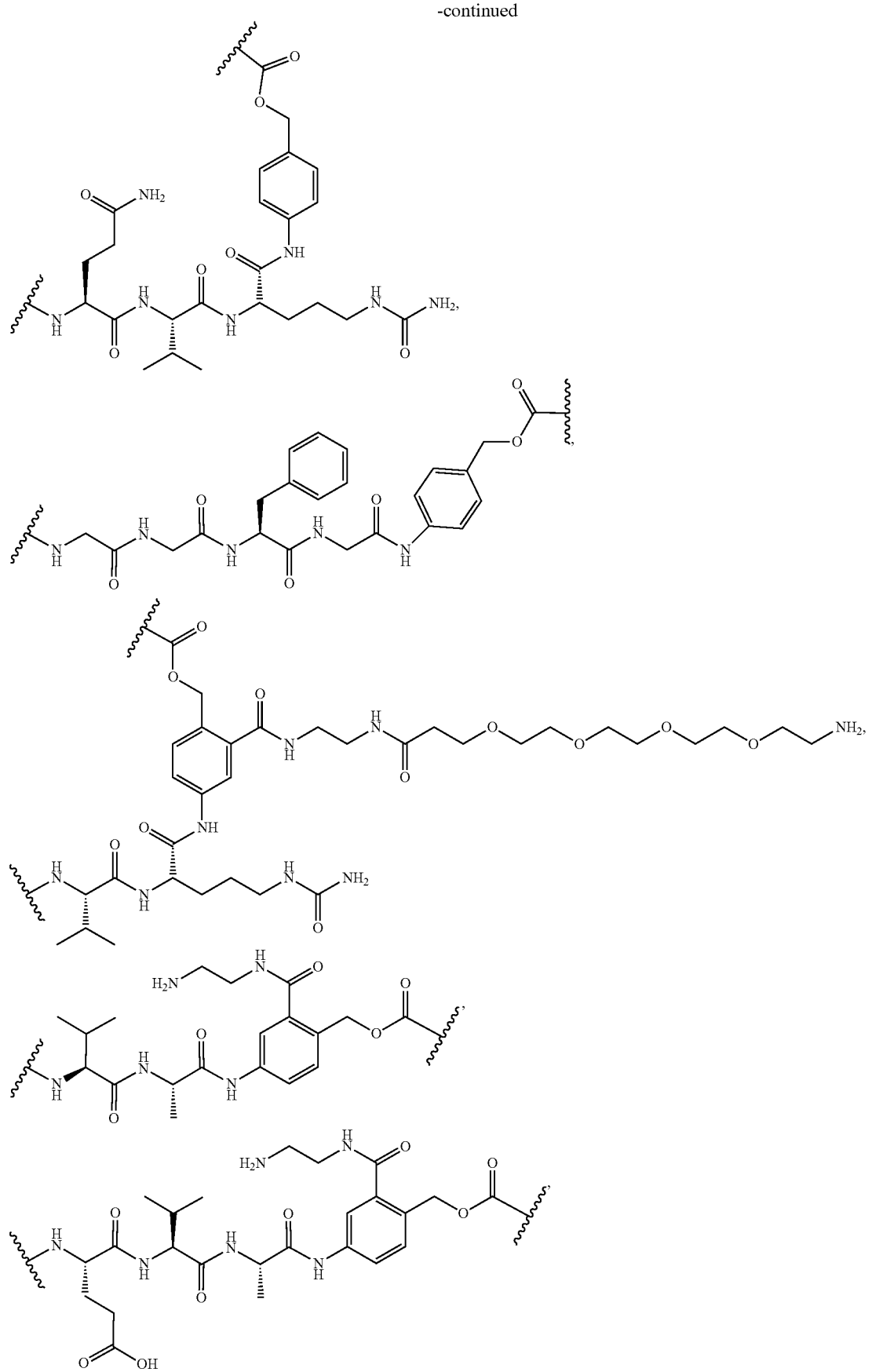

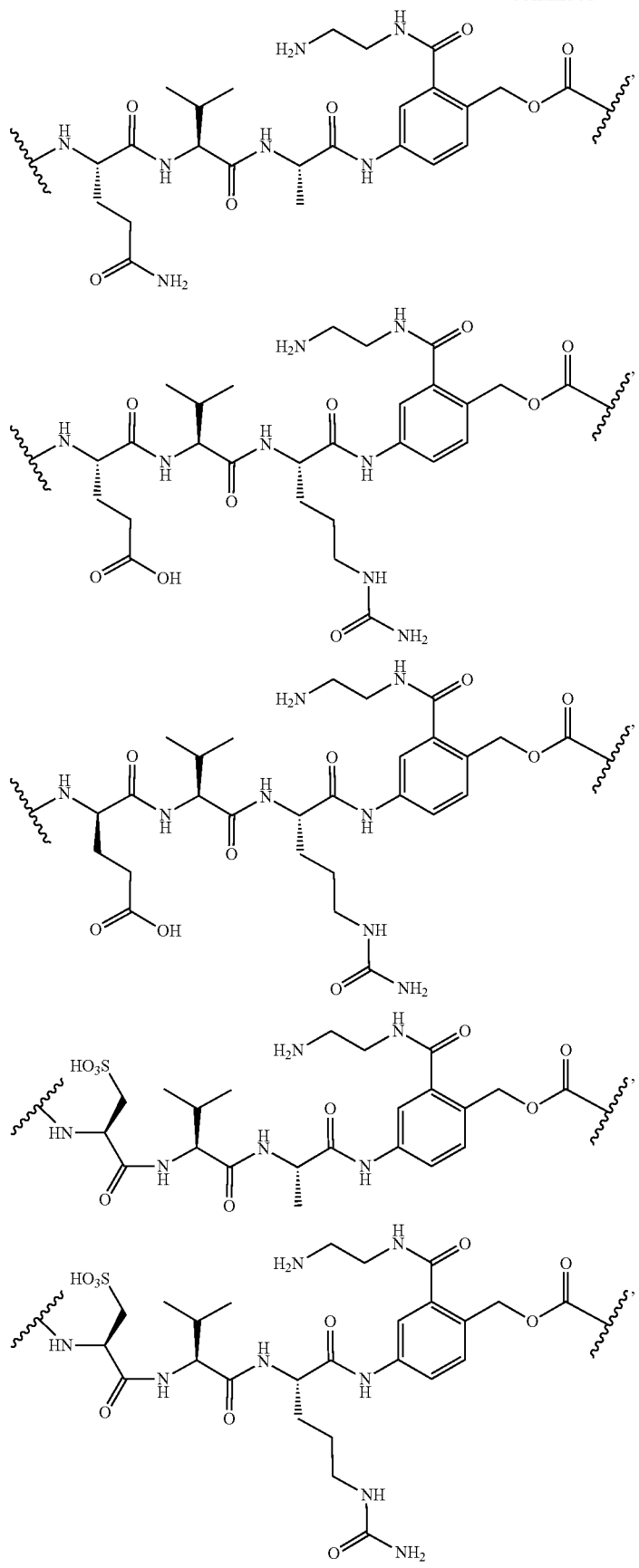

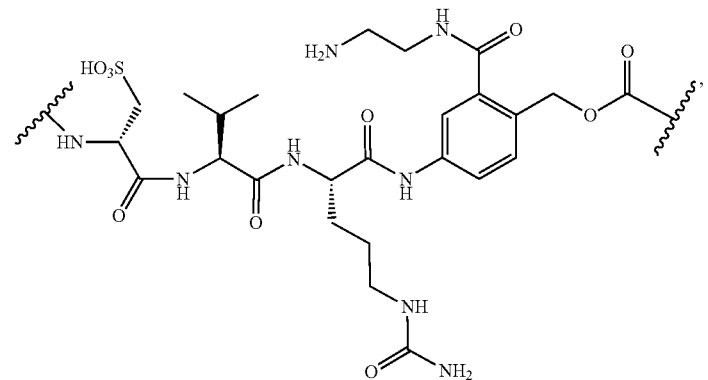
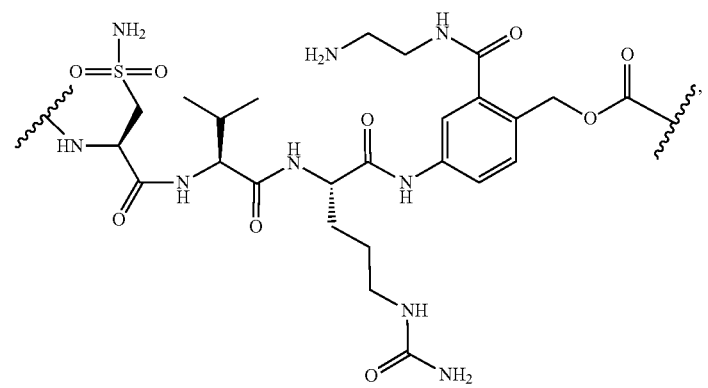
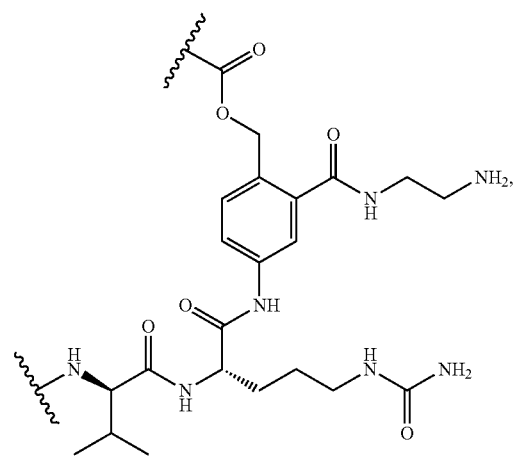
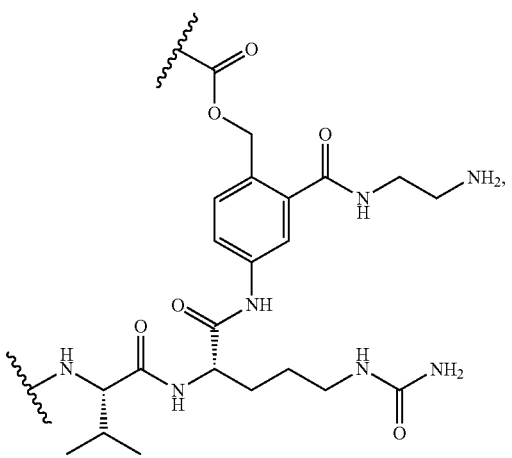
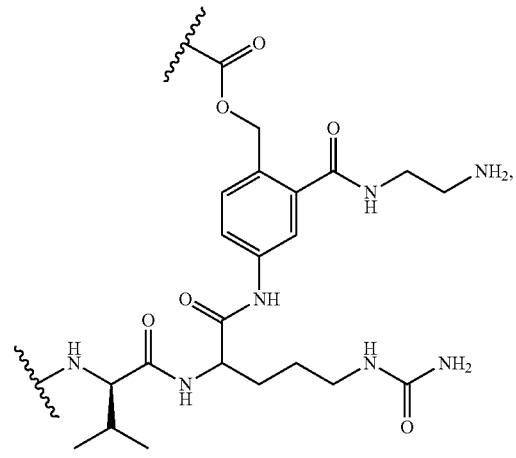

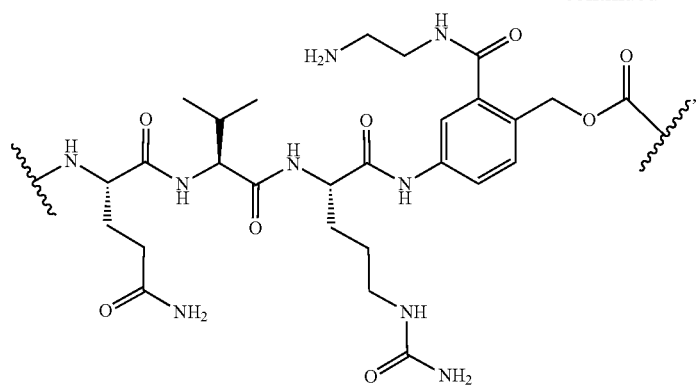
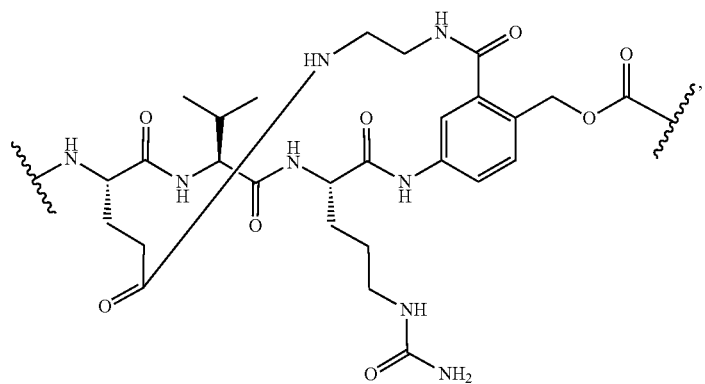
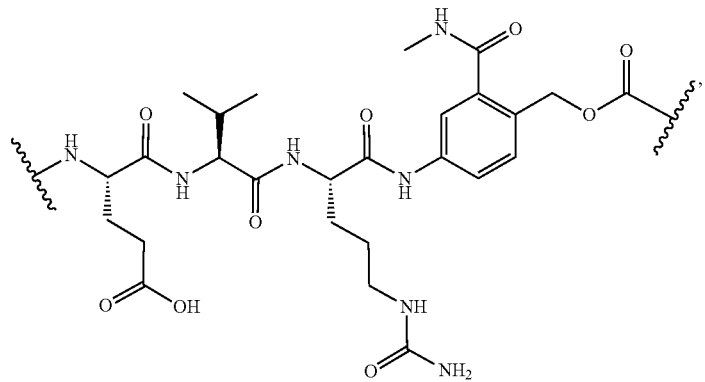
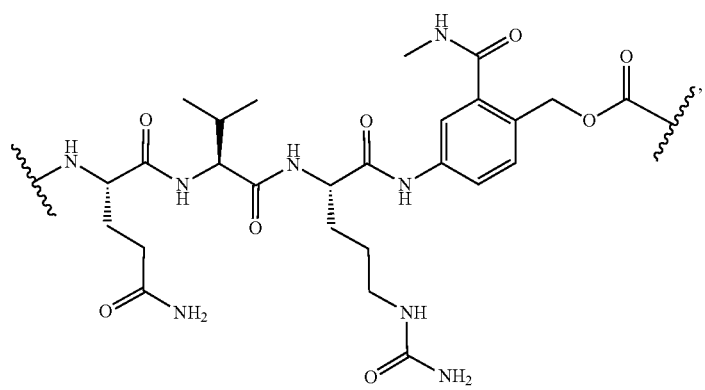

-continued
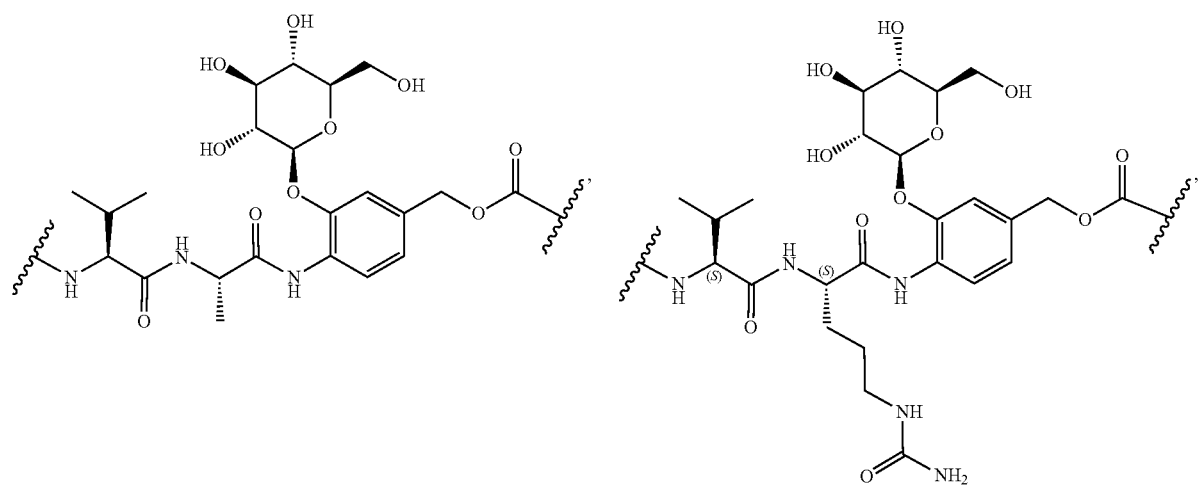
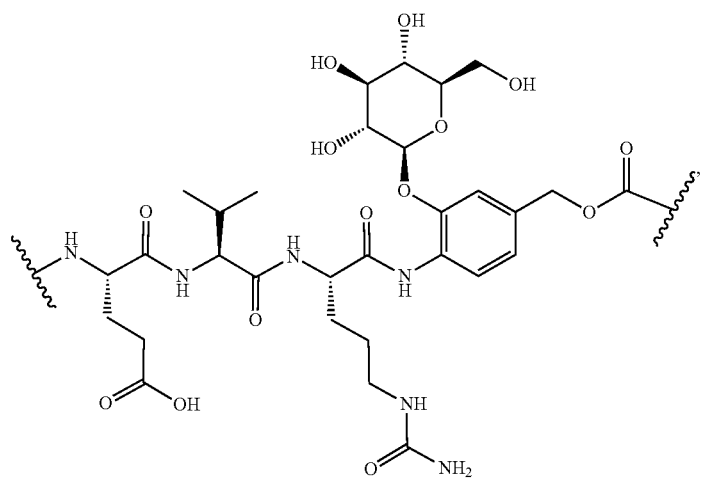
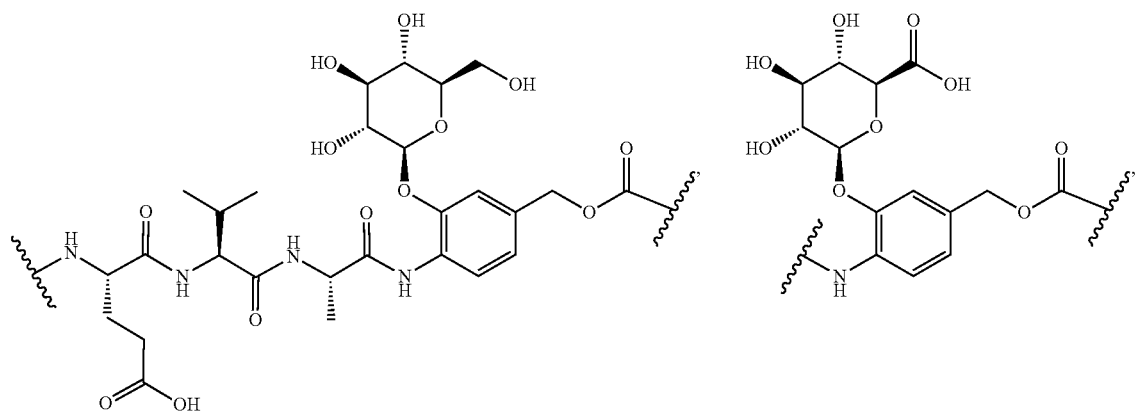

45
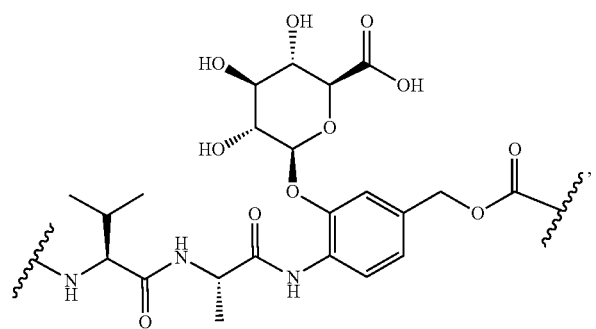
46
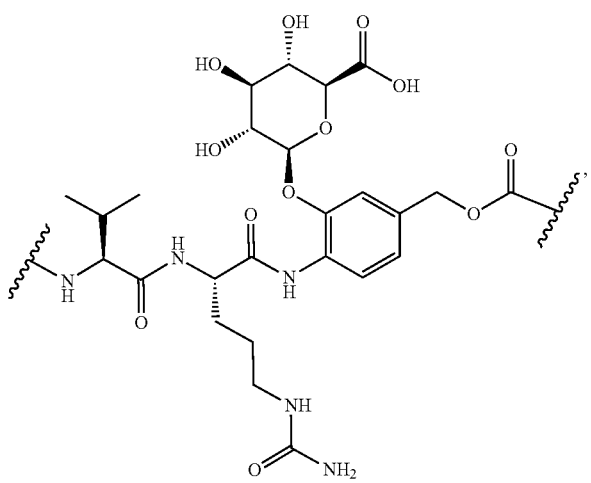
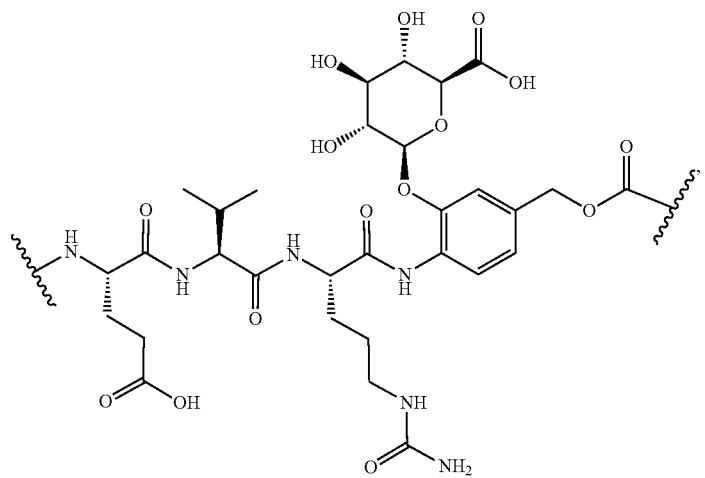
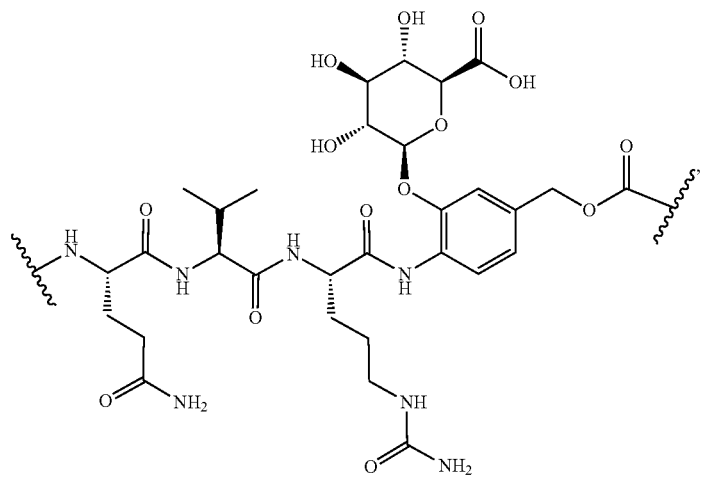

-continued
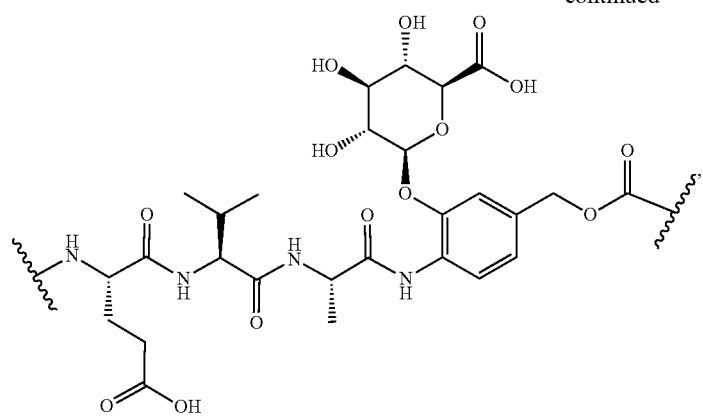
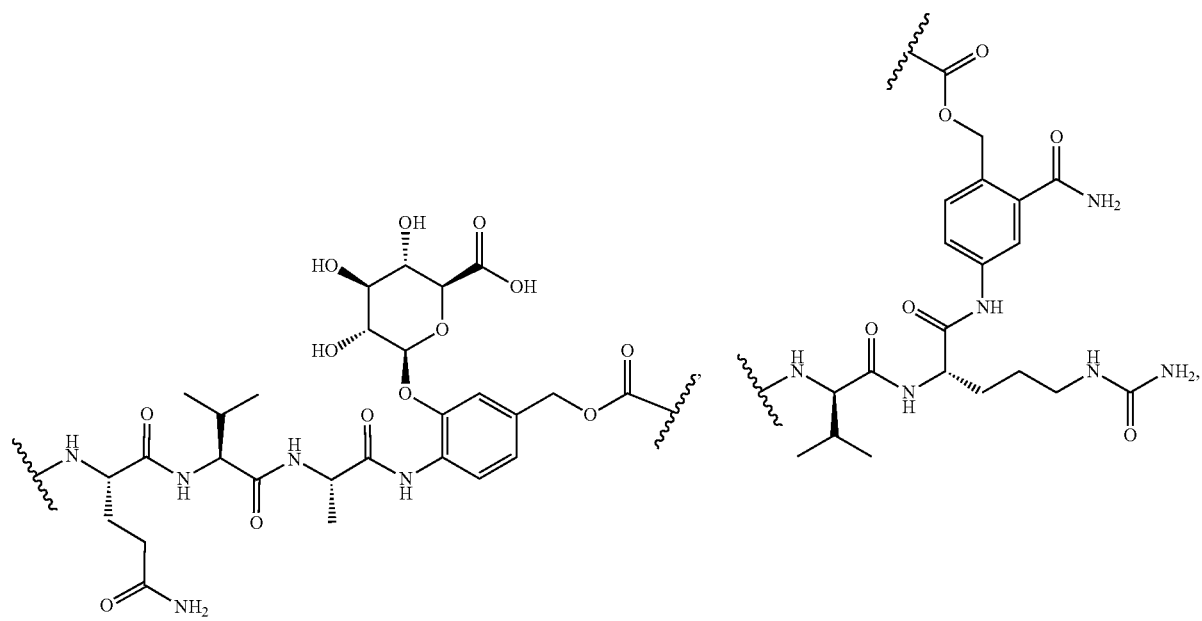
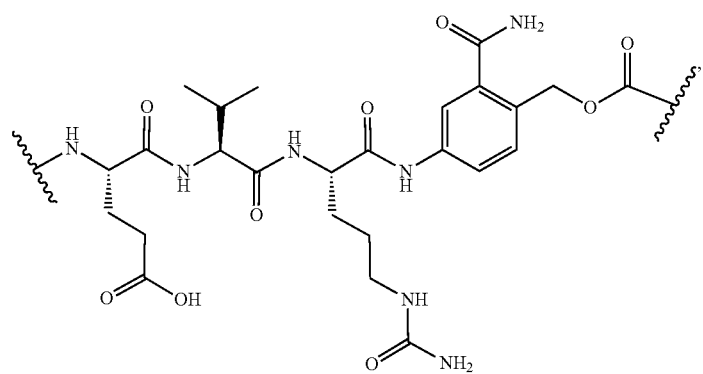

-continued
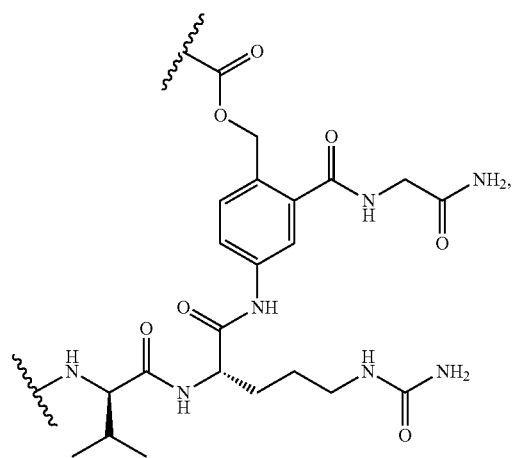
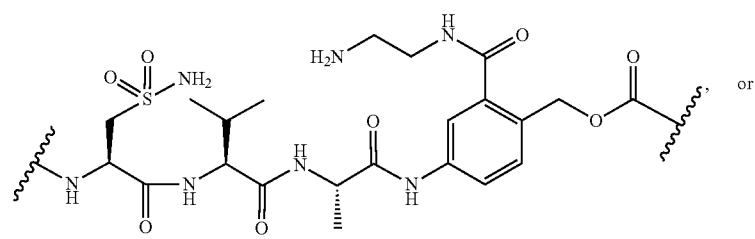
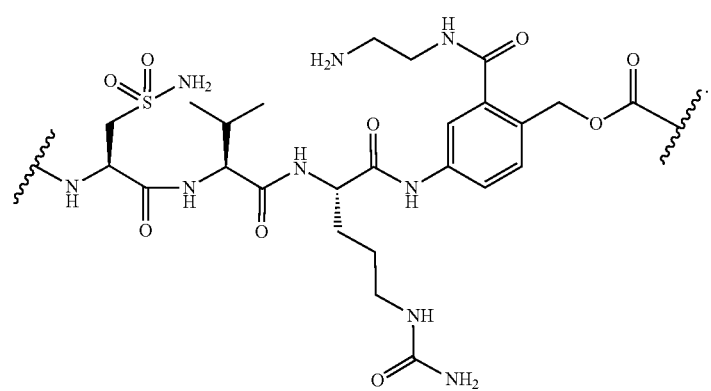

In some embodiments, L² is absent, or L² is a linker that is present and is:
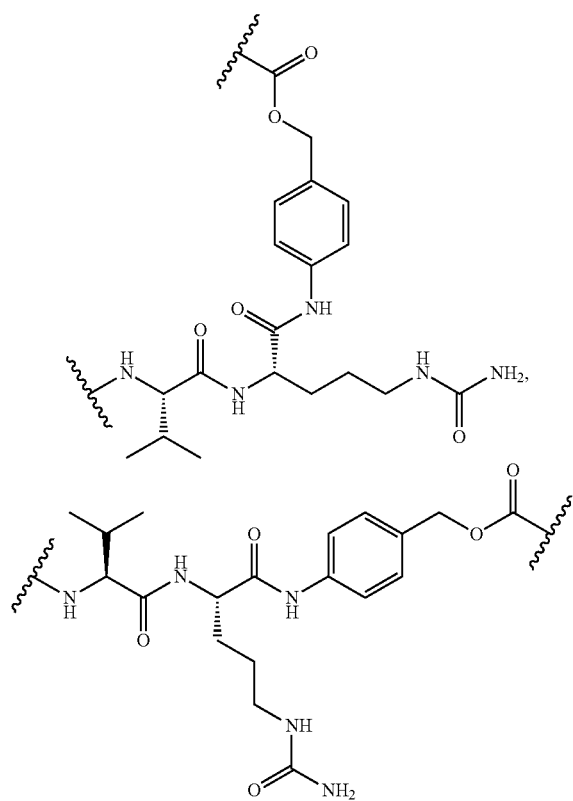
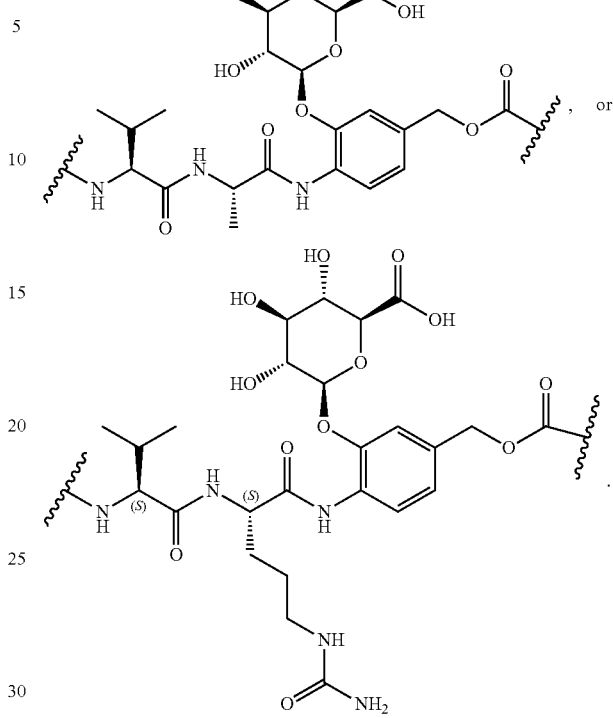
Representative Spacer-Linker Moieties
In some embodiments, L is:
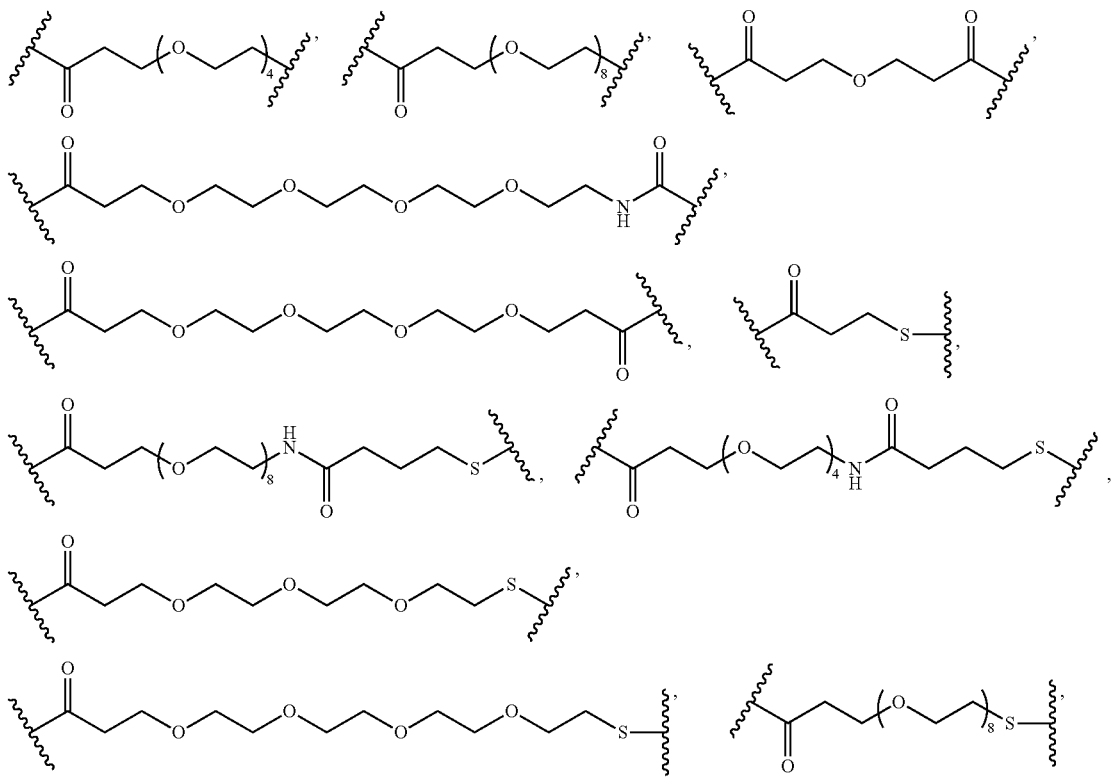

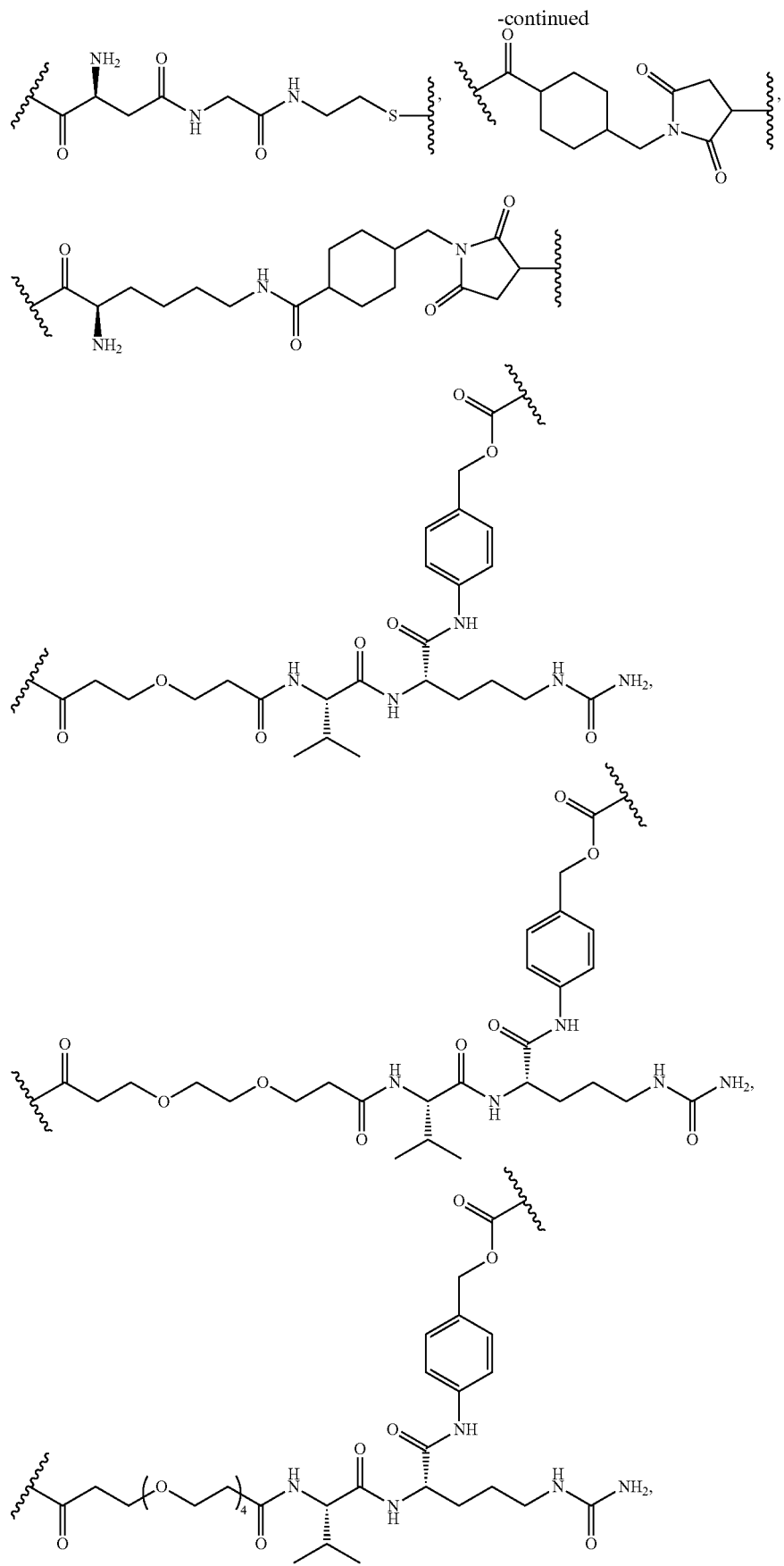

-continued
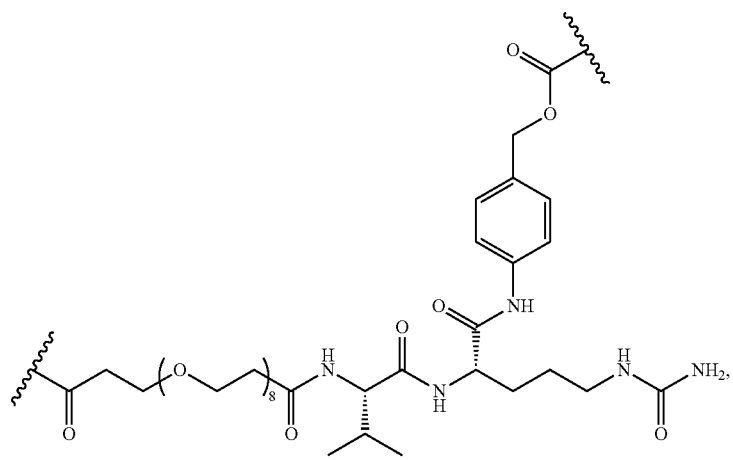
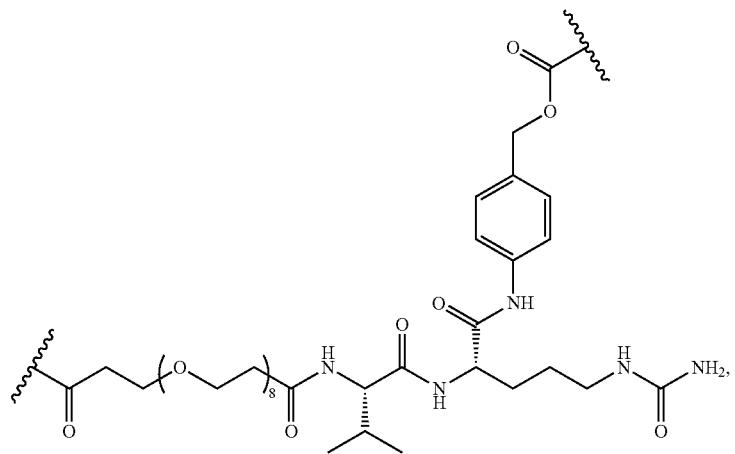
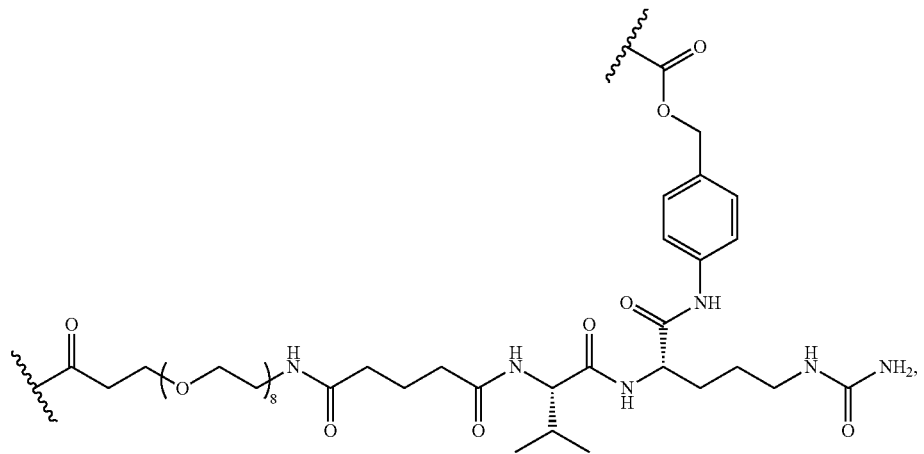

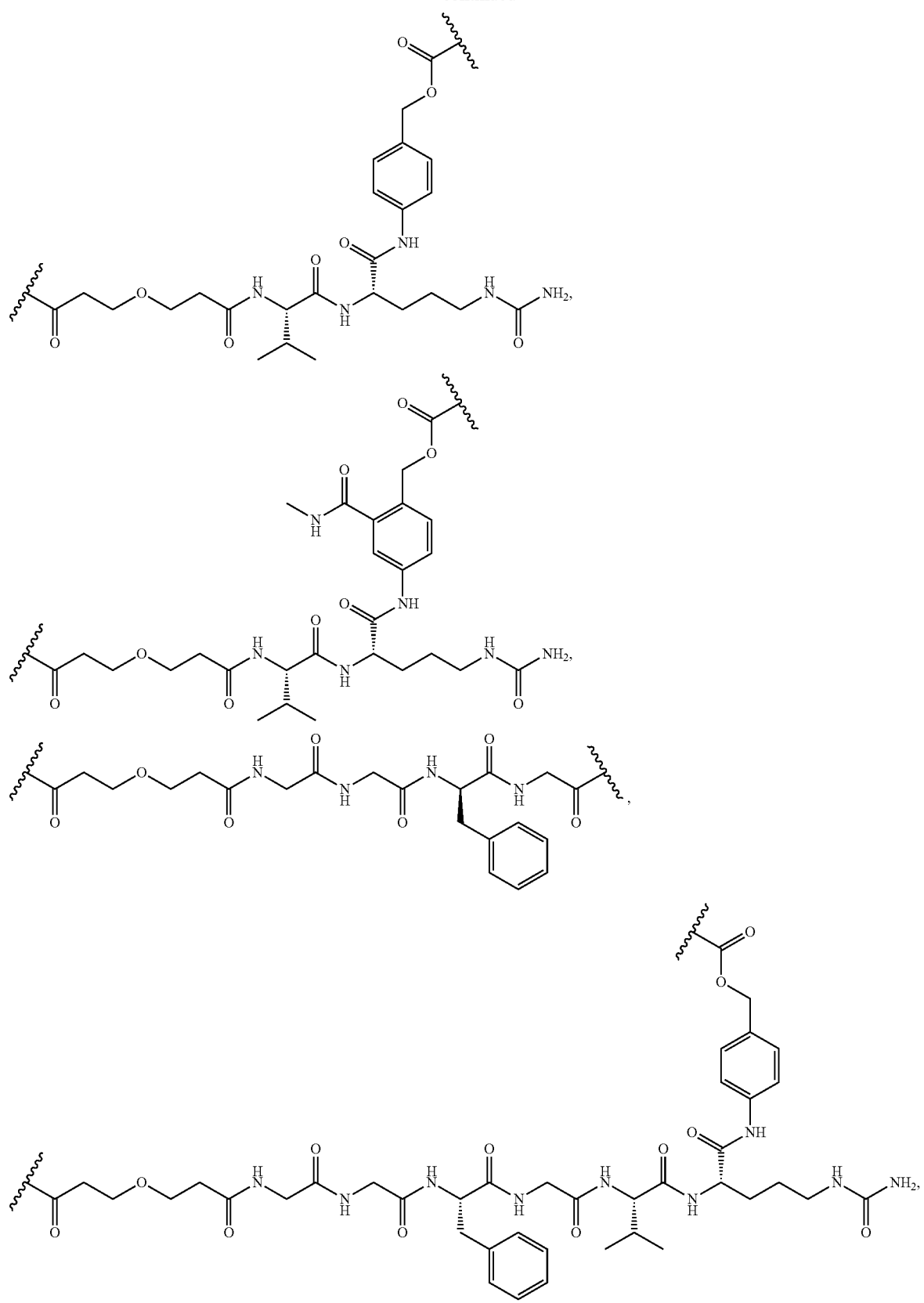

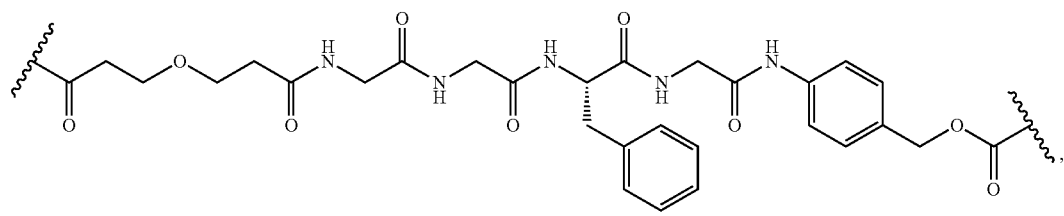
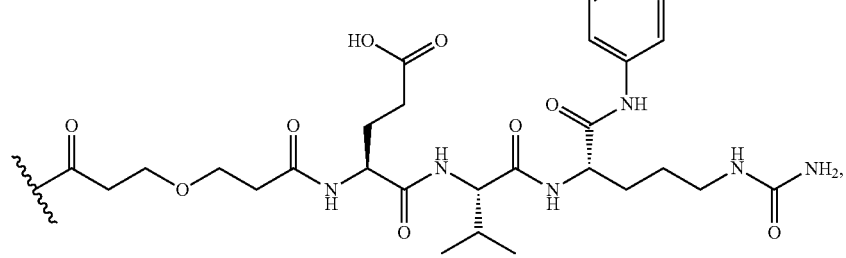
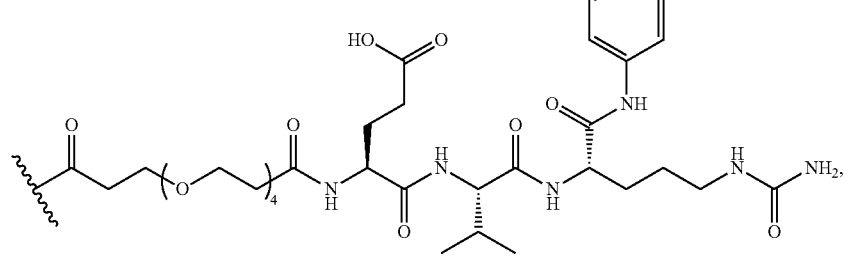
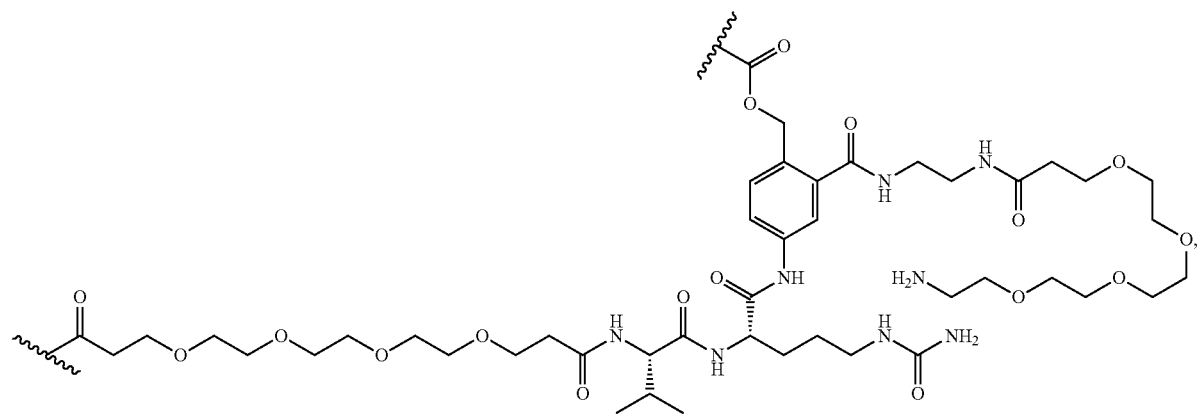

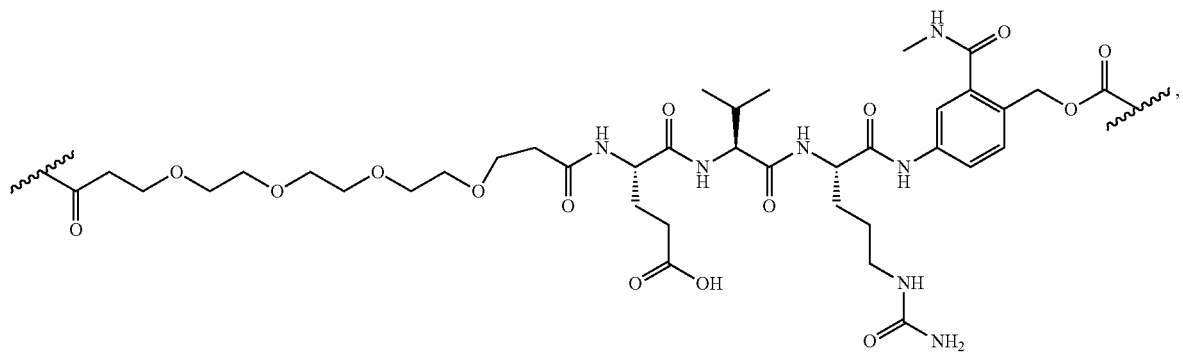
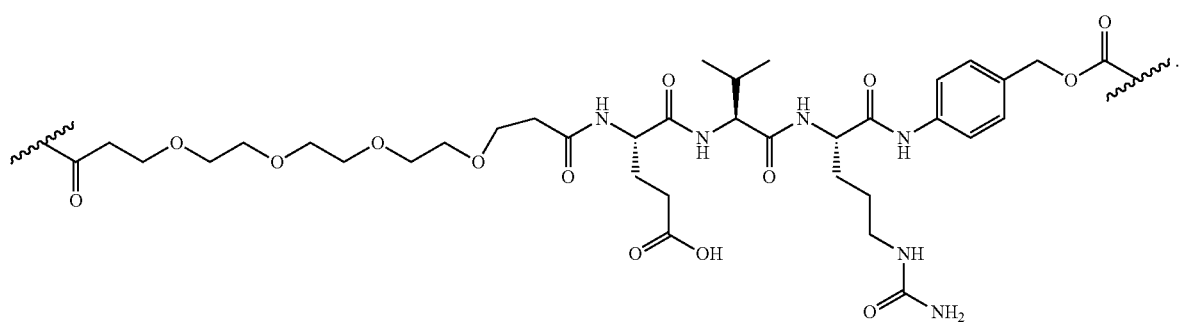
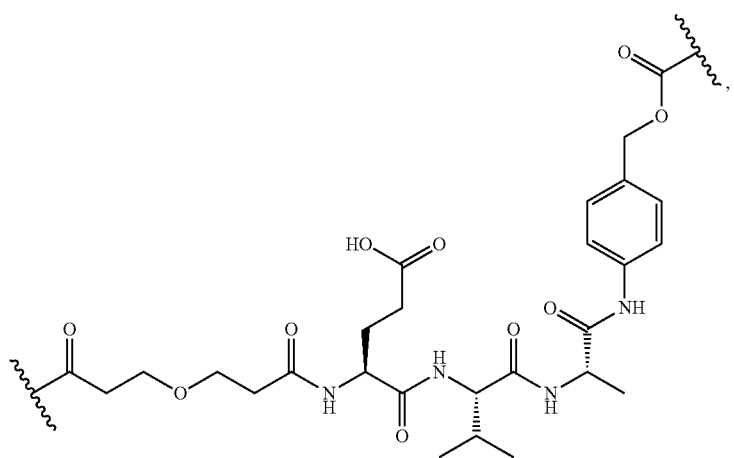
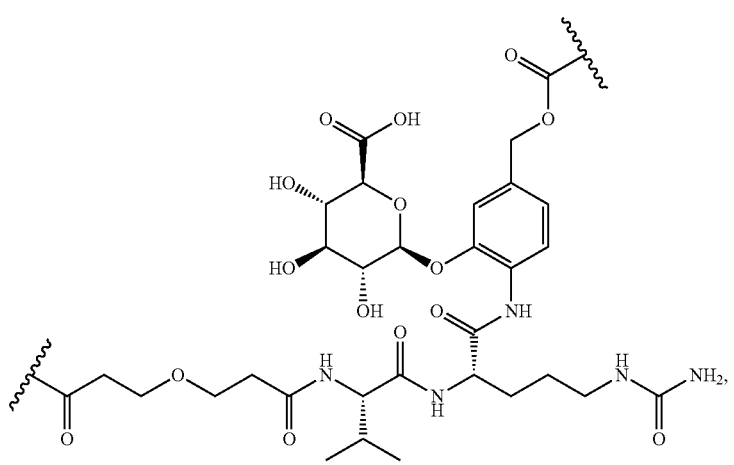

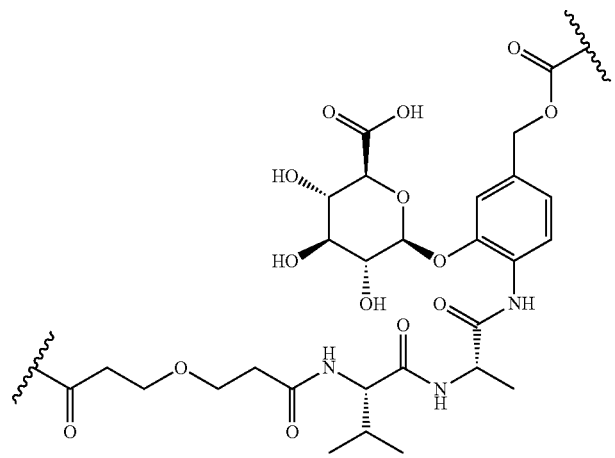
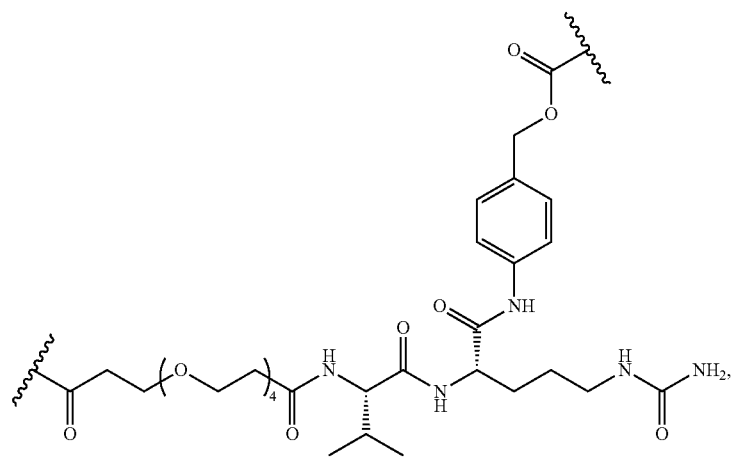
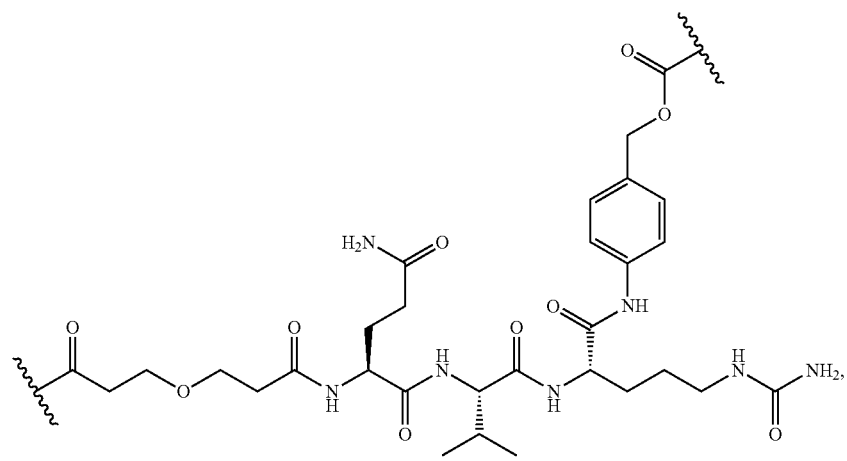

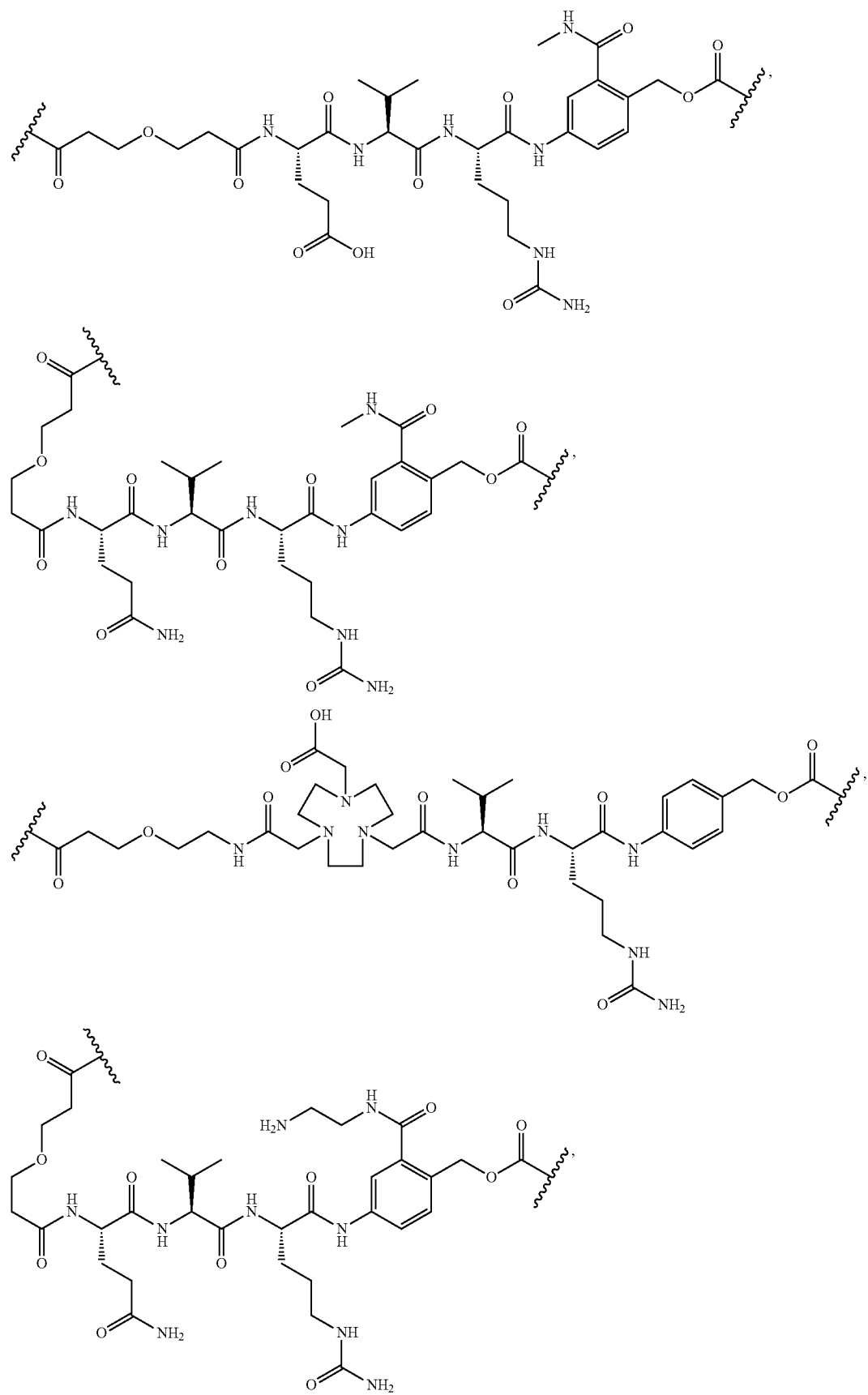

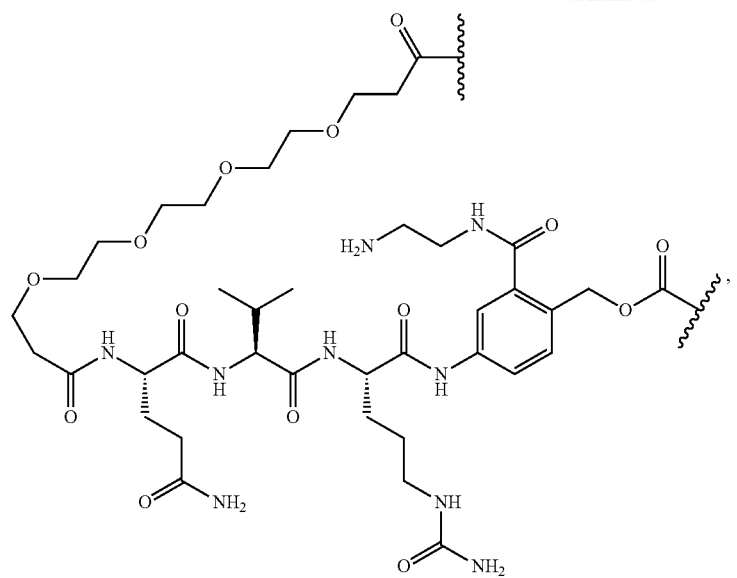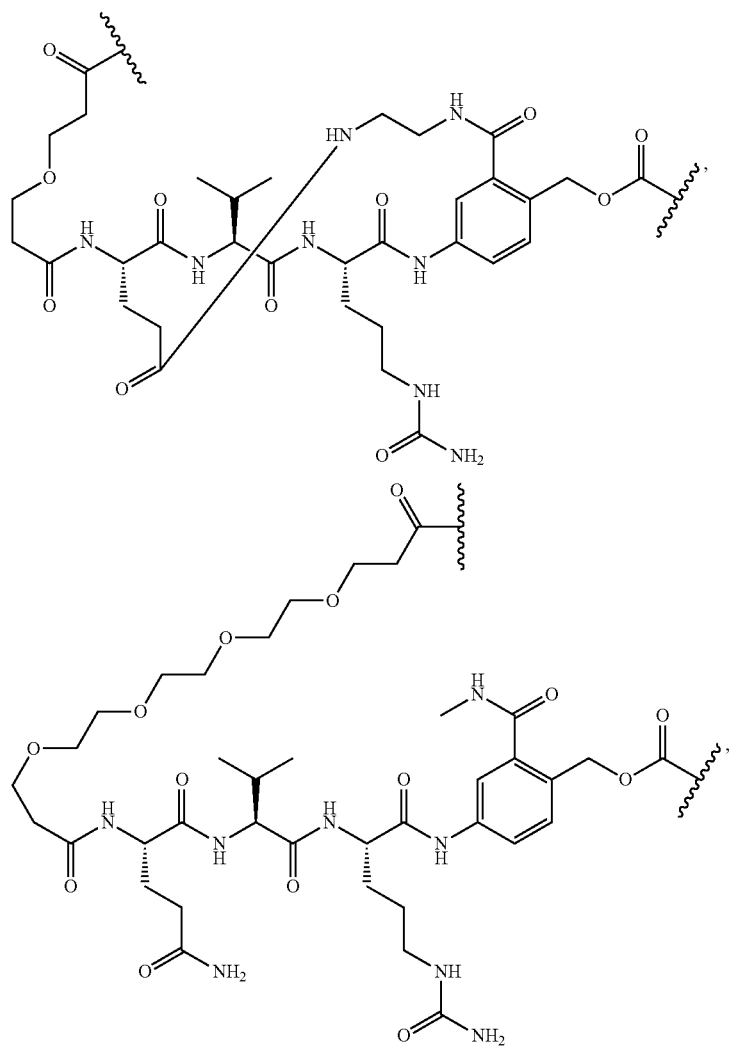

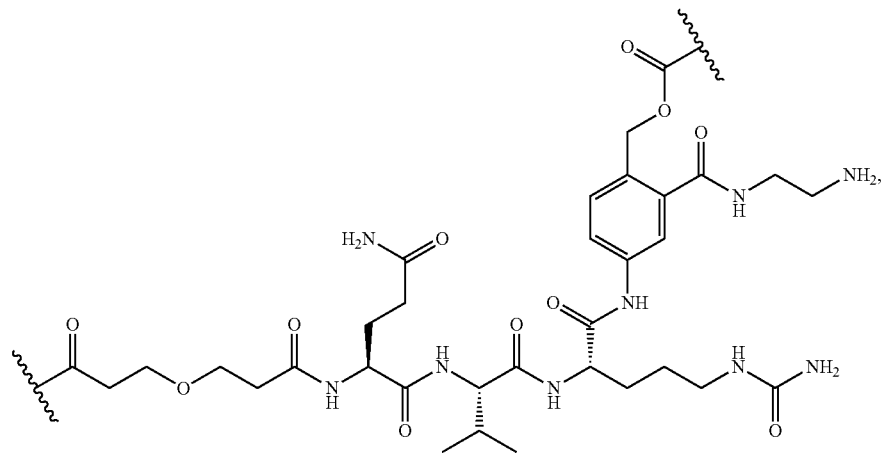
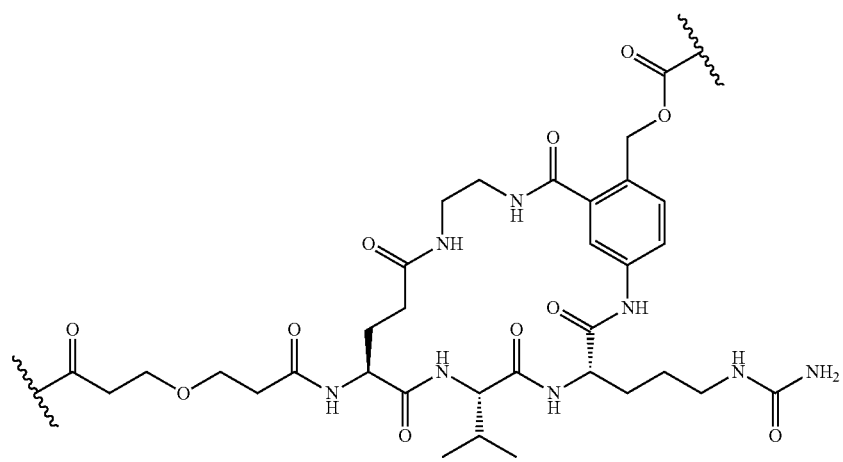
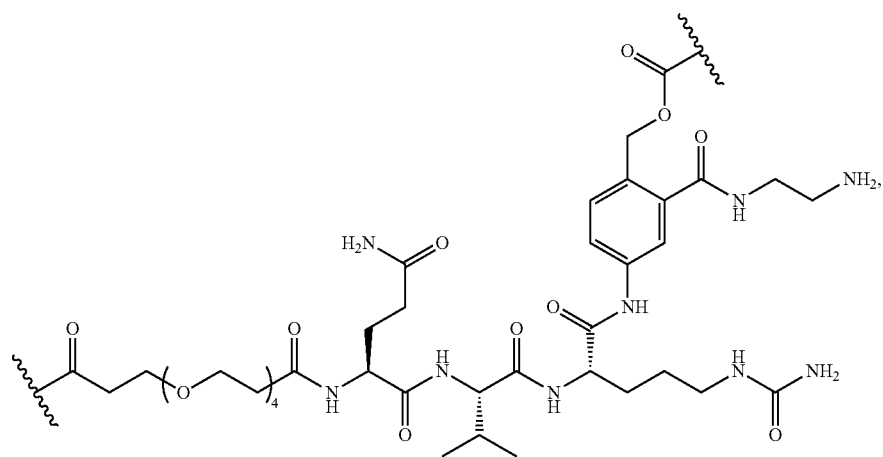

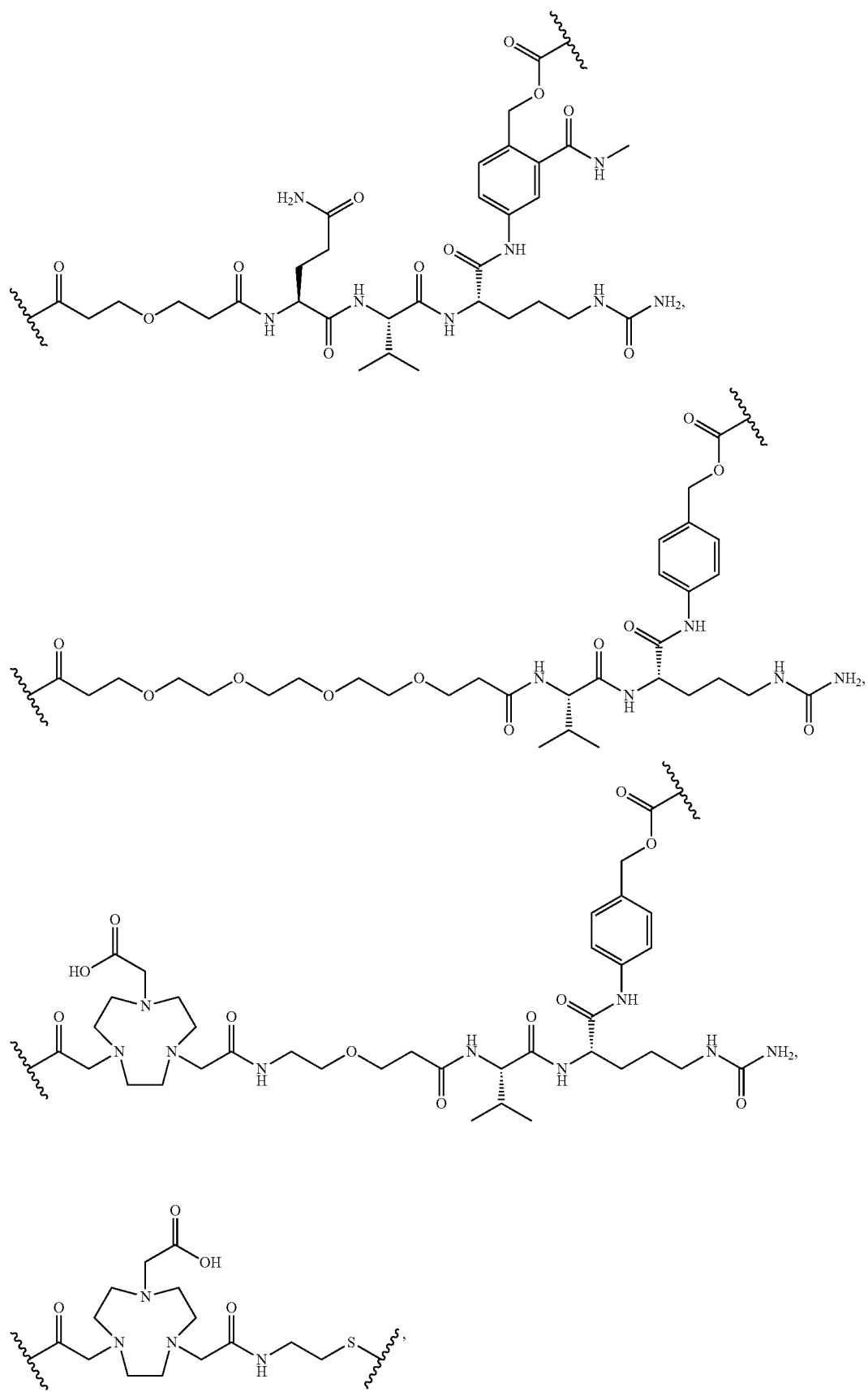

-continued
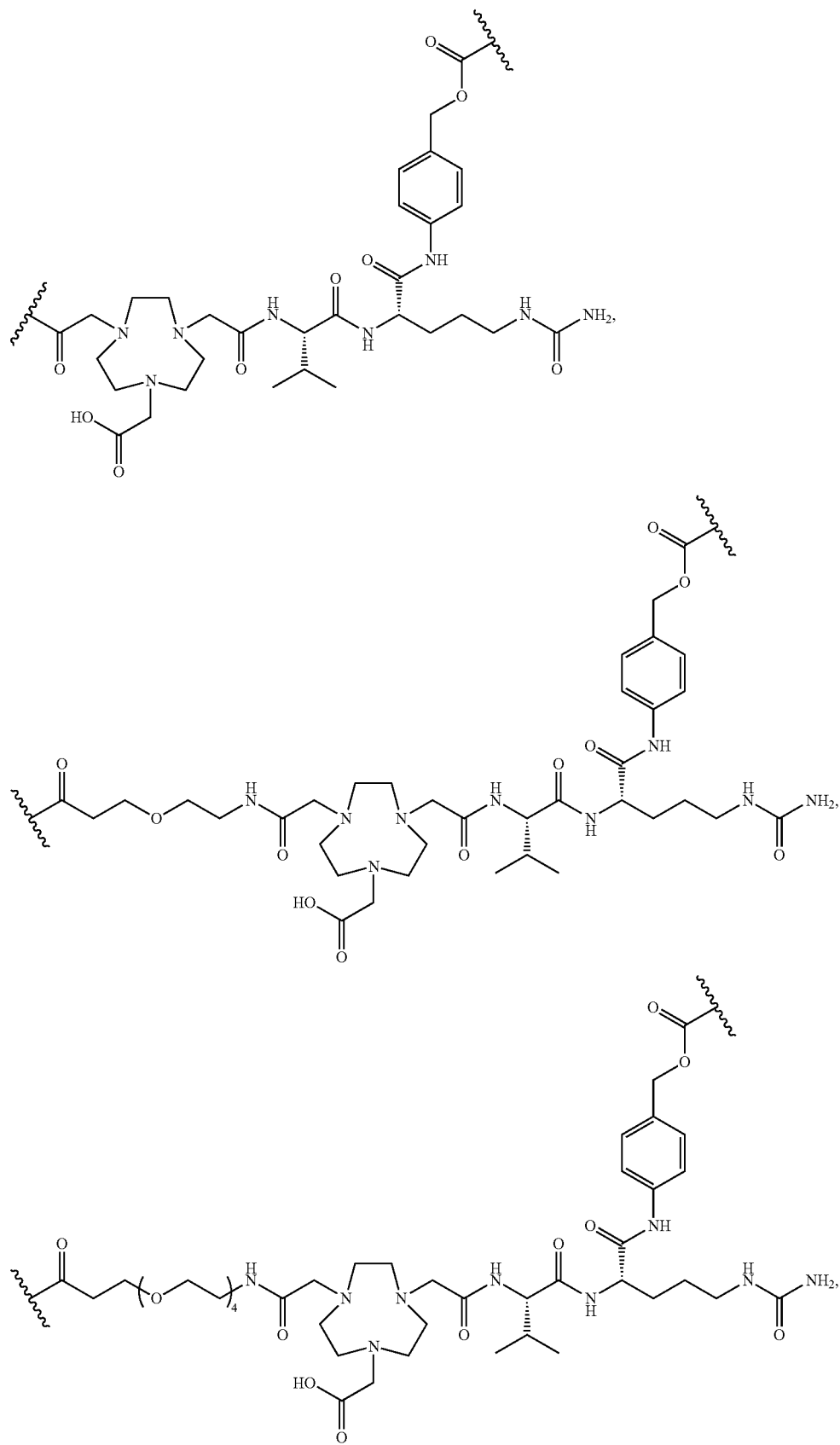

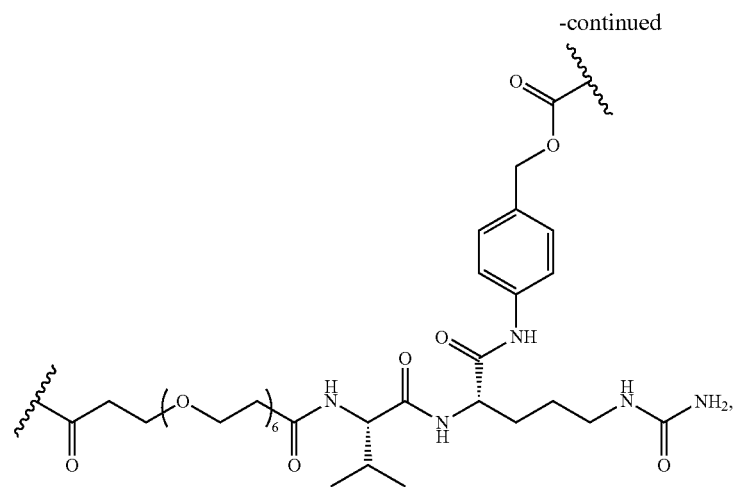
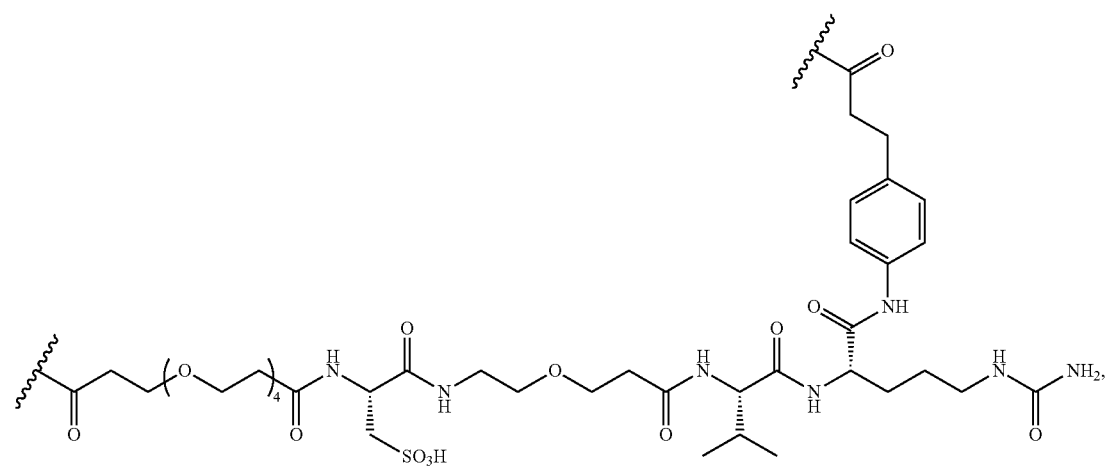
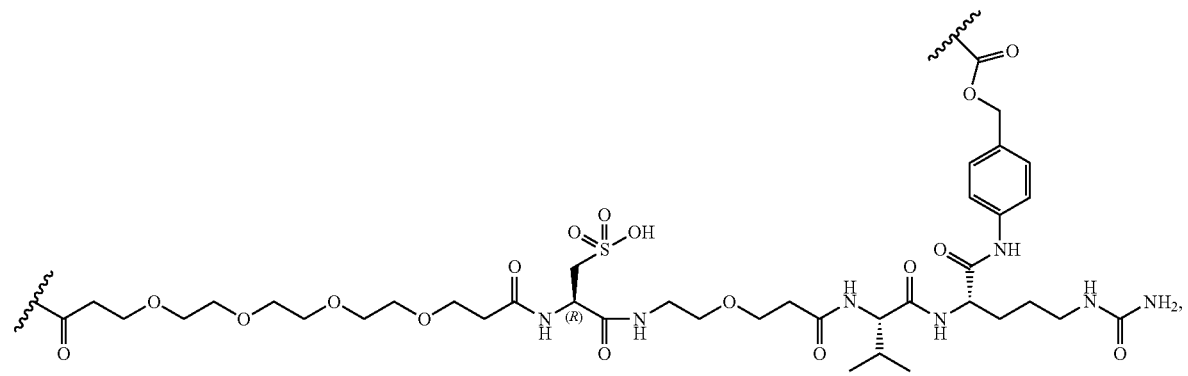

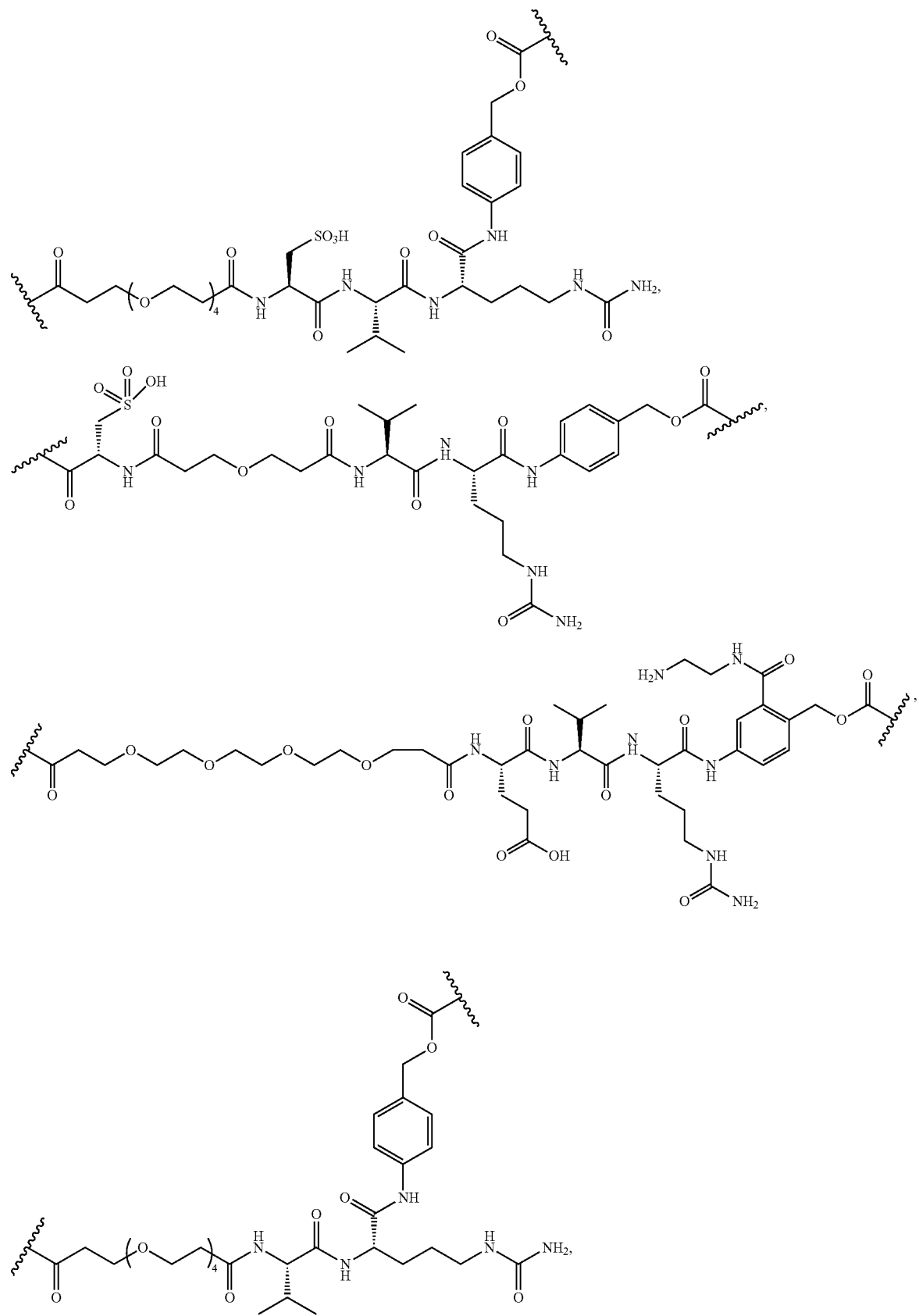

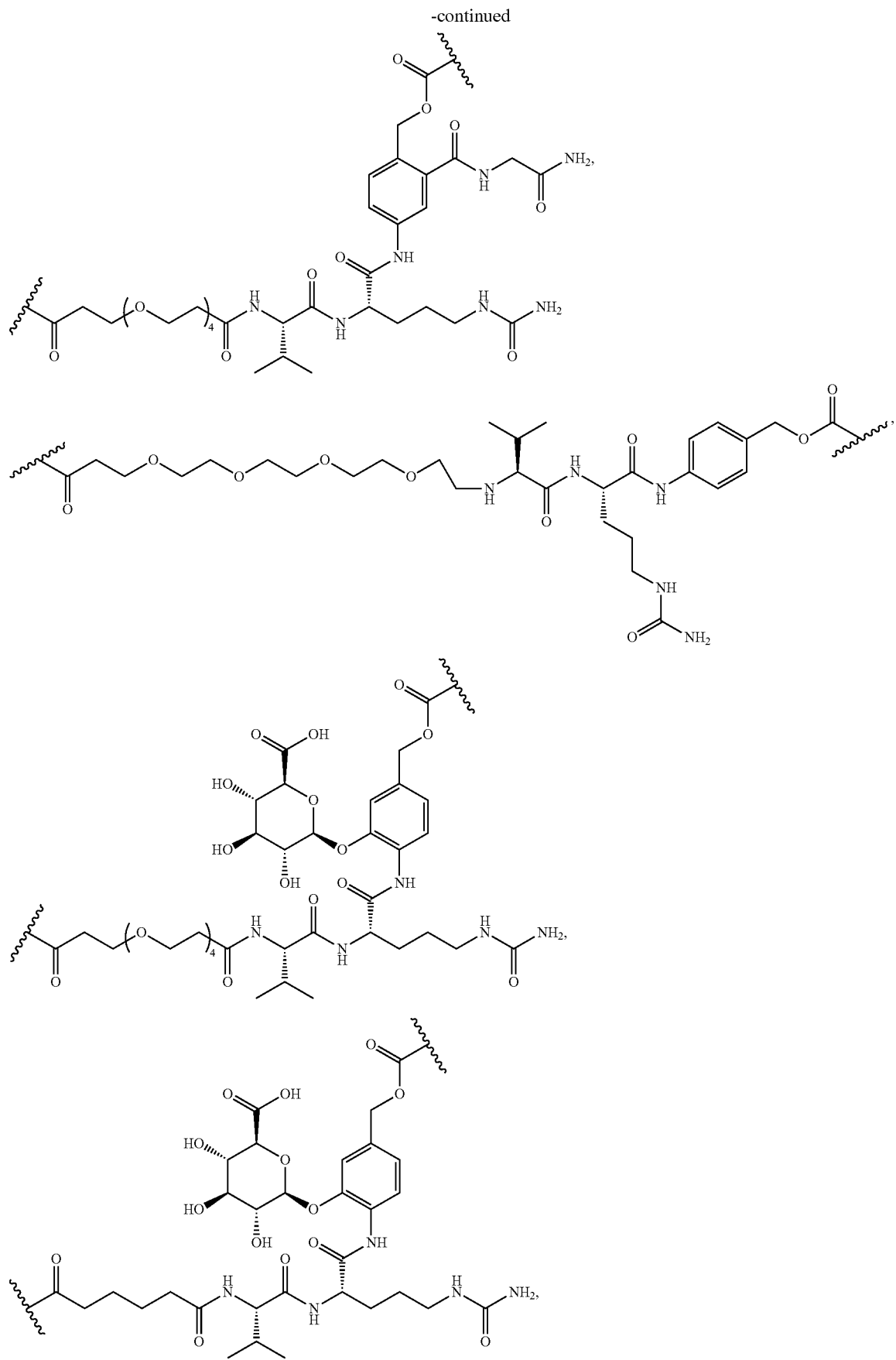

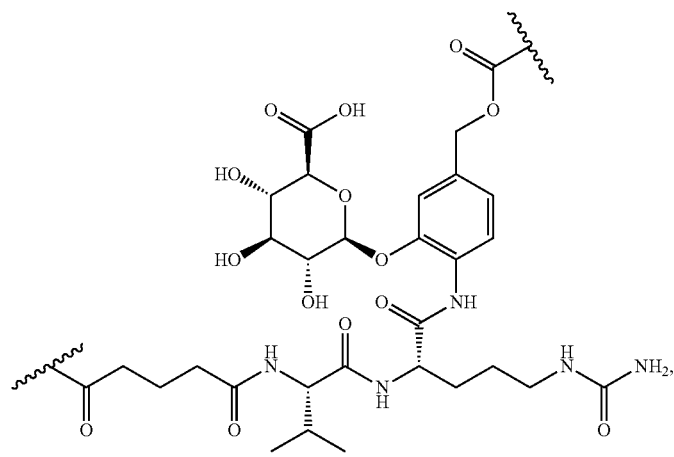
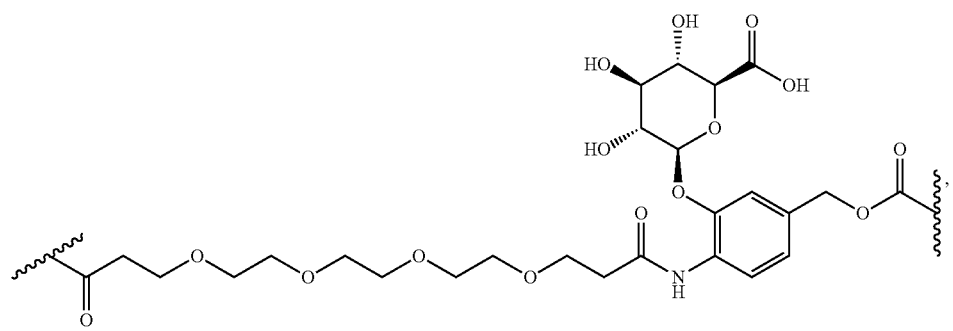
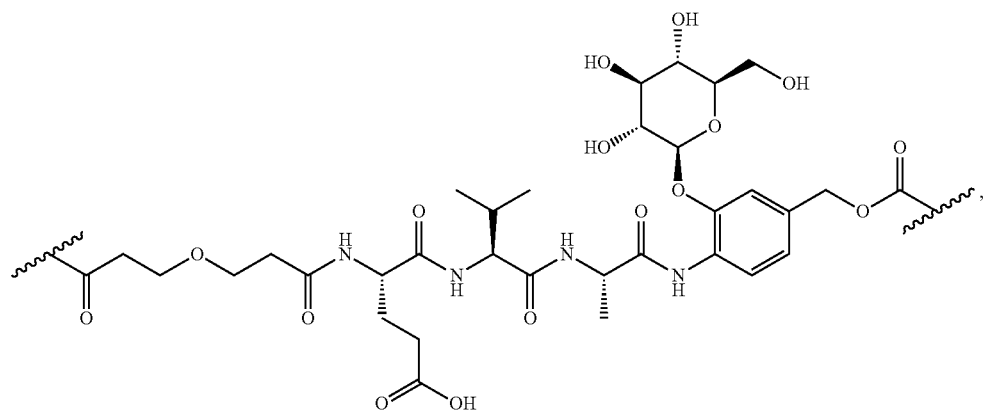
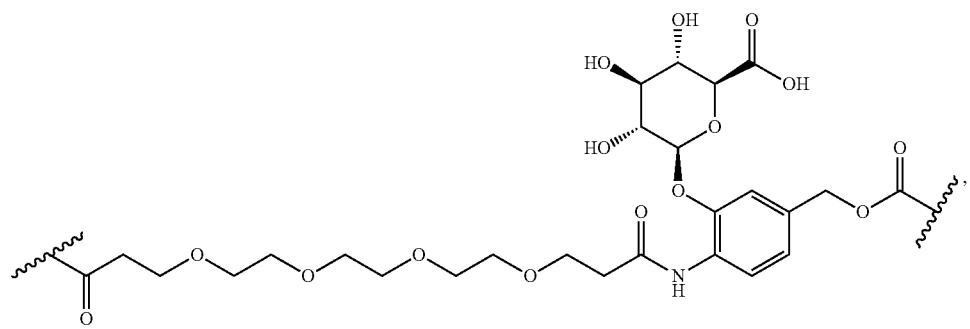

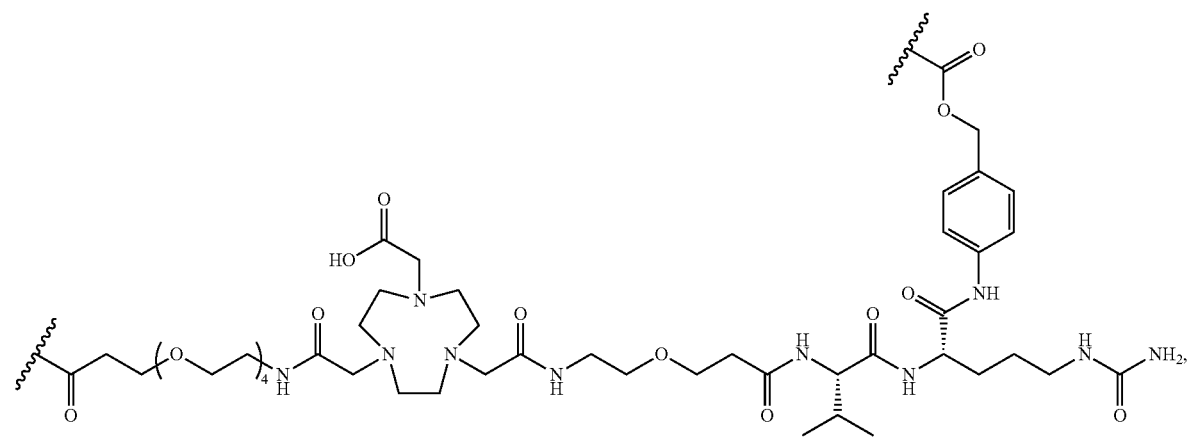
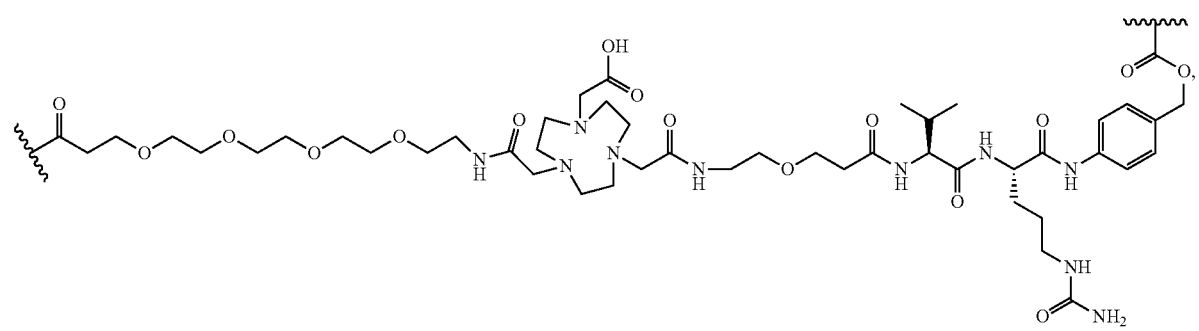
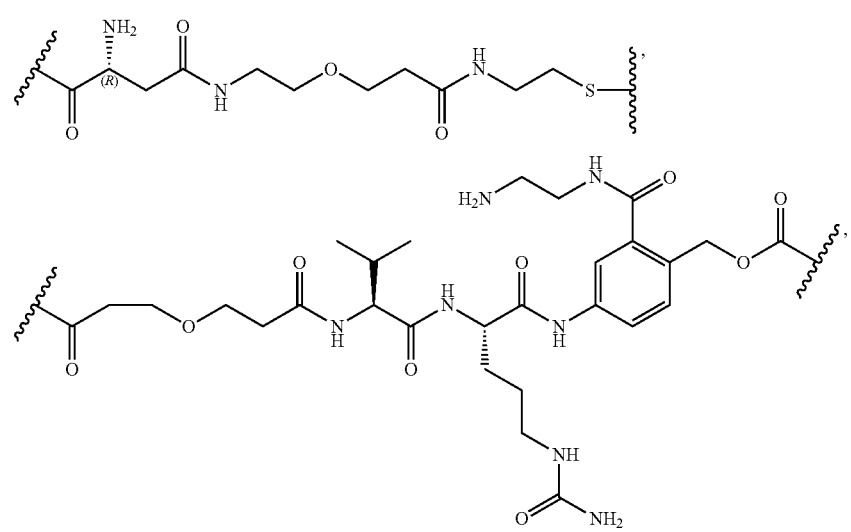
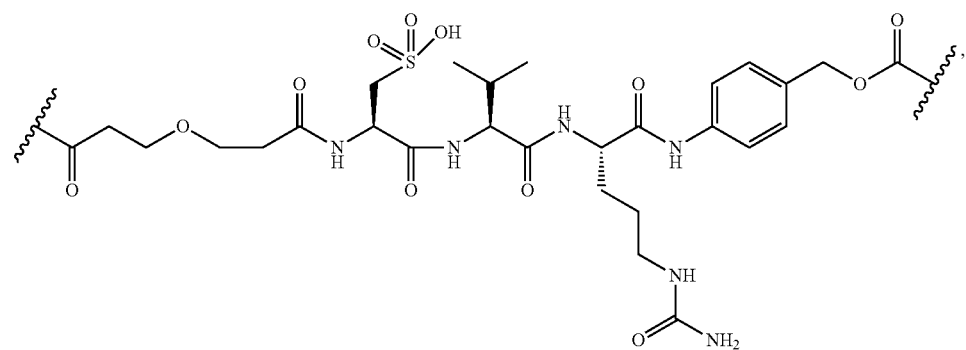

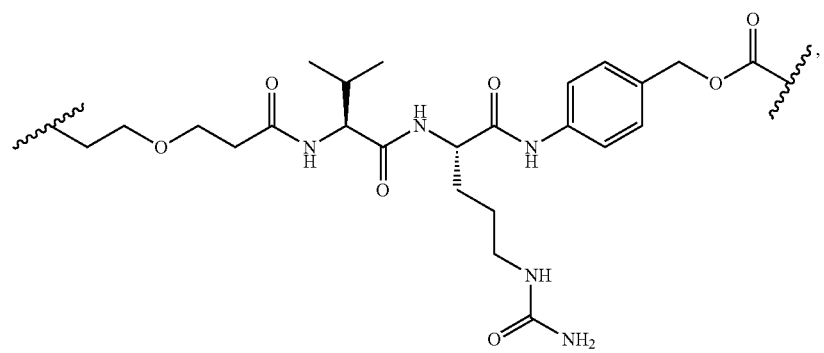
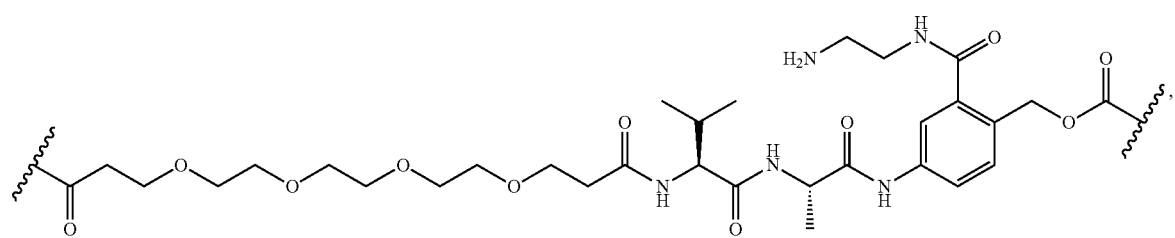
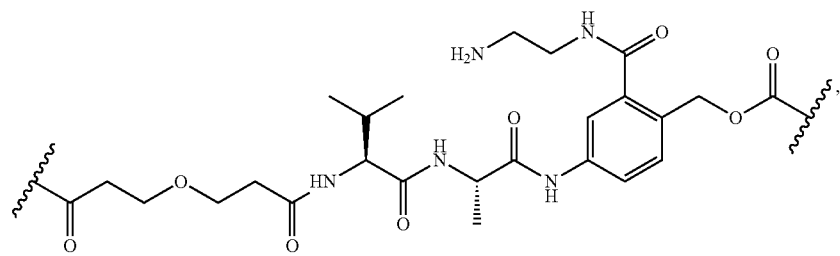
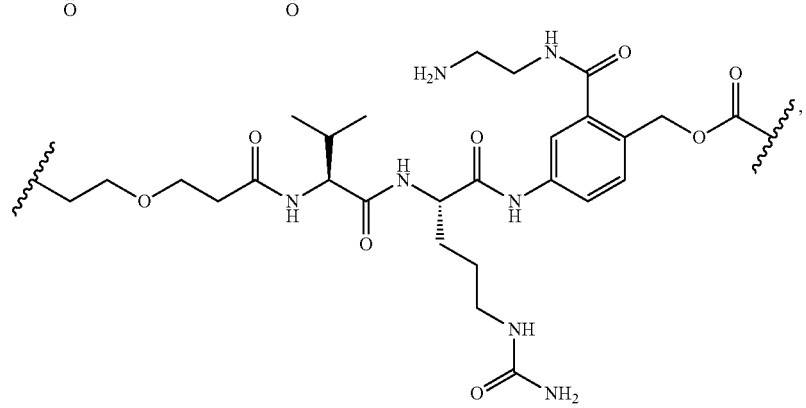
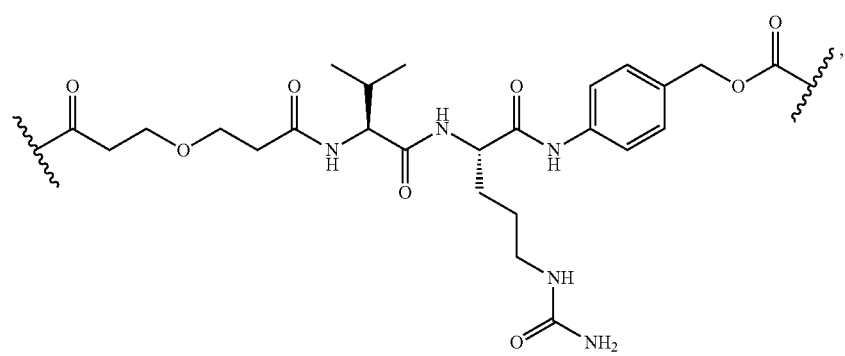

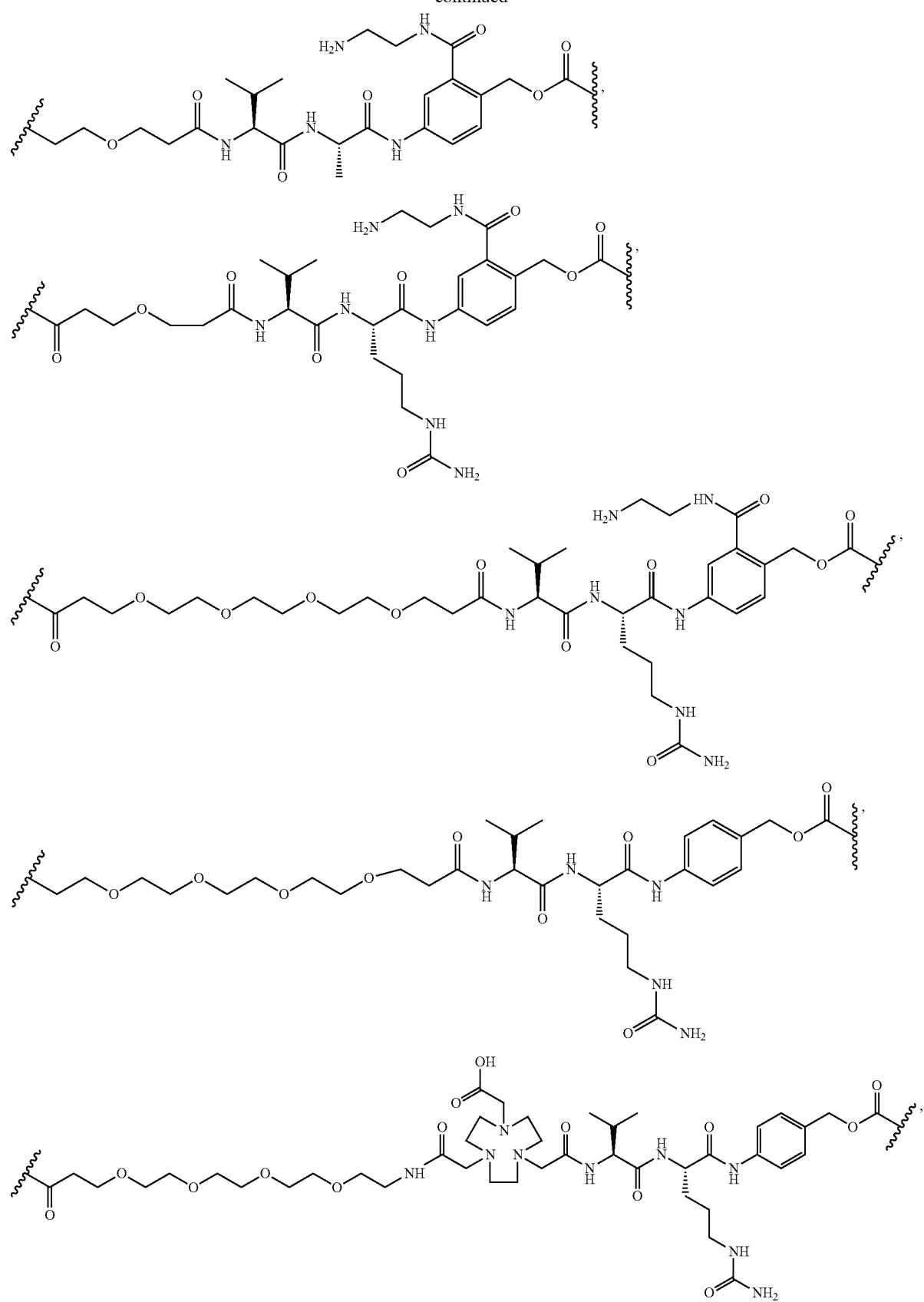

-continued
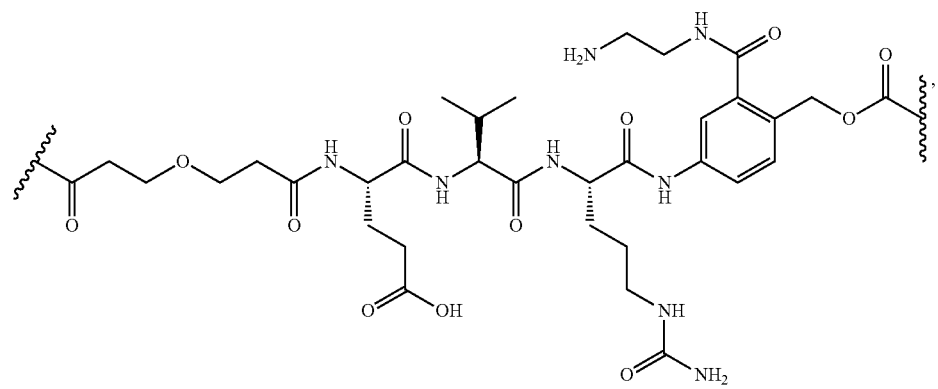
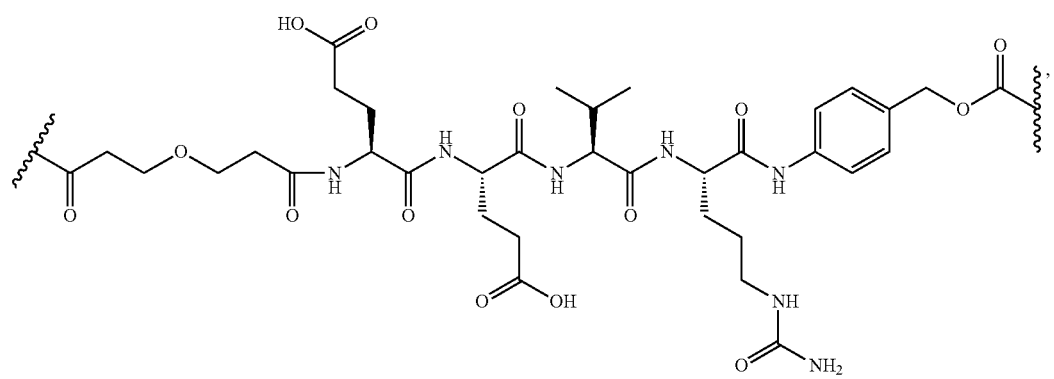
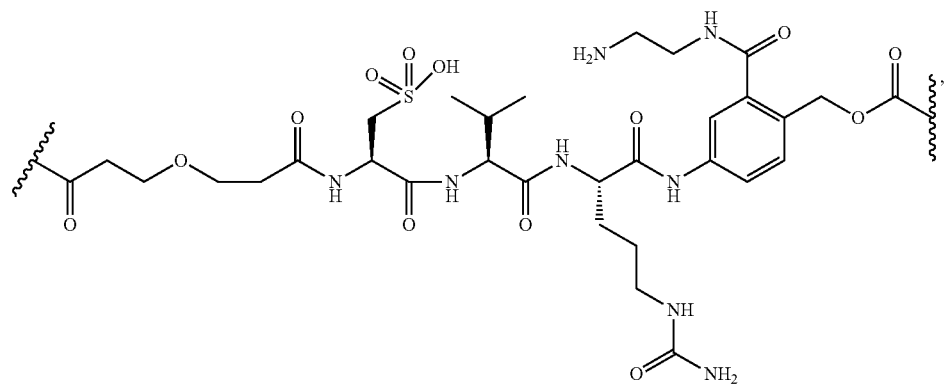
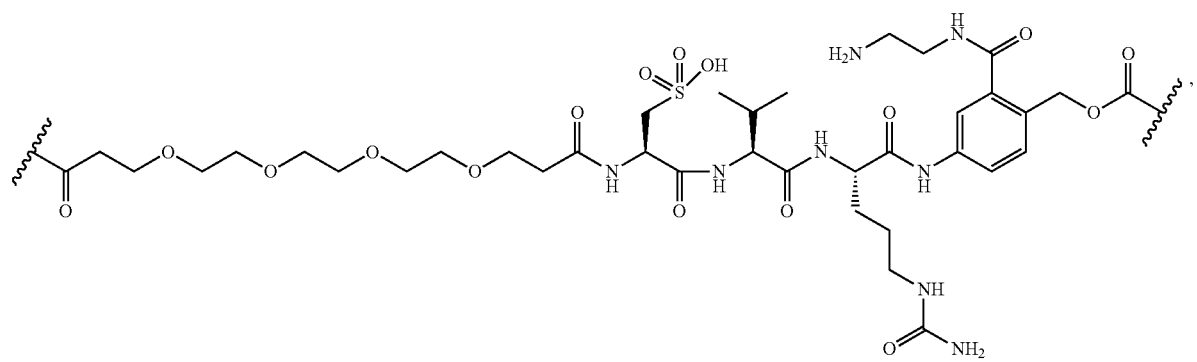

-continued
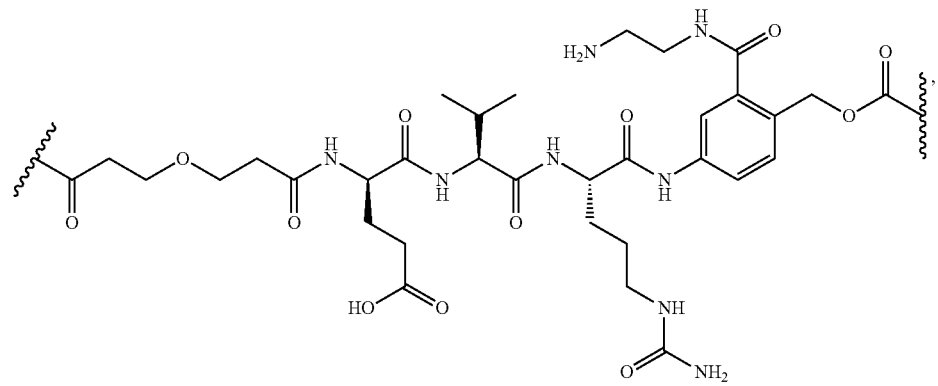
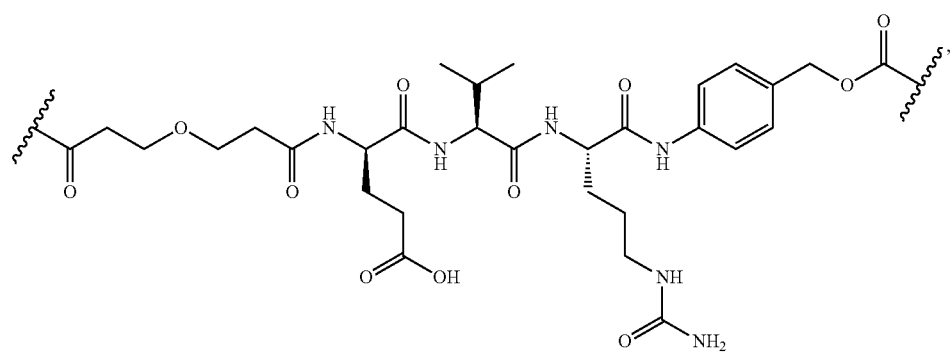
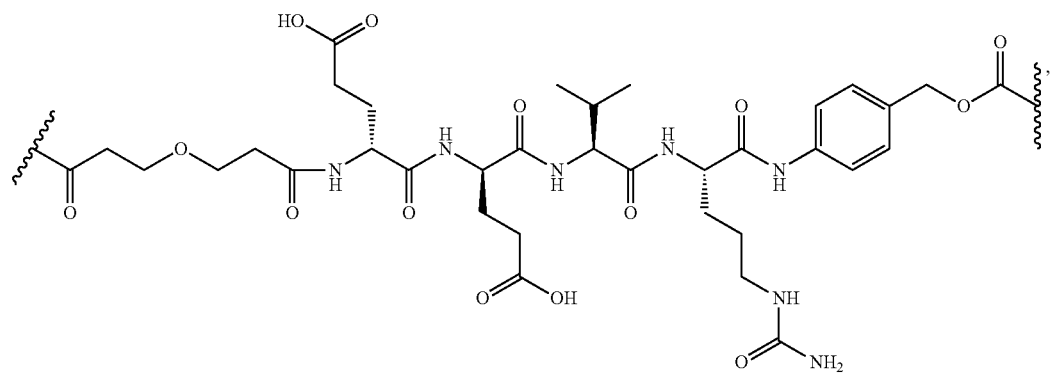
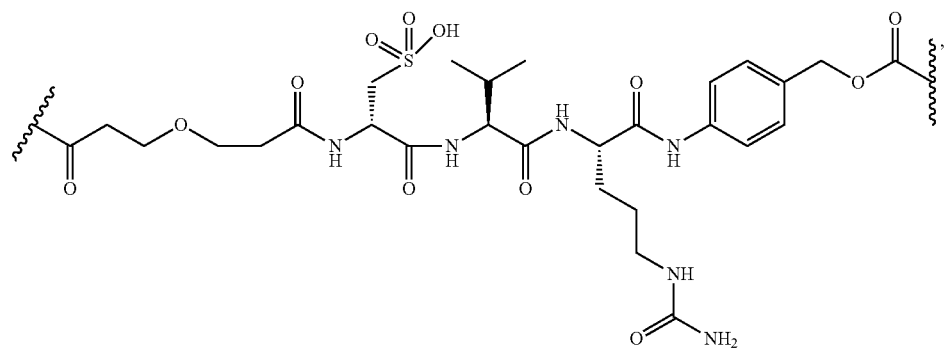

-continued
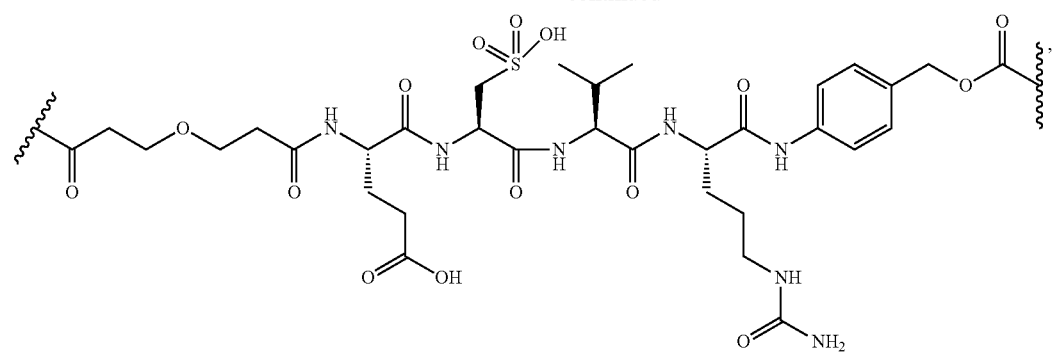
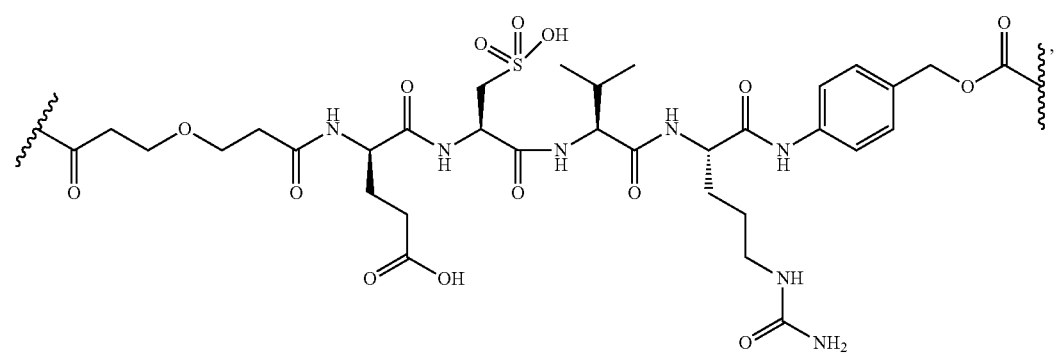
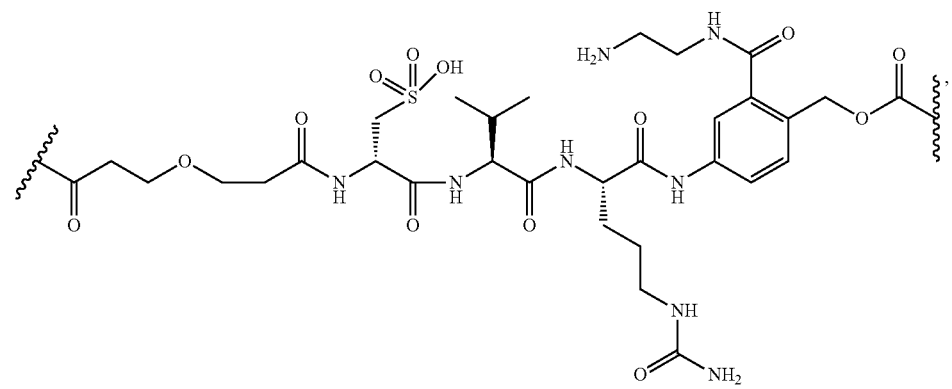
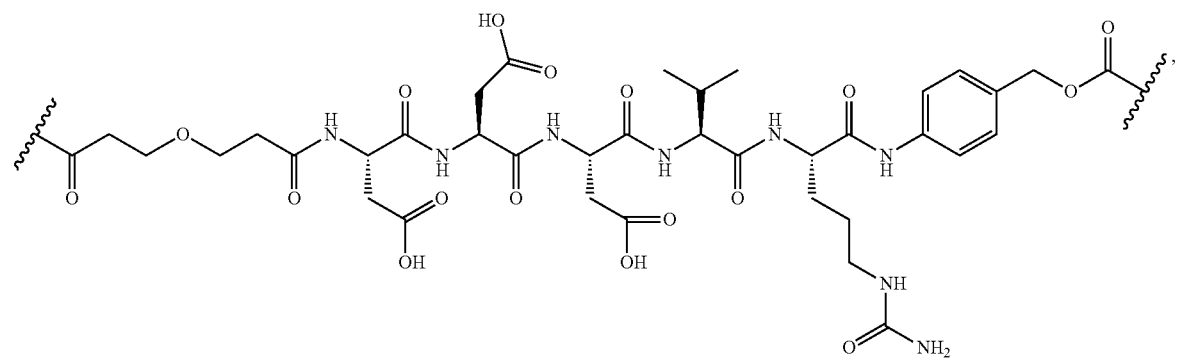

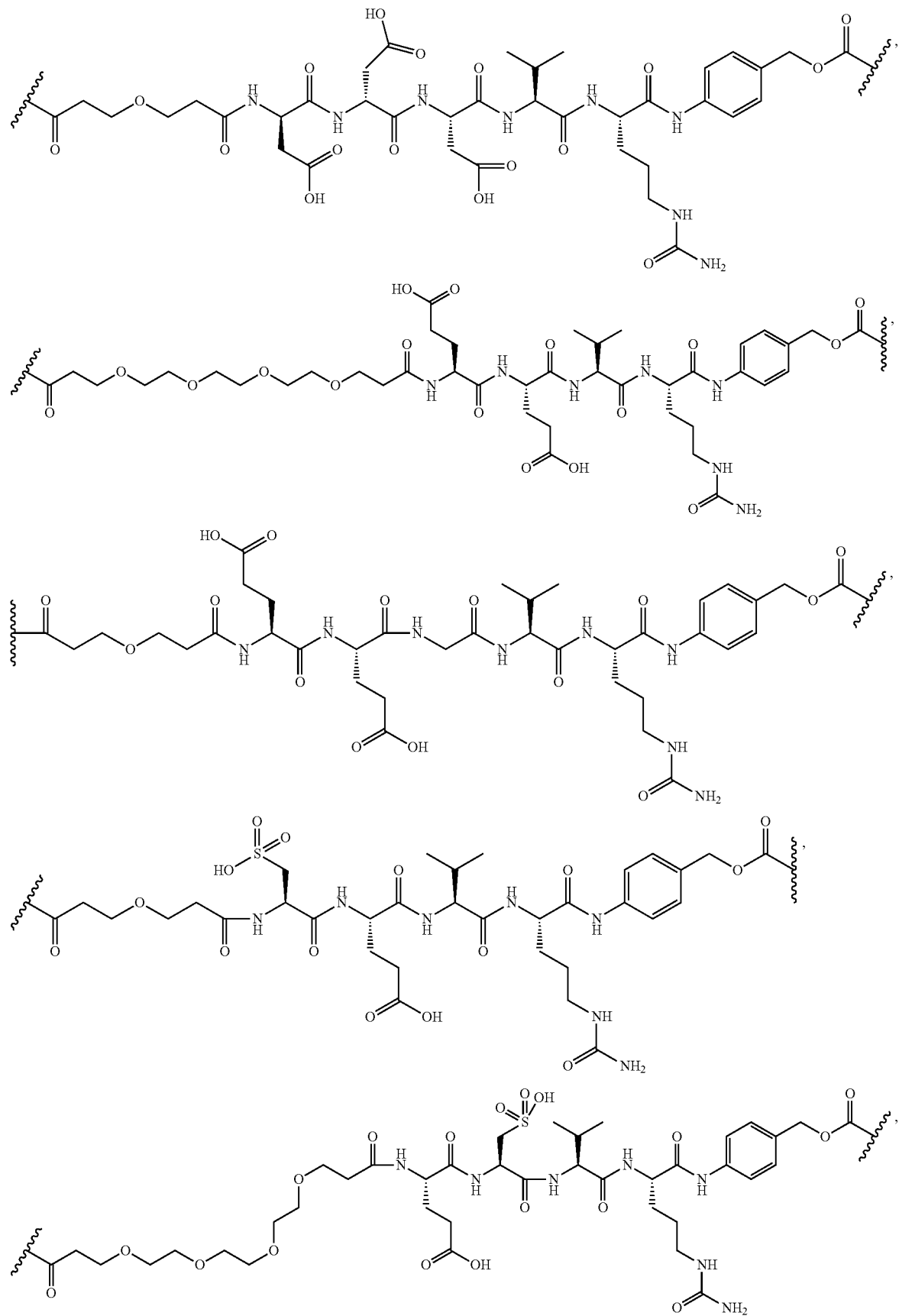

-continued
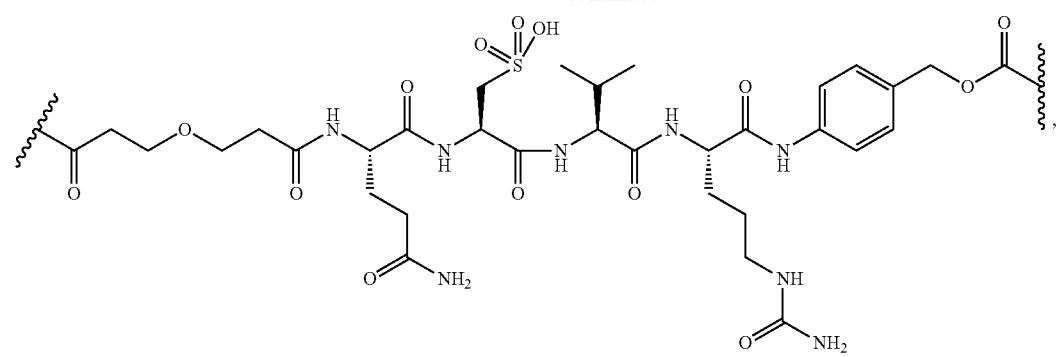
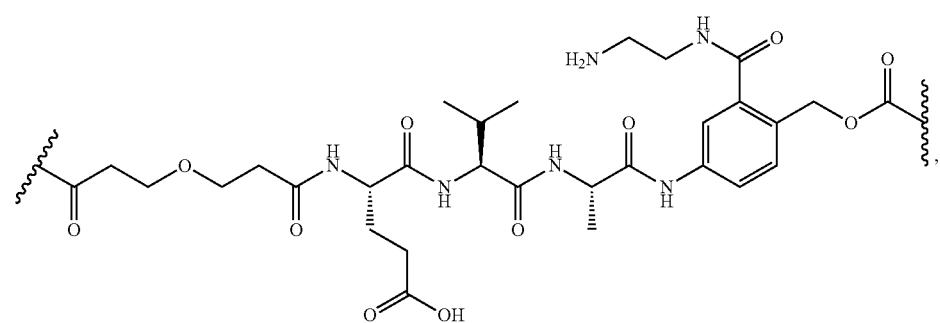
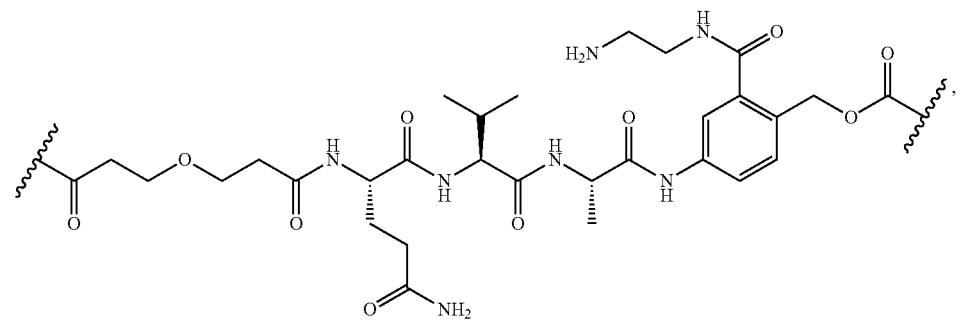
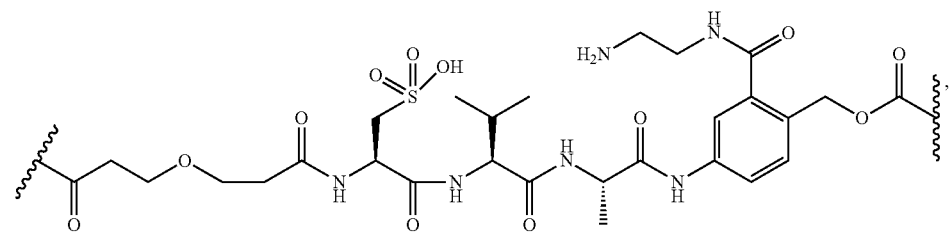
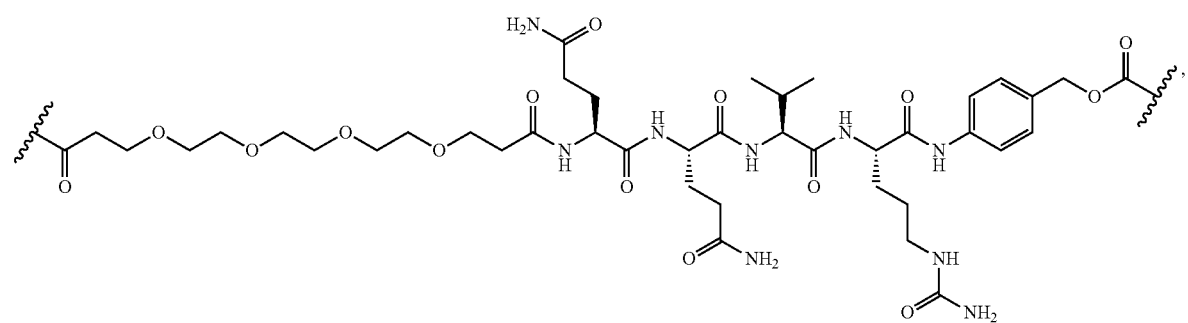

-continued
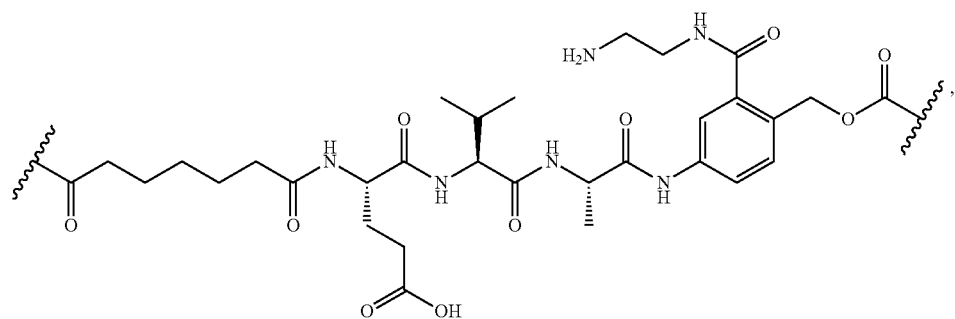
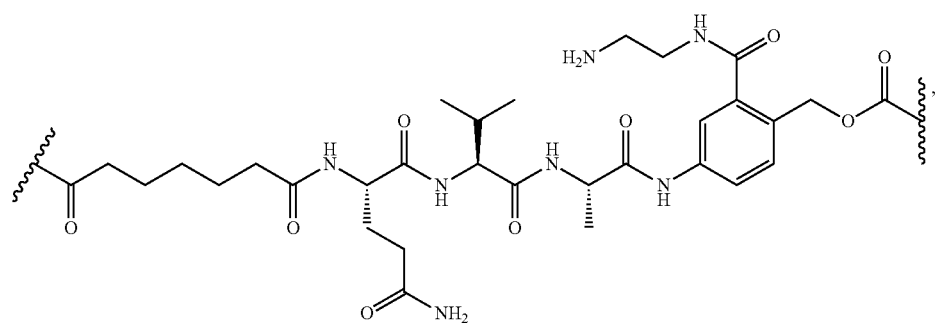
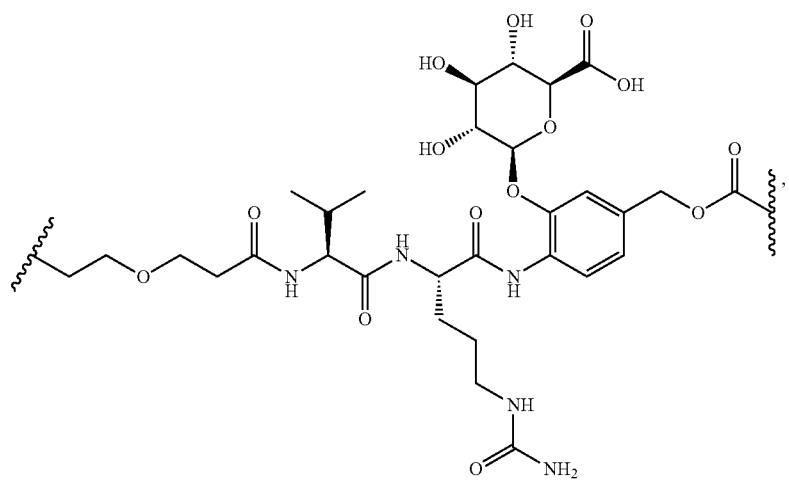
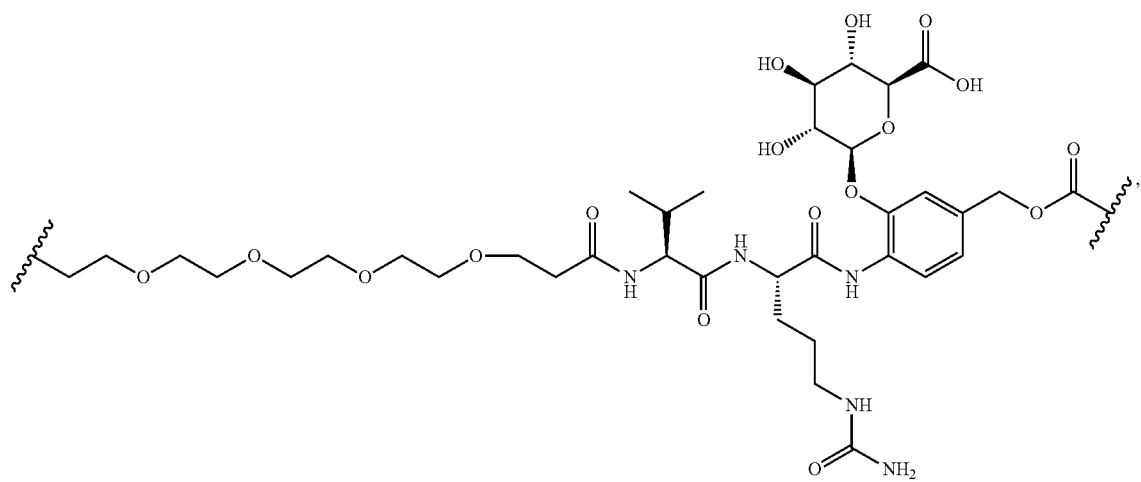

-continued
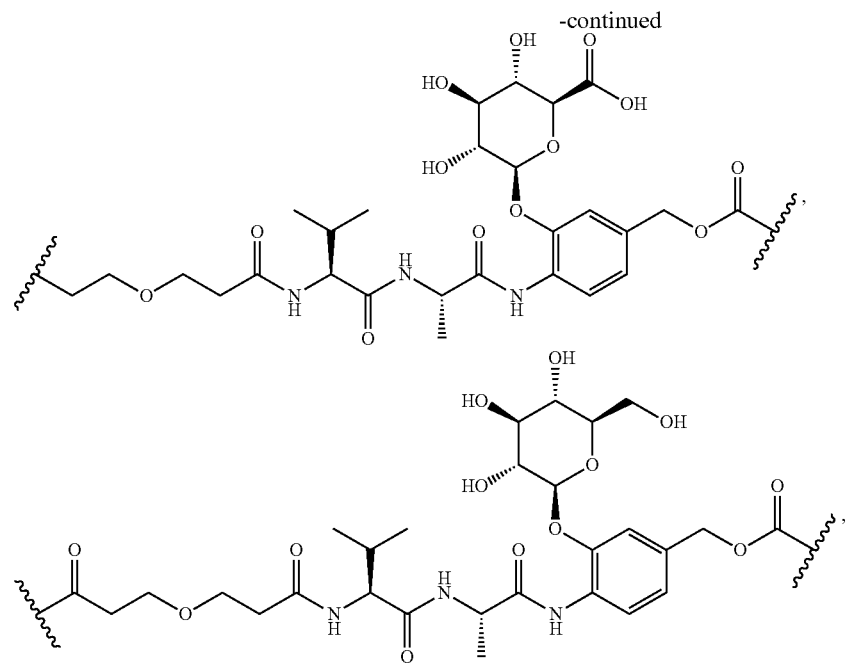
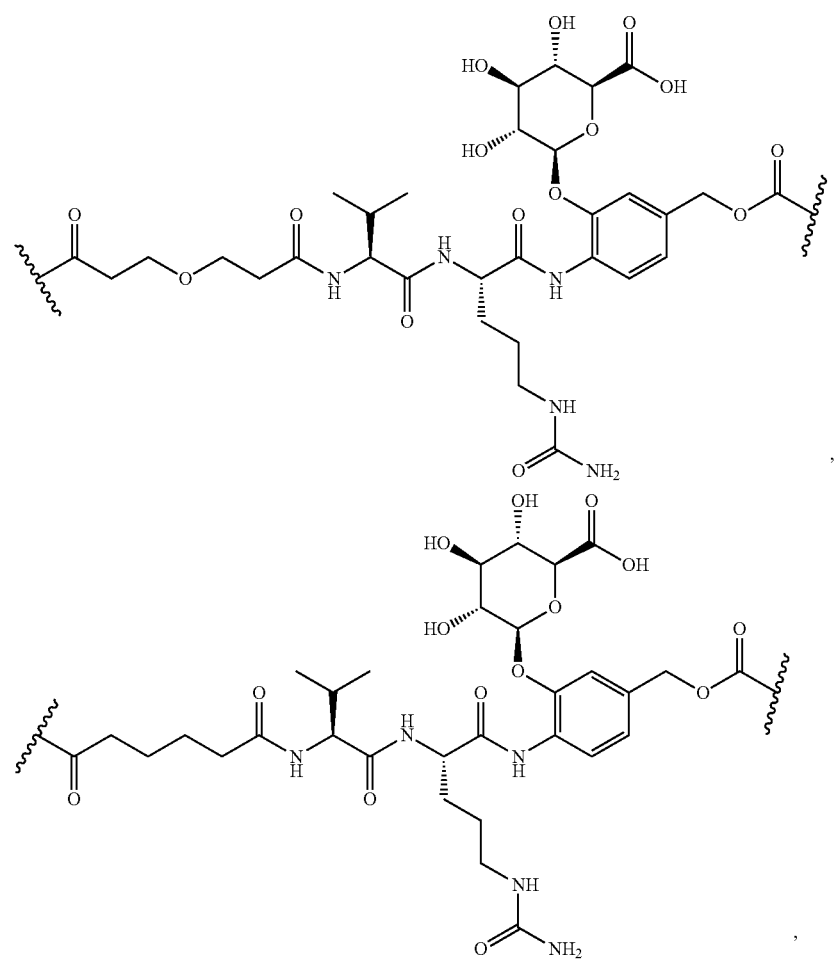

-continued
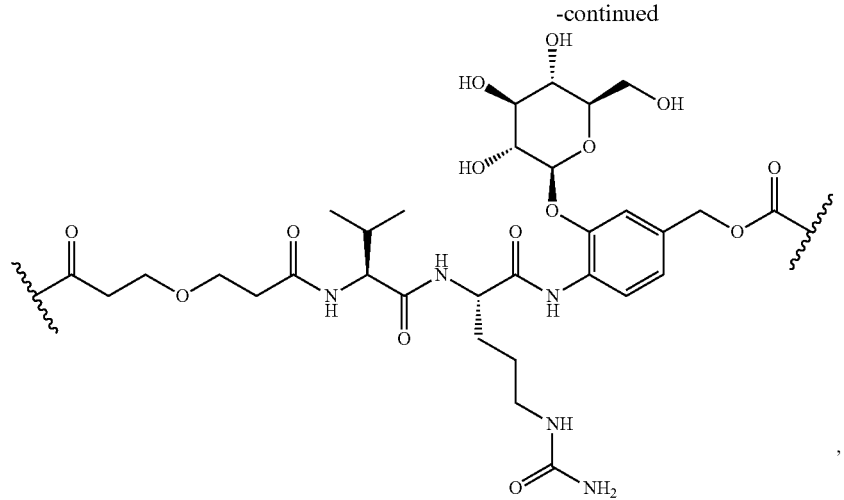
,
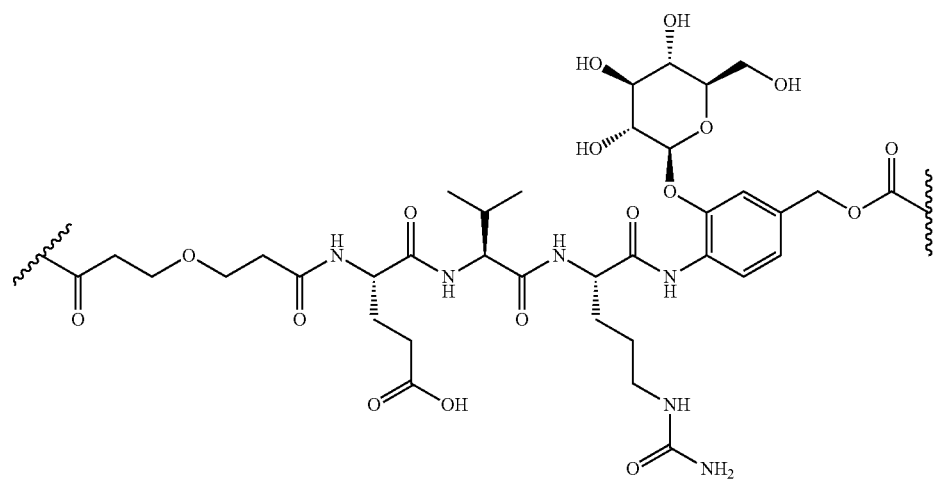
,
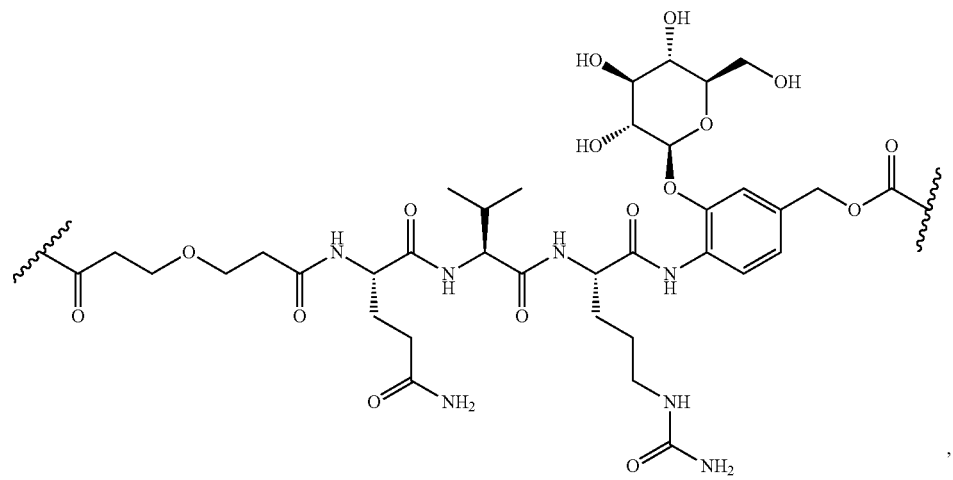
,

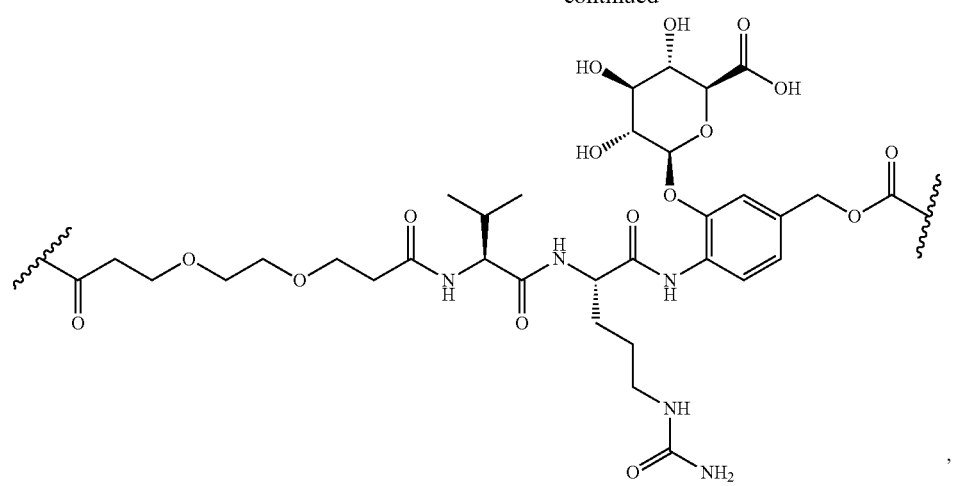
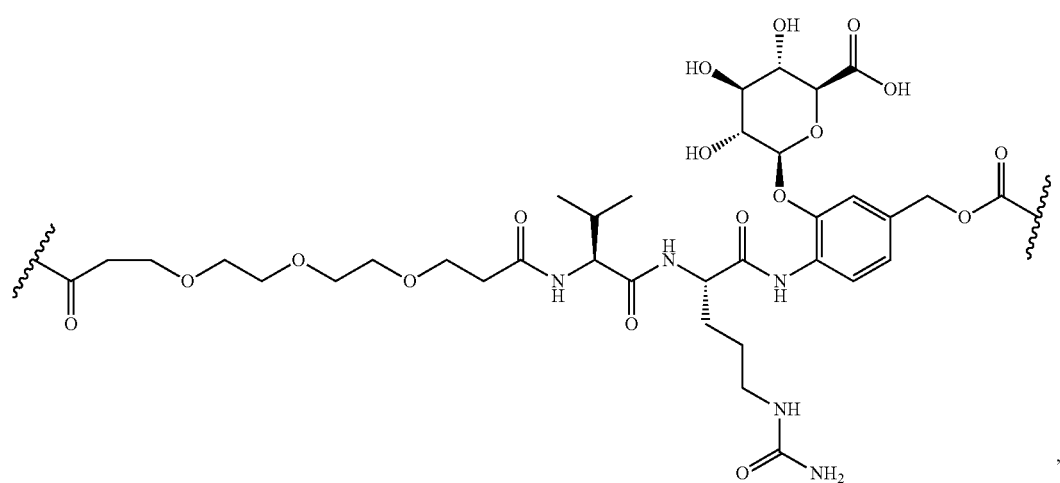
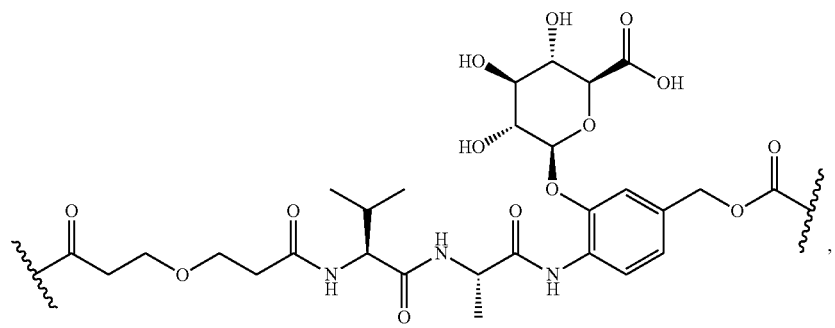

-continued
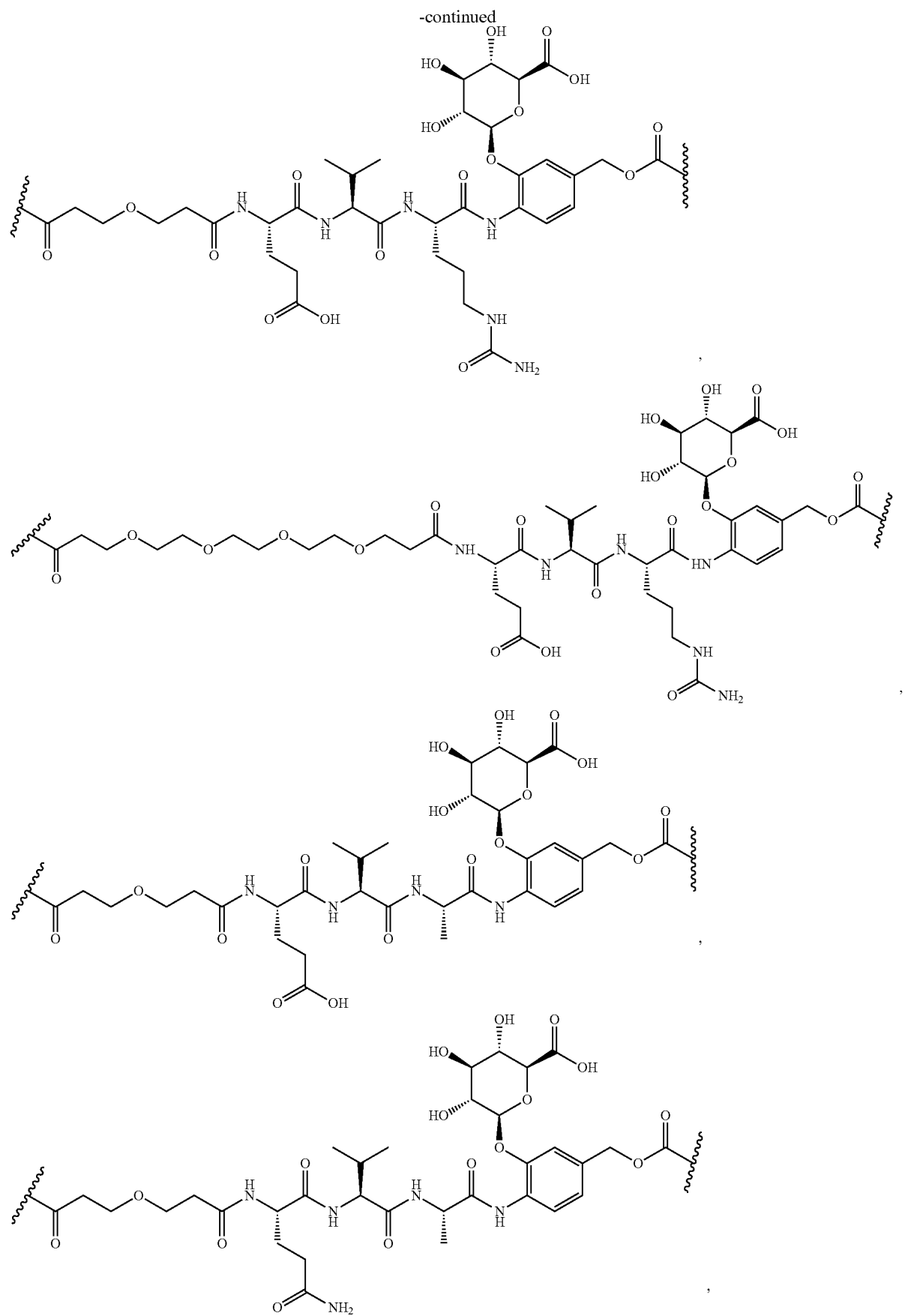

-continued
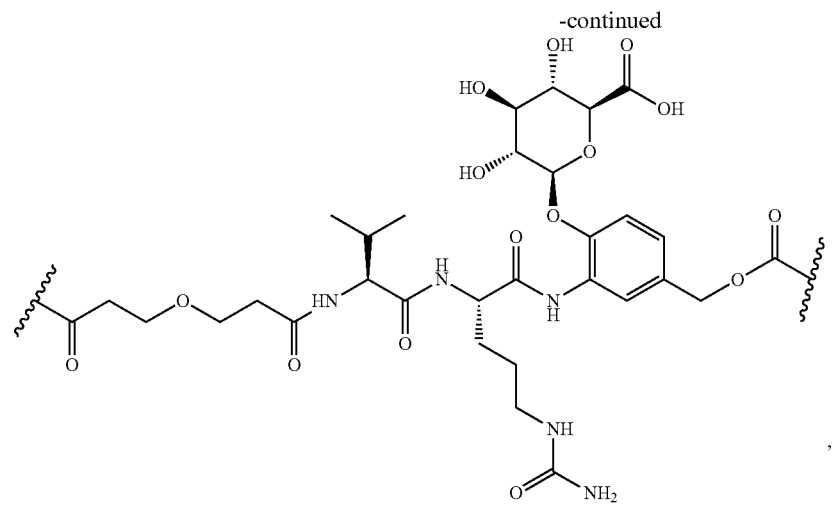
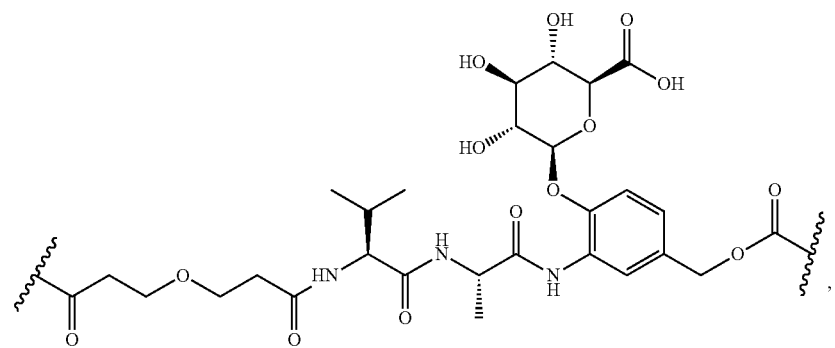
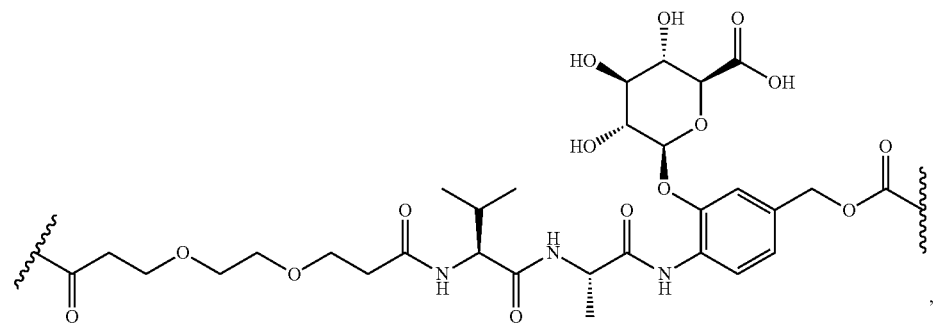
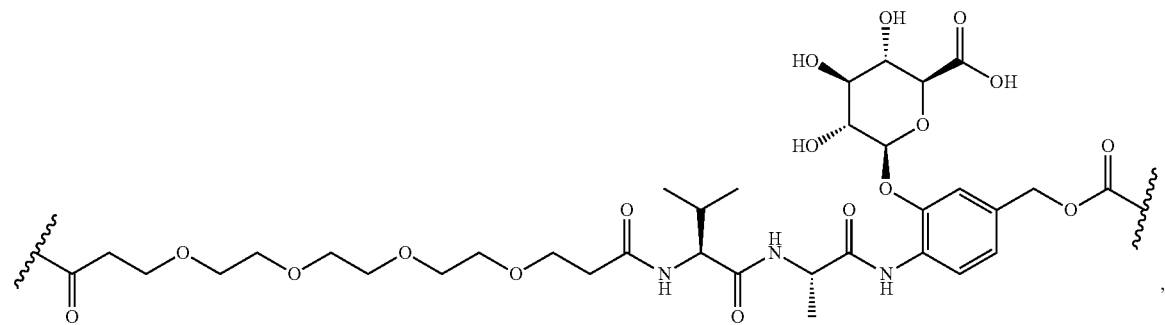

-continued
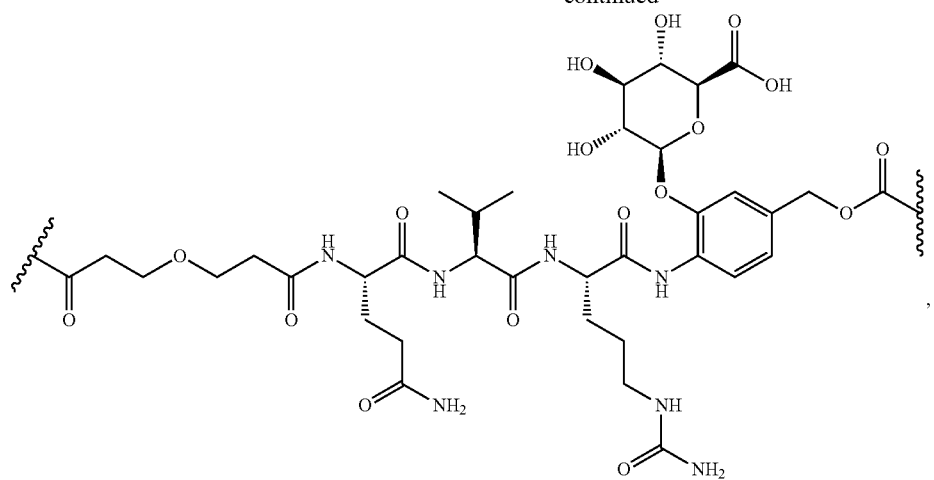
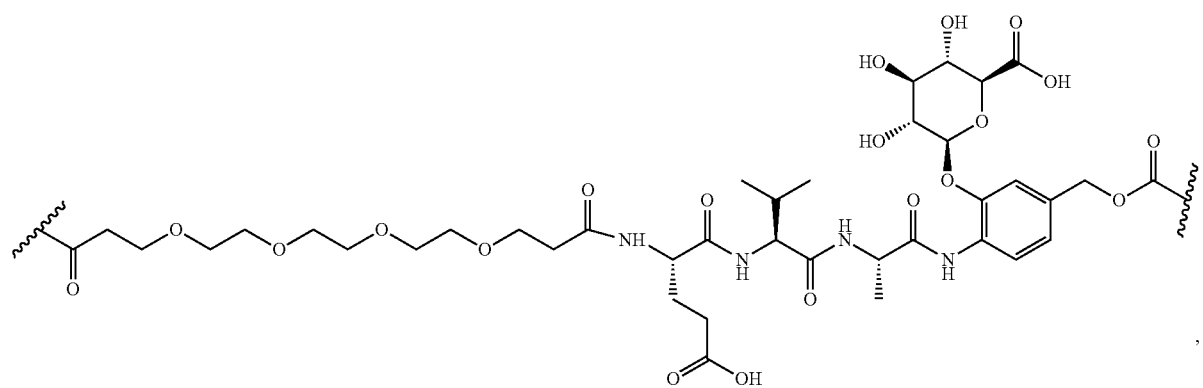
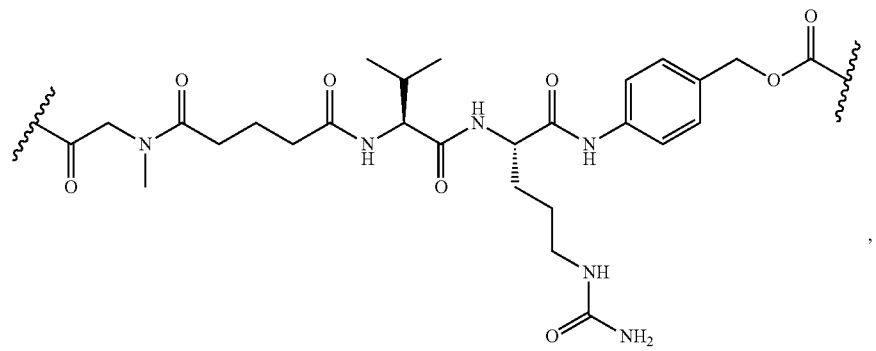
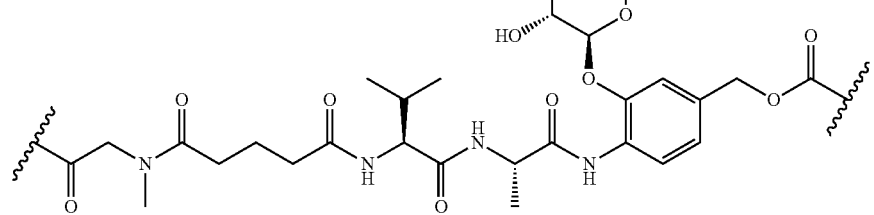

-continued
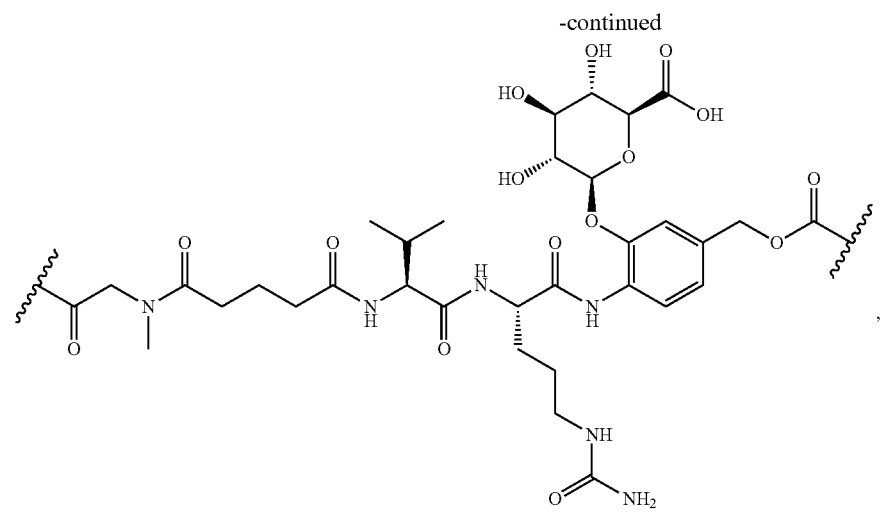
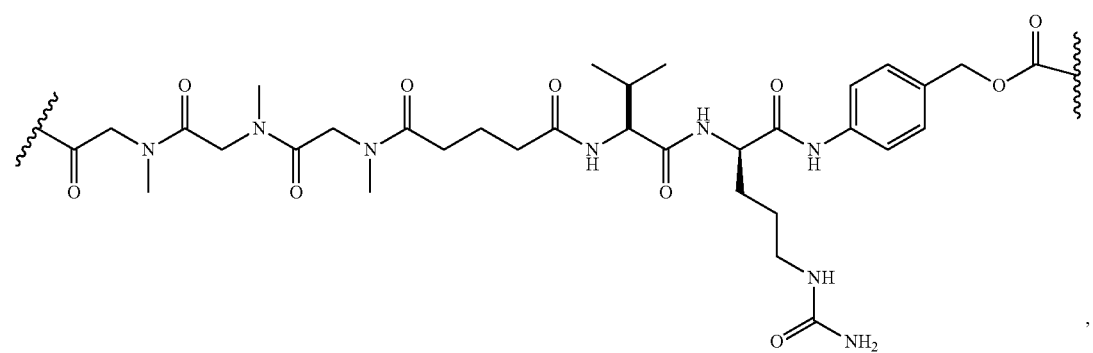
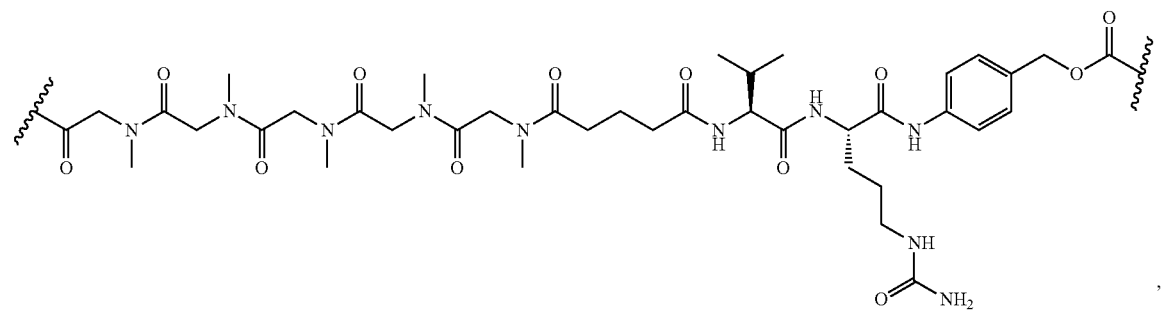
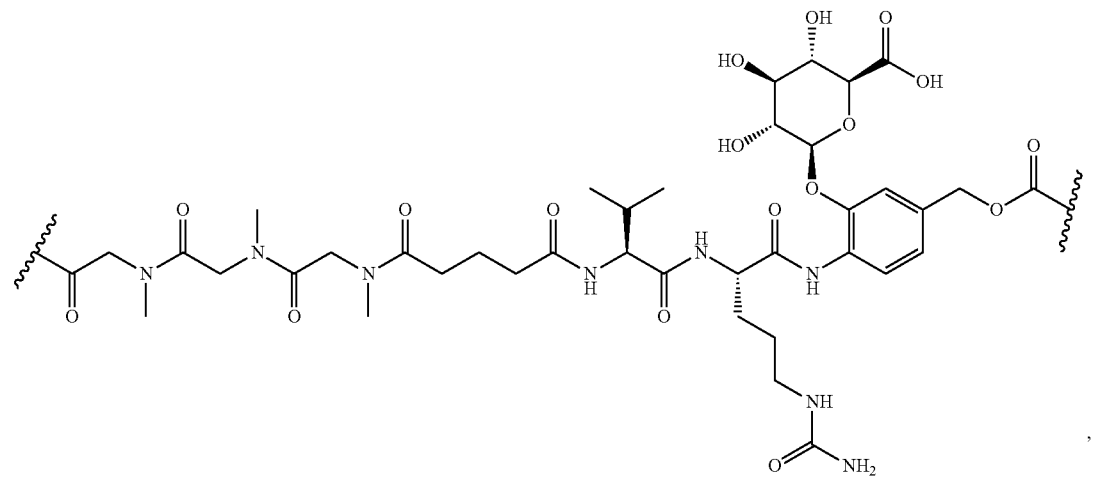

-continued
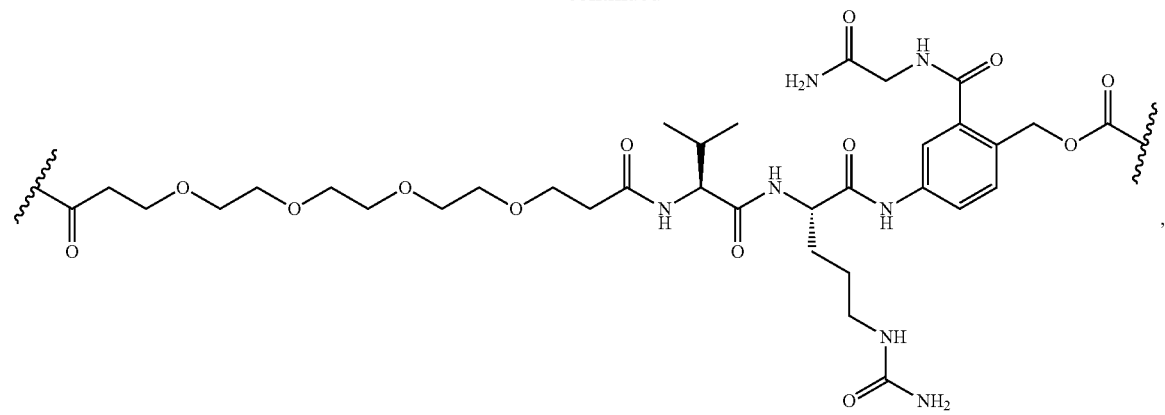
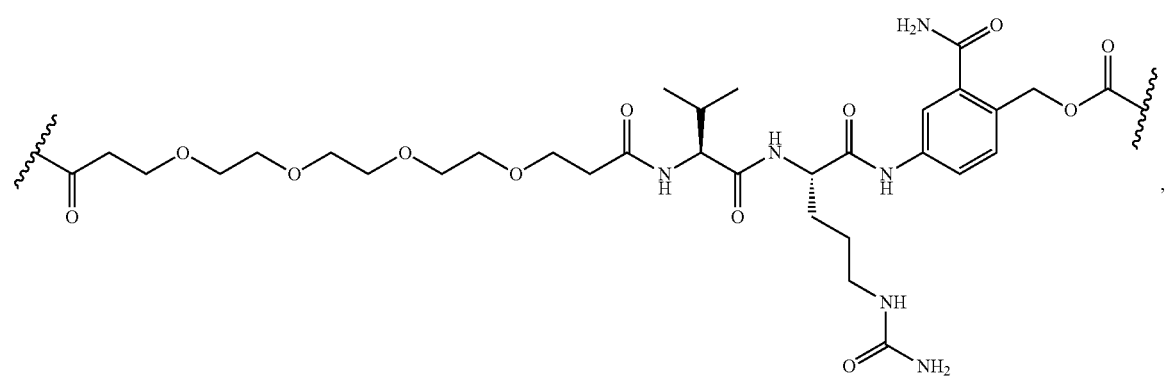
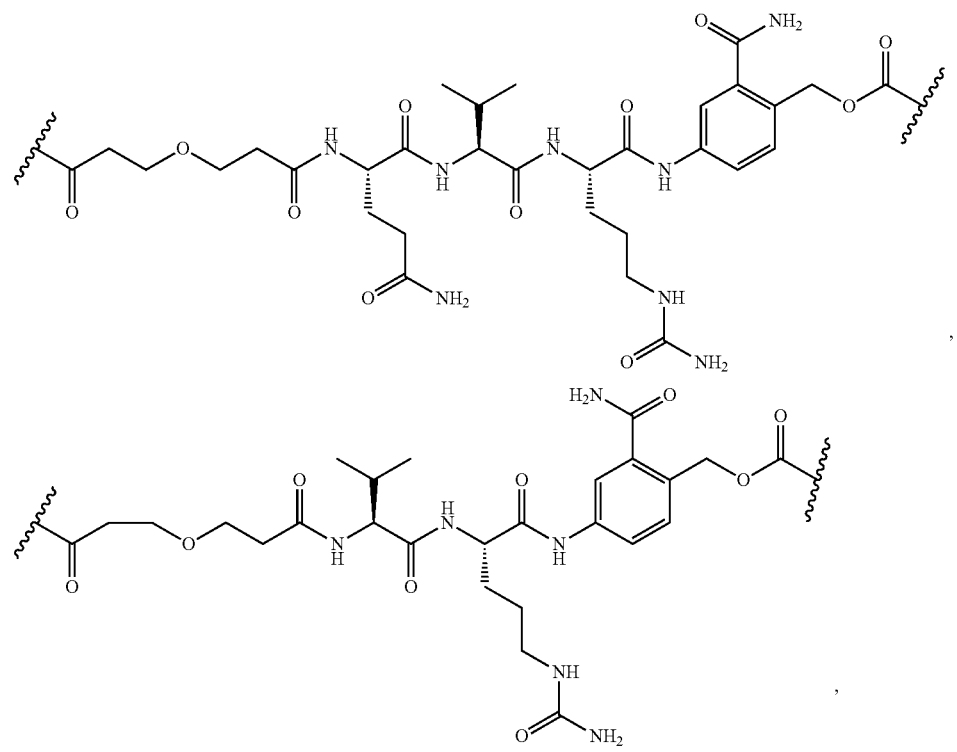

-continued
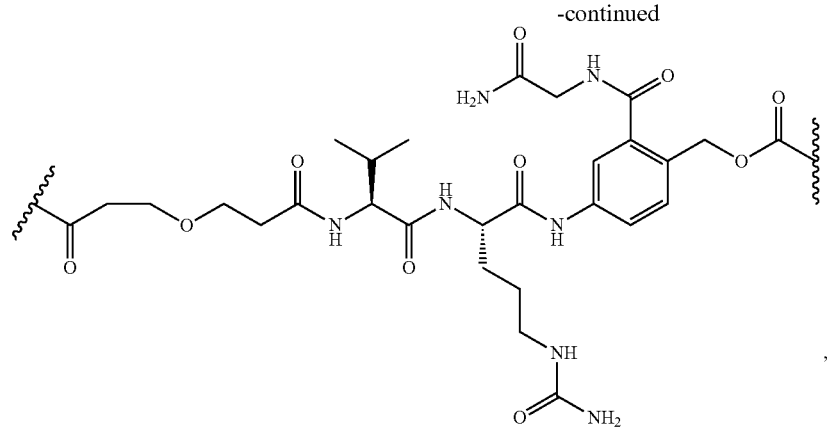
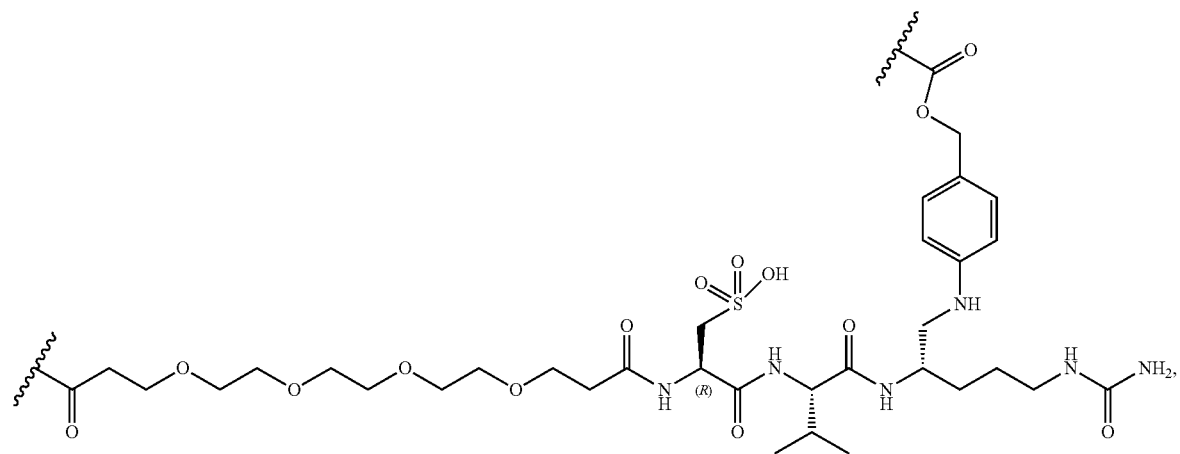
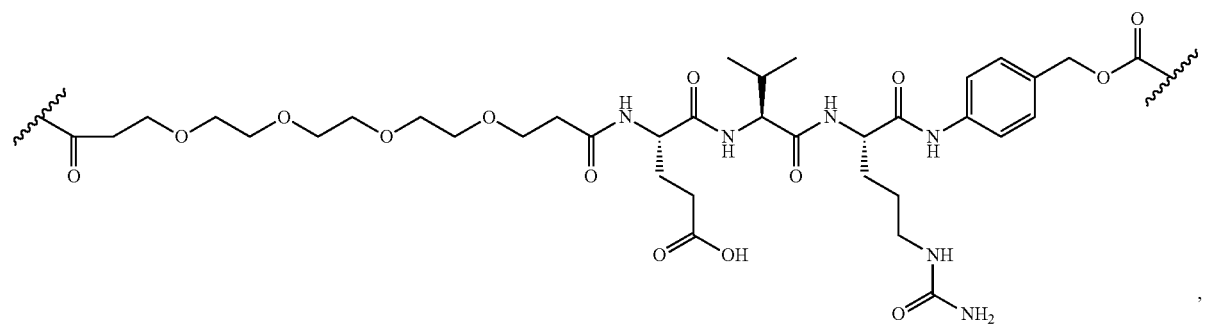
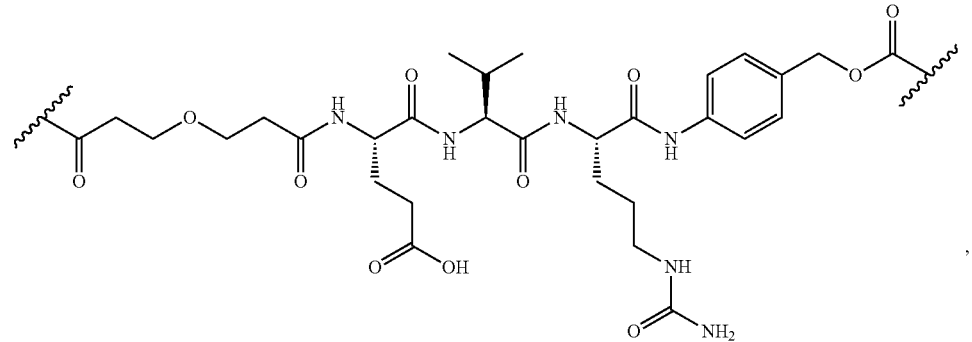

-continued
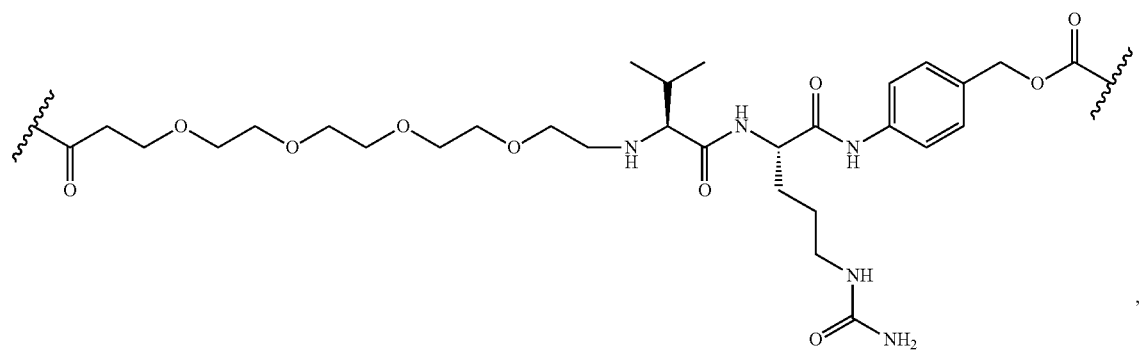
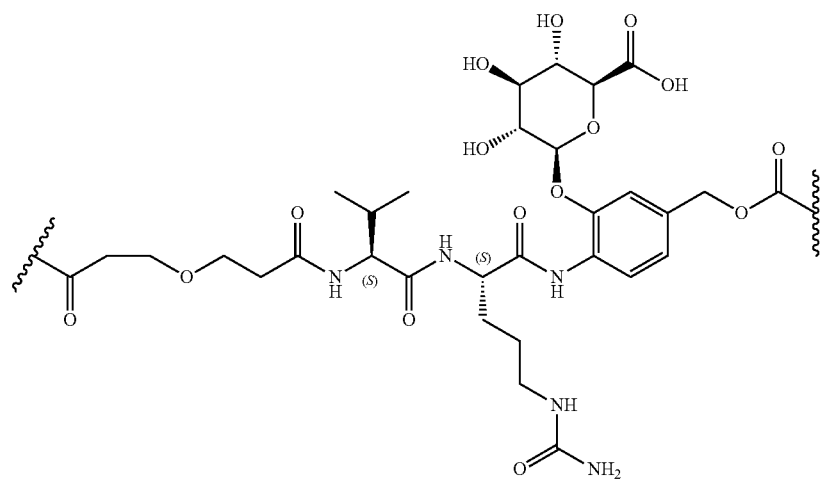
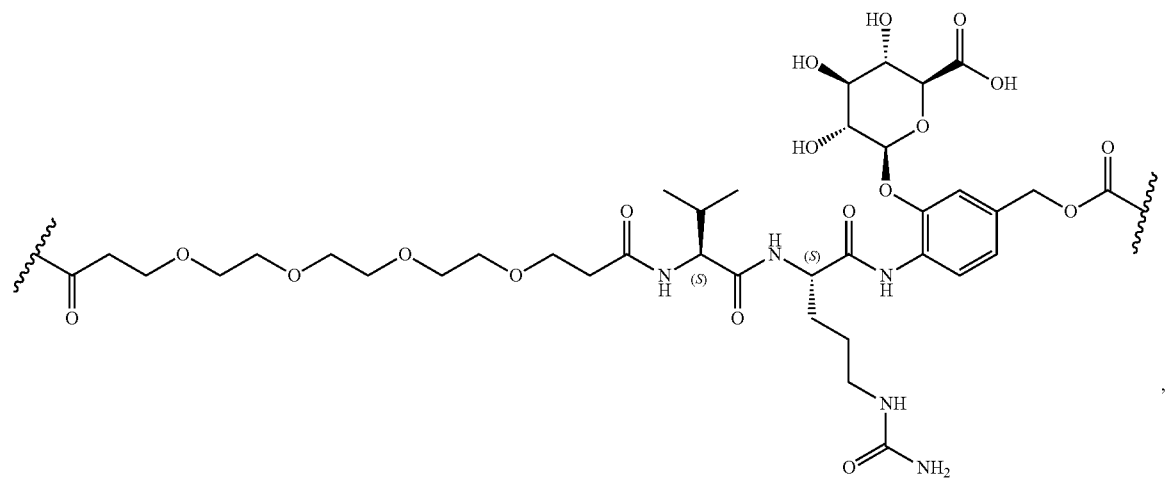

-continued
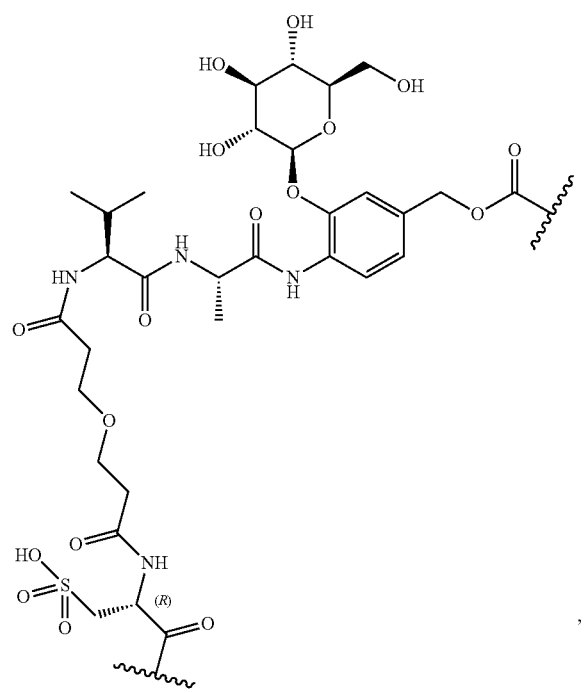
,
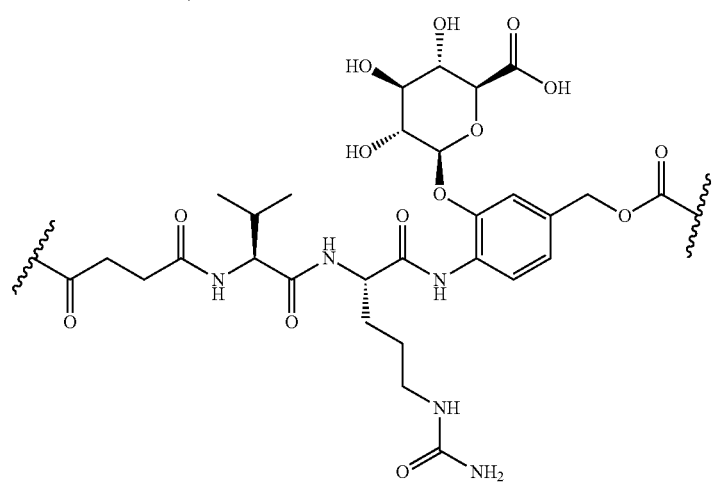
,
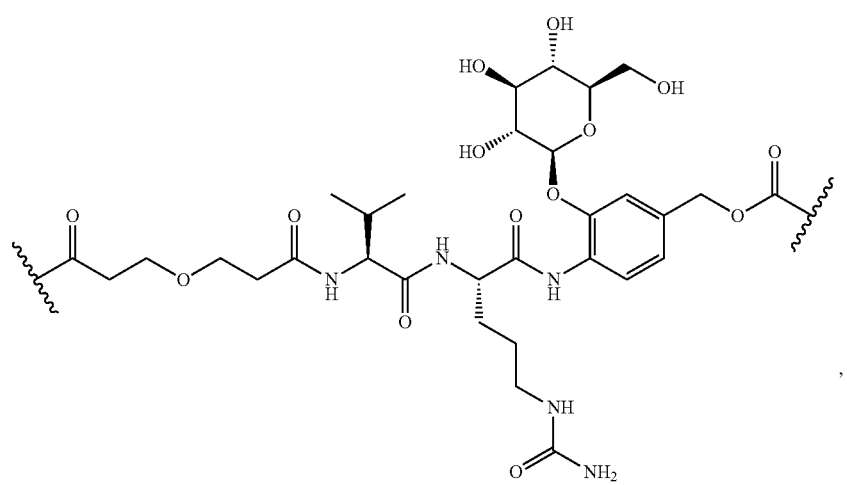
,

-continued
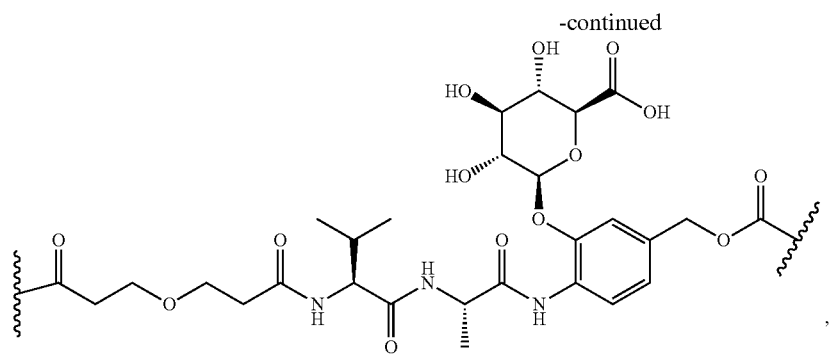
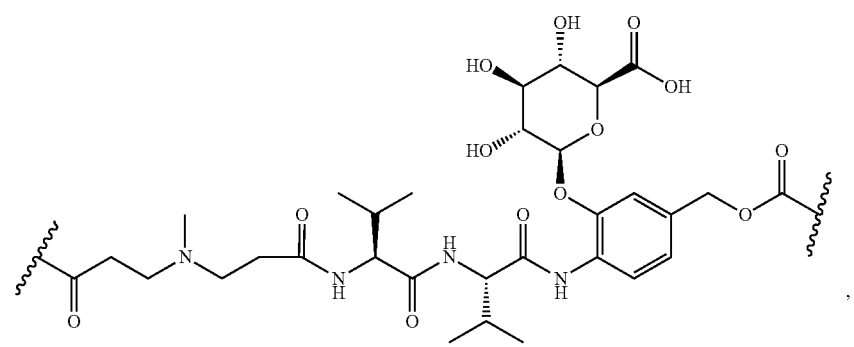
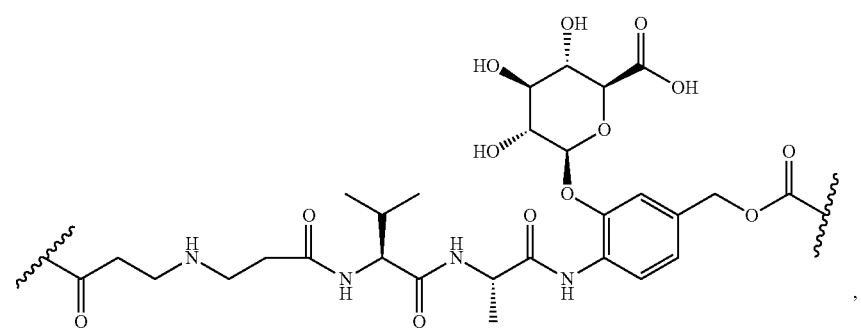
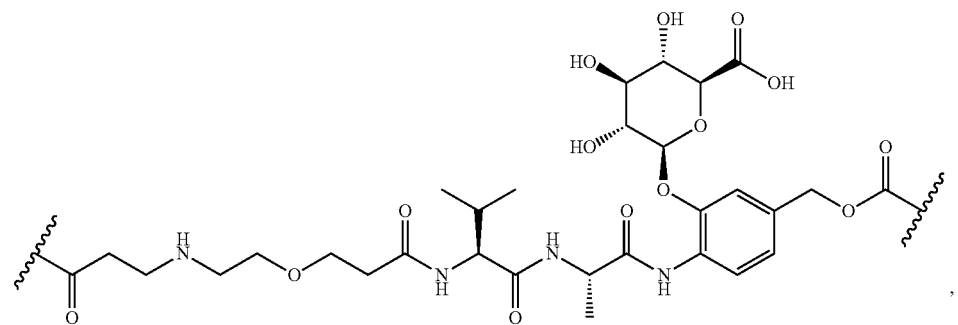
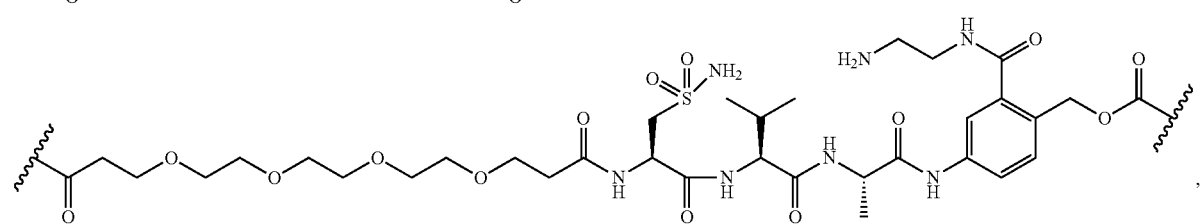

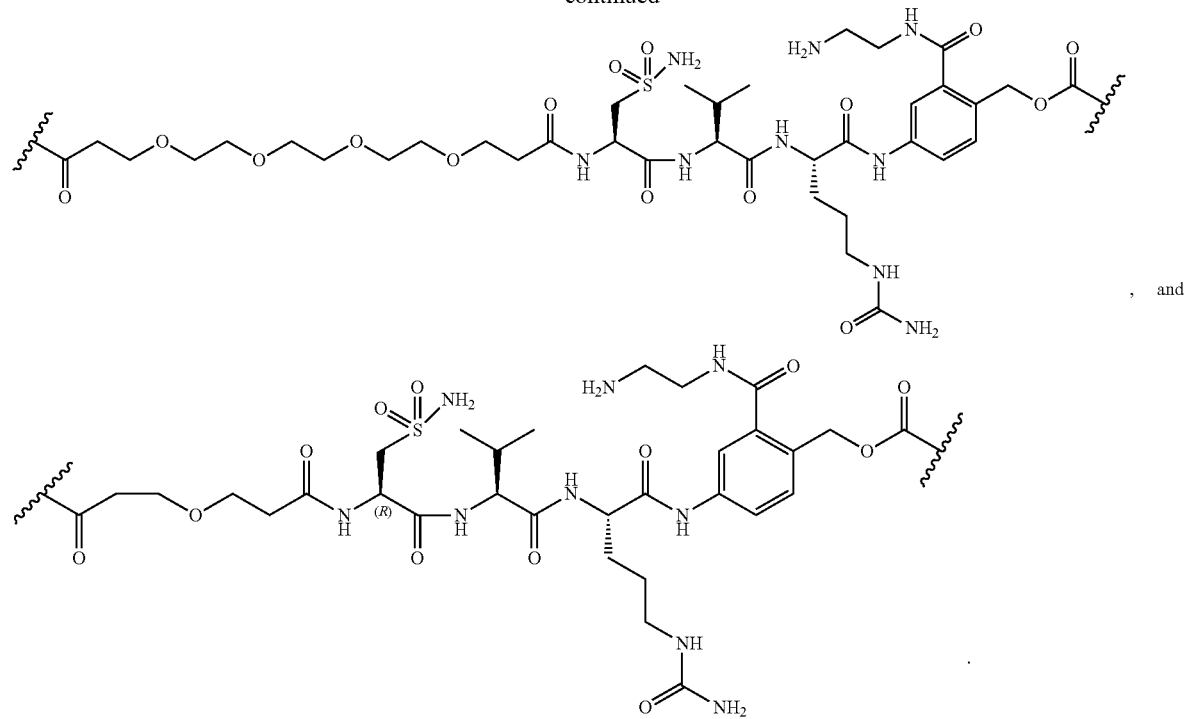
Representative Spacer/Linker and Payload Moieties
In some embodiments, -L-R$^d$ is:
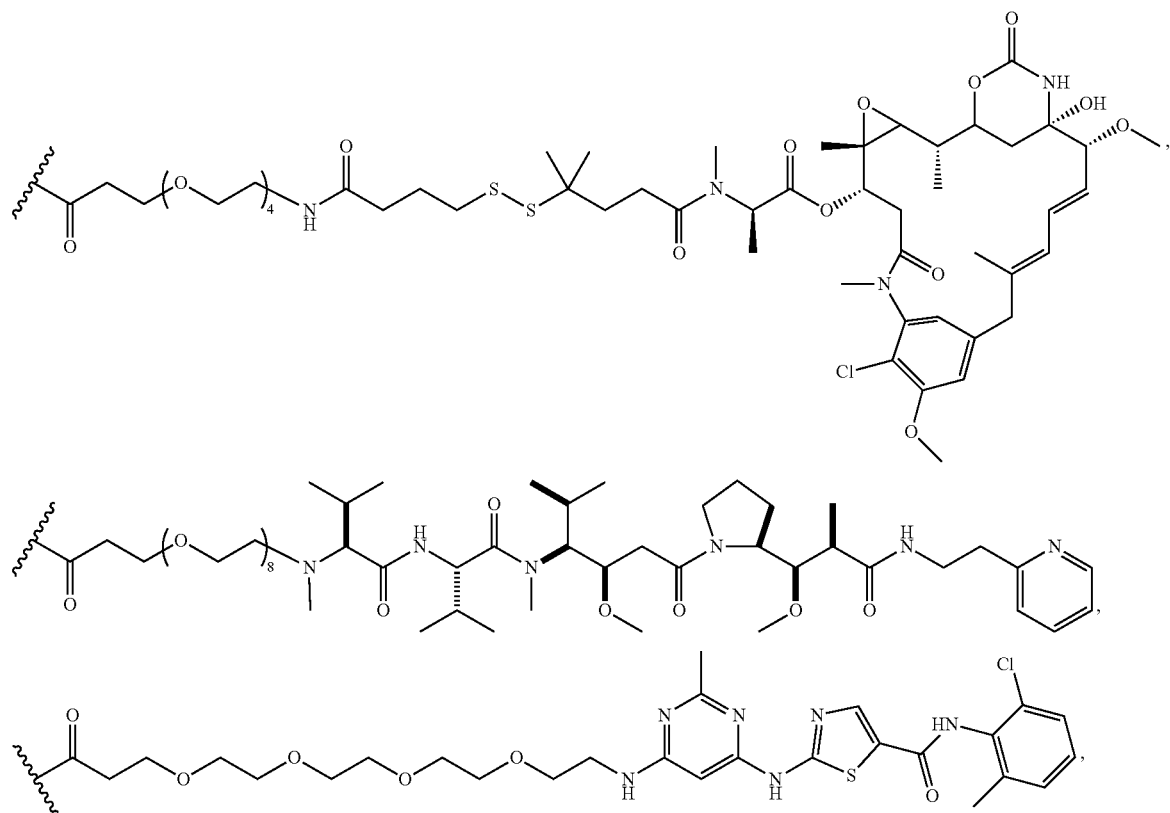

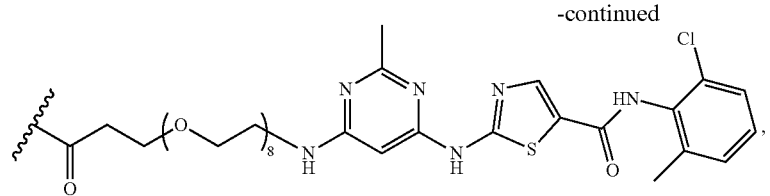
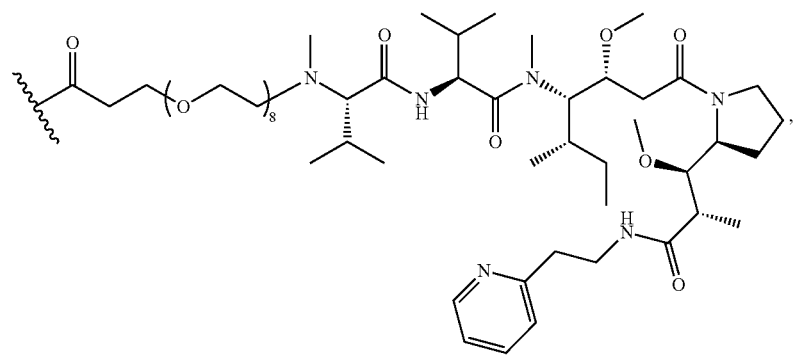
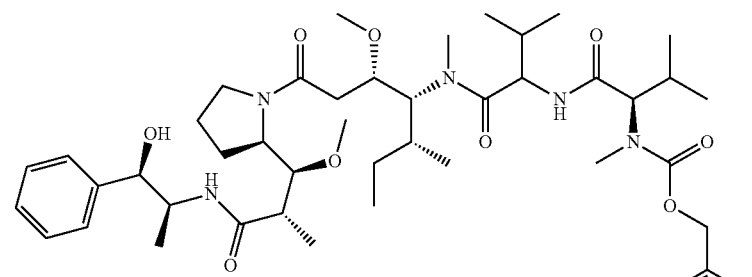
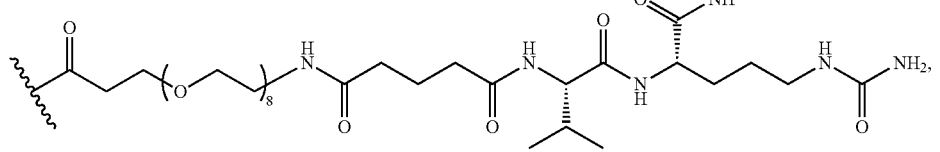
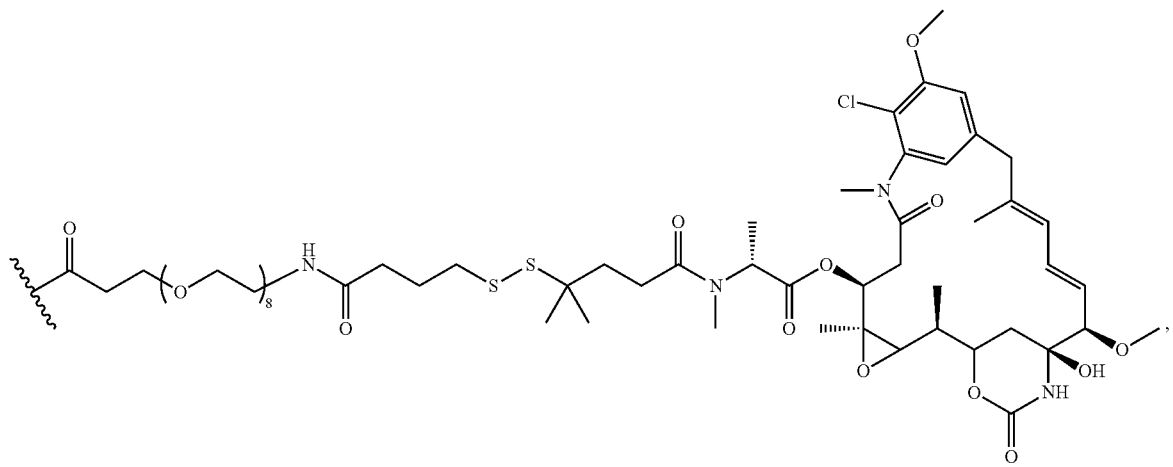

-continued
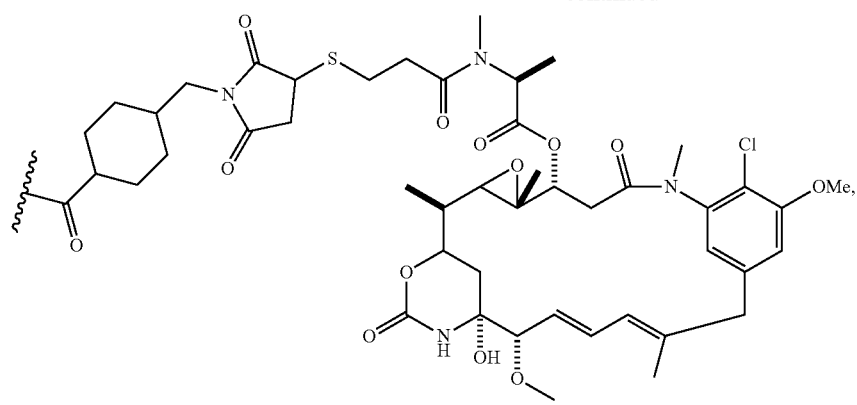
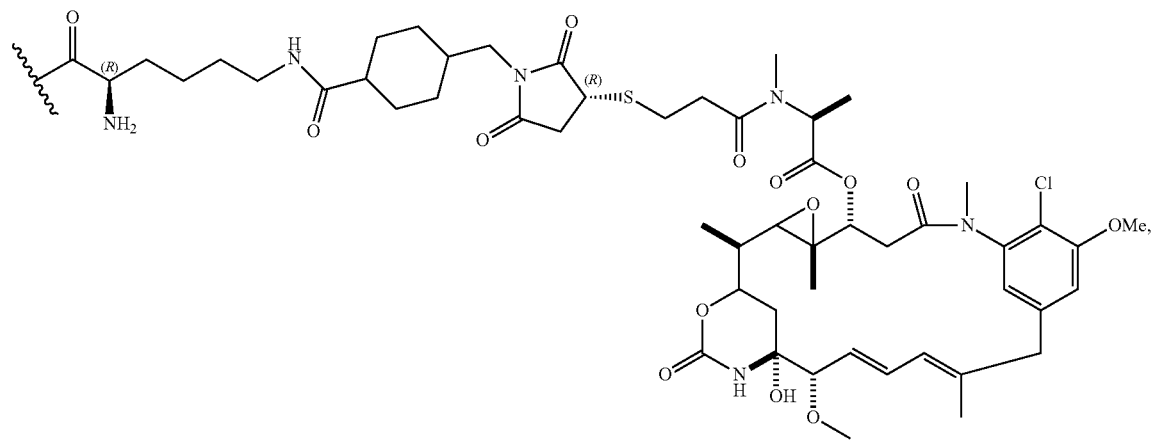
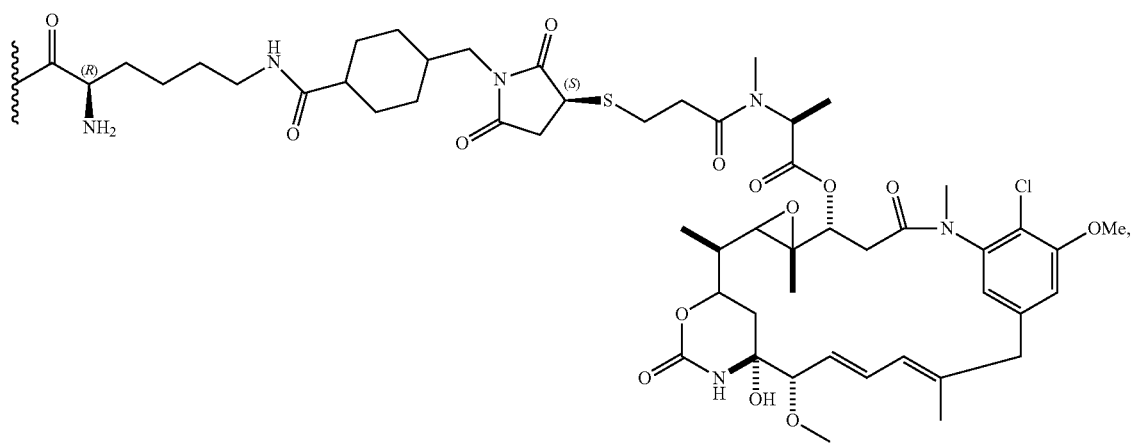

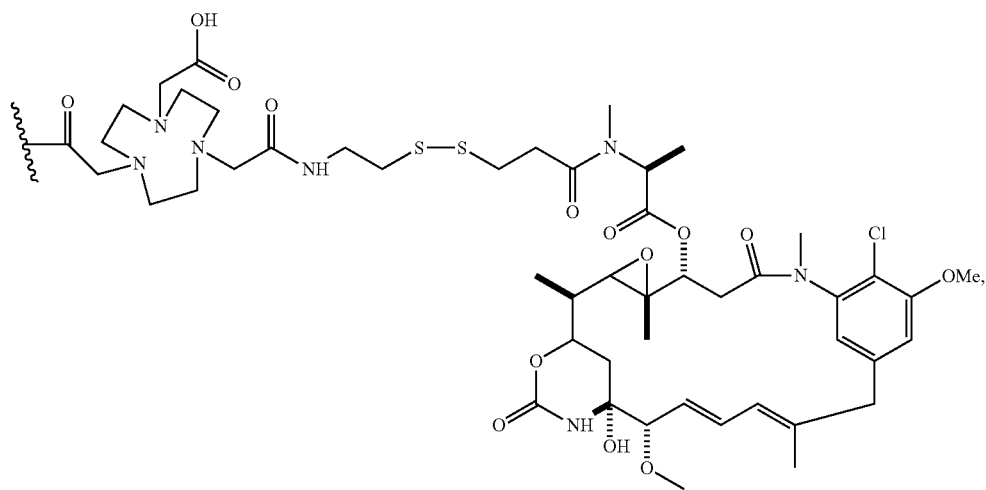
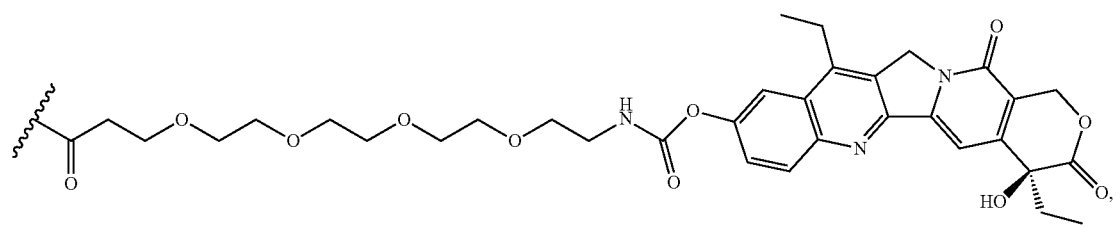
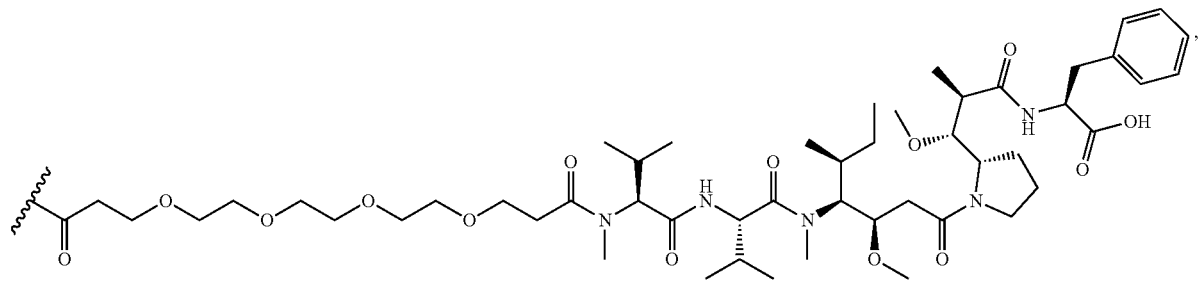
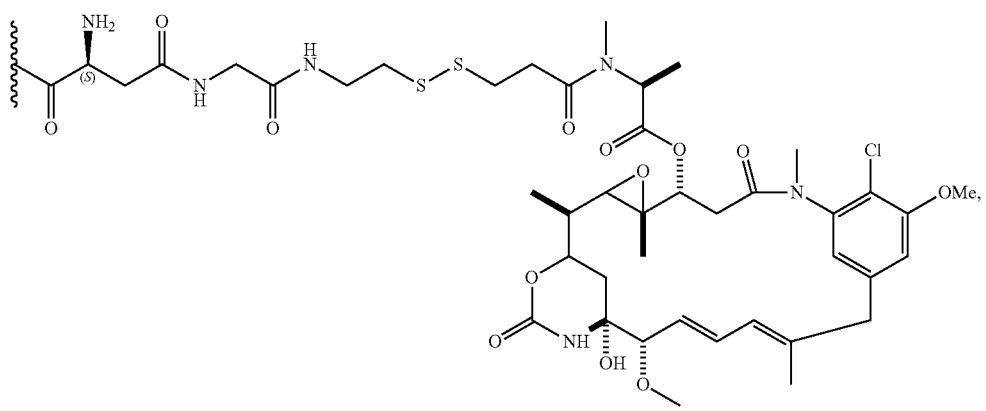

-continued
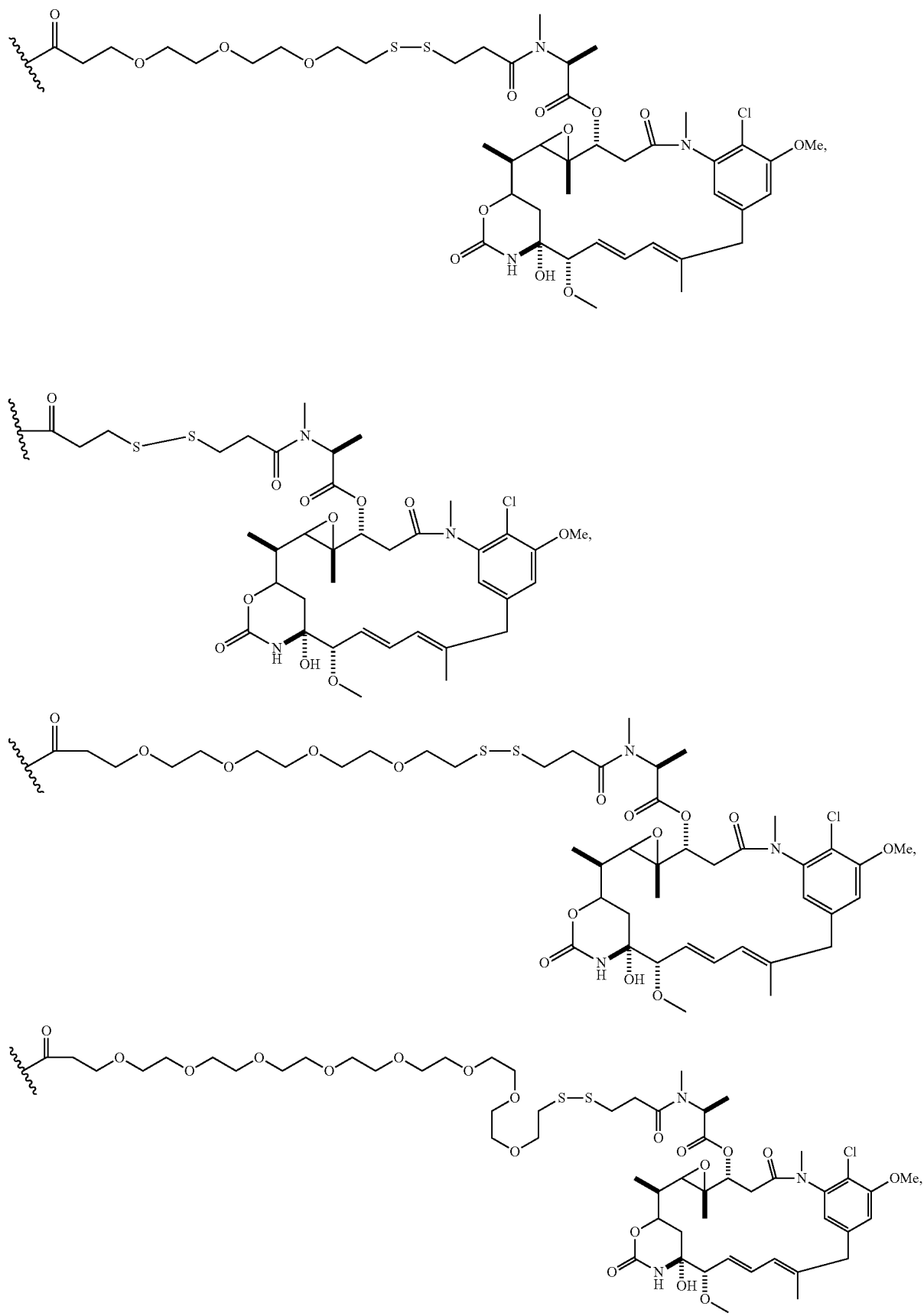

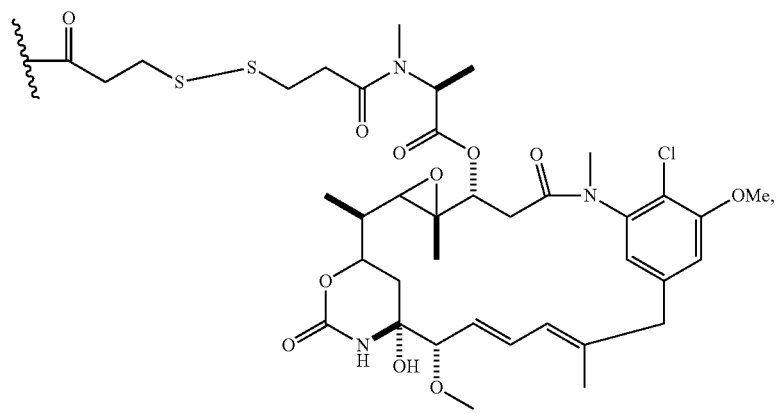
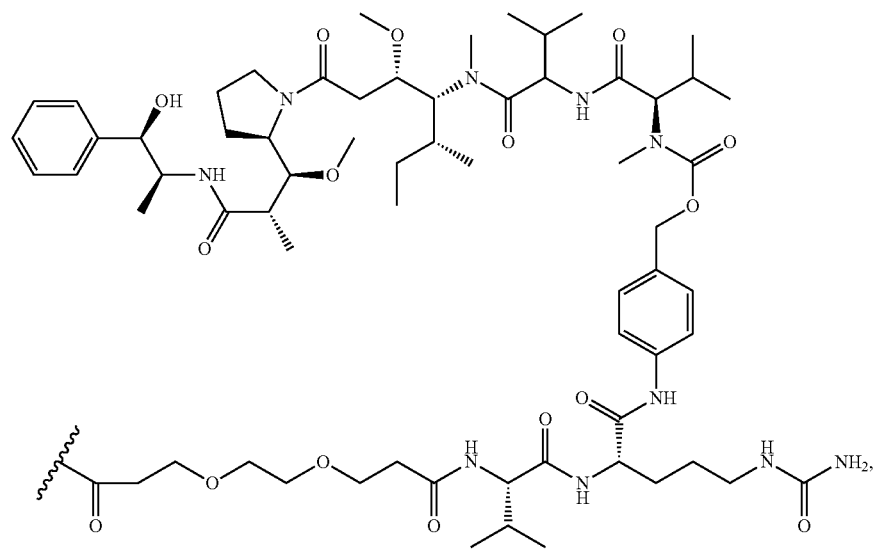
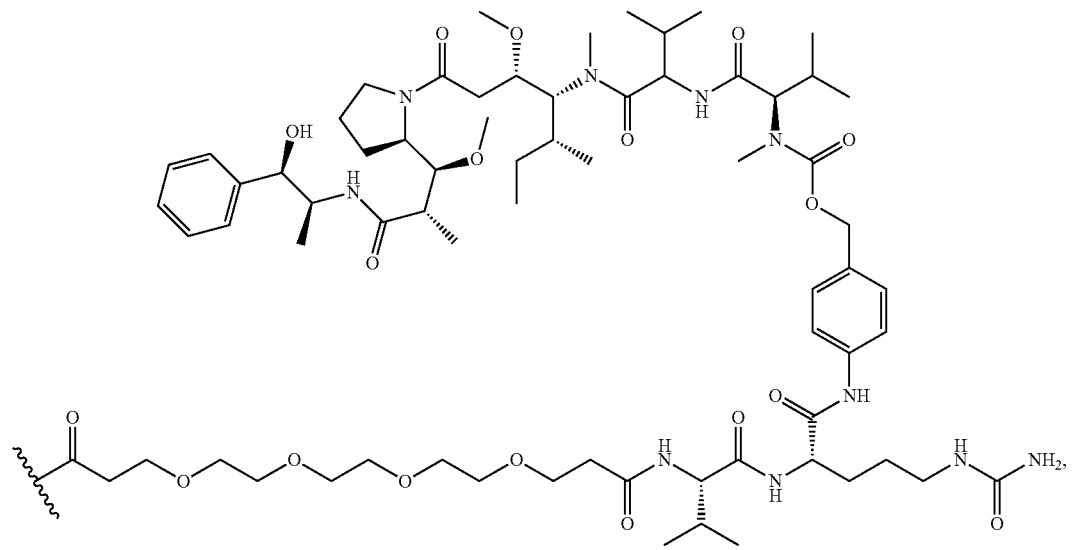

-continued
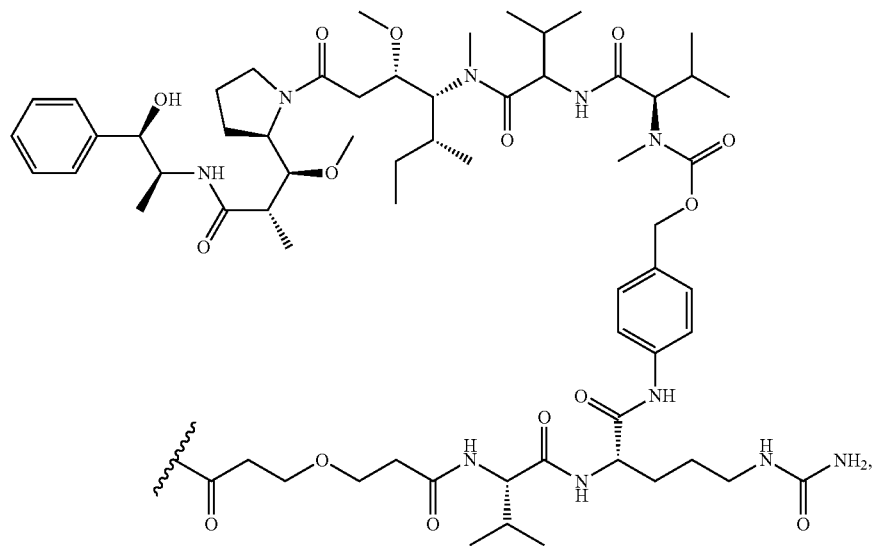
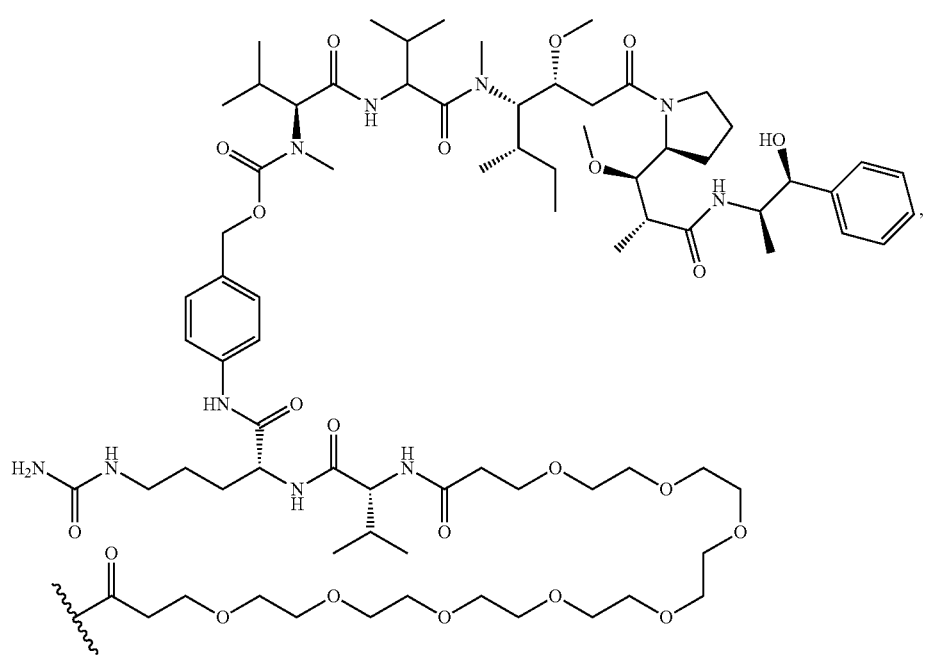

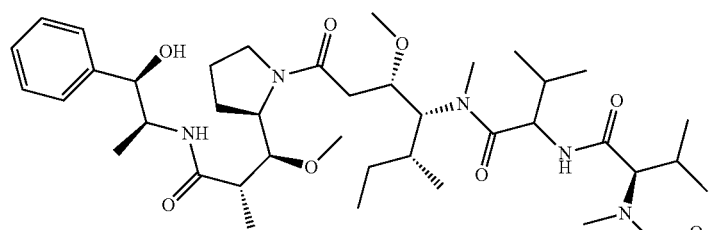
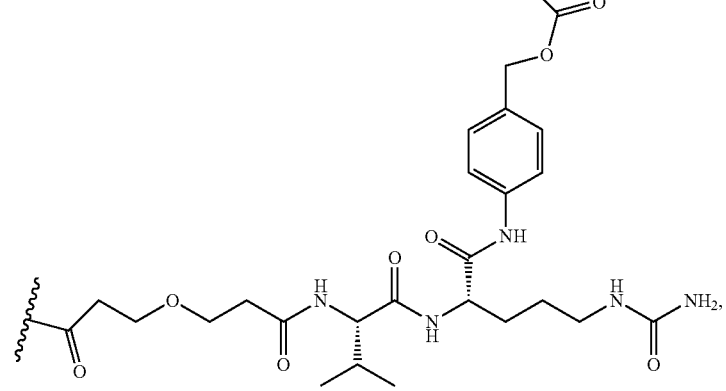
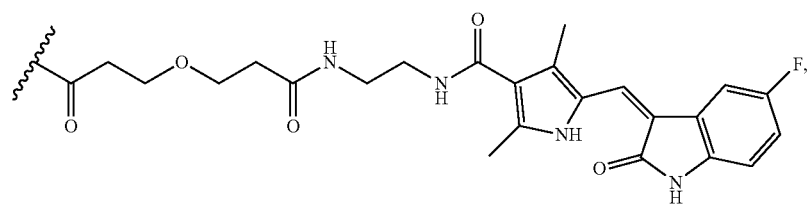
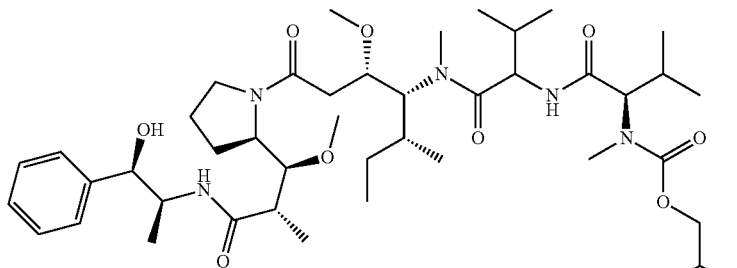
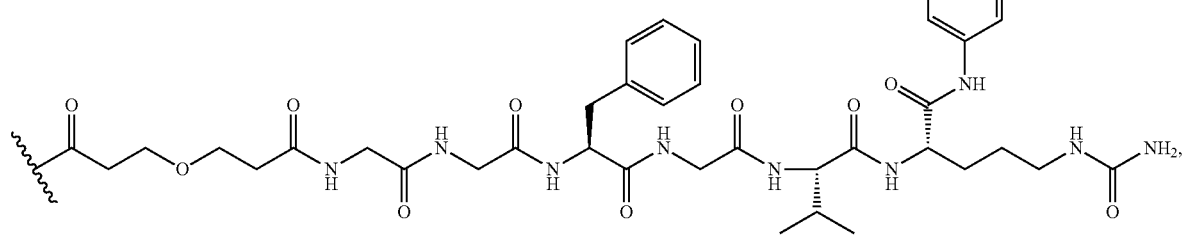

-continued
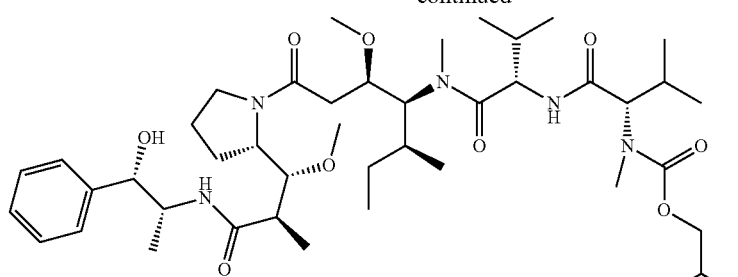
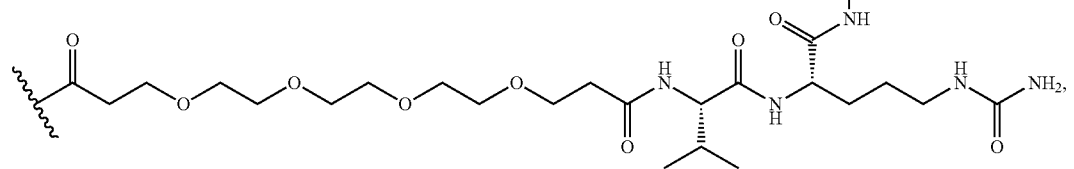
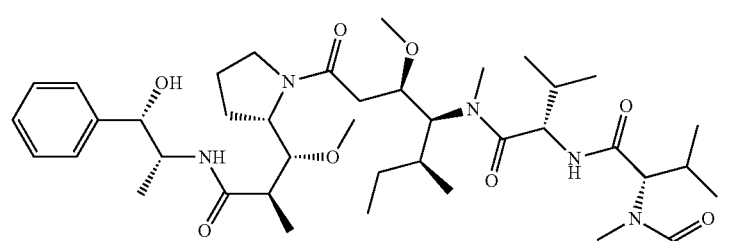
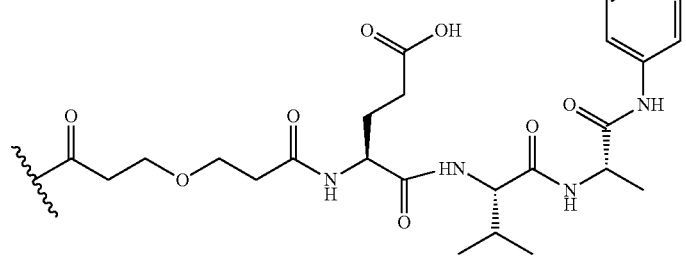

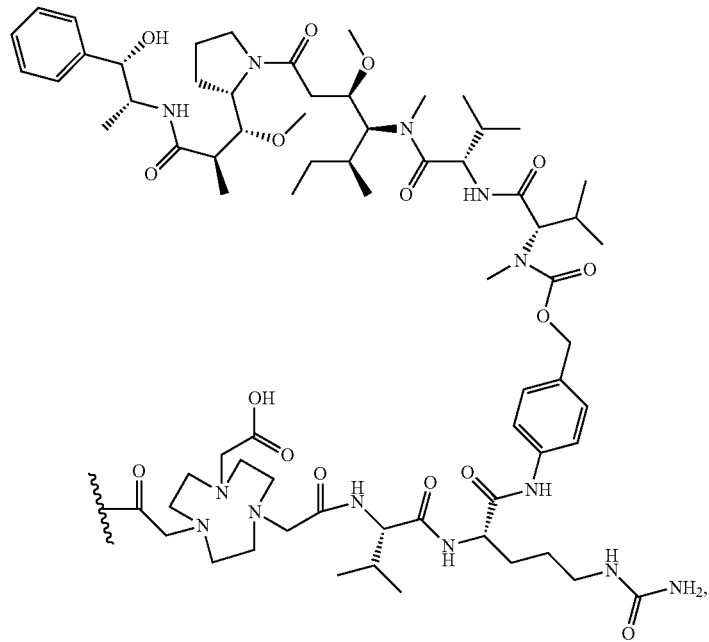
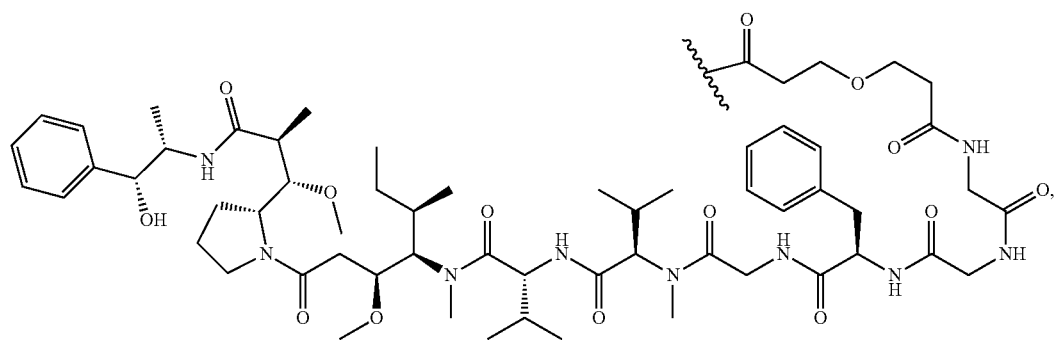
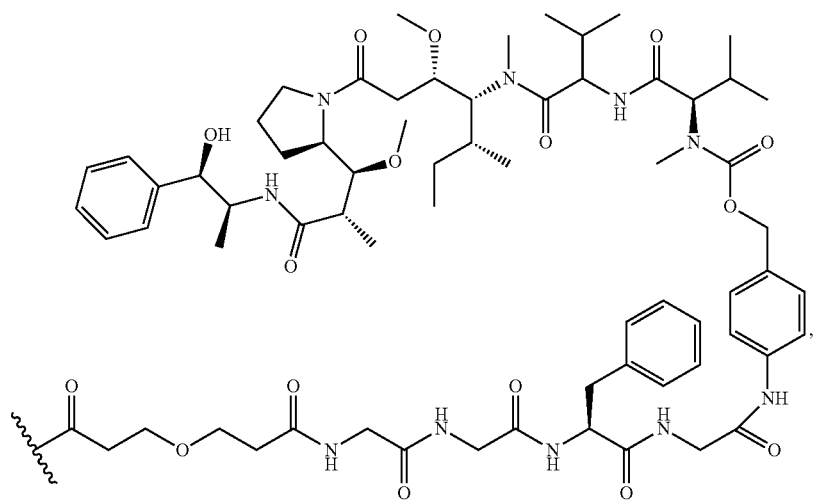

-continued
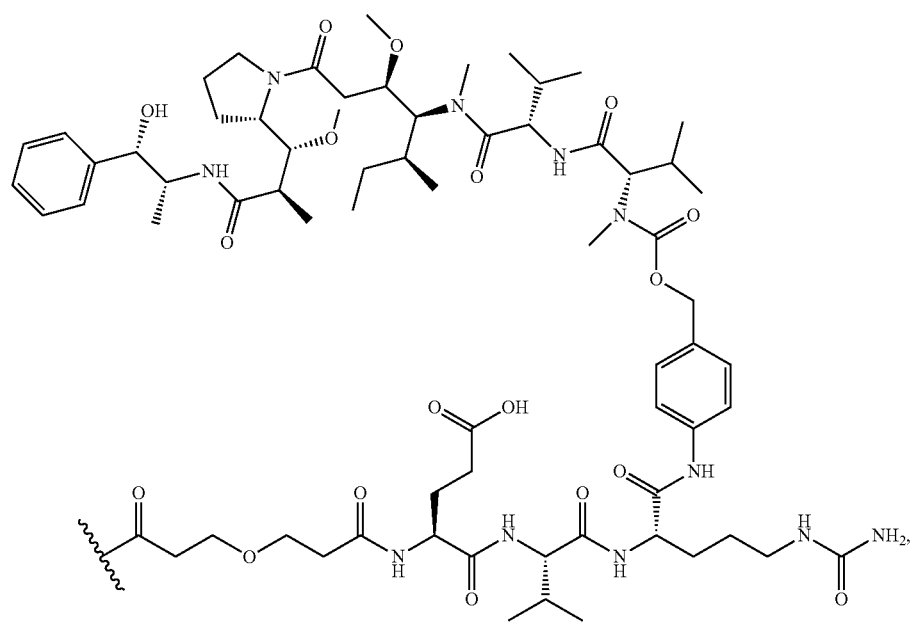
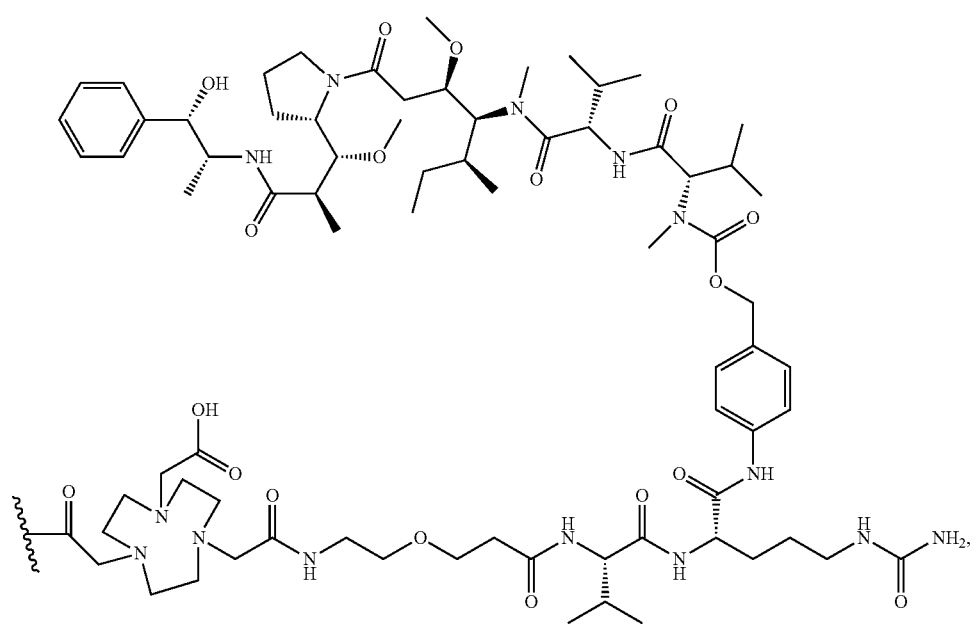

-continued
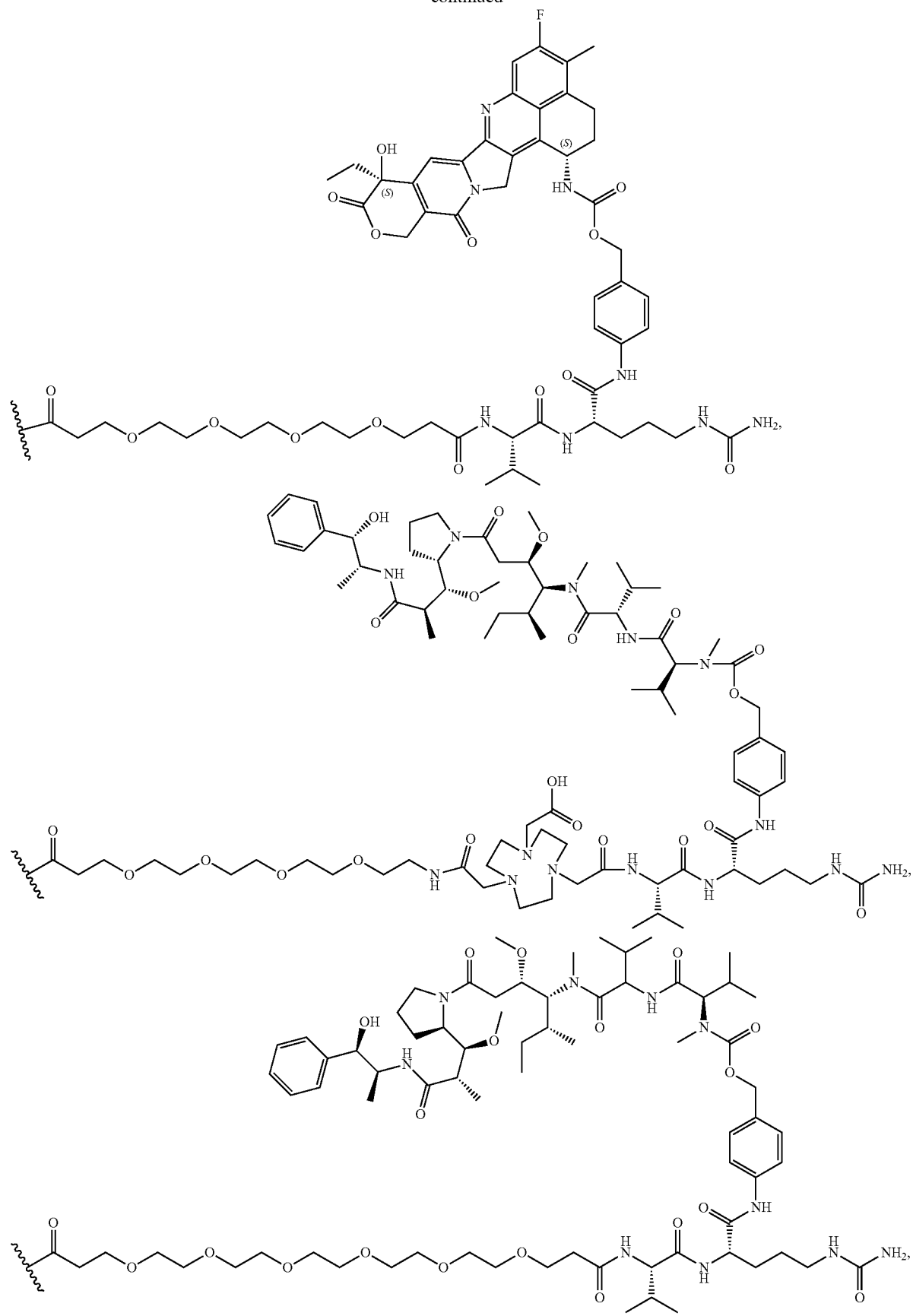

-continued
149
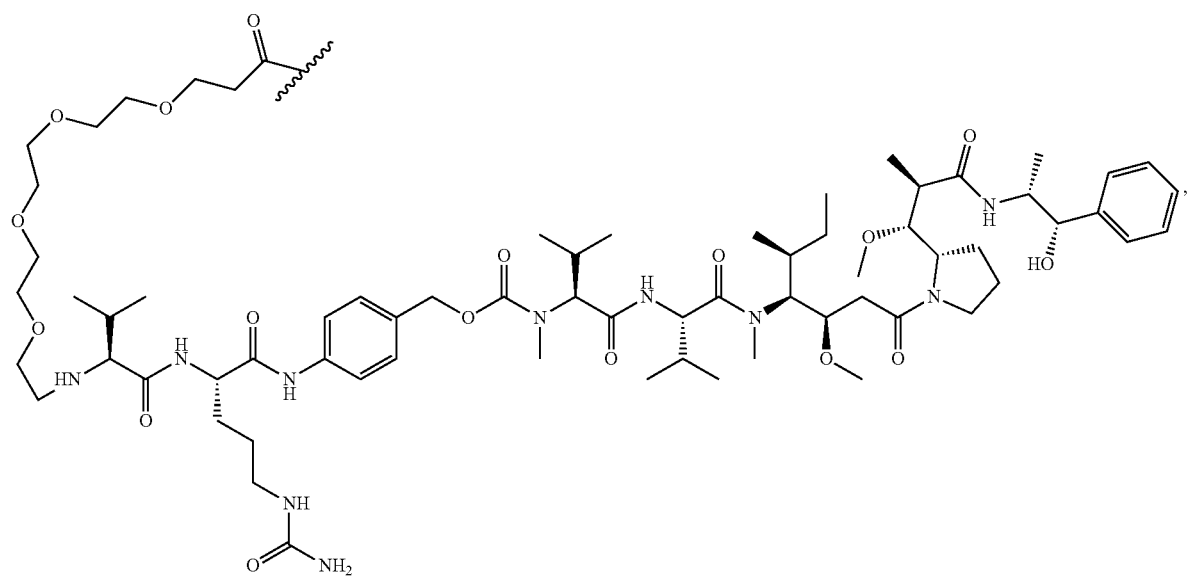
150
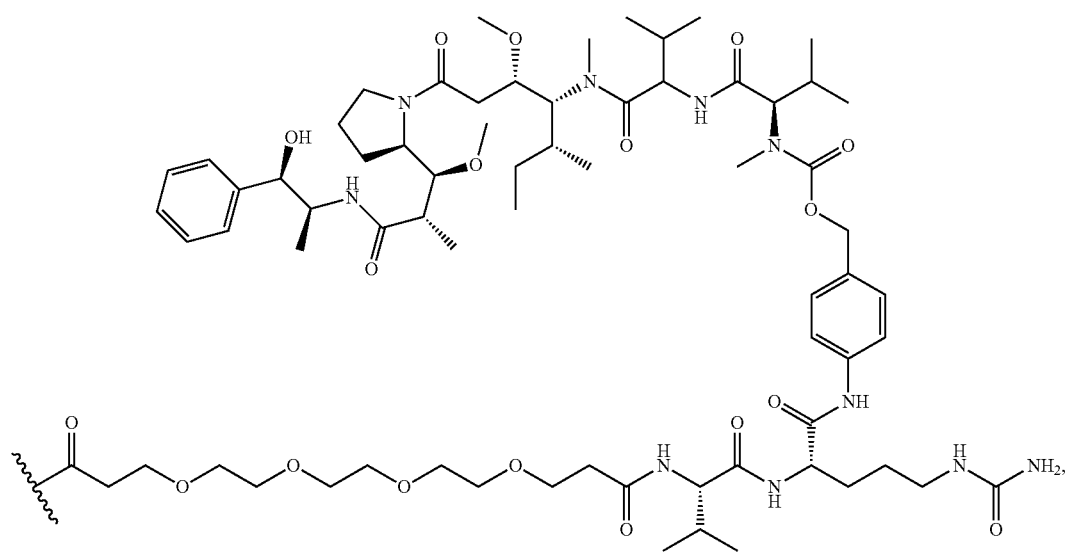
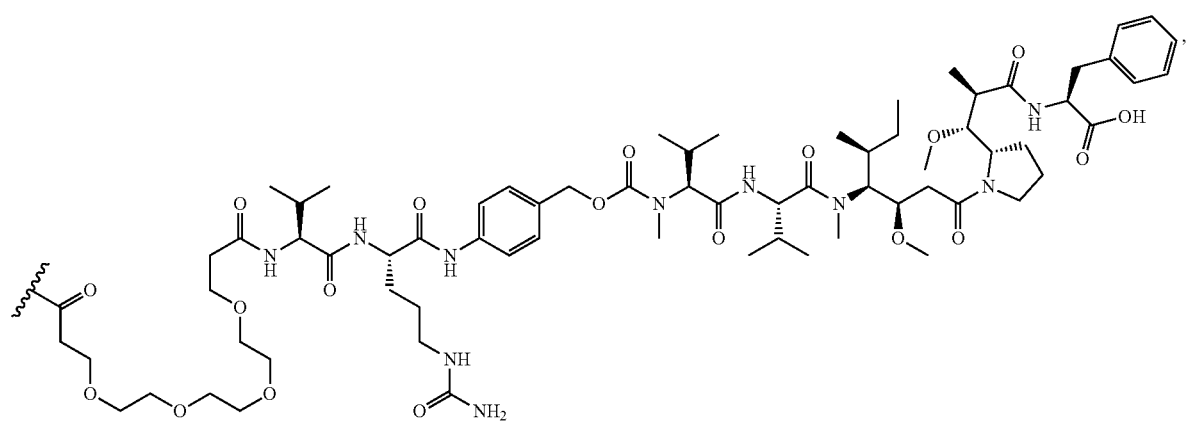

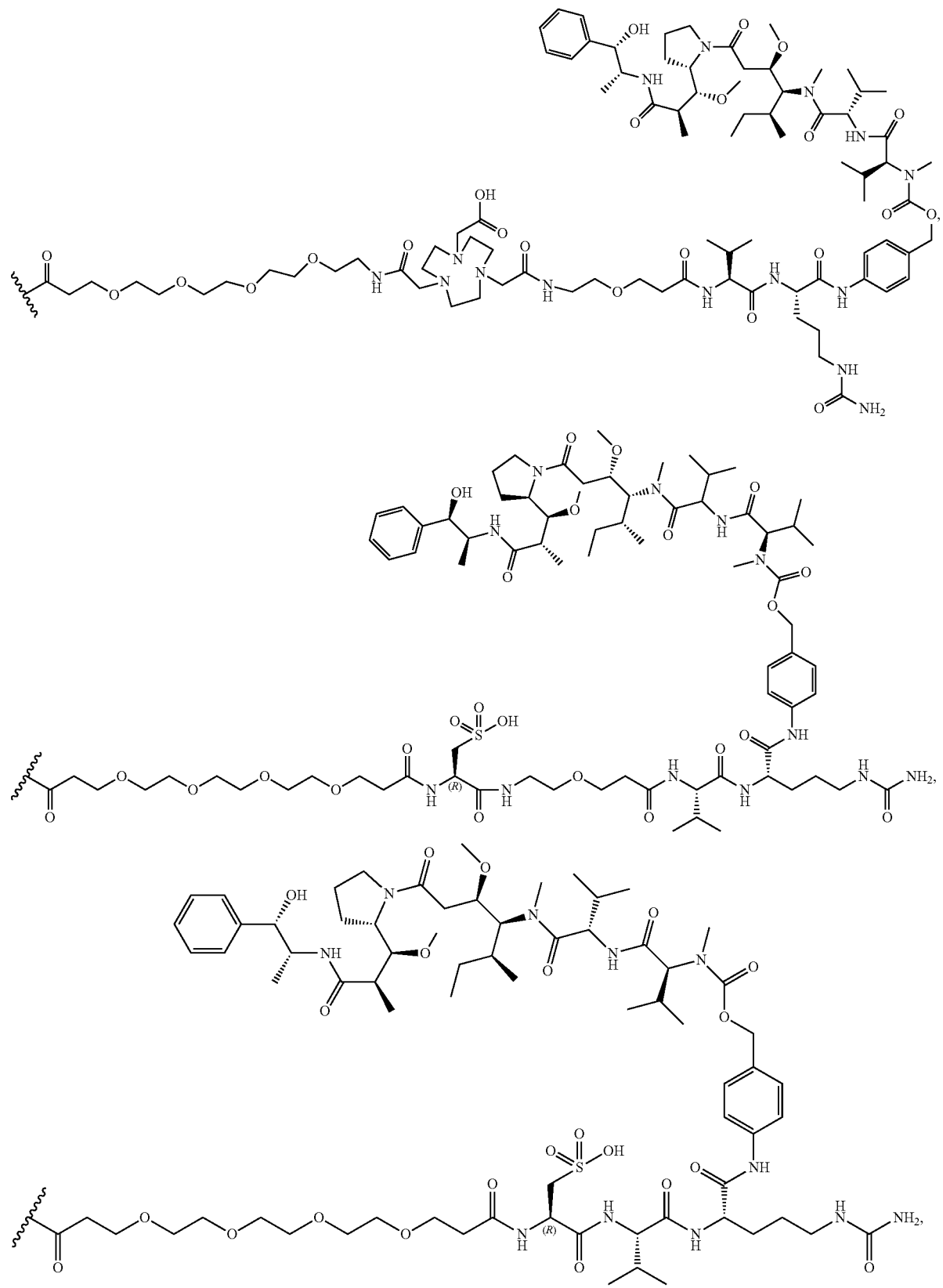

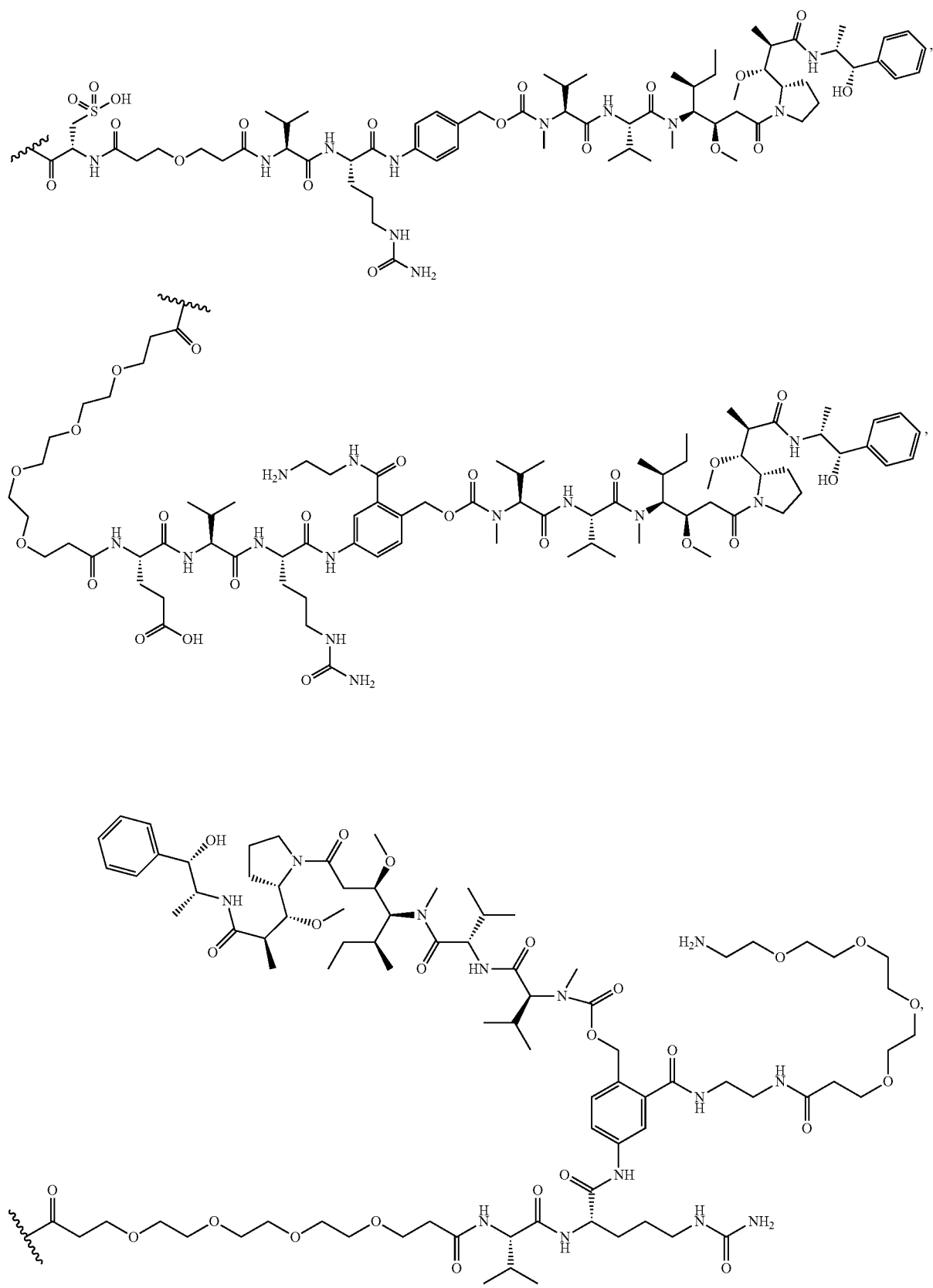

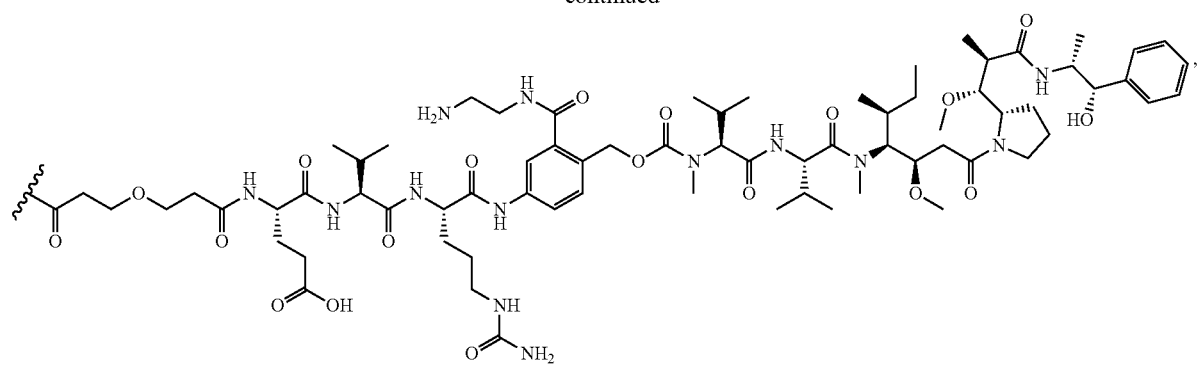
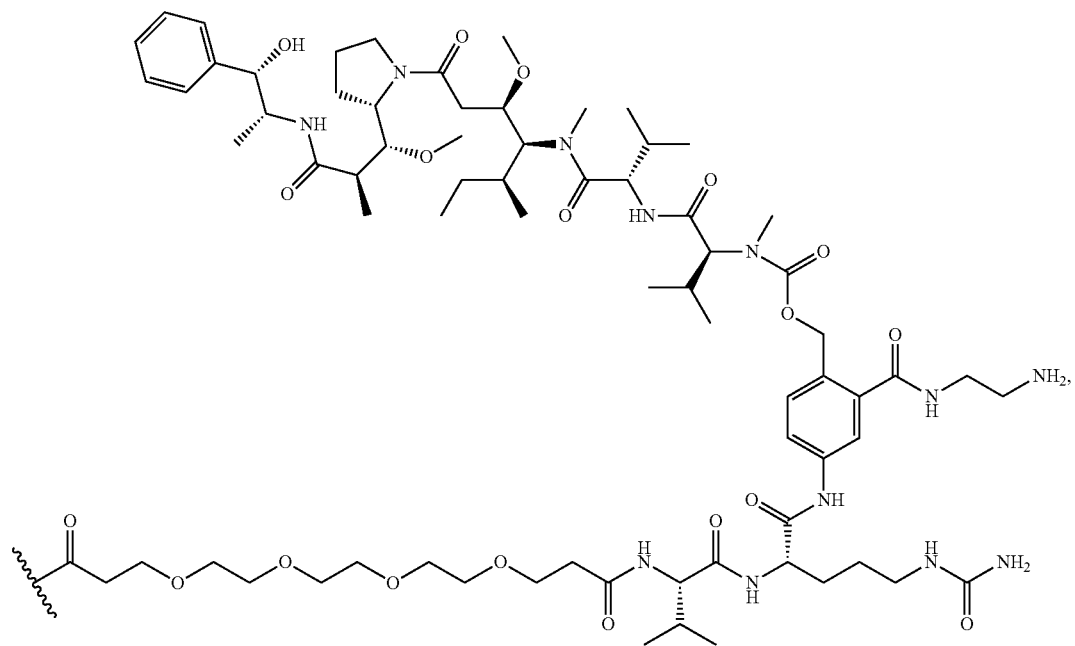
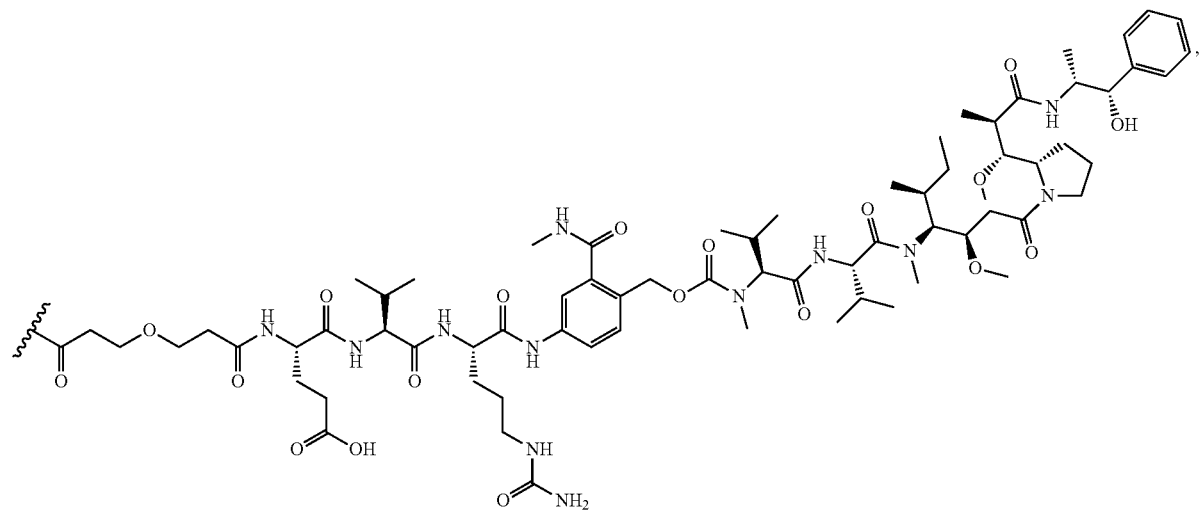

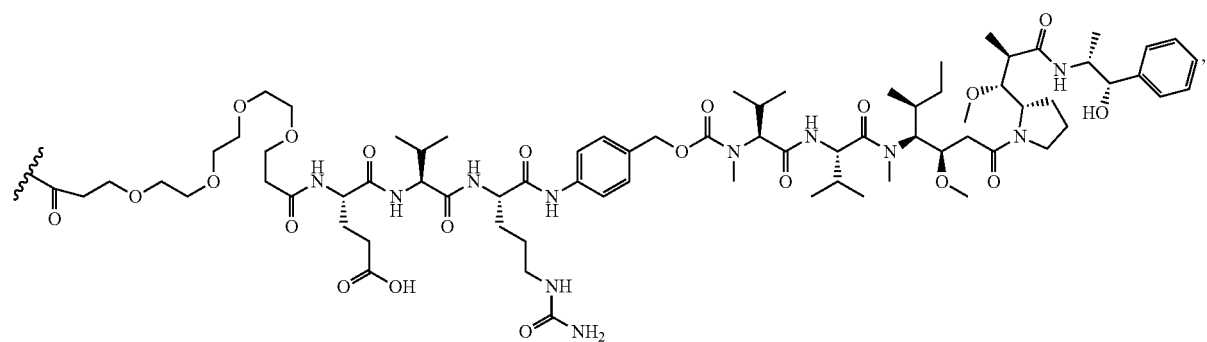
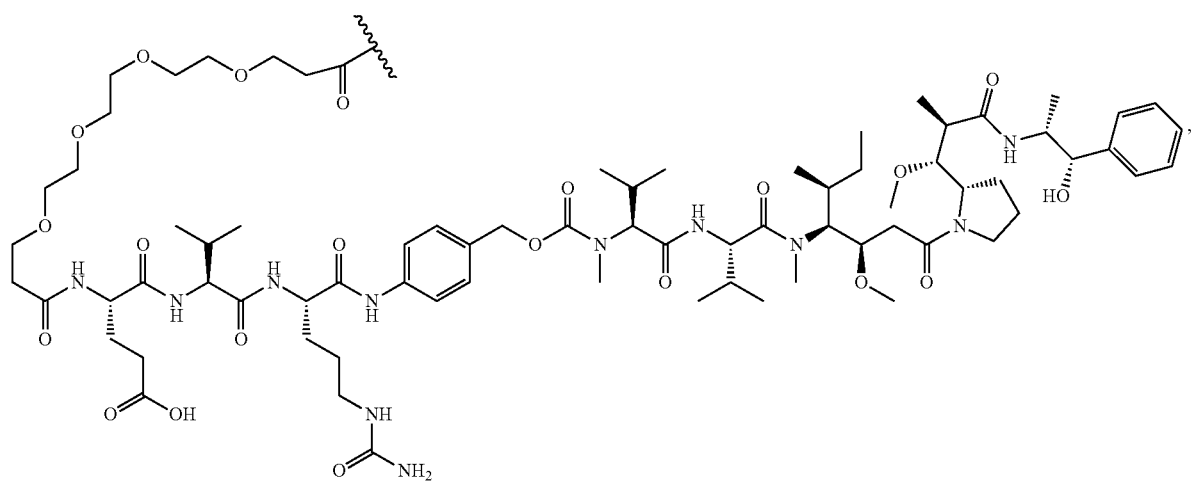
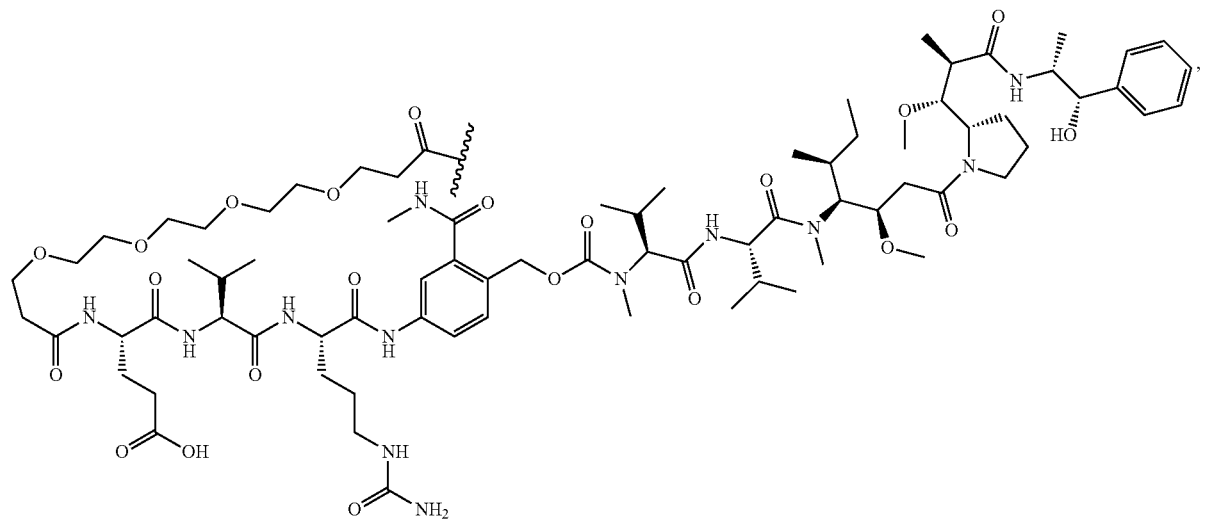

-continued
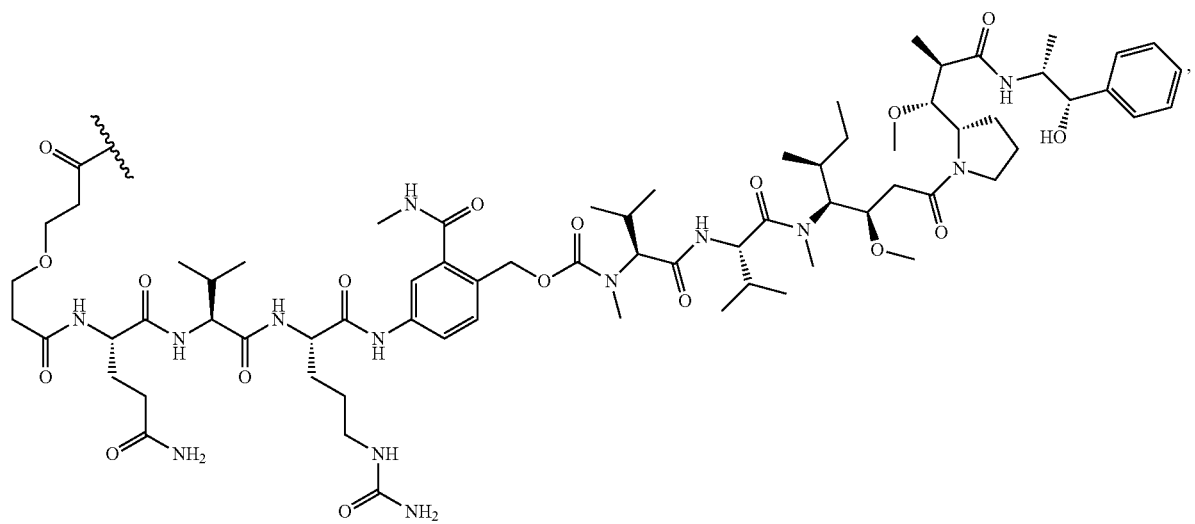
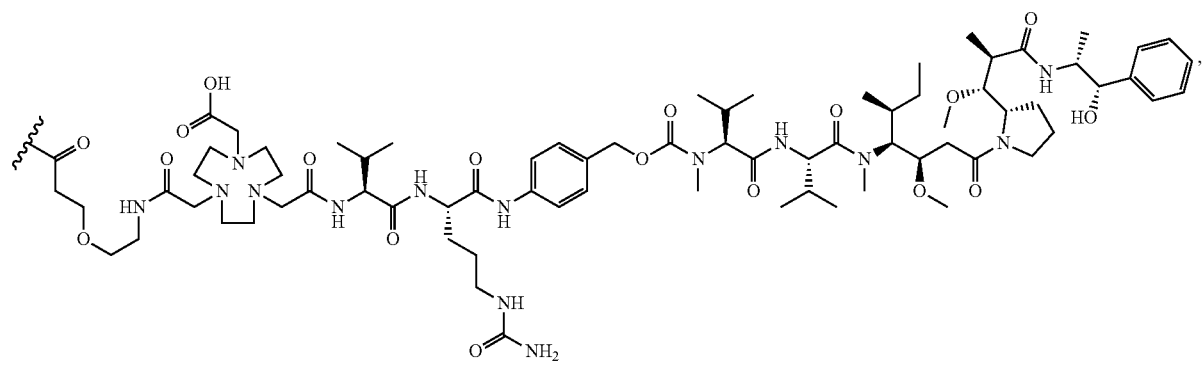
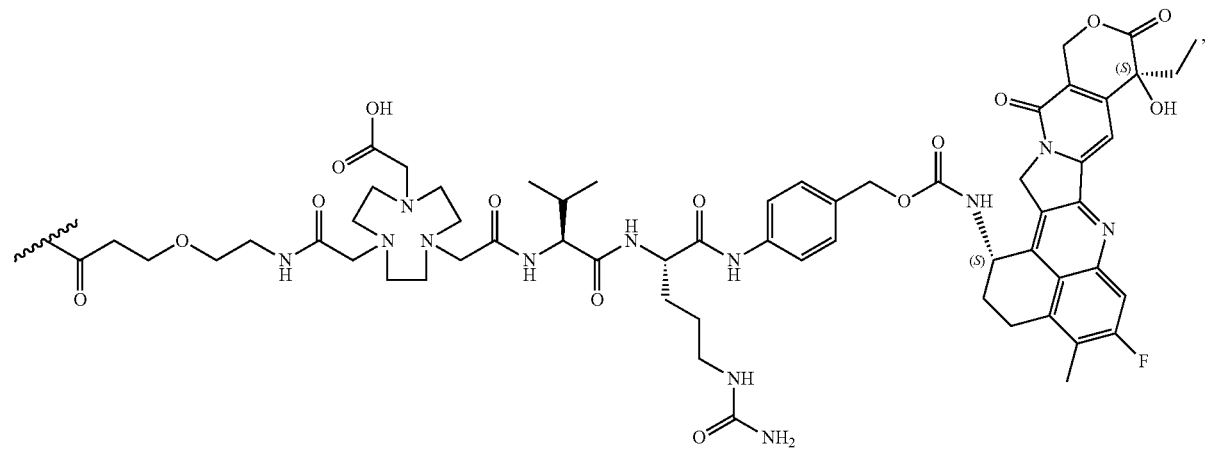

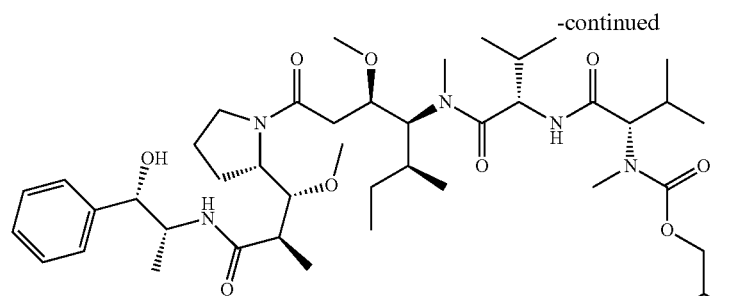
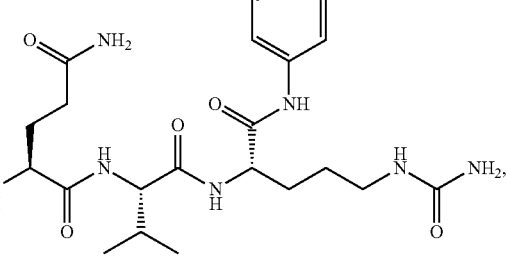
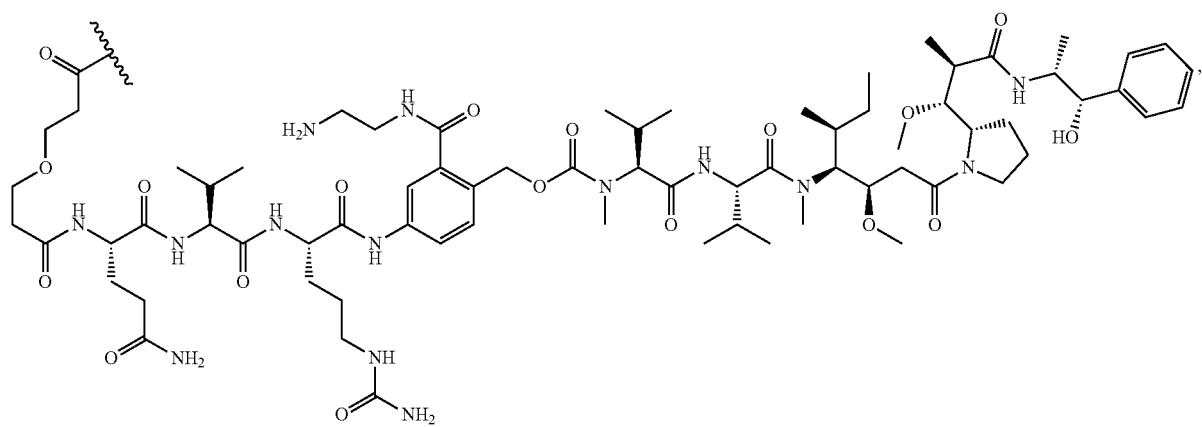
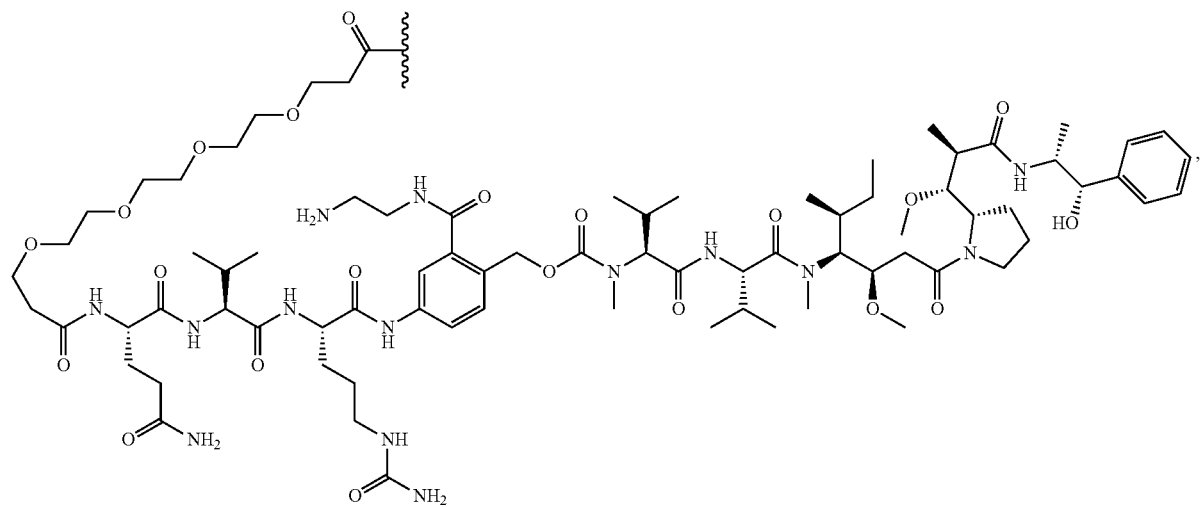

163
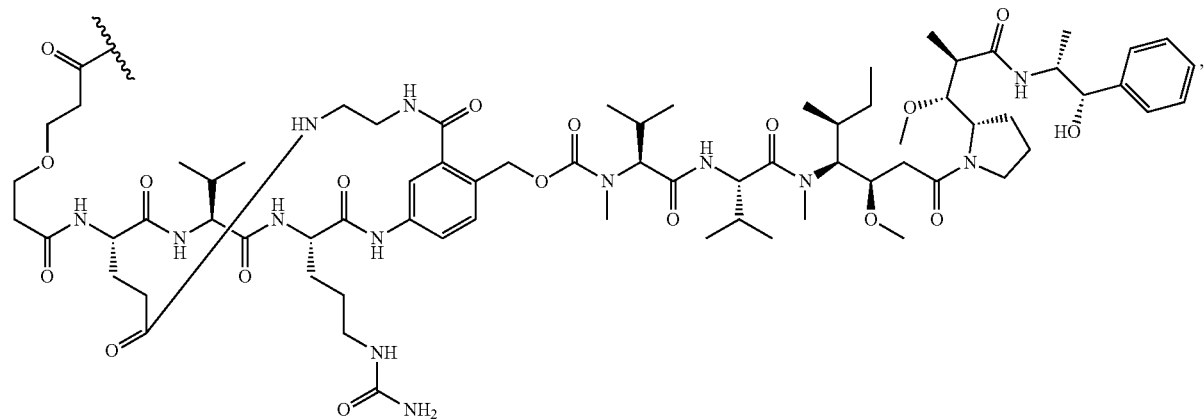
164
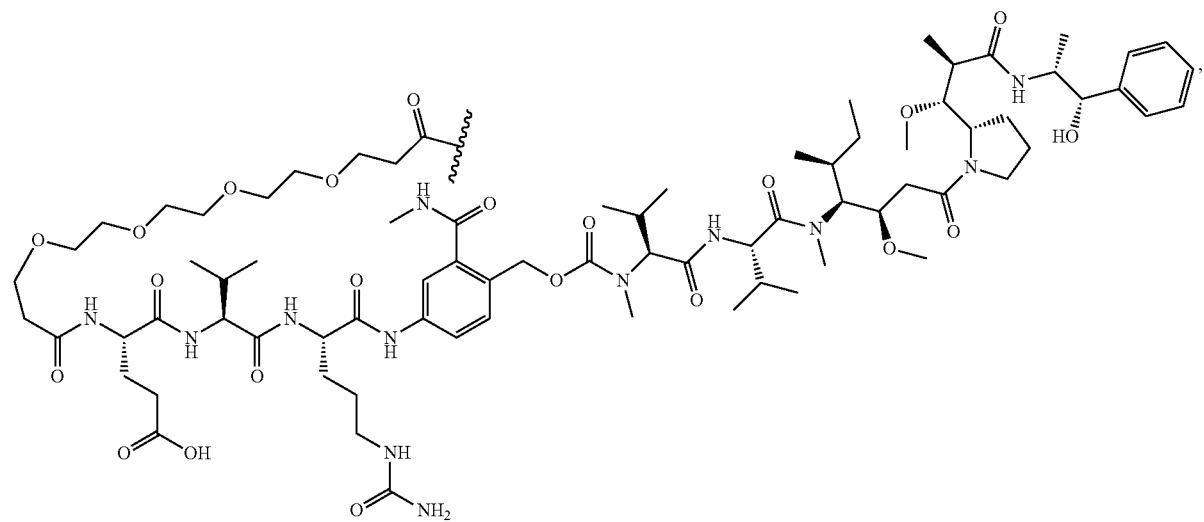
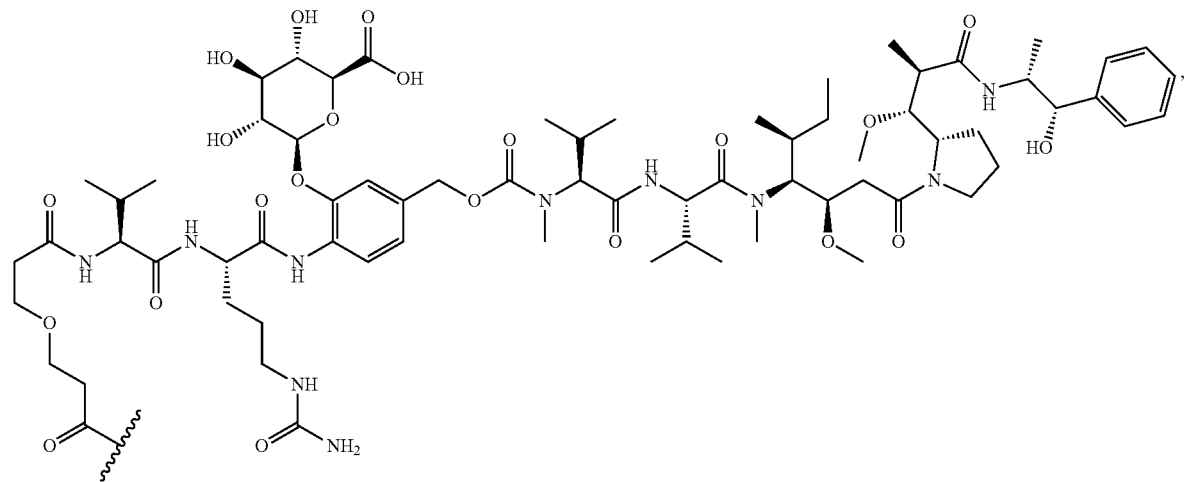

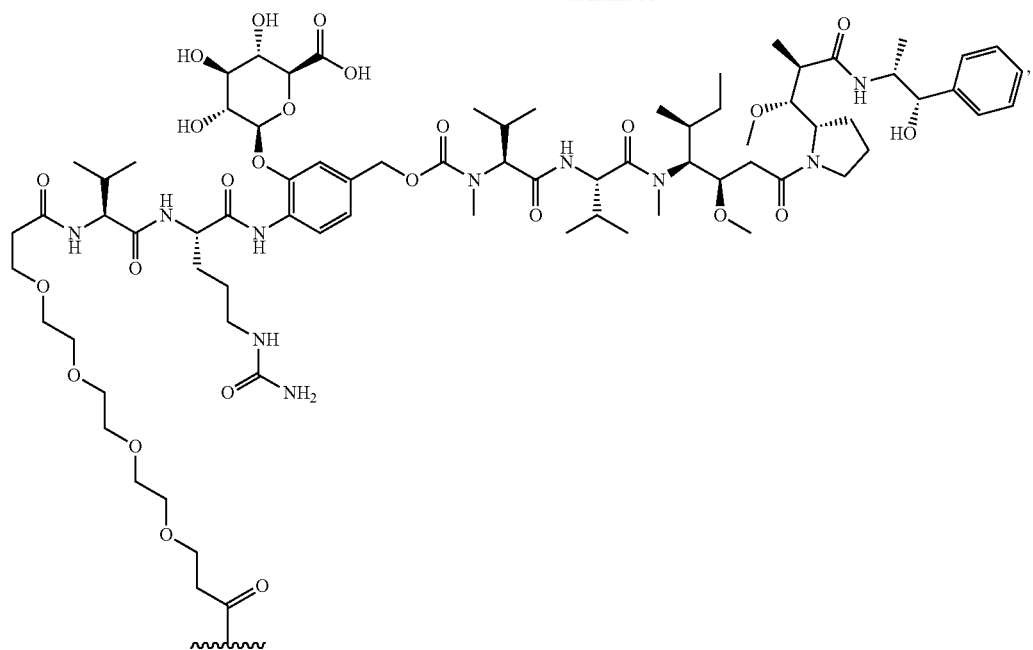
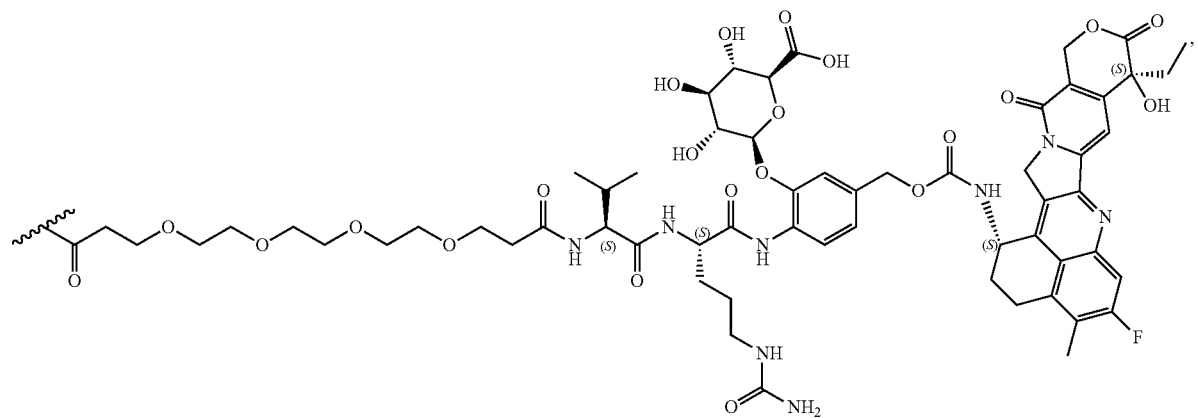
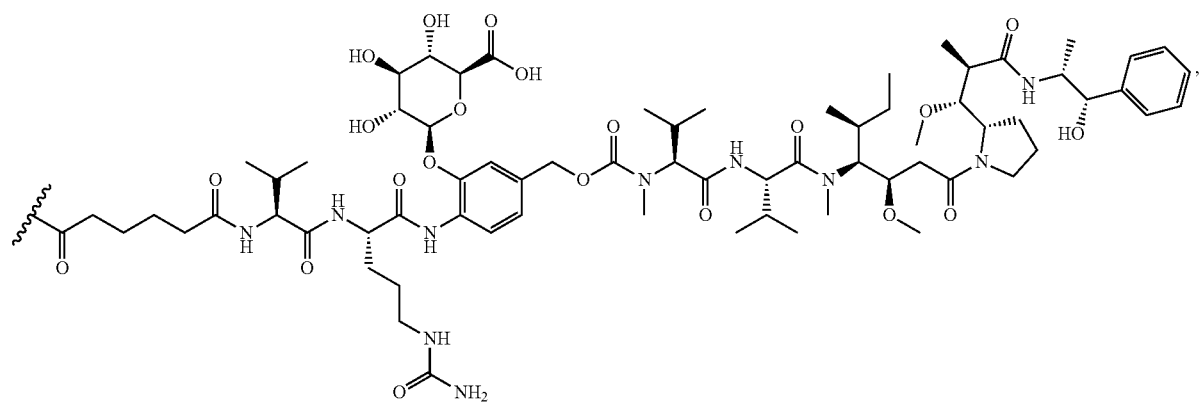
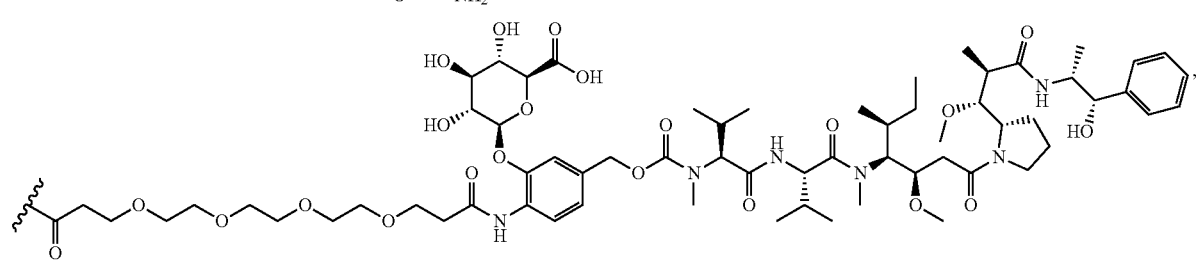

-continued
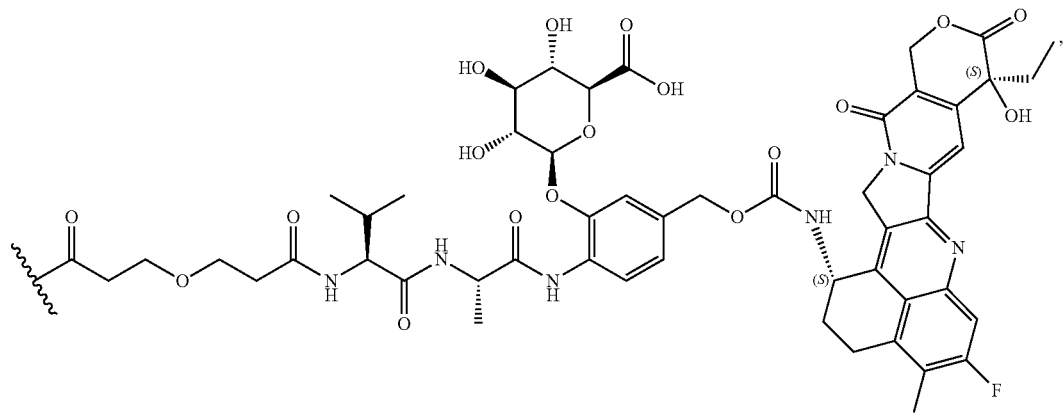
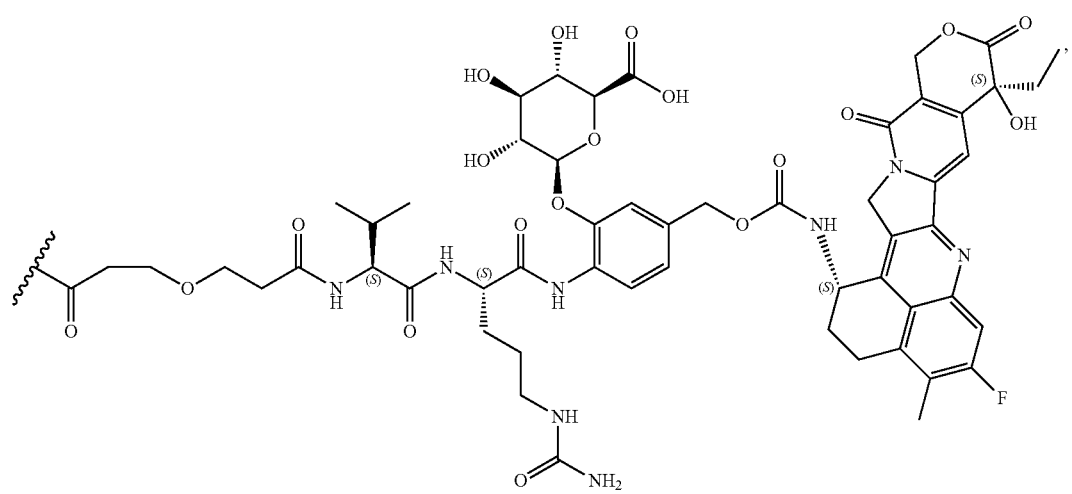
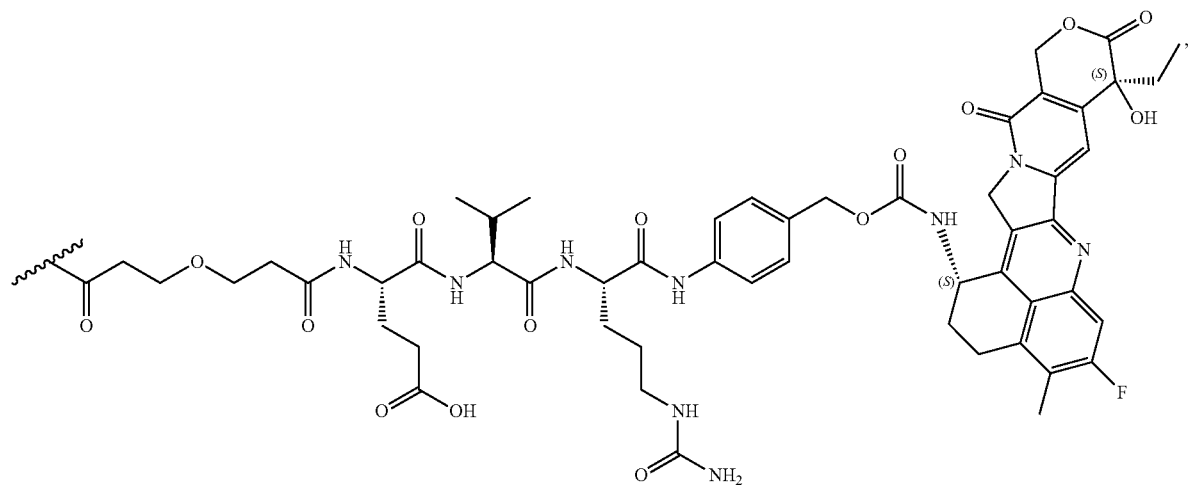

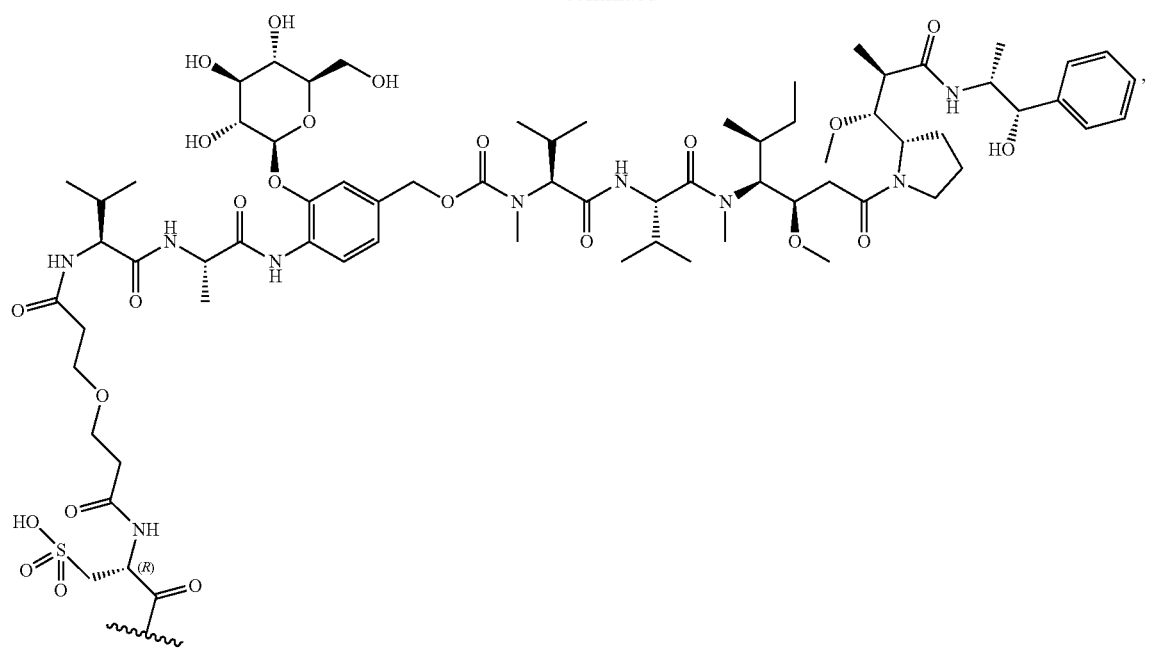
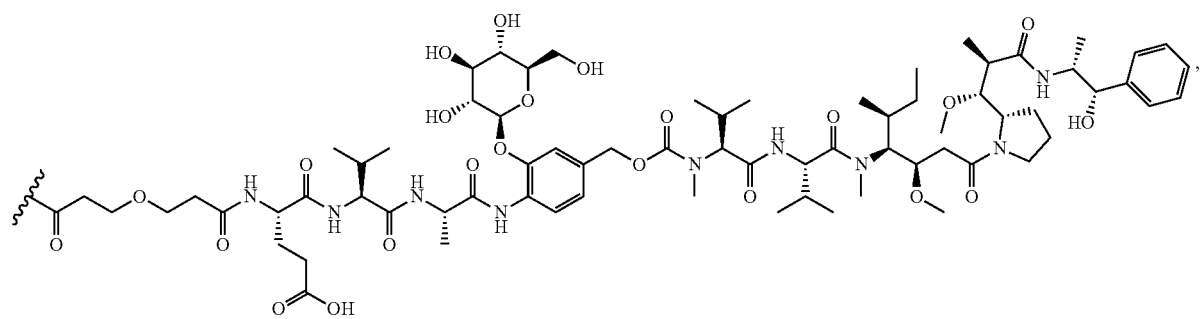
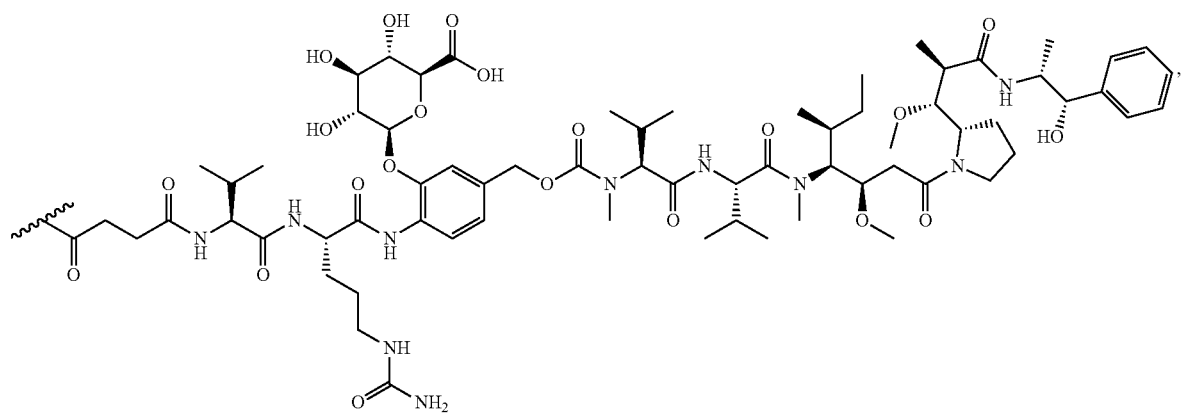

-continued
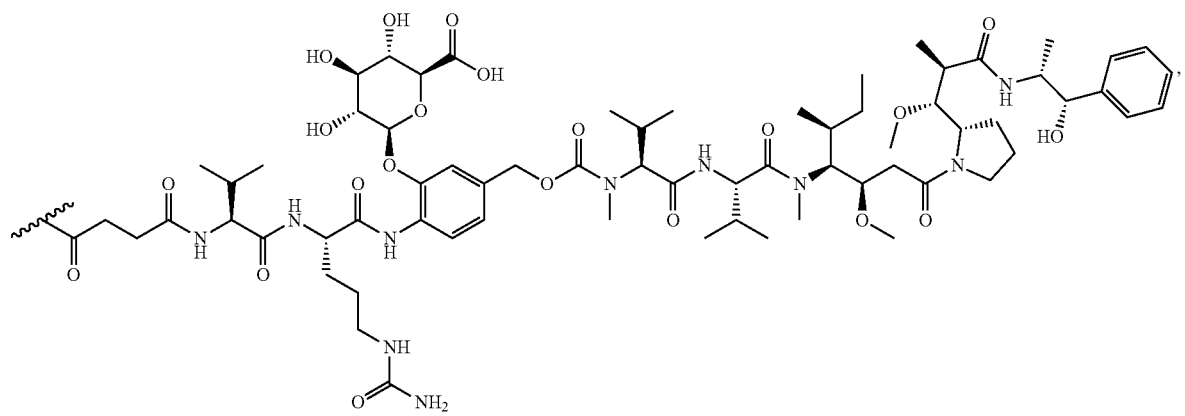
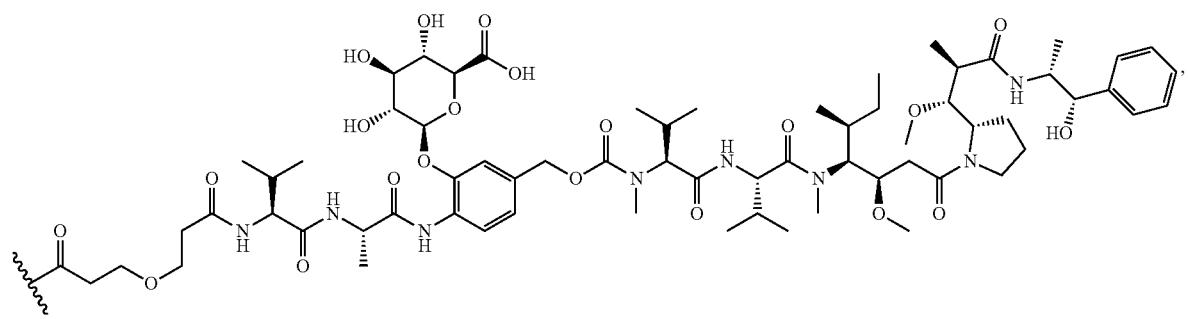
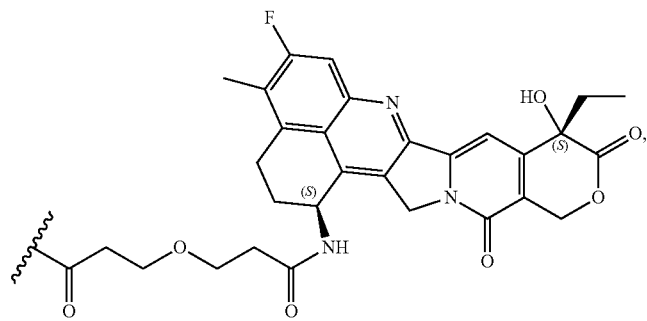
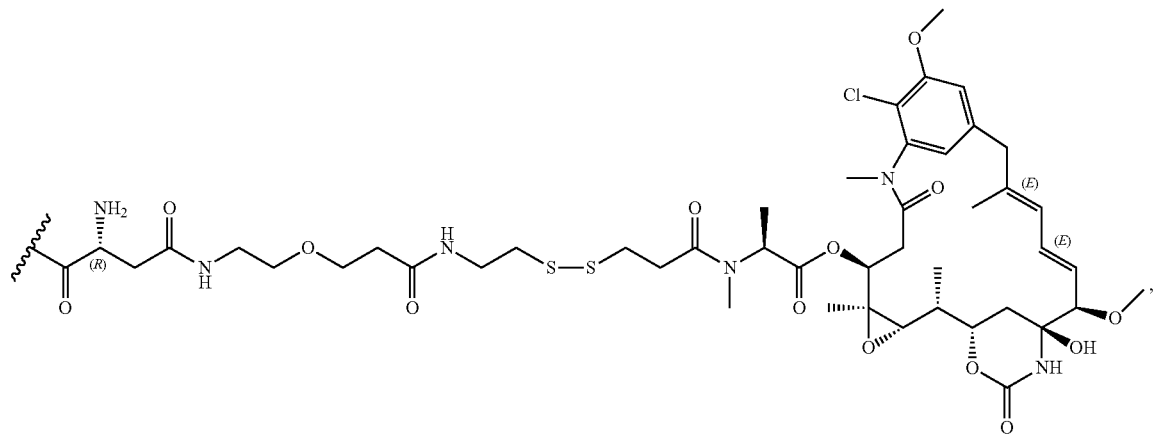

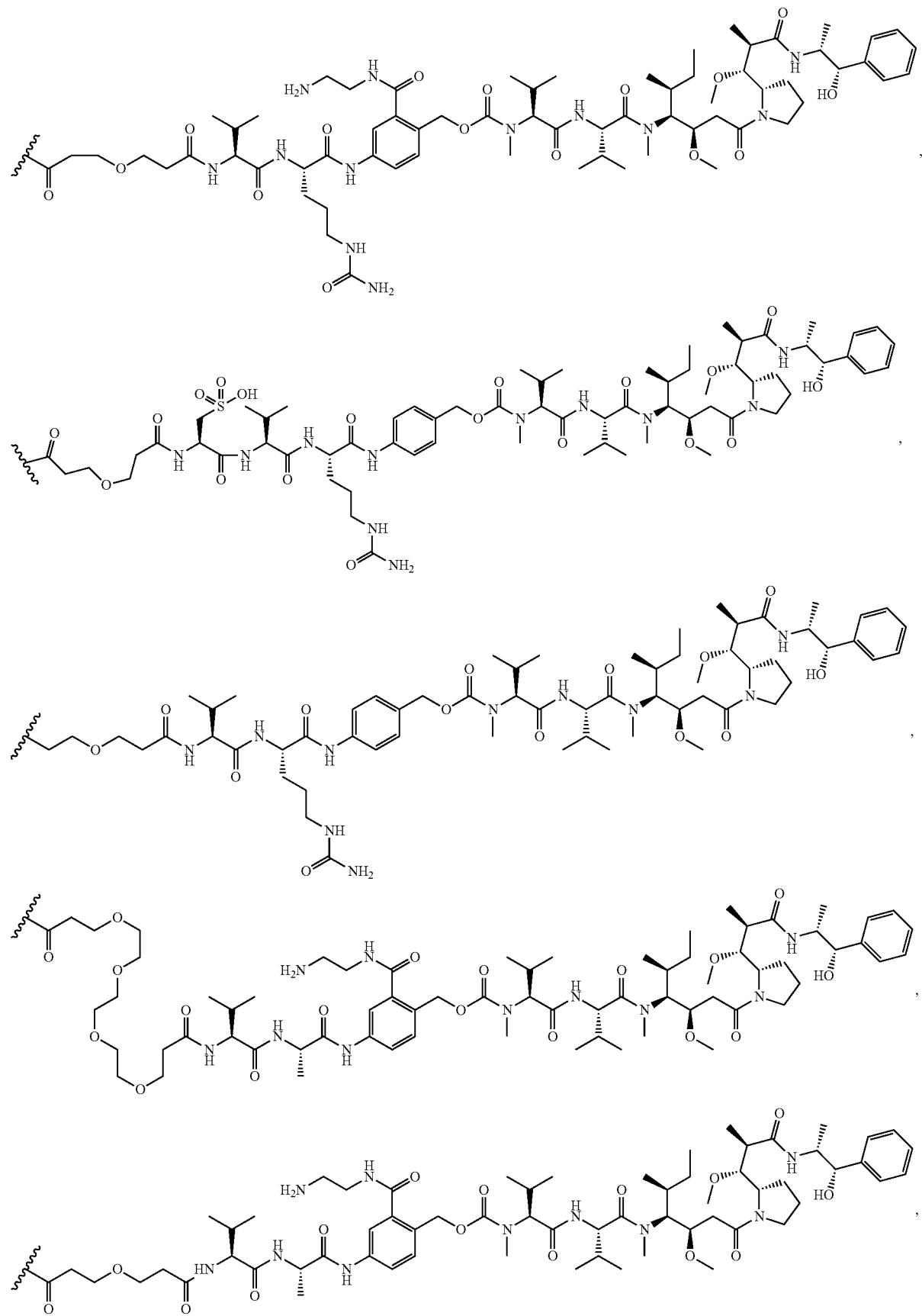

-continued
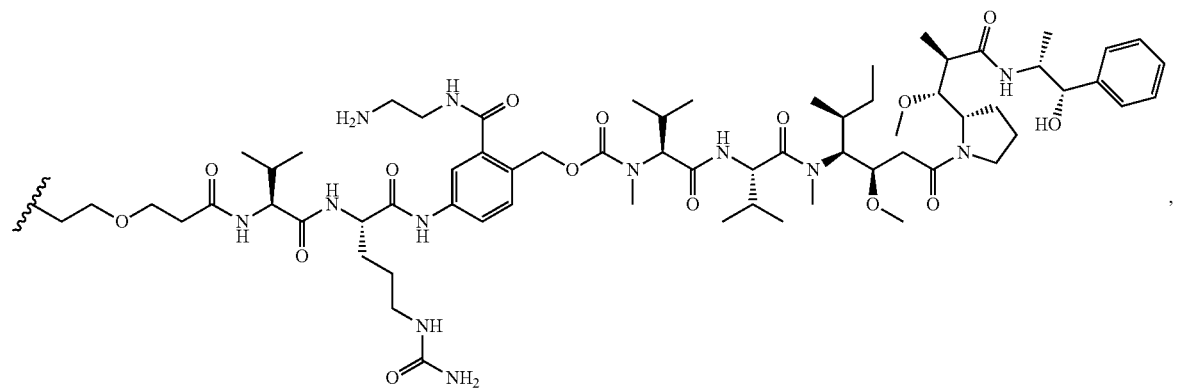
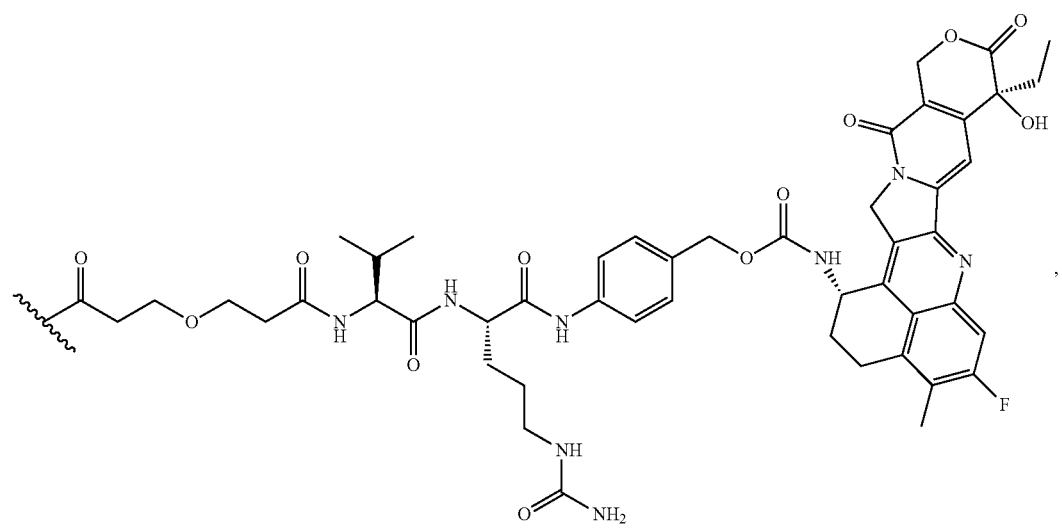
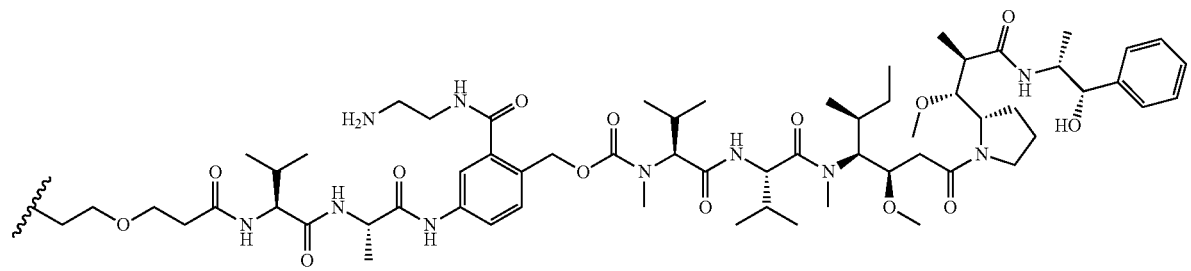
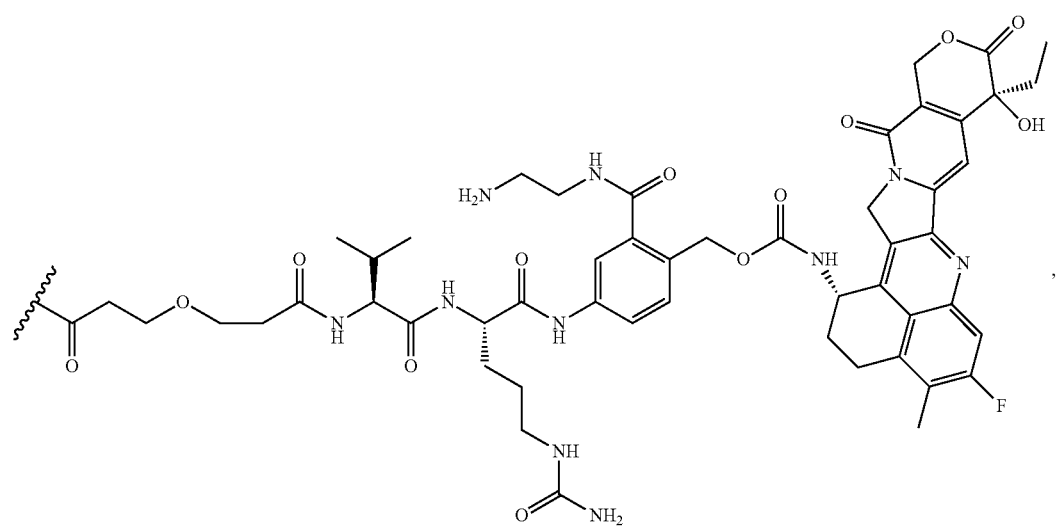

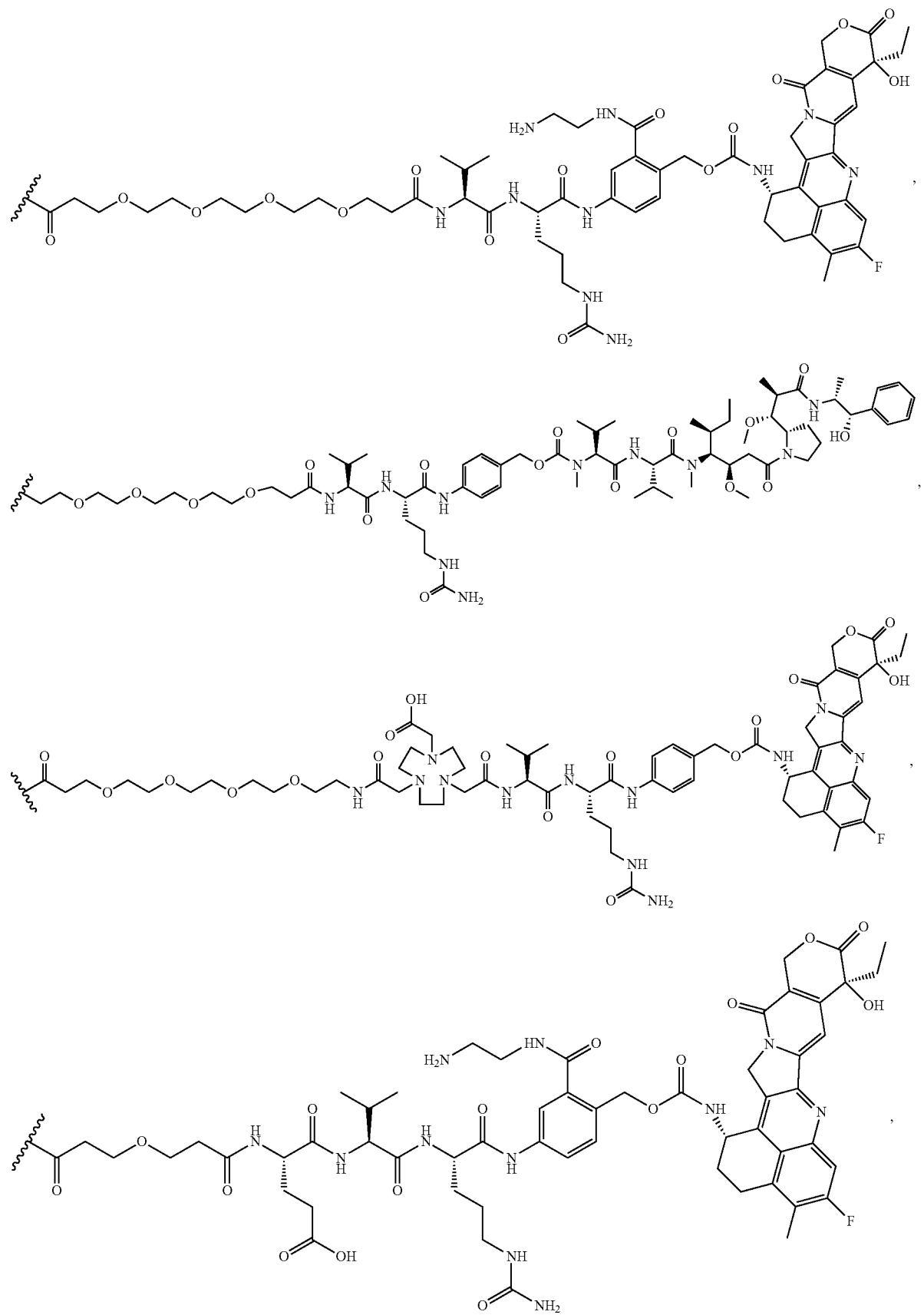

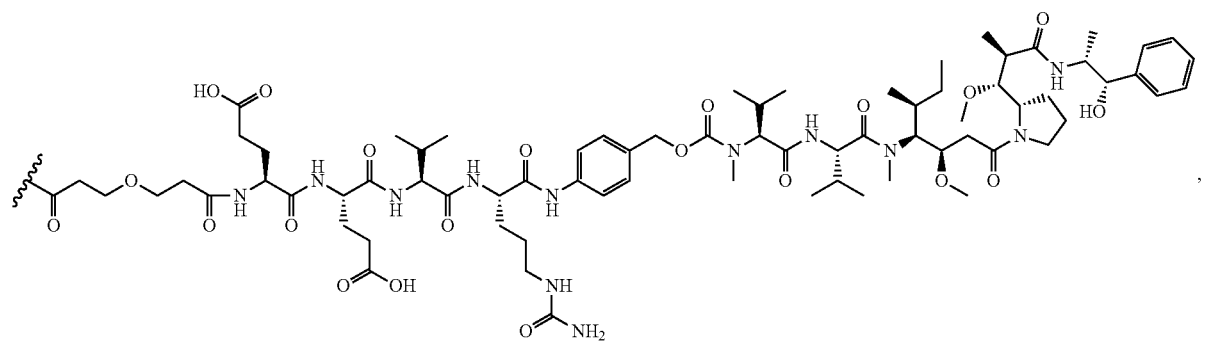 [SMILES: *C(=O)CCOCCC(=O)N[C@H](CCC(=O)O)C(=O)N[C@H](CCC(=O)O)C(=O)N[C@H](C(=O)N[C@@H](CCCNC(N)=O)C(=O)Nc1ccc(COC(=O)N(C)[C@H](C(=O)N[C@H](C(=O)N(C)[C@@H]([C@@H](C)CC)[C@@H](CC(=O)N2CCC[C@H]2[C@H](OC)[C@@H](C)C(=O)N[C@H](C)[C@@H](O)c2ccccc2)OC)C(C)C)C(C)C)cc1)C(C)C]
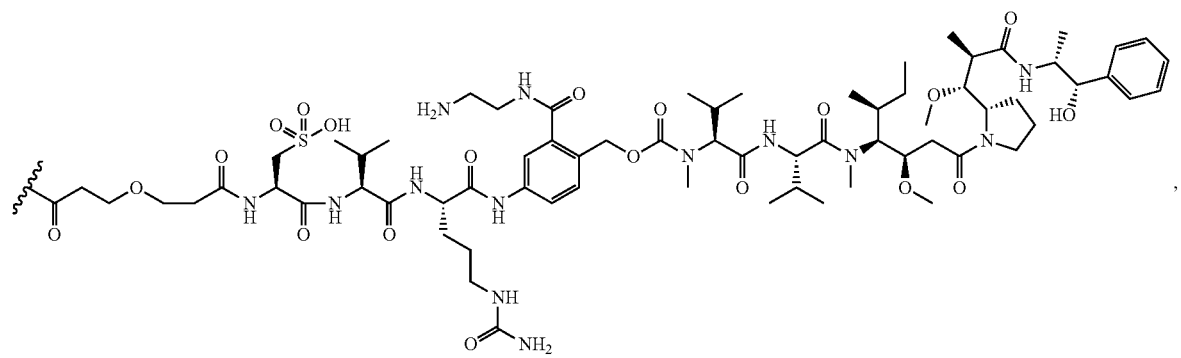
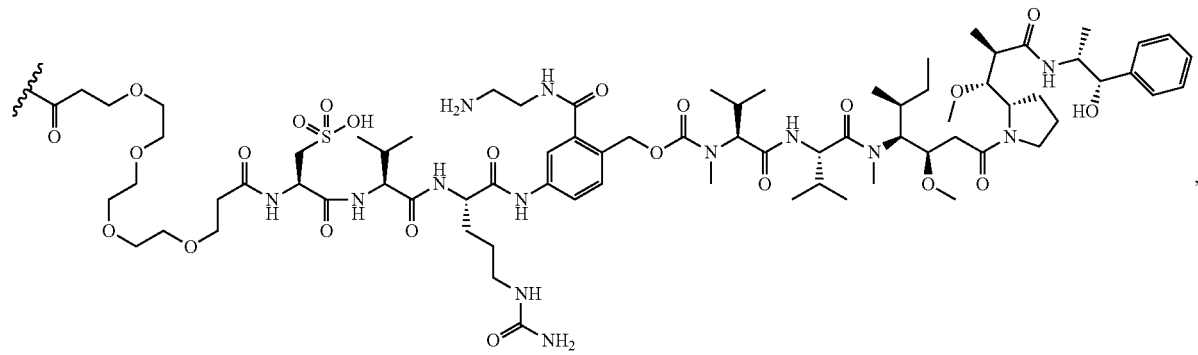
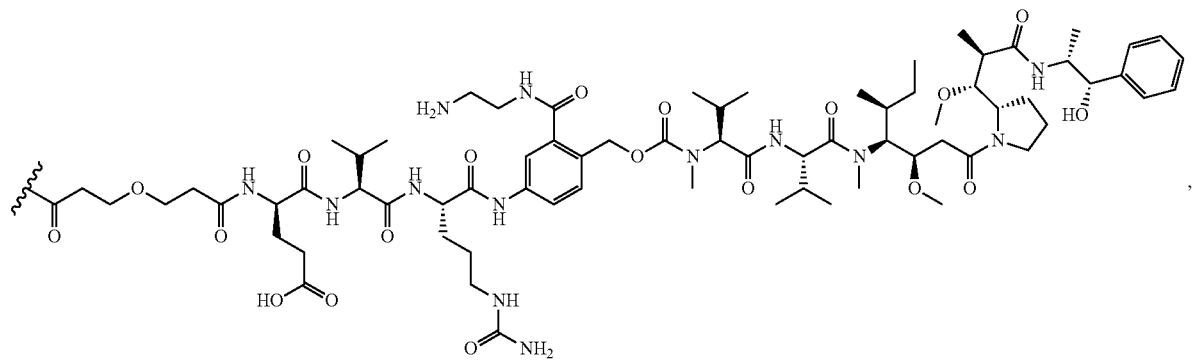

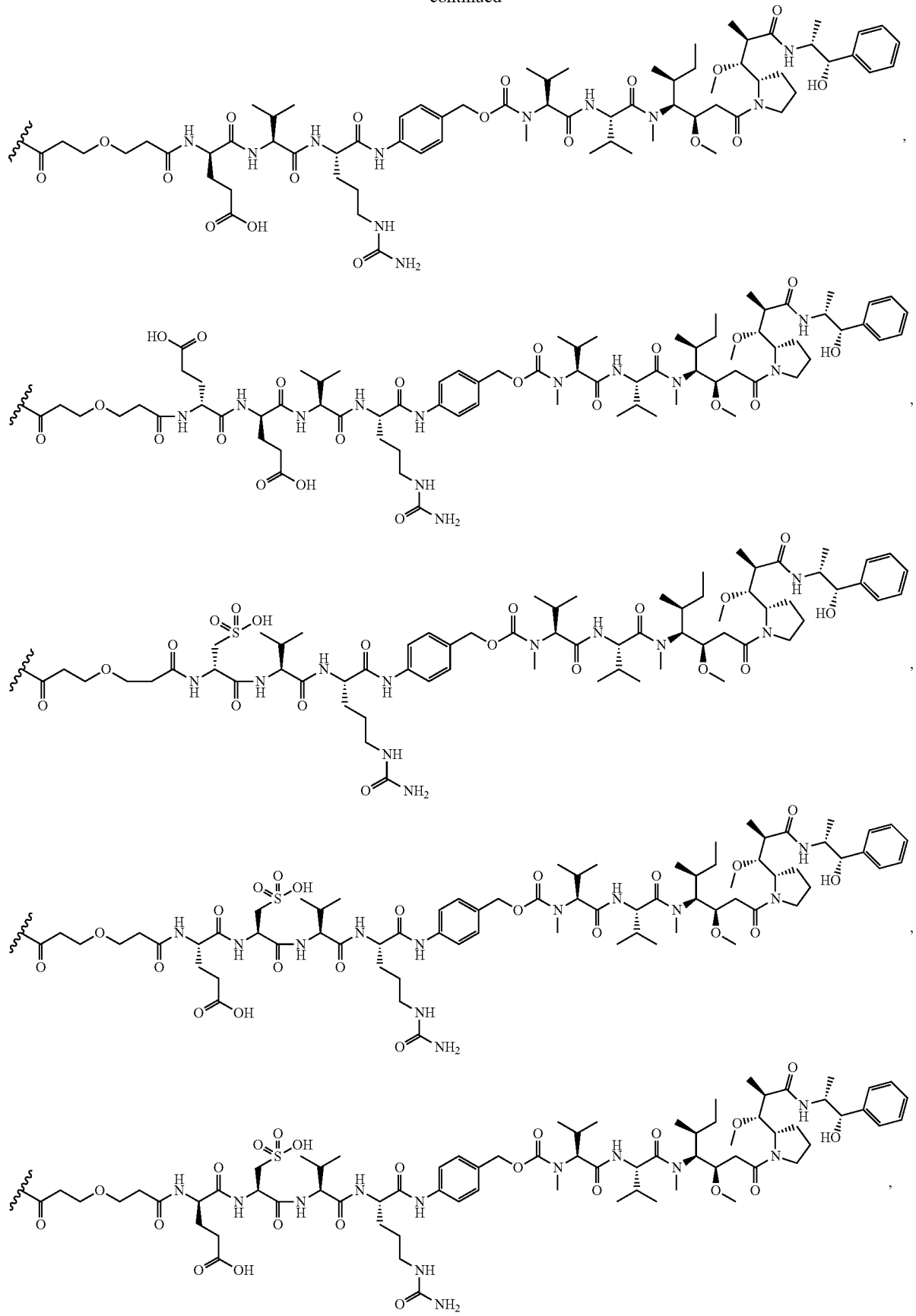

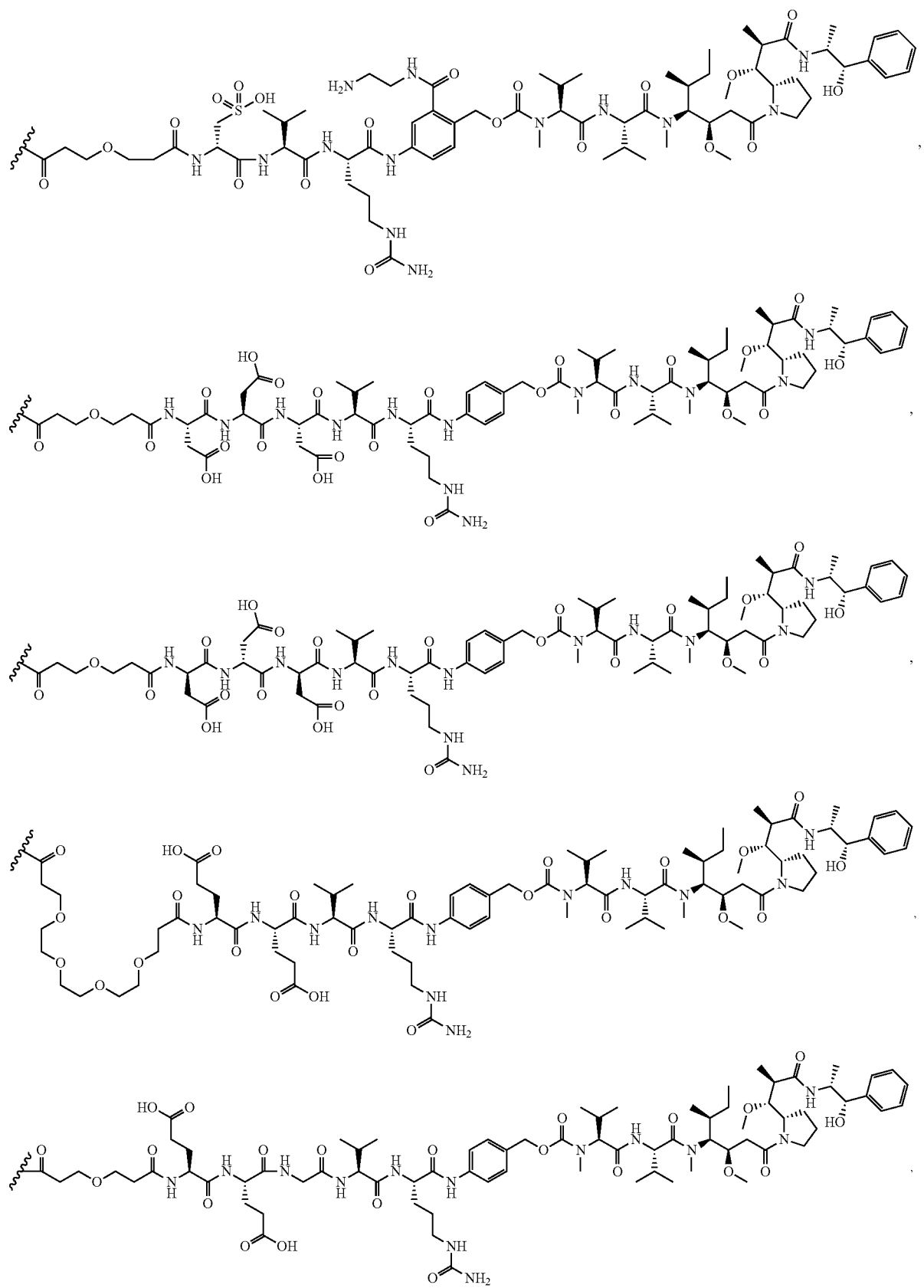

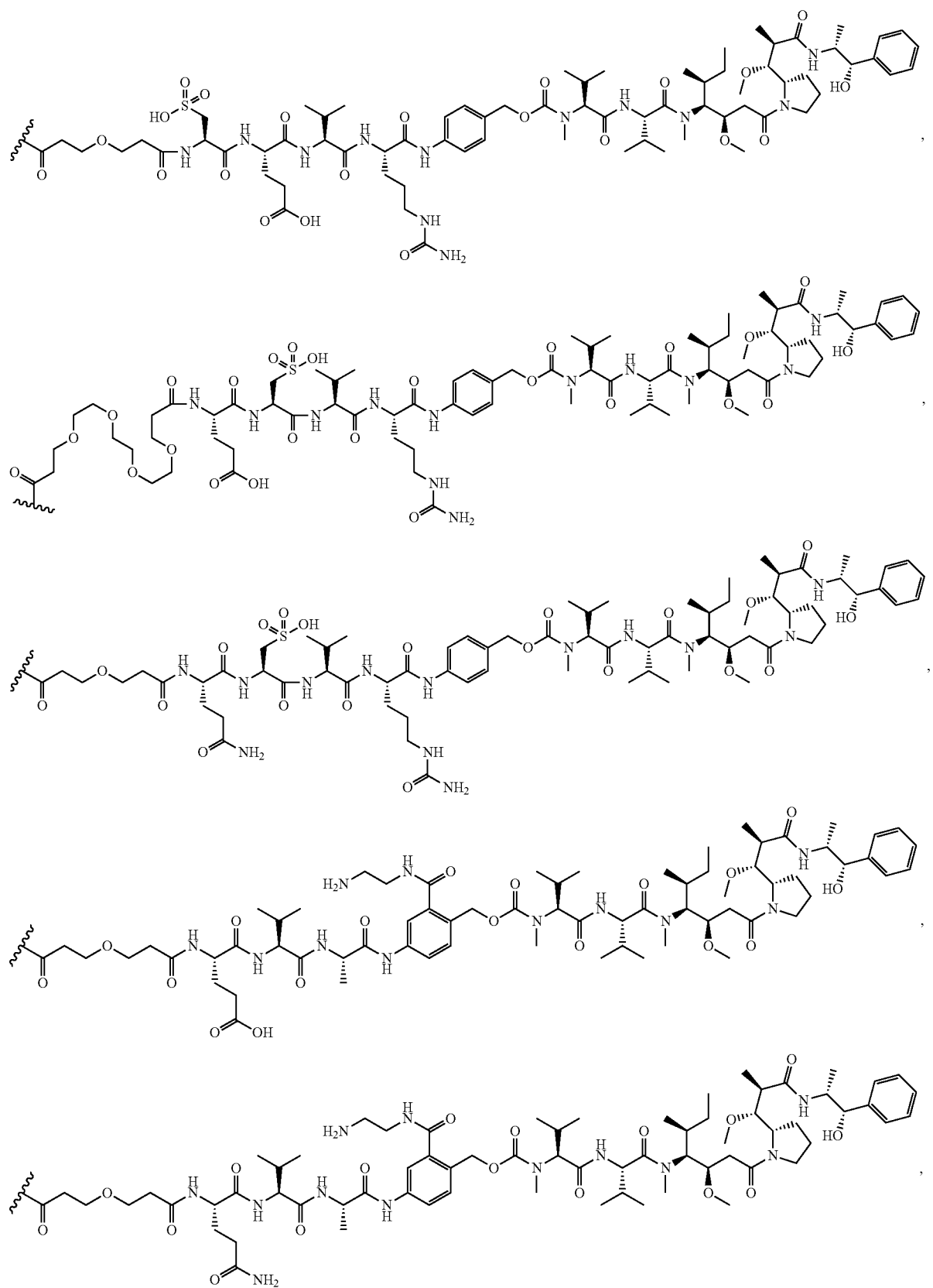

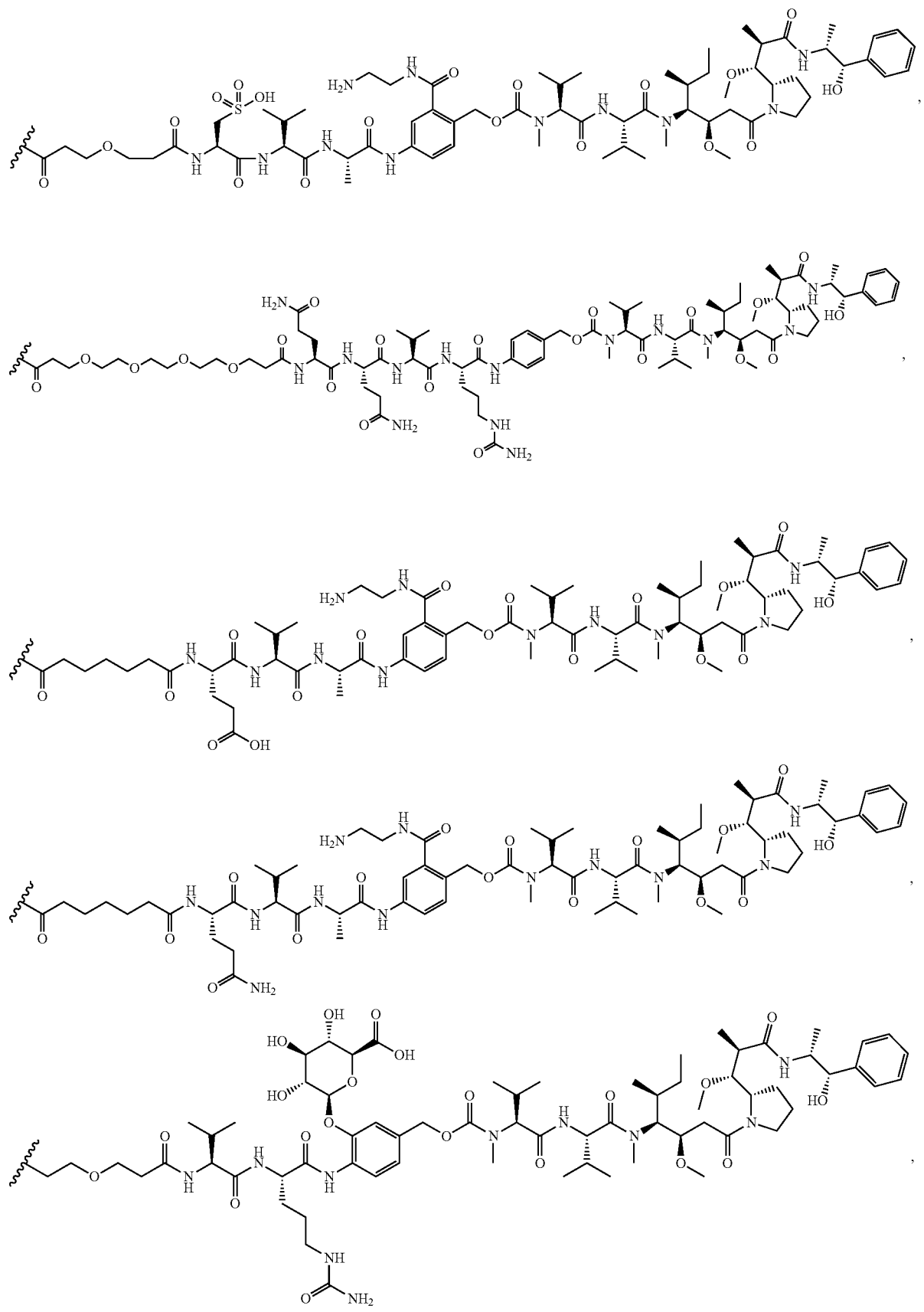

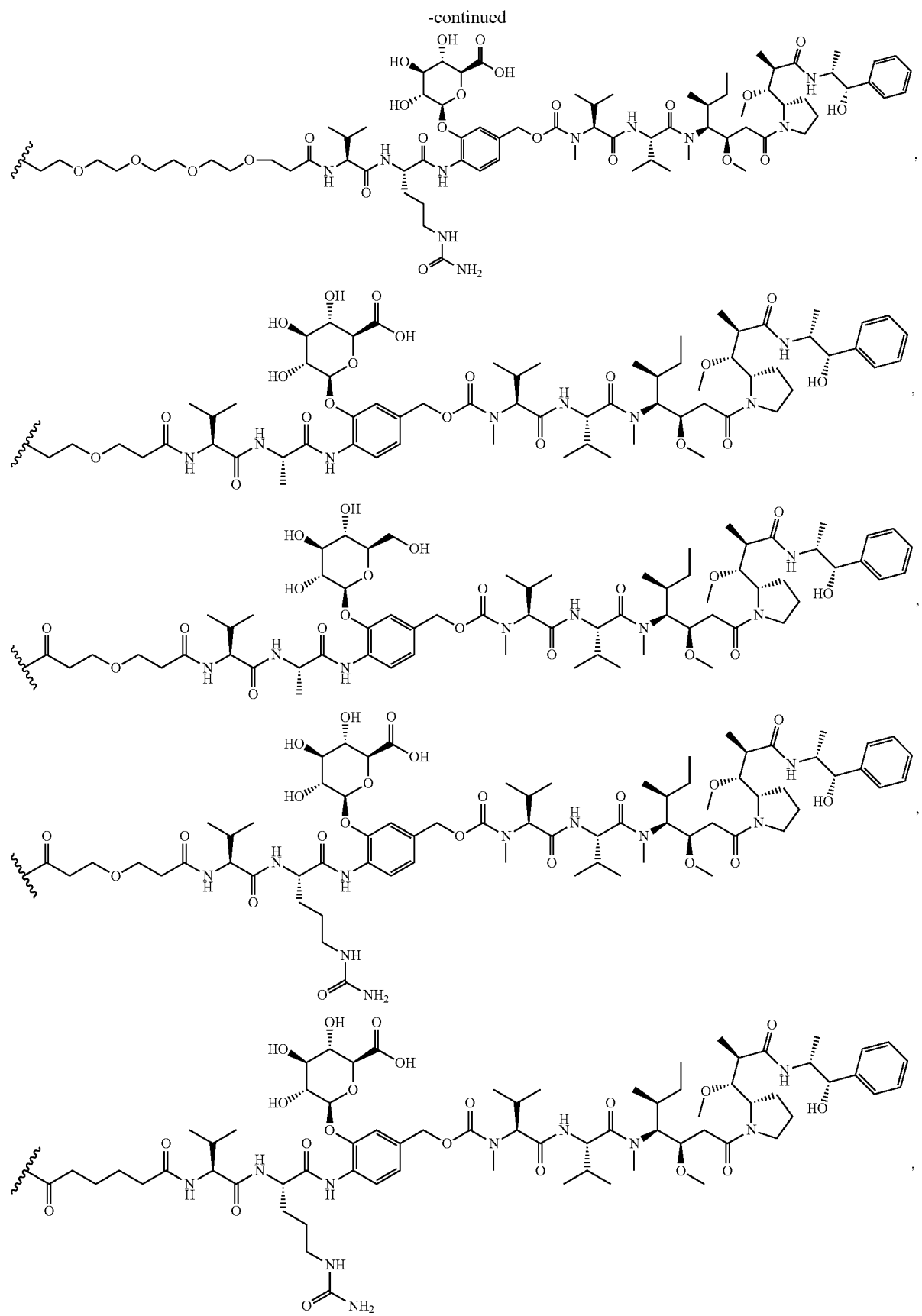

-continued
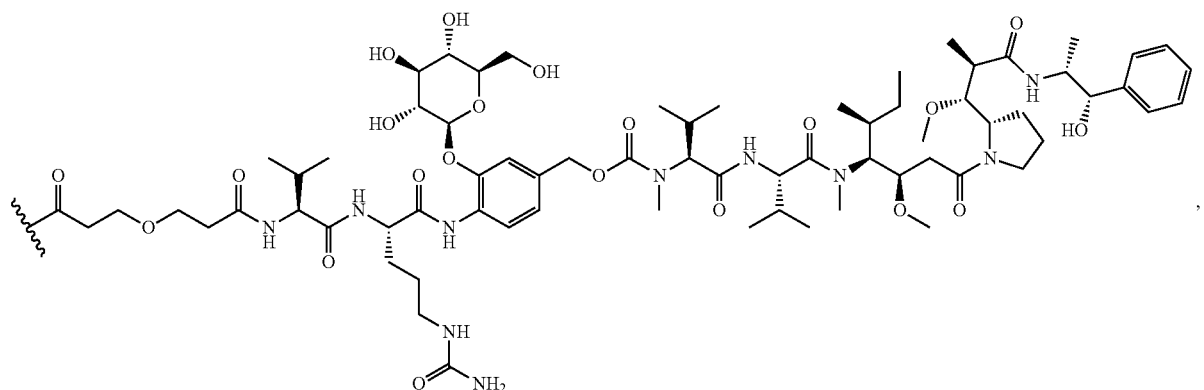
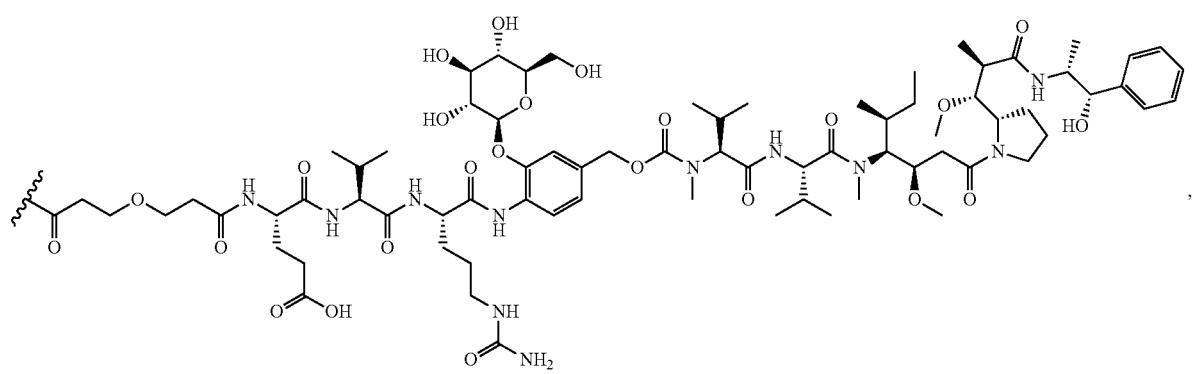
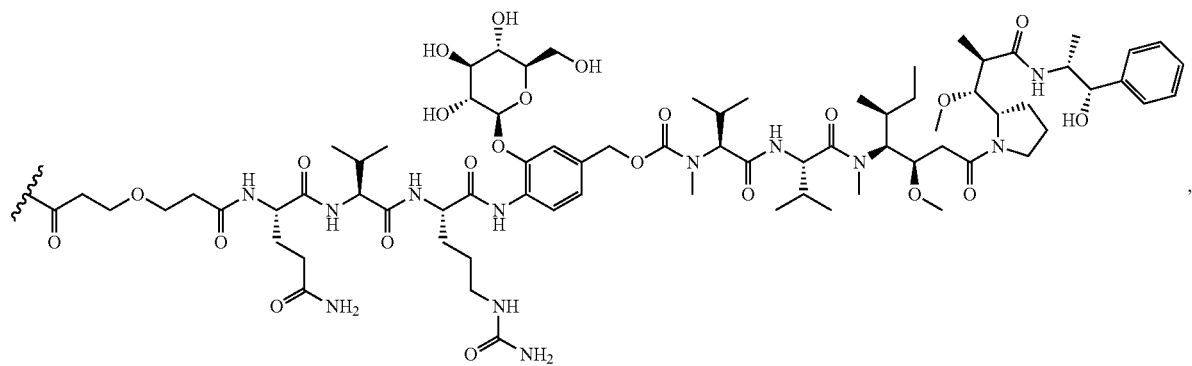
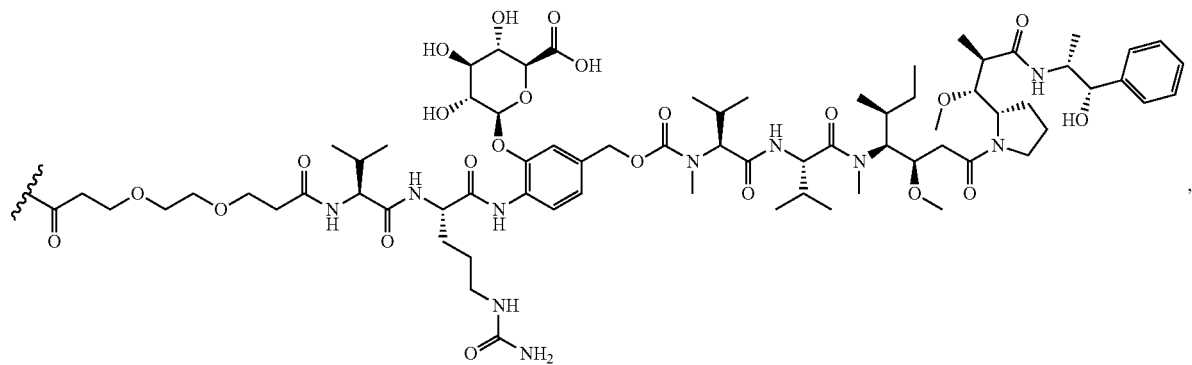

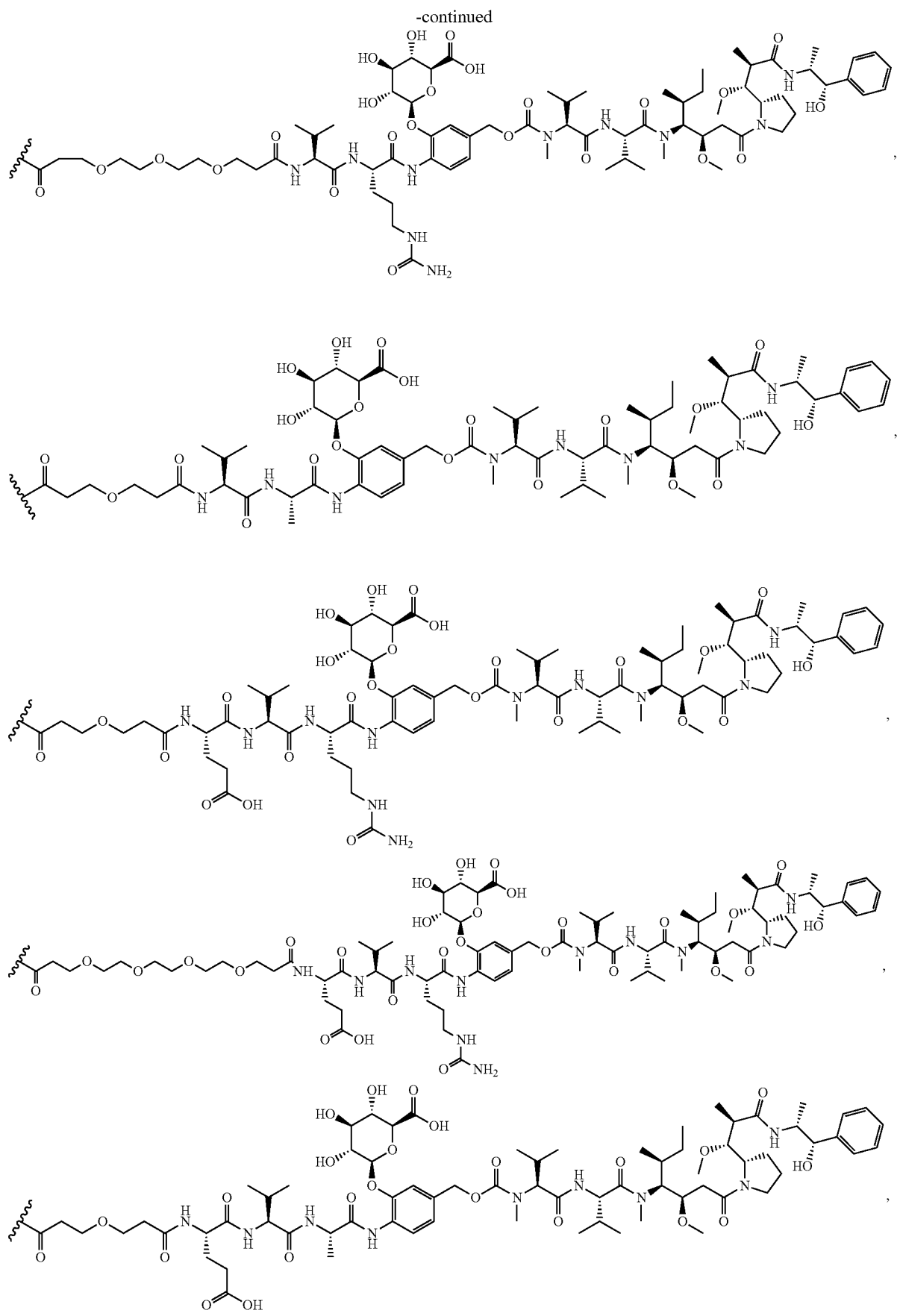

-continued
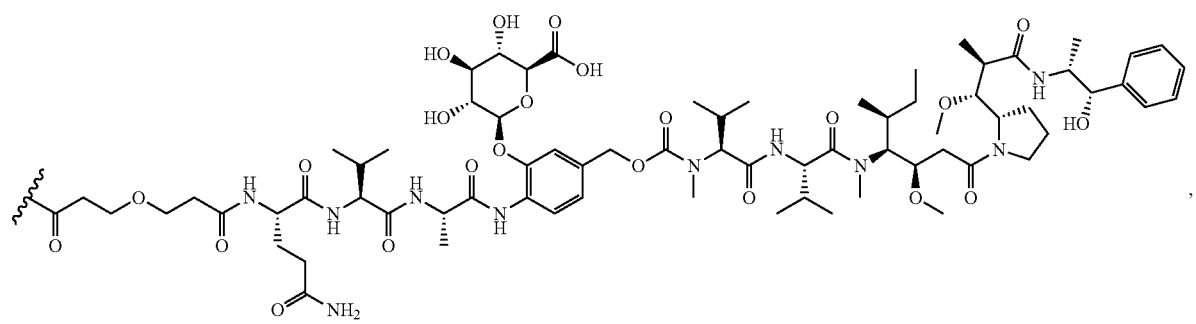
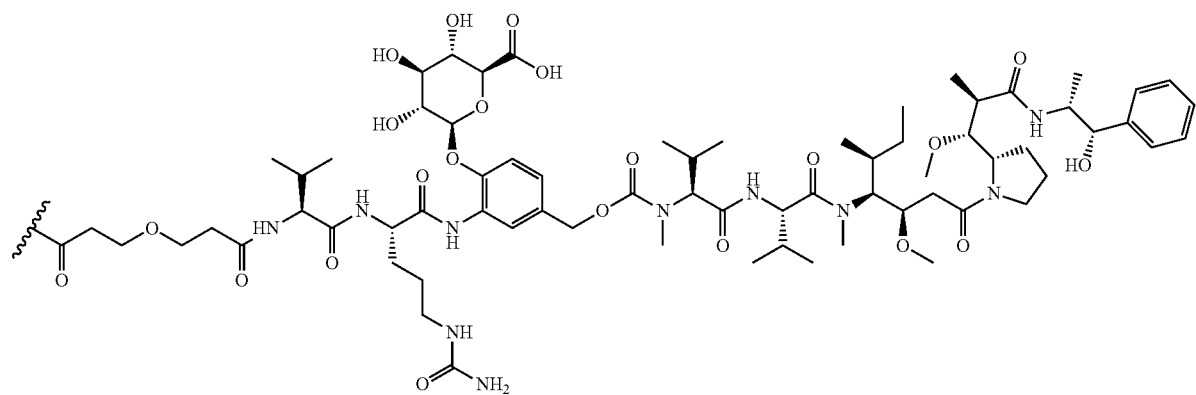
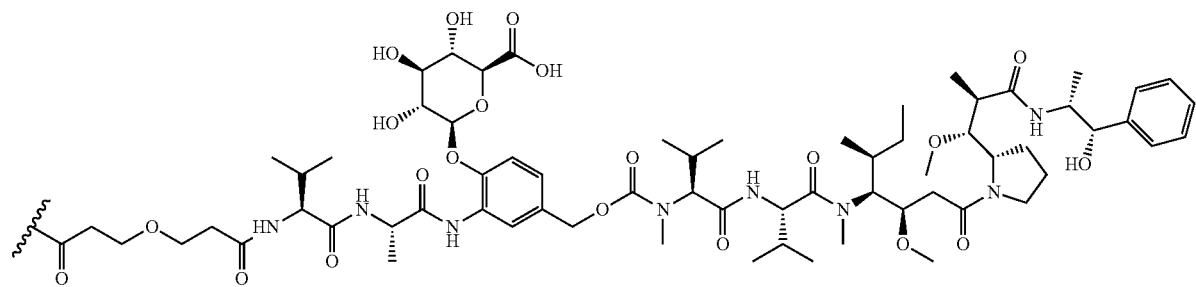
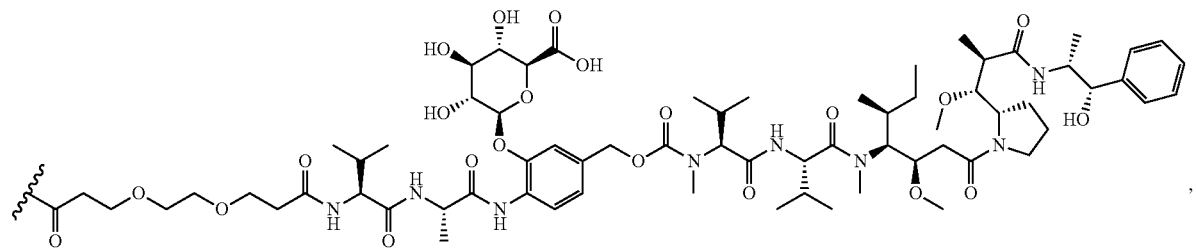
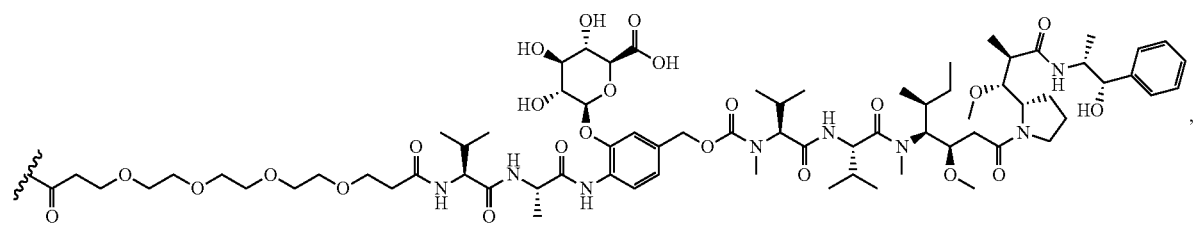

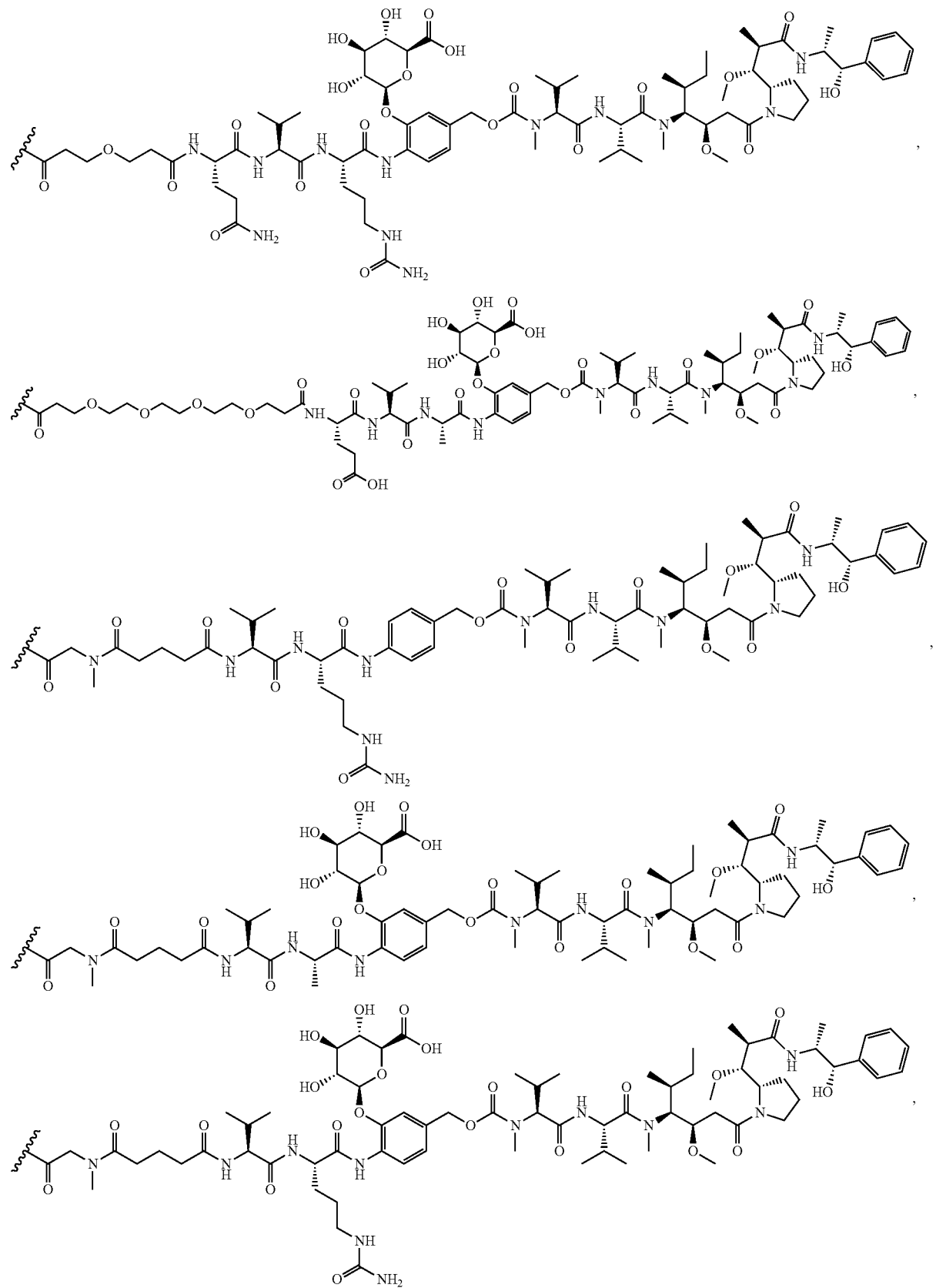

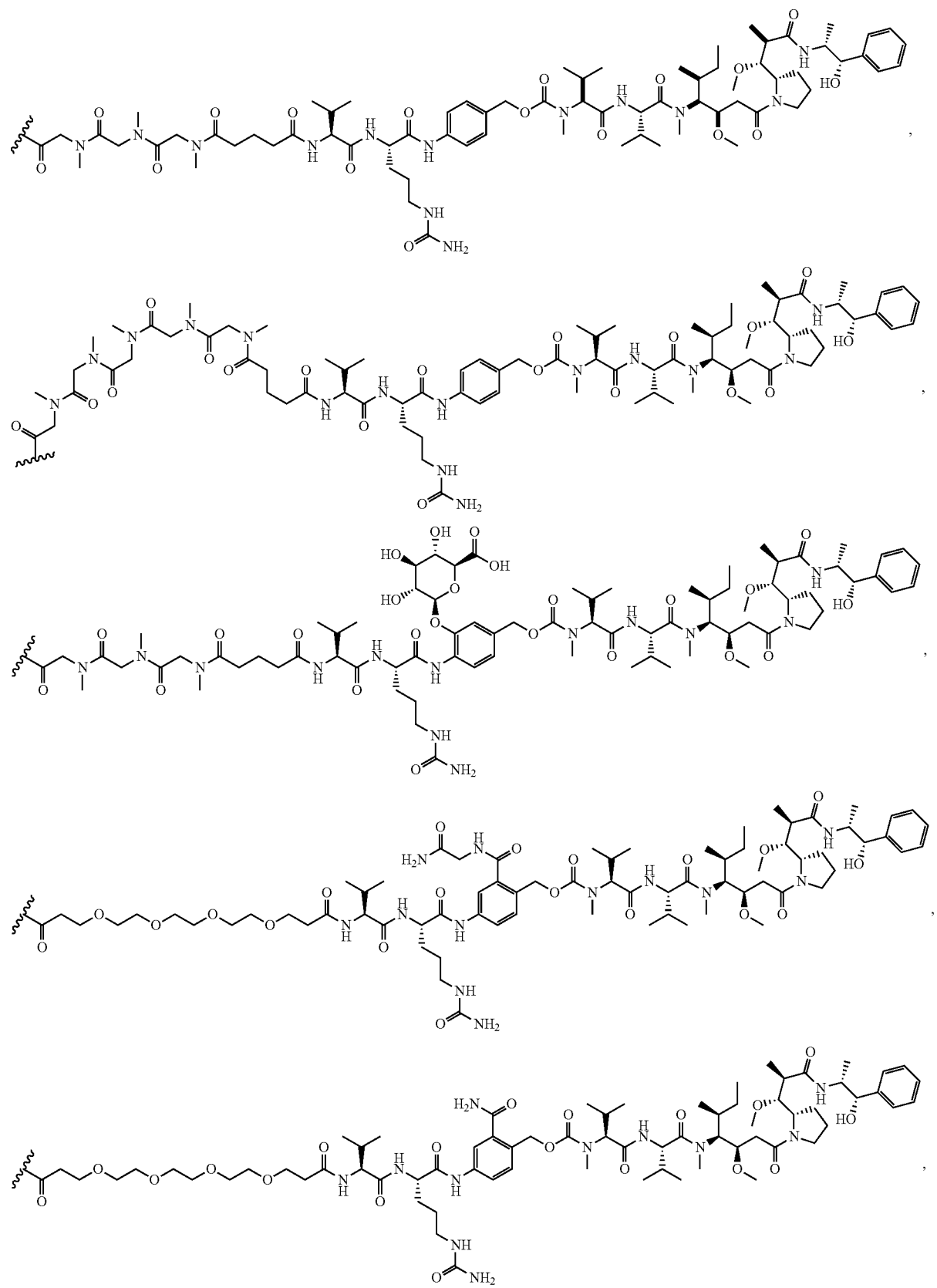

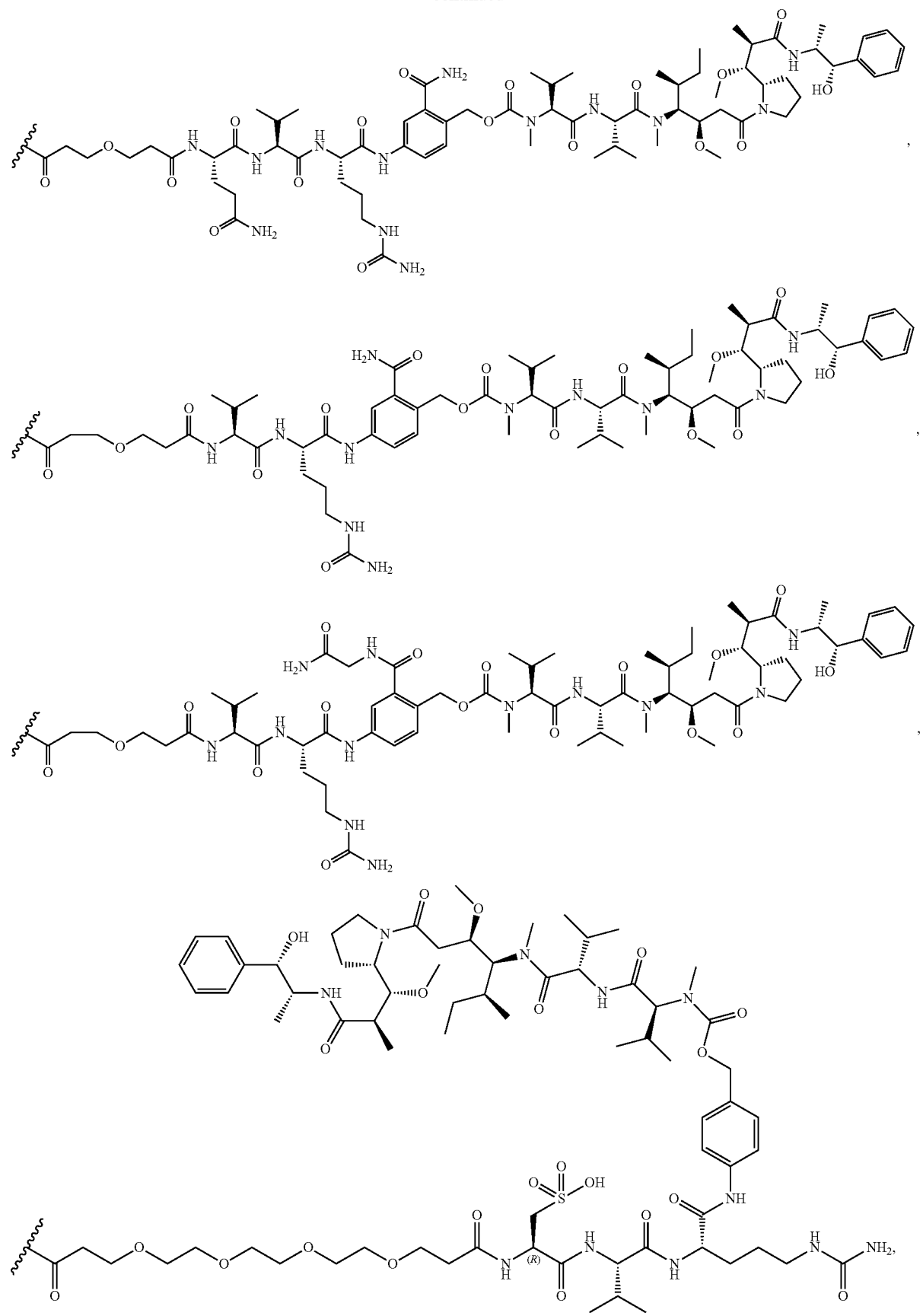

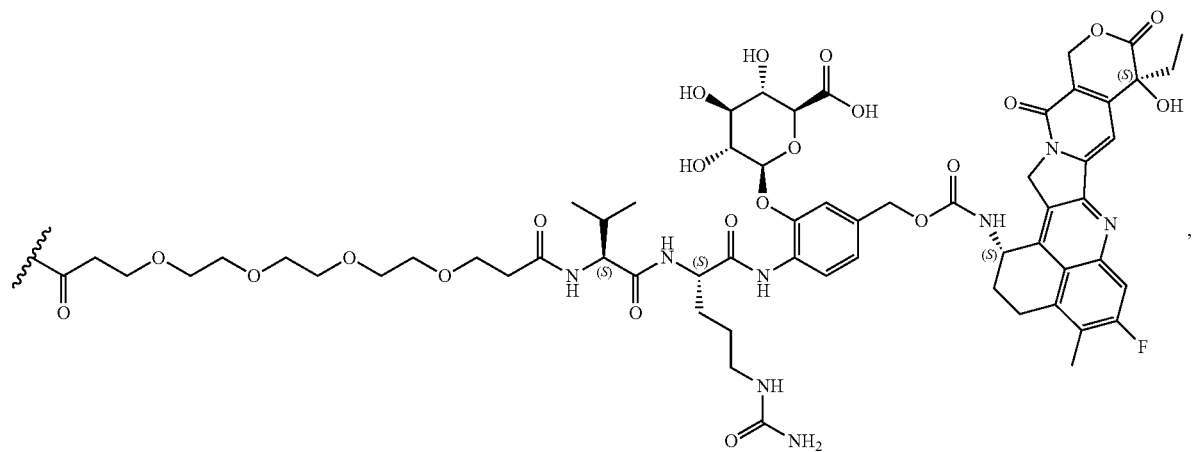
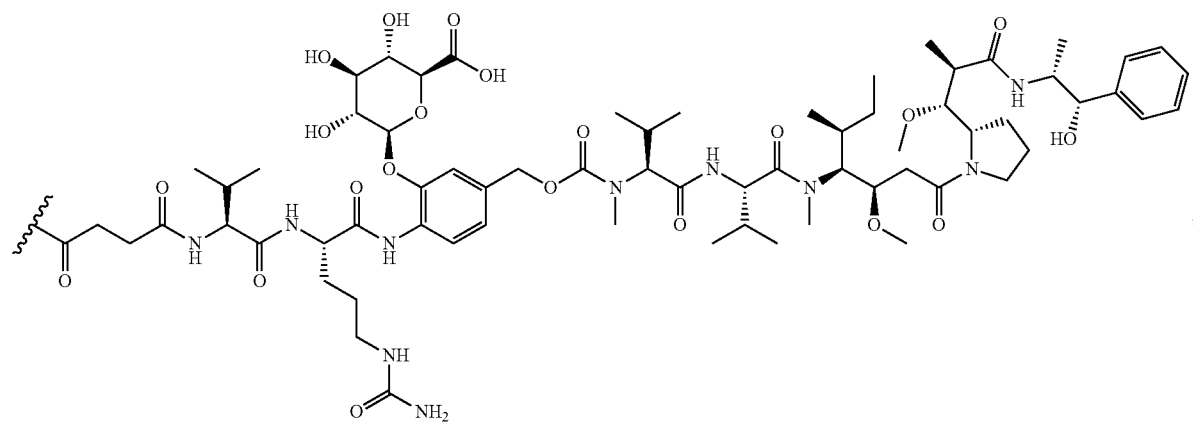
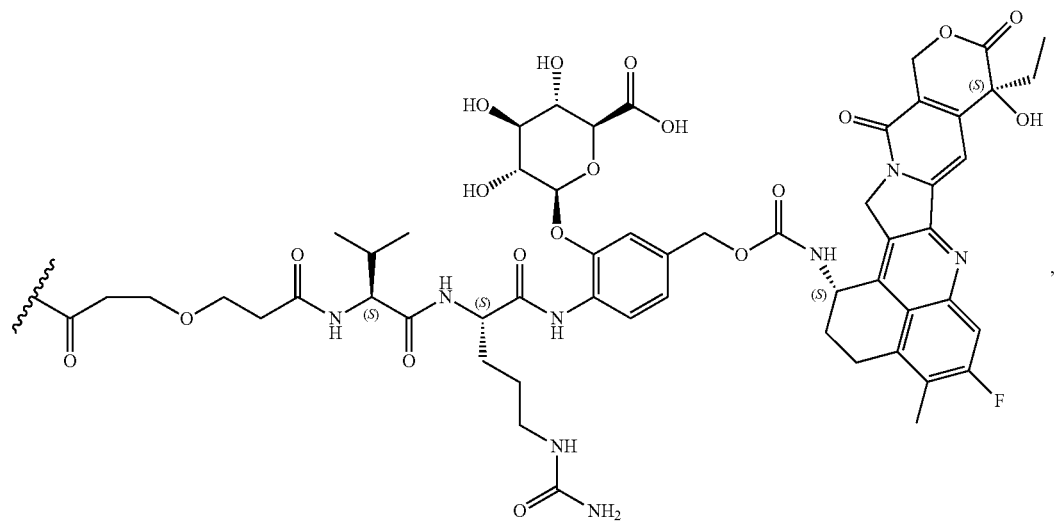

-continued
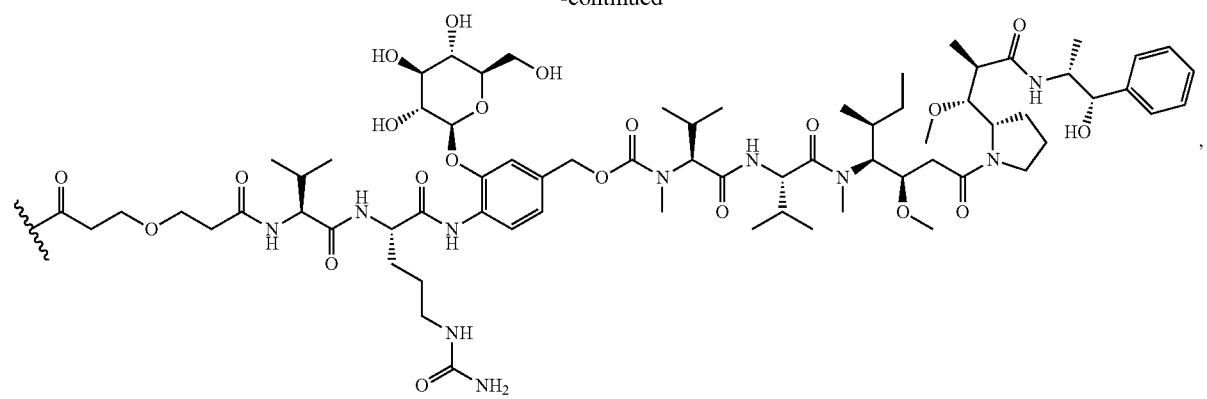
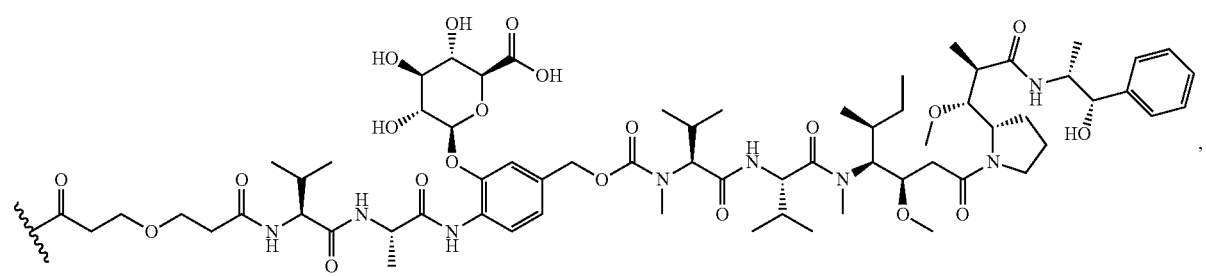
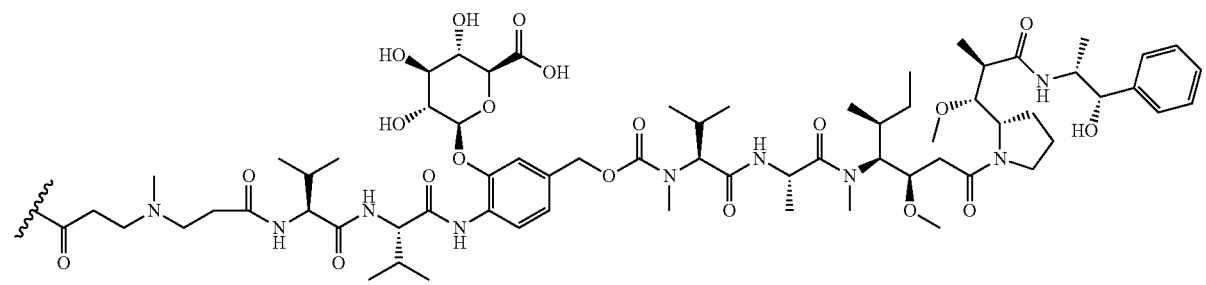
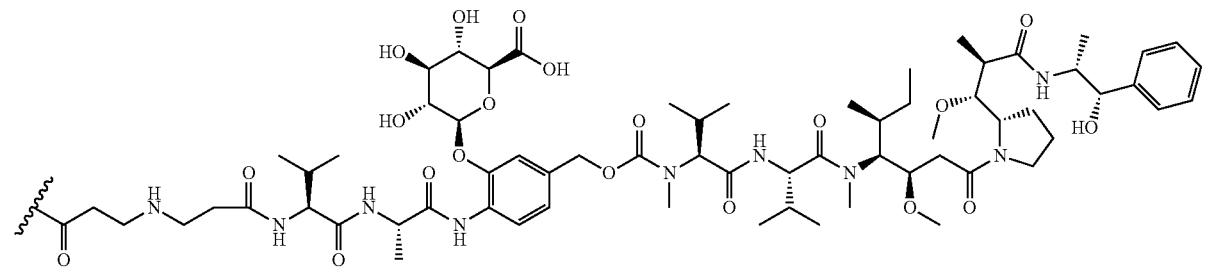
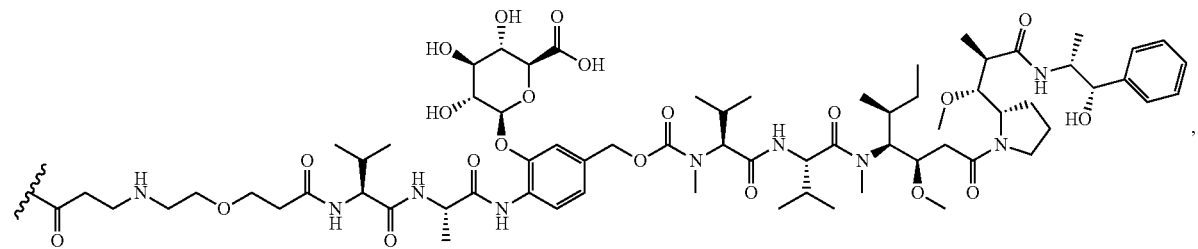

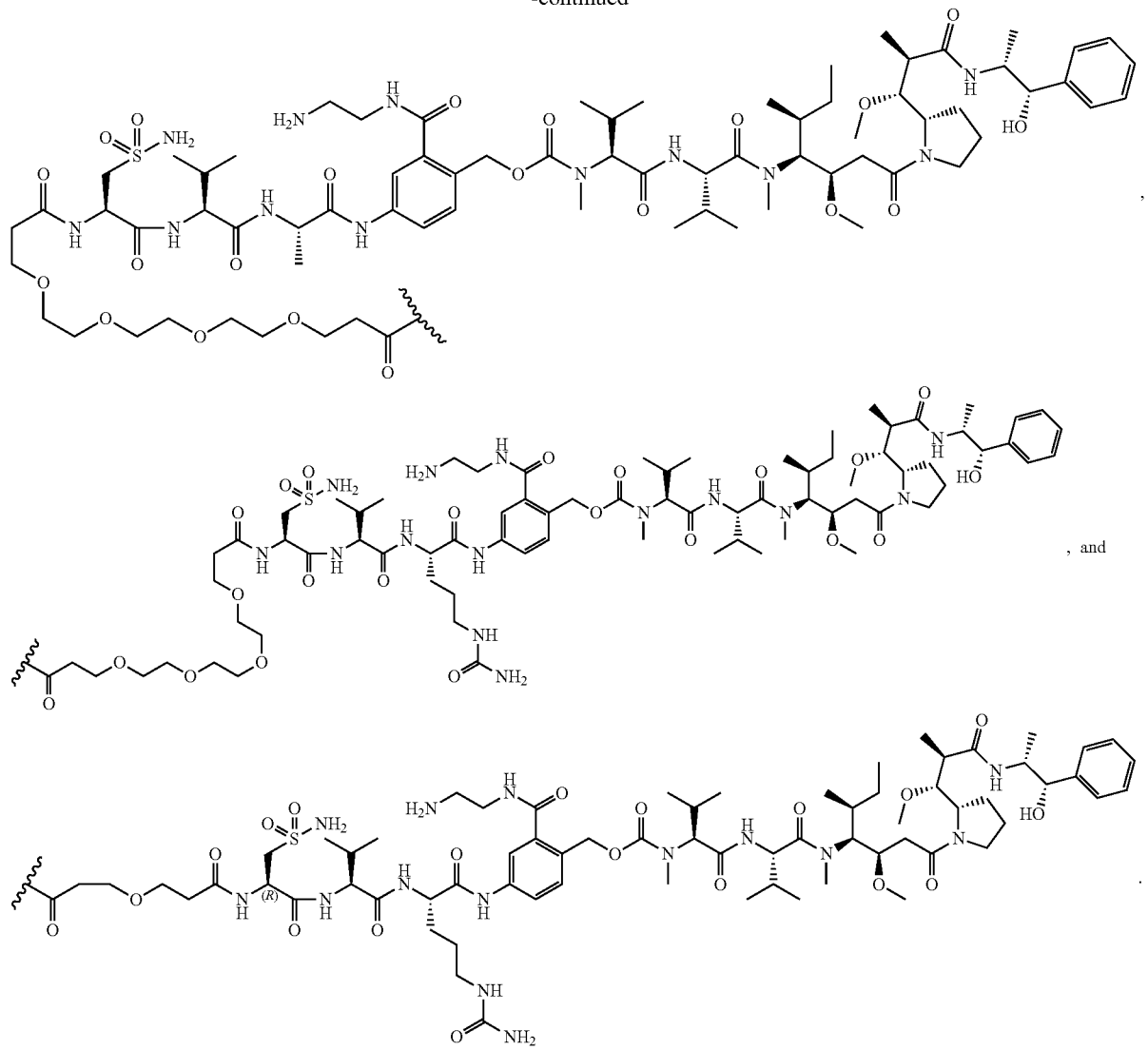

Any combination of the groups described above for the various variables is contemplated herein. Throughout the specification, groups and substituents thereof are chosen by one skilled in the field to provide stable moieties and compounds.

Representative SMDC Conjugates

The compound numbers recited below correspond to those iterated in the examples.

In some embodiments, the compound of Formula (I) is Compound 6.

In some embodiments, the compound of Formula (I) is Compound 7.

In some embodiments, the compound of Formula (I) is Compound 8.

In some embodiments, the compound of Formula (I) is Compound 9.

In some embodiments, the compound of Formula (I) is Compound 10.

In some embodiments, the compound of Formula (I) is Compound 11.

In some embodiments, the compound of Formula (I) is Compound 13.

In some embodiments, the compound of Formula (I) is Compound 14.

In some embodiments, the compound of Formula (I) is Compound 19.

In some embodiments, the compound of Formula (I) is Compound 20.

In some embodiments, the compound of Formula (I) is Compound 21.

In some embodiments, the compound of Formula (I) is Compound 22.

In some embodiments, the compound of Formula (I) is Compound 23.

In some embodiments, the compound of Formula (I) is Compound 24.

In some embodiments, the compound of Formula (I) is Compound 25.

In some embodiments, the compound of Formula (I) is Compound 26.

In some embodiments, the compound of Formula (I) is Compound 27.

In some embodiments, the compound of Formula (I) is Compound 28.

In some embodiments, the compound of Formula (I) is Compound 29.

In some embodiments, the compound of Formula (I) is Compound 30.

In some embodiments, the compound of Formula (I) is Compound 31.

In some embodiments, the compound of Formula (I) is Compound 32.

In some embodiments, the compound of Formula (I) is Compound 33.

In some embodiments, the compound of Formula (I) is Compound 34.

In some embodiments, the compound of Formula (I) is Compound 35.

In some embodiments, the compound of Formula (I) is Compound 36.

In some embodiments, the compound of Formula (I) is Compound 37.

In some embodiments, the compound of Formula (I) is Compound 38.

In some embodiments, the compound of Formula (I) is Compound 39.

In some embodiments, the compound of Formula (I) is Compound 40.

In some embodiments, the compound of Formula (I) is Compound 41.

In some embodiments, the compound of Formula (I) is Compound 42.

In some embodiments, the compound of Formula (I) is Compound 43.

In some embodiments, the compound of Formula (I) is Compound 44.

In some embodiments, the compound of Formula (I) is Compound 45.

In some embodiments, the compound of Formula (I) is Compound 46.

In some embodiments, the compound of Formula (I) is Compound 47.

In some embodiments, the compound of Formula (I) is Compound 48.

In some embodiments, the compound of Formula (I) is Compound 49.

In some embodiments, the compound of Formula (I) is Compound 50.

In some embodiments, the compound of Formula (I) is Compound 51.

In some embodiments, the compound of Formula (I) is Compound 52.

In some embodiments, the compound of Formula (I) is Compound 53.

In some embodiments, the compound of Formula (I) is Compound 54.

In some embodiments, the compound of Formula (I) is Compound 55.

In some embodiments, the compound of Formula (I) is Compound 56.

In some embodiments, the compound of Formula (I) is Compound 57.

In some embodiments, the compound of Formula (I) is Compound 58.

In some embodiments, the compound of Formula (I) is Compound 59.

In some embodiments, the compound of Formula (I) is Compound 60.

In some embodiments, the compound of Formula (I) is Compound 61.

In some embodiments, the compound of Formula (I) is Compound 68.

In some embodiments, the compound of Formula (I) is Compound 69.

In some embodiments, the compound of Formula (I) is Compound 70.

In some embodiments, the compound of Formula (I) is Compound 71.

In some embodiments, the compound of Formula (I) is Compound 72.

In some embodiments, the compound of Formula (I) is Compound 73.

In some embodiments, the compound of Formula (I) is Compound 74.

In some embodiments, the compound of Formula (I) is Compound 75.

In some embodiments, the compound of Formula (I) is Compound 77.

In some embodiments, the compound of Formula (I) is Compound 78.

In some embodiments, the compound of Formula (I) is Compound 81.

In some embodiments, the compound of Formula (I) is Compound 82.

In some embodiments, the compound of Formula (I) is Compound 83.

In some embodiments, the compound of Formula (I) is Compound 84.

In some embodiments, the compound of Formula (I) is Compound 85.

In some embodiments, the compound of Formula (I) is Compound 86.

In some embodiments, the compound of Formula (I) is Compound 87.

In some embodiments, the compound of Formula (I) is Compound 88.

In some embodiments, the compound of Formula (I) is Compound 89.

In some embodiments, the compound of Formula (I) is Compound 90.

In some embodiments, the compound of Formula (I) is Compound 91.

In some embodiments, the compound of Formula (I) is Compound 92.

In some embodiments, the compound of Formula (I) is Compound 93.

In some embodiments, the compound of Formula (I) is Compound 94.

In some embodiments, the compound of Formula (I) is Compound 95.

In some embodiments, the compound of Formula (I) is Compound 96.

In some embodiments, the compound of Formula (I) is Compound 97.

In some embodiments, the compound of Formula (I) is Compound 98.

In some embodiments, the compound of Formula (I) is Compound 99.

In some embodiments, the compound of Formula (I) is Compound 100.

In some embodiments, the compound of Formula (I) is Compound 101.

In some embodiments, the compound of Formula (I) is Compound 102.

In some embodiments, the compound of Formula (I) is Compound 103.

In some embodiments, the compound of Formula (I) is Compound 104.
In some embodiments, the compound of Formula (I) is Compound 105.
In some embodiments, the compound of Formula (I) is Compound 106.
In some embodiments, the compound of Formula (I) is Compound 107.
In some embodiments, the compound of Formula (I) is Compound 108.
In some embodiments, the compound of Formula (I) is Compound 109.
In some embodiments, the compound of Formula (I) is Compound 110.
In some embodiments, the compound of Formula (I) is Compound 111.
In some embodiments, the compound of Formula (I) is Compound 112.
In some embodiments, the compound of Formula (I) is Compound 113.
In some embodiments, the compound of Formula (I) is Compound 114.
In some embodiments, the compound of Formula (I) is Compound 115.
In some embodiments, the compound of Formula (I) is Compound 116.
In some embodiments, the compound of Formula (I) is Compound 117.
In some embodiments, the compound of Formula (I) is Compound 118.
In some embodiments, the compound of Formula (I) is Compound 119.
In some embodiments, the compound of Formula (I) is Compound 120.
In some embodiments, the compound of Formula (I) is Compound 121.
In some embodiments, the compound of Formula (I) is Compound 122.
In some embodiments, the compound of Formula (I) is Compound 123.
In some embodiments, the compound of Formula (I) is Compound 124.
In some embodiments, the compound of Formula (I) is Compound 125.
In some embodiments, the compound of Formula (I) is Compound 126.
In some embodiments, the compound of Formula (I) is Compound 127.
In some embodiments, the compound of Formula (I) is Compound 128.
In some embodiments, the compound of Formula (I) is Compound 129.
In some embodiments, the compound of Formula (I) is Compound 130.
In some embodiments, the compound of Formula (I) is Compound 131.
In some embodiments, the compound of Formula (I) is Compound 132.
In some embodiments, the compound of Formula (I) is Compound 133.
In some embodiments, the compound of Formula (I) is Compound 134.
In some embodiments, the compound of Formula (I) is Compound 135.
In some embodiments, the compound of Formula (I) is Compound 136.
In some embodiments, the compound of Formula (I) is Compound 137.
In some embodiments, the compound of Formula (I) is Compound 138.
In some embodiments, the compound of Formula (I) is Compound 139.
In some embodiments, the compound of Formula (I) is Compound 140.
In some embodiments, the compound of Formula (I) is Compound 141.
In some embodiments, the compound of Formula (I) is Compound 142.
In some embodiments, the compound of Formula (I) is Compound 143.
In some embodiments, the compound of Formula (I) is Compound 144.
In some embodiments, the compound of Formula (I) is Compound 145.
In some embodiments, the compound of Formula (I) is Compound 146.
In some embodiments, the compound of Formula (I) is Compound 147.
In some embodiments, the compound of Formula (I) is Compound 148.
In some embodiments, the compound of Formula (I) is Compound 149.
In some embodiments, the compound of Formula (I) is Compound 150.
In some embodiments, the compound of Formula (I) is Compound 151.
In some embodiments, the compound of Formula (I) is Compound 152.
In some embodiments, the compound of Formula (I) is Compound 153.
In some embodiments, the compound of Formula (I) is Compound 154.
In some embodiments, the compound of Formula (I) is Compound 155.
In some embodiments, the compound of Formula (I) is Compound 156.
In some embodiments, the compound of Formula (I) is Compound 157.
In some embodiments, the compound of Formula (I) is Compound 158.
In some embodiments, the compound of Formula (I) is Compound 159.

Payload Moieties ($R^d$) Comprising Chelated Radionuclides

Radiopharmaceuticals have increasingly become very useful tools for physicians to diagnose, stage, treat, and monitor the progression of several diseases, especially cancer. The primary difference between radiopharmaceuticals and other pharmaceutical drugs is that radiopharmaceuticals contain a radionuclide. The nuclear decay properties of the radionuclide determine whether a radiopharmaceutical will be used clinically as a diagnostic agent or as a therapeutic agent. Diagnostic radiopharmaceuticals require radionuclides that emit either gamma ($\gamma$) rays or positrons ($\beta+$), which subsequently annihilate with nearby electrons to produce two 511 keV annihilation photons emitted approximately 180° away from each other. Gamma ray-emitting radionuclides (e. g. $^{99m}$Tc $^{111}$In, $^{201}$Tl, etc.) are useful for single photon emission computed tomography (SPECT), while positron-emitting radionuclides (e. g. $^{18}$F, $^{89}$Zr, $^{68}$Ga, etc.) are useful for positron emission tomography (PET).

In contrast, therapeutic radiopharmaceuticals require radionuclides that emit particulate radiation, such as alpha ($\alpha$) particles, beta ($\beta$) particles, or Auger electrons. These particles, which strongly interact with target tissues (e.g. cancerous tumor) and lead to extensive localized ionization, can damage chemical bonds in DNA molecules and potentially induce cytotoxicity.

For most nuclear medicine applications, it is desired that a diagnostic radiopharmaceutical is paired with a therapeutic radiopharmaceutical. This concept is commonly known as "theranostics". As a first step in the theranostic concept, a target molecule labeled with a diagnostic radionuclide is used for quantitative imaging of a tumor imaging biomarker, using positron emission tomography (PET) or single photon emission computed tomography (SPECT). When it is demonstrated that, with this targeted molecule, a tumoricidal radiation absorbed dose can be delivered to tumor and metastases, as a second step, the administration of the same or a similar target molecule labeled with a therapeutic radionuclide will be conducted.

In some embodiments, the chemical and pharmacokinetic behaviors of both the diagnostic and therapeutic radiopharmaceuticals match. In some embodiments, the diagnostic and therapeutic radionuclides are a chemically identical radioisotope pair (also known as a "matched pair"). One examples of a matched pair for theranostic radiopharmaceutical applications is the $^{123}$I/$^{131}$I pair, where $^{123}$I-labeled compounds are used for diagnosis, while $^{131}$I-labeled compounds are used for therapy. Other theranostic matched pairs include $^{44}$Sc/$^{47}$Sc, $^{64}$Cu/$^{67}$Cu, $^{72}$As/$^{77}$As, $^{86}$Y/$^{90}$Y, and $^{203}$Pb/$^{212}$Pb, among others. Alternatively, radionuclide pairs from different elements can be utilized for theranostic radiopharmaceutical development when their chemistry is very similar (e.g. $^{99m}$Tc/$^{186/188}$Re) and there is no significant difference in the pharmacokinetic behavior between the diagnostic and therapeutic analogues. Another example is the $^{68}$Ga/$^{177}$Lu pair, where $^{68}$Ga is used for diagnosis and $^{177}$Lu is used for therapy. For example, gastroenteropancreatic endocrine tumors express high amounts of sst2 receptor that can be targeted with somatostatin receptor scintigraphy for diagnostic purposes with a $^{68}$Ga sst2 ligand conjugate ([$^{68}$Ga]Ga-DOTA-TATE (NETSPOT™) or [$^{68}$Ga]Ga-DOTA-TOC (DOTA-(D-Phe1,Tyr3)-octreotide, SomaKit TOC®)), followed by treatment with a $^{177}$Lu sst2 ligand conjugate ([$^{177}$Lu]Lu-DOTA-TATE) for endoradiotherapy.

Chelators for Radionuclides

As used herein, "chelator" and "chelating moiety" are used interchangeably.

In some embodiments, the chelator is capable of binding a radioactive atom. In some embodiments, the binding is direct, e.g., the chelator makes hydrogen bonds or electrostatic interactions with a radioactive atom. In some embodiments, the binding is indirect, e.g., the chelator binds to a molecule that comprises a radioactive atom. In some embodiments, the chelator is or comprises a macrocycle.

In some embodiments, the chelator comprises one or more amine groups. In some embodiments, the metal chelator comprises two or more amine groups. In some embodiments, the chelator comprises three or more amine groups. In some embodiments, the chelator comprises four or more amine groups. In some embodiments, the chelator includes 4 or more N atoms, 4 or more carboxylic acid groups, or a combination thereof. In some embodiments, the chelator does not comprise S. In some embodiments, the chelator comprises a ring. In some embodiments, the ring comprises an O and/or a N atom. In some embodiments, the chelator is a ring that includes 3 or more N atoms, 3 or more carboxylic acid groups, or a combination thereof. In some embodiments, the chelator is polydentate ligand, bidentate ligand, or monodentate ligand. Polydentate ligands range in the number of atoms used to bond to a metal atom or ion. EDTA, a hexadentate ligand, is an example of a polydentate ligand that has six donor atoms with electron pairs that can be used to bond to a central metal atom or ion. Bidentate ligands have two donor atoms which allow them to bind to a central metal atom or ion at two points. Ethylenediamine (en) and the oxalate ion (ox) are examples of bidentate ligands.

In some embodiments, a chelator described herein comprises a cyclic chelating agent or an acyclic chelating agent. In some embodiments, a chelator described herein comprises a cyclic chelating agent. In some embodiments, a chelator described herein comprises an acyclic chelating agent.

In some embodiments, the chelator is or comprises DOTA, HBED-CC, DOTAGA, DOTA(GA)2, NOTA, and DOTAM. In some embodiments, the chelator is or comprises NODAGA, NOTA, DOTAGA, DOTA(GA)2, TRAP, NOPO, NCTA, DFO, DTPA, and HYNIC.

In some embodiments, the chelator comprises a macrocycle, e.g., a macrocycle comprising an O and/or a N atom, DOTA, HBED-CC, DOTAGA, DOTA(GA)2, NOTA, DOTAM, one or more amines, one or more ethers, one or more carboxylic acids, EDTA, DTPA, TETA, DO3A, PCTA, or desferrioxamine.

In some embodiments, $R^d$ is a chelating moiety selected from the group consisting of: 1,4,7,10-tetraazacyclododecane-1,4,7,10-tetraacetic acid (DOTA); 1,4,7,10-tetraazacyclododecane-1,4,7-triacetic acid (DO3A); 1,4,7,10-tetraazacyclododecane-1,7-diacetic acid (DO2A); α,α',α",α'"-tetramethyl-1,4,7,10-tetraazacyclododecane-1,4,7,10-tetraacetic acid (DOTMA); 1,4,7,10-tetrakis(carbamoylmethyl)-1,4,7,10-tetraazacyclododecane (DOTAM); 1,4,7,10-tetraazacyclododecane-1,4,7,10-tetrapropionic acid (DOTPA); 2,2',2"-(10-(2-amino-2-oxoethyl)-1,4,7,10-tetraazacyclododecane-1,4,7-triyl)triacetic acid; benzyl-1,4,7,10-tetraazacyclododecane-1,4,7,10-tetraacetic acid (Bn-DOTA); 6,6'-(((pyridine-2,6-diylbis(methylene))bis((carboxymethyl)azanediyl))-bis(methylene))dipicolinic acid (H$_4$pypa); H$_4$pypa-benzyl; 6,6',6",6'"-(((pyridine-2,6-diylbis(methylene))bis(azanetriyl))-tetrakis(methylene))-tetrapicolinic acid (H$_4$py4pa); H$_4$py4pa-benzyl; H$_4$octapa-benzyl; 3,6,9,12-tetrakis(carboxymethyl)-3,6,9,12-tetraazatetradecanedioic acid (TTHA); or a radionuclide complex thereof.

In some embodiments, $R^d$ is 1,4,7,10-tetraazacyclododecane-1,4,7,10-tetraacetic acid (DOTA); or 1,4,7,10-tetraazacyclododecane-1,4,7-triacetic acid (DO3A); or a radionuclide complex thereof.

In some embodiments, $R^d$ is

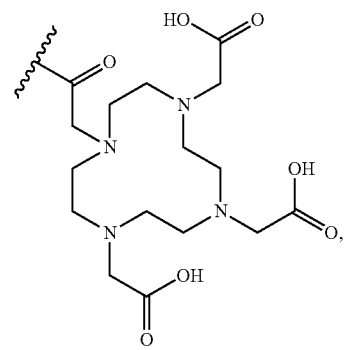

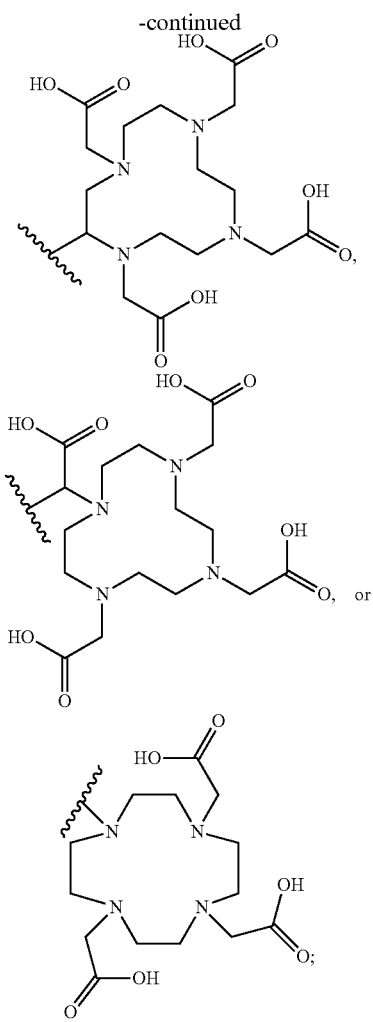

or a radionuclide complex thereof.

In some embodiments, $R^d$ is

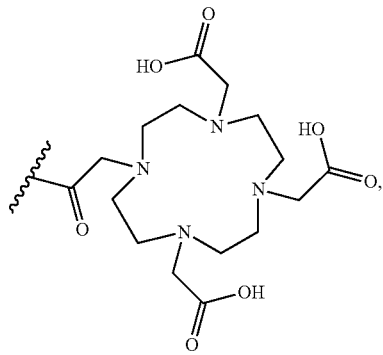 [SMILES: *C(=O)CN1CCN(CC(=O)O)CCN(CC(=O)O)CCN(CC(=O)O)CC1]

or a radionuclide complex thereof

Radionuclides

In some embodiments, the conjugate comprises an Auger electron-emitting radionuclide, α-emitting radionuclide, β-emitting radionuclide, or γ-emitting radionuclide. In some embodiments, the conjugate comprises an Auger electron-emitting radionuclide that is 111-indium ($^{111}$In), 67-gallium ($^{67}$Ga), 68gallium ($^{68}$Ga), 99m-technetium ($^{99m}$Tc), or 195m-platinum ($^{195m}$Pt). In some embodiments, the conjugate comprises an α-emitting radionuclide that is 225-actinium ($^{225}$Ac), 213-bismuth ($^{213}$Bi), 223-Radium ($^{223}$Ra), or 212-lead ($^{212}$Pb). In some embodiments, the conjugate comprises a β-emitting radionuclide that is 90-yttrium ($^{90}$Y), 177-lutetium ($^{177}$Lu), iodine-131 ($^{131}$I), 186-rhenium ($^{186}$Re), 188-rhenium ($^{188}$Re), 64-copper ($^{64}$Cu), 67-copper ($^{67}$Cu), 153-samarium ($^{153}$Sm), 89-strontium ($^{89}$Sr), 198-gold ($^{198}$Au), 169-Erbium ($^{169}$Er), 165-dysprosium ($^{165}$Dy), 99m-technetium ($^{99m}$Tc), 89-zirconium ($^{89}$Zr), or 52-manganese ($^{52}$Mn). In some embodiments, the conjugate comprises a γ-emitting radionuclide that is 60-cobalt ($^{60}$Co), 103-palldium ($^{103}$Pd), 137-cesium ($^{137}$Cs), 169-ytterbium ($^{169}$Yb), 192-iridium ($^{192}$Ir), or 226-radium ($^{226}$Ra).

In some embodiments, the conjugate comprises a radionuclide and a chelator configured to bind the radionuclide, wherein the radionuclide is suitable for positron emission tomography (PET) analysis, single-photon emission computerized tomography (SPECT), or magnetic resonance imaging (MRI). In some embodiments, the radionuclide is copper-64 ($^{64}$Cu), gallium-68 ($^{68}$Ga), 111-indium ($^{111}$In), or technetium-99m ($^{99m}$Tc). Auger electrons (AEs) are very low energy electrons that are emitted by radionuclides that decay by electron capture (EC) (e.g., $^{111}$In, $^{67}$Ga, $^{99m}$Tc, $^{195m}$Pt, $^{125}$I and $^{123}$I). This energy is deposited over nanometre-micrometre distances, resulting in high linear energy transfer that is potent for causing lethal damage in cancer cells. Thus, AE-emitting radiotherapeutic agents have great potential for treatment of cancer.

β-Particles are electrons emitted from the nucleus. They typically have a longer range in tissue (of the order of 1-5 mm) and are the most frequently used.

α-Particles are helium nuclei (two protons and two neutrons) that are emitted from the nucleus of a radioactive atom. Depending on their emission energy, they can travel 50-100 μm in tissue. They are positively charged and are orders of magnitude larger than electrons. The amount of energy deposited per path length travelled (designated 'linear energy transfer') of α-particles is approximately 400 times greater than that of electrons. This leads to substantially more damage along their path than that caused by electrons. An α-particle track leads to a preponderance of complex and largely irreparable DNA double-strand breaks. The absorbed dose required to achieve cytotoxicity relates to the number of α-particles traversing the cell nucleus. With use of this as a measure, cytotoxicity may be achieved with a range of 1 to 20 α-particle traversals of the cell nucleus. The resulting high potency, combined with the short range of α-particles (which reduces normal organ toxicity), has led to substantial interest in developing α-particle-emitting agents. The α-particle emitters typically used include bismuth-212, lead-212, bismuth-213, actinium-225, radium-223 and thorium-227.

In some embodiments, the conjugate comprises a diagnostic or therapeutic radionuclide.

| Representative Radionuclides | | |
|---|---|---|
| Isotope | Radionuclide $t_{1/2}$ (h) | Decay mode |
| $^{60}$Cu | 0.4 | β+ (93%), EC (7%) |
| $^{61}$Cu | 3.3 | β+ (62%), EC (38%) |
| $^{62}$Cu | 0.16 | β+ (98%), EC (2%) |
| $^{64}$Cu | 12.7 | β+ (19%), EC (41%), β− (40%) |
| $^{66}$Ga | 9.5 | β+ (56%), EC (44%) |
| $^{67}$Ga | 78.2 | EC (100%) |

Representative Radionuclides

| Isotope | Radionuclide $t_{1/2}$ (h) | Decay mode |
|---|---|---|
| $^{68}$Ga | 1.1 | β+ (90%), EC (10%) |
| $^{44}$Sc | 3.9 | β+ (94%), EC (6%) |
| $^{47}$Sc | 80.2 | β− (100%) |
| $^{111}$In | 67.2 | EC (100%) |
| $^{114m}$In | 49.5 d | EC (100%) |
| $^{114}$In (daughter) | 73 s | β− (100%) |
| $^{177}$Lu | 159.4 | β− (100%) |
| $^{86}$Y | 14.7 | β+ (33%), EC (66%) |
| $^{90}$Y | 64.1 | β− (100%) |
| $^{89}$Zr | 78.5 | β+ (23%), EC (77%) |
| $^{212}$Bi | 1.1 | α (36%), β− (64%) |
| $^{213}$Bi | 0.76 | α (2.2%), β− (97.8%) |
| $^{212}$Pb (daughter is $^{212}$Bi) | 10.6 | β− (100%) |
| $^{225}$Ac | 240 | α (100%) |

Radionuclides have useful emission properties that can be used for diagnostic imaging techniques, such as single photon emission computed tomography (SPECT, e.g. $^{67}$Ga, $^{99m}$Tc, $^{111}$In, $^{177}$Lu) and positron emission tomography (PET, e.g. $^{68}$Ga, $^{64}$Cu, $^{44}$Sc, $^{86}$Y, $^{89}$Zr), as well as therapeutic applications (e.g. $^{47}$Sc, $^{114m}$In, $^{177}$Lu, $^{90}$Y, $^{212/213}$Bi, $^{212}$Pb, $^{225}$Ac, $^{186/188}$Re). A fundamental component of a radiometal-based radiopharmaceutical is the chelator, the ligand system that binds the radiometal ion in a tight stable coordination complex so that it can be properly directed to a desirable molecular target in vivo. Guidance for selecting the optimal match between chelator and radiometal for a particular use is provided in the art (e.g. see Price et al., "Matching chelators to radiometals for radiopharmaceuticals", Chem. Soc. Rev., 2014, 43, 260-290).

In some embodiments, $R^d$ comprises a chelated radionuclide that is suitable for positron emission tomography (PET) analysis or single-photon emission computerized tomography (SPECT). In some embodiments, $R^d$ comprises a chelated radionuclide that is suitable for single-photon emission computerized tomography (SPECT). In some embodiments, $R^d$ comprises a chelated radionuclide that is suitable for positron emission tomography (PET) analysis. In some embodiments, $R^d$ comprises a chelated radionuclide that is suitable for positron emission tomography imaging, positron emission tomography with computed tomography imaging, or positron emission tomography with magnetic resonance imaging.

Response and toxicity prediction is essential for the rational implementation of cancer therapy. The biological effects of radionuclide therapy are mediated by a well-defined physical quantity, the absorbed dose (D), which is defined as the energy absorbed per unit mass of tissue.

Radiation dosimetry is the measurement, calculation and assessment of the ionizing radiation dose absorbed by an object, usually the human body, and may be thought of as the ability to perform the equivalent of a pharmacodynamic study in treated patients in real time. This applies both internally, due to ingested or inhaled radioactive substances, or externally due to irradiation by sources of radiation. Dosimetry analysis may be performed as part of patient treatment to calculate tumour versus normal organ absorbed dose and therefore the likelihood of treatment success.

In some embodiments, $R^d$ is

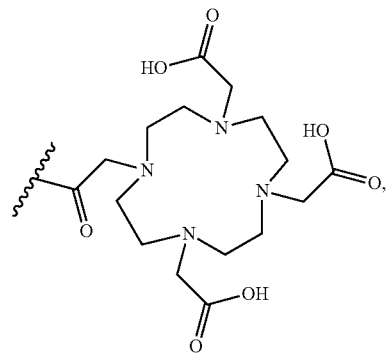 [SMILES: *C(=O)CN1CCN(CC(=O)O)CCN(CC(=O)O)CCN(CC(=O)O)CC1]

or a radionuclide complex thereof.

In some embodiments, -L-$R^d$ is: —CH$_2$CH$_2$NH—$R^d$, —C(=O)CH$_2$NH—$R^d$, —C(=O)CH$_2$CH$_2$NH—$R^d$, —CH$_2$CH$_2$(OCH$_2$CH$_2$)$_2$NH—$R^d$, —CH$_2$CH$_2$(OCH$_2$CH$_2$)$_3$NH—$R^d$, —CH$_2$CH$_2$(OCH$_2$CH$_2$)$_4$NH—$R^d$, —CH$_2$CH$_2$(OCH$_2$CH$_2$)$_5$NH—$R^d$, —CH$_2$CH$_2$(OCH$_2$CH$_2$)$_6$NH—$R^d$, —CH$_2$CH$_2$(OCH$_2$CH$_2$)$_7$NH—$R^d$, —CH$_2$CH$_2$(OCH$_2$CH$_2$)$_8$NH—$R^d$, —C(=O)CH$_2$CH$_2$(OCH$_2$CH$_2$)$_2$NH—$R^d$, —C(=O)CH$_2$CH$_2$(OCH$_2$CH$_2$)$_3$NH—$R^d$, —C(=O)CH$_2$CH$_2$(OCH$_2$CH$_2$)$_4$NH—$R^d$, —C(=O)CH$_2$CH$_2$(OCH$_2$CH$_2$)$_5$NH—$R^d$, —C(=O)CH$_2$CH$_2$(OCH$_2$CH$_2$)$_6$NH—$R^d$, —C(=O)CH$_2$CH$_2$(OCH$_2$CH$_2$)$_7$NH—$R^d$, or —C(=O)CH$_2$CH$_2$(OCH$_2$CH$_2$)$_8$NH—$R^d$;

$R^d$ is

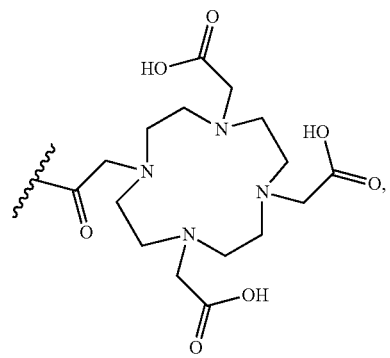 [SMILES: *C(=O)CN1CCN(CC(=O)O)CCN(CC(=O)O)CCN(CC(=O)O)CC1]

or a radionuclide complex thereof.

In some embodiments, -L$^1$-$R^d$ is: -(PEG2)NH—$R^d$, -(PEG3)NH—$R^d$, -(PEG4)NH—$R^d$, -(PEG5)NH—$R^d$, -(PEG6)NH—$R^d$, -(PEG7)NH—$R^d$, -(PEG8)NH—$R^d$, —C(=O)(PEG2)NH—$R^d$, —C(=O)(PEG3)NH—$R^d$, —C(=O)(PEG4)NH—$R^d$, —C(=O)(PEG5)NH—$R^d$, —C(=O)(PEG6)NH—$R^d$, —C(=O)(PEG7)NH—$R^d$, or —C(=O)(PEG8)NH—$R^d$.

$R^d$ is

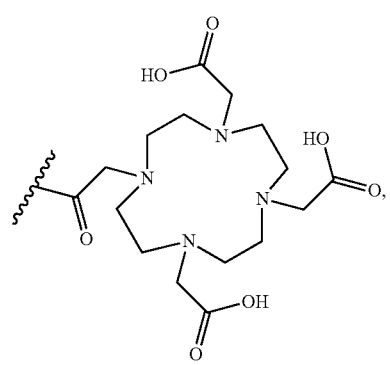 [SMILES: *C(=O)CN1CCN(CC(=O)O)CCN(CC(=O)O)CCN(CC(=O)O)CC1]

or a radionuclide complex thereof.

In some embodiments, -L¹-R$^d$ is:
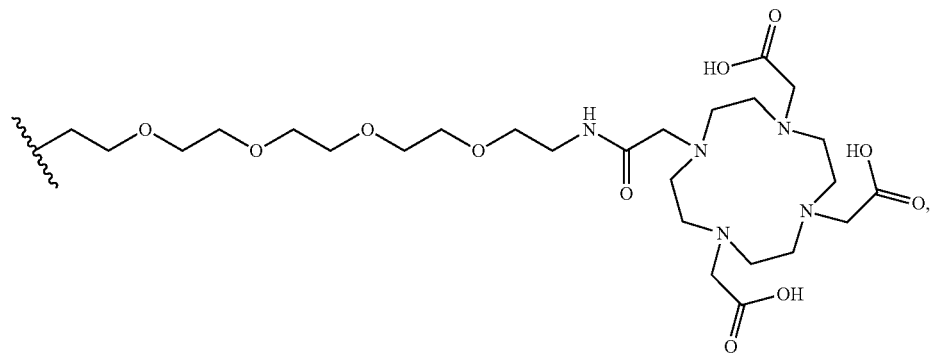
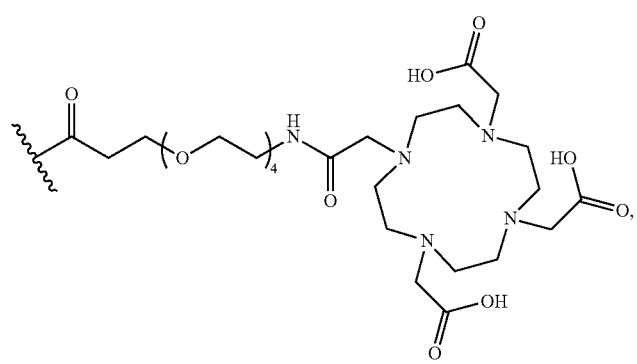
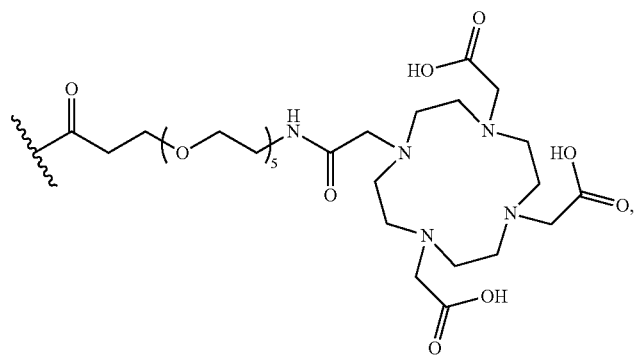
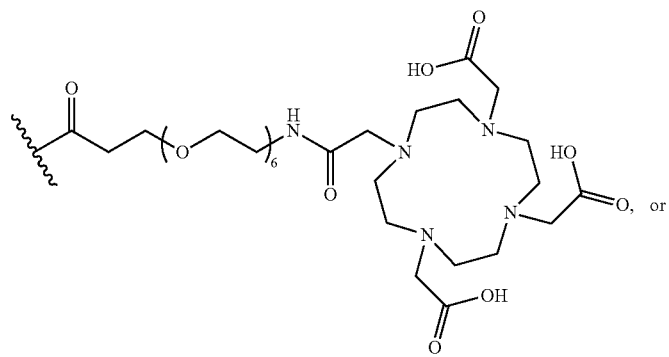

-continued

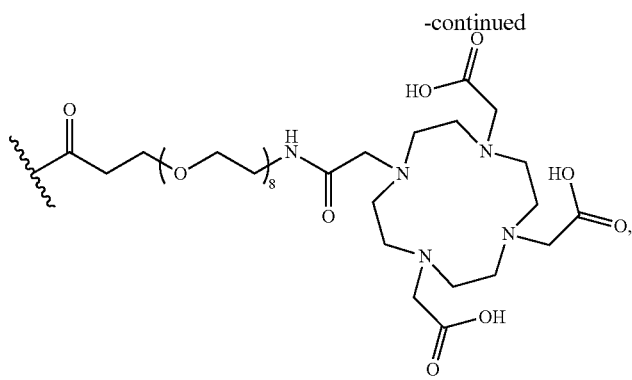

or a radionuclide complex thereof.

In some embodiments, the radionuclide of the radionuclide complex is a lanthanide or an actinide.

In some embodiments, the radionuclide of the radionuclide complex is actinium, bismuth, cesium, cobalt, copper, dysprosium, erbium, gold, indium, iridium, gallium, lead, lutetium, manganese, palladium, platinum, radium, rhenium, samarium, strontium, technetium, ytterbium, yttrium, or zirconium.

In some embodiments, the radionuclide of the radionuclide complex is a diagnostic or therapeutic radionuclide.

In some embodiments, the radionuclide of the radionuclide complex is an Auger electron-emitting radionuclide, α-emitting radionuclide, β-emitting radionuclide, or γ-emitting radionuclide.

In some embodiments, the radionuclide of the radionuclide complex is copper-64 ($^{64}$Cu), 67-copper ($^{67}$Cu), 111-indium ($^{111}$In), 115-indium ($^{115}$In), 67-gallium ($^{67}$Ga), 68-gallium ($^{68}$Ga), 70-gallium ($^{70}$Ga), 225-actinium ($^{225}$Ac), 175-lutetium ($^{175}$Lu), 177-lutetium ($^{177}$Lu), or 212-lead ($^{212}$Pb).

In some embodiments, the radionuclide of the radionuclide complex is 111-indium ($^{111}$In), 115-indium ($^{115}$In), 67-gallium ($^{67}$Ga), 68-gallium ($^{68}$Ga), 70-gallium ($^{70}$Ga), 225-actinium ($^{225}$Ac), 175-lutetium ($^{175}$Lu), or 177-lutetium ($^{177}$Lu).

Synthesis of Compounds

Compounds described herein are synthesized using standard synthetic techniques or using methods known in the art in combination with methods described herein.

Unless otherwise indicated, conventional methods of mass spectroscopy, NMR, and HPLC are employed.

Compounds are prepared using standard organic chemistry techniques such as those described in, for example, March's Advanced Organic Chemistry, 6$^{th}$ Edition, John Wiley and Sons, Inc. Alternative reaction conditions for the synthetic transformations described herein may be employed such as variation of solvent, reaction temperature, reaction time, as well as different chemical reagents and other reaction conditions.

In one aspect, compounds described herein are in the form of pharmaceutically acceptable salts.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19.

In some embodiments, pharmaceutically acceptable salts are obtained by reacting a compound of Formula (I) with an acid. In some embodiments, the compound of Formula (I) (i.e. free base form) is basic and is reacted with an organic acid or an inorganic acid.

In some embodiments, pharmaceutically acceptable salts are obtained by reacting a compound of Formula (I) with a base. In some embodiments, the compound of Formula (I) is acidic and is reacted with a base. In such situations, an acidic proton of the compound of Formula (I) is replaced by a metal ion.

In some embodiments, the compounds of Formula (I) possess one or more stereocenters and each stereocenter exists independently in either the R or S configuration. In some embodiments, the compound of Formula (I) exists in the R configuration. In some embodiments, the compound of Formula (I) exists in the S configuration. The compounds presented herein include all diastereomeric, individual enantiomers, atropisomers, and epimeric forms as well as the appropriate mixtures thereof. The compounds and methods provided herein include all cis, trans, syn, anti, entgegen (E), and zusammen (Z) isomers as well as the appropriate mixtures thereof.

Individual stereoisomers are obtained, if desired, by methods such as, stereoselective synthesis and/or the separation of stereoisomers by chiral chromatographic columns or the separation of diastereomers by either non-chiral or chiral chromatographic columns or crystallization and recrystallization in a proper solvent or a mixture of solvents. In certain embodiments, compounds of Formula (I) are prepared as their individual stereoisomers by reacting a racemic mixture of the compound with an optically active resolving agent to form a pair of diastereoisomeric compounds/salts, separating the diastereomers and recovering the optically pure individual enantiomers. In some embodiments, resolution of individual enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In some embodiments, stereoisomers are obtained by stereoselective synthesis.

In some embodiments, cytotoxic SMDCs of the present invention, described herein, are prepared as described in the schemes A-F. In the schemes below "X" and the carbonyl moieties on either side of "X" represent spacer moiety L¹.
Scheme A
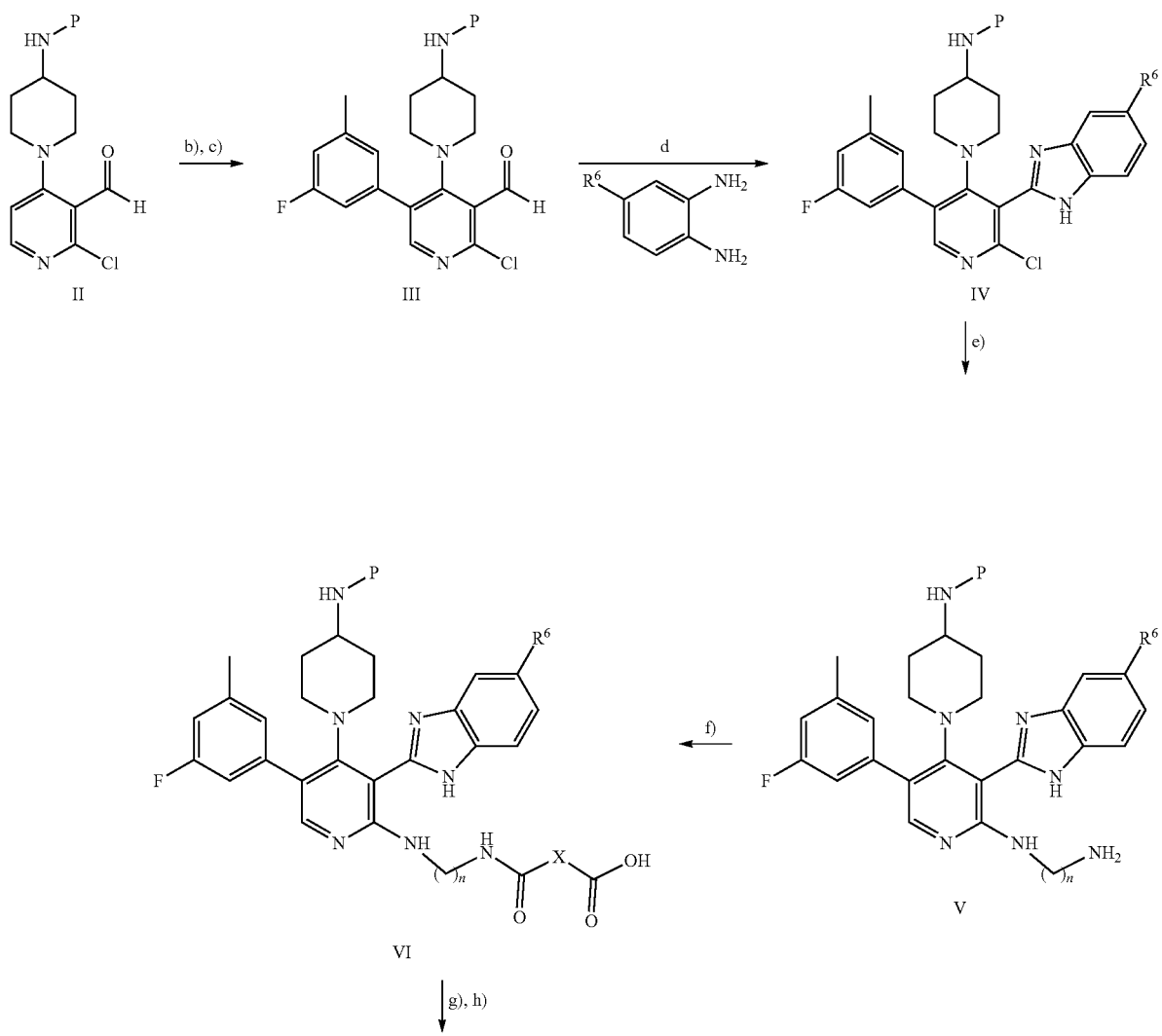

225 226
-continued
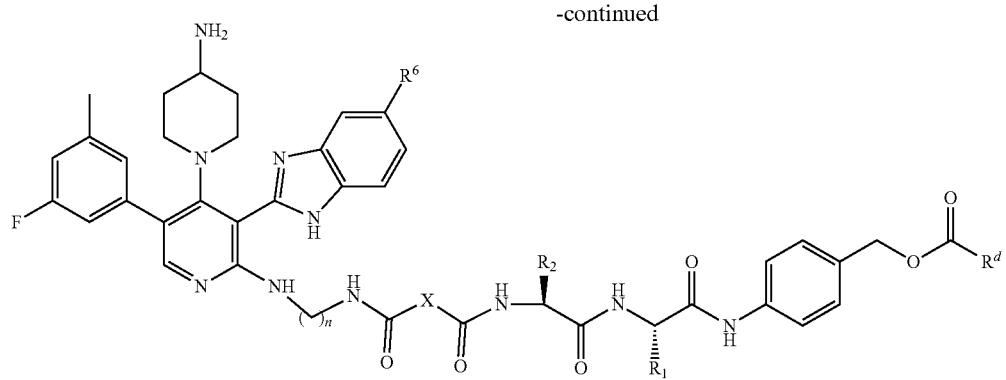
VII
a) DIEA, ACN; b) NBS, DMF; c) (3-fluoro-5-methylphenyl)boronic acid, Pd, toluene/H$_2$O. cat;
d) DMF/H$_2$O; e) NH$_2$(CH$_2$)$_n$NH$_2$, 2,6-lutidine; f) Acid, FDPP, NMM, DMF; g) Val-Cit-PAB-MMAE, FDPP, NMM, DMF; h) deprotection.
P = protecting group
Scheme B
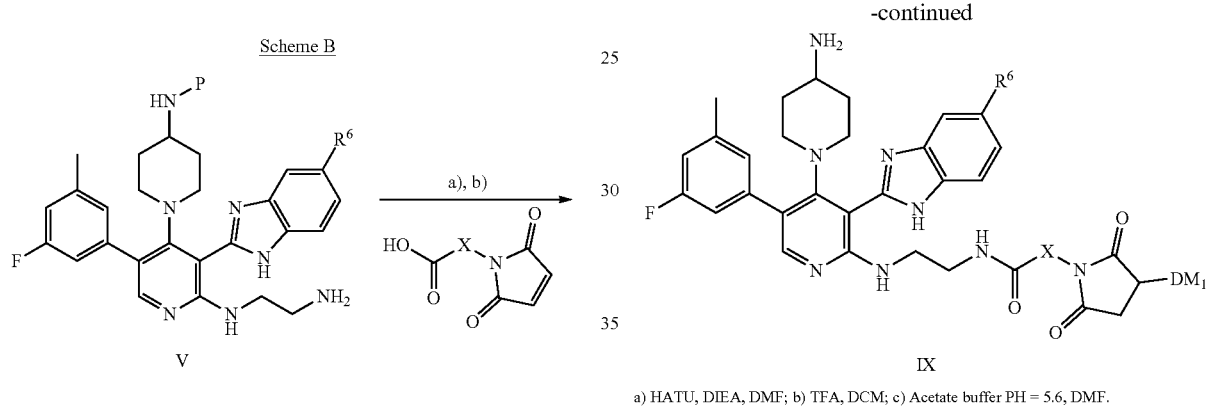
a) HATU, DIEA, DMF; b) TFA, DCM; c) Acetate buffer PH = 5.6, DMF.
Scheme C
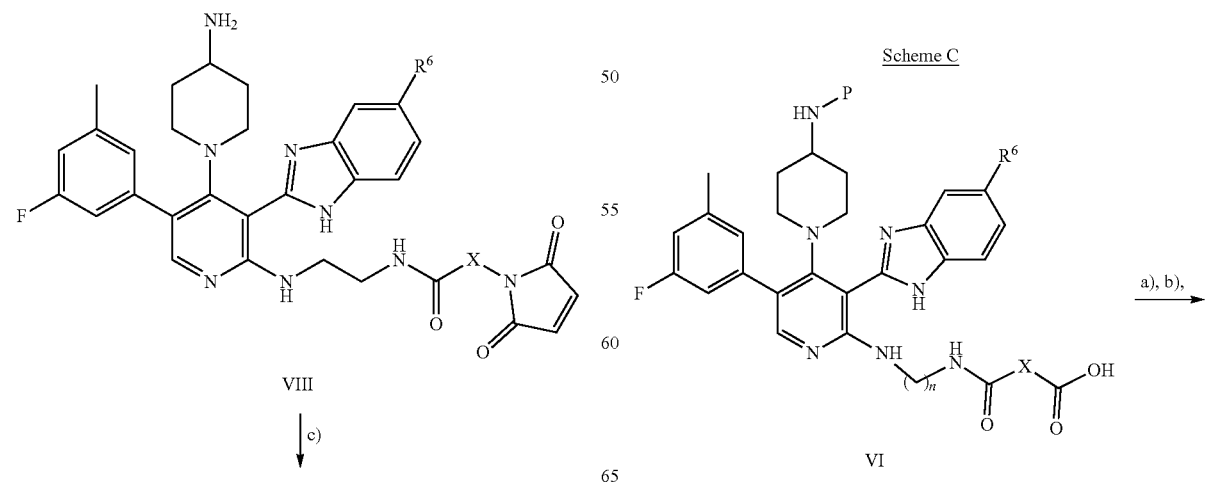

227
-continued
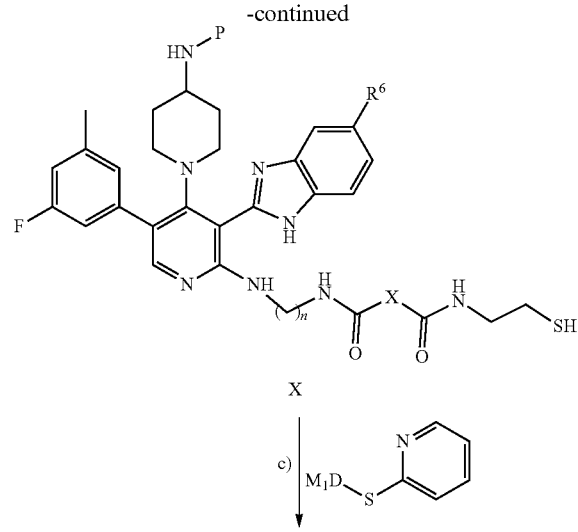
X
228
-continued
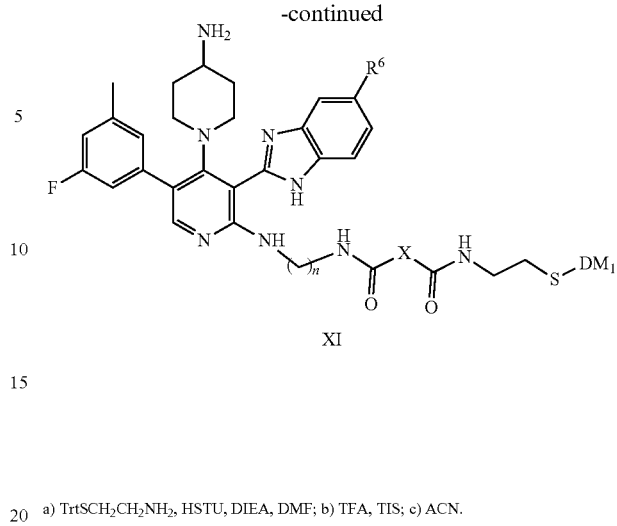
XI
a) TrtSCH$_2$CH$_2$NH$_2$, HSTU, DIEA, DMF; b) TFA, TIS; c) ACN.
Scheme D
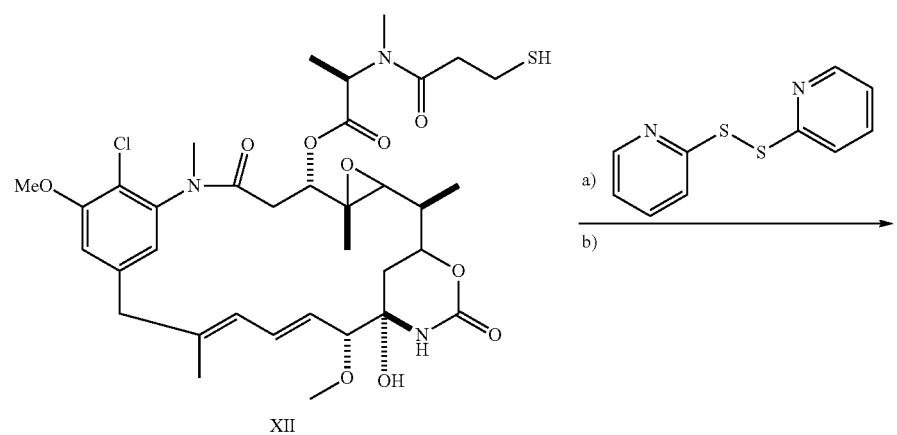
XII
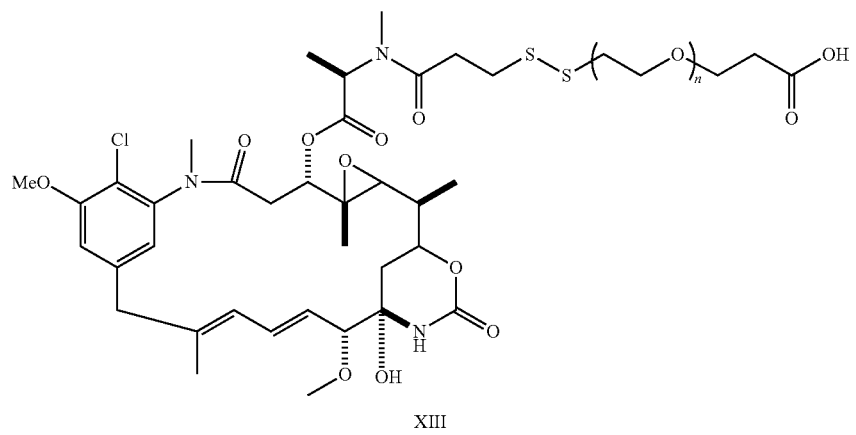
XIII -continued
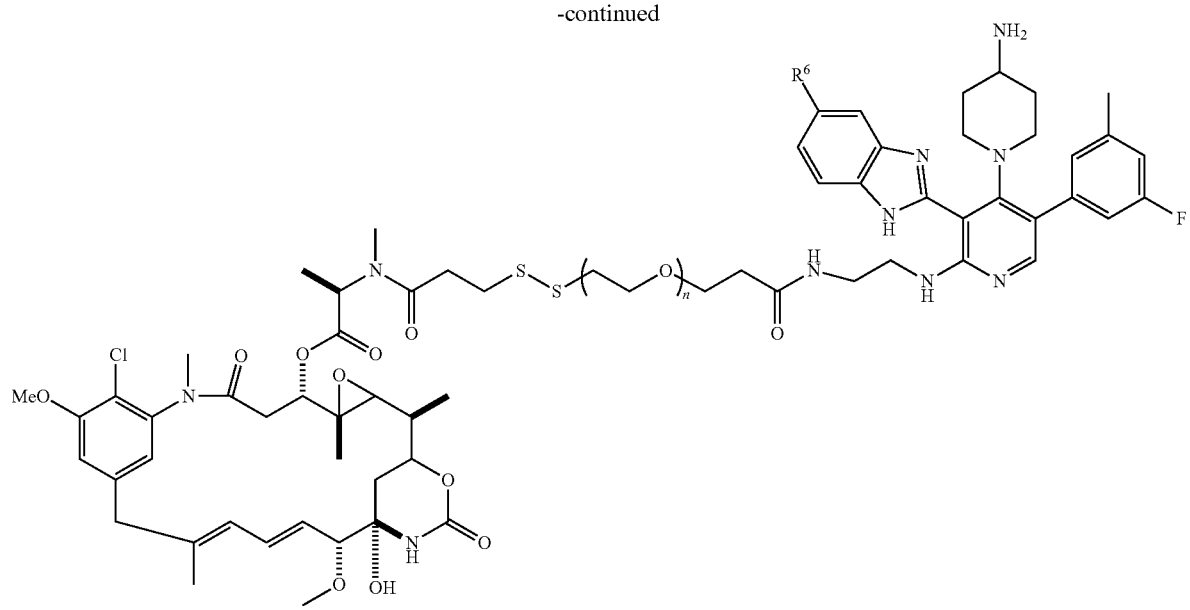
XIV
a) AcOH, DMF, 0.2M NaOAc; b) HO(O)C(CH2CH2O)$_n$CH$_2$CH$_2$SH, MeOH, DCM; c) compound V, HATU, DIEA, DMF; d) ZnBr$_2$, DCM.
Scheme E
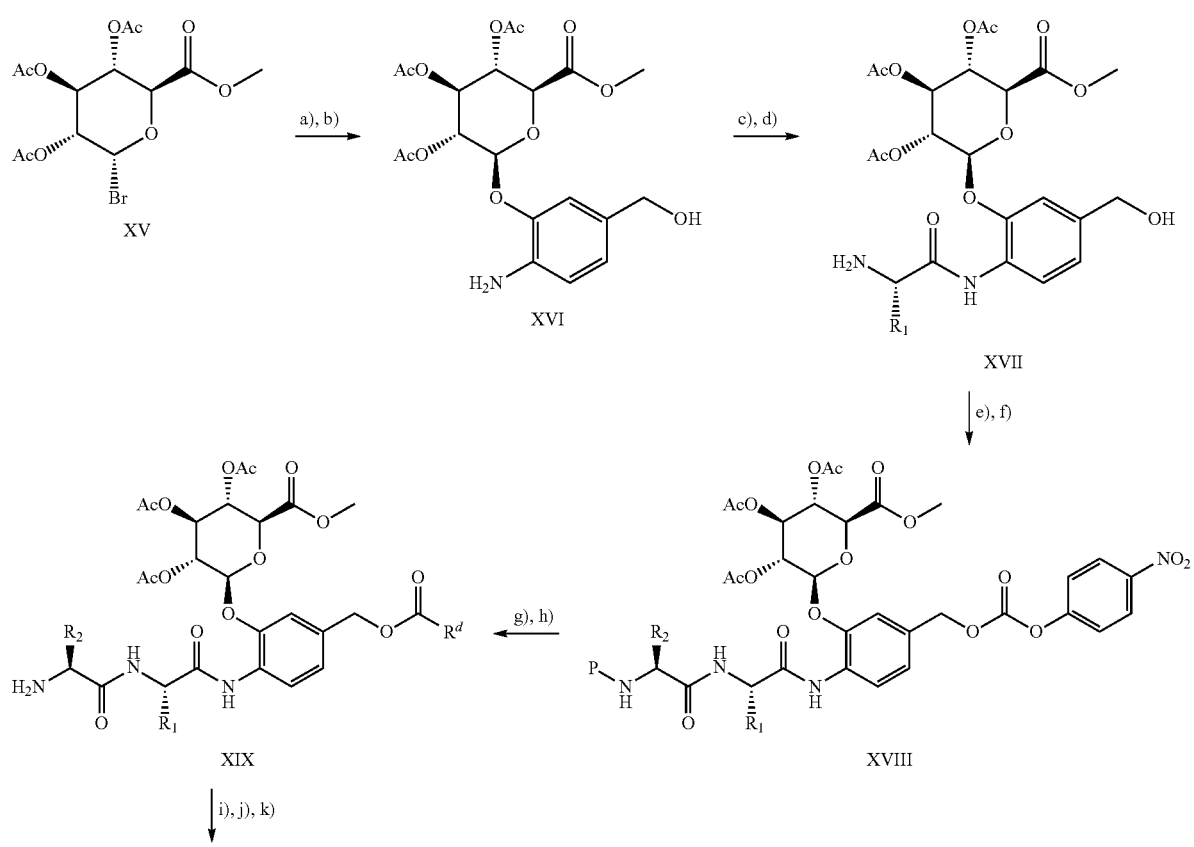

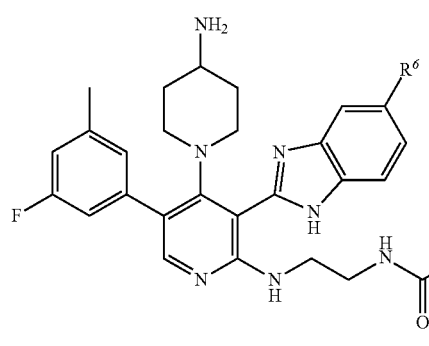
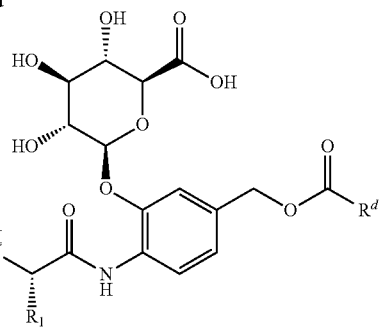

XX a) 3-hydroxy-4-nitrobenzaldehyde, Ag$_2$O; b) H$_2$, Pd/C; c) protected-amino acid, EEDQ; d) deprotection; e) HATU, protected-amino acid; f) (p-NO$_2$C$_6$H$_4$O)$_2$CO, THF; g) R$^d$, HOBT, DIEA; h) deprotection; i) compound VI, FDPP, NMM, DMF; j) LiOH, THF; k) deprotection.

Scheme F

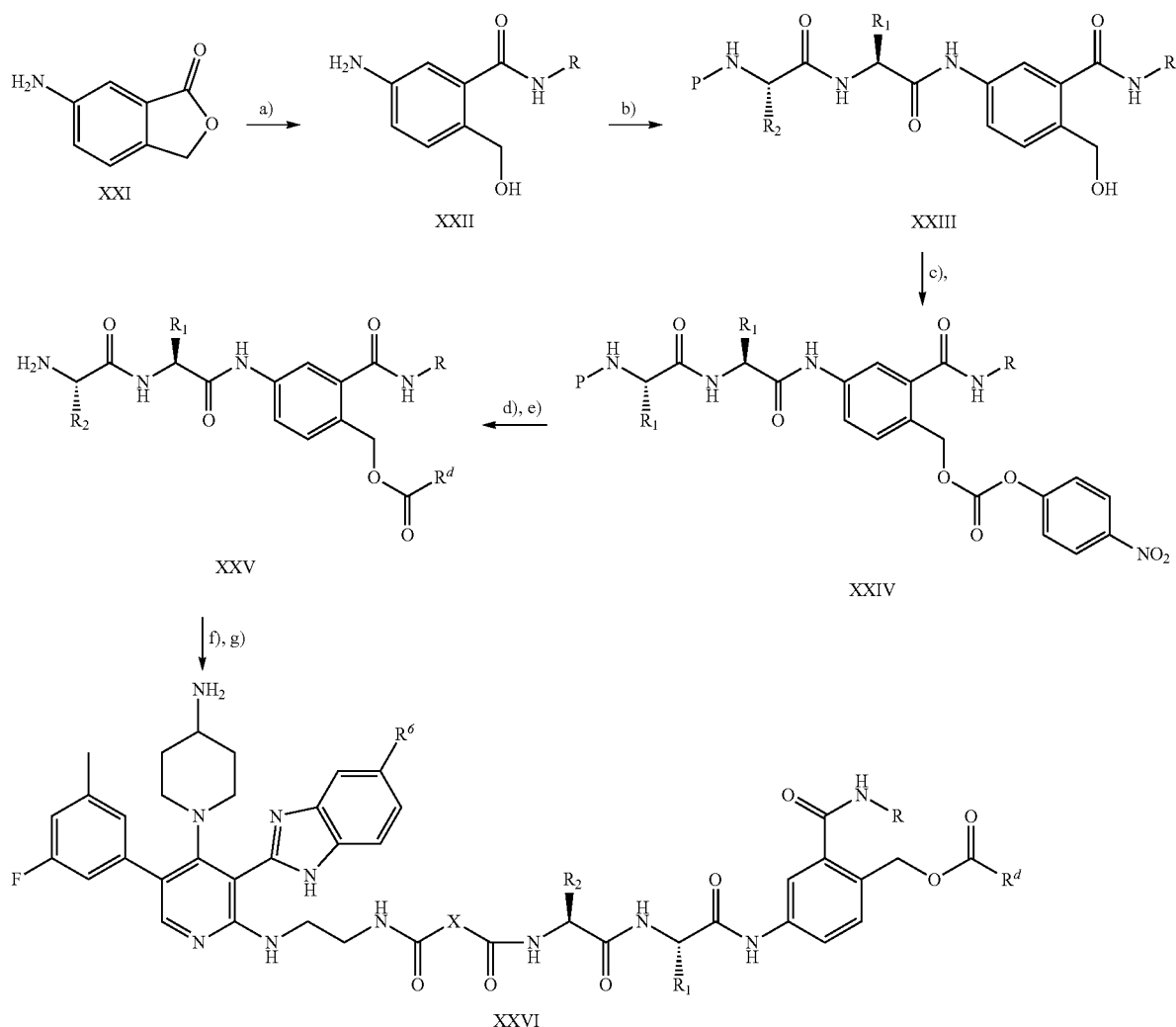

a) NHR, MeOH; b) protected-amino acid, EEDQ, DCM; c) PNP—CO$_3$, DIEA, DMF; d) R$^d$, HOBT, DIEA, DMF; e) deprotection; f) compound V, FDPP, NMM, DMF; g) deprotection.

In some embodiments, radionucleide SMDCs of the present invention, described herein, are prepared as described in the schemes G-H.
Scheme G
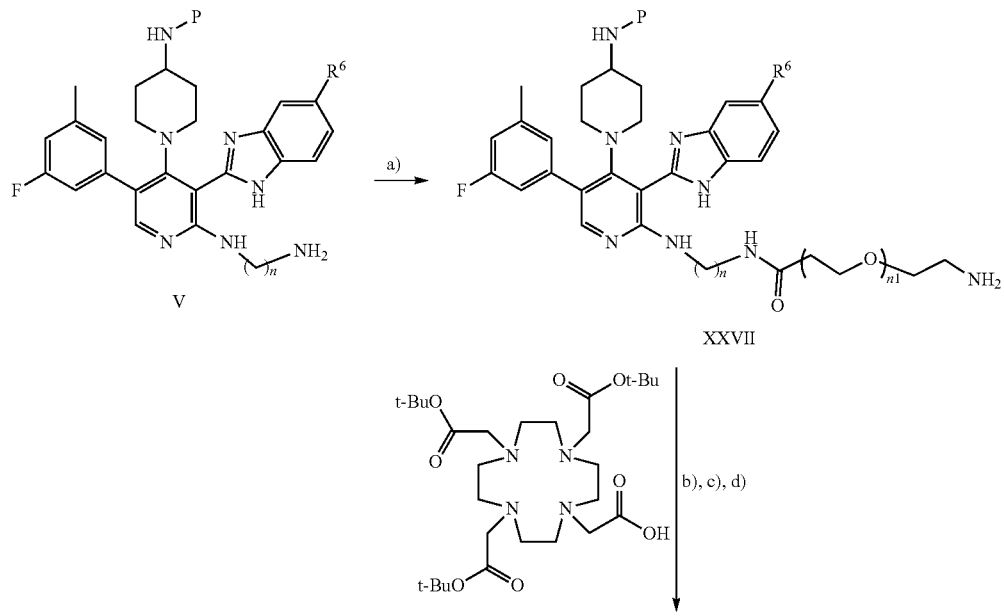
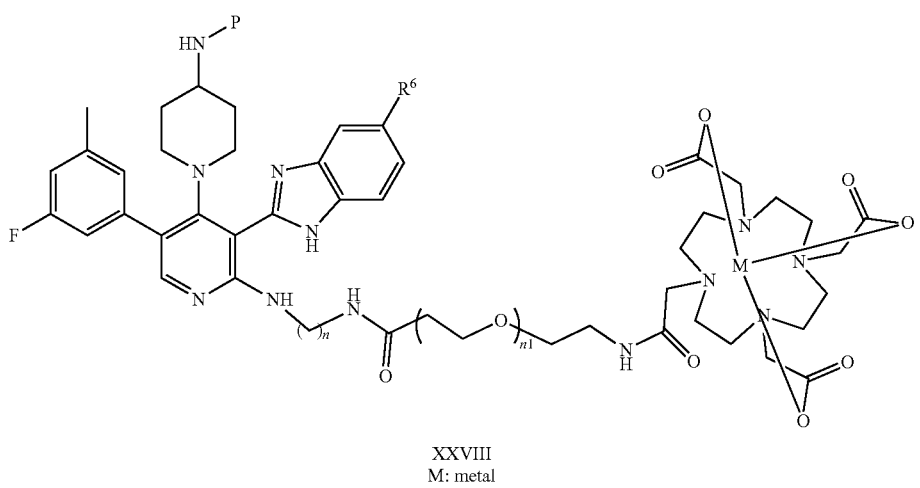
XXVIII
M: metal
a) HO(O)C(CH₂CH₂O)ₙNH₂; b) DOTA(OtBu)₃, HATU, DIEA, DMF; c) TFA; d) Metal chloride, NaHCO₃, ACN/H₂O.

Scheme H

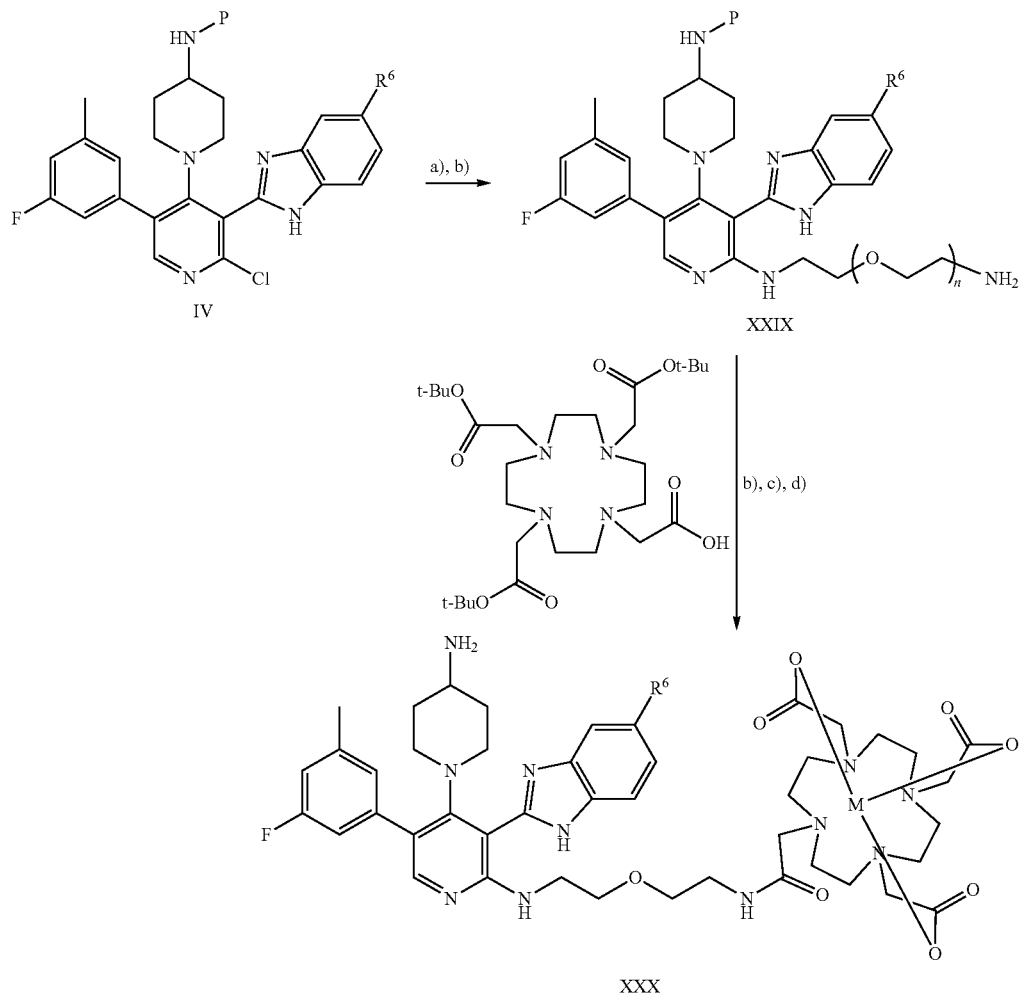

XXX
M: metal a) NH₂(CH₂CH₂O)ₙNHBoc; b) TFA, DCM; c) DOTA(OtBu)₃, HATU, DIEA, DMF; d) TFA; e) Metal chloride, NaHCO₃, ACN/H2O.

Pharmaceutical Compositions

In some embodiments, the compounds described herein are formulated into pharmaceutical compositions.

In some embodiments, the compounds described herein are administered either alone or in combination with pharmaceutically acceptable carriers, excipients or diluents, in a pharmaceutical composition.

Methods of Treatment

In some embodiments, the methods comprise administering to a subject a therapeutically effective amount of a compound of Formula (I) or a pharmaceutically acceptable salt thereof. In some embodiments, the compound of Formula (I) or pharmaceutically acceptable salt thereof is administered in a pharmaceutical composition. In some embodiments, the subject has cancer. In some embodiments, the cancer is a solid tumor or hematological cancer. In some embodiments, the subject has a noncancerous tumor. In some embodiments, the subject has an adenoma.

In embodiments, the treatment is sufficient to reduce or inhibit the growth of the subject's tumor, reduce the number or size of metastatic lesions, reduce tumor load, reduce primary tumor load, reduce invasiveness, prolong survival time, or maintain or improve the quality of life, or combinations thereof.

In some embodiments, provided herein are methods for killing a tumor cell comprising contacting the tumor cell with a compound of Formula (I) or a pharmaceutically acceptable salt thereof.

In one aspect, provided herein are methods and compositions for treating cancers. Cancer includes tissue and organ carcinogenesis including metastases such as for example gastrointestinal cancer, (e.g., gastric cancer, esophageal cancer, pancreatic cancer colorectal cancer, intestinal cancer, anal cancer, liver cancer, gallbladder cancer, or colon cancer; lung cancer; thyroid cancer; skin cancer (e.g., melanoma); oral cancer; urinary tract cancer (e.g. bladder cancer or kidney cancer); blood cancer (e.g. myeloma or leukemia) or prostate cancer. In some embodiments, the present disclosure provides methods and compositions for treating gastrointestinal cancer in a subject in need thereof by administering an effective amount of a non-peptide targeted therapeutic compound disclosed herein to the subject. Non-limiting examples of gastrointestinal cancers that can be treated according to the methods of the present disclosure include gastric cancer, esophageal cancer, pancreatic cancer, lung cancer (small cell lung cancer and/or non small-cell lung cancer), colorectal cancer, intestinal cancer, anal cancer, liver cancer, gallbladder cancer, or colon cancer. In some embodiments, the cancer is Hodkin's lymphoma or B-cell lymphoma.

In one aspect, provided herein are methods and compositions for treating an adenoma.

In one aspect, provided herein are methods and compositions for treating a peptide hormone G protein-coupled receptor expressing cancer. In some embodiments, the peptide hormone G protein-coupled receptor-expressing cancer to be treated is a primary or metastatic cancer of gastrointestinal origin, such as colorectal cancer, stomach cancer, small intestine cancer, or esophageal cancer. In some embodiments, the peptide hormone G protein-coupled receptor-expressing cancer to be treated is primary or metastatic pancreatic cancer. In some embodiments, the peptide hormone G protein-coupled receptor-expressing cancer to be treated is primary or metastatic lung cancer, such as squamous cell carcinoma, adenosquamous carcinoma, or adenocarcinoma. In some embodiments, the peptide hormone G protein-coupled receptor-expressing cancer to be treated is a sarcoma, such as leiomyosarcoma or rhabdomyosarcoma. In some embodiments, the peptide hormone G protein-coupled receptor-expressing cancer to be treated is a primary or metastasized neuroectodermal tumor, such as aphaechromotcytoma or a paraganglioma. In some embodiments, the peptide hormone G protein-coupled receptor-expressing cancer is a primary or a metastasized bronchopulmonary or a gastrointestinal neuroendocrine tumor. In some embodiments, the cancer is colorectal cancer.

In another aspect, provided herein is a method for treating cancer in a mammal comprising administering to the mammal in need thereof, a non-peptide targeted therapeutic compound disclosed herein. In some embodiments, the cancer expresses one or more peptide hormone G protein-coupled receptors. In some embodiments, the cancer comprises a peptide hormone G protein-coupled receptor-positive cancer. In some embodiments, the cancer comprises a solid tumor. In some embodiments, the cancer comprises a sarcoma, carcinoma, or lymphoma. In some embodiments, the cancer comprises a neuroendocrine tumor. In some embodiments, the cancer comprises an insulinoma. In some embodiments, the cancer comprises peptide hormone G protein-coupled receptor-positive (e.g., somatostatin receptor-positive) gastroenteropancreatic neuroendocrine tumors (GEP-NETs).

Methods of Dosing and Treatment Regimens

In one embodiment, compounds of Formula (I), or a pharmaceutically acceptable salt thereof, are used in the preparation of medicaments for the treatment of tumors in a mammal. Methods for treating any of the diseases or conditions described herein in a mammal in need of such treatment, involves administration of pharmaceutical compositions that include at least one compound of Formula (I) or a pharmaceutically acceptable salt thereof in therapeutically effective amounts to said mammal.

In some embodiments, the conjugate or pharmaceutically acceptable salt thereof is administered in combination with another therapeutic agent. In certain embodiments the therapeutic agent is a chemotherapeutic agent. Chemotherapeutic agents include, but are not limited to, lutetium Lu 177 dotatate (LUTATHERA®).

Certain Terminology

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

As used herein, $C_1$-$C_x$ includes $C_1$-$C_2$, $C_1$-$C_3$ ... $C_1$-$C_x$. By way of example only, a group designated as "$C_1$-$C_6$" indicates that there are one to six carbon atoms in the moiety, i.e. groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

An "alkyl" group refers to an aliphatic hydrocarbon group. The alkyl group is branched or straight chain. In some embodiments, the "alkyl" group has 1 to 10 carbon atoms, i.e. a $C_1$-$C_{10}$alkyl. Whenever it appears herein, a numerical range such as "1 to 10" refers to each integer in the given range; e.g., "1 to 10 carbon atoms" means that the alkyl group consist of 1 carbon atom, 2 carbon atoms, 3 carbon atoms, etc., up to and including 10 carbon atoms, although the present definition also covers the occurrence of the term "alkyl" where no numerical range is designated. In some embodiments, an alkyl is a $C_1$-$C_6$alkyl. In one aspect the alkyl is methyl, ethyl, propyl, iso-propyl, n-butyl, iso-butyl, sec-butyl, or t-butyl. Typical alkyl groups include, but are in no way limited to, methyl, ethyl, propyl, isopropyl, butyl, isobutyl, sec-butyl, tertiary butyl, pentyl, neopentyl, or hexyl.

An "alkylene" group refers to a divalent alkyl radical. Any of the above mentioned monovalent alkyl groups may be an alkylene by abstraction of a second hydrogen atom from the alkyl. In some embodiments, an alkylene is a $C_1$-$C_6$alkylene. In other embodiments, an alkylene is a $C_1$-$C_4$alkylene. Typical alkylene groups include, but are not limited to, —CH$_2$—, —CH$_2$CH$_2$—, —CH$_2$CH$_2$CH$_2$—, —CH$_2$CH$_2$CH$_2$CH$_2$—, and the like. In some embodiments, an alkylene is —CH$_2$—.

An "alkoxy" group refers to a (alkyl)O— group, where alkyl is as defined herein.

The term "alkenyl" refers to a type of alkyl group in which at least one carbon-carbon double bond is present. In one embodiment, an alkenyl group has the formula —C(R)=CR$_2$, wherein R refers to the remaining portions of the alkenyl group, which may be the same or different. In some embodiments, R is H or an alkyl. In some embodiments, an alkenyl is selected from ethenyl (i.e., vinyl), propenyl (i.e., allyl), butenyl, pentenyl, pentadienyl, and the like. Non-limiting examples of an alkenyl group include —CH=CH$_2$, —C(CH$_3$)=CH$_2$, —CH=CHCH$_3$, —C(CH$_3$)=CHCH$_3$, and —CH$_2$CH=CH$_2$.

The term "alkynyl" refers to a type of alkyl group in which at least one carbon-carbon triple bond is present. In one embodiment, an alkenyl group has the formula —C≡C—R, wherein R refers to the remaining portions of the alkynyl group. In some embodiments, R is H or an alkyl. In some embodiments, an alkynyl is selected from ethynyl, propynyl, butynyl, pentynyl, hexynyl, and the like. Non-limiting examples of an alkynyl group include —C≡CH, —C≡CCH$_3$—C≡CCH$_2$CH$_3$, —CH$_2$C≡CH.

The term "heteroalkyl" refers to an alkyl group in which one or more skeletal atoms of the alkyl are selected from an atom other than carbon, e.g., oxygen, nitrogen (e.g. —NH—, —N(alkyl)-, sulfur, or combinations thereof. A heteroalkyl is attached to the rest of the molecule at a carbon atom of the heteroalkyl. In one aspect, a heteroalkyl is a $C_1$-$C_6$heteroalkyl.

The term "carbocyclic" or "carbocycle" refers to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, at least one of the two rings of a bicyclic carbocycle is aromatic. In some embodiments, both rings of a bicyclic carbocycle are aromatic. Carbocycles include aryls and cycloalkyls.

As used herein, the term "aryl" refers to an aromatic ring wherein each of the atoms forming the ring is a carbon atom. In one aspect, aryl is phenyl or a naphthyl. In some embodiments, an aryl is a phenyl. In some embodiments, an aryl is a phenyl, naphthyl, indanyl, indenyl, or tetrahydronaphthyl. In some embodiments, an aryl is a $C_6$-$C_{10}$aryl. Depending on the structure, an aryl group is a monoradical or a diradical (i.e., an arylene group).

The term "cycloalkyl" refers to a monocyclic or polycyclic aliphatic, non-aromatic radical, wherein each of the atoms forming the ring (i.e. skeletal atoms) is a carbon atom. In some embodiments, cycloalkyls are spirocyclic or bridged compounds. In some embodiments, cycloalkyls are optionally fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, norbornyl and bicycle[1.1.1] pentyl. In some embodiments, a cycloalkyl is a $C_3$-$C_6$cycloalkyl. In some embodiments, a cycloalkyl is a $C_3$-$C_4$cycloalkyl.

The term "halo" or, alternatively, "halogen" or "halide" means fluoro, chloro, bromo or iodo. In some embodiments, halo is fluoro, chloro, or bromo.

The term "fluoroalkyl" refers to an alkyl in which one or more hydrogen atoms are replaced by a fluorine atom. In one aspect, a fluoroalkyl is a $C_1$-$C_6$fluoroalkyl.

The term "heterocycle" or "heterocyclic" refers to heteroaromatic rings (also known as heteroaryls) and heterocycloalkyl rings containing one to four heteroatoms in the ring(s), where each heteroatom in the ring(s) is selected from O, S and N, wherein each heterocyclic group has from 3 to 10 atoms in its ring system, and with the proviso that any ring does not contain two adjacent O or S atoms. Non-aromatic heterocyclic groups (also known as heterocycloalkyls) include rings having 3 to 10 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d] imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (=O) moieties, such as pyrrolidin-2-one. In some embodiments, at least one of the two rings of a bicyclic heterocycle is aromatic. In some embodiments, both rings of a bicyclic heterocycle are aromatic.

The terms "heteroaryl" or, alternatively, "heteroaromatic" refers to an aryl group that includes one or more ring heteroatoms selected from nitrogen, oxygen and sulfur. Illustrative examples of heteroaryl groups include monocyclic heteroaryls and bicyclic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Monocyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl.

A "heterocycloalkyl" group refers to a cycloalkyl group that includes at least one heteroatom selected from nitrogen, oxygen and sulfur. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl is monocyclic or bicyclic. In some embodiments, a heterocycloalkyl is monocyclic and is a 3, 4, 5, 6, 7, or 8-membered ring. In some embodiments, a heterocycloalkyl is monocyclic and is a 3, 4, 5, or 6-membered ring. In some embodiments, a heterocycloalkyl is monocyclic and is a 3 or 4-membered ring. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "optionally substituted" or "substituted" means that the referenced group is optionally substituted with one or more additional group(s) individually and independently selected from halogen, —CN, —$NH_2$, —NH(alkyl), —N(alkyl)$_2$, —OH, —$CO_2$H, —$CO_2$alkyl, —C(=O)$NH_2$, —C(=O)NH(alkyl), —C(=O)N(alkyl)$_2$, —S(=O)$_2NH_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from halogen, —CN, —$NH_2$, —NH($CH_3$), —N($CH_3$)$_2$, —OH, —$CO_2$H, —$CO_2$($C_1$-$C_4$alkyl), —C(=O)$NH_2$, —C(=O)NH($C_1$-$C_4$alkyl), —C(=O)N($C_1$-$C_4$alkyl)$_2$, —S(=O)$_2NH_2$, —S(=O)$_2$NH($C_1$-$C_4$alkyl), —S(=O)$_2$N($C_1$-$C_4$alkyl)$_2$, $C_1$-$C_4$alkyl, $C_3$-$C_6$cycloalkyl, $C_1$-$C_4$fluoroalkyl, $C_1$-$C_4$heteroalkyl, $C_1$-$C_4$alkoxy, $C_1$-$C_4$fluoroalkoxy, —S$C_1$-$C_4$alkyl, —S(=O)$C_1$-$C_4$alkyl, and —S(=O)$_2C_1$-$C_4$alkyl. In some embodiments, optional substituents are independently selected from halogen, —CN, —$NH_2$, —OH, —NH($CH_3$), —N($CH_3$)$_2$, —$CH_3$, —$CH_2CH_3$, —$CHF_2$, —$CF_3$, —$OCH_3$, —$OCHF_2$, and —$OCF_3$. In some embodiments, substituted groups are substituted with one or two of the preceding groups. In some embodiments, an optional substituent on an aliphatic carbon atom (acyclic or cyclic) includes oxo (=O).

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an agonist.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion). Those of skill in the art are familiar with administration techniques that can be employed with the compounds and methods described herein.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula (I), or a pharmaceutically acceptable salt thereof, and a co-agent, are both administered to a patient simultaneously in the form of a single entity or dosage. The term "non-fixed combination" means that the active ingredients, e.g. a compound of Formula (I), or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "article of manufacture" and "kit" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

EXAMPLES

The following examples are provided for illustrative purposes only and not to limit the scope of the claims provided herein.

Synthesis of Compounds

Example A. 2-{7-[({17-[(2-{[4-(4-aminopiperidin-1-yl)-3-(5-chloro-1H-1,3-benzodiazol-2-yl)-5-(3-fluoro-5-methylphenyl)pyridin-2-yl]amino}ethyl)carbamoyl]-3,6,9,12,15-pentaoxaheptadecan-1-yl}carbamoyl)methyl]-4,10-bis(carboxymethyl)-1,4,7,10-tetraazacyclododecan-1-yl}acetic acid
(Compound 1)

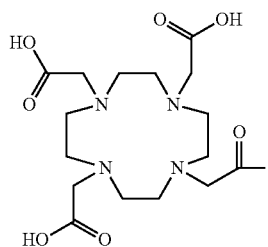
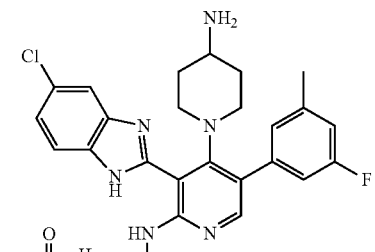

Step A-1 preparation of benzyl (1-(3-(5-chloro-1H-benzo[d]imidazol-2-yl)-2-((2,2-dimethyl-4,23-dioxo-3,8,11,14,17,20-hexaoxa-5,24-diazahexacosan-26-yl)amino)-5-(3-fluoro-5-methylphenyl)pyridin-4-yl)piperidin-4-yl)carbamate: to a mixture of 2,2-dimethyl-4-oxo-3,8,11,14,17,20-hexaoxa-5-azatricosan-23-oic acid (150 mg, 1.29 Eq, 366 μmol), perfluorophenyl diphenylphosphinate (150 mg, 1.38 Eq, 390 μmol) and N-methylmorpholine (NMM) (70 mg, 2.4 Eq, 0.69 mmol) in dimethyl formamide (DMF) (2 mL) was added benzyl (1-(2-((2-aminoethyl)amino)-3-(5-chloro-1H-benzo[d]imidazol-2-yl)-5-(3-fluoro-5-methylphenyl)pyridin-4-yl)piperidin-4-yl)carbamate (178 mg, 1 Eq, 283 μmol). The resulting reaction mixture was stirred at 25° C. for 2 hours. The crude product was purified by Prep-HPLC with the following conditions (Prep-HPLC-013): Column, SunFire Prep C18 OBD Column, 120 g; mobile phase, Water (0.1% trifluoroacetic acid (TFA)) and acetonitrile (CAN) (30.0% ACN up to 98% in 7 min); Total flow rate, 70 mL/min; Detector, UV 220 nm. The collected fractions were combined and concentrated under vacuum to give benzyl (1-(3-(5-chloro-1H-benzo[d]imidazol-2-yl)-2-((2,2-dimethyl-4,23-dioxo-3,8,11,14,17,20-hexaoxa-5,24-diazahexacosan-26-yl)amino)-5-(3-fluoro-5-methylphenyl)pyridin-4-yl)piperidin-4-yl)carbamate (120 mg, 41.5%). MS (M+H)+=1019.5.

Step A-2, preparation of benzyl (1-(2-((1-amino-18-oxo-3,6,9,12,15-pentaoxa-19-azahenicosan-21-yl)amino)-3-(5-chloro-1H-benzo[d]imidazol-2-yl)-5-(3-fluoro-5-methylphenyl)pyridin-4-yl)piperidin-4-yl)carbamate: a mixture of benzyl (1-(3-(5-chloro-1H-benzo[d]imidazol-2-yl)-2-((2,2-dimethyl-4,23-dioxo-3,8,11,14,17,20-hexaoxa-5,24-diazahexacosan-26-yl)amino)-5-(3-fluoro-5-methylphenyl)pyridin-4-yl)piperidin-4-yl)carbamate (118 mg, 1 Eq, 116 μmol) and TFA (1 mL) in dichloromethane (DCM) (3 mL) was stirred at 25° C. for 1 hour. The reaction mixture was concentrated, and the crude product adjusted to a pH of 8 with ammonium bicarbonate (NH$_4$HCO$_3$) and extracted with ethyl acetate (3×30 mL). The collected fractions were combined and concentrated under vacuum to give benzyl (1-(2-((1-amino-18-oxo-3,6,9,12,15-pentaoxa-19-azahenicosan-21-yl)amino)-3-(5-chloro-1H-benzo[d]imidazol-2-yl)-5-(3-fluoro-5-methylphenyl)pyridin-4-yl)piperidin-4-yl)carbamate (95 mg, 89%). MS (M+H)+=919.3.

Step A-3, preparation of tri-tert-butyl 2,2',2''-(10-(24-((4-(4-(((benzyloxy)carbonyl)amino)piperidin-1-yl)-3-(5-chloro-1H-benzo[d]imidazol-2-yl)-5-(3-fluoro-5-methylphenyl)pyridin-2-yl)amino)-2,21-dioxo-6,9,12,15,18-pentaoxa-3,22-diazatetracosyl)-1,4,7,10-tetraazacyclododecane-1,4,7-triyl)triacetate: a mixture of 2-(4,7,10-tris(2-(tert-butoxy)-2-oxoethyl)-1,4,7,10-tetraazacyclododecan-1-yl)acetic acid (70 mg, 1.2 Eq, 0.12 mmol), N,N-diisopropylethylamine (DIEA) (40 mg, 54 μL, 3.2 Eq, 0.31 mmol), and N,N,N',N'-Tetramethyl-O—(N-succinimidyl)uronium hexafluorophosphate (HSTU) (45 mg, 1.3 Eq, 0.13 mmol) in DMF (1 mL) was stirred for 10 min at 25° C., and then benzyl (1-(2-((1-amino-18-oxo-3,6,9,12,15-pentaoxa-19-azahenicosan-21-yl)amino)-3-(5-chloro-1H-benzo[d]imidazol-2-yl)-5-(3-fluoro-5-methylphenyl)pyridin-4-yl)piperidin-4-yl)carbamate (90 mg, 1 Eq, 98 μmol) was added. The resulting reaction mixture was stirred for 1 hour at 25° C. The mixture was purified by Prep-HPLC with the following conditions: Column, SunFire Prep C18 OBD Column, 19*150 mm, 5 um; mobile phase, Water (0.1% TFA) and ACN (30% ACN up to 65% in 7 min); Total flow rate, 20 mL/min; Detector, UV 220 nm. The collected fractions were combined and concentrated under vacuum to give tri-tert-butyl 2,2',2''-(10-(24-((4-(4-(((benzyloxy)carbonyl)amino)piperidin-1-yl)-3-(5-chloro-1H-benzo[d]imidazol-2-yl)-5-(3-fluoro-5-methylphenyl)pyridin-2-yl)amino)-2,21-dioxo-6,9,12,15,18-pentaoxa-3,22-diazatetracosyl)-1,4,7,10-tetraazacyclododecane-1,4,7-triyl)triacetate (62 mg, 43%). MS (M/2+H)+=737.9.

Step A-4, preparation of 2-{7-[({17-[(2-{[4-(4-aminopiperidin-1-yl)-3-(5-chloro-H-1,3-benzodiazol-2-yl)-5-(3-fluoro-5-methylphenyl)pyridin-2-yl]amino}ethyl)carbamoyl]-3,6,9,12,15-pentaoxaheptadecan-1-yl}carbamoyl)methyl]-4,10-bis(carboxymethyl)-1,4,7,10-tetraazacyclododecan-1-yl}acetic acid: a mixture of tri-tert-butyl 2,2',2''-(10-(24-((4-(4-(((benzyloxy)carbonyl)amino)piperidin-1-yl)-3-(5-chloro-1H-benzo[d]imidazol-2-yl)-5-

(3-fluoro-5-methylphenyl)pyridin-2-yl)amino)-2,21-dioxo-6,9,12,15,18-pentaoxa-3,22-diazatetracosyl)-1,4,7,10-tetraazacyclododecane-1,4,7-triyl)triacetate (60 mg, 1 Eq, 41 µmol) and TFA (1 mL) was stirred at 60° C. for 2 hours. The reaction mixture was concentrated and the crude product was purified by Prep-HPLC with the following conditions (Prep-HPLC-013): Column, SunFire Prep C18 OBD Column, 19*150 mm, 5 um; mobile phase, Water (0.05% TFA) and ACN (30.0% ACN up to 50.0% in 7 min); Total flow rate, 20 mL/min; Detector, UV 220 nm. The collected fractions were combined and concentrated under vacuum. The collected fractions were combined and concentrated under vacuum to give 2-{7-[({17-[(2-{[4-(4-aminopiperidin-1-yl)-3-(5-choro-1H-1,3-benzodiazol-2-yl)-5-(3-fluoro-5-methylphenyl)pyridin-2-yl]amino}ethyl)carbamoyl]-3,6,9,12,15-pentaoxaheptadecan-1-yl}carbamoyl)methyl]-4,10-bis(carboxymethyl)-1,4,7,10-tetraazacyclododecan-1-yl}acetic acid (30 mg, 53). MS (M+H)$^+$=1171.7.

Radiochemical Synthesis of $^{111}$In[In]-Compound 1

[$^{111}$In]InCl$_3$ (20.0 MBq, 40.0 µL, 0.1 M HCl) and Compound 1 (2.9 nmol, 2.9 µL, 1.0 mM in DI water) were added to an NH$_4$OAc solution (4.0 µL, 1.0 M). The resulting mixture was heated at 85° C. in a thermal mixer for 30 min. At the end of labeling, Ca-DTPA (4.0 µL, 4 mM) was added. The radiochemical purity was 97.5% as determined by RP-HPLC. The radiotracer solution for in vivo studies was prepared by dilution with 0.9% saline.

The following conjugates were prepared similarly to Example A with appropriate substituting reagents and substrates at different steps and they may require additional functional group modifications via well-known chemistry with appropriate reagents.

| Compound |
|---|
| 2-(7-{[(17-{[(2-{[4-(4-aminopiperidin-1-yl)-3-(5-chloro-1H-1,3-benzodiazol-2-yl)-5-(3-fluoro-5-methylphenyl)pyridin-2-yl]amino}ethoxy)carbonyl]amino}-3,6,9,12,15-pentaoxaheptadecan-1-yl)carbamoyl]methyl}-4,10-bis(carboxymethyl)-1,4,7,10-tetraazacyclododecan-1-yl)acetic acid (Compound 2) $(M + H)^+ = 1225.7$ |
| 2-{7-[({17-[(3-{[4-(4-aminopiperidin-1-yl)-3-(5-chloro-1H-1,3-benzodiazol-2-yl)-5-(3-fluoro-5-methylphenyl)pyridin-2-yl]amino}propyl)carbamoyl]-3,6,9,12,15-pentaoxaheptadecan-1-yl}carbamoyl)methyl]-4,10-bis(carboxymethyl)-1,4,7,10-tetraazacyclododecan-1-yl}acetic acid |

-continued

| Compound |
|---|
| (Compound 3)<br>(M + H)⁺ = 1185.8<br>2-[7-({[21-(4-{[4-(4-aminopiperidin-1-yl)-3-(5-chloro-1H-1,3-benzodiazol-2-yl)-5-(3-fluoro-5-methylphenyl)pyridin-2-yl]amino}piperidin-1-yl)-21-oxo-3,6,9,12,15,18-hexaoxahenicosan-1-yl]carbamoyl}methyl)-4,10-bis(carboxymethyl)-1,4,7,10-tetraazacyclododecan-1-yl]acetic acid 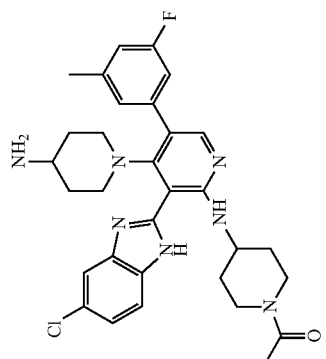 |
| (Compound 4)<br>(M/2 + H)⁺ = 629.5<br>2-(4-{[(14-{[4-(4-aminopiperidin-1-yl)-5-(3-fluoro-5-methylphenyl)-3-[4-(trifluoromethyl)phenyl]pyridin-2-yl]amino}-3,6,9,12-tetraoxatetradecan-1-yl)carbamoyl]methyl}-7,10-bis(carboxymethyl)-1,4,7,10-tetraazacyclododecan-1-yl)acetic acid 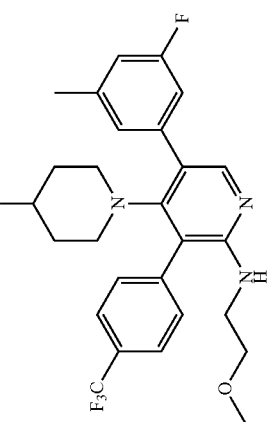 |

-continued
Compound
(Compound 5)
$(M + H)^+ = 1050.5$
(16E,18E)-11-chloro-21-hydroxy-12,20-dimethoxy-2,5,9,16-tetramethyl-8,23-dioxo-4,24-dioxa-9,22-diazatetracyclo[19.3.1.1$^{10,14}$.0$^{3,5}$]hexacosa-10,12,14(26),16,18-pentaen-6-yl 2-(3-{[1-({4-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]cyclohexyl}methyl)-2,5-dioxopyrrolidin-3-yl]sulfanyl}-N-methylpropanamido)propanoate
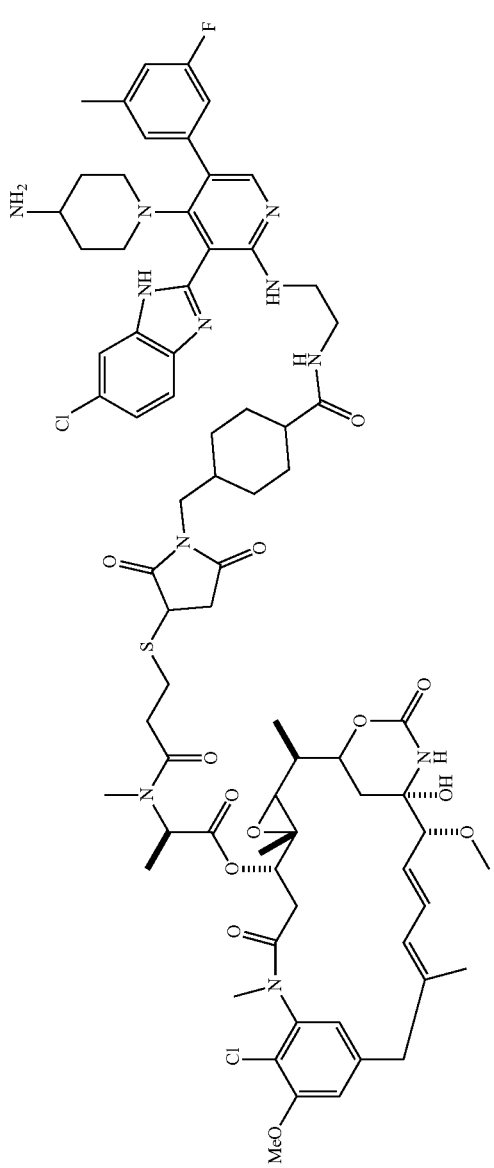

-continued
| Compound |
|---|
| (Compound 6)<br>(M + H)⁺ = 1451.6<br>(16E,18E)-11-chloro-21-hydroxy-12,20-dimethoxy-2,5,9,16-tetramethyl-8,23-dioxo-4,24-dioxa-9,22-diazatetracyclo[19.3.1.1¹⁰,¹⁴.0³,⁵]hexacosa-10,12,14(26),16,18-pentaen-6-yl 2-(3-(3S)-1-[(4-{[(5S)-5-amino-5-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]pentyl]carbamoyl}cyclohexyl)methyl]-2,5-dioxopyrrolidin-3-yl]sulfanyl}-N-methylpropanamido)propanoate |
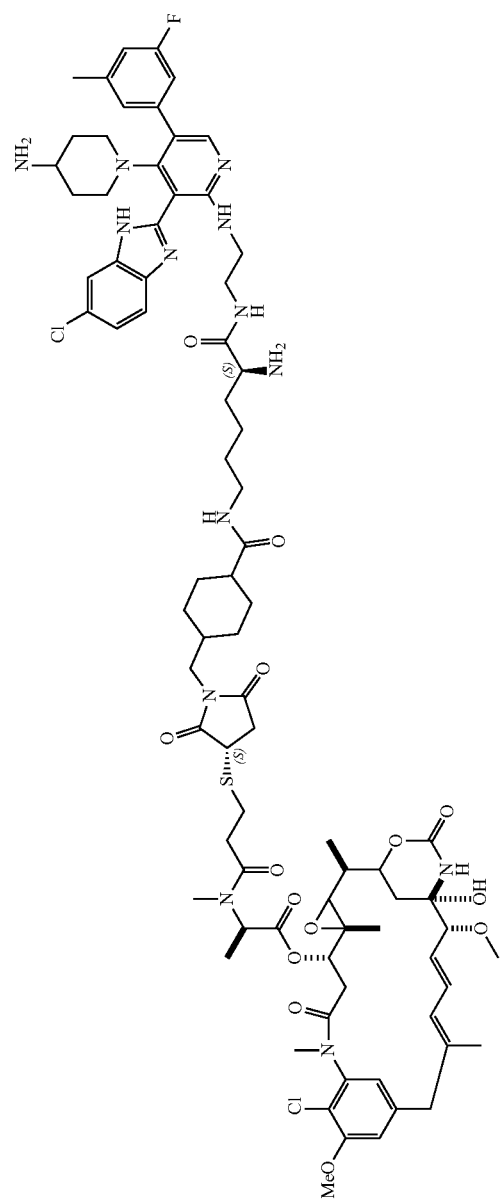

-continued
Compound
(Compound 7)
$(M/2 + H)^+ = 791.0$
(16E,18E)-11-chloro-21-hydroxy-12,20-dimethoxy-2,5,9,16-tetramethyl-8,23-dioxo-4,24-dioxa-9,22-diazatetracyclo[19.3.1.1$^{10,14}$.0$^{3,5}$]hexacosa-10,12,14(26),16,18-pentaen-6-yl 2-(3-{[(3R)-1-[(4-{[(5S)-5-amino-5-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]pentyl]carbamoyl}cyclohexyl)methyl]-2,5-dioxopyrrolidin-3-yl]sulfanyl}-N-methylpropanamido)propanoate
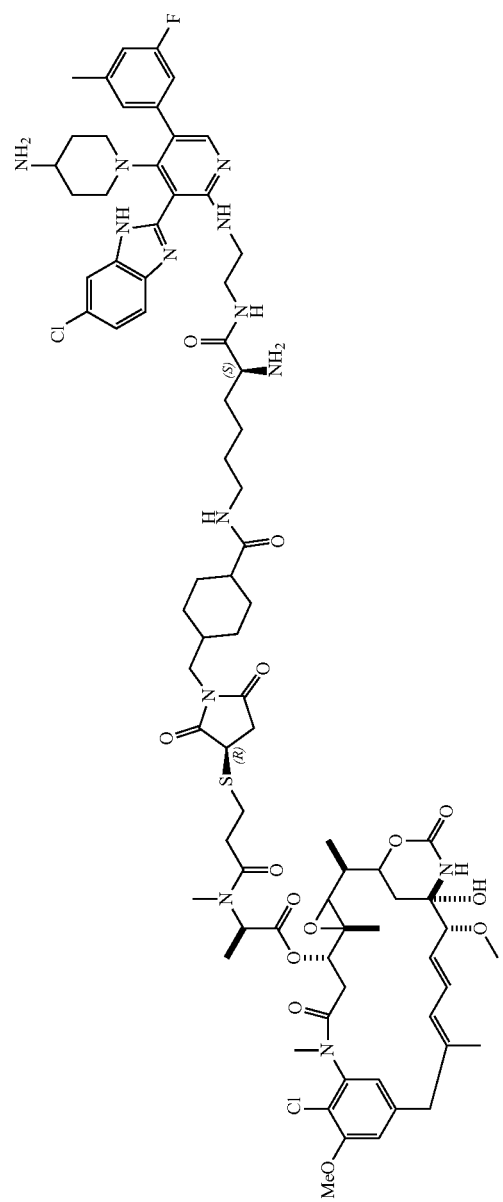

-continued
Compound
(Compound 8)
(M/2 + H)+ = 791.0
2-(4-{[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]methyl}-7-({[2-({2-[(1-{[(16E,18E)-11-chloro-21-hydroxy-12,20-dimethoxy-2,5,9,16-tetramethyl-8,23-dioxo-4,24-dioxa-9,22-diazatetracyclo[19.3.1.1¹⁰,¹⁴.0³,⁵]hexacosa-10,12,14(26),16,18-pentaen-6-yl]oxy}-1-oxopropan-2-yl)(methyl)carbamoyl]ethyl}disulfanyl)ethyl]carbamoyl}methyl)-1,4,7-triazonan-1-yl)acetic acid
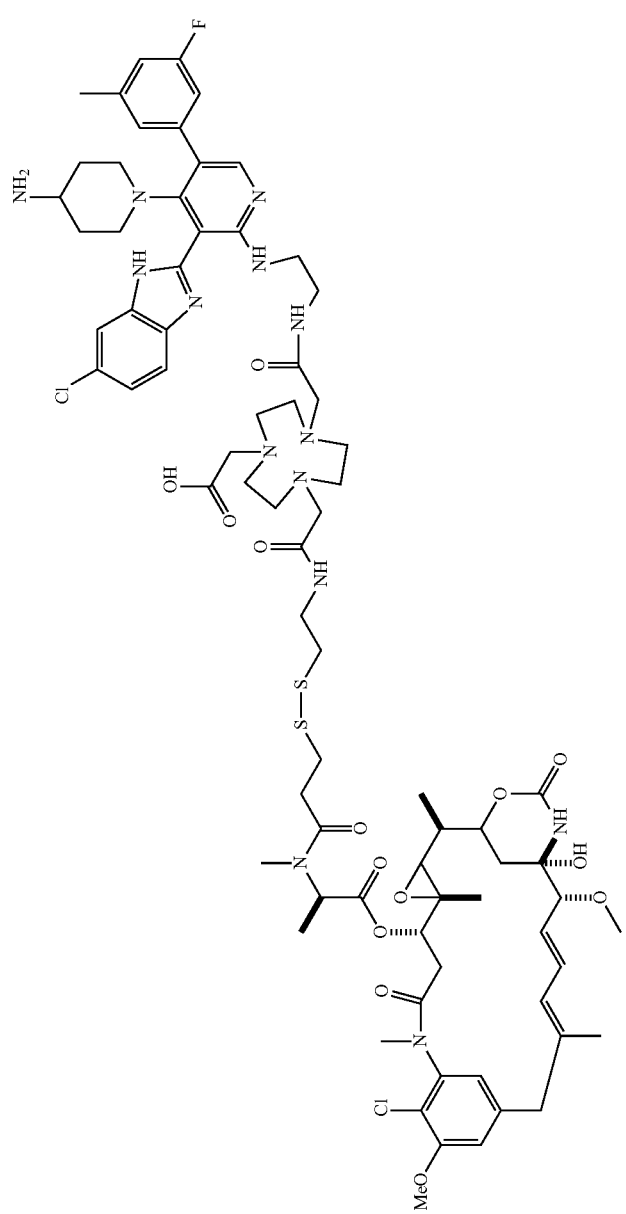

-continued

Compound (Compound 9)
(M/2 + H)⁺ = 788.6
(19S)-10,19-diethyl-19-hydroxy-14,18-dioxo-17-oxa-3,13-diazapentacyclo[11.8.0.0²,¹¹.0⁴,⁹.0¹⁵,²⁰]henicosa-1(21),2,4(9),5,7,10,15(20)-heptaen-7-yl N-{14-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)amino]-3,6,9,12-tetraoxatetradecan-1-yl}carbamate (Compound 10)
(M + H)⁺ = 1159.6
(2S)-2-[(2R)-2-[(R)-[(2S)-1-[(3R,4S,5S)-4-[(2S)-2-[(2S)-2-{1-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]-N-methyl-3,6,9,12-tetraoxapentadecan-15-amido}-3-methylbutanamido]-N,3-dimethylbutanamido]-3-methoxy-5-methylheptanoyl]pyrrolidin-2-yl](methoxy)methyl propanamido]-3-phenylpropanoic acid -continued
Compound
(Compound 11)
(M + H)⁺ = 1484.5
1-[5-({14-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]-3,6,9,12-tetraoxatetradecan-1-yl]carbamoyl}pentyl)-3,3-dimethyl-2-[(1E,3E)-5-[(2E)-1,3,3-trimethyl-2,3-dihydro-1H-indol-2-ylidene]penta-1,3-dien-1-yl]-3H-indol-1-ium
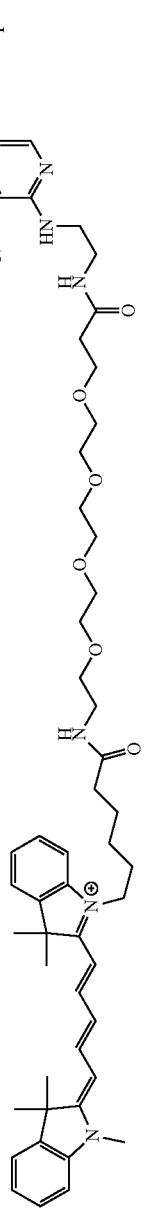

-continued

Compound (Compound 12)
(M + H)⁺ = 1206.6
(2S,5S,6S,16E,18E,20R,21S)-11-chloro-21-hydroxy-12,20-dimethoxy-2,5,9,16-tetramethyl-8,23-dioxo-4,24-dioxa-9,22-diazatetracyclo[19.3.1.1¹⁰,¹⁴.0³,⁵]hexacosa-10,12,14(26),16,18-pentaen-6-yl (2R)-2-{3-[2-{(3R)-3-amino-3-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]propanamido]acetamido}ethyl)disulfanyl]-N-methylpropanamido}propanoate (Compound 13)
(M + H)⁺ = 1462.5
N-(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)-2,5,8,11,14-pentaoxaheptadecan-17-amide (Compound 14)
(M + H)⁺ = 756.4

Example B. N-(2-{[4-(4-aminopiperidin-1-yl)-3-(5-chloro-1H-1,3-benzodiazol-2-yl)-5-(3-fluoro-5-methylphenyl)pyridin-2-yl]amino}ethyl)-1-(2-{3,16,19-trioxo-2,17,18-trioxa-5,8,11,14-tetraaza-1-indatricyclo[9,6,3,2^{5,14}]docosan-8-yl}acetamido)-3,6,9,12,15-pentaoxaoctadecan-18-amide (Compound 15)

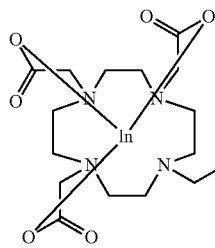 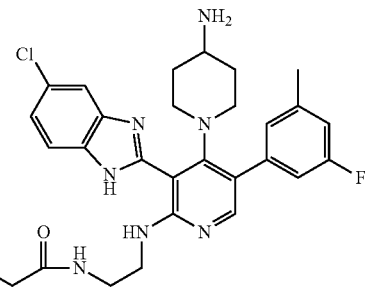

Preparation of N-(2-{[4-(4-aminopiperidin-1-yl)-3-(5-chloro-1H-1,3-benzodiazol-2-yl)-5-(3-fluoro-5-methylphenyl)pyridin-2-yl]amino}ethyl)-1-(2-{3,16,19-trioxo-2,17,18-trioxa-5,8,11,14-tetraaza-1-indatricyclo[9.6.3.2^{5,14}]docosan-8-yl}acetamido)-3,6,9,12,15-pentaoxaoctadecan-18-amide: a mixture of 2,2',2''-(10-(24-((4-(4-aminopiperidin-1-yl)-3-(5-chloro-1H-benzo[d]imidazol-2-yl)-5-(3-fluoro-5-methylphenyl)pyridin-2-yl)amino)-2,21-dioxo-6,9,12,15,18-pentaoxa-3,22-diazatetracosyl)-1,4,7,10-tetraazacyclododecane-1,4,7-triyl)triacetic acid (16 mg, 1 Eq, 14 µmol), Indium trichloride (8 mg, 2 µL, 3 Eq, 0.04 mmol), and Sodium bicarbonate (5 mg, 2 µL, 4 Eq, 0.06 mmol) in ACN (0.2 mL) and Water (0.1 mL) was stirred for 2 hours at 80° C. The mixture was diluted with 4 mL of dimethylsulfoxide (DMSO), filtered, and the filtrate was purified by Prep-HPLC with the following conditions (Prep-HPLC-007): Column, SunFire Prep C18 OBD Column, 19*150 mm 5 um 10 nm; mobile phase, Water (0.05% TFA) and ACN (30% ACN up to 75% in 15 min); Total flow rate, 20 mL/min; Detector, UV 220 nm. The collected fractions were combined and concentrated under vacuum to give N-(2-{[4-(4-aminopiperidin-1-yl)-3-(5-chloro-1H-1,3-benzodiazol-2-yl)-5-(3-fluoro-5-methylphenyl)pyridin-2-yl]amino}ethyl)-1-(2-{3,16,19-trioxo-2,17,18-trioxa-5,8,11,14-tetraaza-1-indatricyclo[9.6.3.2^{5,14}]docosan-8-yl}acetamido)-3,6,9,12,15-pentaoxaoctadecan-18-amide (8.9 mg, 43%). MS (M+H)$^+$=1283.6.

The following conjugates were prepared similarly to Example B with appropriate substituting reagents and substrates at different steps and they may require additional functional group modifications via well-known chemistry with appropriate reagents.

| Compound |
|---|
| N-(3-{[4-(4-aminopiperidin-1-yl)-3-(5-chloro-1H-1,3-benzodiazol-2-yl)-5-(3-fluoro-5-methylphenyl)pyridin-2-yl]amino}propyl)-1-(2-{3,16,19-trioxo-2,17,18-trioxa-5,8,11,14-tetraaza-1-indatricyclo[9.6.3.2⁵,¹⁴]docosan-8-yl}acetamido)-3,6,9,12,15-pentaoxaoctadecan-18-amide 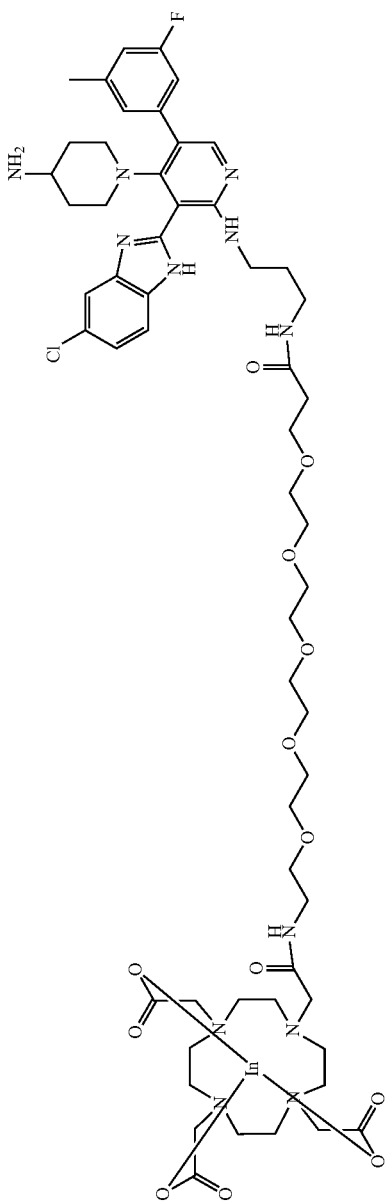 |
| (Compound 16)<br>(M + H)⁺ = 1297.6<br>N-[21-(4-{[4-(4-aminopiperidin-1-yl)-3-(5-chloro-1H-1,3-benzodiazol-2-yl)-5-(3-fluoro-5-methylphenyl)pyridin-2-yl]amino}piperidin-1-yl)-21-oxo-3,6,9,12,15,18-hexaoxahenicosan-1-yl]-2-{3,16,19-trioxo-2,17,18-trioxa-5,8,11,14-tetraaza-1-indatricyclo[9.6.3.2⁵,¹⁴]docosan-8-yl}acetamide 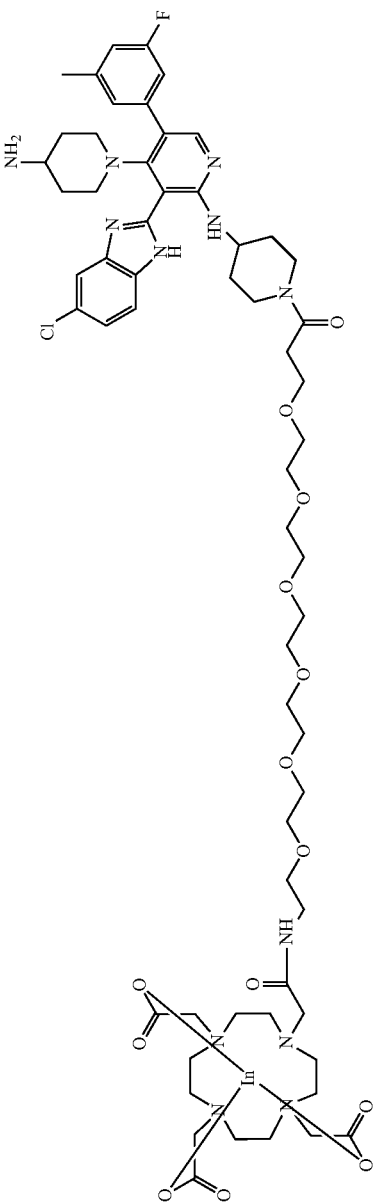 |

-continued
| Compound |
|---|
| 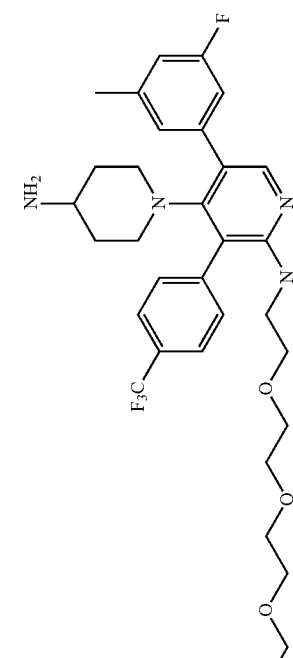<br>(Compound 17)<br>(M + H)⁺ = 1368.4<br>N-(14-{[4-(4-aminopiperidin-1-yl)-5-(3-fluoro-5-methylphenyl)-3-[4-(trifluoromethyl)phenyl]pyridin-2-yl]amino}-3,6,9,12-tetraoxatetradecan-1-yl)-2-{3,16,19-trioxo-2,17,18-trioxa-5,8,11,14-tetraaza-1-indatricyclo[9.6.3.2⁵,¹⁴] docosan-8-yl}acetamide<br>(Compound 18)<br>(M + H)⁺ = 1162.5 |

Example C. (2S,5S,6S,16E,18E,20R,21S)-11-chloro-21-hydroxy-12,20-dimethoxy-2,5,9,16-tetramethyl-8,23-dioxo-4,24-dioxa-9,22-diazatetracyclo[19.3.1.1$^{10,14}$,0$^{3,5}$]hexacosa-10,12,14(26),16,18-pentaen-6-yl (2R)-2-{1-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]-N-methyl-3,6,9-trioxa-12,13-dithiahexadecane-16-amido}propanoate (Compound 19)

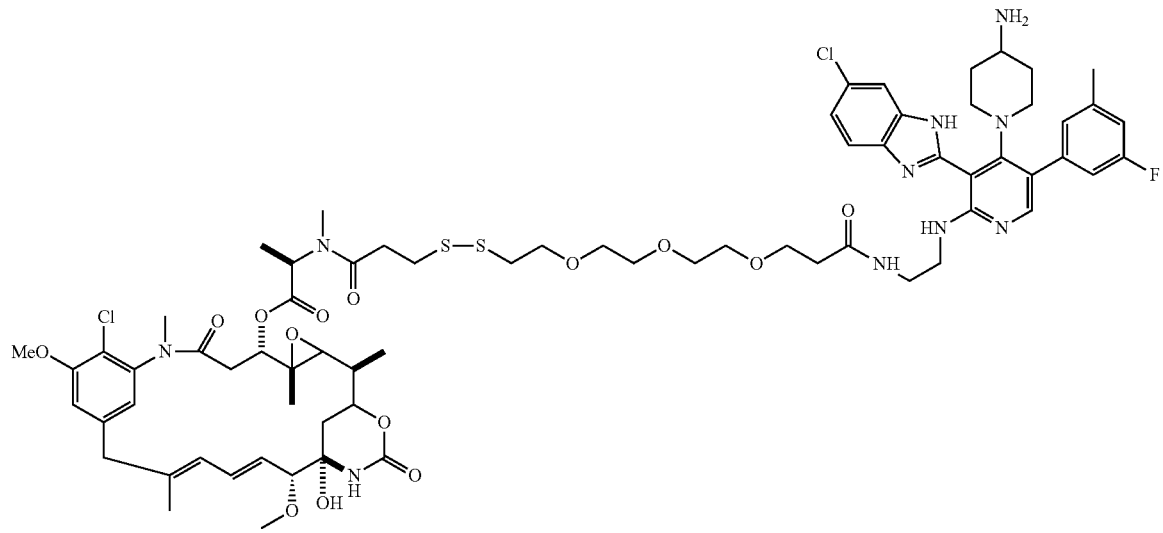

Step C-1 preparation of (14S,33S,2S,4S,10E,12E,14R)-86-chloro-14-hydroxy-85,14-dimethoxy-33,2,7,10-tetramethyl-12,6-dioxo-7-aza-1(6,4)-oxazinana-3(2,3)-oxirana-8(1,3)-benzenacyclotetradecaphane-10,12-dien-4-yl N-methyl-N-(3-(pyridin-2-yldisulfaneyl)propanoyl)-D-alaninate: a mixture of (14S,33S,2S,4S,10E,12E,14R)-86-chloro-14-hydroxy-85,14-dimethoxy-33,2,7,10-tetramethyl-12,6-dioxo-7-aza-1(6,4)-oxazinana-3(2,3)-oxirana-8(1,3)-benzenacyclotetradecaphane-10,12-dien-4-yl N-(3-mercaptopropanoyl)-N-methyl-D-alaninate (50 mg, 1 Eq, 68 μmol) and 1,2-di(pyridin-2-yl)disulfane (45 mg, 3.0 Eq, 0.20 mmol) in DMF (2 mL) and acetic acid (AcOH) (0.2 mL) was stirred for 20 min at 25° C. Sodium acetate (0.5 mL, 0.2 M) was then added to the reaction mixture. The crude product was purified by Prep-HPLC with the following conditions (Prep-HPLC-013): Column, Atlantis Prep T3 OBD Column, 19*150 mm 5 um; mobile phase, Water (0.05% TFA) and ACN (28% Phase B up to 53% in 6 min); 20 mL/min. Detector, UV 220,254 nm. The collected fractions were combined and concentrated under vacuum to give (14S,33S,2S,4S,10E,12E,14R)-86-chloro-14-hydroxy-85,14-dimethoxy-33,2,7,10-tetramethyl-12,6-dioxo-7-aza-1(6,4)-oxazinana-3(2,3)-oxirana-8(1,3)-benzenacyclotetradecaphane-10,12-dien-4-yl N-methyl-N-(3-(pyridin-2-yldisulfaneyl)propanoyl)-D-alaninate (52 mg, 91%). MS (M+H)$^+$=847.

Step C-2, preparation of (2R)-1-(((14S,33S,2S,4S,10E,12E,14R)-86-chloro-14-hydroxy-85,14-dimethoxy-33,2,7,10-tetramethyl-12,6-dioxo-7-aza-1(6,4)-oxazinana-3(2,3)-oxirana-8(1,3)-benzenacyclotetradecaphane-10,12-dien-4-yl)oxy)-2,3-dimethyl-1,4-dioxo-11,14,17-trioxa-7,8-dithia-3-azaicosan-20-oic acid: a mixture of (14S,33S,2S,4S,10E, 12E,14R)-86-chloro-14-hydroxy-85,14-dimethoxy-33,2,7,10-tetramethyl-12,6-dioxo-7-aza-1(6,4)-oxazinana-3(2,3)-oxirana-8(1,3)-benzenacyclotetradecaphane-10,12-dien-4-yl N-methyl-N-(3-(pyridin-2-yldisulfaneyl)propanoyl)-Dalaninate (25 mg, 1 Eq, 30 μmol) and 3-(2-(2-(2-mercaptoethoxy)ethoxy)ethoxy)propanoic acid (14.0 mg, 2.0 Eq, 58.7 μmol) in methanol (MeOH) (2 mL) was stirred for 1 hour at 25° C. The crude product was purified by Prep-HPLC with the following conditions (Prep-HPLC-013): Column, Atlantis Prep T3 OBD Column, 19*150 mm 5 um; mobile phase, Water (0.05% TFA) and ACN (28% Phase B up to 53% in 6 min); 20 mL/min. Detector, UV 220,254 nm. The collected fractions were combined and concentrated under vacuum to give (2R)-1-(((14S,33S,2S, 4S,10E,12E,14R)-86-chloro-14-hydroxy-85,14-dimethoxy-33,2,7,10-tetramethyl-12,6-dioxo-7-aza-1(6,4)-oxazinana-3 (2,3)-oxirana-8(1,3)-benzenacyclotetradecaphane-10,12-dien-4-yl)oxy)-2,3-dimethyl-1,4-dioxo-11,14,17-trioxa-7,8-dithia-3-azaicosan-20-oic acid (31 mg, 97.8%). MS (M+H)$^+$ =975.

Step C-3, preparation of (14S,33S,2S,4S,10E,12E,14R)-86-chloro-14-hydroxy-85,14-dimethoxy-33,2,7,10-tetramethyl-12,6-dioxo-7-aza-1(6,4)-oxazinana-3(2,3)-oxirana-8(1,3)-benzenacyclotetradecaphane-10,12-dien-4-yl (2R)-23-((4-(4-((tertbutoxycarbonyl)amino)piperidin-1-yl)-3-(6-chloro-1H-benzo[d]imidazol-2-yl)-5-(3-fluoro-5-methylphenyl)pyridin-2-yl)amino)-2,3-dimethyl-4,20-dioxo-11,14,17-trioxa-7,8-dithia-3,21-diaza tricosanoate: a mixture of (2R)-1-(((14S,33S,2S,4S,10E,12E,14R)-86-chloro-14-hydroxy-85,14-dimethoxy-33,2,7,10-tetramethyl-12,6-dioxo-7-aza-1(6,4)-oxazinana-3(2,3)-oxirana-8(1,3)-benzenacyclotetradecaphane-10,12-dien-4-yl)oxy)-2, 3-dimethyl-1,4-dioxo-11,14,17-trioxa-7,8-dithia-3-azaicosan-20-oic acid (31 mg, 1 Eq, 32 µmol) and Hexafluorophosphate Azabenzotriazole Tetramethyl Uronium (HATU) (24 mg, 2.0 Eq, 63 µmol) in DMF (2 mL) was stirred for 10 min at 25° C. Tert-butyl (1-(2-((2-aminoethyl) amino)-3-(6-chloro-1H-benzo[d]imidazol-2-yl)-5-(3-fluoro-5-methylphenyl)pyridin-4-yl)piperidin-4-yl)carbamate (21 mg, 1.1 Eq, 35 µmol) was then added to the reaction mixture. The crude product was purified by Prep-HPLC with the following conditions (Prep-HPLC-013): Column, Atlantis Prep T3 OBD Column, 19*150 mm 5 um; mobile phase, Water (0.05% TFA) and ACN (28% Phase B up to 53% in 6 min); 20 mL/min. Detector, UV 220,254 nm. The collected fractions were combined and concentrated under vacuum to give (14S,33S,2S,4S,10E,12E,14R)-86-chloro-14-hydroxy-85,14-dimethoxy-33,2,7,10-tetramethyl-12,6-dioxo-7-aza-1(6,4)-oxazinana-3(2,3)-oxirana-8(1,3)-benzenacyclotetradecaphane-10,12-dien-4-yl (2R)-23-((4-(4-((tert-butoxycarbonyl)amino)piperidin-1-yl)-3-(6-chloro-TH-benzo[d]imidazol-2-yl)-5-(3-fluoro-5-methylphenyl) pyridin-2-yl)amino)-2,3-dimethyl-4,20-dioxo-11,14,17-trioxa-7,8-dithia-3,21-diazatricosanoate (25 mg, 51%). MS (M+H)⁺=1550.7.

Step C-4, preparation of (2S,5S,6S,16E,18E,20R,21S)-11-chloro-21-hydroxy-12,20-dimethoxy-2,5,9,16-tetramethyl-8,23-dioxo-4,24-dioxa-9,22-diazatetracyclo[19.3.1.1$^{10,14}$.0$^{3,5}$]hexacosa-10,12,14(26),16,18-pentaen-6-yl (2R)-2-{1-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]-N-methyl-3,6,9-trioxa-12,13-dithiahexadecan-16-amido}propanoate: a mixture of (14S,33S,2S,4S,10E,12E,14R)-86-chloro-14-hydroxy-85,14-dimethoxy-33,2,7,10-tetramethyl-12,6-dioxo-7-aza-1(6,4)-oxazinana-3(2,3)-oxirana-8(1,3)-benzenacyclotetradecaphane-10,12-dien-4-yl (2R)-23-((4-(4-((tert-butoxycarbonyl)amino)piperidin-1-yl)-3-(6-chloro-1H-benzo[d]imidazol-2-yl)-5-(3-fluoro-5-methylphenyl) pyridin-2-yl)amino)-2,3-dimethyl-4,20-dioxo-11,14,17-trioxa-7,8-dithia-3,21-diazatricosanoate (17 mg, 1 Eq, 11 µmol) and zinc(II) chloride (12 mg, 8.0 Eq, 88 µmol) in DCM (2 mL) was stirred for 3 hours at 25° C. The crude product was purified by Prep-HPLC with the following conditions (Prep-HPLC-013): Column, Atlantis Prep T3 OBD Column, 19*150 mm 5 um; mobile phase, Water (0.05% TFA) and ACN (28% Phase B up to 53% in 6 min); 20 mL/min. Detector, UV 220,254 nm. The collected fractions were combined and concentrated under vacuum to give (2S,5S,6S,16E,18E,20R,21S)-11-chloro-21-hydroxy-12,20-dimethoxy-2,5,9,16-tetramethyl-8,23-dioxo-4,24-dioxa-9,22-diazatetracyclo[19.3.1.1$^{10,14}$.0$^{3,5}$]hexacosa-10,12,14(26),16,18-pentaen-6-yl (2R)-2-{1-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]-N-methyl-3,6,9-trioxa-12,13-dithiahexadecan-16-amido}propanoate (2.1 mg, 11%). MS (M+H)⁺=1451.5.

The following conjugates were prepared similarly to Example C with appropriate substituting reagents and substrates at different steps and they may require additional functional group modifications via well-known chemistry with appropriate reagents.

| Compound |
|---|
| 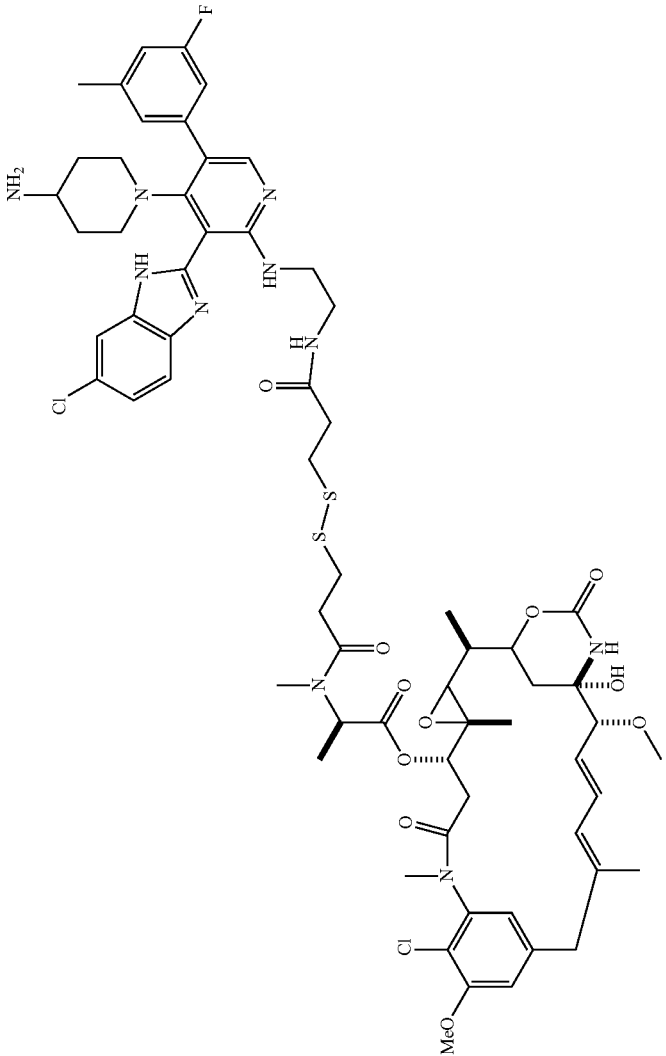 (2S,5S,6S,16E,18E,20R,21S)-11-chloro-21-hydroxy-12,20-dimethoxy-2,5,9,16-tetramethyl-8,23-dioxo-4,24-dioxa-9,22-diazatetracyclo[19.3.1.1$^{10,14}$.0$^{3,5}$]hexacosa-10,12,14(26),16,18-pentaen-6-yl (2R)-2-[3-({2-[({2-[({4-(4-aminopiperidin-1-yl)-3-(6-chloro-1H-1,3-benzodiazol-2-yl)-5-(3-fluoro-5-methylphenyl)pyridin-2-yl]amino}ethyl)-carbamoyl]ethyl}disulfanyl)ethyl]propanamido]propanoate |

-continued

| Compound |
|---|
| (Compound 20)<br>(M + H)⁺ = 1317.6<br>(2S,5S,6S,16E,18E,20R,21S)-11-chloro-21-hydroxy-12,20-dimethoxy-2,5,9,16-tetramethyl-8,23-dioxo-4,24-dioxa-9,22-diazatetracyclo[19.3.1.1¹⁰,¹⁴.0³,⁵]hexacosa-10,12,14(26),16,18-pentaen-6-yl (2R)-2-{1-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]-N-methyl-3,6,9,12-tetraoxa-15,16-dithianonadecan-19-amido}propanoate |

-continued
Compound
(Compound 21)
(M + H)⁺ = 1495.4
(2S,5S,6S,16E,18E,20R,21S)-11-chloro-21-hydroxy-12,20-dimethoxy-2,5,9,16-tetramethyl-8,23-dioxo-4,24-dioxa-9,22-diazatetracyclo[19.3.1.1¹⁰,¹⁴.0³,⁵]hexacosa-10,12,14(26),16,18-pentaen-6-yl (2R)-2-{1-[(2-{[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]-N-methyl-3,6,9,12,15,18,21,24-octaoxa-27,28-dithiahentriacontan-31-amido}propanoate
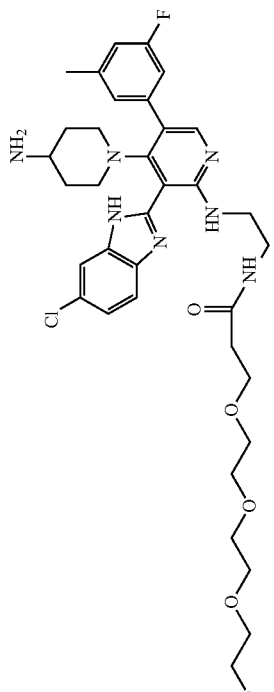

| Compound |
|---|
| (Compound 22)<br>(M + H)⁺ = 1671.55<br>(16E,18E)-11-chloro-21-hydroxy-12,20-dimethoxy-2,5,9,16-tetramethyl-8,23-dioxo-4,24-dioxa-9,22-diazatetracyclo[19.3.1.1¹⁰,¹⁴.0³,⁵]hexacosa-10,12,14(26),16,18-pentaen-6-yl 2-[3-({2-[(2-{[4-(4-aminopiperidin-1-yl)-3-(6-carbamoyl-1H-1,3-benzodiazol-2-yl)-5-(3-fluoro-5-methylphenyl)pyridin-2-yl]amino}ethyl)carbamoyl]ethyl]disulfanyl)-N-methylpropanamido]propanoate<br>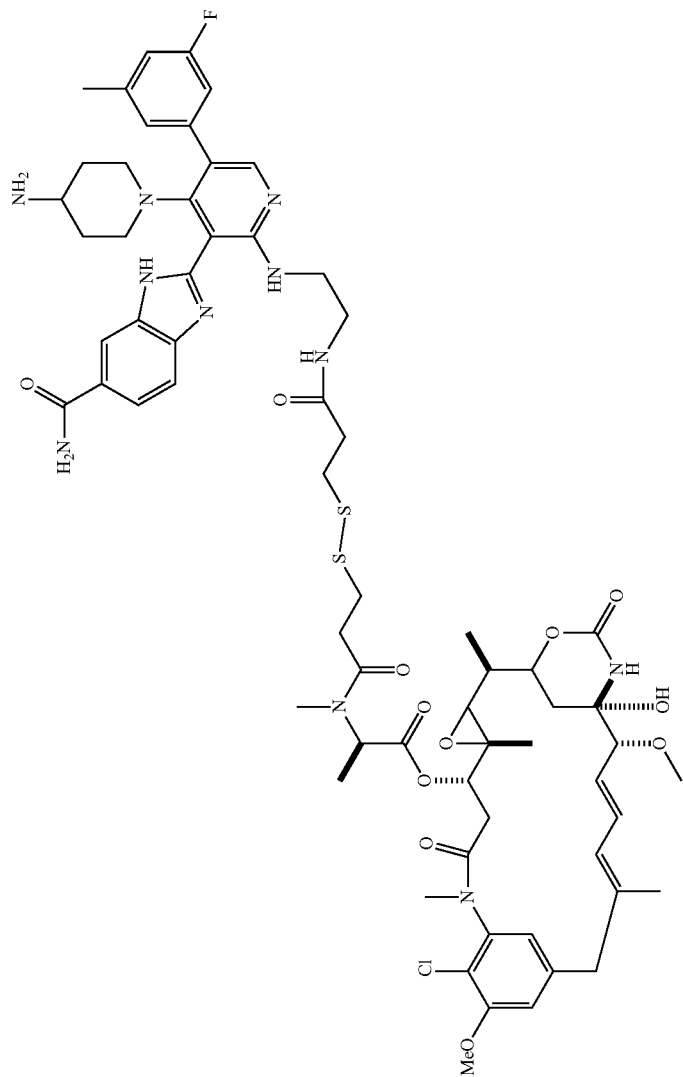 |

| Compound |
| --- |
| (Compound 23)<br>(M + H)⁺ = 1328<br>(1S,2R,3S,5S,6S,20R,21S,16E,18E)-11-chloro-21-hydroxy-12,20-dimethoxy-2,5,16-trimethyl-9-methyl-8,23-dioxo-4,24-dioxa-9,22-diazatetracyclo[19.3.1.1¹⁰,¹⁴.0³,⁵]hexacosa-10(26),11,13,16,18-pentaen-6-yl (S)-2-(N-methyl{2-[2-(3-{2-[(R)-3-{[N-2-[4-(4-amino-1-piperidyl)-3-(6-chloro-1H-1,3-benzimidazol-2-yl)-5-(3-fluoro-5-tolyl)-2-pyridyl]amino]ethylcarbamoyl]-3-aminopropionylamino]ethoxy}propionylamino)ethyl]dithio]ethyl}carbonylamino)propionate |
| 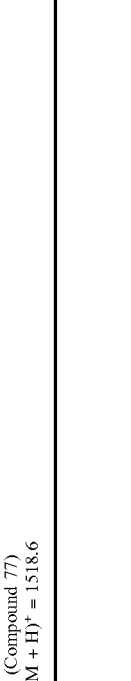<br>(Compound 77)<br>(M + H)⁺ = 1518.6 |

Example D. {4-[(2S)-2-[(2S)-2-[3-(2-{2-[(2-{[4-(4-aminopiperidin-1-yl)-3-(6-chloro-1H-1,3-benzodiazol-2-yl)-5-(3-fluoro-5-methylphenyl)-139-pyrrolid-2-yl}amino)ethyl)carbamoyl]ethoxy}ethoxy)propanamido]-3-methylbutanamido]-5-(carbamoylamino)pentanamido]phenyl}methyl N-[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]-139-pyrrolidine-1-yl]-3-methoxy-5-methyl-1-oxoheptan-4-yl](methyl)carbamoyl}-2-methylpropyl]carbamoyl}-2-methylpropyl]-N-methylcarbamate (Compound 24)

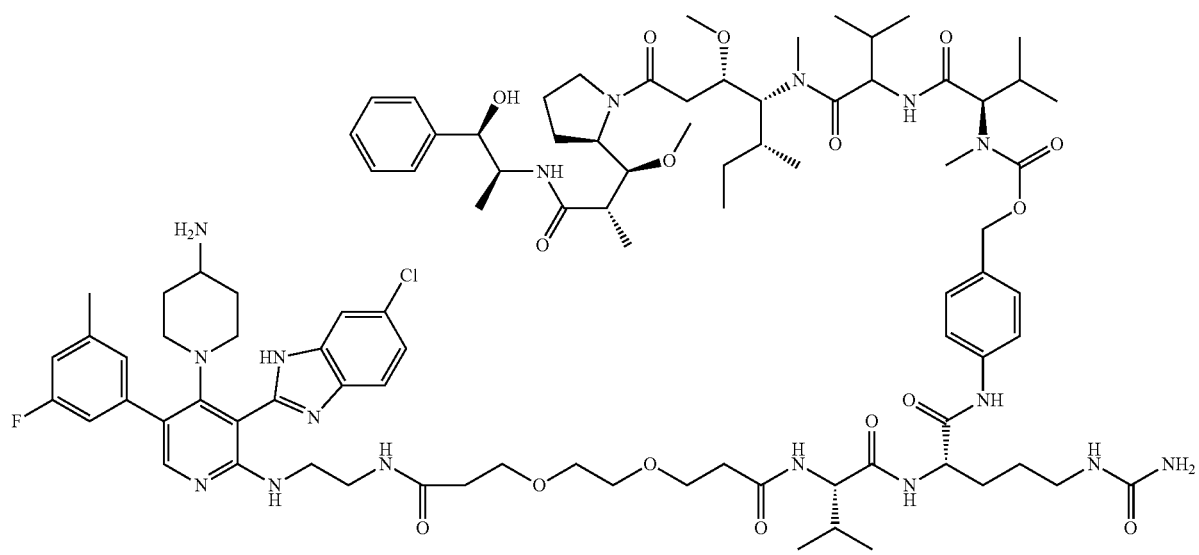 [SMILES: CC[C@@H](C)[C@H]([C@H](CC(=O)N1CCC[C@@H]1[C@@H](OC)[C@H](C)C(=O)N[C@@H](C)[C@H](O)c1ccccc1)OC)N(C)C(=O)C(NC(=O)[C@@H](C(C)C)N(C)C(=O)OCc1ccc(NC(=O)[C@H](CCCNC(N)=O)NC(=O)[C@@H](NC(=O)CCOCCOCCC(=O)NCCNc2ncc(-c3cc(C)cc(F)c3)c(N3CCC(N)CC3)c2-c2nc3ccc(Cl)cc3[nH]2)C(C)C)cc1)C(C)C]

Step D-1, preparation of 4-((S)-2-((S)-2-((tert-butoxycarbonyl)amino)-3-methylbutanamido)-5-ureidopentanamido)benzyl ((2R)-1-((1-(((3S,4R,5R)-1-((R)-2-((1S,2S)-3-(((1R,2S)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)amino)-3-methyl-1-oxobutan-2-yl)(methyl)carbamate: to a DMF (1 mL) solution of N-((3S,4R,5R)-1-((R)-2-((1S,2S)-3-(((1R,2S)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N,3-dimethyl-2-((R)-3-methyl-2-(methylamino)butanamido)butanamide (100 mg, 1 Eq, 139 μmol), tert-butyl ((S)-3-methyl-1-(((S)-1-((4-(((((4-nitrophenoxy)carbonyl)oxy)methyl)phenyl)amino)-1-oxo-5-ureidopentan-2-yl)amino)-1-oxobutan-2-yl)carbamate (108 mg, 1.2 Eq, 167 μmol) and HOBt (25.6 mg, 1.2 Eq, 167 μmol) was added DIEA (54.0 mg, 72.8 μL, 3 Eq, 418 μmol). The reaction mixture was stirred at 20° C. for 6 hours. The reaction mixture was then diluted with ethyl acetate, washed with water and brine, and concentrated to give crude product 4-((S)-2-((S)-2-((tert-butoxycarbonyl)amino)-3-methylbutanamido)-5-ureidopentanamido)benzyl ((2R)-1-((1-(((3S,4R,5R)-1-((R)-2-((1S,2S)-3-(((1R,2S)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)amino)-3-methyl-1-oxobutan-2-yl)(methyl)carbamate. MS (M+H)$^+$=1223.9. This material was used for the next step without further purification.

Step D-2, preparation of 4-((S)-2-((S)-2-amino-3-methylbutanamido)-5-ureidopentanamido)benzyl ((2R)-1-((1-(((3S,4R,5R)-1-((R)-2-((1S,2S)-3-(((1R,2S)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)amino)-3-methyl-1-oxobutan-2-yl)(methyl)carbamate: to a DCM (0.6 mL) solution of 4-((S)-2-((S)-2-((tert-butoxycarbonyl)amino)-3-methylbutanamido)-5-ureidopentanamido)benzyl ((2R)-1-((1-(((3S,4R,5R)-1-((R)-2-((1S,2S)-3-(((1R,2S)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)amino)-3-methyl-1-oxobutan-2-yl)(methyl)carbamate (170 mg, 1 Eq, 139 μmol) was added 2,2,2-trifluoroacetic acid (15.8 mg, 1 Eq, 139 μmol). The resulting mixture was stirred at 0° C. for 30 min. The reaction crude was concentrated and then purified by C$_{18}$ reverse phase chromatography eluting with MeCN (0.1% TFA)/water (0.1% TFA). The collected fractions were combined and concentrated under vacuum to give 4-((S)-2-((S)-2-amino-3-methylbutanamido)-5-ureidopentanamido)benzyl ((2R)-1-((1-(((3S,4R,5R)-1-((R)-2-((1S,2S)-3-(((1R,2S)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)amino)-3-methyl-1-oxobutan-2-yl)(methyl)carbamate (71.8 mg, 46.0%). MS (M+H)$^+$=1124.1.

Step D-3, preparation of tert-butyl (6S,9S)-1-amino-6-((4-((5R,11R,12S)-11-((R)-sec-butyl)-12-(2-((R)-2-((1S, 2S)-3-(((1R,2S)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenyl)carbamoyl)-9-isopropyl-1,8,11-trioxo-14,17-dioxa-2,7,10-triazaicosan-20-oate: to a DMF (0.5 mL) solution of 3-(2-(3-(tert-butoxy)-3-oxopropoxy)ethoxy)propanoic acid (6.0 mg, 1 Eq, 23 µmol) and 2-(3H-[1,2,3]triazolo[4,5-b]pyridin-3-yl)-1,1,3,3-tetramethylisouronium hexafluorophosphate(V) (13 mg, 1.5 Eq, 34 µmol) was added N-ethyl-N-isopropylpropan-2-amine (12 mg, 16 µL, 4 Eq, 91 µmol) and 4-((S)-2-((S)-2-amino-3-methylbutanamido)-5-ureidopentanamido)benzyl ((2R)-1-((1-(((3S,4R,5R)-1-((R)-2-((1S,2S)-3-(((1R,2S)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)amino)-3-methyl-1-oxobutan-2-yl)(methyl)carbamate-2,2,2-trifluoroacetaldehyde (1/1) (28 mg, 1 Eq, 23 µmol). The reaction mixture was stirred at 20° C. for 2 hours. The reaction mixture was diluted with ethyl acetate, washed with water and brine, and concentrated to give crude product tert-butyl (6S,9S)-1-amino-6-((4-((5R,11R,12S)-11-((R)-sec-butyl)-12-(2-((R)-2-((1S,2S)-3-(((1R,2S)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenyl)carbamoyl)-9-isopropyl-1,8,11-trioxo-14,17-dioxa-2,7,10-triazaicosan-20-oate. MS (M+H)$^+$=1369.4. This material was used for the next step without further purification.

Step D-4, preparation of (6S,9S)-1-amino-6-((4-((5R,11R,12S)-11-((R)-sec-butyl)-12-(2-((R)-2-((1S,2S)-3-(((1R,2S)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenyl)carbamoyl)-9-isopropyl-1,8,11-trioxo-14,17-dioxa-2,7,10-triazaicosan-20-oic acid: to a DCM (0.6 mL) solution of tert-butyl (6S,9S)-1-amino-6-((4-((5R,11R,12S)-11-((R)-sec-butyl)-12-(2-((R)-2-((1S,2S)-3-(((1R,2S)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenyl)carbamoyl)-9-isopropyl-1,8,11-trioxo-14,17-dioxa-2,7,10-triazaicosan-20-oate (31 mg, 1 Eq, 23 µmol) was made added TFA (0.7 g, 0.5 mL, 3e+2 Eq, 6 mmol). The resulting mixture was stirred at 20° C. for 30 min. The reaction crude was concentrated and purified by C18 reverse phase chromatography eluting with ACN (0.1% TFA)/water (0.1% TFA). The collected fractions were combined and concentrated under vacuum to give (6S,9S)-1-amino-6-((4-((5R,11R,12S)-11-((R)-sec-butyl)-12-(2-((R)-2-((1S,2S)-3-(((1R,2S)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenyl)carbamoyl)-9-isopropyl-1,8,11-trioxo-14,17-dioxa-2,7,10-triazaicosan-20-oic acid (13.6 mg, 46%). MS (M+H)$^+$=1312.3

Step D-5, preparation of 4-((2S,5S)-19-((4-(4-((tert-butoxycarbonyl)amino)piperidin-1-yl)-3-(6-chloro-1H-benzo[d]imidazol-2-yl)-5-(3-fluoro-5-methylphenyl)pyridin-2-yl)amino)-5-isopropyl-4,7,16-trioxo-2-(3-ureidopropyl)-10,13-dioxa-3,6,17-triazanonadecanamido)benzyl ((2R)-1-((1-(((3S,4R,5R)-1-((R)-2-((1S,2S)-3-(((1R,2S)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)amino)-3-methyl-1-oxobutan-2-yl)(methyl)carbamate: to a DMF (0.2 mL) solution of (6S,9S)-1-amino-6-((4-((5R,11R,12S)-11-((R)-sec-butyl)-12-(2-((R)-2-((1S,2S)-3-(((1R,2S)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenyl)carbamoyl)-9-isopropyl-1,8,11-trioxo-14,17-dioxa-2,7,10-triazaicosan-20-oic acid (13.6 mg, 1 Eq, 9.94 µmol) and 2-(3H-[1,2,3]triazolo[4,5-b]pyridin-3-yl)-1,1,3,3-tetramethylisouronium hexafluorophosphate(V) (5.67 mg, 1.5 Eq, 14.9 µmol) was added N-ethyl-N-isopropylpropan-2-amine (5.14 mg, 6.93 µL, 4 Eq, 39.8 µmol) followed by tert-butyl (1-(2-((2-aminoethyl)amino)-3-(6-chloro-TH-benzo[d]imidazol-2-yl)-5-(3-fluoro-5-methylphenyl)pyridin-4-yl)piperidin-4-yl)carbamate (6.50 mg, 1.1 Eq, 10.9 µmol). The reaction mixture was stirred at 20° C. for 2 hours. The reaction mixture was diluted with ethyl acetate, washed with water and brine, and concentrated to give 4-((2S,5S)-19-((4-(4-((tert-butoxycarbonyl)amino)piperidin-1-yl)-3-(6-chloro-1H-benzo[d]imidazol-2-yl)-5-(3-fluoro-5-methylphenyl)pyridin-2-yl)amino)-5-isopropyl-4,7,16-trioxo-2-(3-ureidopropyl)-10,13-dioxa-3,6,17-triazanonadecanamido)benzyl ((2R)-1-((1-(((3S,4R,5R)-1-((R)-2-((1S,2S)-3-(((1R,2S)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)amino)-3-methyl-1-oxobutan-2-yl)(methyl)carbamate. MS (M+H)$^+$=1888.0. This material was used for the next step without further purification.

Step D-6, preparation of {4-[(2S)-2-[(2S)-2-[3-(2-{2-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]ethoxy}ethoxy)propanamido]-3-methylbutanamido]-5-(carbamoylamino)pentanamido]phenyl}methyl N-[(1S)-1-{[(1S)-1-{[(3R,4S,5S)-1-[(2S)-2-(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl]-N-methylcarbamate: to a DCM (0.6 mL) solution of 4-((2S,5S)-19-((4-(4-((tert-butoxycarbonyl)amino)piperidin-1-yl)-3-(6-chloro-1H-benzo[d]imidazol-2-yl)-5-(3-fluoro-5-methylphenyl)pyridin-2-yl)amino)-5-isopropyl-4,7,16-trioxo-2-(3-ureidopropyl)-10,13-dioxa-3,6,17-triazanonadecanamido)benzyl ((2R)-1-((1-(((3S,4R,5R)-1-((R)-2-((1S,2S)-3-(((1R,2S)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)amino)-3-methyl-1-oxobutan-2-yl)(methyl)carbamate (18.8 mg, 1 Eq, 9.96 µmol) was added TFA (0.7 g, 0.5 mL, 7e+2 Eq, 6 mmol). The resulting mixture was stirred at 0° C. for 30 min. The reaction crude was concentrated and then purified by C18 reverse phase chromatography eluting with ACN (0.1% TFA)/water (0.1% TFA). The collected fractions were combined and concentrated under vacuum to give {4-[(2S)-2-[(2S)-2-[3-(2-{2-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]ethoxy}ethoxy)propanamido]-3-methylbutanamido]-5-(carbamoylamino)pentanamido]phenyl}methyl N-[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl]-N-methylcarbamate (10.5 mg, 59.0%). MS (M+H)$^+$=1788.3.

The following conjugates were prepared similarly to Example D with appropriate substituting reagents and substrates at different steps and they may require additional functional group modifications via well-known chemistry with appropriate reagents.

| Compound |
|---|
| {4-[(2S)-2-[(2S)-2-{1-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]-3,6,9,12-tetraoxapentadecan-15-amido}-3-methylbutanamido]-5-(carbamoylamino)pentanamido]phenyl}methyl N-[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl]-N-methylcarbamate |

-continued

Compound (Compound 25)
(M + H)⁺ = 1876.6

{4-[(2S)-2-[(2S)-2-(3-{2-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]ethoxy}propanamido)-3-methylbutanamido]-5-(carbamoylamino)pentanamido]phenyl}methyl N-[(1S)-1-{[(1S)-1-{[(3R,4S,5S)-1-[(2S)-2-{[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl][(methyl)carbamoyl]-2-methylpropyl]carbamoyl}-2-methylpropyl]-N-methylcarbamate

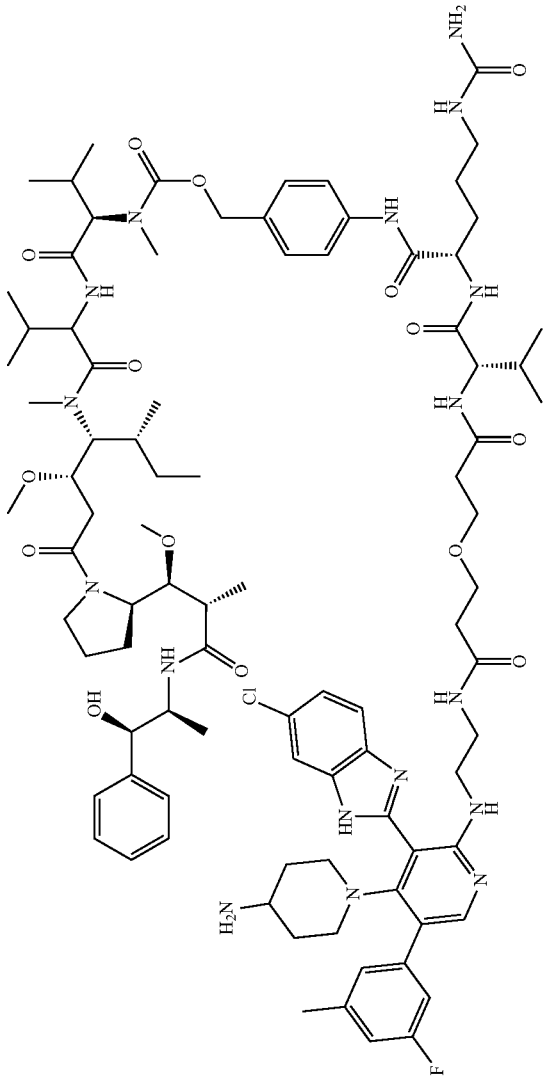

-continued

Compound (Compound 26)
(M + H)⁺ = 1745.9
{4-[(2S)-2-[(2S)-2-{1-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]-3,6,9,12,15,18,21,24-octaoxaheptacosan-27-amido}-3-methylbutanamido]-5-(carbamoylamino)pentanamido]phenyl}methyl N-[(1S)-1-{[(1S)-1-{[(3R,4S,5S)-1-{(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl]-N-methylcarbamate

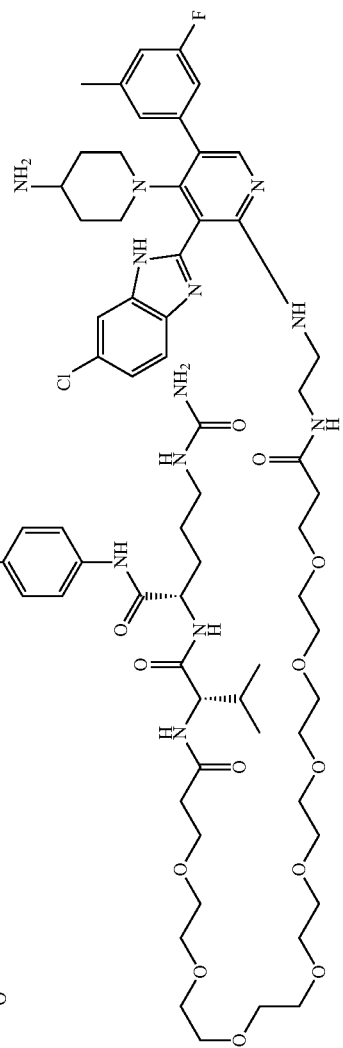

-continued

| Compound |
|---|
| (Compound 27)<br>(M/2 + H)+ = 1027.2<br>{4-[(2S)-2-[(2S)-2-(3-{2-[(2-{[4-(4-aminopiperidin-1-yl)-3-(6-carbamoyl-1H-1,3-benzodiazol-2-yl)-5-(3-fluoro-5-methylphenyl)pyridin-2-yl]amino}ethyl)carbamoyl]ethoxy}propanamido)-3-methylbutanamido]-5-(carbamoylamino)pentanamido]phenyl} methyl N-[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl]-2-methylpropyl]-N-methylcarbamate<br>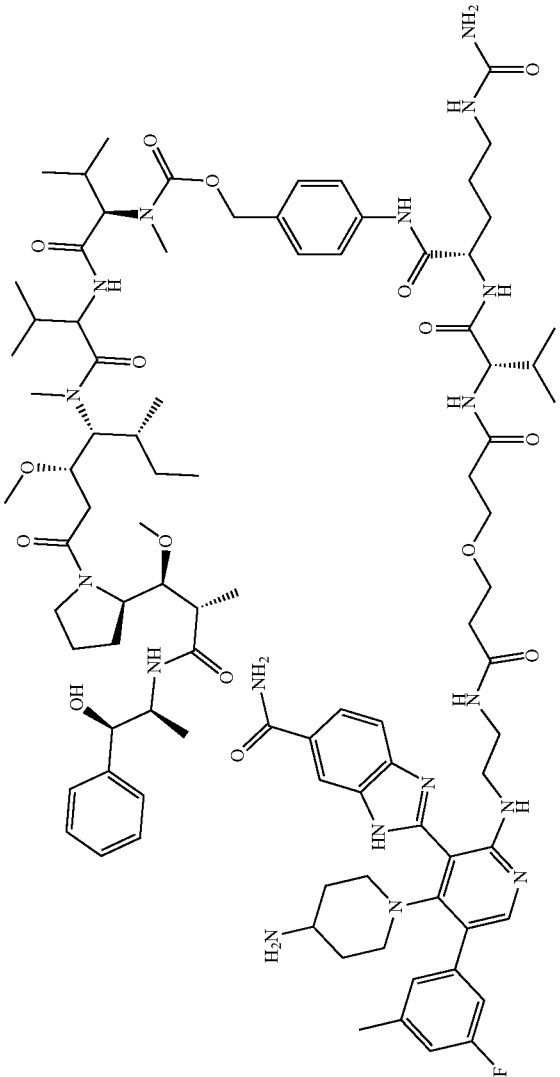 |

| Compound |
| --- |
| (Compound 28)<br>(M + H)+ = 1753.9<br>N-(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)-3-[2-({2-[(5-{[(3Z)-5-fluoro-2-oxo-2,3-dihydro-1H-indol-3-ylidene]methyl}-2,4-dimethyl-1H-pyrrol-3-yl)formamido]ethyl}carbamoyl)ethoxy]propenamide<br>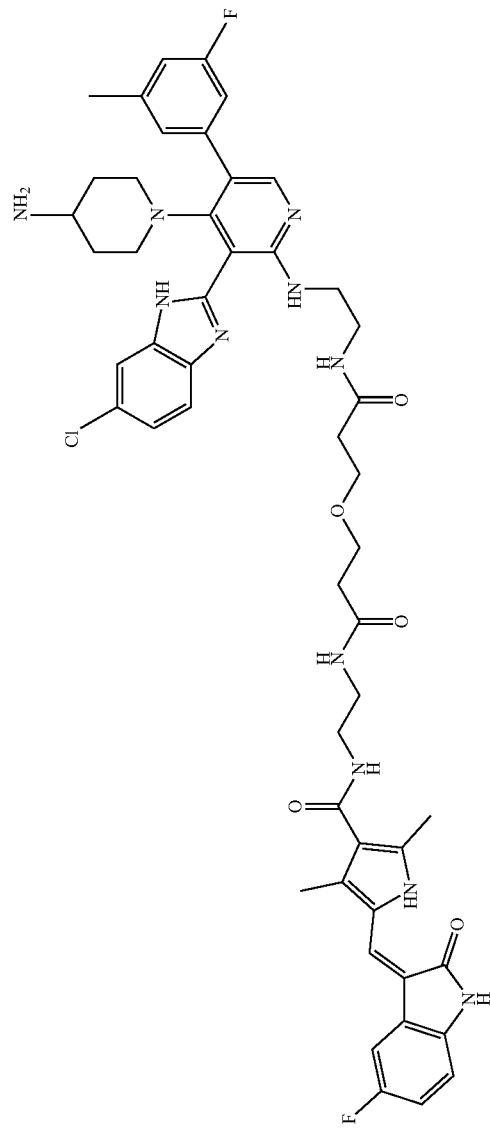 |

-continued

Compound (Compound 29)
(M + H)⁺ = 963.9
{4-[(2S)-2-[(2S)-2-[(2S)-2-[2-[(2S)-2-[2-[2-(3-{2-[2-{[(4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]ethoxy}propanamido)acetamido]-3-phenylpropanamido]acetamido}-3-methylbutanamido]-5-(carbamoylamino)pentanamido]phenyl}methyl N-[(1S)-1-{[(1S)-1-{[(3R,4S,5S)-1-{(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl]-N-methylcarbamate

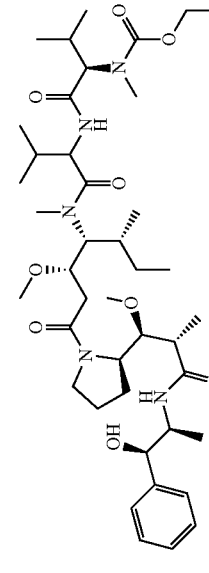

-continued

| Compound |
|---|
| (Compound 30)<br>(M/2 + H)+ = 1031.9<br>{4-[(2S)-5-(carbamoylamino)-2-[(2S)-2-{1-[(2-{[3-(6-chloro-1H-1,3-benzodiazol-2-yl)-5-(3-fluoro-5-methylphenyl)-4-(4-hydroxypiperidin-1-yl)pyridin-2-yl]amino}ethyl)carbamoyl]-3,6,9,12-tetraoxapentadecan-15-amido}-3-methylbutanamido]pentanamido]phenyl}methyl N-{(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl]-N-methylcarbamate |

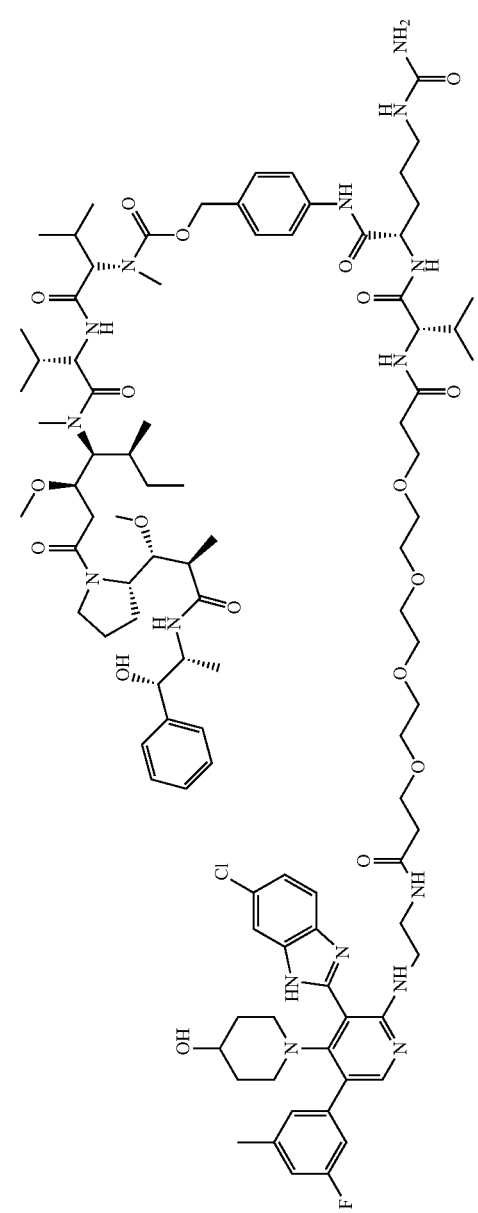

-continued

Compound (Compound 31)
{4-[(2S)-2-[(16S)-1-{(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]-16-(propan-2-yl)-3,6,9,12-tetraoxa-15-azaheptadecan-17-amido]-5-(carbamoylamino)pentanamido]phenyl}methyl N-[(1S)-1-{[(1S)-1-{[(2S)-2-{[(1R,2R)-2-{[(1S,2R)-1-hydroxy-1-phenylpropan-2-yl]carbamoyl}-1-methoxypropyl]pyrrolidin-1-yl]-3-methoxy-5-methyl-1-oxoheptan-4-yl}(methyl)carbamoyl]-2-methylpropyl}carbamoyl]-2-methylpropyl]-N-methylcarbamate (Compound 69)
N-{2-[4-(4-amino-1-piperidyl)-3-(6-chloro-1H-1,3-benzimidazol-2-yl)-5-(3-fluoro-5-tolyl)-2-pyridyl]amino]ethyl}-3-(2-{N-(10S,23S)-10-ethyl-18-fluoro-10-hydroxy-19-methyl-5,9-dioxo-8-oxa-4,15-diazahexacyclo[14.7.1.0²,¹⁴.0⁴,¹³.0⁶,¹¹.0²⁰,²⁴]tetracosa-1,6(11),12,14,16,18,20(24)-heptaen-23-ylcarbamoyl}ethoxy)propionamide
$(M + H)^+ = 1847.0$ (Compound 78)
$(M + H)^+ = 1056.8$ Example E. (4S)-4-(3-{2-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]ethoxy}propanamido)-4-{[(1S)-1-{[(1S)-1-({4-[(({[(1S)-1-{[(1S)-1-{[(3R,4S,5S)-1-[(2S)-2-[(1R,2R)-2-{[(1S,2R)-1-hydroxy-1-phenylpropan-2-yl]carbamoyl]-1-methoxy-2-methylethyl]pyrrolidin-1-yl]-3-methoxy-5-methyl-1-oxoheptan-4-yl](methyl)carbamoyl]-2-methylpropyl}carbamoyl]-2-methylpropyl](methyl)carbamoyl}oxy)methyl]phenyl}carbamoyl)ethyl}carbamoyl]-2-methylpropyl]carbamoyl}butanoic acid (Compound 32)

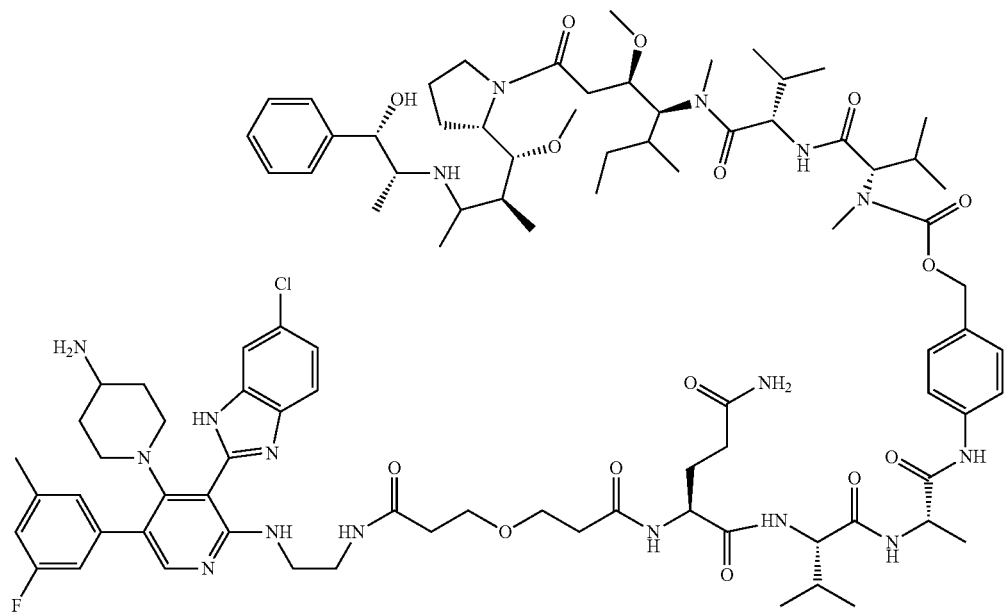 [SMILES: CCC(C)[C@@H]([C@@H](CC(=O)N1CCC[C@H]1[C@H](OC)[C@@H](C)C(C)N[C@H](C)[C@@H](O)c1ccccc1)OC)N(C)C(=O)[C@@H](NC(=O)[C@H](C(C)C)N(C)C(=O)OCc1ccc(NC(=O)[C@H](C)NC(=O)[C@@H](NC(=O)[C@H](CCC(N)=O)NC(=O)CCOCCC(=O)NCCNc2ncc(-c3cc(C)cc(F)c3)c(N3CCC(N)CC3)c2-c2nc3ccc(Cl)cc3[nH]2)C(C)C)cc1)C(C)C]

Step E-1. preparation of 4-((S)-2-((S)-2-((((9H-fluoren-9-yl)methoxy)carbonyl)amino)-3-methylbutanamido)propanamido)benzyl ((S)-1-(((S)-1-(((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)amino)-3-methyl-1-oxobutan-2-yl)(methyl)carbamate: to a mixture of (S)—N-((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N,3-dimethyl-2-((S)-3-methyl-2-(methylamino)butanamido)butanamide (150 mg, 1 Eq, 209 μmol) in DMF (1.5 mL) was added (9H-fluoren-9-yl)methyl ((S)-3-methyl-1-(((S)-1-((4-((((4-nitrophenoxy)carbonyl)oxy)methyl)phenyl)amino)-1-oxopropan-2-yl)amino)-1-oxobutan-2-yl)carbamate (160 mg, 1.13 Eq, 235 μmol), 1H-benzo[d][1,2,3]triazol-1-ol hydrate (50 mg, 1.6 Eq, 0.33 mmol) and N-ethyl-Nisopropylpropan-2-amine (100 mg, 3.70 Eq, 774 μmol). The reaction mixture was stirred at 20° C. for 5 hours. The mixture was directly purified by MPLC with the following conditions: Column, C18 120 g, Spherical 20-40 μm; Mobile phase, Water (0.05% FA) and ACN (5% ACN to 5% ACN in 1 min, 30% ACN up to 90% in 10 min, 95% ACN to 95% in 2 min); Total flow rate, 70 mL/min; Detector, UV 220 nm. The collected fractions were combined and concentrated under vacuum to give 4-((S)-2-((S)-2-((((9H-fluoren-9-yl)methoxy)carbonyl)amino)-3-methylbutanamido)propanamido)benzyl ((S)-1-(((S)-1-(((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)amino)-3-methyl-1-oxobutan-2-yl)(methyl)carbamate (130 mg, 49.4%). MS (M+H)=1259.8.

Step E-2, preparation of 4-((S)-2-((S)-2-amino-3-methylbutanamido)propanamido)-benzyl ((S)-1-(((S)-1-(((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)amino)-3-methyl-1-oxobutan-2-yl)(methyl)carbamate: to a mixture of 4-((S)-2-((S)-2-((((9H-fluoren-9-yl)methoxy)carbonyl)-amino)-3-methylbutanamido)propanamido)benzyl ((S)-1-(((S)-1-(((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)amino)-3-methyl-1-oxobutan-2-yl)(methyl)carbamate (125 mg, 1 Eq, 99.2 μmol) in ACN (1.5 mL) was added 1,8-Diazabicyclo[5.4.0]undec-7-ene (DBU) (50 mg, 50 μL, 3.3 Eq, 0.33 mmol). The reaction mixture was stirred at 20° C. for 1 hour. The mixture was directly purified by MPLC with the following conditions: Column, WelFlash™, C18 120 g, Spherical 20-40 μm; Mobile phase, Water (0.05% FA) and ACN (5% ACN to 5% ACN in 1 min, 30% ACN up to 90% in 10 min, 95% ACN to 95% in 2 min); Total flow rate, 70 mL/min; Detector, UV 220 nm. The collected fractions were combined and concentrated under vacuum to give 4-((S)-2-((S)-2-amino-3-methylbutanamido)-propanamido)benzyl ((S)-1-(((S)-1-(((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)amino)-3-methyl-1-oxobutan-2-yl)(methyl)carbamate (110 mg, 91%, 85% Purity). MS (M+H)$^+$=1037.8.

Step E-3, preparation of tert-butyl (S)-4-((((9H-fluoren-9-yl)methoxy)carbonyl)amino)-5-(((S)-1-(((S)-1-((4-((5S,8S,11S,12S)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenyl)amino)-1-oxopropan-2-yl)amino)-3-methyl-1-oxobutan-2-yl)amino)-5-oxopentanoate: to a mixture of (S)-2-((((9H-fluoren-9-yl)methoxy)carbonyl)amino)-5-(tert-butoxy)-5-oxopentanoic acid (35 mg, 1.1 Eq, 82 μmol) in DMF (1 mL) was added HATU (33 mg, 1.1 Eq, 87 μmol) and DIEA (30 mg, 40 μL, 3.0 Eq, 0.23 mmol). The reaction mixture was stirred at 20 C for 10 min and then 4-((S)-2-((S)-2-amino-3-methylbutanamido)propanamido)benzyl ((S)-1-(((S)-1-(((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)amino)-3-methyl-1-oxobutan-2-yl)(methyl)carbamate (80 mg, 1 Eq, 77 μmol) was added and the reaction mixture was stirred at 20° C. for an additional 1.5 hours. The mixture was directly purified by MPLC with the following conditions: Column, C18 120 g, Spherical 20-40 μm; Mobile phase, Water (0.05% TFA) and ACN (5% ACN to 5% ACN in 1 min, 30% ACN up to 78% in 9 min, 90% ACN to 90% in 3 min); Total flow rate, 70 mL/min; Detector, UV 220 nm. The collected fractions were combined and concentrated under vacuum to give tert-butyl (S)-4-((((9H-fluoren-9-yl)methoxy)carbonyl)amino)-5-(((S)-1-(((S)-1-((4-((5S,8S,11S,12S)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenyl)amino)-1-oxopropan-2-yl)amino)-3-methyl-1-oxobutan-2-yl)amino)-5-oxopentanoate (60 mg, 54%). MS (M+H)$^+$=1445.0.

Step E-4, preparation of tert-butyl (S)-4-amino-5-(((S)-1-(((S)-1-((4-((5S,8S,11S,12S)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenyl)amino)-1-oxopropan-2-yl)amino)-3-methyl-1-oxobutan-2-yl)amino)-5-oxopentanoate: to a mixture of tert-butyl (S)-4-((((9H-fluoren-9-yl)methoxy)carbonyl)amino)-5-(((S)-1-(((S)-1-((4-((5S,8S,11S,12S)-11-((S)-secbutyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenyl)amino)-1-oxopropan-2-yl)amino)-3-methyl-1-oxobutan-2-yl)amino)-5-oxopentanoate (55 mg, 1 Eq, 38 μmol) in ACN (1 mL) was added DBU (20 mg, 20 μL, 3.5 Eq, 0.13 mmol). The reaction mixture was stirred at 20° C. for 1 hour. The mixture was directly purified by MPLC with the following conditions: Column, WelFlash™, C18 120 g, Spherical 20-40 μm; Mobile phase, Water (0.05% TFA) and ACN (5% ACN to 5% ACN in 1 min, 30% ACN up to 80% in 9 min, 90% ACN to 90% in 3 min); Total flow rate, 70 mL/min; Detector, UV 220 nm. The collected fractions were dried by lyophilization. The collected fractions were combined and concentrated under vacuum to give tert-butyl (S)-4-amino-5-(((S)-1-(((S)-1-((4-((5S,8S,11S,12S)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenyl)amino)-1-oxopropan-2-yl)amino)-3-methyl-1-oxobutan-2-yl)amino)-5-oxopentanoate (40 mg, 86%). MS (M+H)$^+$=1223.2.

Step E-5, preparation of 3-(3-((2-((4-(4-((tert-butoxycarbonyl)amino)piperidin-1-yl)-3-(6-chloro-1Hbenzo[d]imidazol-2-yl)-5-(3-fluoro-5-methylphenyl)pyridin-2-yl)amino)ethyl)amino)-3-oxopropoxy)propanoic acid: a mixture of 3,3'-oxydipropionic acid (150 mg, 1.10 Eq, 925 μmol), HATU (384 mg, 1.20 Eq, 1.01 mmol), and Diisopropylethylamine (327 mg, 437 μL, 3.01 Eq, 2.53 mmol) in DMF (5 mL) was stirred for 10 min at 25° C. and then tert-butyl (1-(2-((2-aminoethyl)amino)-3-(6-chloro-1H-benzo[d]imidazol-2-yl)-5-(3-fluoro-5-methylphenyl)pyridin-4-yl)piperidin-4-yl)carbamate (500 mg, 1 Eq, 842 μmol) was added. The resulting reaction mixture was stirred at 25° C. for 2 hours. The reaction was then quenched with water (200 mL). The resulting solution was extracted with ethyl acetate (3×200 mL). The organic layers was dried over anhydrous sodium sulfate and concentrated under vacuum. The residue was applied onto a silica gel column with ethyl acetate/petroleum ether (1:1). The collected fractions were combined and concentrated under vacuum to give 3-(3-((2-((4-(4-((tert-butoxycarbonyl)amino)piperidin-1-yl)-3-(6-chloro-1H-benzo[d]imidazol-2-yl)-5-(3-fluoro-5-methylphenyl)pyridin-2-yl)amino)ethyl)amino)-3-oxopropoxy)propanoic acid (290 mg, 46.7%). MS (M+H)$^+$=738.5.

Step E-6, preparation of tert-butyl (S)-4-(3-(3-((2-((4-(4-((tert-butoxycarbonyl)amino)piperidin-1-yl)-3-(6-chloro-1H-benzo[d]imidazol-2-yl)-5-(3-fluoro-5-methylphenyl)pyridin-2-yl)amino)ethyl)amino)-3-oxopropoxy)propanamido)-5-(((S)-1-(((S)-1-((4-((5S,8S,11S,12S)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenyl)amino)-1-oxopropan-2-yl)amino)-3-methyl-1-oxobutan-2-yl)amino)-5-oxopentanoate: to a mixture of 3-(3-((2-((4-(4-((tert-butoxycarbonyl)amino)piperidin-1-yl)-3-(6-chloro-1H-benzo[d]imidazol-2-yl)-5-(3-fluoro-5-methylphenyl)pyridin-2-yl)amino)ethyl)amino)-3-oxopropoxy)propanoic acid (25 mg, 1.0 Eq, 34 μmol) in DMF (1 mL) was added 4-methylmorpholine (12 mg, 3.6 Eq, 0.12 mmol) and perfluorophenyl diphenylphosphinate (16 mg, 1.3 Eq, 42 μmol). The reaction mixture was stirred at 20° C. for 10 min, and then tert-butyl (S)-4-amino-5-(((S)-1-(((S)-1-((4-((5S,8S,11S,12S)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenyl)amino)-1-oxopropan-2-yl)amino)-3-methyl-1-oxobutan-2-yl)amino)-5-oxopentanoate (40 mg, 1 Eq, 33 μmol) was added and the reaction mixture was stirred at 20° C. for additional 2 h. The mixture was diluted with 20 mL of water, extracted with ethyl acetate (20 mL×3), the combined organic layers were washed with water (10 mL×2) and brine (20 mL), dried over anhydrous Na$_2$SO$_4$ and concentrated under reduced pressure to give tert-butyl (S)-4-(3-(3-((2-((4-(4-((tert-butoxycarbonyl)amino)piperidin-1-yl)-3-(6-chloro-TH-benzo[d]imidazol-2-yl)-5-(3-fluoro-5-methylphenyl)pyridin-2-yl)amino)ethyl)amino)-3-oxopropoxy)propanamido)-5-(((S)-1-(((S)-1-((4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenyl)amino)-1-oxopropan-2-yl)amino)-3-methyl-1-oxobutan-2-yl)amino)-5-oxopentanoate (50 mg, 79%). MS (M+H)$^+$=1942.2. This material was used for the next step without further purification.

Step E-7, preparation of (4S)-4-(3-{2-[(2-{[4-(4-aminopiperidin-1-yl)-3-(6-chloro-TH-1,3-benzodiazol-2-yl)-5-(3-fluoro-5-methylphenyl)pyridin-2-yl]amino}ethyl)carbamoyl]ethoxy}propanamido)-4-{[(1S)-1-{[(1S)-1-({4-[({[(S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl](methyl)carbamoyl}oxy)methyl]phenyl}carbamoyl)ethyl]carbamoyl}-2-methylpropyl]carbamoyl}butanoic acid: to a mixture of tert-butyl (S)-4-(3-3-((2-((4-(4-((tert-butoxycarbonyl)amino)piperidin-1-yl)-3-(6-chloro-TH-benzo[d]imidazol-2-yl)-5-(3-fluoro-5-methylphenyl)pyridin-2-yl)amino)ethyl)amino)-3-oxopropoxy)propanamido)-5-(((S)-1-(((S)-1-((4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenyl)amino)-1-oxopropan-2-yl)amino)-3-methyl-1-oxobutan-2-yl)amino)-5-oxopentanoate (45 mg, 1 Eq, 23 μmol) in DCM (0.2 mL) was added TFA (0.2 mL) at 0° C. and the reaction mixture was stirred for 30 min. The pH value of the reaction mixture was adjusted to 7.0 by DIEA at 0° C. and blow dried with nitrogen. The crude product was purified by Prep-HPLC with the following conditions: Column: SunFire prep OBD 19*150 mm 5 um; Mobile Phase A: Water (0.05% TFA); Mobile Phase B: ACN; Gradient: 20% B to 53% B in 15 min; Flow rate: 20 mL/min; Wave Length: 220 nm. The collected fractions were dried by lyophilization to give (4S)-4-(3-{2-[(2-{[4-(4-aminopiperidin-1-yl)-3-(6-chloro-TH-1,3-benzodiazol-2-yl)-5-(3-fluoro-5-methylphenyl)pyridin-2-yl]amino}ethoxy}propanamido)-4-{[(1S)-1-{[(1S)-1-({4-[({[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl](methyl)carbamoyl}oxy)methyl]phenyl}carbamoyl)ethyl]carbamoyl}-2-methylpropyl]carbamoyl}butanoic acid (8.4 mg, 17%). MS (M+H)$^+$=1790. The following conjugates were prepared similarly to Example E with appropriate substituting reagents and substrates at different steps and they may require additional functional group modifications via well-known chemistry with appropriate reagents.

| Compound |
|---|
| 2-(4-{[(2-{[4-(4-aminopiperidin-1-yl)-3-(6-chloro-1H-1,3-benzodiazol-2-yl)-5-(3-fluoro-5-methyl)phenyl]pyridin-2-yl]amino}ethyl)carbamoyl]methyl}-7-({[(1S)-1-{[(1S)-4-(carbamoylamino)-1-({4-[{[(1S)-1-{[(3R,4S,5S)-1-{[(3R,2R)-2-{[(1S,2R)-1-hydroxy-1-phenylpropan-2-yl]carbamoyl}-1-methoxy-2-methylethyl]pyrrolidin-1-yl}-3-methoxy-5-methyl-1-oxoheptan-4-yl](methyl)carbamoyl}-2-methylpropyl]carbamoyl}-2-methylpropyl](methyl)carbamoyl]oxy}methyl]phenyl}carbamoyl)butyl]carbamoyl}-2-methylpropyl](methyl)carbamoyl]methyl)-1,4,7-triazonan-1-yl)acetic acid 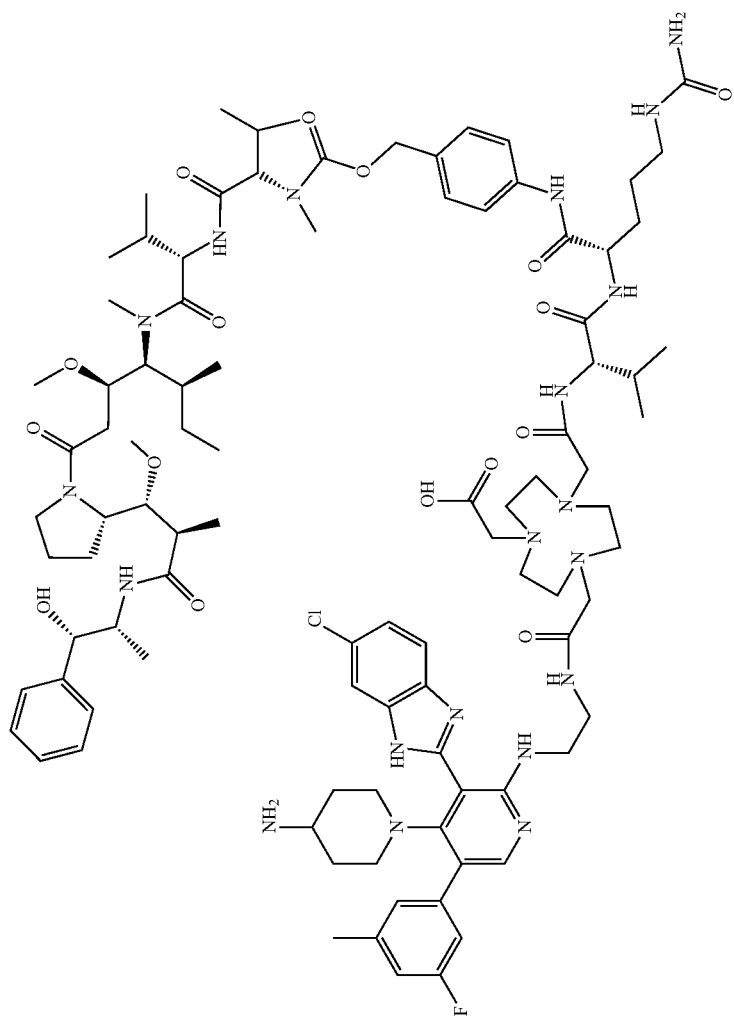 |

-continued

| Compound |
|---|
| (Compound 33)<br>(M + H)+ = 1884.6<br>(2S)-2-[(2S)-2-{2-[(2S)-2-{2-[2-(3-{2-[2-({[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]ethoxy}propanamido)acetamido]-3-phenylpropanamido]-N-methylacetamido}-3-methylbutanamido]-N-[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl]-N,3-dimethylbutanamide |

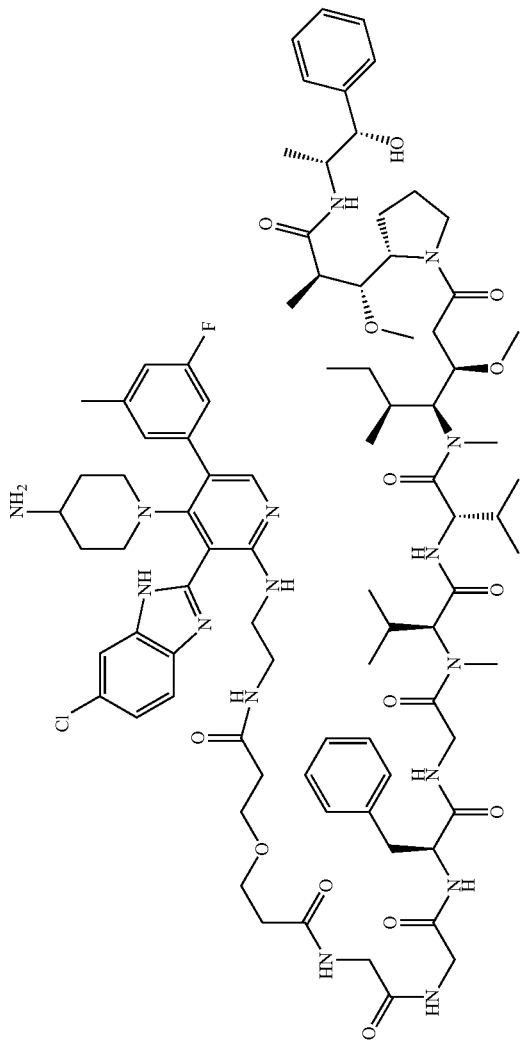

-continued

| Compound |
|---|
| (Compound 34)<br>(M + H)+ = 1658.1<br>(4-{2-[(2S)-2-{2-[2-(3-{2-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]ethoxy}propanamido)acetamido]-3-phenylpropanamido}acetamido)phenyl)methyl N-[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl]](methyl)carbamoyl}-2-methylpropyl]carbamoyl}-2-methylpropyl]-N-methylcarbamate |

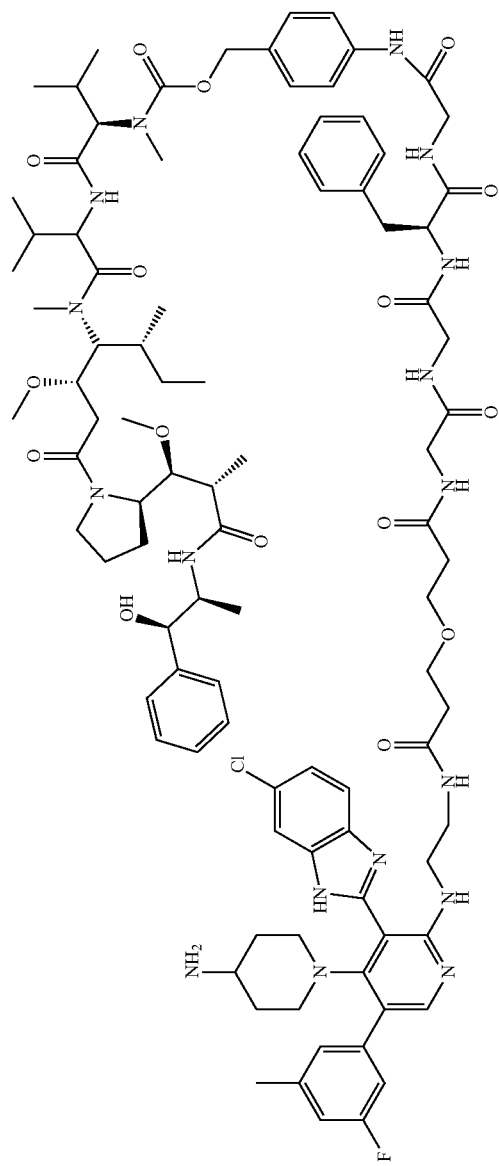

-continued

| Compound |
|---|
| (Compound 35)<br>(M + H)⁺ = 1807.7<br>(4S)-4-(3-{2-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]ethoxy}propanamido)-4-{[(1S)-1-{[(1S)-4-(carbamoylamino)-1-({4-[{[(1S)-1-{[(1S)-1-{[(3R,4S,5S)-1-{(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl]-2-methylpropyl}carbamoyl]-2-methylpropyl}(methyl)carbamoyl]oxy}methyl]phenyl}carbamoyl)butyl]carbamoyl}-2-methylpropyl]carbamoyl}butanoic acid |

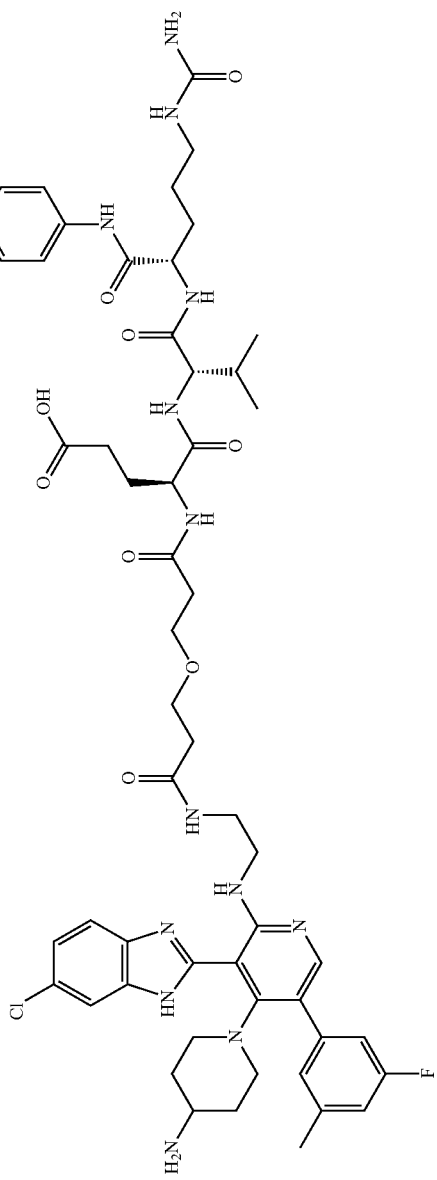

-continued

| Compound |
|---|
| (Compound 36)<br>(M + H)⁺ = 1873.1<br>2-(4-{[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]methyl}-7-({2-(2-{[(1S)-1-{[(1S)-4-(carbamoylamino)-1-({4-[{[(1S)-1-{[(1S)-1-{[(2S)-2-{[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl]-2-methylpropyl}carbamoyl]-2-methylpropyl](methyl)carbamoyl]oxy)methyl]phenyl}carbamoyl)butyl]carbamoyl}-2-methylpropyl]carbamoyl}ethoxy)ethyl]carbamoyl}methyl)-1,4,7-triazonan-1-yl)acetic acid |

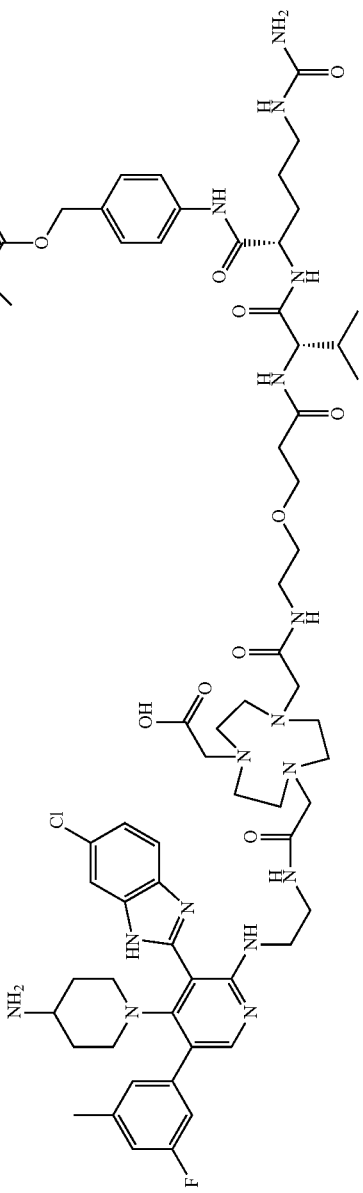

-continued
Compound
(Compound 37)
$(M + H)^+$ = 2000.1
{4-[(2S)-2-[(2S)-2-[1-[(2-[[4-(4-aminopiperidin-1-yl)-3-(6-chloro-1H-1,3-benzodiazol-2-yl)-5-(3-fluoro-5-methylphenyl)pyridin-2-yl]amino]ethyl)carbamoyl]-3,6,9,12-tetraoxapentadecan-15-amido]-3-methylbutanamido]-5-(carbamoylamino)pentanamido]phenyl}methyl N-[(10S,23S)-10-ethyl-18-fluoro-10-hydroxy-19-methyl-5,9-dioxo-8-oxa-4,15-diazahexacyclo[14.7.1.0²,¹⁴.0⁴,¹³.0⁶,¹¹.0²⁰,²⁴]tetracosa-1,6(11),12,14,16,18,20(24)-heptaen-23-yl]carbamate
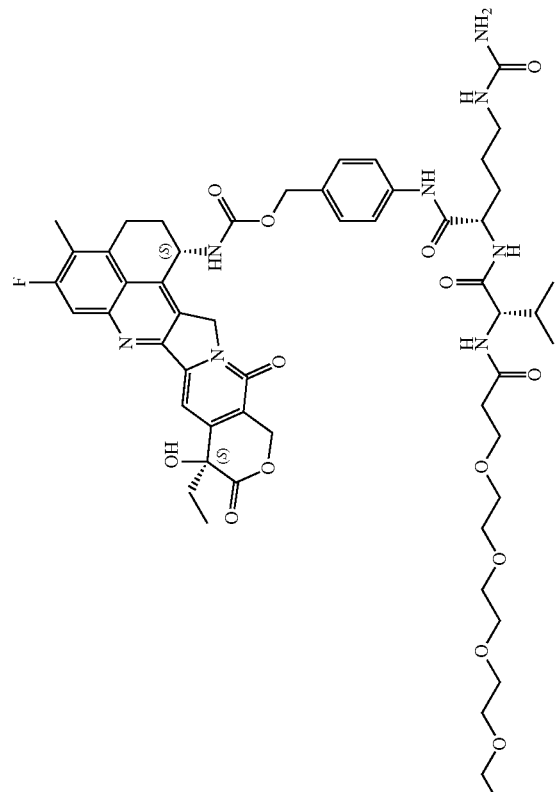

-continued

Compound (Compound 38)
(M + H)⁺ = 1594.8
2-{4-[{{14-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]-3,6,9,12-tetraoxatetradecan-1-yl}carbamoyl)methyl]-7-({[(1S)-1-{[(1S)-4-(carbamoylamino)-1-({4-[{[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl]carbamoyl]oxy}methyl)phenyl]carbamoyl}butyl]carbamoyl}-2-methylpropyl]carbamoyl}methyl)-1,4,7-triazonan-1-yl]acetic acid

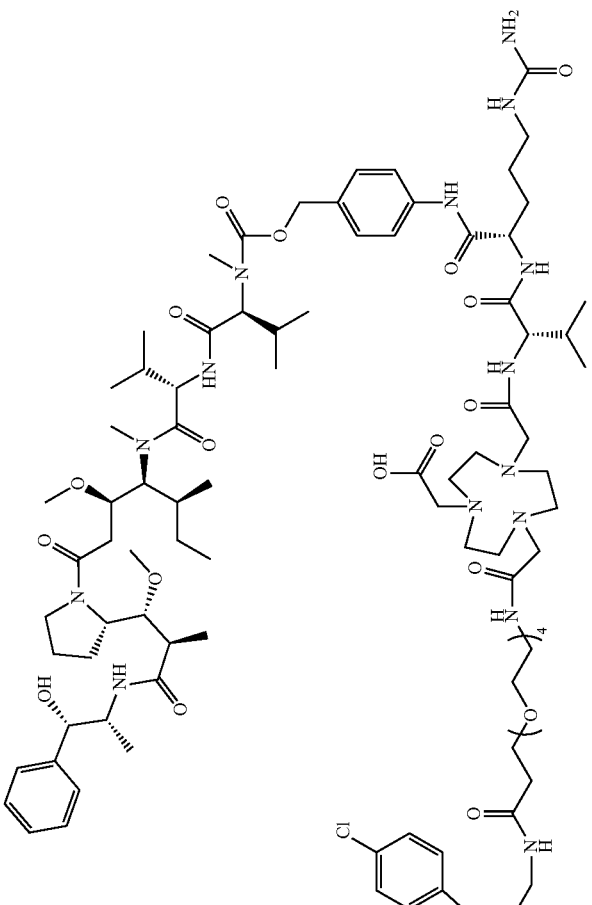

| -continued |
|---|
| Compound |
| (Compound 39)<br>(M + H)⁺ = 2131.2<br>{4-[(2S)-2-[(2S)-2-{1-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]-3,6,9,12,15,18-hexaoxahenicosan-21-amido]-3-methylbutanamido]-5-(carbamoylamino)pentanamido]phenyl} methyl N-[(1S)-1-{[(1S)-1-{[(3R,4S,5S)-1-{(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl]-N-methylcarbamate |

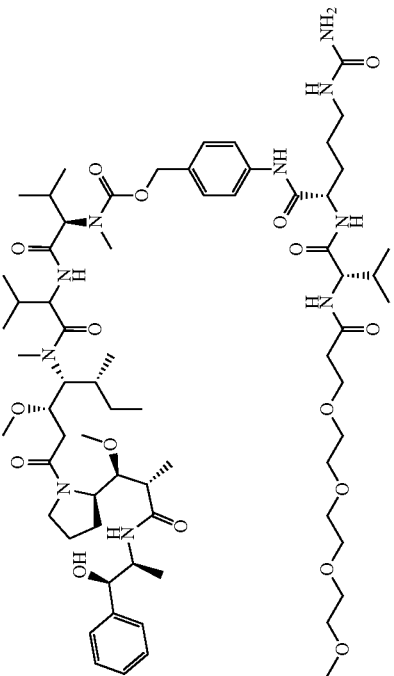

-continued

| Compound |
|---|
| (Compound 40)<br>(M + H)⁺ = 1964.1<br>{4-[(2S)-5-(carbamoylamino)-2-[(2S)-2-{[(2S)-2-{1-[(2-{[3-(6-chloro-1H-1,3-benzodiazol-2-yl)-5-(3-fluoro-5-methylphenyl)-4-[4-(methylamino)piperidin-1-yl]pyridin-2-yl]amino}ethyl)carbamoyl]-3,6,9,12-tetraoxapentadecan-15-amido}-3-methylbutanamido]pentanamido]phenyl}methyl N-[(1S)-1-{[(1S)-1-{[(3R,4S,5S)-1-[(2S)-2-{[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl]-N-methylcarbamate |

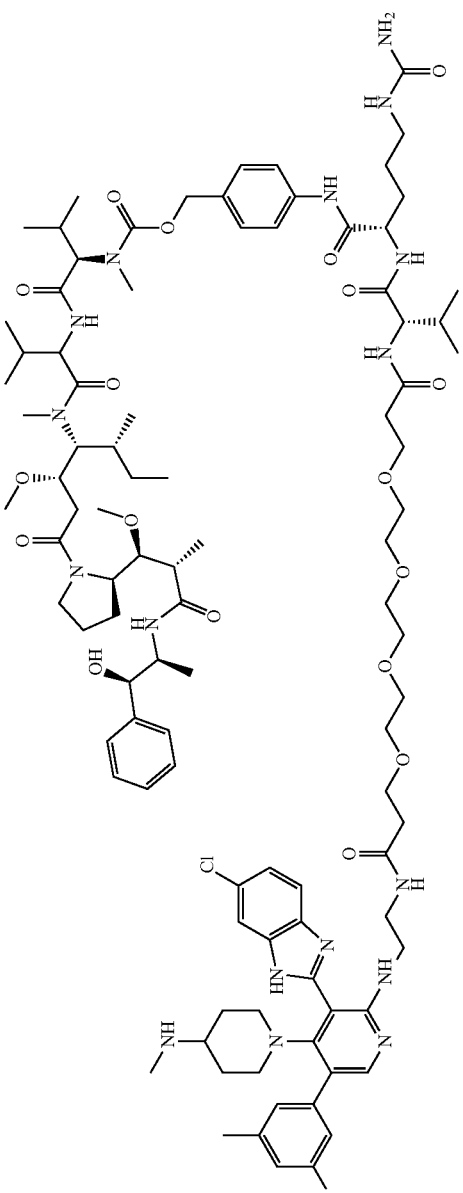

-continued

Compound (Compound 41)
(M/2 + H)+ = 1890.1
(2S)-2-[(2R)-2-[(R)-[(2S)-1-[(3R,4S,5S)-4-[(2S)-2-[(2S)-2-[[{4-[(2S)-2-[(2S)-2-{1-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]-3,6,9,12-tetraoxapentadecan-15-amido]-3-methylbutanamido]-5-(carbamoylamino)pentanamido]phenyl}methoxy)carbonyl](methyl)amino]-3-methylbutanamido]-N,3-dimethylbutanamido]-3-methoxy-5-methylheptanoyl]pyrrolidin-2-yl](methoxy)methyl propanamido]-3-phenylpropanoic acid

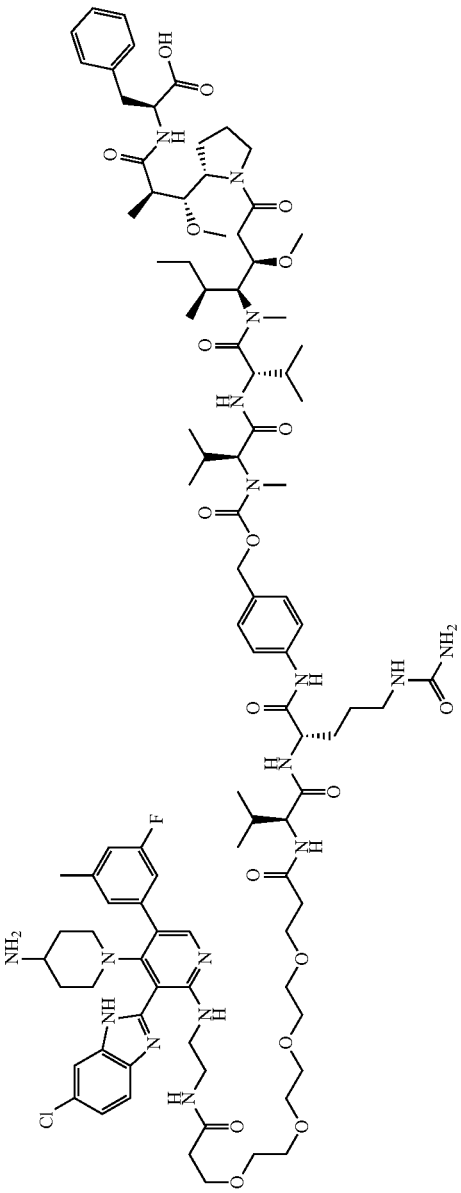

| Compound |
|---|
| (Compound 42)<br>(M/2 + H)⁺ = 945.8<br>2-{4-[{[14-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]-3,6,9,12-tetraoxatetradecan-1-yl]carbamoyl}methyl]-7-({[2-(2-{[(1S)-1-{[(1S)-4-(carbamoylamino)-1-({4-[{[(1S)-1-{[(1S)-1-{[(3R,4S,5S)-1-{(2S)-2-{[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl}(methyl)carbamoyl]-2-methylpropyl}carbamoyl]-2-methylpropyl}carbamoyl]oxy}methyl]phenyl}carbamoyl)butyl]carbamoyl}-2-methylpropyl]carbamoyl}ethoxy)ethyl]carbamoyl}methyl)-1,4,7-triazonan-1-yl}acetic acid<br>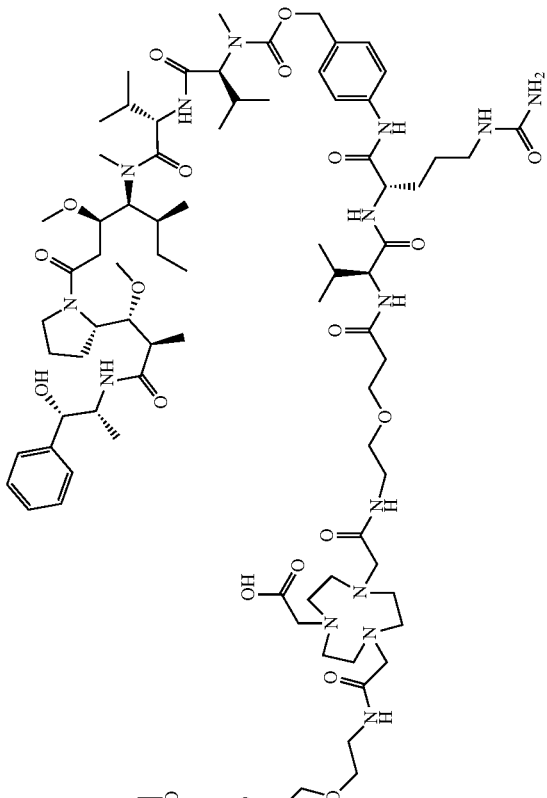 |

—continued

-continued

| Compound |
|---|
| (Compound 43)<br>(M + H)⁺ = 2249.3<br>(2R)-2-{1-[(2-{[(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]-3,6,9,12-tetraoxapentadecan-15-amido}-2-{[2-(2-{[(1S)-1-{[(1S)-4-(carbamoylamino)-1-({4-[{[[(1S)-1-{[(1S)-1-{[(3R,4S,5S)-1-{(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl](methyl)carbamoyl]oxy}methyl]phenyl}carbamoyl)butyl]carbamoyl}-2-methylpropyl]carbamoyl]ethoxy}ethyl]carbamoyl]ethane-1-sulfonic acid |

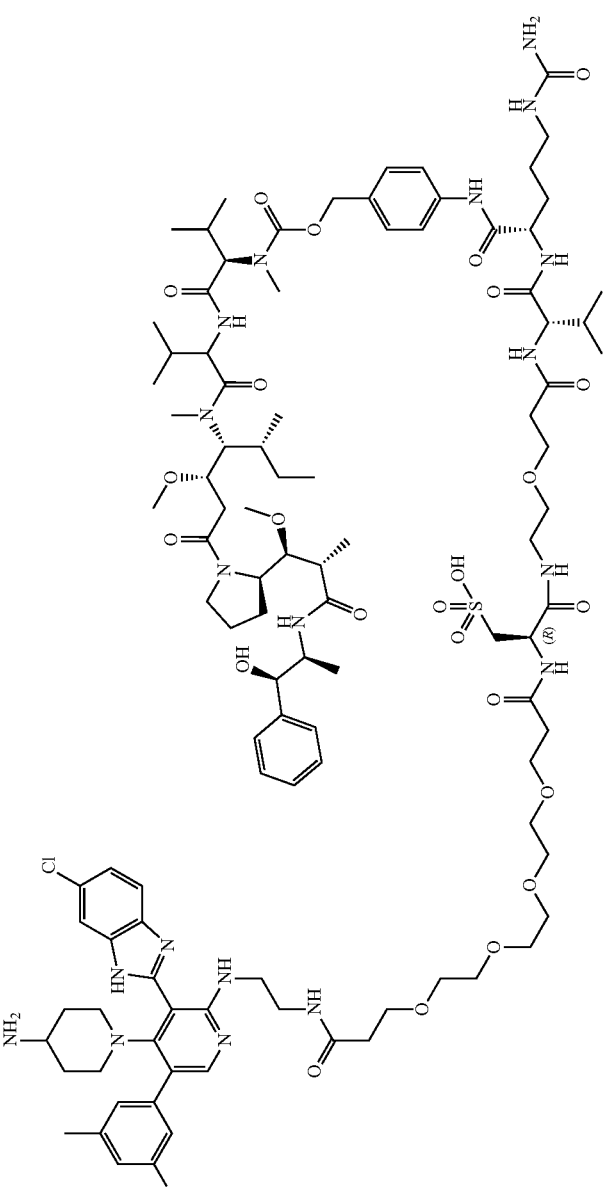

-continued

Compound (Compound 44)
(M + H)⁺ = 2142.1
(2R)-2-{1-[(2-{[(4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]-3,6,9,12-tetraoxapentadecan-15-amido}-2-{[(1S)-1-{[(1S)-4-(carbamoylamino)-1-({4-[({[(1S)-1-{[(1S)-2-{[(3R,4S,5S)-1-{[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl]oxy}methyl)phenyl]carbamoyl}butyl]carbamoyl}-2-methylpropyl]carbamoyl}ethane-1-sulfonic acid

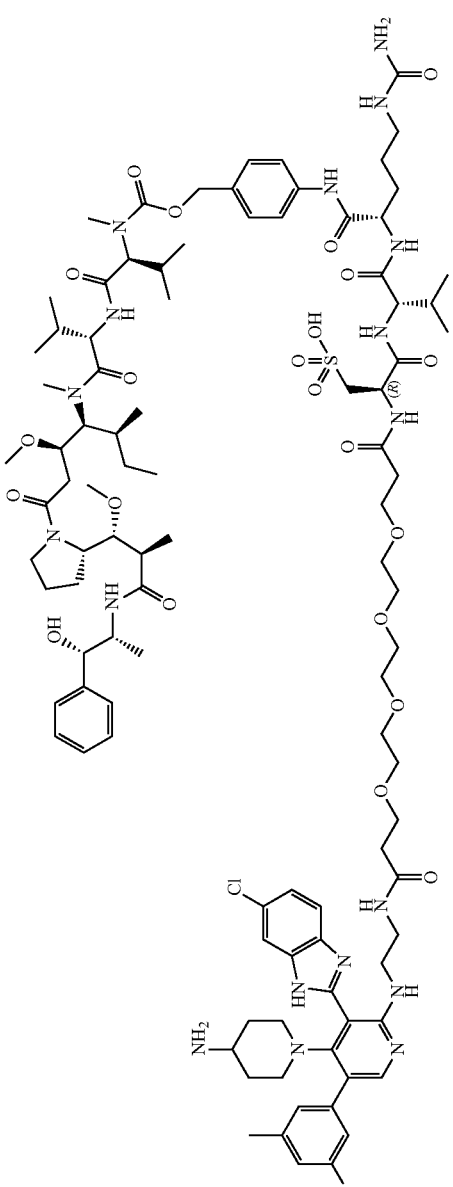

-continued

| Compound |
|---|
| (Compound 45)<br>(M + H)+ = 2027.4<br>{4-[(2S)-2-[(2S)-2-(2-{4,7-bis[{{14-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl]carbamoyl}-3,6,9,12-tetraoxatetradecan-1-yl}carbamoyl)methyl]-1,4,7-triazonan-1-yl}acetamido)-3-methylbutanamido]-5-(carbamoylamino)pentanamido]phenyl}methyl N-[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl]-2-methylpropyl]-N-methylcarbamate |

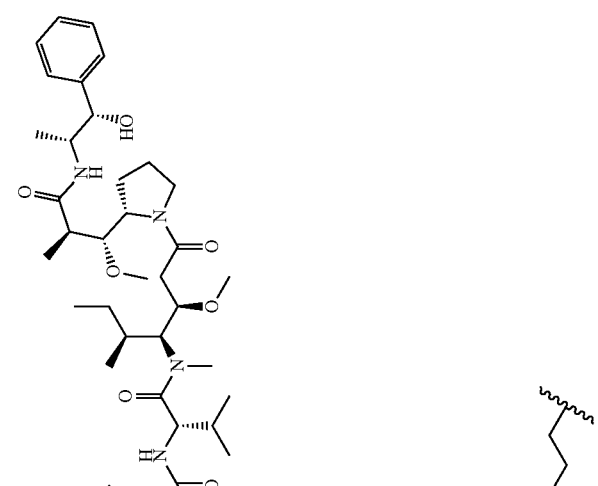

-continued

| Compound |
|---|
| (Compound 46)<br>(M + H)⁺ = 2857.6<br>(4S)-4-{[(1S)-1-{[(1S)-1-({3-[(2-aminoethyl)carbamoyl]-4-{[{(1S)-1-[((3R,4S,5S)-1-[(2S)-2-[((1R,2R)-2-{[((1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl](methyl)phenyl]carbamoyl}-4-{1-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]-3,6,9,12-tetraoxapentadecan-15-amido}butanoic acid |

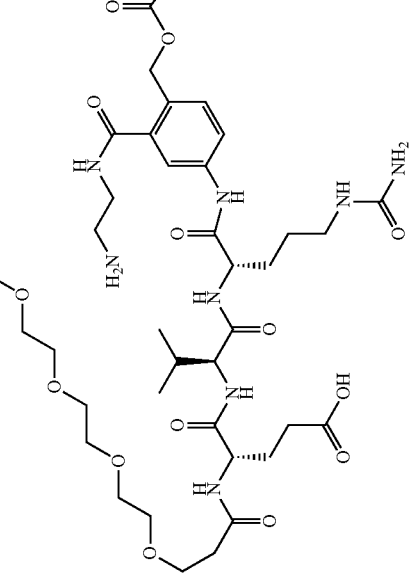

-continued

Compound (Compound 47)
(M + H)+ = 2091.1
(2-[[2-(1-amino-3,6,9,12-tetraoxapentadecan-15-amido)ethyl]carbamoyl]-4-[(2S)-2-[(2S)-2-{1-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]-3,6,9,12-tetraoxapentadecan-15-amido}-3-methylbutanamido]-5-(carbamoylamino)pentanamido]phenyl)methyl N-((1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl]-N-methylcarbamate

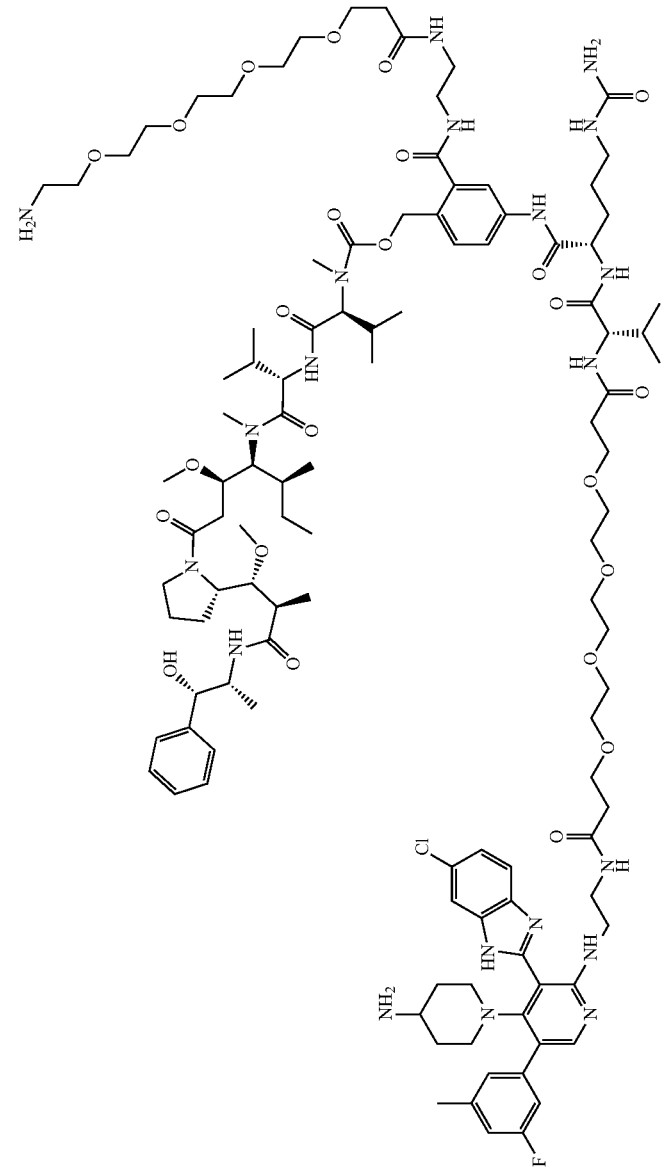

-continued

| Compound |
|---|
| (Compound 48)<br>(M + H)⁺ = 2209.2<br>(4S)-4-{[(1S)-1-{[(1S)-1-({3-[(2-aminoethyl)carbamoyl]-4-{[[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl[(methyl)carbamoyl]oxy}methyl)phenyl]carbamoyl}-4-(carbamoylamino)butyl]carbamoyl}-2-methylpropyl]carbamoyl}-4-(3-{2-[(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]ethoxy}propanamido)butanoic acid |

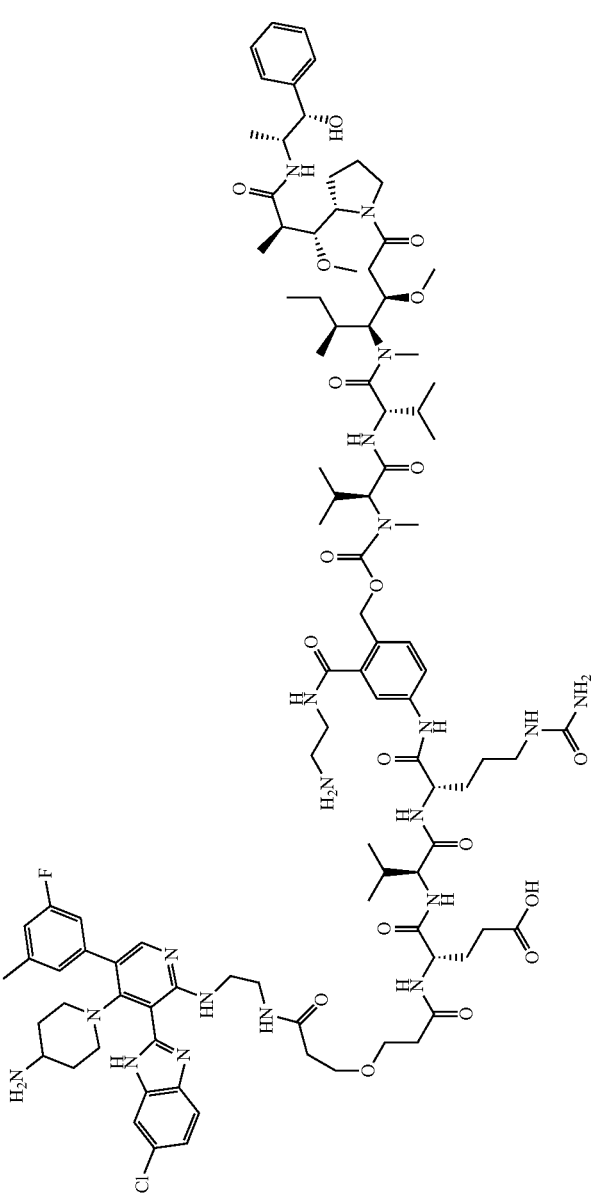

-continued

| Compound |
|---|
| (Compound 49)<br>(M + H)+ = 1958.0<br>{2-[(2-aminoethyl)carbamoyl]-4-[(2S)-2-[(2S)-2-{1-[(2-[[4-(4-aminopiperidin-1-yl)-3-(6-chloro-1H-1,3-benzodiazol-2-yl)-5-(3-fluoro-5-methylphenyl)pyridin-2-yl]amino}ethyl]carbamoyl]-3,6,9,12-tetraoxapentadecan-15-amido]-3-methylbutanamido]-5-(carbamoylamino)pentanamido]phenyl}methyl N-[(1S)-1-{[(1S)-1-{[(3R,4S,5S)-1-[(2S)-2-[(1R,2R)-2-[{(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl)carbamoyl}-2-methylpropyl]-N-methylcarbamate |

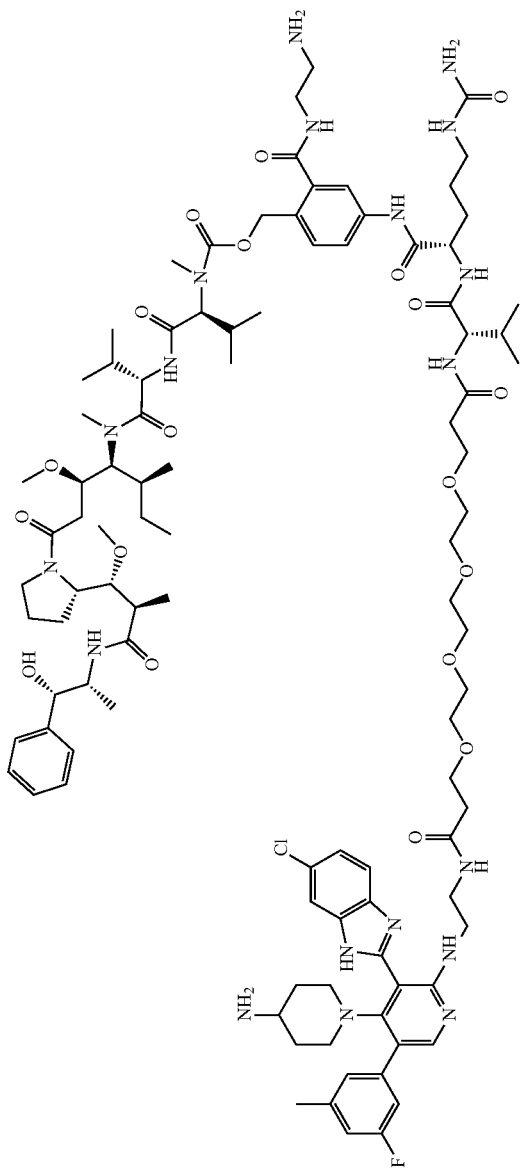

-continued

| Compound |
|---|
| (Compound 50)<br>(M + H)$^+$ = 1962.1<br>(4S)-4-(3-{2-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]ethoxy}propanamido)-4-{[(1S)-1-{[(1S)-4-(carbamoylamino)-1-({4-[{{[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxyethyl]pyrrolidin-1-yl]-3-methoxy-5-methyl-1-oxoheptan-4-yl]carbamoyl}-2-methylpropyl]carbamoyl]-2-methylpropyl}(methyl)carbamoyl]oxy}methyl]phenyl}carbamoyl)butyl]carbamoyl}-2-methylpropyl]-3-(methylcarbamoyl)phenyl}carbamoyl}butyl)carbamoyl]-2-methylpropyl}oxy)methyl]-3-(methylcarbamoyl)butanoic acid |

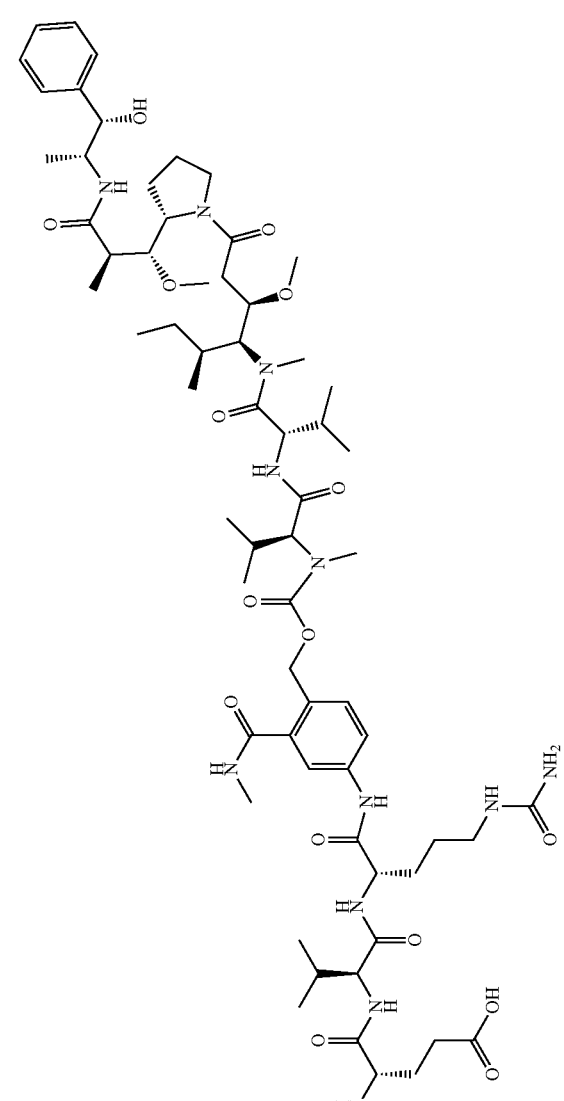

-continued

| Compound |
|---|
| (Compound 51)<br>(M + H)+ = 1930.0<br>(4S)-4-{1-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]-3,6,9,12-tetraoxapentadecan-15-amido}-4-{[(1S)-1-{[(1S)-4-(carbamoylamino)-1-({4-[{[(1S)-1-{[(3R,4S,5S)-1-{[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl]-2-methylpropyl}carbamoyl]oxy}methyl]phenyl}carbamoyl)butyl]carbamoyl}-2-methylpropyl](methyl)carbamoyl]-2-methylpropyl}carbamoyl]butanoic acid |

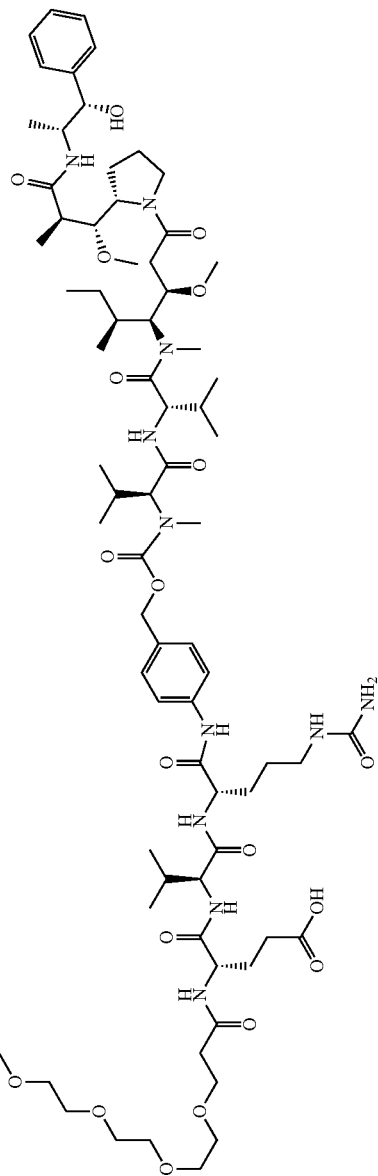

-continued

Compound (Compound 52)
(M + H)+ = 2005.0

(4S)-4-{1-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]-3,6,9,12-tetraoxapentadecan-15-amido}-4-{[(1S)-1-{[(1S)-4-(carbamoylamino)-1-({4-[{[(1S)-1-{[(1S)-2-{[(3R,4S,5S)-1-{[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}oxy)methyl]-3-(methylcarbamoyl)phenyl}carbamoyl)butyl]carbamoyl}-2-methylpropyl]carbamoyl}butanoic acid

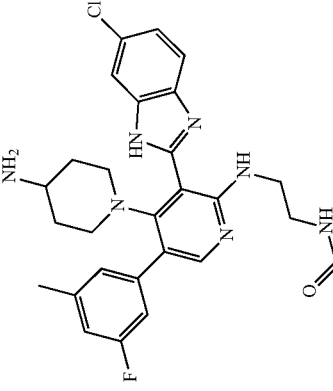

-continued

| Compound |
|---|
| (Compound 53)<br>(M + H)⁺ = 2061.1<br>{4-[(2S)-2-[(2S)-2-[(2S)-2-(3-{2-[(2-{[(2-{[(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]ethoxy}propanamido)-4-carbamoylbutanamido]-3-methylbutanamido]-5-(carbamoylamino)pentanamido]-2-(methylcarbamoyl)phenyl}methyl N-[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl][(methyl)carbamoyl]-2-methylpropyl}[methyl]propyl]-N-methylcarbamate |

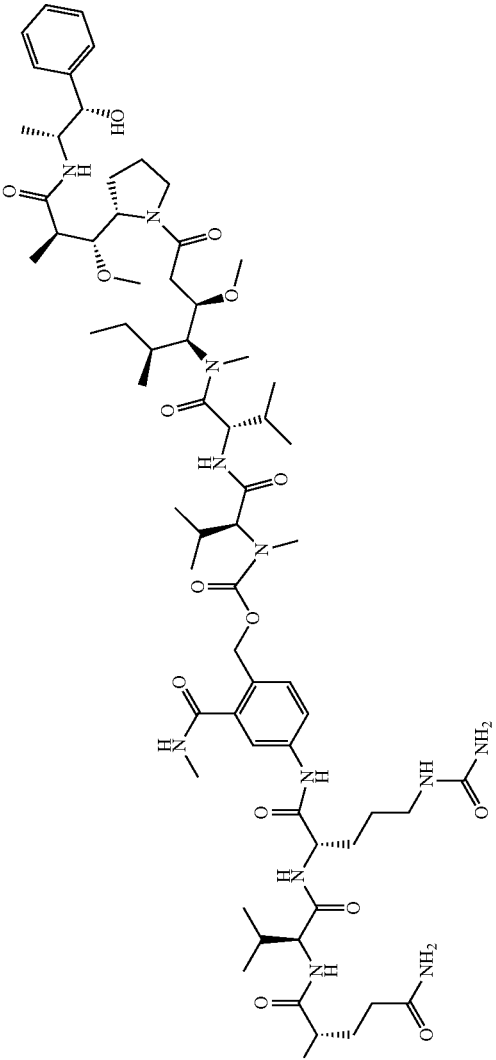

-continued

| Compound |
|---|
| (Compound 54)<br>(M + H)⁺ = 1928.1<br>2-(4-{[(2-{2-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]ethoxy}ethyl)carbamoyl]methyl}-7-{[{(1S)-1-{[(1S)-4-(carbamoylamino)-1-({4-[({(1S)-1-{[(1S)-1-{[(3R,4S,5S)-1-[(2S)-2-[(1R,2R)-2-[(1S,2R)-1-hydroxy-1-phenylpropan-2-yl]carbamoyl]-1-methoxy-2-methylethyl]pyrrolidin-1-yl]-3-methoxy-5-methyl-1-oxoheptan-4-yl](methyl)carbamoyl]-2-methylpropyl]carbamoyl]-2-methylpropyl](methyl)carbamoyl]oxy)methyl]phenyl]carbamoyl}butyl]carbamoyl}-2-methylpropyl]carbamoyl]methyl}-1,4,7-triazonan-1-yl)acetic acid |

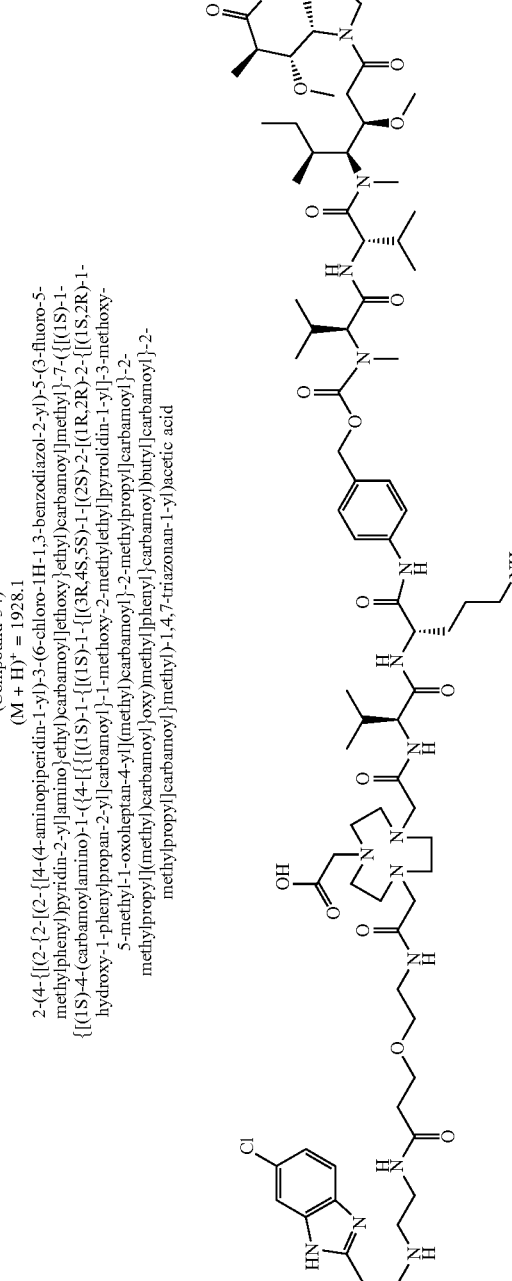

| Compound |
|---|
| (Compound 55)<br>(M + H)+ = 1999.3<br>(2R)-2-[(2-{[(4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]-2-[3-(2-{[(1S)-1-{[(1S)-4-(carbamoylamino)-1-({4-[{[(1S)-1-{[(1S)-1-{[(3R,4S,5S)-1-[(2S)-2-{[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-methylpropyl](methyl)carbamoyl}oxy)methyl]phenyl}carbamoyl)butyl]carbamoyl}-2-methylpropyl]carbamoyl}ethoxy)propanamido]ethane-1-sulfonic acid<br>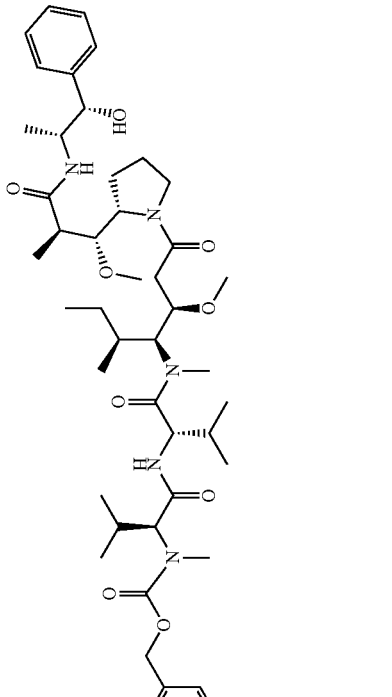 |

-continued

| Compound |
|---|
| (Compound 70)<br>(M + H)⁺ = 1893.9<br>(4S)-4-(3-{2-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]ethoxy}propanamido)-4-{[(1S)-1-{[(1S)-4-(carbamoylamino)-1-({4-[({[(10S,23S)-10-ethyl-18-fluoro-10-hydroxy-19-methyl-5,9-dioxo-8-oxa-4,15-diazahexacyclo[14.7.1.0²,¹⁴.0⁴,¹³.0⁶,¹¹.0²⁰,²⁴]tetracosa-1,6(11),12,14,16,18,20(24)-heptaen-23-yl]carbamoyl}oxy)methyl]phenyl}carbamoyl)butyl]carbamoyl}-2-methylpropyl]carbamoyl}butanoic acid 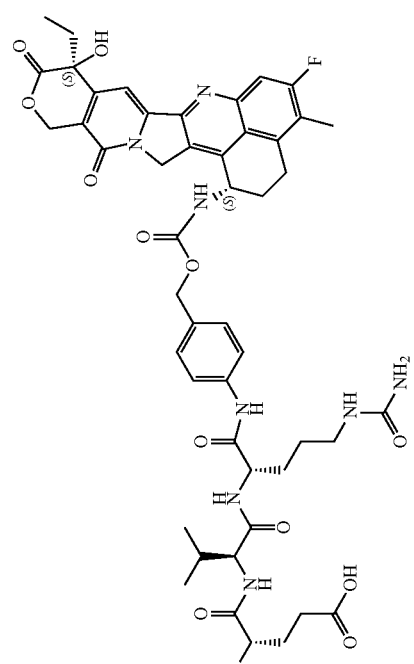 |

-continued

| Compound |
|---|
| (Compound 71)<br>(M + H)⁺ = 1589.6<br>2-(4-{[(2-{2-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]ethoxy}ethyl)carbamoyl]methyl}-7-({[(1S)-1-{[(1S)-4-(carbamoylamino)-1-({4-[({[(10S,23S)-10-ethyl-18-fluoro-10-hydroxy-19-methyl-5,9-dioxo-8-oxa-4,15-diazahexacyclo[14.7.1.0²,¹⁴.0⁴,¹³.0⁶,¹¹.0²⁰,²⁴]tetracosa-1,6(11),12,14,16,18,20(24)-heptaen-23-yl]carbamoyl}oxy)methyl]phenyl}carbamoyl)butyl]carbamoyl}-2-methylpropyl]carbamoyl]methyl)-1,4,7-triazonan-1-yl)acetic acid 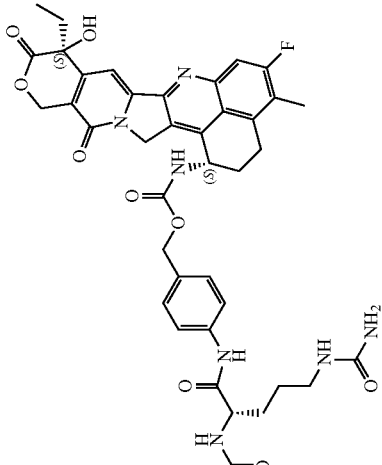 |

| Compound |
| --- |
| (Compound 72)<br>(M + H)+ = 1716.7<br>(2S,3S,4S,5R,6S)-6-{2-[(2S)-2-[(2S)-2-(3-{2-[(2S)-2-{3-(6-chloro-1H-1,3-benzodiazol-2-yl)-5-(3-fluoro-5-methylphenyl)pyridin-2-yl]amino}ethyl)carbamoyl]ethoxy}propanamido)-3-methylbutanamido]-5-(carbamoylamino)pentanamido]-5-[{[(10S,23S)-10-ethyl-18-fluoro-10-hydroxy-19-methyl-5,9-dioxo-8-oxa-4,15-diazahexacyclo[14.7.1.0²,¹⁴.0⁴,¹³.0⁶,¹¹.0²⁰,²⁴]tetracosa-1,6(11),12,14,16,18,20(24)-heptaen-23-yl]carbamoyl}oxy)methyl]phenoxy}-3,4,5-trihydroxyoxane-2-carboxylic acid |

-continued

| Compound |
|---|
| (Compound 73)<br>(M + H)+ = 1652.6<br>(2S,3S,4S,5R,6S)-6-{2-[(2S)-2-[(2S)-2-{1-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]-3,6,9,12-tetraoxapentadecan-15-amido}-3-methylbutanamido]-5-(carbamoyl)amino)pentanamido]-5-[{[(10S,23S)-10-ethyl-18-fluoro-10-hydroxy-19-methyl-5,9-dioxo-8-oxa-4,15-diazahexacyclo[14.7.1.0²,¹⁴.0⁴,¹³.0⁶,¹¹.0²⁰,²⁴]tetracosa-1,6(11),12,14,16,18,20(24)-heptaen-23-yl]carbamoyl}oxy)methyl]phenoxy}-3,4,5-trihydroxyoxane-2-carboxylic acid |

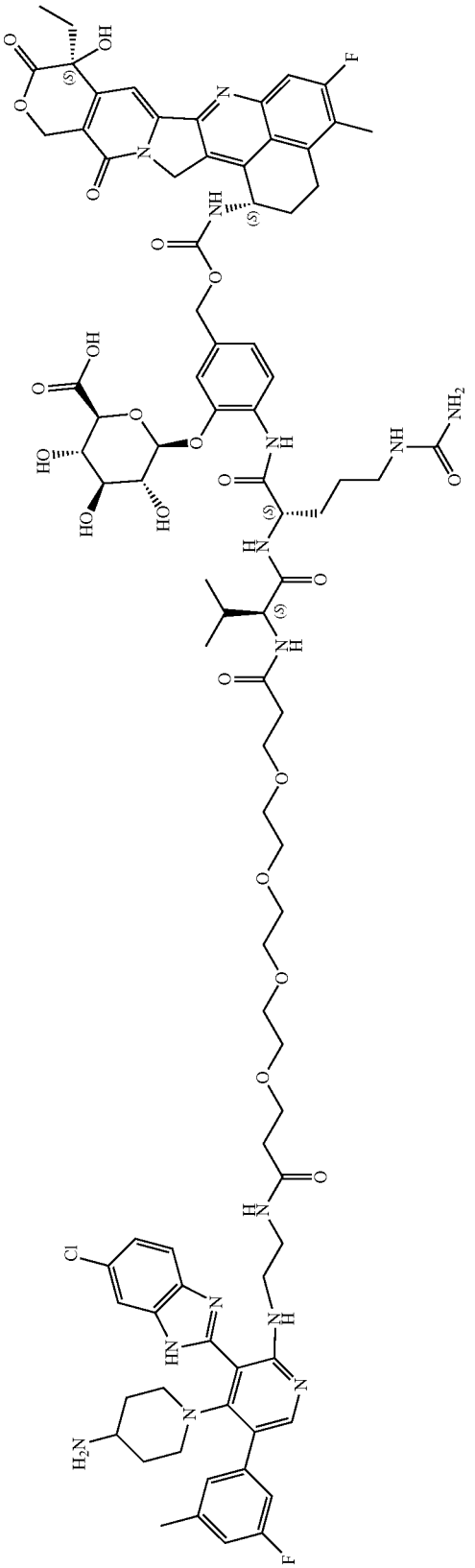

| Compound |
| --- |
| (Compound 74)<br>(M + H)⁺ = 1784.7<br>(2S,3S,4S,5R,6S)-6-{2-[(2S)-2-{(2S)-2-[(2S)-2-{3-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]propanamido}-3-methylbutanamido]-5-(carbamoylamino)pentanamido]-5-[{{[(1S)-1-{[(3R,4S,5S)-1-{(2S)-2-[(1R,2R)-2-{[(1S,2R)-1-hydroxy-1-phenylpropan-2-yl]carbamoyl}-1-methoxy-2-methylethyl]pyrrolidin-1-yl}-3-methoxy-5-methyl-1-oxoheptan-4-yl](methyl)carbamoyl}-2-methylpropyl]carbamoyl}-2-methylpropyl]-(methyl)carbamoyl]-oxy}methyl]phenoxy}-3,4,5-trihydroxyoxane-2-carboxylic acid |

-continued

| Compound |
|---|
| (Compound 75)<br>(M + H)⁺ = 1890.9<br>(2R)-2-{1-[(2-{[(1-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]-3,6,9,12-tetraoxapentadecan-15-amido}-2-{[(1S)-1-{[(1S)-4-(carbamoylamino)-1-({4-[({[(1S)-1-{[(3R,4S,5S)-1-{[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl](methyl)carbamoyl]oxy}methyl)phenyl]carbamoyl}butyl]carbamoyl}-2-methylpropyl]carbamoyl}ethane-1-sulfonic acid |

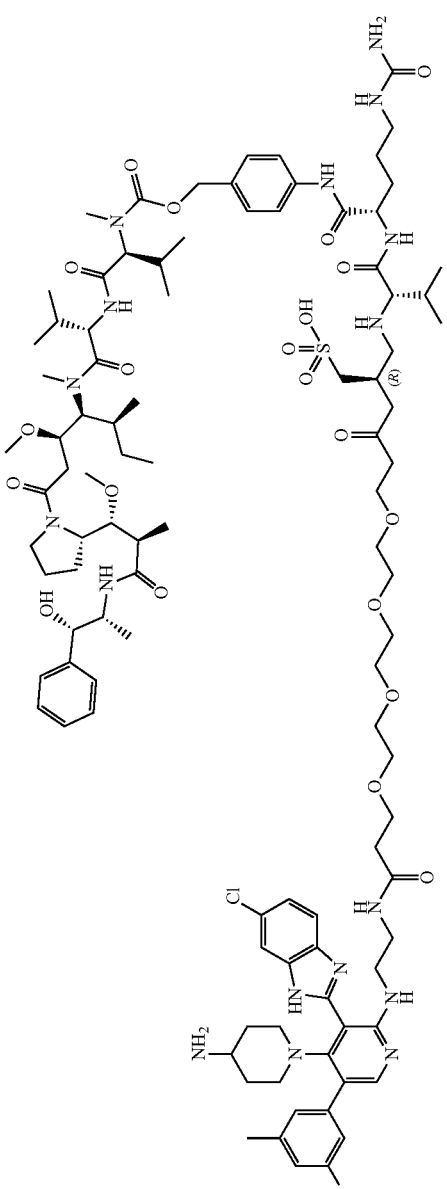

-continued

| Compound |
|---|
| (Compound 81)<br>(M + H)+ = 1014.4<br>1-(S)-1-[N-(S)-1-{[(1S,2R)-4-[(S)-2-{(1R,2R)-2-[N-(1R,2S)-2-hydroxy-1-methyl-2-phenylethylcarbamoyl]-1-methoxypropyl]-1-pyrrolidinyl]-1-[(S)-1-methylpropyl]-2-methoxy-4-oxobutyl]-N-methylcarbamoyl}-2-methylpropylcarbamoyl]-1-methyl [2-(N-2-aminoethylcarbamoyl)-4-[(S)-2-[(S)-2-[3-(2-{N-2-[4-(4-amino-1-piperidyl)-3-(6-chloro-1H-1,3-benzimidazol-2-yl)-5-(3-fluoro-5-tolyl)-2-pyridylamino]ethylcarbamoyl}ethoxy)propionylamino]-3-methylbutyrylamino]-5-ureidovalerylamino]phenyl]methanecarbamate |

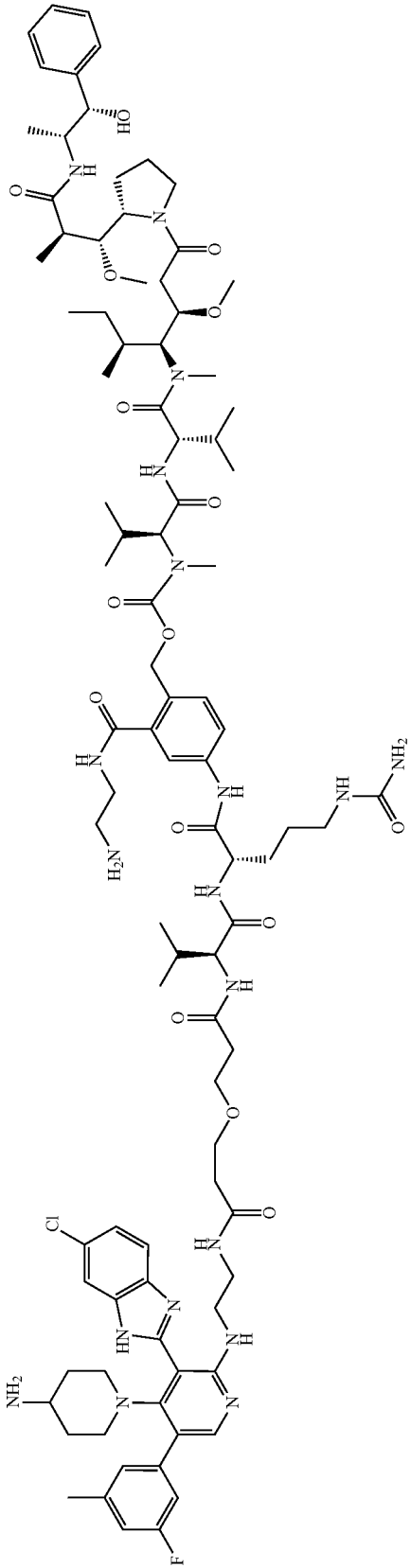

-continued

| Compound |
|---|
| (Compound 82)<br>(M + H)⁺ = 1829.0<br>(R)-2-[N-(S)-1-[N-(S)-1-[N-p-({[(S)-1-[N-(S)-1-{[(1S,2R)-2-{[(1R,2S)-2-[N-(1R,2S)-2-hydroxy-1-methyl-2-phenylethylcarbamoyl]-1-methoxypropyl]-1-pyrrolidinyl]-1-[(S)-1-methylpropyl]-2-methoxy-4-oxobutyl]-N-methylcarbamoyl}-2-methylpropyl]carbamoyl]-1-(S)-1-methylpropyl](methyl)(aminocarbonyloxy)}methyl)phenylcarbamoyl]-4-ureidobutylcarbamoyl]-2-methylpropylcarbamoyl]-2-[3-(2-{N-2-[4-(4-amino-1-piperidyl)-3-(6-chloro-1H-1,3-benzimidazol-2-yl)-5-(3-fluoro-5-tolyl)-2-pyridylamino]ethylcarbamoyl]ethoxy)propionylamino]ethanesulfonic acid |

-continued

| Compound |
|---|
| (Compound 83)<br>(M + H)⁺ = 1894.1<br>1-(S)-1-[N-(S)-1-[[(1S,2R)-4-[(S)-2-{(1R,2R)-2-[N-(1R,2S)-2-hydroxy-1-methyl-2-phenylethylcarbamoyl]-1-methoxypropyl}-1-pyrrolidinyl]-1-[(S)-1-methylpropyl]-2-methoxy-4-oxobutyl]-N-methylcarbamoyl]-2-methylpropylcarbamoyl]-2-methylpropyl 1-methyl {p-[(S)-2-[(S)-2-[3-(2-{2-[4-(4-amino-1-piperidyl)-3-(6-chloro-1H-1,3-benzimidazol-2-yl)-5-(3-fluoro-5-tolyl)-2-pyridylamino]ethylamino}ethoxy)propionylamino]-3-methylbutyrylamino]-5-ureidovalerylamino]phenyl}methanecarbamate |

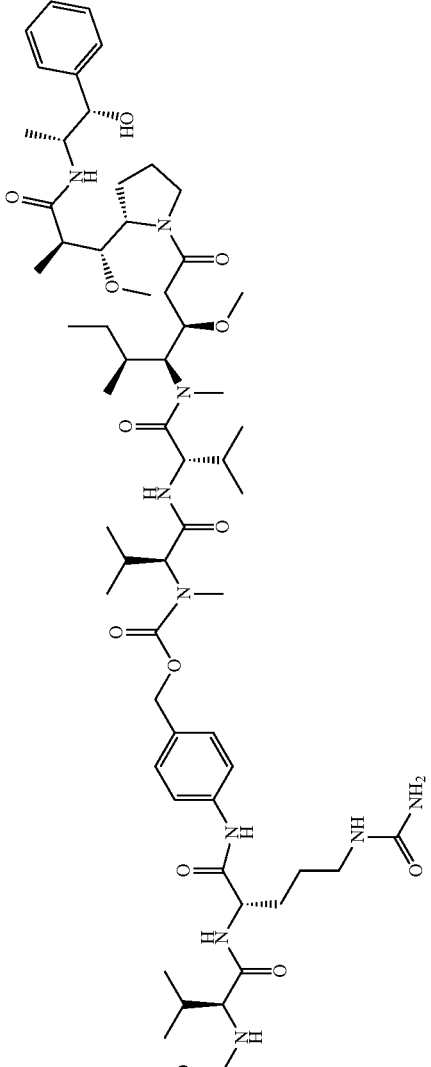

-continued

| Compound |
|---|
| (Compound 84)<br>(M + H)⁺ = 1714.9<br>1-(S)-1-[N-(S)-1-{[(1S,2R)-4-[(S)-2-{(1R,2R)-2-[N-(1R,2S)-2-hydroxy-1-methyl-2-phenylethylcarbamoyl]-1-methoxypropyl}-1-pyrrolidinyl]-1-(S)-1-methylpropyl]-2-methoxy-4-oxobutyl]-N-methylcarbamoyl}-2-methylpropylcarbamoyl]-1-methyl [2-(N-2-aminoethylcarbamoyl)-4-[(S)-2-{(S)-2-(14-{N-2-[4-(4-amino-1-piperidyl)-3-(6-chloro-1H-1,3-benzimidazol-2-yl)-5-(3-fluoro-5-tolyl)-2-pyridylamino]ethylcarbonylamino}-3,6,9,12-tetraoxatetradecylcarbonylamino)-3-methylbutyrylamino]propionylamino]phenyl]methanecarbamate |

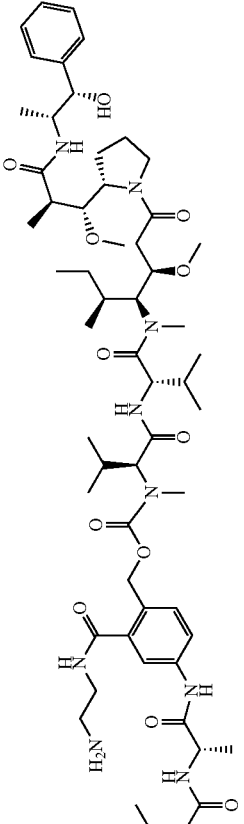

| (Compound 85)<br>(M + H)⁺ = 1875.0<br>1-(S)-1-[N-(S)-1-{[(1S,2R)-4-[(S)-2-{(1R,2R)-2-[N-(1R,2S)-2-hydroxy-1-methyl-2-phenylethylcarbamoyl]-1-methoxypropyl}-1-pyrrolidinyl]-1-(S)-1-methylpropyl]-2-methoxy-4-oxobutyl]-N-methylcarbamoyl}-2-methylpropylcarbamoyl]-1-methyl [2-(N-2-aminoethylcarbamoyl)-4-[(S)-2-{[3-(2-{N-2-[4-(4-amino-1-piperidyl)-3-(6-chloro-1H-1,3-benzimidazol-2-yl)-5-(3-fluoro-5-tolyl)-2-pyridylamino]ethoxy}ethoxy)propionylamino]-3-methylbutyrylamino]propionylamino]phenyl]methanecarbamate |

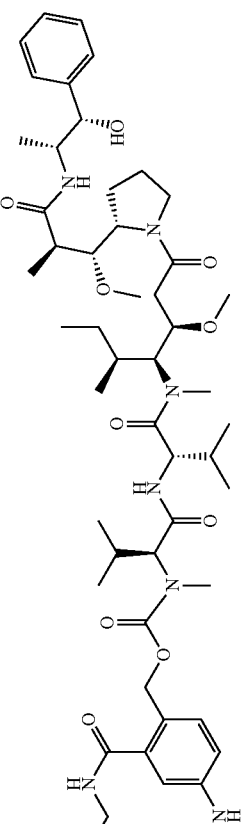

| -continued |
|---|
| Compound |
| (Compound 86)<br>(M + H)⁺ = 1742.9<br>1-(S)-1-[N-(S)-1-[[(1S,2R)-4-[(S)-2-{(1R,2R)-2-[N-(1R,2S)-2-hydroxy-1-methyl-2-phenylethylcarbamoyl]-1-methoxypropyl}-1-pyrrolidinyl]-1-[(S)-1-methylpropyl]-2-methoxy-4-oxobutyl]-N-methylcarbamoyl]-2-methylpropylcarbamoyl]-1-[(S)-1-methylpropyl 1-methyl [2-(N-2-aminoethylcarbamoyl)-4-[(S)-2-[[(S)-2-[3-(2-{2-[4-(4-amino-1-piperidyl)-3-(6-chloro-1H-1,3-benzimidazol-2-yl)-5-(3-fluoro-5-tolyl)-2-pyridylamino]ethylamino}ethoxy)propionylamino]-3-methylbutyrylamino]-5-ureidovalerylamino]phenyl]methanecarbamate |

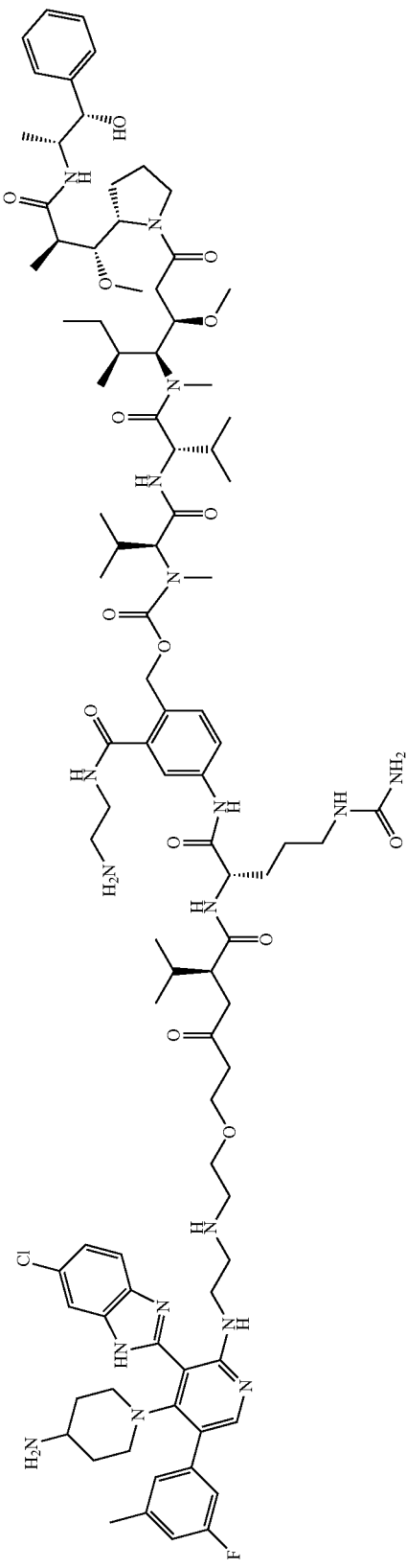

-continued
Compound
(Compound 87)
(M + H)⁺ = 1801.0
(10S,23S)-10-ethyl-18-fluoro-10-hydroxy-19-methyl-5,9-dioxo-8-oxa-4,15-diazahexacyclo[14.7.1.0²,¹⁴.0⁴,¹³.0⁶,¹¹.0²⁰,²⁴]tetracosa-1,6(11),12,14,16,18,20(24)-heptaen-23-yl {p-[(S)-2-[(S)-2-[3-(2-{N-2-[4-(4-amino-1-piperidyl)-3-(6-chloro-1H-1,3-benzimidazol-2-yl)-5-(3-fluoro-5-tolyl)-2-pyridyl]aminoethylcarbamoyl}ethoxy)propionylamino]-3-methylbutyrylamino]-5-ureidovalerylamino]phenyl}methanecarbamate
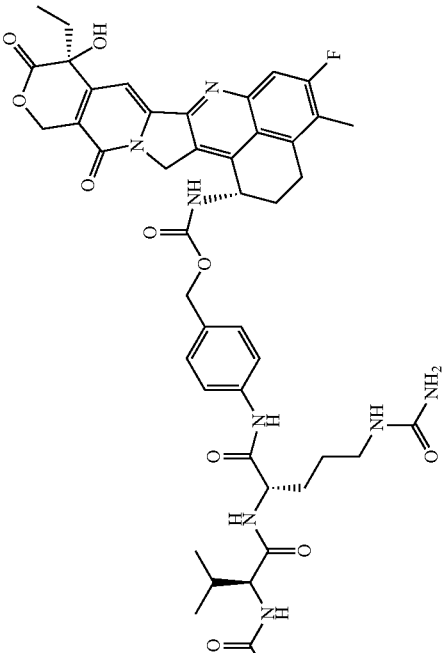

-continued

Compound (Compound 88)
(M + H)⁺ = 1460.8
1-(S)-1-[N-(S)-1-{[(1S,2R)-4-[(S)-2-{[(1R,2R)-2-[N-(1R,2S)-2-hydroxy-1-methyl-2-phenylethyl]carbamoyl]-1-methoxypropyl]-1-pyrrolidinyl]-1-[(S)-1-methylpropyl]-2-methoxy-4-oxobutyl]-N-methylcarbamoyl]-2-methylpropyl]carbamoyl]-1-[(S)-1-methylpropyl 1-methyl] [2-(N-2-aminoethylcarbamoyl)-4-[(S)-2-[(S)-2-[3-(2-{2-[4-(4-amino-1-piperidyl)-3-(6-chloro-1H-1,3-benzimidazol-2-yl)-5-(3-fluoro-5-tolyl)-2-pyridylamino]ethylamino}ethoxy)propionylamino]-3-methylbutyrylamino]propionylamino]phenyl]methanecarbamate -continued
Compound
(Compound 89)
(M + H)+ = 1714.9
(10S,23S)-10-ethyl-18-fluoro-10-hydroxy-19-methyl-5,9-dioxo-8-oxa-4,15-diazahexacyclo[14.7.1.0²,¹⁴.0⁴,¹³.0⁶,¹¹.0²⁰,²⁴]tetracosa-1,6(11),12,14,16,18,20(24)-heptaen-23-yl [2-(N-2-aminoethylcarbamoyl)-4-[(S)-2-[(S)-2-[3-(2-[N-2-[4-(4-amino-1-piperidyl)-3-(6-chloro-1H-1,3-benzimidazol-2-yl)-5-(3-fluoro-5-tolyl)-2-pyridylamino]ethylcarbamoyl]ethoxy)propionylamino]-3-methylbutyrylamino]-5-ureidovalerylamino]phenyl]methanecarbamate
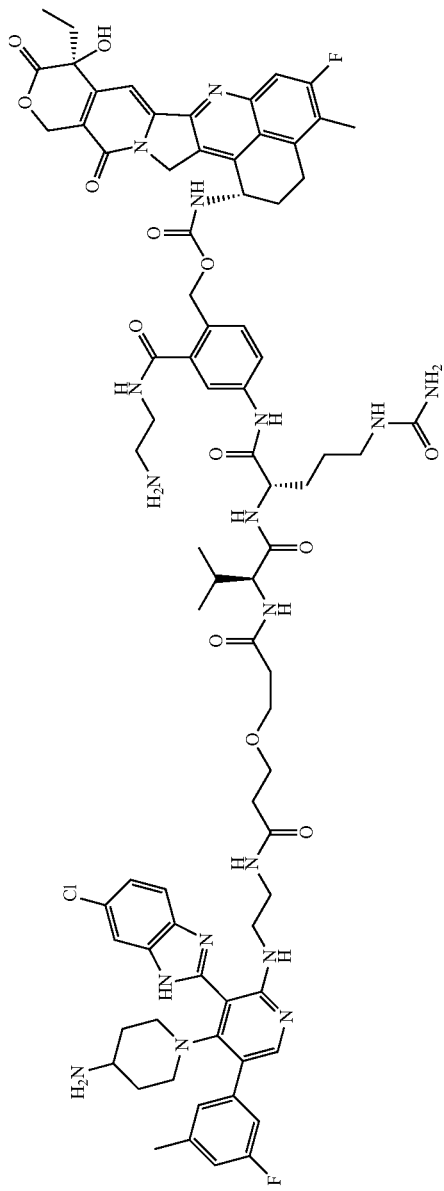

| Compound | |
|---|---|
| | (Compound 90)<br>(M + H)+ = 1546.6<br>(10S,23S)-10-ethyl-18-fluoro-10-hydroxy-19-methyl-5,9-dioxo-8-oxa-4,15-diazahexacyclo[14.7.1.0²,¹⁴.0⁴,¹³.0⁶,¹¹.0²⁰,²⁴]tetracosa-1,6(11),12,14,16,18,20(24)-heptaen-23-yl [2-(N-2-aminoethylcarbamoyl)-4-[(S)-2-[(S)-2-(14-{N-2-[4-(4-amino-1-piperidyl)-3-(6-chloro-1H-1,3-benzimidazol-2-yl)-5-(3-fluoro-5-tolyl)-2-pyridylamino]ethylcarbamoyl}-3,6,9,12-tetraoxatetradecylcarbonylamino)-3-methylbutyrylamino]-5-ureidovalerylamino]phenyl]methanecarbamate |
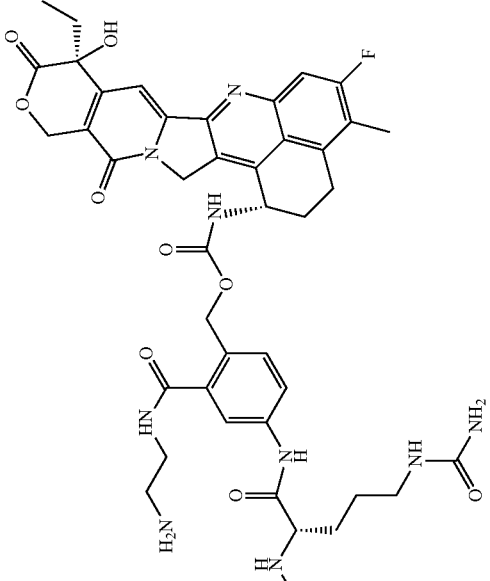

-continued

Compound (Compound 91)
(M + H)+ = 1678.7
1-(S)-1-[N-(S)-1-{[(1S,2R)-4-[(S)-2-{(1R,2R)-2-[N-(1R,2S)-2-hydroxy-1-methyl-2-phenylethylcarbamoyl]-1-methoxypropyl}-1-pyrrolidinyl]-1-[(S)-1-methylpropyl]-2-methoxy-4-oxobutyl]-N-methylcarbamoyl]-2-methylpropylcarbamoyl}-1-methyl {p-[(S)-2-[(S)-2-[3-(2-{2-[2-{2-[4-(4-amino-1-piperidyl)-3-(6-chloro-1H-1,3-benzimidazol-2-yl)-5-(3-fluoro-5-tolyl)-2-pyridylamino]ethylamino}ethoxy]ethoxy]ethoxy)propionylamino]-3-methylbutyrylamino]-5-ureidovalerylamino]phenyl}methanecarbamate

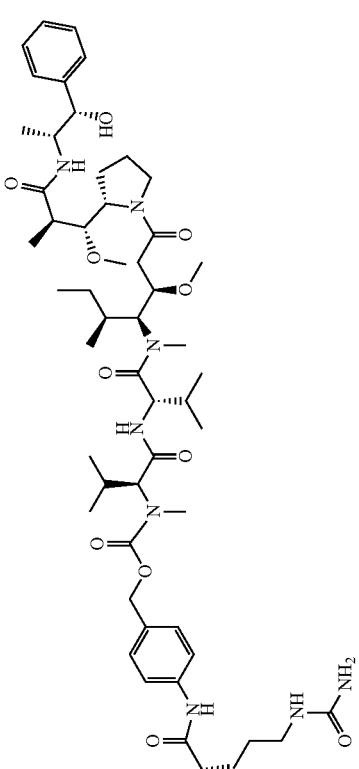

-continued

| Compound |
|---|
| (Compound 92)<br>(M + H)+ = 1847.0<br>{4-[(N-14-{N-2-[4-(4-amino-1-piperidyl)-3-(6-chloro-1H-1,3-benzimidazol-2-yl)-5-(3-fluoro-5-tolyl)-2-pyridylamino]ethylcarbamoyl}-3,6,9,12-tetraoxatetradecylcarbamoyl)methyl]-7-{[N-(S)-1-[N-(S)-1-{N-p-[{[(10S,23S)-10-ethyl-18-fluoro-10-hydroxy-19-methyl-5,9-dioxo-8-oxa-4,15-diazahexacyclo[14.7.1.0²,¹⁴.0⁴,¹³.0⁶,¹¹.0²⁰,²⁴]tetracosa-1,6(11),12,14,16,18,20(24)-heptaen-23-yl}(aminocarbonyloxy)methyl]phenyl]carbamoyl}-4-ureidobutyl]carbamoyl]-2-methylpropylcarbamoyl]methyl}-1,4,7-triazonan-1-yl}acetic acid |

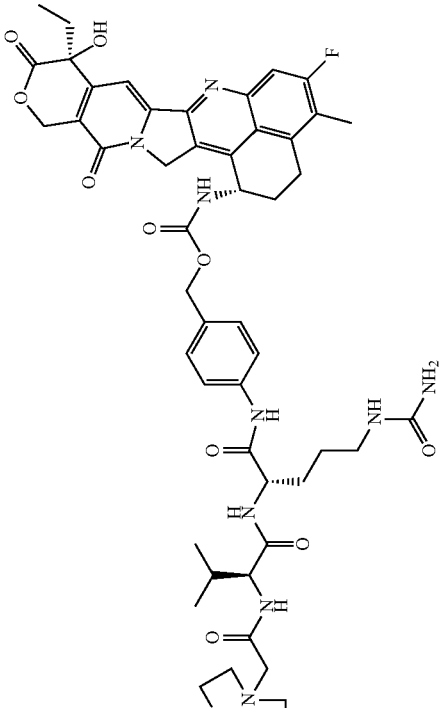

-continued

| Compound |
|---|
| (Compound 93)<br>$(M + H)^+ = 617.3$<br>(S)-4-[N-(S)-1-[N-(S)-1-[N-3-(N-2-aminoethylcarbamoyl)-4-[[{(10S,23S)-10-ethyl-18-fluoro-10-hydroxy-19-methyl-5,9-dioxo-8-oxa-4,15-diazahexacyclo[14.7.1.0². ¹⁴.0⁴.¹³.0⁶,¹¹.0²⁰,²⁴]tetracosa-1,6(11),12,14,16,18,20(24)-heptaen-23-yl}(aminocarbonyloxy))methyl]phenylcarbamoyl]-4-ureidobutylcarbamoyl]-2-methylpropylcarbamoyl]-4-[3-(2-{N-2-[4-(4-amino-1-piperidyl)-3-(6-chloro-1H-1,3-benzimidazol-2-yl)-5-(3-fluoro-5-tolyl)-2-pyridylamino]ethylcarbamoyl}ethoxy)propionylamino]butyric acid |

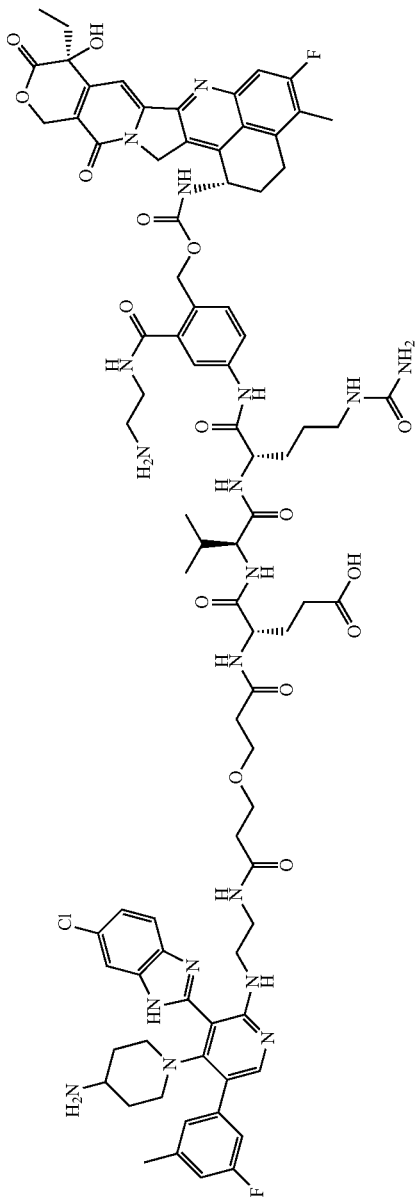

-continued

Compound (Compound 94)
(M + H)⁺ = 1675.9
1-(S)-1-[N-(S)-1-{[(1S,2R)-4-[(S)-2-{(1R,2R)-2-[N-(1R,2S)-2-hydroxy-1-methyl-2-phenylethyl]carbamoyl]-1-methoxypropyl}-1-pyrrolidinyl]-1-methylpropyl]-2-methoxy-4-oxobutyl]-N-methylcarbamoyl]-2-methylpropylcarbamoyl]-2-methylpropyl 1-methyl {p-[(S)-2-[(S)-2-{4-[({N-2-[4-(4-amino-1-piperidyl)-3-(6-chloro-1H-1,3-benzimidazol-2-yl)-5-(3-fluoro-5-tolyl)-2-pyridyl]amino}ethyl}carbamoyl]methyl)-N-methylcarbamoyl]butyrylamino}-3-methylbutyrylamino]-5-ureidovalerylamino]phenyl}methanecarbamate

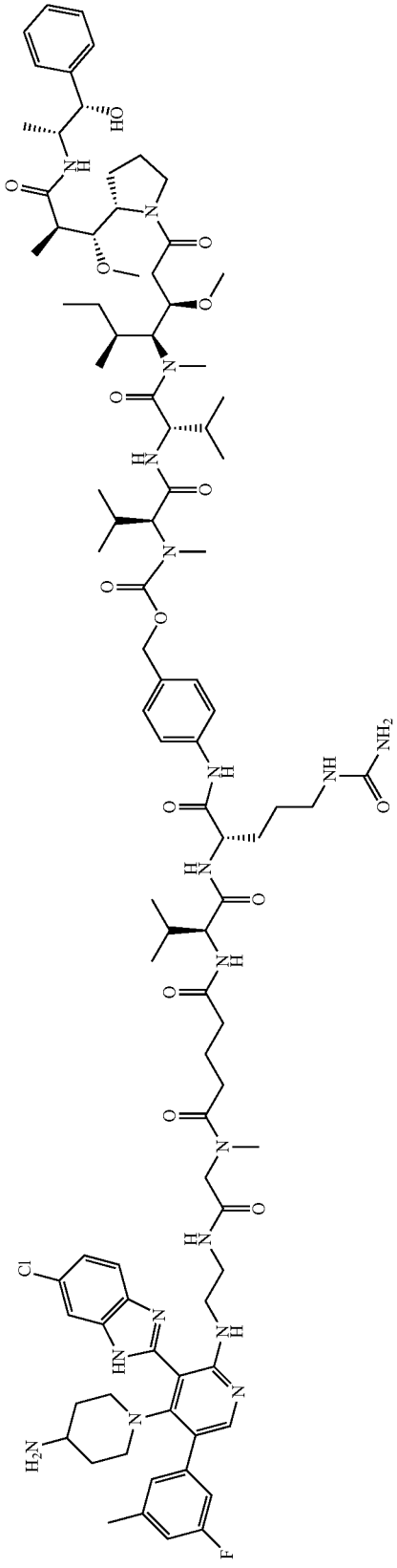

-continued

Compound (Compound 95)
(M + H)+ = 1783.9
1-(S)-1-[N-(S)-1-[[(1S,2R)-4-[(S)-2-{[(1R,2R)-2-[N-(1R,2S)-2-hydroxy-1-methyl-2-phenylethylcarbamoyl]-1-methoxypropyl]-1-pyrrolidinyl]-1-[(S)-1-methylpropyl]-2-methoxy-4-oxobutyl]-N-methylcarbamoyl]-2-methylpropylcarbamoyl]-2-methylpropyl 1-methyl {p-[(S)-2-[(S)-2-(4-{[{[{[N-2-[4-(4-amino-1-piperidyl)-3-(6-chloro-1H-1,3-benzimidazol-2-yl)-5-(3-fluoro-5-tolyl)-2-pyridylamino]ethylcarbamoyl}methyl)-N-methylcarbamoyl]methyl}-N-methylcarbamoyl]methyl}-N-methylcarbamoyl]butyrylamino)-3-methylbutyrylamino]-5-ureidovalerylamino]phenyl}methanecarbamate

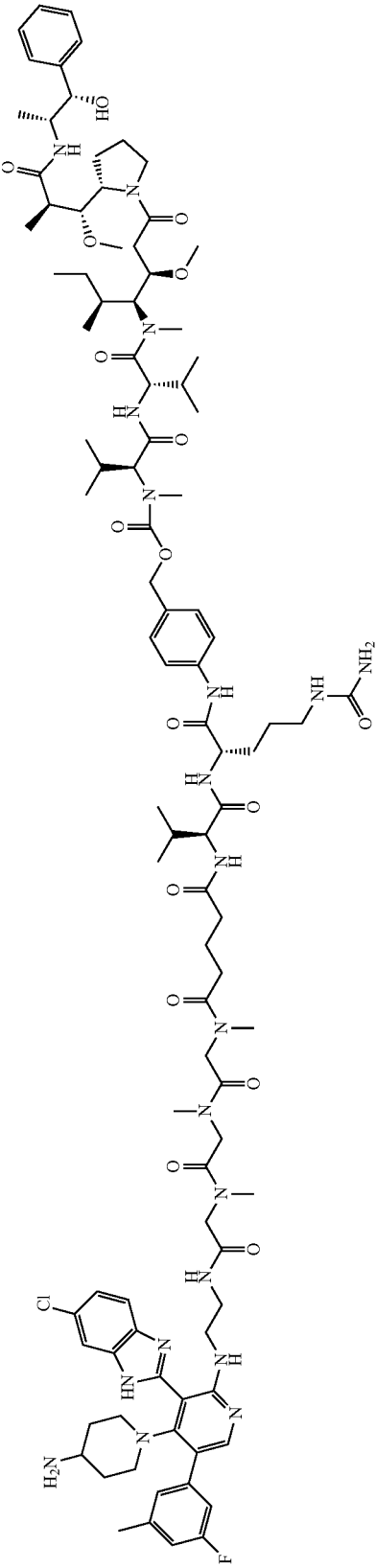

-continued

| Compound |
|---|
| (Compound 96)<br>(M + H)⁺ = 1926.0<br>1-(S)-1-[N-(S)-1-{[(1S,2R)-4-[(S)-2-{(1R,2R)-2-[N-(1R,2S)-2-hydroxy-1-methyl-2-phenylethylcarbamoyl]-1-methoxypropyl}-1-pyrrolidinyl]-1-[(S)-1-methylpropyl]-2-methoxy-4-oxobutyl]-N-methylcarbamoyl}-2-methylpropylcarbamoyl]-2-methylpropyl 1-methyl {p-[(S)-2-[(S)-2-[4-({[{[{[{[{N-2-[4-(4-amino-1-piperidyl)-3-(6-chloro-1H-1,3-benzimidazol-2-yl)-5-(3-fluoro-5-tolyl)-2-pyridyl]amino}ethylcarbamoyl]methyl}-N-methylcarbamoyl]methyl}-N-methylcarbamoyl]methyl}-N-methylcarbamoyl]methyl}-3-methylbutyrylamino]-5-ureidovalerylamino]phenyl}methanecarbamate |

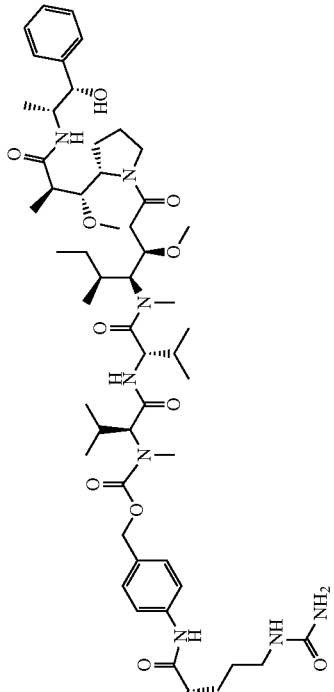

-continued

| Compound |
| --- |
| (Compound 97)<br>(M + H)⁺ = 2068.1<br>(S)-4-[N-(S)-1-[N-(S)-1-[N-p-({[(S)-1-[N-(S)-1-{[(S)-1-methoxy-1-methyl-2-phenylethylcarbamoyl]-1-methoxypropyl}-1-pyrrolidinyl]-1-[(S)-1-methylpropyl]-2-methoxy-4-oxobutyl]-N-methylcarbamoyl}-2-methylpropylcarbamoyl]-2-methylpropyl](methyl)(aminocarbonyloxy)}methyl)phenylcarbamoyl]-4-ureidobutylcarbamoyl]-2-methylpropylcarbamoyl]-4-[(S)-2-[3-(2-{N-2-[4-(4-amino-1-piperidyl)-3-(6-chloro-1H-1,3-benzimidazol-2-yl)-5-(3-fluoro-5-tolyl)-2-pyridylamino]ethylcarbamoyl}ethoxy)propionylamino]-4-carboxybutyryrylamino]butyric acid |

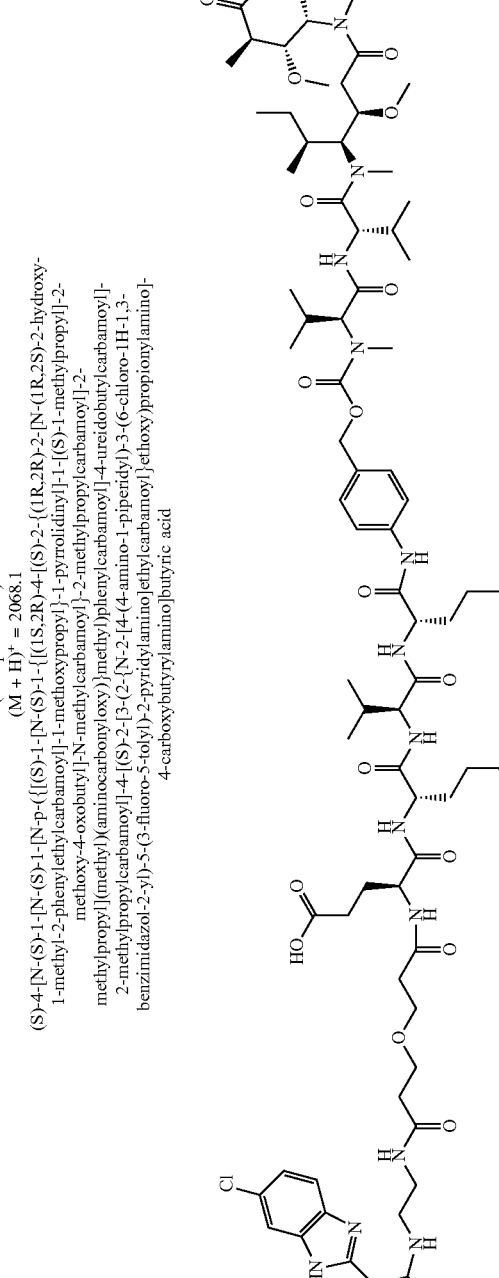

-continued

| Compound |
|---|
| (Compound 98)<br>(M + H)$^+$ = 2001.0<br>(R)-2-[N-(S)-1-[N-(S)-1-[N-3-(N-2-aminoethylcarbamoyl)-4-({[(S)-1-[N-(S)-1-{[(1S,2R)-4-[(S)-2-{(1R,2R)-2-[N-(1R,2S)-2-hydroxy-1-methyl-2-phenylethylcarbamoyl]-1-methoxypropyl]-1-pyrrolidinyl]-1-[(S)-1-methylpropyl]-2-methoxy-4-oxobutyl]-N-methylcarbamoyl}-2-methylpropylcarbamoyl]-2-methylpropyl](methyl)(aminocarbonyloxy)}methyl)phenylcarbamoyl]-4-ureidobutylcarbamoyl]-2-methylpropylcarbamoyl]-2-[3-(2-{N-2-[4-(4-amino-1-piperidyl)-3-(6-chloro-1H-1,3-benzimidazol-2-yl)-5-(3-fluoro-5-tolyl)-2-pyridylamino]ethylcarbamoyl}ethoxy)propionylamino]ethanesulfonic acid |

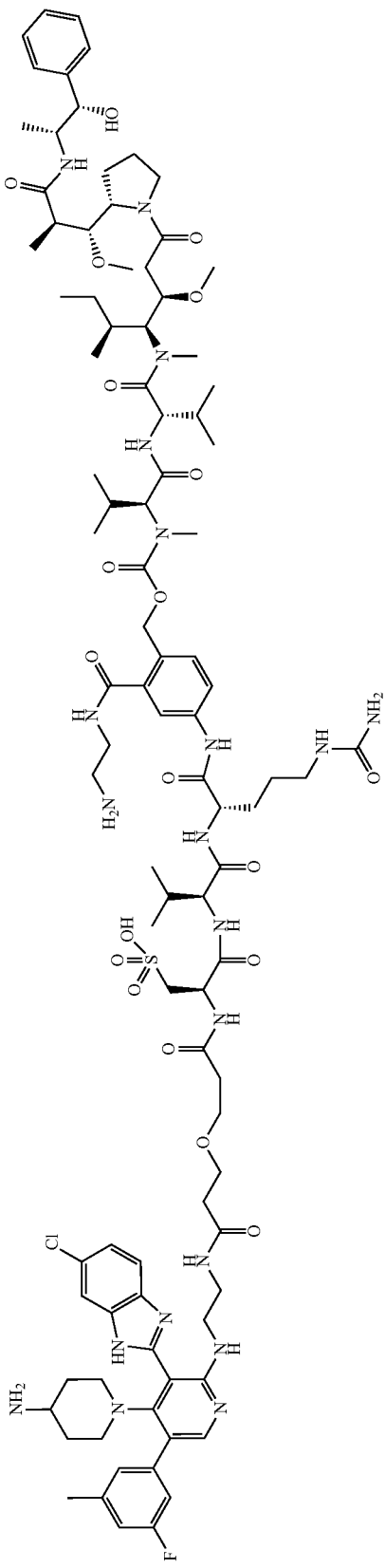

| Compound |
|---|
| (Compound 99)<br>(M + H)⁺ = 1980.0<br>(R)-2-[N-(S)-1-[N-(S)-1-[N-3-(N-2-aminoethylcarbamoyl)-4-({[(S)-1-[N-(S)-1-{[(1S,2R)-4-[(S)-2-{(1R,2R)-2-[N-(1R,2S)-2-hydroxy-1-methyl-2-phenylethylcarbamoyl]-1-methoxypropyl}-1-pyrrolidinyl]-1-[(S)-1-methylpropyl]-2-methoxy-4-oxobutyl]-N-methylcarbamoyl}-2-methylpropylcarbamoyl]-2-methylpropyl](methyl)(aminocarbonyloxy)}methyl)phenylcarbamoyl]-4-ureidobutylcarbamoyl]-2-methylpropylcarbamoyl]-2-(14-{N-2-[4-(4-amino-1-piperidyl)-3-(6-chloro-1H-1,3-benzimidazol-2-yl)-5-(3-fluoro-5-tolyl)-2-pyridylamino]ethylcarbamoyl]-3,6,9,12-tetraoxatetradecylcarbonylamino)ethanesulfonic acid 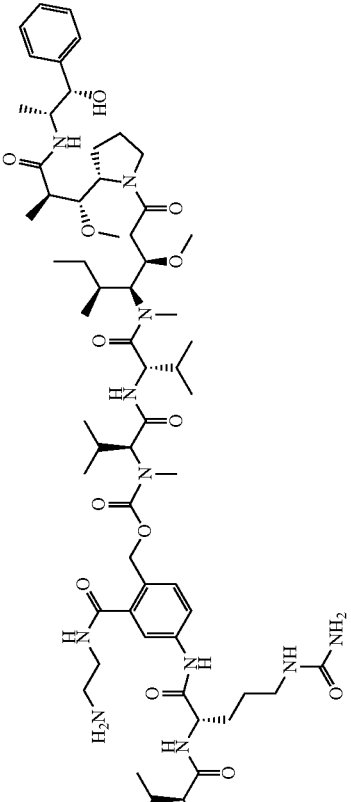 |

-continued

| Compound |
|---|
| (Compound 100)<br>(M + H)⁺ = 2112.0<br>(R)-4-[N-(S)-1-[N-(S)-1-[N-3-(N-2-aminoethylcarbamoyl)-4-({[(S)-1-[N-(S)-1-{[(1S,2R)-4-[(S)-2-{(1R,2R)-2-[N-(1R,2S)-2-hydroxy-1-methyl-2-phenylethylcarbamoyl]-1-methoxypropyl]}-1-pyrrolidinyl]-1-[(S)-1-methylpropyl]-2-methoxy-4-oxobutyl]-N-methylcarbamoyl]-2-methylpropylcarbamoyl]-2-methylpropyl](methyl)(aminocarbonyloxy)}methyl)phenylcarbamoyl]-4-ureidobutylcarbamoyl]-2-methylpropylcarbamoyl]-4-[3-(2-{N-2-[4-(4-amino-1-piperidyl)-3-(6-chloro-1H-1,3-benzimidazol-2-yl)-5-(3-fluoro-5-tolyl)-2-pyridylamino]ethylcarbamoyl}ethoxy)propionylamino]butyric acid |

-continued

| Compound |
|---|
| (Compound 101)<br>(M + H)⁺ = 1958.0<br>(R)-4-[N-(S)-1-[N-(S)-1-[N-p-({[(S)-1-[N-(S)-1-[N-p-({[(S)-1-[N-(S)-1-{[(1S,2R)-4-[(S)-2-{(1R,2R)-2-[N-(1R,2S)-2-hydroxy-1-methyl-2-phenylethylcarbamoyl]-1-methoxypropyl}-1-pyrrolidinyl]-1-[(S)-1-methylpropyl]-2-methoxy-4-oxobutyl]-N-methylcarbamoyl}-2-methylpropyl]carbamoyl]-2-methylpropyl](methyl)(aminocarbonyloxy)}methyl)phenyl]carbamoyl]-4-ureidobutyl]carbamoyl]-2-methylpropyl]carbamoyl]-4-[3-(2-{N-2-[4-(4-amino-1-piperidyl)-3-(6-chloro-1H-1,3-benzimidazol-2-yl)-5-(3-fluoro-5-tolyl)-2-pyridylamino]ethylcarbamoyl}ethoxy)propionylamino]butyric acid |

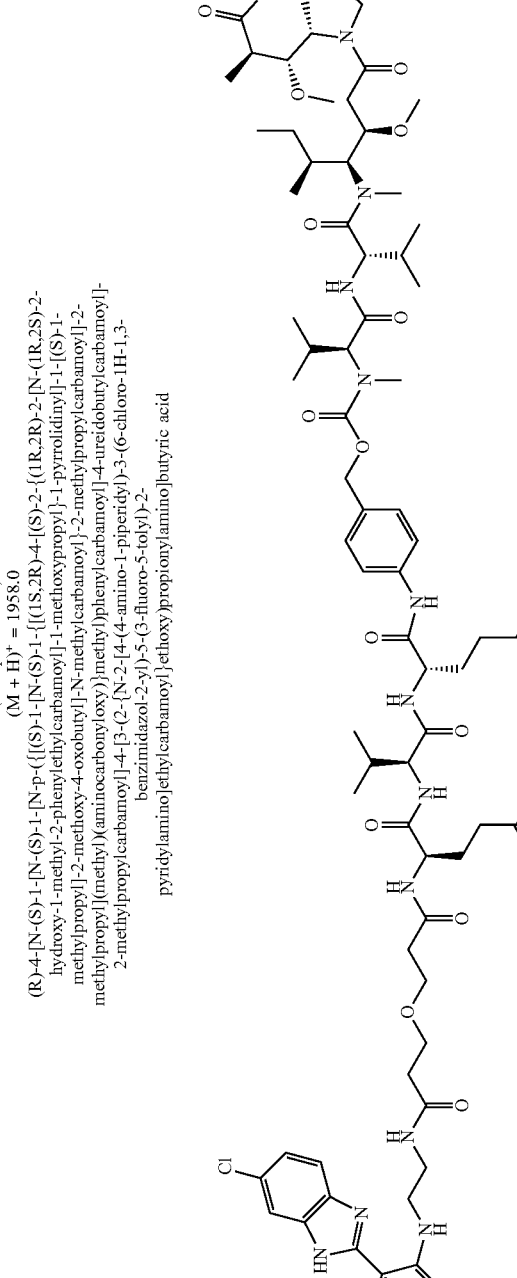

-continued

Compound (Compound 102)
(M + H)⁺ = 1872.0
(R)-4-[N-(S)-1-[N-(S)-1-[N-(S)-1-[N-p-({[(S)-1-[N-(S)-1-{[(1S,2R)-2-{[(1R,2R)-2-[N-(1R,2S)-2-hydroxy-1-methyl-2-phenylethylcarbamoyl]-1-methoxypropyl}-1-pyrrolidinyl]-1-[(S)-1-methylpropyl]-2-methoxy-4-oxobutyl]-N-methylcarbamoyl}-2-methylpropyl]carbamoyl]-2-methylpropyl](methyl)(aminocarbonyloxy)}methyl)phenyl]carbamoyl]-4-ureidobutylcarbamoyl]-2-methylpropylcarbamoyl]-4-[(R)-2-[3-(2-{N-2-[4-(4-amino-1-piperidy)-3-(6-chloro-1H-1,3-benzimidazol-2-yl)-5-(3-fluoro-5-tolyl)-2-pyridylamino]ethylcarbamoyl}ethoxy)propionylamino]-4-carboxybutyrylamino]butyric acid

| Compound |
| --- |
| (Compound 103)<br>(M + H)⁺ = 2001.0<br>(S)-2-[N-(S)-1-[N-(S)-1-[N-p-({[(S)-1-[N-(S)-1-{[(1S,2R)-4-[(S)-2-{(1R,2R)-2-[N-(1R,2S)-2-hydroxy-1-methyl-2-phenylethylcarbamoyl]-1-pyrrolidinyl}-1-methoxypropyl]-1-methylpropyl]-1-[(S)-1-methylpropyl]-2-methoxy-4-oxobutyl]-N-methylcarbamoyl}-2-methylpropylcarbamoyl]-2-methylpropyl](methyl)(aminocarbonyloxy)}methyl)phenylcarbamoyl]-4-ureidobutylcarbamoyl]-2-methylpropylcarbamoyl]-2-[3-(2-{N-2-[4-(4-amino-1-piperidyl)-3-(6-chloro-1H-1,3-benzimidazol-2-yl)-5-(3-fluoro-5-tolyl)-2-pyridylamino]ethylcarbamoyl}ethoxy)propionylamino]ethanesulfonic acid |

-continued

Compound (Compound 104)
(M + H)⁺ = 1897.7
(S)-4-[N-(R)-1-[N-(S)-1-[N-(S)-1-[N-(S)-1-[N-p-({[(S)-1-[N-(S)-2-{[(1S,2R)-4-[(S)-2-{[(1R,2R)-2-[N-(1R,2S)-2-hydroxy-1-methyl-2-phenylethylcarbamoyl]-1-pyrrolidinyl]-1-methoxypropyl}-1-methoxypropyl]-N-methylcarbamoyl}-1-(S)-1-methylpropyl]-2-methoxy-4-oxobutyl]-N-methylcarbamoyl}-2-methylpropyl]carbamoyl]-2-methylpropyl](methyl)(aminocarbonyloxy)}methyl)phenyl]carbamoyl]-4-ureidobutylcarbamoyl]-2-methylpropylcarbamoyl]-2-sulfoethylcarbamoyl]-4-[3-(2-{N-2-[4-(4-amino-1-piperidyl)-3-(6-chloro-1H-1,3-benzimidazol-2-yl)-5-(3-fluoro-5-tolyl)-2-pyridylamino]ethylcarbamoyl}ethoxy)propionylamino]butyric acid

| Compound |
|---|
| (Compound 105)<br>(M + H)+ = 2022.9<br>(R)-4-[N-(R)-1-[N-(S)-1-[N-(S)-1-[N-(S)-1-[N-p-({[(S)-1-[N-(S)-1-{[(1S,2R)-4-[(S)-2-{(1R,2R)-2-[N-(1R,2S)-2-hydroxy-1-methyl-2-phenylethylcarbamoyl]-1-methoxypropyl]-1-pyrrolidinyl]-1-[(S)-1-methylpropyl]-2-methoxy-4-oxobutyl]-N-methylcarbamoyl}-2-methylpropyl]carbamoyl]-1-(S)-methylpropyl](methyl)(aminocarbonyloxy)}methyl)phenylcarbamoyl]-4-ureidobutylcarbamoyl]-2-methylpropyl]carbamoyl]-2-sulfoethylcarbamoyl]-4-[3-(2-{N-2-[4-(4-amino-1-piperidyl)-3-(6-chloro-1H-1,3-benzimidazol-2-yl)-5-(3-fluoro-5-tolyl)-2-pyridylamino]ethylcarbamoyl}ethoxy)propionylamino]butyric acid |

-continued

Compound (Compound 106)
(M + H)⁺ = 2022.9
(S)-2-[N-(S)-1-[N-(S)-1-[N-(S)-1-[N-3-(N-2-aminoethylcarbamoyl)-4-({[(S)-1-[N-(S)-1-[[(1S,2R)-4-[(S)-2-{(1R,2R)-2-[N-(1R,2S)-2-hydroxy-1-methyl-2-phenylethylcarbamoyl]-1-methoxypropyl]-1-pyrrolidinyl]-1-[(S)-1-methylpropyl]-2-methoxy-4-oxobutyl]-N-methylcarbamoyl]-2-methylpropylcarbamoyl]-2-methylpropyl](methyl)(aminocarbonyloxy)}methyl)phenylcarbamoyl]-4-ureidobutylcarbamoyl]-2-methylpropylcarbamoyl]-2-[3-(2-{N-2-[4-(4-amino-1-piperidyl)-3-(6-chloro-1H-1,3-benzimidazol-2-yl)-5-(3-fluoro-5-tolyl)-2-pyridylamino]ethylcarbamoyl}ethoxy)propionylamino]ethanesulfonic acid

| Compound |
| --- |
| (Compound 107)<br>(M + H)⁺ = 1980.0<br>(S)-3-[N-(S)-1-[N-(S)-1-[N-p-({[(S)-1-[N-(S)-1-{[(1S,2R)-4-[(S)-2-{(1R,2R)-2-[N-(1R,2S)-2-hydroxy-1-methyl-2-phenylethylcarbamoyl]-1-methoxypropyl}-1-pyrrolidinyl]-1-[(S)-1-methylpropyl]-2-methoxy-4-oxobutyl]-N-methylcarbamoyl}-2-methylpropylcarbamoyl]-2-methylpropyl](methyl)(aminocarbonyloxy)]methyl)phenylcarbamoyl]-4-ureidobutyl]carbamoyl]-2-methylpropylcarbamoyl]-3-[(S)-2-[(S)-2-[3-(2-{N-2-[4-(4-amino-1-piperidyl)-3-(6-chloro-1H-1,3-benzimidazol-2-yl)-5-(3-fluoro-5-tolyl)-2-pyridylamino]ethyl]carbamoyl}ethoxy)propionylamino]-3-carboxypropionylamino]-3-carboxypropionylamino]propionic acid |

-continued

| Compound |
|---|
| (Compound 108)<br>(M + H)⁺ = 2088.0<br>(R)-3-[N-(S)-1-[N-(S)-1-[N-(S)-1-[N-p-({[(S)-1-[N-(S)-1-{[(1S,2R)-2-{(1R,2R)-2-[N-(1R,2S)-2-hydroxy-1-methyl-2-phenylethylcarbamoyl]-1-pyrrolidinyl}-1-methoxypropyl]-N-methylcarbamoyl}-1-[(S)-1-methylpropyl]-2-methoxy-4-oxobutyl]-N-methylcarbamoyl]-2-methylpropyl]carbamoyl}-1-(S)-1-methylpropyl](aminocarbonyloxy)}methyl)phenylcarbamoyl]-4-ureidobutylcarbamoyl]-2-methylpropyl]carbamoyl]-3-[(R)-2-[(R)-2-[3-(2-{N-2-[4-(4-amino-1-piperidyl)-3-(6-chloro-1H-1,3-benzimidazol-2-yl)-5-(3-fluoro-5-tolyl)-2-pyridylamino]ethylcarbamoyl}ethoxy)propionylamino]-3-carboxypropionylamino]-3-carboxypropionylamino]propionic acid |

| Compound |
| --- |
| (Compound 109)<br>(M + H)⁺ = 2088.0<br>(S)-4-[N-(S)-1-[N-(S)-1-[N-p-({[(S)-1-[N-(S)-1-{[(1S,2R)-4-[(S)-2-{(1R,2R)-2-[N-(1R,2S)-2-hydroxy-1-methyl-2-phenylethylcarbamoyl]-1-methoxypropyl}-1-pyrrolidinyl]-1-[(S)-1-methylpropyl]-2-methoxy-4-oxobutyl]-N-methylcarbamoyl}-2-methylpropylcarbamoyl]-2-methylpropyl](methyl)(aminocarbonyloxy)}methyl)phenylcarbamoyl]-4-ureidobutylcarbamoyl]-2-methylpropylcarbamoyl]-4-[(S)-2-(14-{N-2-[4-(4-amino-1-piperidyl)-3-(6-chloro-1H-1,3-benzimidazol-2-yl)-5-(3-fluoro-5-tolyl)-2-pyridylamino]ethylcarbamoyl}-3,6,9,12-tetraoxatetradecylcarbonylamino)-4-carboxybutyrylamino]butyric acid<br>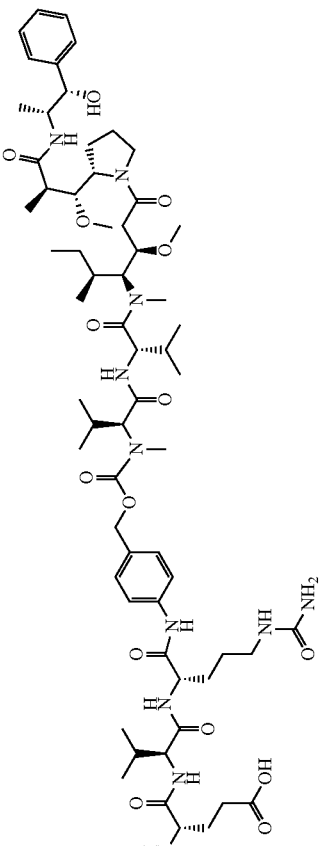 |

| Compound |
| --- |
| (Compound 110)<br>(M + H)⁺ = 2133.1<br>(S)-4-({[N-(S)-1-[N-(S)-1-[N-(S)-1-[N-p-({[(S)-1-[N-(S)-1-{[(1S,2R)-4-{(S)-2-{(1R,2R)-2-[N-(1R,2S)-2-hydroxy-1-methyl-2-phenylethyl]carbamoyl]-1-pyrrolidinyl]-1-methoxypropyl]-1-methoxypropyl]-N-methylcarbamoyl}-2-methylpropyl]carbamoyl]-1-(S)-1-methylpropyl]-2-methoxy-4-oxobutyl]-N-methylcarbamoyl}-2-methylpropyl]carbamoyl]-2-methylpropyl](methyl)(aminocarbonyloxy)}methyl)phenyl]carbamoyl]-4-ureidobutyl]carbamoyl]-2-methylpropyl]carbamoyl]methyl]carbamoyl)-4-{(S)-2-[3-(2-{N-2-[4-(4-amino-1-piperidyl)-3-(6-chloro-1H-1,3-benzimidazol-2-yl)-5-(3-fluoro-5-tolyl)-2-pyridylamino]ethyl]carbamoyl}ethoxy)propionylamino]-4-carboxybutyryl]amino}butyric acid |

-continued

| Compound |
|---|
| (Compound 111)<br>(M + H)⁺ = 2058.0<br>1-(S)-1-[N-(S)-1-{[(1S,2R)-4-[(S)-2-{(1R,2R)-2-[N-(1R,2S)-2-hydroxy-1-methyl-2-phenylethylcarbamoyl]-1-methoxypropyl}-1-pyrrolidinyl]-1-[(S)-1-methylpropyl]-2-methoxy-4-oxobutyl]-N-methylcarbamoyl]-2-methylpropylcarbamoyl}-2-methylpropyl 1-methyl {4-[(S)-2-[(S)-2-[(S)-2-[3-(2-{N-2-[4-(4-amino-1-piperidyl)-3-(6-chloro-1H-1,3-benzimidazol-2-yl)-5-(3-fluoro-5-tolyl)-2-pyridylamino]ethylcarbamoyl}ethoxy)propionylamino]-4-carbamoylbutyrylamino]-3-methylbutyrylamino]-5-ureidovalerylamino]-2-carbamoylphenyl}methanecarbamate 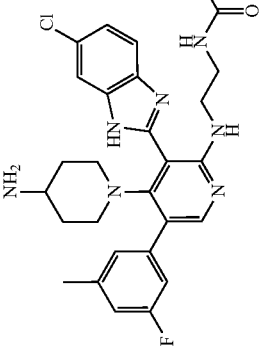 |

| Compound |
| --- |
| (Compound 112)<br>(M + H)⁺ = 1914.0<br>(S)-4-[N-(S)-1-[N-(S)-1-[N-p-({[(S)-1-[N-(S)-1-{[(1S,2R)-4-[(S)-2-{(1R,2R)-2-[N-(1R,2S)-2-hydroxy-1-methyl-2-phenylethylcarbamoyl]-1-methoxypropyl}-1-pyrrolidinyl]-1-[(S)-1-methylpropyl]-2-methoxy-4-oxobutyl]-N-methylcarbamoyl}-2-methylpropylcarbamoyl]-2-methylpropyl](aminocarbonyloxy)}methyl)phenylcarbamoyl]-4-ureidobutylcarbamoyl]-2-methylpropylcarbamoyl]-4-[(R)-2-[3-(2-{N-2-[4-(4-amino-1-piperidyl)-3-(6-chloro-1H-1,3-benzimidazol-2-yl)-5-(3-fluoro-5-tolyl)-2-pyridylamino]ethylcarbamoyl}ethoxy)propionylamino]-3-sulfopropionylamino]butyric acid |

-continued

Compound (Compound 113)
(M + H)+ = 2022.9
(S)-4-[N-(R)-1-[N-(S)-1-[N-(S)-1-[N-p-({[(S)-1-[N-(S)-1-[{(1S,2R)-4-[(S)-2-{(1R,2R)-2-[N-(1R,2S)-2-hydroxy-1-methyl-2-phenylethylcarbamoyl]-1-methoxypropyl}-1-pyrrolidinyl]-1-[(S)-1-methylpropyl]-2-methoxy-4-oxobutyl]-N-methylcarbamoyl}-2-methylpropyl]carbamoyl]-1-methylpropyl](methyl)(aminocarbonyloxy)}methyl)phenylcarbamoyl]-4-ureidobutylcarbamoyl]-2-methylpropylcarbamoyl]-2-sulfoethylcarbamoyl]-4-{14-[N-2-[4-(4-amino-1-piperidyl)-3-(6-chloro-1H-1,3-benzimidazol-2-yl)-5-(3-fluoro-5-tolyl)-2-pyridylamino]ethylcarbamoyl]-3,6,9,12-tetraoxatetradecyl}carbonylamino)butyric acid

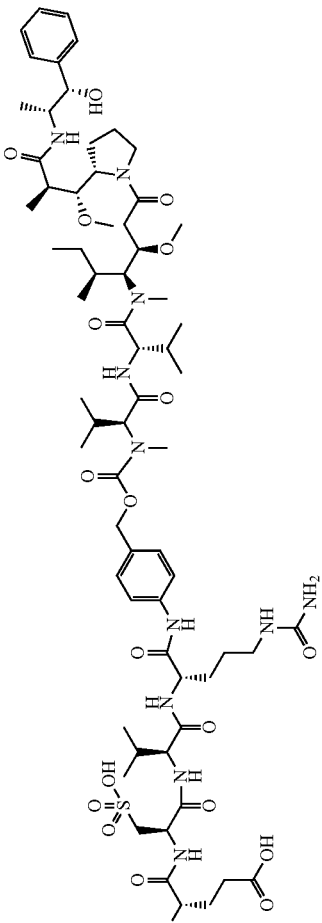

-continued

Compound (Compound 114)
(M + H)⁺ = 2155.0
(R)-2-[N-(S)-1-[N-(S)-1-[N-(S)-1-[N-p-({[(S)-1-[N-(S)-1-[N-p-({[(S)-1-[N-(S)-1-{[(1S,2R)-4-[(S)-2-{(1R,2R)-2-[N-(1R,2S)-2-hydroxy-1-methyl-2-phenylethylcarbamoyl]-1-methoxypropyl]-1-pyrrolidinyl]-1-[(S)-1-methylpropyl]-2-methoxy-4-oxobutyl]-N-methylcarbamoyl}-2-methylpropyl]carbamoyl]-2-methylpropyl](methyl)(aminocarbonyloxy)}methyl)phenyl]carbamoyl]-4-ureidobutylcarbamoyl]-2-methylpropylcarbamoyl]-2-[(S)-2-[3-(2-{N-2-[4-(4-amino-1-piperidyl)-3-(6-chloro-1H-1,3-benzimidazol-2-yl)-5-(3-fluoro-5-tolyl)-2-pyridylamino]ethylcarbamoyl;ethoxy)propionylamino]-4-carbamoylbutyrylamino]ethanesulfonic acid -continued

| Compound |
|---|
| (Compound 115)<br>(M + H)⁺ = 2022.0<br>(S)-4-[N-(S)-1-[N-(S)-1-[N-3-(N-2-aminoethylcarbamoyl)-4-({[(S)-1-[N-(S)-1-{[(1S,2R)-4-{(S)-2-{(1R,2R)-2-[N-(1R,2S)-2-hydroxy-1-methyl-2-phenylethylcarbamoyl]-1-methoxypropyl}-1-pyrrolidinyl]-1-[(S)-1-methylpropyl]-2-methoxy-4-oxobutyl]-N-methylcarbamoyl}-2-methylpropylcarbamoyl]-2-methylpropyl](methyl)(aminocarbonyloxy)}methyl)phenyl]carbamoyl]ethylcarbamoyl]-4-[3-(2-{N-2-[4-(4-amino-1-piperidyl)-3-(6-chloro-1H-1,3-benzimidazol-2-yl)-5-(3-fluoro-5-tolyl)-2-pyridylamino]ethylcarbamoyl}ethoxy)propionylamino]butyric acid |
| (Compound 116)<br>(M + H)⁺ = 1872.0<br>(R)-2-[N-(S)-1-[N-(S)-1-[N-3-(N-2-aminoethylcarbamoyl)-4-({[(S)-1-[N-(S)-1-{[(1S,2R)-4-{(S)-2-{(1R,2R)-2-[N-(1R,2S)-2-hydroxy-1-methyl-2-phenylethylcarbamoyl]-1-methoxypropyl}-1-pyrrolidinyl]-1-[(S)-1-methylpropyl]-2-methoxy-4-oxobutyl]-N-methylcarbamoyl}-2-methylpropylcarbamoyl]-2-methylpropyl](methyl)(aminocarbonyloxy)}methyl)phenyl]carbamoyl]ethylcarbamoyl]-2-methylpropylcarbamoyl]-2-[3-(2-{N-2-[4-(4-amino-1-piperidyl)-3-(6-chloro-1H-1,3-benzimidazol-2-yl)-5-(3-fluoro-5-tolyl)-2-pyridylamino]ethylcarbamoyl}ethoxy)propionylamino]ethanesulfonic acid |

-continued

| Compound |
|---|
| (Compound 117)<br>(M + H)⁺ = 1893.9<br>1-(S)-1-[N-(S)-1-{[(1S,2R)-4-[(S)-2-{(1R,2R)-2-[N-(1R,2S)-2-hydroxy-1-methyl-2-phenylethyl]carbamoyl]-1-methoxypropyl]-1-pyrrolidinyl]-1-[(S)-1-methylpropyl]-2-methoxy-4-oxobutyl]-N-methylcarbamoyl}-2-methylpropyl]carbamoyl]-2-methylpropyl 1-methyl [2-(N-2-aminoethylcarbamoyl)-4-[(S)-2-[(S)-2-[(S)-2-[3-(2-{N-2-[4-(4-amino-1-piperidyl)-3-(6-chloro-1H-1,3-benzimidazol-2-yl)-5-(3-fluoro-5-tolyl)-2-pyridylamino]ethylcarbamoyl}ethoxy)propionylamino]-4-carbamoylbutyrylamino]-3-methylbutyrylamino]propionylamino]phenyl]methanecarbamate<br>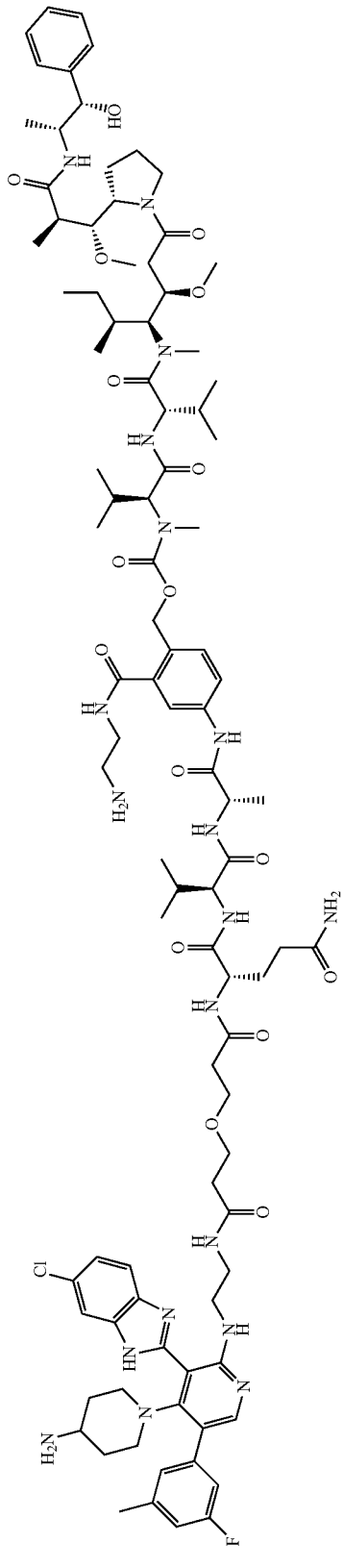 |

| Compound |
|---|
| (Compound 118)<br>(M + H)⁺ = 1871.0<br>1-(S)-1-[N-(S)-1-{[(1S,2R)-4-[(S)-2-{(1R,2R)-2-[N-(1R,2S)-2-hydroxy-1-methyl-2-phenylethylcarbamoyl]-1-methoxypropyl}-1-pyrrolidinyl]-1-[(S)-1-methylpropyl]-2-methoxy-4-oxobutyl]-N-methylcarbamoyl}-2-methylpropylcarbamoyl]-2-methylpropyl 1-methyl {p-[(S)-2-[(S)-2-[(S)-2-(14-{N-2-[4-(4-amino-1-piperidyl)-3-(6-chloro-1H-1,3-benzimidazol-2-yl)-5-(3-fluoro-5-tolyl)-2-pyridylamino]ethylcarbamoyl]-3,6,9,12-tetraoxatetradecylcarbonylamino]-4-carbamoylbutyrylamino]-4-carbamoylbutyrylamino]-3-methylbutyrylamino]-5-ureidovalerylamino]phenyl}methanecarbamate 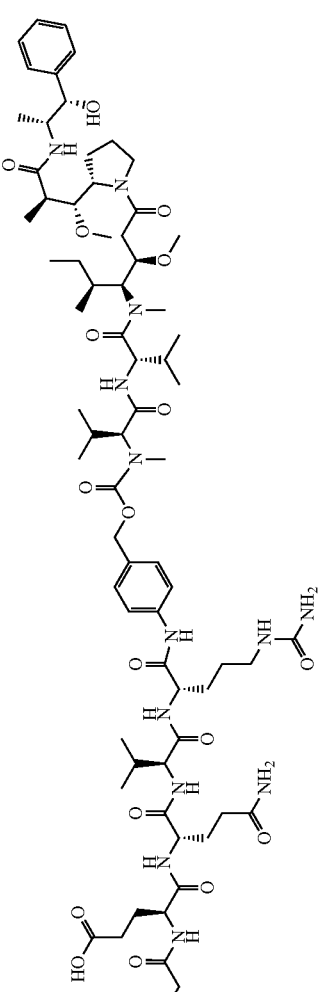 |

-continued

| Compound |
|---|
| (Compound 119)<br>(M + H)⁺ = 2131.1<br>(S)-4-[N-(S)-1-[N-(S)-1-[N-(S)-1-[N-3-(N-2-aminoethylcarbamoyl)-4-{[[(S)-1-[N-(S)-1-{[(1S,2R)-4-[(S)-2-{(1R,2R)-2-[N-(1R,2S)-2-hydroxy-1-methyl-2-phenylethylcarbamoyl]-1-methoxypropyl}-1-pyrrolidinyl]-1-[(S)-1-methylpropyl]-2-methoxy-4-oxobutyl]-N-methylcarbamoyl]-2-methylpropylcarbamoyl]-2-methylpropyl](methyl)(aminocarbonyloxy)}methyl)phenylcarbamoyl]-2-methylpropylcarbamoyl]-4-(5-{N-2-[4-(4-amino-1-piperidyl)-3-(6-chloro-1H-1,3-benzimidazol-2-yl)-5-(3-fluoro-5-tolyl)-2-pyridylamino]ethylcarbamoyl}pentylcarbonylamino)butyric acid |

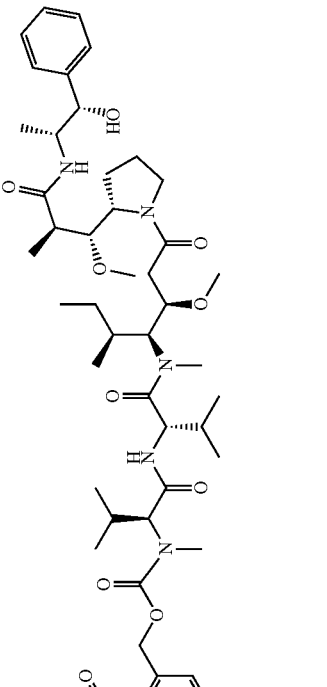

-continued

| Compound |
|---|
| 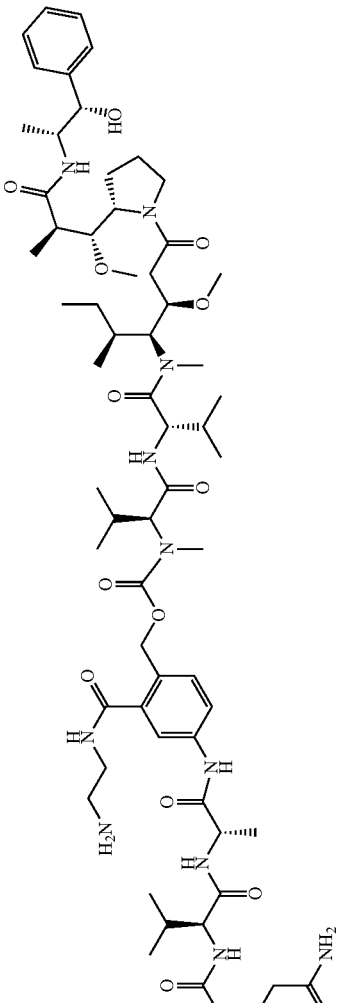 (Compound 120) $(M + H)^+ = 1870.0$ 1-(S)-1-[N-(S)-1-{[(1S,2R)-4-[(S)-2-{(1R,2R)-2-[N-(1R,2S)-2-hydroxy-1-methyl-2-phenylethyl]carbamoyl]-1-[(1S,2R)-1-methoxypropyl]-1-pyrrolidinyl]-1-[(S)-1-methylpropyl]-2-methoxy-4-oxobutyl]-N-methylcarbamoyl}-2-methylpropyl]carbamoyl]-1-[(S)-1-methylpropyl [2-(N-2-aminoethyl)carbamoyl]-4-[(S)-2-[(S)-2-(5-{N-2-[4-(4-amino-1-piperidyl)-3-(6-chloro-1H-1,3-benzimidazol-2-yl)-5-(3-fluoro-5-tolyl)-2-pyridylamino]ethyl]carbamoyl]pentylcarbonyl]amino)-4-carbamoylbutyrylamino]-3-methylbutyrylamino]propionylamino]phenyl]methanecarbamate |

-continued

| Compound |
|---|
| (Compound 121)<br>(M + H)⁺ = 1869.0<br>1-(S)-1-[N-(S)-1-{[(1S,2R)-4-[(S)-2-{(1R,2R)-2-[N-(1R,2S)-2-hydroxy-1-methyl-2-phenylethylcarbamoyl]-1-methoxypropyl}-1-pyrrolidinyl]-1-[(S)-1-methylpropyl]-2-methoxy-4-oxobutyl]-N-methylcarbamoyl}-2-methylpropylcarbamoyl]-2-methylpropyl 1-methyl {4-[(S)-2-[(S)-2-[3-(2-{N-2-[4-(4-amino-1-piperidyl)-3-(6-chloro-1H-1,3-benzimidazol-2-yl)-5-(3-fluoro-5-tolyl)-2-pyridylamino]ethylcarbamoyl}ethoxy)propionylamino]-3-methylbutyrylamino]-5-ureidovalerylamino]-2-carbamoylphenyl}methanecarbamate |

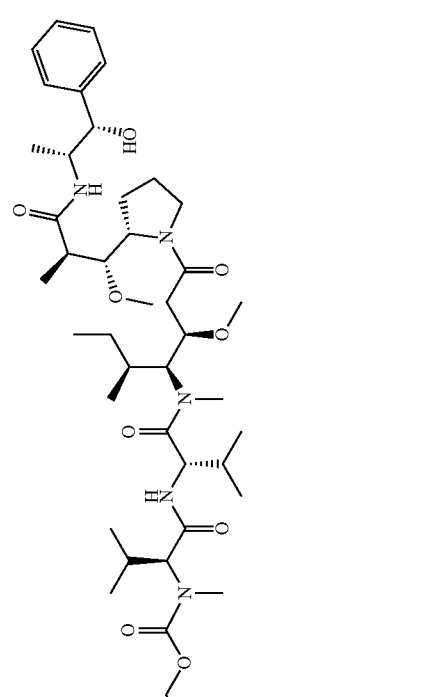

-continued

Compound (Compound 122)
(M + H)⁺ = 1786.0
1-(S)-1-[N-(S)-1-[[(1S,2R)-4-[(S)-2-{[(1R,2R)-2-[N-(1R,2S)-2-hydroxy-1-methyl-2-phenylethylcarbamoyl]-1-methoxypropyl]-1-pyrrolidinyl}-1-[(S)-1-methylpropyl]-2-methoxy-4-oxobutyl]-N-methylcarbamoyl]-2-methylpropylcarbamoyl]-2-methylpropyl 1-methyl {4-[(S)-2-[(S)-2-(14-{N-2-[4-(4-amino-1-piperidyl)-3-(6-chloro-1H-1,3-benzimidazol-2-yl)-5-(3-fluoro-5-tolyl)-2-pyridyl]amino]ethylcarbamoyl]-3,6,9,12-tetraoxatetradecylcarbonylamino)-3-methylbutyrylamino]-5-ureidovalerylamino]-2-carbamoylphenyl}methanecarbamate

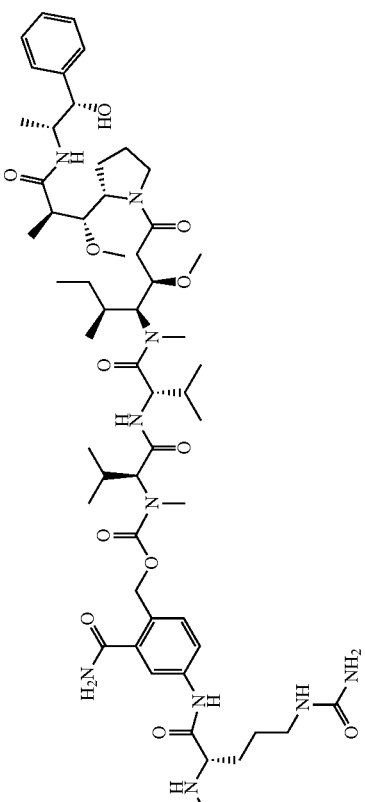

-continued

Compound (Compound 123)
(M + H)⁺ = 1918.0
1-(S)-1-[N-(S)-1-[[(1S,2R)-4-[(S)-2-{(1R,2R)-2-[N-(1R,2S)-2-hydroxy-1-methyl-2-phenylethyl)carbamoyl]-1-methoxypropyl}-1-pyrrolidinyl]-1-methylpropyl]-2-methoxy-4-oxobutyl]-N-methylcarbamoyl]-2-methylpropylcarbamoyl]-1-[(S)-1-methylpropyl 1-methyl {4-[(S)-2-[(S)-2-(14-{N-2-[4-(4-amino-1-piperidyl)-3-(6-chloro-1H-1,3-benzimidazol-2-yl)-5-(3-fluoro-5-tolyl)-2-pyridyl]amino]ethylcarbamoyl}-3,6,9,12-tetraoxatetradecylcarbonylamino)-3-methylbutyrylamino]-5-ureidovalerylamino]-[(carbamoylmethyl)carbamoyl]phenyl}methanecarbamate

| Compound |
| --- |
| (Compound 124)<br>(M + H)⁺ = 1975.0<br>1-(S)-1-[N-(S)-1-{[(1S,2R)-4-[(S)-2-{(1R,2R)-2-[N-(1R,2S)-2-hydroxy-1-methyl-2-phenylethyl)carbamoyl]-1-methoxypropyl}-1-pyrrolidinyl]-1-methylpropyl]-2-methoxy-4-oxobutyl]-N-methylcarbamoyl}-2-methylpropylcarbamoyl]-2-methylpropyl 1-methyl {4-[(S)-2-[(S)-2-[3-(2-{N-2-[4-(4-amino-1-piperidyl)-3-(6-chloro-1H-1,3-benzimidazol-2-yl)-5-(3-fluoro-5-tolyl)-2-pyridylamino]ethyl}carbamoyl)ethoxy)propionylamino]-3-methylbutyrylamino]-5-ureidovalerylamino]-2-[((carbamoylmethyl)carbamoyl)phenyl]methanecarbamate |

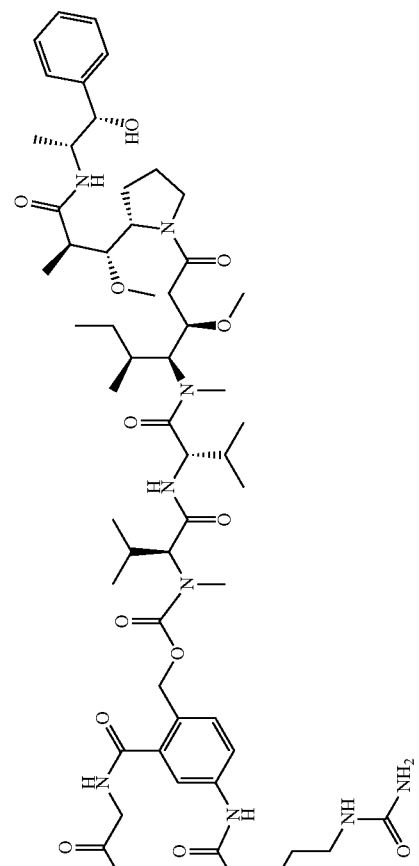

-continued

| Compound |
|---|
| (Compound 125)<br>(M + H)⁺ = 1843.0<br>(R)-2-[N-(S)-1-[N-(S)-1-[N-3-(N-2-aminoethylcarbamoyl)-4-({[(S)-1-[N-(S)-1-{[(1S,2R)-4-(S)-2-{(1R,2R)-2-[N-(1R,2S)-2-hydroxy-1-methyl-2-phenylethylcarbamoyl]-1-methoxypropyl]-1-pyrrolidinyl]-1-[(S)-1-methylpropyl]-2-methoxy-4-oxobutyl]-N-methylcarbamoyl}-2-methylpropyl]carbamoyl]-2-methylpropyl](methyl)(aminocarbonyloxy)}methyl)phenylcarbamoyl]-4-ureidobutyl]carbamoyl]-2-methylpropyl]carbamoyl]-2-(14-{N-2-[4-(4-amino-1-piperidyl)-5-(3-fluoro-5-tolyl)-2-pyridylamino]ethylcarbamoyl}-3,6,9,12-tetraoxatetradecylcarbonylamino)ethanesulfonamide |
| (Compound 157)<br>(M + H)⁺ = 2111.0<br>(R)-2-[N-(S)-1-[N-(S)-1-[N-3-(N-2-aminoethylcarbamoyl)-4-({[(S)-1-[N-(S)-1-{[(1S,2R)-4-(S)-2-{(1R,2R)-2-[N-(1R,2S)-2-hydroxy-1-methyl-2-phenylethylcarbamoyl]-1-methoxypropyl]-1-pyrrolidinyl]-1-[(S)-1-methylpropyl]-2-methoxy-4-oxobutyl]-N-methylcarbamoyl}-2-methylpropyl]carbamoyl]-2-methylpropyl](methyl)(aminocarbonyloxy)}methyl)phenylcarbamoyl]-2-methylpropyl]carbamoyl]-2-(14-{N-2-[4-(4-amino-1-piperidyl)-3-(6-chloro-1H-1,3-benzimidazol-2-yl)-5-(3-fluoro-5-tolyl)-2-pyridylamino]ethylcarbamoyl}-3,6,9,12-tetraoxatetradecylcarbonylamino)ethanesulfonamide |

-continued

| Compound |
|---|
| (Compound 158)<br>(M + H)⁺ = 2025.0<br>(R)-2-[N-(S)-1-[N-(S)-1-[N-3-(N-2-aminoethylcarbamoyl)-4-({[(S)-1-[N-(S)-1-{[(1S,2R)-4-[(S)-2-{(1R,2R)-2-[N-(1R,2S)-2-hydroxy-1-methyl-2-phenylethylcarbamoyl]-1-methoxypropyl]-1-pyrrolidinyl]-1-[(S)-1-methylpropyl]-2-methoxy-4-oxobutyl]-N-methylcarbamoyl}-2-methylpropylcarbamoyl]-2-methylpropyl](methyl)(aminocarbonyloxy)}methyl)phenylcarbamoyl]-4-ureidobutylcarbamoyl]-2-methylpropylcarbamoyl]-2-[3-(2-{N-2-[4-(4-amino-1-piperidyl)-3-(6-chloro-1H-1,3-benzimidazol-2-yl)-5-(3-fluoro-5-tolyl)-2-pyridylamino]ethylcarbamoyl}ethoxy)propionylamino]ethanesulfonamide |
| (Compound 159)<br>(M + H)⁺ = 1979.0 |

Example F. {4-[(2S)-2-[(2S)-2-[(2S)-2-(3-{2-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]ethoxy}propanamido)-4-carbamoylbutanamido]-3-methylbutanamido]-5-(carbamoylamino)pentanamido]phenyl}methyl N-[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl]-2-methylpropyl]carbamoyl}-2-methylpropyl]-N-methylcarbamate (Compound 56)

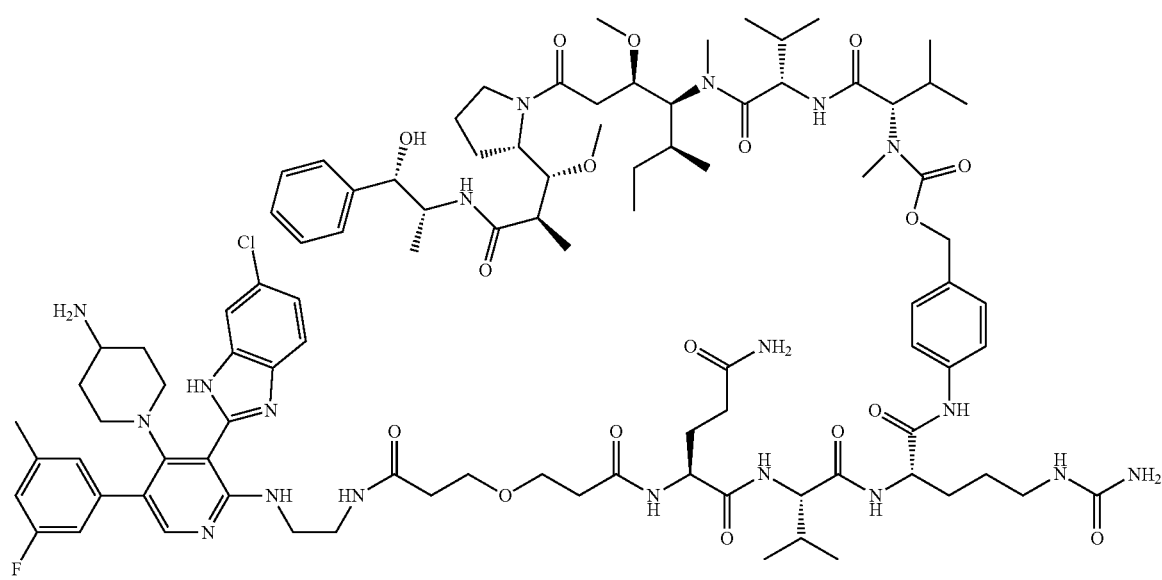 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)[C@H](CCC(N)=O)NC(=O)CCOCCC(=O)NCCNc2ncc(-c3cc(C)cc(F)c3)c(N3CCC(N)CC3)c2-c2nc3ccc(Cl)cc3[nH]2)C(C)C)cc1)C(C)C]

Step F-1 tert-butyl (4S)-4-(((((9H-fluoren-9-yl)methoxy)carbonyl)amino)-5-(((2S)-1-(((2S)-1-((4-((5S,11S,14S,17S,18R)-17-((S)-sec-butyl)-18-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8,11,14-tetraisopropyl-4,10,16-trimethyl-3,6,9,12,15-pentaoxo-2,19-dioxa-4,7,10,13,16-pentaazaicosyl)phenyl)amino)-1-oxo-5-ureidopentan-2-yl)amino)-3-methyl-1-oxobutan-2-yl)amino)-5-oxopentanoate: a mixture of (S)-2-(((((9H-fluoren-9-yl)methoxy)carbonyl)amino)-5-(tert-butoxy)-5-oxopentanoic acid (40 mg, 1.6 Eq, 94 μmol), HATU (40 mg, 1.8 Eq, 0.11 mmol), and DIEA (40 mg, 54 μL, 5.2 Eq, 0.31 mmol) in DMF (1 mL) was stirred at 20° C. for 10 minutes, then 4-((S)-2-((S)-2-amino-3-methylbutanamido)-5-ureidopentanamido)benzyl ((3R,4S,7S,10S,16S)-4-((S)-sec-butyl)-3-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-7,10,13-triisopropyl-5,11,17-trimethyl-6,9,12,15-tetraoxo-2-oxa-5,8,11,14-tetraazaoctadecan-16-yl)(methyl)carbamate (80 mg, 1 Eq, 60 μmol) was added and the reaction mixture was stirred at 20° C. for 1 hour. The mixture was directly purified by MPLC with the following conditions: Column, WelFlash™, C18 120 g, Spherical 20-40 μm; Mobile phase, Water (0.05% FA) and ACN (5% ACN to 5% ACN in 1 min, 30% ACN up to 80% in 7 min, 95% ACN to 95% in 3 min); Total flow rate, 70 mL/min; Detector, UV 220 nm. The collected fractions were combined and concentrated under vacuum to give tert-butyl (4S)-4-(((((9H-fluoren-9-yl)methoxy)carbonyl)amino)-5-(((2S)-1-(((2S)-1-((4-((5S,11S,14S,17S,18R)-17-((S)-sec-butyl)-18-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8,11,14-tetraisopropyl-4,10,16-trimethyl-3,6,9,12,15-pentaoxo-2,19-dioxa-4,7,10,13,16-pentaazaicosyl)phenyl)amino)-1-oxo-5-ureidopentan-2-yl)amino)-3-methyl-1-oxobutan-2-yl)amino)-5-oxopentanoate (90 mg, 86%). MS (M+H)$^+$ =1531.6.

Step F-2, preparation of tert-butyl (4S)-4-amino-5-(((2S)-1-(((2S)-1-((4-((5S,11S,14S,17S,18R)-17-((S)-secbutyl)-18-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8,11,14-tetraisopropyl-4,10,16-trimethyl-3,6,9,12,15-pentaoxo-2,19-dioxa-4,7,10,13,16-pentaazaicosyl)phenyl)amino)-1-oxo-5-ureidopentan-2-yl)amino)-3-methyl-1-oxobutan-2-yl)amino)-5-oxopentanoate: a mixture of tert-butyl (4S)-4-(((((9H-fluoren-9-yl)methoxy)carbonyl)amino)-5-(((2S)-1-(((2S)-1-((4-((5S,11S,14S,17S,18R)-17-((S)-sec-butyl)-18-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8,11,14-tetraisopropyl-4,10,16-trimethyl-3,6,9,12,15-pentaoxo-2,19-dioxa-4,7,10,13,16-pentaazaicosyl)phenyl)amino)-1-oxo-5-ureidopentan-2-yl)amino)-3-methyl-1-oxobutan-2-yl)amino)-5-oxopentanoate (85 mg, 1 Eq, 49 μmol) and 2,3,4,6,7,8,9,10-octahydropyrimido[1,2-a]azepine (25 mg, 3.4 Eq, 0.16 mmol) in DMF (1 mL) was stirred at 20° C. for 1 hour. The mixture was directly purified by MPLC with the following conditions: Column, Wel-Flash™, C18 120 g, Spherical 20-40 μm; Mobile phase, Water (0.05% FA) and ACN (5% ACN to 5% ACN in 1 min, 20% ACN up to 70% in 7 min, 95% ACN to 95% in 3 min); Total flow rate, 70 mL/min; Detector, UV 220 nm. The collected fractions were combined and concentrated under vacuum to give tert-butyl (4S)-4-amino-5-(((2S)-1-(((2S)-1-((4-((5S,11S,14S,17S,18R)-17-((S)-sec-butyl)-18-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8,11,14-tetraisopropyl-4,10,16-trimethyl-3,6,9,12,15-pentaoxo-2,19-dioxa-4,7,10,13,16-pentaazaicosyl)phenyl)amino)-1-oxo-5-ureidopentan-2-yl)amino)-3-methyl-1-oxobutan-2-yl)amino)-5-oxopentanoate (70 mg, 94%). MS (M+H)⁺=1531.6.

Step F-3, preparation of tert-butyl (S)-4-(3-(3-((2-((4-(4-((tert-butoxycarbonyl)amino)piperidin-1-yl)-3-(6-chloro-1H-benzo[d]imidazol-2-yl)-5-(3-fluoro-5-methylphenyl)pyridin-2-yl)amino)ethyl)amino)-3-oxopropoxy)propanamido)-5-(((S)-1-(((S)-1-((4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenyl)amino)-1-oxo-5-ureidopentan-2-yl)amino)-3-methyl-1-oxobutan-2-yl)amino)-5-oxopentanoate: a mixture of 3-(3-((2-((4-(4-((tert-butoxycarbonyl)amino)piperidin-1-yl)-3-(6-chloro-1H-benzo[d]imidazol-2-yl)-5-(3-fluoro-5-methylphenyl)pyridin-2-yl)amino)ethyl)amino)-3-oxopropoxy)propanoic acid (40 mg, 1.3 Eq, 54 μmol), 4-methylmorpholine (20 mg, 4.6 Eq, 0.20 mmol), and Pentafluorophenyldiphenylphosphinate (25 mg, 1.5 Eq, 65 μmol) in DMF (1 mL) was stirred at 20° C. for 10 minutes, then tert-butyl (4S)-4-amino-5-(((2S)-1-(((2S)-1-((4-((5S,11S,14S,17S,18R)-17-((S)-sec-butyl)-18-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8,11,14-tetraisopropyl-4,10,16-trimethyl-3,6,9,12,15-pentaoxo-2,19-dioxa-4,7,10,13,16-pentaazaicosyl)phenyl)amino)-1-oxo-5-ureidopentan-2-yl)amino)-3-methyl-1-oxobutan-2-yl)amino)-5-oxopentanoate (65 mg, 1 Eq, 43 μmol) was added and the reaction mixture was stirred at 20° C. for 1 hour. The mixture was diluted with 20 mL of water, extracted with EtOAc (20 mL×3), the combined organic layers were washed with water (10 mL×2) and brine (20 mL), dried over anhydrous Na₂SO₄ and concentrated under reduced pressure to give tert-butyl (S)-4-(3-(3-((2-((4-(4-((tert-butoxycarbonyl)amino)piperidin-1-yl)-3-(6-chloro-1H-benzo[d]imidazol-2-yl)-5-(3-fluoro-5-methylphenyl)pyridin-2-yl)amino)ethyl)amino)-3-oxopropoxy)propanamido)-5-(((S)-1-(((S)-1-((4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenyl)amino)-1-oxo-5-ureidopentan-2-yl)amino)-3-methyl-1-oxobutan-2-yl)amino)-5-oxopentanoate (70 mg, 81%). MS (M/2+H)⁺=1015.2. This material was used for the next step without further purification.

Step F-4, preparation of 4-((S)-2-((S)-2-(((((9H-fluoren-9-yl)methoxy)carbonyl)amino)-3-methylbutanamido)propanamido)benzyl ((S)-1-(((S)-1-(((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)amino)-3-methyl-1-oxobutan-2-yl)(methyl)carbamate: to a mixture of (4S)-4-(3-{2-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]ethoxy}propanamido)-4-{[(1S)-1-{[(1S)-4-(carbamoylamino)-1-({4-[({[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl](methyl)carbamoyl}oxy)methyl]phenyl}carbamoyl)butyl]carbamoyl}-2-methylpropyl]carbamoyl}butanoic acid (35 mg, 80% Wt, 1 Eq, 15 μmol) in DMF (1 mL) was added ammonium chloride (20 mg, 25 Eq, 0.37 mmol), 1H-benzo[d][1,2,3]triazol-1-ol hydrate (3 mg, 1 Eq, 0.02 mmol), 3-(((ethylimino)methylene)amino)-N,N-dimethylpropan-1-amine hydrochloride (5 mg, 2 Eq, 0.03 mmol), and N,Ndimethylpyridin-4-amine (3 mg, 2 Eq, 0.02 mmol). The reaction mixture was stirred at 20° C. for 6 hours. The crude product was purified by Prep-HPLC with the following conditions: Column: SunFire prep OBD 19*150 mm 5 um; Mobile Phase A: Water (0.05% TFA); Mobile Phase B: ACN; Gradient: 25% B to 55% B in 16 min; Flow rate: 20 mL/min; Wave Length: 220 nm. The collected fractions were dried by lyophilization to give {4-[(2S)-2-[(2S)-2-[(2S)-2-(3-{2-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]ethoxy}propanamido)-4-carbamoylbutanamido]-3-methylbutanamido]-5-(carbamoylamino)pentanamido]phenyl}methyl N-[(1S)-1-{1[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl]-N-methylcarbamate (10.3 mg, 31%). MS (M+H)⁺=1872.1.

The following conjugates were prepared similarly to Example F with appropriate substituting reagents and substrates at different steps and they may require additional functional group modifications via well-known chemistry with appropriate reagents.

| Compound |
|---|
| {2-[(2-aminoethyl)carbamoyl]-4-[(2S)-2-[(2S)-2-[(2S)-2-(3-{2-[[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]ethoxy}propanamido)-4-carbamoylbutanamido]-3-methylbutanamido]-5-(carbamoylamino)pentanamido]phenyl}methyl N-[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl]-N-methylcarbamate 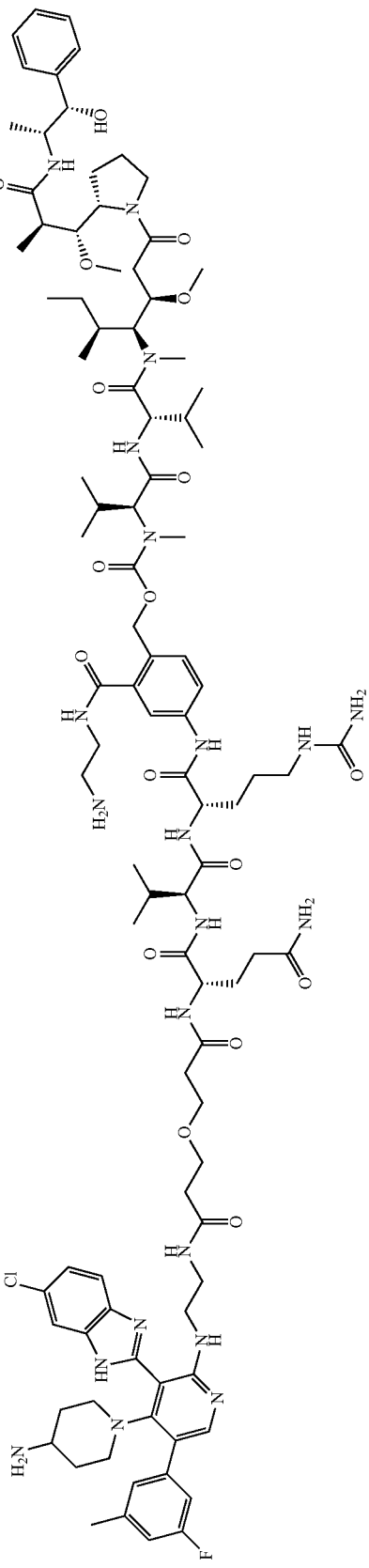 |

-continued

| Compound |
|---|
| (Compound 57)<br>(M + H)⁺ = 1958.1<br>{2-[(2-aminoethyl)carbamoyl]-4-[(2S)-2-[(2S)-2-[(2S)-2-{1-[(2-{[4-(4-aminopiperidin-1-yl)-5-(3-fluoro-5-methylphenyl)pyridin-2-yl]amino}ethyl)carbamoyl]-3,6,9,12-tetraoxapentadecan-15-amido}-3-(6-chloro-1H-1,3-benzodiazol-2-yl)propanamido]-5-(carbamoylamino)pentanamido]phenyl}methyl N-[(1S)-1-{[(1S)-1-{[(2S)-1-{[(3R,4S,5S)-1-{[(1S)-1-{[(2S)-2-{[(1S,2R)-2-{[(1S,2R)-1-hydroxy-1-phenylpropan-2-yl]carbamoyl}-1-methylpropyl]carbamoyl}pyrrolidin-1-yl]-3-methoxy-5-methyl-1-oxoheptan-4-yl](methyl)carbamoyl}-2-methylpropyl]carbamoyl}-2-methylpropyl]-N-methylcarbamate |

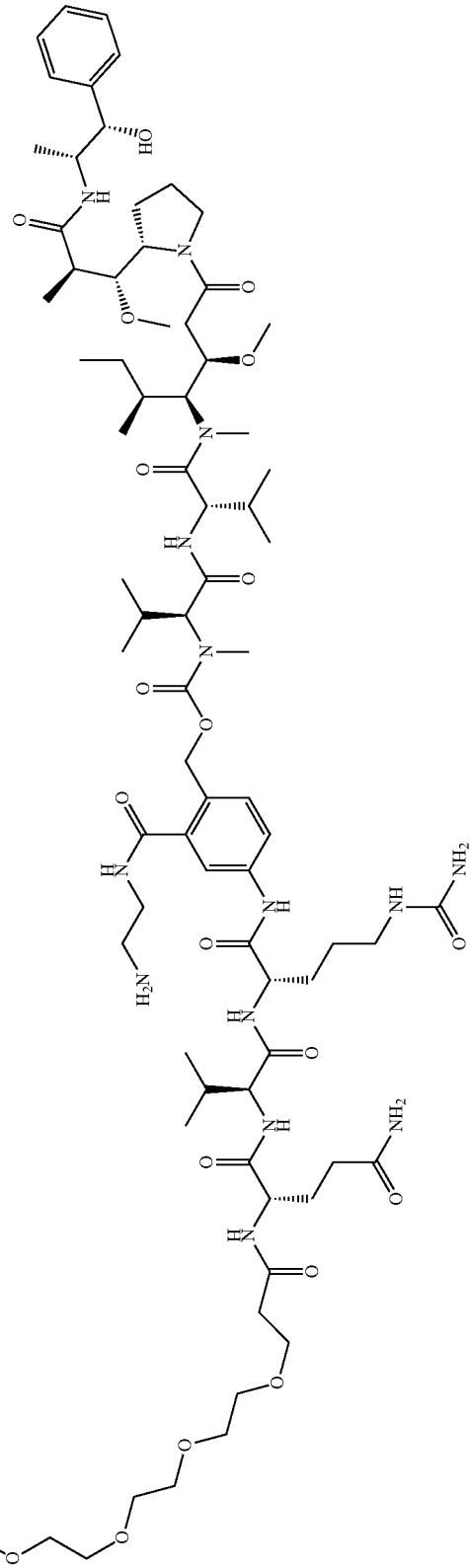

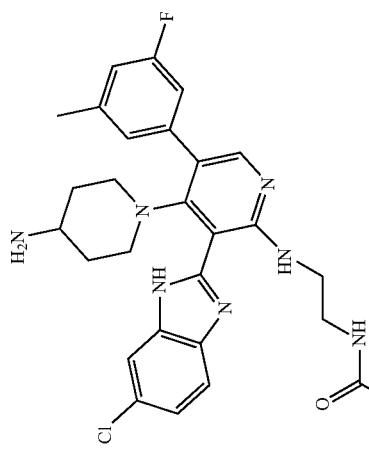

| Compound |
|---|
| (Compound 58)<br>(M + H)+ = 2090.1<br>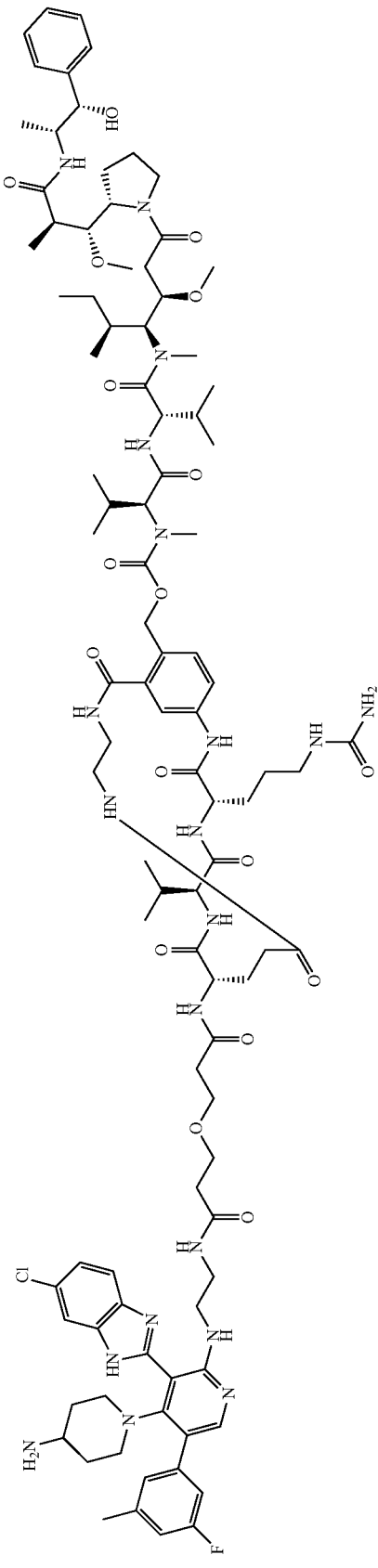<br>[(4S,7S,10S)-10-(3-{2-[(2S)-2-[[4-(4-aminopiperidin-1-yl)-3-(6-chloro-1H-1,3-benzodiazol-2-yl)-5-(3-fluoro-5-methylphenyl)pyridin-2-yl]amino]ethyl)carbamoyl]ethoxy}propanamido)-4-[3-(carbamoylamino)propyl]-3,6,9,13,18-pentaoxo-7-(propan-2-yl)-2,5,8,14,17-pentaazabicyclo[17.3.1]tricosa-1(23),19,21-trien-20-yl]methyl N-[(1S)-1-{[(3R,4S,5S)-1-[(2S)-2-{[(1S,2R)-2-{[(1S,2R)-1-hydroxy-1-phenylpropan-2-yl]carbamoyl}-2-methylpropyl]carbamoyl}-2-methylpropyl]carbamoyl]-1-methoxy-2-methylpentan-4-yl](methyl)carbamoyl}pyrrolidin-1-yl]-3-methoxy-5-methyl-1-oxoheptan-4-yl](methyl)carbamoyl]-2-methylpropyl]-N-methylcarbamate |
| (Compound 59)<br>(M + H)+ = 1941.0<br>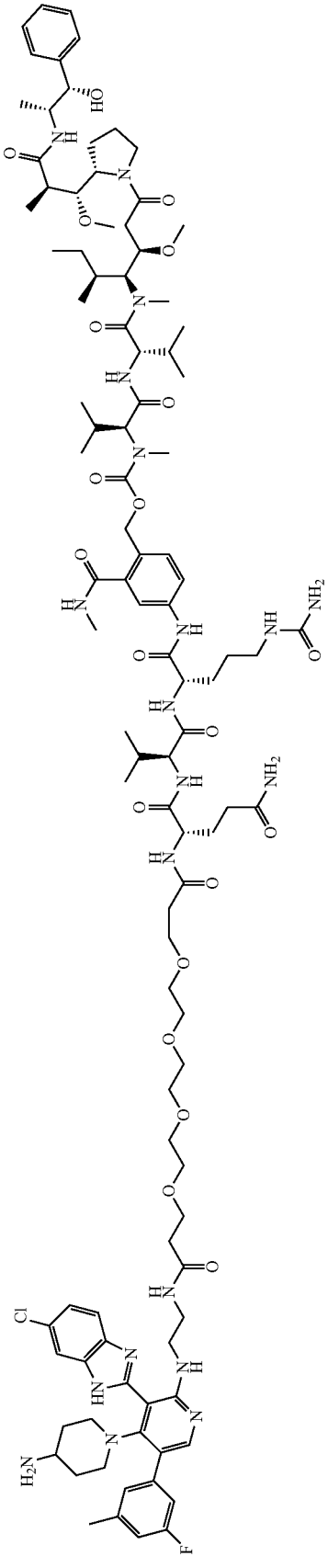<br>{4-[(2S)-2-[(2S)-2-{1-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]-3,6,9,12-tetraoxapentadecan-15-amido}-4-carbamoylbutanamido]-3-methylbutanamido]-5-(carbamoylamino)pentanamido]-2-(methylcarbamoyl)phenyl]methyl N-[(1S)-1-{[(3R,4S,5S)-1-[(2S)-2-{[(1R,2R)-2-{[(1S,2R)-1-hydroxy-1-phenylpropan-2-yl]carbamoyl}-2-methylpropyl]carbamoyl]-1-methoxy-2-methylpentan-4-yl](methyl)carbamoyl}pyrrolidin-1-yl]-3-methoxy-5-methyl-1-oxoheptan-4-yl](methyl)carbamoyl]-2-methylpropyl]-N-methylcarbamate |

-continued

| Compound |
|---|
| (Compound 60) $(M + H)^+ = 2060.1$ |

Example G. (2S,3S,4S,5R,6S)-6-{2-[(2S)-2-[(2S)-2-(3-{2-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]ethoxy}propanamido)-3-methylbutanamido]-5-(carbamoylamino)pentanamido]-5-[({[(1S)-1-1[(1S)-1-1 [(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl]-2-methylpropyl]carbamoyl}-2-methylpropyl](methyl)carbamoyl}oxy)methyl]phenoxy}-3,4,5-trihydroxyoxane-2-carboxylic acid (Compound 61)

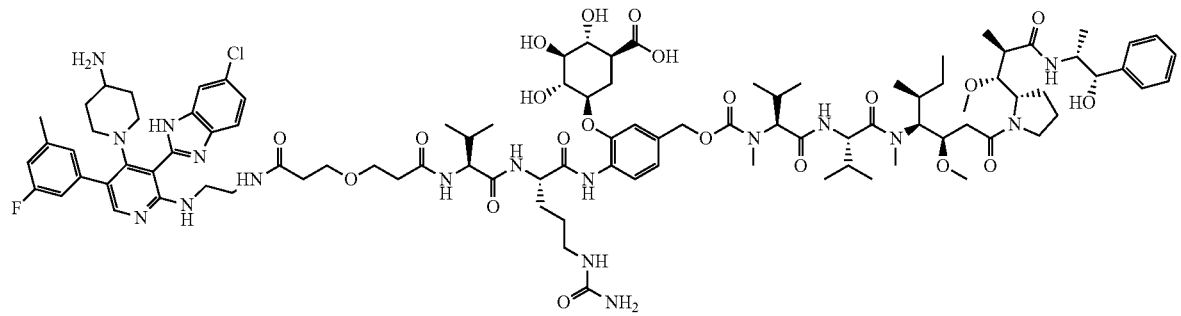 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCOCCC(=O)NCCNc2ncc(-c3cc(C)cc(F)c3)c(N3CCC(N)CC3)c2-c2nc3ccc(Cl)cc3[nH]2)C(C)C)c(O[C@@H]2C[C@H](C(=O)O)[C@@H](O)[C@H](O)[C@H]2O)c1)C(C)C]

Step G-1. preparation of (2S,3R,4S,5S,6S)-2-(5-formal-2-nitrophenoxy)-6-(methoxycarbonyl)tetrahydro-2H-pyran-3,4,5-triyl triacetate: a mixture of 3-hydroxy-4-nitrobenzaldehyde (2.334 g, 1 Eq, 13.97 mmol), (2R,3R,4S,5S,6S)-2-bromo-6-(methoxycarbonyl)tetrahydro-2H-pyran-3,4,5-triyl triacetate (16.64 g, 3.000 Eq, 41.90 mmol), and silver (I) oxide (25.9 g, 8.00 Eq, 112 mmol) in ACN (140 mL) was stirred at 25° C. for 24 hours in the dark. The mixture was filtered and the filtrate concentrated under reduced pressure. The crude product was purified by MPLC with the following conditions: Silica gel column 120 g, petroleum ether/ethyl acetate (PE/EtOAc) system, the ratio of EtOAc from 0% to 85% in 15 min, Flow rate: 70 mL/min; Wave Length: 254 nm. The collected fractions were combined and concentrated under vacuum to give (2S,3R,4S,5S,6S)-2-(5-formyl-2-nitrophenoxy)-6-(methoxycarbonyl)tetrahydro-2H-pyran-3,4,5-triyl triacetate (3.8 g, 56%). MS (M+H)$^+$=484.4.

Step G-2, preparation of (2S,3R,4S,5S,6S)-2-(2-amino-5-(hydroxymethyl)phenoxy)-6-(methoxycarbonyl)tetrahydro-2H-pyran-3,4,5-triyl triacetate: to a mixture of (2S,3R,4S,5S,6S)-2-(5-formyl-2-nitrophenoxy)-6-(methoxycarbonyl)tetrahydro-2H-pyran-3,4,5-triyl triacetate (3.8 g, 1 Eq, 7.9 mmol) and Triethylamine (0.16 g, 0.22 mL, 0.20 Eq, 1.6 mmol) in ethyl acetate (210 mL) in an inert atmosphere of nitrogen was added Pearlman's catalyst (85 mg, 0.10 Eq, 0.80 mmol). The reaction mixture was flushed with hydrogen three times, followed by flushing with hydrogen, and stirred for 24 hours at 25° C. under the pressure of H$_2$ gas. The reaction mixture was filtered through a diatomite cushion and the filtrate was concentrated under reduced pressure to give (2S,3R,4S,5S,6S)-2-(2-amino-5-(hydroxymethyl)phenoxy)-6-(methoxycarbonyl)tetrahydro-2Hpyran-3,4,5-triyl triacetate (2.7 g, 75%). MS (M+H)$^+$=456.4.

Step G-3, preparation of (2S,3R,4S,5S,6S)-2-(2-((S)-2-((S)-2-((tert-butoxycarbonyl)amino)-3-methylbutanamido)-5-ureidopentanamido)-5-(hydroxymethyl)phenoxy)-6-(methoxycarbonyl)tetrahydro-2H-pyran-3,4,5-triyl triacetate: to a mixture of (2S,3R,4S,5S,6S)-2-(2-amino-5-(hydroxymethyl)phenoxy)-6-(methoxycarbonyl)tetrahydro-2H-pyran-3,4,5-triyl triacetate (1.05 g, 1 Eq, 2.31 mmol), 2-Ethoxy-1-ethoxycarbonyl-1,2-dihydroquinoline (EEDQ) (685 mg, 1.20 Eq, 2.77 mmol) in DCM (10 mL) was added (S)-2-((S)-2-((tert-butoxycarbonyl)amino)-3-methylbutanamido)-5-ureidopentanoic acid (865 mg, 1.00 Eq, 2.31 mmol) at room temperature and the reaction mixture was stirred at 25° C. for 24 hours in the dark. The reaction mixture was concentrated under reduced pressure. The crude product was purified by MPLC with the following conditions: Silica gel column 120 g, PE/EtOAc system, the ratio of EtOAc from 0% to 85% in 15 min, Flow rate: 70 mL/min; Wave Length: 254 nm. The collected fractions were combined and concentrated under vacuum to give (2S,3R,4S,5S,6S)-2-(2-((S)-2-((S)-2-((tert-butoxycarbonyl)amino)-3-methylbutanamido)-5-ureidopentanamido)-5-(hydroxymethyl)phenoxy)-6-(methoxycarbonyl)tetrahydro-2H-pyran-3,4,5-triyl triacetate (1.36 g, 72.7%). MS (M+H)$^+$=812.2.

Step G-4, preparation of (2S,3R,4S,5S,6S)-2-(2-((S)-2-((S)-2-((tert-butoxycarbonyl)amino)-3-methylbutanamido)-5-ureidopentanamido)-5-((((4-nitrophenoxy)carbonyl)oxy)methyl)phenoxy)-6-(methoxycarbonyl)tetrahydro-2Hpyran-3,4,5-triyl triacetate: a mixture of (2S,3R,4S,5S,6S)-2-(2-((S)-2-((S)-2-((tert-butoxycarbonyl)amino)-3-methylbutanamido)-5-ureidopentanamido)-5-(hydroxymethyl)phenoxy)-6-(methoxycarbonyl)tetrahydro-2H-pyran-3,4,5-triyl triacetate (460 mg, 1 Eq, 567 μmol), Carbonicacid,bis(4-nitrophenyl)ester (260 mg, 1.51 Eq, 855 μmol), and N-ethyl-N-isopropylpropan-2-amine (150 mg, 2.05 Eq, 1.16 mmol) in tetrahydrofuran (THF) (4.6 mL) was stirred for 24 hours at room temperature. The reaction mixture was concentrated under reduced pressure. The crude product was purified by MPLC with the following conditions: Silica gel column 120 g, PE/EtOAc system, the ratio of EtOAc from 0% to 85% in 15 min, Flow rate: 70 mL/min; Wave Length: 254 nm. The collected fractions were combined and concentrated under vacuum to give (2S,3R,4S,5S,6S)-2-(2-((S)-2-((S)-2-((tert-butoxycarbonyl)amino)-3- methylbutanamido)-5-ureidopentanamido)-5-((((4-nitrophenoxy)carbonyl)oxy)methyl)phenoxy)-6-(methoxycarbonyl)tetrahydro-2H-pyran-3,4,5-triyl triacetate (400 mg, 72.3%). MS (M+H)⁺=977.1.

Step G-5, preparation of (2S,3R,4S,5S,6S)-2-(2-((S)-2-((S)-2-((tert-butoxycarbonyl)amino)-3-methylbutanamido)-5-ureidopentanamido)-5-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-6-(methoxycarbonyl)tetrahydro-2H-pyran-3,4,5-triyl triacetate: a mixture of (2S,3R,4S,5S,6S)-2-(2-((S)-2-((S)-2-((tert-butoxycarbonyl)amino)-3-methylbutanamido)-5-ureidopentanamido)-5-((((4-nitrophenoxy)carbonyl)oxy)methyl)phenoxy)-6-(methoxycarbonyl)tetrahydro-2H-pyran-3,4,5-triyl triacetate (170 mg, 1 Eq, 174 μmol), (S)—N-((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N,3-dimethyl-2-((S)-3-methyl-2-(methylamino)butanamido) butanamide (100 mg, 0.800 Eq, 139 μmol), 1H-benzo[d][1,2,3]triazol-1-ol (30 mg, 1.3 Eq, 0.22 mmol), and DIEA (70 mg, 94 μL, 3.1 Eq, 0.54 mmol) in DMF (1.7 mL) was stirred at 25° C. for 2 hours. The mixture was directly purified by MPLC with the following conditions: Column, WelFlash™, C18 120 g, Spherical 20-40 μm; Mobile phase, Water (0.05% NH·HO) and ACN (5% ACN to 5% ACN in 1 min, 30% ACN up to 98% in 6 min, 98% ACN to 98% in 3 min); Total flow rate, 70 mL/min; Detector, UV 254 nm. The collected fractions were combined and concentrated under vacuum to give (2S,3R,4S,5S,6S)-2-(2-((S)-2-((S)-2-((tert-butoxycarbonyl)amino)-3-methylbutanamido)-5-ureidopentanamido)-5-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-6-(methoxycarbonyl)tetrahydro-2H-pyran-3,4,5-triyl triacetate (80 mg, 30%). MS (M+H)⁺=1556.5.

Step G-6, preparation of (2S,3R,4S,5S,6S)-2-(2-((S)-2-((S)-2-amino-3-methylbutanamido)-5-ureidopentanamido)-5-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-6-(methoxycarbonyl)tetrahydro-2H-pyran-3,4,5-triyl triacetate: a mixture of (2S,3R,4S,5S,6S)-2-(2-((S)-2-((S)-2-((tert-butoxycarbonyl)amino)-3-methylbutanamido)-5-ureidopentanamido)-5-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-6-(methoxycarbonyl)tetrahydro-2H-pyran-3,4,5-triyl triacetate (76 mg, 1 Eq, 49 μmol) and TFA (0.5 mL) in DCM (0.5 mL) was stirred at 0° C. for 2 min. The mixture was adjusted to a pH 9.0 with DIEA and blown dry with nitrogen to give (2S,3R,4S,5S,6S)-2-(2-((S)-2-((S)-2-amino-3-methylbutanamido)-5-ureidopentanamido)-5-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-6-(methoxycarbonyl)tetrahydro-2H-pyran-3,4,5-triyl triacetate (60 mg, 84%). MS (M+H)⁺=1456.5. This material was used for the next step without further purification.

Step G-7, preparation of (2S,3R,4S,5S,6S)-2-(2-((2S,5S)-16-((4-(4-((tert-butoxycarbonyl)amino)piperidin-1-yl)-3-(6-chloro-1H-benzo[d]imidazol-2-yl)-5-(3-fluoro-5-methylphenyl)pyridin-2-yl)amino)-5-isopropyl-4,7,13-trioxo-2-(3-ureidopropyl)-10-oxa-3,6,14-triazahexadecanamido)-5-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-6-(methoxycarbonyl)tetrahydro-2H-pyran-3,4,5-triyl triacetate: a mixture of (2S,3R,4S,5S,6S)-2-(2-((S)-2-((S)-2-amino-3-methylbutanamido)-5-ureidopentanamido)-5-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-6-(methoxycarbonyl)tetrahydro-2H-pyran-3,4,5-triyl triacetate (60 mg, 1 Eq, 41 μmol), Pentafluorophenyldiphenylphosphinate (20 mg, 1.3 Eq, 52 μmol), 4-methylmorfolin (13 mg, 14 μL, 3.1 Eq, 0.13 mmol), and 3-(3-((2-((4-(4-((tert-butoxycarbonyl)amino)piperidin-1-yl)-3-(6-chloro-1H-benzo[d]imidazol-2-yl)-5-(3-fluoro-5-methylphenyl)pyridin-2-yl)amino)ethyl)amino)-3-oxopropoxy)propanoic acid (30 mg, 0.99 Eq, 41 μmol) in DMF (0.6 mL) was stirred for 2 hours at 25° C. The mixture was directly purified by MPLC with the following conditions: Column, WelFlash™, C18 120 g, Spherical 20-40 μm; Mobile phase, Water (0.05% NH·HO) and ACN (5% ACN to 5% ACN in 2 min, 30% ACN up to 98% in 12 min, 98% ACN to 98% in 1 min); Total flow rate, 70 mL/min; Detector, UV 220 nm. The collected fractions were combined and concentrated under vacuum to give (2S,3R,4S,5S,6S)-2-(2-((2S,5S)-16-((4-(4-((tert-butoxycarbonyl)amino)piperidin-1-yl)-3-(6-chloro-1H-benzo[d]imidazol-2-yl)-5-(3-fluoro-5-methylphenyl)pyridin-2-yl)amino)-5-isopropyl-4,7,13-trioxo-2-(3-ureidopropyl)-10-oxa-3,6,14-triazahexadecanamido)-5-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-6-(methoxycarbonyl)tetrahydro-2H-pyran-3,4,5-triyl triacetate (64 mg, 71%). MS (M/2+H)⁺=1088.6.

Step G-8, preparation of (2S,3S,4S,5R,6S)-6-(2-((2S,5S)-16-((4-(4-((tertbutoxycarbonyl)amino)piperidin-1-yl)-3-(6-chloro-1Hbenzo[d]imidazol-2-yl)-5-(3-fluoro-5-methylphenyl)pyridin-2-yl)amino)-5-isopropyl-4,7,13-trioxo-2-(3-ureidopropyl)-10-oxa-3,6,14-triazahexadecanamido)-5-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-3,4,5-trihydroxytetrahydro-2H-pyran-2-carboxylic acid: a mixture of (2S,3R,4S,5S,6S)-2-(2-((2S,5S)-16-((4-(4-((tert-butoxycarbonyl)amino)piperidin-1-yl)-3-(6-chloro-1Hbenzo[d]imidazol-2-yl)-5-(3-fluoro-5-methylphenyl)pyridin-2-yl)amino)-5-isopropyl-4,7,13-trioxo-2-(3-ureidopropyl)-10-oxa-3,6,14-triazahexadecanamido)-5-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8- diisopropyl-4,10-dimethyl-3,6,9-trioxo-2,13-dioxa-4,7,10-triazatetradecyl)phenoxy)-6-(methoxy carbonyl)tetrahydro-2H-pyran-3,4,5-triyl triacetate (64 mg, 1 Eq, 29 μmol), and lithium hydroxide (4 mg, 6 Eq, 0.2 mmol) in THF (0.6 mL) and $H_2O$ (0.6 mL) was stirred for 2 hours at 25° C. The residue was diluted with water (10 ml), then adjusted to a pH 6-7 with AcOH (1 M). The resulting solution was extracted with ethyl acetate (3×2 mL). The organic layers were dried over anhydrous sodium sulfate and concentrated under vacuum to give (2S,3S,4S,5R,6S)-6-(2-((2S,5S)-16-((4-(4-((tert-butoxycarbonyl)amino)piperidin-1-yl)-3-(6-chloro-1H-benzo[d]imidazol-2-yl)-5-(3-fluoro-5-methylphenyl)pyridin-2-yl)amino)-5-isopropyl-4,7,13-trioxo-2-(3-ureidopropyl)-10-oxa-3,6,14-triazahexadecanamido)-5-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-3,4,5-trihydroxytetrahydro-2H-pyran-2-carboxylic acid (50 mg, 15 μmol, 52%, 62% Purity). MS $(M/2+H)^+=1019.2$. This material was used for the next step without further purification.

Step G-9, preparation of (2S,3S,4S,5R,6S)-6-{2-[(2S)-2-[(2S)-2-(3-{2-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]ethoxy}propanamido)-3-methylbutanamido]-5-(carbamoylamino)pentanamido]-5-[({[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl](methyl)carbamoyl}oxy)methyl]phenoxy}-3,4,5-trihydroxyoxane-2-carboxylic acid: a mixture of (2S,3S,4S,5R,6S)-6-(2-((2S,5S)-16-((4-(4-((tert-butoxycarbonyl)amino)piperidin-1-yl)-3-(6-chloro-1Hbenzo[d]imidazol-2-yl)-5-(3-fluoro-5-methylphenyl)pyridin-2-yl)amino)-5-isopropyl-4,7,13-trioxo-2-(3-ureidopropyl)-10-oxa-3,6,14-triazahexadecanamido)-5-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-3,4,5-trihydroxytetrahydro-2H-pyran-2-carboxylic acid (50 mg, 52% Wt, 1 Eq, 13 μmol) and TFA (0.2 mL) in DCM (1.0 mL) was stirred at 0° C. for 30 min. The crude product was purified by Prep-HPLC with the following conditions: Column: SunFire prep OBD 19*150 mm 5 um; Mobile Phase A: Water (0.05% NH·HO); Mobile Phase B: ACN; Gradient: 25% B to 65% B in 8 min; Flow rate: 20 mL/min; Wave Length: 220 nm. The collected fractions were dried by lyophilization to give (2S,3S,4S,5R,6S)-6-{2-[(2S)-2-[(2S)-2-(3-{2-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]ethoxy}propanamido)-3-methylbutanamido]-5-(carbamoylamino)pentanamido]-5-[({[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl](methyl)carbamoyl}oxy)methyl]phenoxy}-3,4,5-trihydroxyoxane-2-carboxylic acid (8.1 mg, 33%). MS $(M+H)^+=1936.0$.

The following conjugates were prepared similarly to Example G with appropriate substituting reagents and substrates at different steps and they may require additional functional group modifications via well-known chemistry with appropriate reagents.

| Compound |
|---|
| (2S,3S,4S,5R,6S)-6-{2-[(2S)-2-[(2S)-2-{1-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]-3,6,9,12-tetraoxapentadecan-15-amido}-3-methylbutanamido]-5-(carbamoylamino)pentanamido]-5-{({[(1S)-1-{[(1S)-1-{[(3R,4S,5S)-1-[(2S)-2-{[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl](methyl)carbamoyl}oxy)methyl]phenoxy}-3,4,5-trihydroxyoxane-2-carboxylic acid |

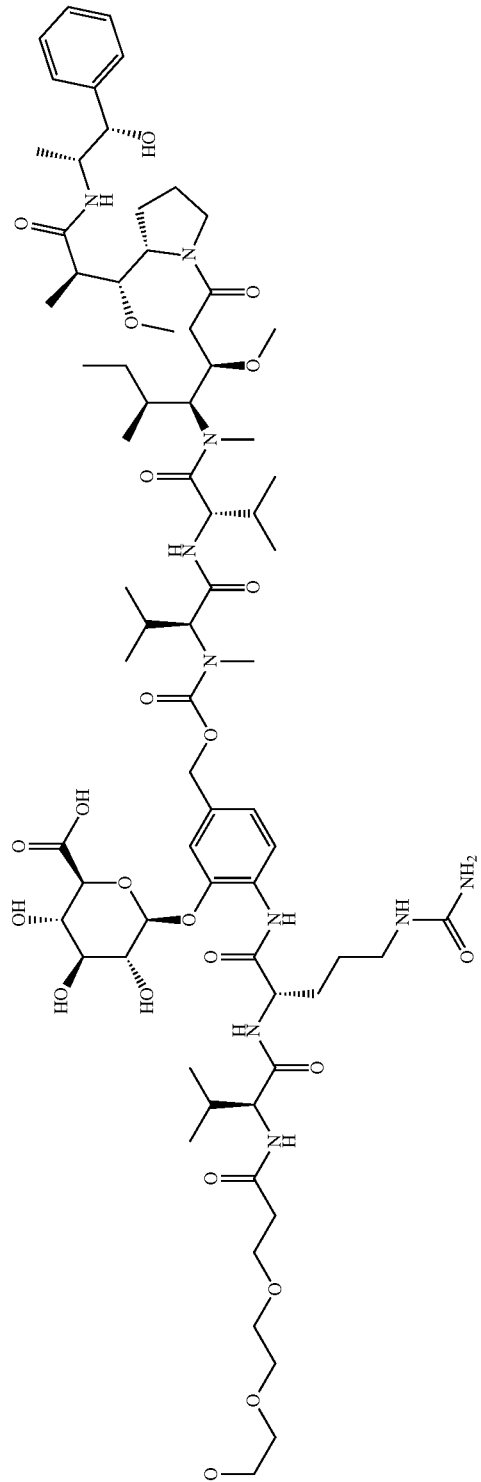
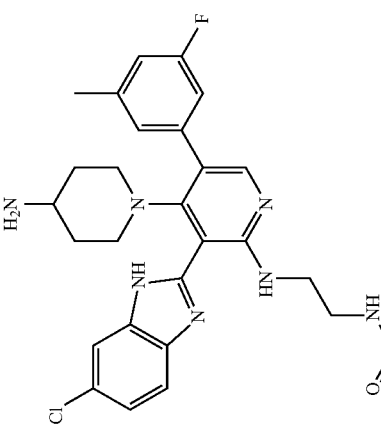

-continued

Compound (Compound 62)
(M + H)⁺ = 2068.07

(2S,3S,4S,5R,6S)-6-{2-[(2S)-2-[(2S)-2-{5-[2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]pentanamido}-3-methylbutanamido]-5-(carbamoylamino)pentanamido]-5-[({[(1S)-1-{[(3R,4S,5S)-1-{(2S)-2-[(1R,2R)-2-{[(1S,2R)-1-hydroxy-1-phenylpropan-2-yl]carbamoyl}-[[(1S,2R)-2-methoxy-2-methylpropyl]carbamoyl]-2-methylpropyl](methyl)carbamoyl}-2-methylpropyl](methyl)carbamoyl]oxy)methyl]phenoxy}-3,4,5-trihydroxyoxane-2-carboxylic acid

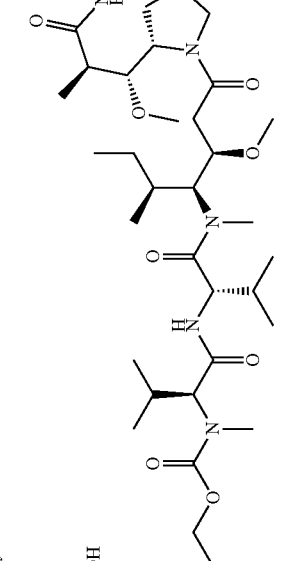

-continued

| Compound |
|---|
| (Compound 63)<br>(M + H)⁺ = 1920.2 |
| (2S,3S,4S,5R,6S)-6-(2-{1-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]-3,6,9,12-tetraoxapentadecan-15-amido}-5-[({[(1S)-1-{[(1S)-1-{[(3R,4S,5S)-1-{(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl[(methyl)carbamoyl](methyl)carbamoyl]-2-methylpropyl}(methyl)carbamoyl]oxy)methyl]phenoxy)-3,4,5-trihydroxyoxane-2-carboxylic acid |

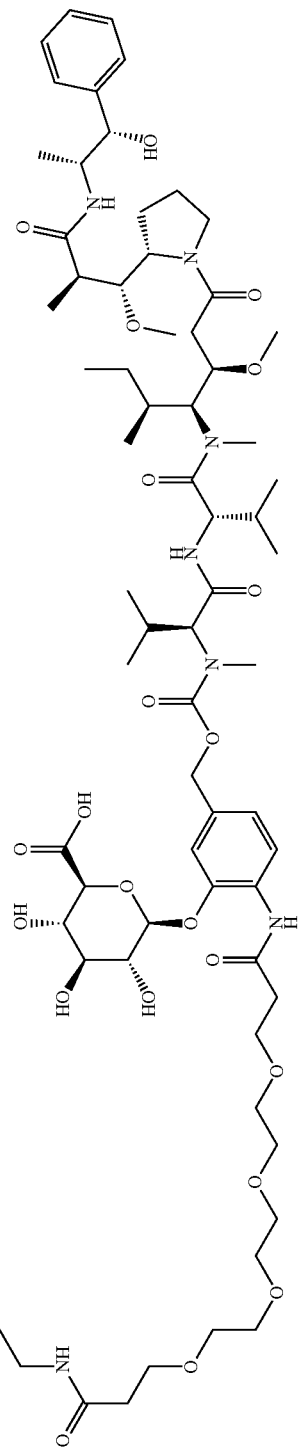

-continued

| Compound |
|---|
| (Compound 64)<br>(M/2 + H)⁺ = 1811.9<br>(2S,3S,4S,5R,6S)-6-{2-[(2S)-2-[(2S)-2-{(2S)-2-{3-{2-{(2S)-2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]ethoxy}propanamido]-3-methylbutanamido]-5-{[{(10S,23S)-10-ethyl-18-fluoro-10-hydroxy-19-methyl-5,9-dioxo-4,15-diazahexacyclo[14.7.1.0²,¹⁴.0⁴,¹³.0⁶,¹¹.0²⁰,²⁴]tetracosa-1,6(11),12,14,16,18,20(24)-heptaen-23-yl]carbamoyl}oxy)methyl]phenoxy}-3,4,5-trihydroxyoxane-2-carboxylic acid |
| (Compound 65)<br>(M + H)⁺ = 1566.6<br>(2R)-2-[2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]-2-[3-(2-{[(1S)-1-{[(1S)-1-{[(1S)-1-({4-[({[(1S)-1-({(1S)-1-{[(3R,4S,5S)-1-{(2S)-2-{[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl](methyl)carbamoyl}-2-methylpropyl]carbamoyl}ethoxy)phenyl](methyl)carbamoyl]oxy}methyl)phenyl]carbamoyl}-2-[{(2S,3R,4S,5S,6R)-3,4,5-trihydroxy-6-(hydroxymethyl)oxan-2-yl]oxy}methyl]-2-{[(1S,2R)-2-{[(1S,2R)-2-methoxy-2-methylethyl](methyl)carbamoyl]oxy}methyl]carbamoyl]ethyl]carbamoyl]oxan-2-yl]oxy}phenyl]carbamoyl}ethyl]carbamoyl}ethyl)propanamido]ethane-1-sulfonic acid |

-continued

Compound (Compound 66)
(M + H)⁺ = 1986.0

(4S)-4-(3-{2-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]ethoxy}propanamido)-4-{[(1S)-1-{[(1S)-1-({4-[({(1S)-1-[({(1S)-1-{[(3R,4S,5S)-1-[(2S)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl](methyl)carbamoyl]oxy}methyl)-2-{[(2S,3R,4S,5S,6R)-3,4,5-trihydroxy-6-(hydroxymethyl)oxan-2-yl]oxy}phenyl]carbamoyl}ethyl](methyl)carbamoyl}-2-methylpropyl]carbamoyl}butanoic acid

| Compound | |
|---|---|
| (Compound 67)<br>(M + H)⁺ = 1964.0<br>(2S,3S,4S,5R,6S)-6-{2-[(2S)-2-[(2S)-2-[(2S)-2-(3-{2-[(2-{[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]ethoxy}ethoxy)-3-methylbutanamido]-5-(carbamoylamino)pentanamido]-5-[({[(10S,23S)-10-ethyl-18-fluoro-10-hydroxy-19-methyl-5,9-dioxo-8-oxa-4,15-diazahexacyclo[14.7.1.0²,¹⁴.0⁴,¹³.0⁶,¹¹.0²⁰,²⁴]tetracosa-1,6(11),12,14,16,18,20(24)-heptaen-23-yl]carbamoyl}oxy)methyl]phenoxy}-3,4,5-trihydroxyoxane-2-carboxylic acid | 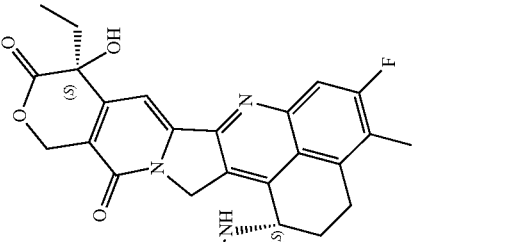 |

-continued
Compound
(Compound 126)
(M + H)+ = 1652.6
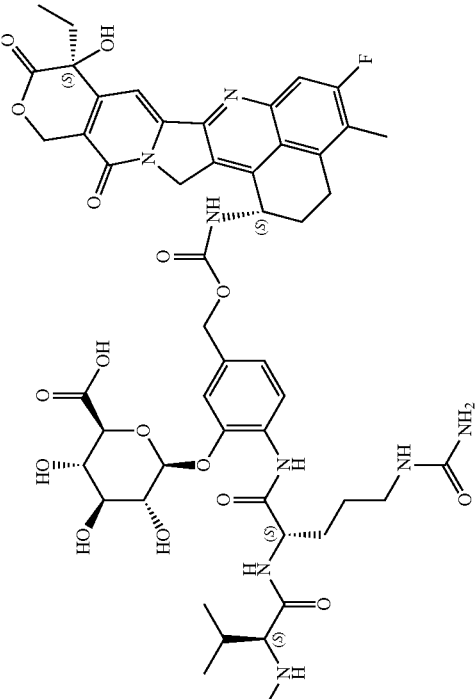
(2S,3S,4S,5R,6S)-6-{2-[(2S)-2-[(2S)-2-{1-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]-3,6,9,12-tetraoxapentadecan-15-amido}-3-methylbutanamido]-5-[({[(10S,23S)-10-ethyl-18-fluoro-10-hydroxy-19-methyl-5,9-dioxo-8-oxa-4,15-diazahexacyclo[14.7.1.0²,¹⁴.0⁴,¹³.0⁶,¹¹.0²⁰,²⁴]tetracosa-1,6(11),12,14,16,18,20(24)-heptaen-23-yl]carbamoyl}oxy)methyl]phenoxy}-3,4,5-trihydroxyoxane-2-carboxylic acid

| Compound |
|---|
| -continued |
| (Compound 127)<br>(M + H)+ = 1784.7<br>(2S,3S,4S,5R,6S)-6-[(((S)-1-[N-(S)-1-{[(1S,2R)-4-[(S)-2-{(1R,2R)-2-[N-(1R,2S)-2-hydroxy-1-methyl-2-phenylethylcarbamoyl]-1-methoxypropyl}-1-pyrrolidinyl]-1-[(S)-1-methylpropyl]-2-methoxy-4-oxobutyl]-N-methylcarbamoyl]-2-methylpropyl}(methyl)(aminocarbonyloxy)]methyl)-2-[(S)-2-[3-(2-{2-[4-(4-amino-1-piperidyl)-3-(6-chloro-1H-1,3-benzimidazol-2-yl)-5-(3-fluoro-5-methylphenyl)amino]phenoxy}-5-ureidovalerylamino]-3-methylbutyrylamino]ethoxy)propionylamino]ethylamino]ethoxy)propionylamino}-5-ureidovalerylamino]ethoxy)propionylamino]ethylamino]-2-pyridyl)-2-tolyl)-3,4,5-trihydroxytetrahydro-2H-pyran-2-carboxylic acid |
| (Compound 128)<br>(M + H)+ = 1906.9<br>(2S,3S,4S,5R,6S)-6-[5-({[(S)-1-[N-(S)-1-{[(1S,2R)-4-[(S)-2-{(1R,2R)-2-[N-(1R,2S)-2-hydroxy-1-methyl-2-phenylethylcarbamoyl]-1-methoxypropyl}-1-pyrrolidinyl]-1-[(S)-1-methylpropyl]-2-methoxy-4-oxobutyl]-N-methylcarbamoyl]-2-methylpropyl}(methyl)(aminocarbonyloxy)]methyl)-2-[(S)-2-[3-(2-{2-[2-[4-(4-amino-1-piperidyl)-3-(6-chloro-1H-1,3-benzimidazol-2-yl)-5-(3-fluoro-5-methylphenyl)amino]phenoxy]ethoxy]ethoxy]ethylamino]-3-methylbutyrylamino]-5-ureidovalerylamino]-2-pyridyl)amino]-3-methylbutyrylamino]-5-ureidovalerylamino]-2-pyridylamino]phenoxy}-5-ureidovalerylamino)ethoxy]ethoxy]ethylamino]-2-pyridylamino]-5-methylbutyrylamino)propionylamino]-3-methylbutyrylamino]ethoxy)propionylamino]ethylamino]ethoxy)ethoxy)ethoxy)ethylamino]-2-pyridylamino]-5-methylbutyrylamino)propionylamino]-3-methylbutyrylamino)ethoxy]ethoxy]ethylamino]-2-pyridylamino]-5-methylbutyrylamino)propionylamino]-3-methylbutyrylamino]ethoxy)propionylamino]ethylamino]ethoxy]ethoxy]ethoxy]ethylamino]-2-pyridylamino]-5-methylbutyrylamino)propionylamino]-3-methylbutyrylamino]-3,4,5-trihydroxytetrahydro-2H-pyran-2-carboxylic acid |

| Compound |
|---|
| (Compound 129)<br>(M + H)⁺ = 2039.0<br>(2S,3S,4S,5R,6S)-6-[5-{[{(S)-1-[N-(S)-1-{[(1S,2R)-4-[(S)-2-{[(1R,2R)-2-[N-(1R,2S)-2-hydroxy-1-methyl-2-phenylethylcarbamoyl]-1-pyrrolidinyl]-1-(S)-1-methylpropyl]-2-methoxy-4-oxobutyl]-N-methylpropylcarbamoyl}-2-methylpropyl](methyl)(aminocarbonyloxy)methyl)-2-[(S)-2-[(S)-2-[3-(2-{2-[4-(4-amino-1-piperidyl)-3-(6-chloro-1H-1,3-benzimidazol-2-yl)-5-(3-fluoro-5-tolyl)-2-pyridylamino]ethylamino}ethoxy)propionylamino]-3-methylbutyrylamino]phenoxy]-3,4,5-trihydroxytetrahydro-2H-pyran-2-carboxylic acid |
| (Compound 130)<br>(M + H)⁺ = 1820.9<br>1-(S)-1-[N-(S)-1-{[(1S,2R)-4-[(S)-2-{[(1R,2R)-2-[N-(1R,2S)-2-hydroxy-1-methyl-2-phenylethylcarbamoyl]-1-pyrrolidinyl]-1-(S)-1-methylpropyl]-2-methoxy-4-oxobutyl]-N-methylcarbamoyl}-2-methylpropylcarbamoyl]-2-methylpropyl {3-[(2S,3R,4S,5S,6R)-3,4,5-trihydroxy-6-(hydroxymethyl)tetrahydro-2H-pyran-2-yloxy]-4-[(S)-2-[(S)-2-[3-(2-{N-2-[4-(4-amino-1-piperidyl)-3-(6-chloro-1H-1,3-benzimidazol-2-yl)-5-(3-fluoro-5-tolyl)-2-pyridylamino]ethoxy)propionylamino]ethoxy]propionylamino]-3-methylbutyrylcarbamoyl]ethoxy)propionylamino]-3-methylbutyrylamino]phenyl}methanecarbamate |

-continued

| Compound |
|---|
| (Compound 131)<br>(M + H)⁺ = 1834.9<br><br>(2S,3S,4S,5R)-6-[5-({[(S)-1-[N-(S)-1-{[(1S,2R)-4-[(S)-2-{[(1R,2R)-2-[N-(1R,2S)-2-[N-(1R,2S)-2-hydroxy-1-methyl-2-phenylethylcarbamoyl]-1-methylpropyl]-1-methoxypropyl]-1-pyrrolidinyl]-1-[(S)-1-methylpropyl]-2-methoxy-4-oxobutyl]-N-methylcarbamoyl]-2-methylpropyl]carbamoyl]-2-methylpropyl](aminocarbonyloxy)}methyl)-2-[(S)-2-[(S)-2-[3-(2-{[N-2-[4-(4-amino-1-piperidyl)-3-(6-chloro-1H-1,3-benzimidazol-2-yl)-5-(3-fluoro-5-tolyl)-2-pyridylamino]ethylcarbamoyl}ethoxy)propionylamino]-5-ureidovalerylamino]phenoxy]-3,4,5-trihydroxytetrahydro-2H-pyran-2-carboxylic acid |

-continued

Compound (Compound 132)
(M + H)⁺ = 1935.2

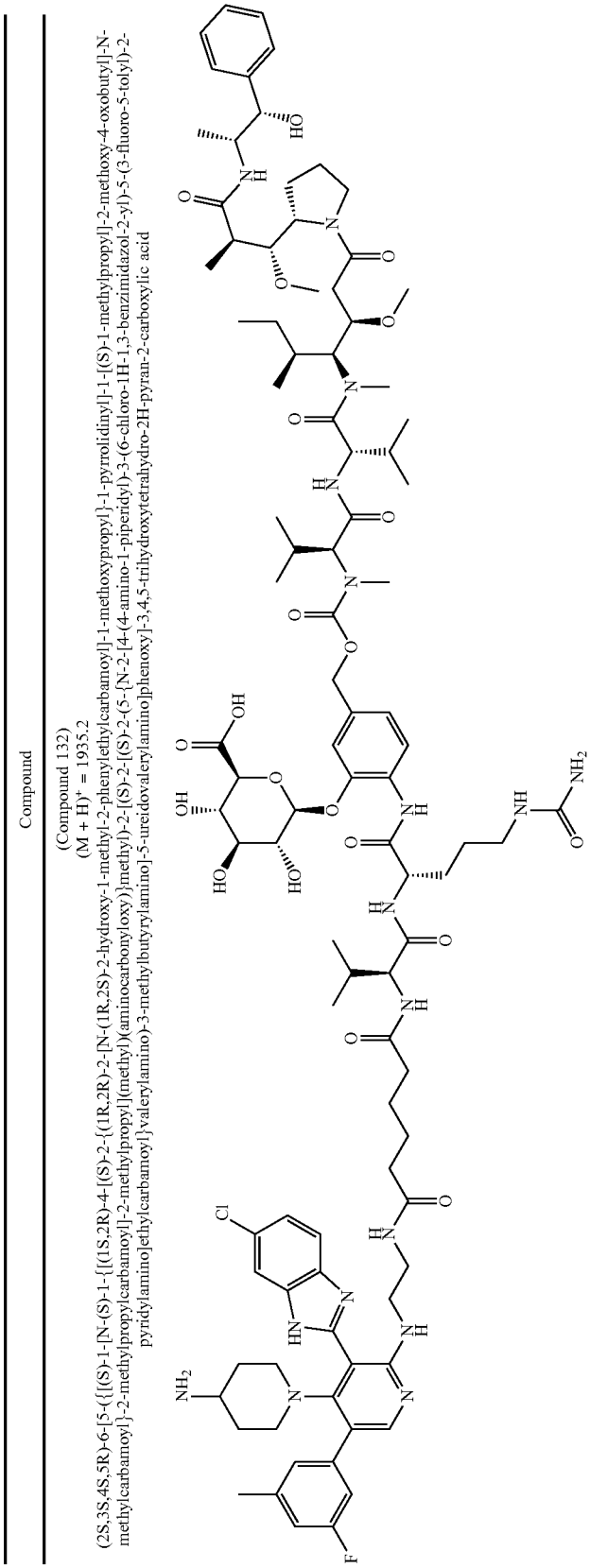

(2S,3S,4S,5R)-6-[5-({[(S)-1-[N-(S)-1-{[(1S,2R)-4-[(S)-2-{[(1R,2R)-2-[N-(1R,2S)-2-hydroxy-1-methyl-2-phenylethylcarbamoyl]-1-methylpropyl]-2-methoxy-4-oxobutyl]-N-methylcarbamoyl]-2-methylpropyl]-2-methoxyethylcarbamoyl]-1-pyrrolidinyl]-1-[(S)-1-methylpropyl]-2-methoxyethylcarbamoyl)-N-methyl]carbamoyl}-2-methylpropyl](methyl)(aminocarbonyloxy)]methyl)-2-[(S)-2-[(S)-2-(5-{N-2-[4-(4-amino-1-piperidyl)-3-(6-chloro-1H-1,3-benzimidazol-2-yl)-5-(3-fluoro-5-tolyl)-2-pyridyl]aminoethylcarbamoyl}valerylamino)-5-methylbutyrrylamino]phenoxy]-3,4,5-trihydroxytetrahydro-2H-pyran-2-carboxylic acid -continued

| Compound |
|---|
| (Compound 133)<br>(M + H)⁺ = 1919.0 |

1-(S)-1-[N-(S)-1-{[(1S,2R)-4-[(S)-2-{(1R,2R)-2-[N-(1R,2S)-2-hydroxy-1-methyl-2-phenylethylcarbamoyl]-1-[(S)-1-methylpropyl]-2-methoxy-4-oxobutyl]-N-methylcarbamoyl]-1-[(S)-1-methylpropyl]-1-pyrrolidinyl]-1-[(S)-1-methylpropyl]-2-methoxy-1-methyl-2-phenylethylcarbamoyl]-2-methoxy-1-methylpropyl 1-methyl {3-[(2S,3R,4S,5S,6R)-3,4,5-trihydroxy-6-(hydroxymethyl)tetrahydro-2H-pyran-2-yloxy]-4-[(S)-2-[3-(2-{[S)-2-[3-{2-{N-2-[4-(4-amino-1-piperidyl)-3-(6-chloro-1H-1,3-benzimidazol-2-yl)-5-(3-fluoro-5-tolyl)-2-pyridylamino]ethoxy}propionylamino]-3-methylbutyrylamino]-5-ureidovalerylamino]phenyl}methanecarbamate -continued

| Compound |
|---|
| (Compound 134)<br>(M + H)⁺ = 1921.0<br>(S)-4-[N-(S)-1-[N-(S)-1-[N-4-({[(S)-1-[N-(S)-1-{[(1S,2R)-4-{(S)-2-{(1R,2R)-2-[N-(1R,2S)-2-[N-(1R,2S)-2-hydroxy-1-methyl-2-phenylethyl]carbamoyl]-1-pyrrolidinyl]-1-methoxypropyl]-1-[(S)-1-methylpropyl]-2-methoxy-4-oxobutyl]-2-methylpropyl]carbamoyl]-2-methylpropyl](methyl)(aminocarbonyloxy)}methyl)-2-[(2S,3R,4S,5S,6R)-3,4,5-trihydroxy-6-(hydroxymethyl)tetrahydro-2H-pyran-2-yloxy]phenylcarbamoyl]-4-ureidobutyl]carbamoyl]-2-methylpropyl]carbamoyl]-4-[3-(2-{N-2-[4-(4-amino-1-piperidyl)-3-(6-chloro-1H-1,3-benzimidazol-2-yl)-5-(3-fluoro-5-tolyl)-2-pyridylamino]ethylcarbamoyl]ethoxy)propionylamino]butyric acid |

-continued

| Compound |
|---|
| (Compound 135)<br>(M + H)⁺ = 2050.0<br><br>1-(S)-1-[N-(S)-1-{[(1S,2R)-4-[(S)-2-{[(1R,2R)-2-[N-(1R,2S)-2-hydroxy-1-methyl-2-phenylethyl]carbamoyl]-1-pyrrolidinyl]-1-methoxypropyl]-1-(S)-1-methylpropyl]-2-methoxy-4-oxobutyl]-N-methylcarbamoyl}-2-methylpropyl]carbamoyl]-2-methylpropyl 1-methyl {3-[(2S,3R,4S,5S,6R)-3,4,5-trihydroxy-6-(hydroxymethyl)tetrahydro-2H-pyran-2-yloxy]-4-[(S)-2-[(S)-2-[(N-2-[4-(4-amino-1-piperidyl)-3-(6-chloro-1H-1,3-benzimidazol-2-yl)-5-(3-fluoro-5-tolyl)-2-pyridylamino]-5-methylbutyrylamino]-3-methylbutyrylamino]-4-carbamoylamino]ethoxy)propionylamino]-4-carbamoylamino]ethyl]carbamoyl]ethoxy)propionylamino]-2-pyridylamino]phenyl}methanecarbamate |
| (Compound 136)<br>(M + H)⁺ = 2049.0<br><br>(2S,3S,4S,5R,6S)-6-[5-{[[(S)-1-[N-(S)-1-{[(1S,2R)-4-[(S)-2-{[(1R,2R)-2-[N-(1R,2S)-2-hydroxy-1-methyl-2-phenylethyl]carbamoyl]-1-pyrrolidinyl]-1-methoxypropyl]-1-(S)-1-methylpropyl]-2-methoxy-4-oxobutyl]-N-methylcarbamoyl]-2-methylpropyl]carbamoyl]-2-methylpropyl](methyl)(aminocarbonyloxy)]methyl)-2-[(S)-2-{(S)-2-[3-[2-(S)-2-{3-[2-{N-2-[4-(4-amino-1-piperidyl)-3-(6-chloro-1H-1,3-benzimidazol-2-yl)-5-(3-fluoro-5-tolyl)-2-pyridylamino]propionylamino]-5-methylbutyrylamino]-3-methylbutyrylamino]phenoxy]-3,4,5-trihydroxytetrahydro-2H-pyran-2-carboxylic acid |

-continued

| Compound |
|---|
| (Compound 137)<br>(M + H)⁺ = 1979.0<br>(2S,3S,4S,5R,6S)-6-[5-({[(S)-1-[N-(S)-1-{[(1S,2R)-4-[(S)-2-{[(1R,2R)-2-[N-(1R,2S)-2-hydroxy-1-methyl-2-phenylethylcarbamoyl]-1-methoxypropyl]-1-pyrrolidinyl]-1-[(S)-1-methylpropyl]-2-methoxy-4-oxobutyl]-N-methylcarbamoyl]-2-methylpropyl]-2-methylpropyl](methyl)(aminocarbonyloxy)]methyl}-2-methylpropyl](methyl)carbamoyl]-2-methylpropyl}-2-[(S)-2-[(S)-2-(11-{N-2-[4-(4-amino-1-piperidyl)-3-(6-chloro-1H-1,3-benzimidazol-2-yl)-5-(3-fluoro-5-tolyl)-2-pyridylamino]ethylcarbamoyl}-3,6,9-trioxaundecyl carbonylamino]-5-methylbutyrylamino]-5-ureidovalerylamino)phenoxy]-3,4,5-trihydroxytetrahydro-2H-pyran-2-carboxylic acid |
| (Compound 138)<br>(M + H)⁺ = 2023.0<br>(2S,3S,4S,5R,6S)-6-[5-({[(S)-1-[N-(S)-1-{[(1S,2R)-4-[(S)-2-{[(1R,2R)-2-[N-(1R,2S)-2-hydroxy-1-methyl-2-phenylethylcarbamoyl]-1-methoxypropyl]-1-pyrrolidinyl]-1-[(S)-1-methylpropyl]-2-methoxy-4-oxobutyl]-N-methylcarbamoyl]-2-methylpropyl](methyl)(aminocarbonyloxy)]methyl}-2-methylpropyl](methyl)carbamoyl]-2-methylpropyl}-2-[(S)-2-[(S)-2-[3-(2-{[N-2-[3-(6-chloro-1H-1,3-benzimidazol-2-yl)-5-(3-fluoro-5-tolyl)-4-(4-hydroxy-1-piperidyl)-2-pyridylamino]ethoxy}propionylamino)propionylamino]-3-methylbutyrylamino]-3-methylbutyrylamino]phenoxy]-3,4,5-trihydroxytetrahydro-2H-pyran-2-carboxylic acid |

-continued

| Compound |
|---|
| (Compound 139)<br>(M + H)⁺ = 1849.9<br>(2S,3S,4S,5R,6S)-6-[5-({[(S)-1-[N-(S)-1-{[(1S,2R)-2-[(S)-2-[N-(1R,2R)-2-[N-(1R,2S)-2-{(1R,2S)-2-hydroxy-1-methyl-2-phenylethylcarbamoyl]-1-pyrrolidinyl]-1-(S)-1-methylpropyl)-2-methoxy-4-oxobutyl]-N-methylcarbamoyl]-2-methylpropyl](methyl)(aminocarbonyloxy)}methyl)-2-[(S)-2-[(S)-2-{4-[(N-2-[4-(4-amino-1-piperidyl)-3-(6-chloro-1H-1,3-benzimidazol-2-yl)-5-(3-fluoro-5-tolyl)-2-pyridyl]amino]propionylamino]phenoxy]-3,4,5-trihydroxytetrahydro-2H-pyran-2-carboxylic acid |
| (Compound 140)<br>(M + H)⁺ = 1889.9<br>(2S,3S,4S,5R,6S)-6-[5-({[(S)-1-[N-(S)-1-{[(1S,2R)-2-[(S)-2-[N-(1R,2R)-2-[N-(1R,2S)-2-{(1R,2S)-2-hydroxy-1-methyl-2-phenylethylcarbamoyl]-1-pyrrolidinyl]-1-(S)-1-methylpropyl)-2-methoxy-4-oxobutyl]-N-methylcarbamoyl]-2-methylpropyl](methyl)(aminocarbonyloxy)}methyl)-2-[(S)-2-{4-[((N-2-[4-(4-amino-1-piperidyl)-3-(6-chloro-1H-1,3-benzimidazol-2-yl)-5-(3-fluoro-5-tolyl)-2-pyridylamino]butyrylamino]-5-ureidovaleryl)amino]phenoxy]-3,4,5-trihydroxytetrahydro-2H-pyran-2-carboxylic acid |

-continued

| Compound |
|---|
| (Compound 141)<br>(M + H)⁺ = 1976.3<br>(2S,3S,4S,5R,6S)-6-[5-{[{(S)-1-[N-(S)-1-{[(1S,2R)-4-[(S)-2-{(1R,2R)-2-[N-(1R,2S)-2-[N-(1R,2S)-2-hydroxy-1-methyl-2-phenylethylcarbamoyl]-1-methoxypropyl]-1-pyrrolidinyl]-1-methoxypropyl]-1-(S)-1-methylpropyl]-2-methoxy-4-oxobutyl]-N-methylcarbamoyl]-2-methylpropyl]carbamoyl}(methyl)(aminocarbonyloxy)}methyl)-2-{(S)-2-[4-{[{({N-2-[4-amino-1-piperidyl)-3-(6-chloro-1H-1,3-benzimidazol-2-yl)-5-(3-fluoro-5-tolyl)-2-pyridyl]amino}ethylcarbamoyl]methyl}-N-methylcarbamoyl]methyl]-N-methylcarbamoyl}butyrylamino]-3-methylbutyrylamino]-5-ureidovalerylamino]phenoxy]-3,4,5-trihydroxytetrahydro-2H-pyran-2-carboxylic acid |
| (Compound 142)<br>(M + H)⁺ = 2118.0<br>(2S,3S,4S,5R,6S)-6-[5-({[(S)-1-[N-(S)-1-{[(1S,2R)-4-[(S)-2-{(1R,2R)-2-[N-(1R,2S)-2-{(1R,2S)-2-hydroxy-1-methyl-2-phenylethylcarbamoyl]-1-methoxypropyl]-1-pyrrolidinyl]-1-(S)-1-methylpropyl]-2-methoxy-4-oxobutyl]-N-methylpropylcarbamoyl]-2-methylpropyl](methyl)(aminocarbonyloxy)}methyl)-2-[(S)-2-[(S)-2-[3-(2-{N-2-[4-(4-amino-1-piperidyl)-3-(6-chloro-1H-1,3-benzimidazol-2-yl)-5-(3-fluoro-5-tolyl)-2-pyridyl]amino}ethylcarbamoyl]-3-methylbutyrylamino]-4-carboxybutyrylamino]ethoxy)propionylamino]-3-methylbutyrylamino]-5-ureidovalerylamino]phenoxy]-3,4,5-trihydroxytetrahydro-2H-pyran-2-carboxylic acid |

| Compound |
| --- |
| (Compound 143)<br>(M + H)⁺ = 2064.0<br>(S)-4-[N-(S)-1-[N-(S)-1-[N-4-({[(S)-1-[N-(S)-1-{[(1S,2R)-4-[(S)-2-{(1R,2R)-2-[N-(1R,2S)-2-[N-(1R,2S)-2-hydroxy-1-methyl-2-phenylethylcarbamoyl]-1-pyrrolidinyl]-1-(S)-1-methylpropyl]-2-methoxy-4-oxobutyl]-N-methylcarbamoyl]-2-methylpropylcarbamoyl](methyl)amino carbonyloxy}methyl)-2-[(2S,3R,4S,5S,6S)-6-carboxy-3,4,5-trihydroxytetrahydro-2H-pyran-2-yloxy]phenylcarbamoyl]-4-ureidobutylcarbamoyl]-2-methylpropylcarbamoyl]-4-{N-2-[4-(4-amino-1-piperidyl)-3-(6-chloro-1H-1,3-benzimidazol-2-yl)-5-(3-fluoro-5-tolyl)-2-pyridylamino]ethylcarbamoyl]-3,6,9,12-tetraoxatetradecyl)carbonylamino)butyric acid |
| (Compound 144)<br>(M + H)⁺ = 2196.1<br>(2S,3S,4S,5R,6S)-6-[5-({[(S)-1-[N-(S)-1-[N-(S)-1-{[(1S,2R)-4-[(S)-2-{(1R,2R)-2-[N-(1R,2S)-2-hydroxy-1-methyl-2-phenylethylcarbamoyl]-1-pyrrolidinyl]-1-(S)-1-methylpropyl]-2-methoxy-4-oxobutyl]-N-methylcarbamoyl]-2-methylpropylcarbamoyl](methyl)methyl}-2-[(S)-2-[(S)-2-[3-(2-{(S)-2-[3-(2-{N-2-[4-(4-amino-1-piperidyl)-3-(6-chloro-1H-1,3-benzimidazol-2-yl)-5-(3-fluoro-5-tolyl)-2-pyridylamino]propionylamino}phenoxy]-4-carboxybutyrylamino]-3-methylbutyrylamino}ethoxy)propionylamino]-4-carboxybutyrylamino]ethoxy)propionylamino]-3-methylbutyrylcarbamoyl]-3,4,5-trihydroxytetrahydro-2H-pyran-2-carboxylic acid |

| Compound |
|---|
| (Compound 145)<br>(M + H)+ = 1977.9<br>(2S,3S,4S,5R,6S)-6-[5-({[(S)-1-[N-(S)-1-{[(1S,2R)-4-[(S)-2-{(1R,2R)-2-[N-(1R,2S)-2-hydroxy-1-methyl-2-phenylethylcarbamoyl]-1-pyrrolidinyl]-1-(S)-1-methylpropyl]-2-methoxy-4-oxobutyl]-N-methylcarbamoyl]-2-methylpropyl](methyl)(aminocarbonyloxy)}methyl]-2-[(S)-2-[(S)-2-(3-(2-{[N-2-[4-(4-amino-1-piperidyl)-3-(6-chloro-1H-1,3-benzimidazol-2-yl)-5-(3-fluoro-5-tolyl)-2-pyridyl]amino]ethylcarbamoyl]-3-methylbutyrylamino]-4-carbamoylbutyrylamino]propionylamino]phenoxy]-3,4,5-trihydroxytetrahydro-2H-pyran-2-carboxylic acid |
| (Compound 146)<br>(M + H)+ = 1976.9<br>(2S,3S,4S,5R,6S)-6-[4-({[(S)-1-[N-(S)-1-{[(1S,2R)-4-[(S)-2-{(1R,2R)-2-[N-(1R,2S)-2-hydroxy-1-methyl-2-phenylethylcarbamoyl]-1-pyrrolidinyl]-1-(S)-1-methylpropyl]-2-methoxy-4-oxobutyl]-N-methylcarbamoyl]-2-methylpropyl](methyl)(aminocarbonyloxy)}methyl]-2-[(S)-2-[(S)-2-[3-(2-{[N-2-[4-(4-amino-1-piperidyl)-3-(6-chloro-1H-1,3-benzimidazol-2-yl)-5-(3-fluoro-5-tolyl)-2-pyridyl]amino]ethylcarbamoyl]-2-methylpropyl](methyl)(aminocarbonyloxy)}methyl]-2-[(S)-2-[(S)-2-[3-(2-{[N-2-[4-(4-amino-1-piperidyl)-5-ureidovalerylamino]-3-methylbutyrylamino]ethoxy)propionylamino]ethylcarbamoyl]phenoxy]-3,4,5-trihydroxytetrahydro-2H-pyran-2-carboxylic acid |

-continued

| Compound |
|---|
| (Compound 147)<br>(M + H)⁺ = 1934.9<br>(2S,3S,4S,5R,6S)-6-[4-({[(S)-1-[N-(S)-1-[[(1S,2R)-4-[(S)-2-{[(1R,2R)-2-[N-(1R,2S)-2-hydroxy-1-methyl-2-phenylethylcarbamoyl]-1-(S)-1-methylpropyl]-2-methoxy-4-oxobutyl]-N-methylcarbamoyl]-2-methylpropyl](methyl)(aminocarbonyloxy)}methyl)-2-[(S)-2-[3-(2-{N-2-[4-(4-amino-1-piperidyl)-3-(6-chloro-1H-1,3-benzimidazol-2-yl)-2-pyridylamino]ethylcarbamoyl}-3-methylbutyryl]amino]propionylamino]phenoxy]-3,4,5-trihydroxytetrahydro-2H-pyran-2-carboxylic acid |
| (Compound 148)<br>(M + H)⁺ = 1848.9<br>(2S,3S,4S,5R,6S)-6-[5-({[(S)-1-[N-(S)-1-[[(1S,2R)-4-[(S)-2-{[(1R,2R)-2-[N-(1R,2S)-2-hydroxy-1-methyl-2-phenylethylcarbamoyl]-1-(S)-1-methylpropyl]-2-methoxy-4-oxobutyl]-N-methylcarbamoyl]-2-methylpropyl](methyl)(aminocarbonyloxy)}methyl)-2-[(S)-2-{3-[2-(2-{N-2-[4-(4-amino-1-piperidyl)-3-(6-chloro-1H-1,3-benzimidazol-2-yl)-5-(3-fluoro-5-tolyl)-2-pyridyl](methylcarbamoyl)-2-methylbutyryl]amino]propionylamino]ethoxy)ethoxy]propionylamino}-3-methylbutyrylamino]propionylamino]phenoxy]-3,4,5-trihydroxytetrahydro-2H-pyran-2-carboxylic acid |

-continued

| Compound |
|---|
| (Compound 149)<br>(M + H)⁺ = 1892.9<br>(2S,3S,4S,5R,6S)-6-[5-({[(S)-1-[N-(S)-1-{[(1S,2R)-4-[(S)-2-{[(1R,2R)-2-[N-(1R,2S)-2-hydroxy-1-methyl-2-phenylethyl]carbamoyl]-1-methoxypropyl]-1-pyrrolidinyl]-1-methoxy-4-oxobutyl]-2-methoxy-4-oxobutyl]-N-methylcarbamoyl]-2-methylpropyl]-2-methylpropyl](methyl)(aminocarbonyloxy)]methyl)-2-[(S)-2-(14-{N-2-[4-(4-amino-1-piperidyl)-3-(6-chloro-1H-1,3-benzimidazol-2-yl)-5-(3-fluoro-5-tolyl)-2-pyridyl]amino]-3-methylbutyryl]amino]propionyl]amino]-3,6,9,12-tetraoxatetradecyl]carbonyl]amino]-3-methylbutyryl]carbonyl]amino]-pyridyl]amino]ethyl]carbamoyl]-3,4,5-trihydroxytetrahydro-2H-pyran-2-carboxylic acid |
| (Compound 150)<br>(M + H)⁺ = 1981.0<br>(2S,3S,4S,5R,6S)-6-[5-({[(S)-1-[N-(S)-1-{[(1S,2R)-4-[(S)-2-{[(1R,2R)-2-[N-(1R,2S)-2-hydroxy-1-methyl-2-phenylethyl]carbamoyl]-1-methoxypropyl]-1-pyrrolidinyl]-1-methoxy-4-oxobutyl]-N-methylcarbamoyl]-2-methylpropyl](methyl)(aminocarbonyloxy)]methyl)-2-[(S)-2-[(S)-2-[3-(2-{N-2-[4-(4-amino-1-piperidyl)-3-(6-chloro-1H-1,3-benzimidazol-2-yl)-5-(3-fluoro-5-tolyl)-2-pyridyl]amino]-5-ureidovalerylamino]-3-methylbutyrylamino]-4-carbamoylbutyrylamino]ethoxy)propionylamino]-4-carbamoylbutyrylamino]-3-methylbutyrylamino]ethoxy)propionylamino]ethyl]carbamoyl]-3,4,5-trihydroxytetrahydro-2H-pyran-2-carboxylic acid |

-continued

| Compound |
|---|
| (Compound 151)<br>(M + H)⁺ = 2063.0<br>(S)-4-[N-(S)-1-[N-(S)-1-[N-(S)-1-[N-4-({[(S)-1-[N-(S)-1-{[(1S,2R)-4-[(S)-2-{(1R,2R)-2-[N-(1R,2S)-2-hydroxy-1-methyl-2-phenylethylcarbamoyl]-1-pyrrolidinyl]-1-[(S)-1-methylpropyl]-2-methoxy-4-oxobutyl]-N-methylcarbamoyl]-2-methylpropyl}carbamoyl]-2-methylpropyl](methyl)(aminocarbonyloxy)}methyl)-2-[(2S,3R,4S,5S,6S)-6-carboxy-3,4,5-trihydroxytetrahydro-2H-pyran-2-yloxy]phenylcarbamoyl]ethylcarbamoyl]-4-{N-2-[4-(4-amino-1-piperidyl)-3-(6-chloro-1H-1,3-benzimidazol-2-yl)-5-(3-fluoro-5-tolyl)-2-pyridylamino]butyric acid<br>tetraoxatetradecyl carbonylamino)butyric acid |
| (Compound 152)<br>(M + H)⁺ = 2110.0<br>(2S,3S,4S,5R,6S)-6-[5-({[(S)-1-[N-(S)-1-{[(1S,2R)-4-[(S)-2-{(1R,2R)-2-[N-(1R,2S)-2-hydroxy-1-methyl-2-phenylethylcarbamoyl]-1-pyrrolidinyl]-1-[(S)-1-methylpropyl]-2-methoxy-4-oxobutyl]-N-methylcarbamoyl]-2-methylpropyl}carbamoyl](methyl)(aminocarbonyloxy)}methyl)-2-[(S)-2-[(S)-2-{3-[2-{4-[4-amino-1-piperidyl)-3-(6-chloro-1H-1,3-benzimidazol-2-yl)-5-(3-fluoro-5-tolyl)-2-pyridylamino]phenoxy]-3,4,5-trihydroxytetrahydro-2H-pyran-2-carboxylic acid<br>2-yl)-5-(3-fluoro-5-tolyl)-2-pyridylamino]phenoxy]-3-methylbutyrylamino]propionylamino]ethyl}-N-methylcarbamoyl)ethoxy]propionylamino)ethyl]-3-methylbutyrylamino]propionylamino-3-methylbutyrylamino)ethyl}-N-methylcarbamoyl)ethoxy]propionylamino)ethyl]-3-methylbutyrylamino]propionylamino |

-continued

| Compound |
|---|
| (Compound 153)<br>(M + H)⁺ = 1862.91<br>(2S,3S,4S,5R,6S)-6-[5-({[(S)-1-[N-(S)-1-[[(1S,2R)-2-[N-(S)-2-{[(1R,2R)-2-[N-(1R,2S)-2-hydroxy-1-methyl-2-phenylethylcarbamoyl]-1-methoxypropyl]-1-pyrrolidinyl]-1-(S)-1-methylpropyl]-2-methoxy-4-oxobutyl]-N-methylpropylcarbamoyl]-2-methylpropyl](methyl)(aminocarbonyloxy)}methyl]-2-[(S)-2-{(S)-2-{3-[(2-{N-2-{N-2-[4-(4-amino-1-piperidyl)-3-(6-chloro-1H-1,3-benzimidazol-2-yl)-5-(3-fluoro-5-tolyl)-2-pyridylamino]ethyl}carbamoyl]ethyl)-N-methylbutyrylamino]propionylamino}-3-methylbutyrylamino]propionylamino]phenoxy]-3,4,5-trihydroxytetrahydro-2H-pyran-2-carboxylic acid |
| (Compound 154)<br>(M + H)⁺ = 1861.9<br>(2S,3S,4S,5R,6S)-6-[5-({[(S)-1-[N-(S)-1-[[(1S,2R)-2-[N-(S)-2-{[(1R,2R)-2-[N-(1R,2S)-2-hydroxy-1-methyl-2-phenylethylcarbamoyl]-1-methoxypropyl]-1-pyrrolidinyl]-1-(S)-1-methylpropyl]-2-methoxy-4-oxobutyl]-N-methylpropylcarbamoyl]-2-methylpropyl](methyl)(aminocarbonyloxy)}methyl]-2-[(S)-2-{3-(2-{N-2-[4-(4-amino-1-piperidyl)-3-(6-chloro-1H-1,3-benzimidazol-2-yl)-5-(3-fluoro-5-tolyl)-2-pyridylamino]propionylamino}ethylcarbamoyl]ethyl}amino]-3-methylbutyrylamino]propionylamino]phenoxy]-3,4,5-trihydroxytetrahydro-2H-pyran-2-carboxylic acid |

-continued

| Compound |
|---|
| (Compound 155)<br>(M + H)⁺ = 1847.9<br>(2S,3S,4S,5R,6S)-6-[5-({[(S)-1-[N-(S)-1-{[(1S,2R)-2-[N-(S)-2-{(1R,2R)-2-[(1R,2S)-2-hydroxy-1-methyl-2-phenylethylcarbamoyl]-1-methylpropyl}-1-[(S)-1-methylpropyl]-2-methoxy-4-oxobutyl]-N-methylcarbamoyl]-2-methylpropyl}(methyl)(aminocarbonyloxy)]methyl)-2-[(S)-2-{3-[2-(S)-[3-[2-{N-2-[4-(4-amino-1-piperidyl)-3-(6-chloro-1H-1,3-benzimidazol-2-yl)-5-(3-fluoro-5-tolyl)-2-pyridylamino]ethylamino]ethoxy]propionylamino]-3-methylbutyrylamino)phenoxy]-3,4,5-trihydroxytetrahydro-2H-pyran-2-carboxylic acid |
| (Compound 156)<br>(M + H)⁺ = 1891.9 |

Example H. (2S,3S,4S,5R,6S)-6-{2-[(2S)-2-[(2S)-2-(3-{2-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]ethoxy}propanamido)-3-methylbutanamido]propanamido]-5-[({[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl}carbamoyl}-2-methylpropyl](methyl)carbamoyl}oxy)methyl]phenoxy}-3,4,5-trihydroxyoxane-2-carboxylic acid (Compound 68)

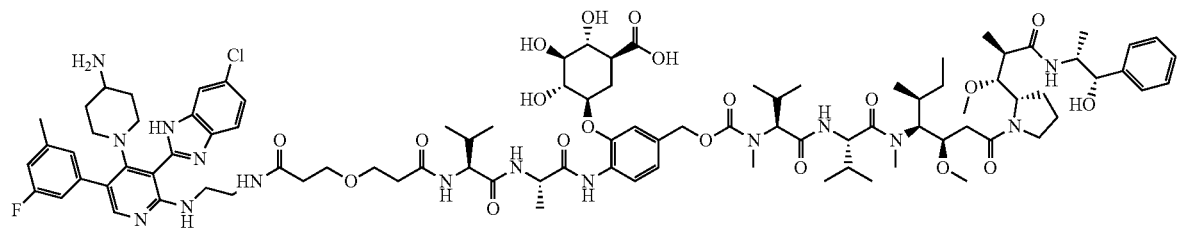 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](C)NC(=O)[C@@H](NC(=O)CCOCCC(=O)NCCNc2ncc(-c3cc(C)cc(F)c3)c(N3CCC(N)CC3)c2-c2nc3ccc(Cl)cc3[nH]2)C(C)C)c(O[C@@H]2C[C@H](C(=O)O)[C@@H](O)[C@H](O)[C@H]2O)c1)C(C)C]

Step H-1. preparation of (2S,3R,4S,5S,6S)-2-(2-((S)-2-((tert-butoxycarbonyl)amino)propanamido)-5-(hydroxymethyl)phenoxy)-6-(methoxycarbonyl)tetrahydro-2H-pyran-3,4,5-triyl triacetate: a mixture of (2S,3R,4S,5S,6S)-2-(2-amino-5-(hydroxymethyl)phenoxy)-6-(methoxycarbonyl)tetrahydro-2H-pyran-3,4,5-triyl triacetate (800 mg, 1 Eq, 1.76 mmol), (tert-butoxycarbonyl)-L-alanine (400 mg, 1.20 Eq, 2.11 mmol) and EEDQ (520 mg, 1.20 Eq, 2.10 mmol) in DMF (10 mL) was stirred for 24 h at 25° C. The reaction was then quenched with water (100 mL) and the resulting solution was extracted with ethyl acetate (3×100 mL). The organic layers were dried over anhydrous sodium sulfate and concentrated under vacuum. The residue was applied onto a silica gel column with ethyl acetate/petroleum ether (3:1). The collected fractions were combined and concentrated under vacuum to give (2S,3R,4S,5S,6S)-2-(2-((S)-2-((tert-butoxycarbonyl)amino)propanamido)-5-(hydroxymethyl)phenoxy)-6-(methoxycarbonyl)tetrahydro-2H-pyran-3,4,5-triyl triacetate (770 mg, 70.0%). MS (M+H)$^+$=627.5.

Step H-2, preparation of (2S,3R,4S,5S,6S)-2-(2-((S)-2-aminopropanamido)-5-(hydroxymethyl)phenoxy)-6-(methoxycarbonyl)tetrahydro-2H-pyran-3,4,5-triyl triacetate: a mixture of (2S,3R,4S,5S,6S)-2-(2-((S)-2-((tert-butoxycarbonyl)amino)propanamido)-5-(hydroxymethyl)phenoxy)-6-(methoxycarbonyl)tetrahydro-2H-pyran-3,4,5-triyl triacetate (770 mg, 1 Eq, 1.23 mmol) and TFA (2 mL) in DCM (6 mL) was stirred at 25° C. for 30 min. The resulting solution was concentrated under vacuum. The resulting mixture was dissolved in 20 mL DCM, and washed with 2 mL of Sat. NaHCO$_3$. The organic layer was dried over anhydrous sodium sulfate and concentrated to give (2S,3R,4S,5S,6S)-2-(2-((S)-2-aminopropanamido)-5-(hydroxymethyl)phenoxy)-6-(methoxycarbonyl)tetrahydro-2H-pyran-3,4,5-triyl triacetate (650 mg, 100%). MS (M+H)$^+$=527.2. This material was used for the next step without further purification.

Step H-3, preparation of (2S,3R,4S,5S,6S)-2-(2-((S)-2-((S)-2-((((9H-fluoren-9-yl)methoxy)carbonyl)amino)-3-methylbutanamido)propanamido)-5-(hydroxymethyl)phenoxy)-6-(methoxycarbonyl)tetrahydro-2H-pyran-3,4,5-triyl triacetate: a mixture of (2S,3R,4S,5S,6S)-2-(2-((S)-2-aminopropanamido)-5-(hydroxymethyl)phenoxy)-6-(methoxycarbonyl)tetrahydro-2H-pyran-3,4,5-triyl triacetate (650 mg, 1 Eq, 1.23 mmol), HATU (580 mg, 1.24 Eq, 1.53 mmol), and Diisopropylethylamine (480 mg, 642 µL, 3.01 Eq, 3.71 mmol) in DMF (6.5 mL) was stirred for 10 min at 25° C. Then (((9H-fluoren-9-yl)methoxy)carbonyl)-L-valine (420 mg, 1.00 Eq, 1.24 mmol) was added and the resulting reaction mixture was stirred for 1 h at 25° C. The reaction was then quenched with water (100 mL) and the resulting solution was extracted with ethyl acetate (3×100 mL). The organic layers were dried over anhydrous sodium sulfate and concentrated under vacuum. The residue was applied onto a silica gel column with ethyl acetate/petroleum ether (2:1). The collected fractions were combined and concentrated under vacuum to give (2S,3R,4S,5S,6S)-2-(2-((S)-2-((S)-2-((((9H-fluoren-9-yl)methoxy)carbonyl)amino)-3-methylbutanamido)propanamido)-5-(hydroxymethyl)phenoxy)-6-(methoxycarbonyl)tetrahydro-2H-pyran-3,4,5-triyl triacetate (620 mg, 59.2%). MS (M+H)$^+$=848.3.

Step H-4, preparation of (2S,3R,4S,5S,6S)-2-(2-((S)-2-((S)-2-((((9H-fluoren-9-yl)methoxy)carbonyl)amino)-3-methylbutanamido)propanamido)-5-((((4-nitrophenoxy)carbonyl)oxy)methyl)phenoxy)-6-(methoxycarbonyl)tetrahydro-2H-pyran-3,4,5-triyl triacetate: a mixture of (2S,3R,4S,5S,6S)-2-(2-((S)-2-((S)-2-((((9H-fluoren-9-yl)methoxy)carbonyl)amino)-3-methylbutanamido)propanamido)-5-(hydroxymethyl)phenoxy)-6-(methoxycarbonyl)tetrahydro-2H-pyran-3,4,5-triyl triacetate (520 mg, 1 Eq, 613 µmol) and Carbonicacid,bis(4-nitrophenyl)ester (280 mg, 1.50 Eq, 920 µmol) in THF (5 mL) was stirred for 24 hour under nitrogen atmosphere at 25° C. 70% product was detected by LCMS. The reaction mixture was worked up with the next batch. MS (M+H)$^+$ =1013.

Step H-5, preparation of (2S,3R,4S,5S,6S)-2-(2-((S)-2-((S)-2-((((9H-fluoren-9-yl)methoxy)carbonyl)amino)-3-methylbutanamido)propanamido)-5-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10- triazatetradecyl)phenoxy)-6-(methoxycarbonyl)tetrahydro-2H-pyran-3,4,5-triyl triacetate: a mixture of (2S,3R,4S,5S,6S)-2-(2-((S)-2-((S)-2-(((((9H-fluoren-9-yl)methoxy)carbonyl)amino)-3-methylbutanamido)propanamido)-5-(((((4-nitrophenoxy)carbonyl)oxy)methyl)phenoxy)-6-(methoxycarbonyl)tetrahydro-2H-pyran-3,4,5-triyl triacetate (320 mg, 1 Eq, 316 µmol), (S)—N-((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N,3-dimethyl-2-((S)-3-methyl-2-(methylamino)butanamido)butanamide (205 mg, 0.904 Eq, 286 µmol), 1-Hydroxy-1H-benzotriazole (52 mg, 53 µL, 1.2 Eq, 0.38 mmol), and N-ethyl-N-isopropylpropan-2-amine (123 mg, 3.01 Eq, 952 µmol) in DMF (3.5 mL) was stirred at 25° C. for 16 h. 68% product was detected by LCMS. The reaction mixture was worked up with the next batch. MS (M+H)$^+$=1591.6.

Step H-6, preparation of (2S,3R,4S,5S,6S)-2-(2-((S)-2-((S)-2-amino-3-methylbutanamido)propanamido)-5-((5R,11R,12S)-11-((R)-sec-butyl)-12-(2-((R)-2-((1S,2S)-3-(((1R,2S)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-6-(methoxycarbonyl)tetrahydro-2H-pyran-3,4,5-triyl triacetate: to a mixture of (2S,3R,4S,5S,6S)-2-(2-((S)-2-((S)-2-(((((9H-fluoren-9-yl)methoxy)carbonyl)amino)-3-methylbutanamido)propanamido)-5-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-6-(methoxycarbonyl)tetrahydro-2H-pyran-3,4,5-triyl triacetate (120 mg, 1 Eq, 75.4 µmol) in DMF (2.8 mL) was added Piperidine (45.0 mg, 52.0 µL, 7.01 Eq, 528 µmol) at 0° C. and the resulting reaction mixture stirred for 5 h at 0° C. The mixture was directly purified by MPLC with the following conditions: Column, WelFlash™, C18 120 g, Spherical 20-40 µm; Mobile phase, Water (0.05% NH·HO) and ACN(5% ACN to 5% ACN in 1 min, 20% ACN up to 98% in 8 min, 98% ACN to 98% in 1 min); Total flow rate, 70 mL/min; Detector, UV 220 nm. The collected fractions were combined and concentrated under vacuum to give (2S,3R,4S,5S,6S)-2-(2-((S)-2-((S)-2-amino-3-methylbutanamido)propanamido)-5-((5R,11R,12S)-11-((R)-sec-butyl)-12-(2-((R)-2-((1S,2S)-3-(((1R,2S)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-6-(methoxycarbonyl)tetrahydro-2H-pyran-3,4,5-triyl triacetate (120 mg, 58%). MS (M+H)$^+$=1369.6.

Step H-7, preparation of (2S,3R,4S,5S,6S)-2-(2-((2S,5S)-16-((4-(4-((tert-butoxycarbonyl)amino)piperidin-1-yl)-3-(6-chloro-1H-benzo[d]imidazol-2-yl)-5-(3-fluoro-5-methylphenyl)pyridin-2-yl)amino)-5-isopropyl-2-methyl-4,7,13-trioxo-10-oxa-3,6,14-triazahexadecanamido)-5-((5R,11R,12S)-11-((R)-sec-butyl)-12-(2-((R)-2-((1S,2S)-3-(((1R,2S)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-6-(methoxycarbonyl)tetrahydro-2H-pyran-3,4,5-triyl triacetate: a mixture of (2S,3R,4S,5S,6S)-2-(2-((S)-2-((S)-2-amino-3-methylbutanamido)propanamido)-5-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-6-(methoxycarbonyl)tetrahydro-2H-pyran-3,4,5-triyl triacetate (100 mg, 1 Eq, 73.0 µmol), 3-(3-((2-((4-(4-((tert-butoxycarbonyl)amino)piperidin-1-yl)-3-(6-chloro-1H-benzo[d]imidazol-2-yl)-5-(3-fluoro-5-methylphenyl)pyridin-2-yl)amino)ethyl)amino)-3-oxopropoxy)propanoic acid (55 mg, 1.0 Eq, 74 µmol), perfluorophenyl diphenylphosphinate (34 mg, 1.2 Eq, 88 µmol), and 4-methylmorfolin (22 mg, 24 µL, 3.0 Eq, 0.22 mmol) in DMF (1 mL) was stirred for 10 min at 25° C. Then to this was added (2S,3R,4S,5S,6S)-2-(2-((S)-2-((S)-2-amino-3-methylbutanamido)propanamido)-5-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-6-(methoxycarbonyl)tetrahydro-2H-pyran-3,4,5-triyl triacetate (100 mg, 1 Eq, 73.0 µmol). The resulting reaction mixture was stirred for 1 h at 25° C. The mixture was directly purified by MPLC with the following conditions: Column, Flash™, C18 120 g, Spherical 20-40 µm; Mobile phase, Water (0.05% NH·HO) and ACN (5% ACN to 5% ACN in 2 min, 30% ACN up to 98% in 12 min, 98% ACN to 98% in 1 min); Total flow rate, 70 mL/min; Detector, UV 220 nm. The collected fractions were combined and concentrated under vacuum to give (2S,3R,4S,5S,6S)-2-(2-((2S,5S)-16-((4-(4-((tert-butoxycarbonyl)amino)piperidin-1-yl)-3-(6-chloro-1H-benzo[d]imidazol-2-yl)-5-(3-fluoro-5-methylphenyl)pyridin-2-yl)amino)-5-isopropyl-2-methyl-4,7,13-trioxo-10-oxa-3,6,14-triazahexadecanamido)-5-((5R,11R,12S)-11-((R)-secbutyl)-12-(2-((R)-2-((1S,2S)-3-(((1R,2S)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenoxy)-6-(methoxycarbonyl)tetrahydro-2H-pyran-3,4,5-triyl triacetate (20 mg, 13%). MS (M/2+H)$^+$=1050.5; MS (M+H)$^+$=2099.5.

Step H-8, preparation of (2S,3S,4S,5R,6S)-6-(2-((2S,5S)-16-((4-(4-((tert-butoxycarbonyl)amino)piperidin-1-yl)-3-(6-chloro-1H-benzo[d]imidazol-2-yl)-5-(3-fluoro-5-methylphenyl)pyridin-2-yl)amino)-5-isopropyl-2-methyl-4,7,13-trioxo-10-oxa-3,6,14-triazahexadecanamido)-5-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)allyl)-5,8-diisopropyl-4,10-dimethyl-3,6,9-trioxo-2,13-dioxa-4,7,10-triazatetradecyl)phenoxy)-3,4,5-trihydroxytetrahydro-2H-pyran-2-carboxylic acid: a mixture of (2S,3R,4S,5S,6S)-2-(2-((2S,5S)-16-((4-(4-((tert-butoxycarbonyl)amino)piperidin-1-yl)-3-(6-chloro-1Hbenzo[d]imidazol-2-yl)-5-(3-fluoro-5-methylphenyl)pyridin-2-yl)amino)-5-isopropyl-2-methyl-4,7,13-trioxo-10-oxa-3,6,14-triazahexadecanamido)-5-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)allyl)-5,8-diisopropyl-4,10-dimethyl-3,6,9-trioxo-2,13-dioxa-4,7,10-triazatetradecyl)phenoxy)-6-(methoxycarbonyl)tetrahydro-2H-pyran-3,4,5-triyl triacetate (18 mg, 1 Eq, 8.6 µmol) and lithium hydroxide (2 mg, 1e+1 Eq, 0.08 mmol) in THF (0.1 mL) and H$_2$O (0.02 mL) was stirred for 30 min at 25° C. The residue was diluted with water (10 ml), then adjusted to a pH 6-7 with AcOH (1 M). The resulting solution was extracted with ethyl acetate (3×2 mL). The organic layers was dried over anhydrous sodium sulfate and concentrated under vacuum to give (2S,3S,4S,5R,6S)-6-(2-((2S,5S)-16-((4-(4-((tert-butoxycarbonyl)amino)piperidin-1-yl)-3-(6-chloro-1H-benzo[d]imidazol-2-yl)-5-(3-fluoro-5-methylphenyl)pyridin-2-yl)amino)-5-isopropyl-2-methyl-4,7,13-trioxo-10-oxa-3,6,14-triazahexadecanamido)-5-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)allyl)-5,8-diisopropyl-4,10-dimethyl-3,6,9-trioxo-2,13-dioxa-4,7,10-triazatetradecyl)phenoxy)-3,4,5-trihydroxytetrahydro-2H-pyran-2-carboxylic acid (20 mg, 84%). MS (M/2+H)$^+$=975; MS (M+H)$^+$=1949. This material was used for the next step without further purification.

Step H-9, preparation of (2S,3S,4S,5R,6S)-6-{2-[(2S)-2-[(2S)-2-(3-{2-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]ethoxy}propanamido)-3-methylbutanamido]propanamido]-5-[({[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl](methyl)carbamoyl}oxy)methyl]phenoxy}-3,4,5-trihydroxyoxane-2-carboxylic acid: a mixture of (2S,3S,4S,5R,6S)-6-(2-((2S,5S)-16-((4-(4-((tert-butoxycarbonyl)amino)piperidin-1-yl)-3-(6-chloro-1Hbenzo[d]imidazol-2-yl)-5-(3-fluoro-5-methylphenyl)pyridin-2-yl)amino)-5-isopropyl-2-methyl-4,7,13-trioxo-10-oxa-3,6,14-triazahexadecanamido)-5-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)allyl)-5,8-diisopropyl-4,10-dimethyl-3,6,9-trioxo-2,13-dioxa-4,7,10-triazatetradecyl)phenoxy)-3,4,5-trihydroxytetrahydro-2H-pyran-2-carboxylic acid (20 mg, 1 Eq, 10 µmol) and TFA (0.1 mL) in DCM (0.5 mL) was stirred at 25° C. for 30 min. The crude product was purified by Prep-HPLC with the following conditions (Prep-HPLC-013): Column, Atlantis Prep T3 OBD Column, 19*150 mm 5 um; mobilephase, Water(0.1% TFA) and ACN (28% Phase B up to 53% in 10 min); 20 mL/min. Detector, UV 220,254 nm. The collected fractions were combined and concentrated under vacuum to give (2S,3S,4S,5R,6S)-6-{2-[(2S)-2-[(2S)-2-(3-{2-[(2-{[4-(4-aminopiperidin-1-yl)-3-(6-chloro-1H-1,3-benzodiazol-2-yl)-5-(3-fluoro-5-methylphenyl)pyridin-2-yl]amino}ethyl)carbamoyl]ethoxy}propanamido)-3-methylbutanamido]propanamido]-5-[({[(1S)-1-{[(1S)-1-{[(3R,4S,5S)-1-[(2S)-2-[(1R,2R)-2-{[(1S,2R)-1-hydroxy-1-phenylpropan-2-yl]carbamoyl}-1-methoxy-2-methylethyl]pyrrolidin-1-yl]-3-methoxy-5-methyl-1-oxoheptan-4-yl](methyl)carbamoyl}-2-methylpropyl]carbamoyl}-2-methylpropyl](methyl)carbamoyl}oxy)methyl]phenoxy}-3,4,5-trihydroxyoxane-2-carboxylic acid (4.7 mg, 21%). MS (M+H)$^+$=1850.0.

Biological Assays

Example I: SSTR Assay

General overview: All five SSTR subtypes are Gi coupled G-protein coupled receptors (GPCRs) that lead to decreases in intracellular cyclic AMP (cAMP) when activated by an agonist. Therefore, measurement of intracellular cAMP levels can be used to assess whether compounds of the invention are agonists of SSTR subtypes (John Kelly, Troy Stevens, W. Joseph Thompson, and Roland Seifert, *Current Protocols in Pharmacology*, 2005, 2.2.1-2.2). One example of an intracellular cAMP assay is described below. Functional Assay for SSTR2 Agonists Four days prior to the assay, 2,000 Chinese hamster ovary cells (CHO-K1, ATCC #CCL-61) stably expressing the human somatostatin receptor subtype 2 are plated in each well of a 96-well tissue culture-treated plate in Ham's F12 growth media (ThermoFisher #10-080-CM) supplemented with 10% donor bovine serum (Gemini Bio-Products #100-506), 100 U/mL penicillin; 100 ug/mL streptomycin; 2 mM L-glutamine (Gemini Bio-Products #400-110) and 0.2 mg/mL hygromycin B (GoldBio #31282-04-9). The cells are cultured at 37° C., 5% $CO_2$ and 95% humidity. cAMP is measured with HTRF dynamic cAMP assay (Cisbio, #62AM5PEJ) per manufacturer's instructions. On the day of the assay, the media is aspirated and the cells are treated with 50 µL of stimulation buffer supplemented with 10.2 mM 3-Isobutyl-1-methylxanthine (IBMX, Millipore Sigma #15879) and 1.6 µM NKH477 (Tocris #1603), plus various dilutions of SMDCs of the present invention. The cells are incubated for 20 minutes at 37° C. (the final concentration of the compounds of the invention are typically 0-10,000 nM). The cells are treated with 50 µL of lysis buffer (HRTF cAMP kit, Cisbio) and incubated at room temperature for 30 minutes with rotary shaking at 600 rpm, and then diluted with 150 µL of stimulation buffer and shaken for an additional five minutes at 300 rpm. The lysate is transferred to 384-well plates and incubated for 1-24 hours at room temperature, and cAMP accumulation is detected by d2-labeled cAMP and Anti-cAMP-Cryptate. The time-resolved fluorescent signal is read using a m1000 Pro (Tecan) or CLARIOStar (BMG Labtech) microplate reader, where the samples are excited with light at 340 nm and emission light is measured at 620 nm and 665 nm. The data is expressed as a calculation of the fluorescence ratio (665 nm/620 nm). The intracellular cAMP concentrations are calculated by regression to a standard curve and are plotted vs. the concentration of the compounds of the invention. The $EC_{50}$ of the compounds are calculated using standard methods. All data manipulations are in GraphPad Prism v9 (GraphPad, San Diego, CA).

Example J: Internalization Assay Protocol

SMDCs of the present invention were assessed in vitro using the human PathHunter CHO-K1 SST2 β-arrestin2 and PathHunter CHO-K1 SST2 Internalization Assays from DiscoverX. The CHO-K cells were seeded in 20 µLs of cell culture medium in a white-walled 384 well tissue culture-compatible plate at a density of 2500 cells/well. After a 48-hour incubation, cells were treated with 5 µLs of a 1:3 serially diluted SST2 SMDC prepared at 5× concentration with a final top compound concentration of 10 uM for 90 min at 37 C and in 5% CO2. 11 dilutions were tested as well as one treatment that was compound free. After incubation, the media containing treatments were discarded and 20 µL of a working solution of Beta-Glo from Promega Beta-Glo Assay System was added to each well. The plate was then incubated for 60 min at room temperature in the dark. Luminescence was measured using a Tecan plate reader. $IC_{50}$ curves were generated using the nonlinear regression analysis (four-parameters) with GraphPad Prism 9. Results were the average of duplicates and are corrected for background.

Example K: H524 Assay Protocol

SMDCs of the present invention were assessed in an in vitro assay evaluating the inhibition of cell proliferation. NCI-H524 (ATCC) human small cell lung cancer cells were plated in 96-well V-bottom plates (Costar) at a concentration of 5,000 cells/well. 24 h later, the cells were treated for 2 h with a SMDC. SMDC starting dose was 1 uM and two-fold serial dilutions were done for a total of 11 points. After 2 h of treatment, cells were spun down, and the drug-containing media was removed, and fresh complete media was added and used to resuspend the cells, which were spun again. After removal of the media, the cells were resuspended in complete medium and incubated for an additional 70 h. Cell proliferation was assessed using the CellTiter Glo Assay according to the standard protocol (Promega). Luminescence was measured using a TECAN plate reader. Percent proliferation inhibition was calculated using the following formula: % inhibition=(Luminescence Control−Luminescence Treatment)/Luminescence Control*100. $IC_{50}$ curves were generated using the nonlinear regression analysis (four-parameter) with GraphPad Prism 9. Illustrative biological activity of compounds is demonstrated in the following Tables.

TABLE 1

Representative Activity

| Compound # | hSST2 cAMP Avg $EC_{50}$ (nM) | Internalization $EC_{50}$ (nM) | H524 $EC_{50}$ (nM) |
| --- | --- | --- | --- |
| 1 | 0.075 | n.d. | n.d. |
| 2 | 0.17 | n.d. | n.d. |
| 3 | 0.14 | n.d. | n.d. |
| 4 | 0.20 | n.d. | n.d. |
| 5 | 0.66 | n.d | n.d. |
| 6 | 0.22 | 5.3 | 11.7 |
| 7 | 0.15 | 21 | 354.8 |
| 8 | 0.12 | 23.6 | 446.7 |
| 9 | 0.13 | 7.7 | 378.9 |
| 10 | 0.44 | 3.15 | 17.4 |
| 11 | 0.086 | 13.4 | 104.7 |
| 12 | 0.39 | 2.9 | n.d. |
| 13 | 0.075 | 6.3 | 41.8 |
| 14 | 0.048 | n.d. | n.d. |
| 15 | 0.057 | n.d. | n.d. |
| 16 | 0.11 | n.d. | n.d. |
| 17 | 0.10 | n.d. | n.d. |
| 18 | 1.8 | n.d. | n.d. |
| 19 | 0.44 | 7.1 | 20 |
| 20 | 0.27 | 6.3 | 31.6 |
| 21 | 0.41 | 17.2 | 22.4 |
| 22 | 0.36 | 26 | 27.1 |
| 23 | 0.66 | 244.8 | 131.9 |
| 24 | 0.2 | 12 | 13.4 |
| 25 | 0.34 | 27 | 25 |
| 26 | 0.3 | 11.6 | 10.6 |
| 27 | 0.2 | 27.8 | 65.5 |
| 28 | 2 | 704.4 | 1288 |
| 29 | 0.065 | 2.2 | >10,000 |
| 30 | 0.56 | 7.1 | 28.6 |
| 31 | 1700 | >1000 | 1055 |
| 32 | 0.37 | 33.3 | 154.7 |
| 33 | 0.63 | 34.9 | 274.3 |
| 34 | 0.16 | 21.8 | 3141.6 |
| 35 | 0.58 | 6.1 | 17.4 |
| 36 | 0.25 | 12.9 | 44.1 |
| 37 | 0.071 | 13.7 | 101.9 |
| 38 | 0.11 | 1 | 59.4 |
| 39 | 0.12 | 18.7 | 35.9 |
| 40 | 0.36 | 26.4 | 46.5 |
| 41 | 0.48 | 24.6 | 27.8 |
| 42 | 0.12 | 8.6 | 57.3 |
| 43 | 0.29 | 18.1 | 82.6 |
| 44 | 0.089 | 17.2 | 101.2 |
| 45 | 0.12 | 21 | 32 |
| 46 | 0.54 | 26.1 | 85.9 |
| 47 | 0.091 | 9 | 18.7 |
| 48 | 0.26 | 6.9 | 12.4 |
| 49 | 0.14 | 5.5 | 17.3 |
| 50 | 0.15 | 7.7 | 5.8 |
| 51 | 0.22 | 6.3 | 130 |
| 52 | 0.24 | 9.1 | 48 |
| 53 | 0.16 | 13 | 100 |
| 54 | 0.17 | 10 | 17 |
| 55 | 0.17 | 8.3 | 35 |
| 56 | 0.23 | 15.1 | 10.3 |
| 57 | 0.38 | 5.7 | 15 |
| 58 | 0.37 | 5 | 11 |
| 59 | 0.35 | 6.5 | 14 |
| 60 | 0.1 | 13 | 35 |
| 61 | 0.11 | 12.7 | 33.2 |
| 62 | 0.2 | 14 | 61.2 |
| 63 | 0.16 | 16 | 13 |
| 64 | 0.1 | 12 | 9500 |
| 65 | 0.27 | 1.5 | 250 |
| 66 | 0.13 | 15 | 300 |
| 67 | 0.19 | 6.7 | 41 |
| 68 | 0.14 | 10.8 | 11.2 |
| 69 | 0.25 | 7.8 | 14.5 |
| 70 | 0.44 | 17 | 68 |
| 71 | 0.29 | 1.6 | 270 |
| 72 | 0.28 | 3.9 | 31 |
| 73 | 0.49 | n.d. | n.d. |
| 74 | 0.31 | n.d. | n.d. |
| 75 | 0.54 | 8.9 | 16.5 |
| 77 | 0.21 | 5.2 | 17 |
| 78 | 0.23 | 0.77 | 170 |
| 81 | 0.12 | 21 | 32 |
| 82 | 0.31 | 6 | 0.79 |
| 83 | 0.11 | 2.9 | 20 |
| 84 | 0.51 | 9.7 | 24 |
| 85 | 0.25 | 13 | 2.2 |
| 86 | 0.36 | 15 | 1.1 |
| 87 | 0.4 | 26 | 42 |
| 88 | 0.3 | 1.3 | 55 |
| 89 | 0.71 | 66 | 60 |
| 90 | 0.22 | 4.8 | 71 |
| 91 | 0.18 | 5.6 | 190 |
| 92 | 0.56 | 27 | 110 |
| 93 | 0.48 | 4.5 | 130 |
| 94 | 0.16 | 2.4 | 260 |
| 95 | 0.26 | 2.2 | 5.1 |
| 96 | 0.47 | 4.9 | 21 |
| 97 | 0.3 | 4.5 | 35 |
| 98 | 0.25 | 2.9 | 120 |
| 99 | 0.19 | 2.8 | 4.6 |
| 100 | 0.14 | 3.3 | 6.4 |
| 101 | 0.22 | 6.7 | 34 |
| 102 | 0.067 | 19 | 130 |
| 103 | 0.26 | 24 | 620 |
| 104 | 0.062 | 2.8 | 24 |
| 105 | 0.18 | 14 | 290 |
| 106 | 0.25 | 16 | 460 |
| 107 | 0.15 | 2.2 | 4 |
| 108 | 1.9 | 53 | 3300 |
| 109 | 0.7 | 11 | 2500 |
| 110 | 0.57 | 13 | 110 |
| 111 | 1.2 | 22 | 360 |
| 112 | 0.16 | 2.9 | 10 |
| 113 | 0.33 | 30 | 200 |
| 114 | 0.22 | 10 | 100 |
| 115 | 0.08 | 3.6 | 23 |
| 116 | 0.1 | 3.9 | 6.6 |
| 117 | 0.081 | 2.6 | 3.7 |
| 118 | 0.068 | 3.8 | 0.65 |
| 119 | 0.14 | 5.4 | 16 |
| 120 | 0.19 | 2.7 | 2.4 |
| 121 | 0.45 | 3 | 0.62 |
| 122 | 0.18 | 3.8 | 7.9 |
| 123 | 0.13 | 7.0 | 18 |
| 124 | 0.16 | 5.6 | 5.3 |
| 125 | 0.17 | 3.9 | 3.4 |
| 126 | 0.29 | 3.4 | 100 |
| 127 | 0.26 | 13 | n.d. |
| 128 | 0.18 | 8.7 | 31 |

TABLE 1-continued

Representative Activity

| Compound # | hSST2 cAMP Avg EC$_{50}$ (nM) | Internalization EC$_{50}$ (nM) | H524 EC$_{50}$ (nM) |
|---|---|---|---|
| 129 | 0.34 | 21 | 290 |
| 130 | 0.29 | 25 | 140 |
| 131 | 0.13 | 5.2 | 4 |
| 132 | 0.2 | 5.7 | 22 |
| 133 | 0.11 | 6 | 34 |
| 134 | 0.18 | 4.6 | 3.8 |
| 135 | 0.15 | 2.8 | 38 |
| 136 | 0.23 | 6.7 | 5.8 |
| 137 | 0.51 | 4.6 | 6.7 |
| 138 | 0.16 | 5.2 | 12 |
| 139 | 360 | 3000 | 3200 |
| 140 | 0.33 | 1.8 | 5.4 |
| 141 | 0.22 | 2.3 | 11 |
| 142 | 0.25 | 4.4 | 91 |
| 143 | 0.14 | 3 | 100 |
| 144 | 0.21 | 6.9 | 120 |
| 145 | 0.25 | 7.9 | 150 |
| 146 | 0.072 | 2.1 | 4.8 |
| 147 | 0.14 | 2.5 | 3.2 |
| 148 | 0.086 | 4.5 | 7.9 |
| 149 | 0.099 | 5.2 | 5 |
| 150 | 0.18 | 5.6 | 9.3 |
| 151 | 0.28 | 2.2 | 8.9 |
| 152 | 0.2 | 5.8 | 91 |
| 153 | 0.51 | 14 | 98 |
| 154 | 0.16 | 25 | 29 |
| 155 | 0.24 | 29 | 71 |
| 156 | 0.24 | 25 | 76 |
| 157 | 0.17 | 12 | 1.9 |
| 158 | 0.24 | 12 | 3 |
| 159 | 0.3 | 10 | 2.6 | n.d. = not determined

Comparative Activity

The compounds of the present invention (25 and 68) employ an ethylene diamine moiety to connect the targeting ligand to the linker or spacer of the SMDC. The inventors unexpectedly discovered that utilization of the ethylene diamine moiety significantly improves internalization and H524 activity of the conjugate in comparison to conjugates utilizing a piperazine moiety to connect the targeting ligand to the linker or spacer. This is illustrated in the comparative examples below, wherein internalization increases 5 to 10-fold for SMDCs with the ethylene diamine moiety compared to the corresponding conjugates with a piperazine moiety as shown in Table 2.

The structures of comparative compounds 1 (Comp. 1) and 2 (Comp. 2) with the piperazine moeity are shown below:

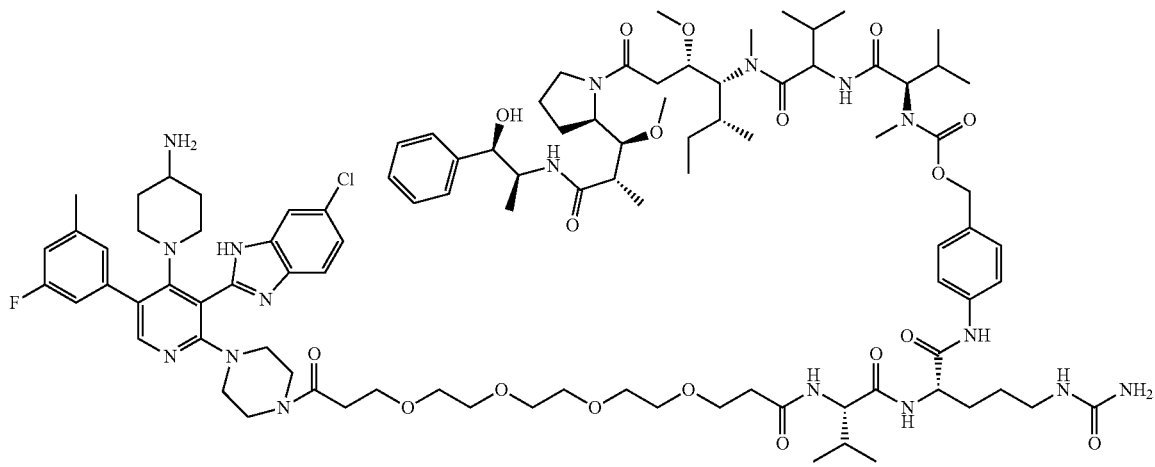

Comp. 1

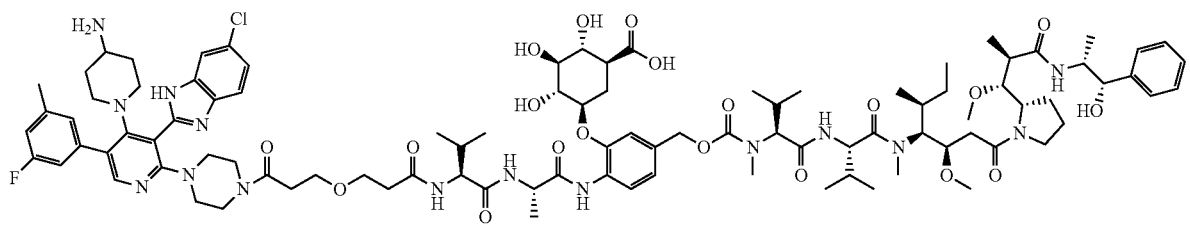

Comp. 2

The structures of their corresponding SMDCs of the present invention with the ethylene diamine moiety are shown below:

Compound 25
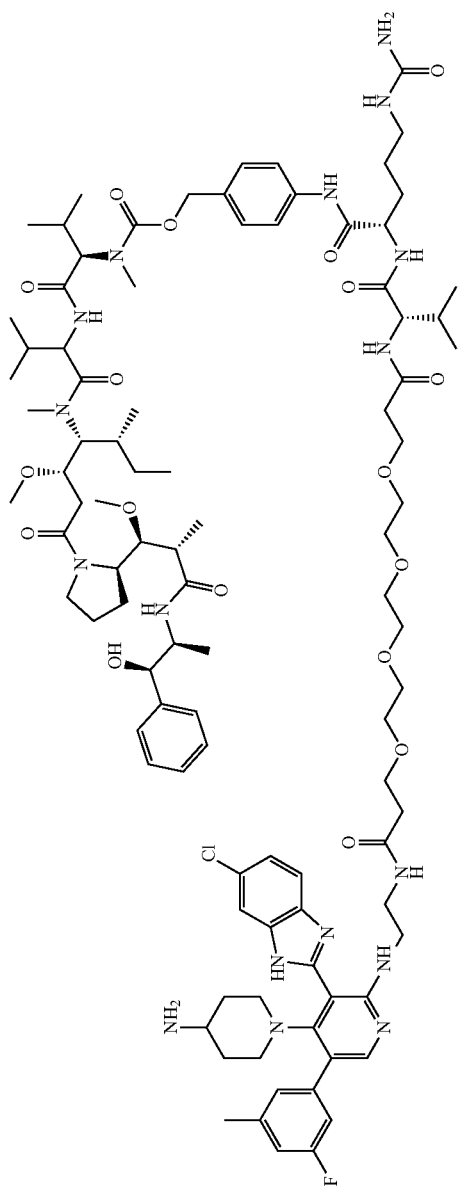
Compound 68
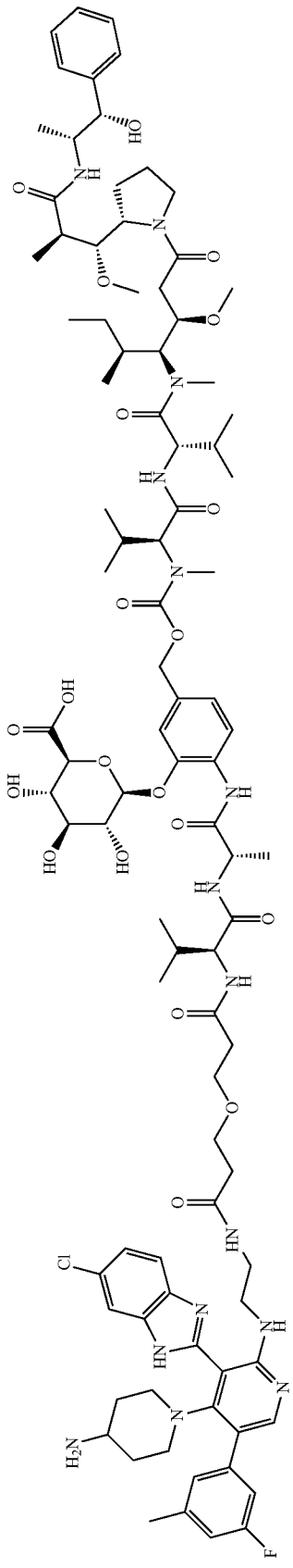

TABLE 2

Comparative Activity

| Compound # | hSST2 cAMP Avg EC$_{50}$ (nM) | Internalization EC$_{50}$ (nM) | H524 EC$_{50}$ (nM) |
|---|---|---|---|
| Comp. 1 | 0.44 | 130 | 180 |
| 25 | 0.34 | 27 | 25 |
| Comp. 2 | 0.39 | 100 | 590 |
| 68 | 0.14 | 10.8 | 11.2 |

Example L: H524 Tumor Biodistribution Model

In this example, 5 million H524 (Small Cell Lung Cancer) cells in 1:1 Matrigel: cold Media (RPMI1640) were injected into the subcutaneous (SQ) flank of female Athymic nude mice. Tumor volumes and body weights were measured twice a week. The tumors were allowed to grow until they reached 250-500 mm$^3$ in size before animals were randomized into groups (n=3/time point). Animals were injected intravenously with a SMDC of the present invention at a single dose of 500 nmol/kg. Plasma and tissues were collected after perfusion of the whole body with saline to remove any vascular signal at 1, 4, 24 and 72 hours post compound administration and the concentration of conjugate and MMAE were measured by LC/MS-MS. Tumor and plasma levels of SMDC and MMAE are shown in Tables 4. BLQ: Below Limit of Quantitation.

TABLE 3

Tumor and plasma concentrations of compound 68 and MMAE in H524 tumor bearing nude mice following intravenous administration of 500 nmol/kg compound 68.

| | Compoud 68 | | MMAE | |
|---|---|---|---|---|
| Time (h) | Tumor (nM) | Plasma (nM) | Tumor (nM) | Plasma (nM) |
| 1 h | 212 | 1388 | 17.5 | 8.82 |
| 4 h | 91.3 | 446 | 197 | 1.94 |
| 24 h | 15.5 | 36.9 | 299 | 0.416 |
| 72 h | BLQ | 0.68 | 231 | BLQ |

TABLE 4

Tumor and plasma concentrations of compound 49 and MMAE in H524 tumor bearing nude mice following intravenous administration of 500 nmol/kg compound 49.

| | Compoud 49 | | MMAE | |
|---|---|---|---|---|
| Time (h) | Tumor (nM) | Plasma (nM) | Tumor (nM) | Plasma (nM) |
| 1 h | 88.1 | 354 | 38 | 9.2 |
| 4 h | 46.5 | 41.6 | 65.7 | 1.36 |
| 24 h | BLQ | 0.783 | 83.5 | BLQ |
| 72 h | BLQ | BLQ | 62.7 | BLQ |

TABLE 5

Tumor and plasma concentrations of compound 61 and MMAE in H524 tumor bearing nude mice following intravenous administration of 500 nmol/kg compound 61.

| | Compound 61 | | MMAE | |
|---|---|---|---|---|
| Time (h) | Tumor (nM) | Plasma (nM) | Tumor (nM) | Plasma (nM) |
| 4 h | 181 | 1099 | 75.0 | 0.754 |
| 24 h | 37.0 | 56.5 | 320 | BLQ |
| 72 h | BLQ | BLQ | 267 | BLQ |
| 168 h | BLQ | BLQ | 97.8 | BLQ |

TABLE 6

Tumor and plasma concentrations of compound 107 and MMAE in H524 tumor bearing nude mice following intravenous administration of 500 nmol/kg compound 107.

| | Compound 107 | | MMAE | |
|---|---|---|---|---|
| Time (h) | Tumor (nM) | Plasma (nM) | Tumor (nM) | Plasma (nM) |
| 4 h | 94.2 | 83.1 | 123 | 2.26 |
| 24 h | 9.26 | 0.441 | 242 | BLQ |
| 72 h | 1.64 | BLQ | 141 | BLQ |
| 168 h | BLQ | BLQ | 90.1 | BLQ |
| 240 | BLQ | BLQ | 25.2 | BLQ |

Example M: Biodistribution of $^{111}$In-Compound 1 in Female Swiss Nude Mice Harboring Tumors Derived from the AR42J Rat Pancreatic Cancer Cell Line Study outline: 24 hours prior to the start of the biodistribution study, $^{111}$In-Compound 1 was radiolabeled as described herein. On the day of the study animals received a single IV injection of 200 uL into the caudal vein via a catheter with $^{111}$In-labeled Compound 1 (1 nmol) as described in Table 2. The blocking study (Group 6) combined 1 nmol of $^{111}$In-Compound 1 with 100 nmol $^{115}$In-Compound 1.

TABLE 7

Study Details

| Group | # of animals | Readout Time | MBq/ animal | nmol/ animal | Route/ Schedule |
|---|---|---|---|---|---|
| 1 | 6 | 0.5 hours | 30-35 | 1 | IV / Q1Dx1 |
| 2 | 4 | 1 hours | 5-7 | 1 | IV / Q1Dx1 |
| 3 | 4 | 2 hours | 5-7 | 1 | IV / Q1Dx1 |
| 4 | 4 | 6 hours | 5-7 | 1 | IV / Q1Dx1 |
| 5 | 6 | 22 hours | 5-7 | 1 | IV / Q1Dx1 |
| 6 | 4 | 2 hours | 5-7 + 0 | 1 + 100 | IV / Q1Dx1 |

After drug administration, animals were euthanized at specific timepoints (0.5 hour, 1 hour, 2 hours, 6, hours, 22 hours) and organs (blood, tumor, heart, kidneys, pituitary gland, brain, liver, spleen, lungs, gut, adrenals, pancreas, stomach, bone (femur) and tail) were collected, weighed, and radioactivity was assessed in each organ/tissue. Activity was quantitated and expressed as % ID/g (Percentage of Initial Dose/gram of tissue).

Biodistribution Results:

In the AR42J xenograft tumor model, $^{111}$In-Compound 1 showed high and sustained uptake in the SST2R positive tumors. The uptake of $^{111}$In-Compound 1 was demonstrated to be SST2R-specific through competition studies, where co-administration of 100-fold molar excess of non-radioactive $^{115}$In-Compound 1 significantly reduced tumor uptake of $^{111}$In labeled Compound-15 (FIG. 1). Only the kidneys showed non-specific uptake of $^{111}$In-Compound 1, which was not blocked by co-administration of excess of non-radioactive $^{115}$In-Compound 1, suggesting urinary excretion is the primary pathway of $^{111}$In-Compound-1 elimination.

The examples and embodiments described herein are for illustrative purposes only and various modifications or changes suggested to persons skilled in the art are to be included within the spirit and purview of this application and scope of the appended claims.

What is claimed is:

1. A compound that has the structure of Formula (I), or a pharmaceutically acceptable salt thereof:

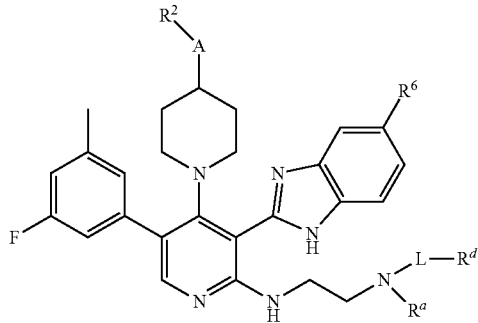

Formula (I)

wherein:
A is —N(H)— or —O—;
$R^a$ is hydrogen or $C_1$-$C_6$alkyl;
$R^2$ is hydrogen or $C_1$-$C_6$alkyl;
$R^6$ is chloro or —C(=O)NH$_2$;
L is -$L^1$-$L^2$-;
 $L^1$ is an optional spacer; and
 $L^2$ is an optional linker;
 wherein at least one of $L^1$ or $L^2$ is present; and
$R^d$ is a payload moiety comprising a chemotherapeutic agent.

2. The compound of claim 1, or a pharmaceutically acceptable salt thereof, wherein:
$L^2$ is present, and is -($L^{2a}$)$_w$-$L^{2b}$- or -$L^{2c}$-;
each $L^{2a}$ is independently selected from the group consisting of natural and unnatural amino acids, wherein any free amine of an amino acid is optionally independently substituted with —CH$_3$;
$L^{2b}$ is absent or —N($R^{10}$)(unsubstituted or substituted benzyl)-OC(=O)—; wherein substituted benzyl is substituted with —C(=O)NHR$^{12}$ or a monosaccharide;
each $R^{10}$ is independently selected from the group consisting of hydrogen and $C_1$-$C_6$alkyl;
each $R^{12}$ is independently selected from the group consisting of hydrogen, $C_4$-$C_{20}$polyethylene glycol, and unsubstituted or substituted $C_1$-$C_6$alkyl, wherein the substituted $C_1$-$C_6$alkyl is substituted with —NHR$^{13}$, —C(=O)NHR$^{13}$, or —NHC(=O) R$^{13}$;
each $R^{13}$ is independently selected from the group consisting of hydrogen, $C_4$-$C_{20}$polyethylene glycol, and $C_4$-$C_{20}$polyethylene glycol-NH$_2$;
or when $R^{13}$ is present and at least one free carboxylic group of an amino acid of $L^{2a}$ is present, then $R^{13}$ and the free carboxylic group of the amino acid of $L^{2a}$ are taken together to form a ring;
w is 1, 2, 3, 4, 5, or 6; and
each $L^{2c}$ is N-maleimidomethyl-cyclohexane-1-carbonyl (MCC) or —S—.

3. The compound of claim 2, or a pharmaceutically acceptable salt thereof, wherein $L^{2b}$ is selected from the group consisting of:

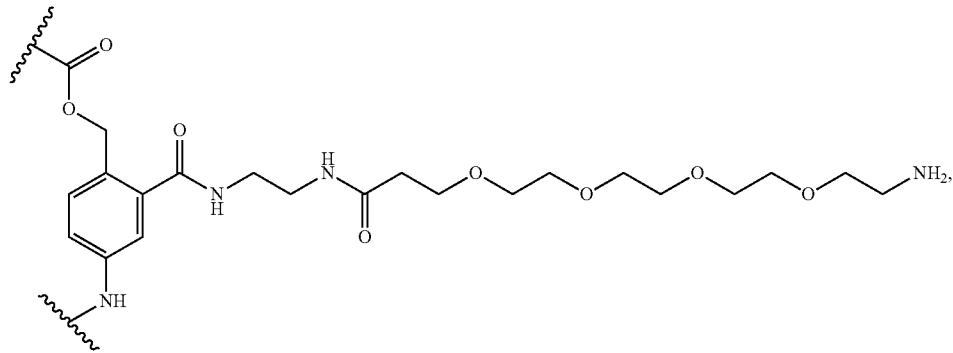

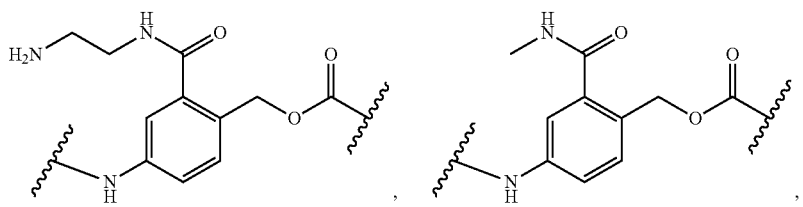

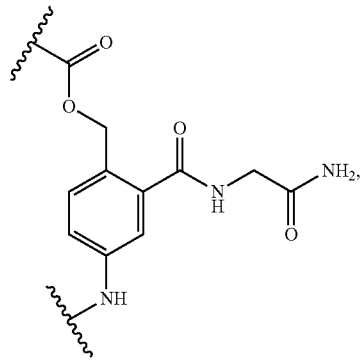
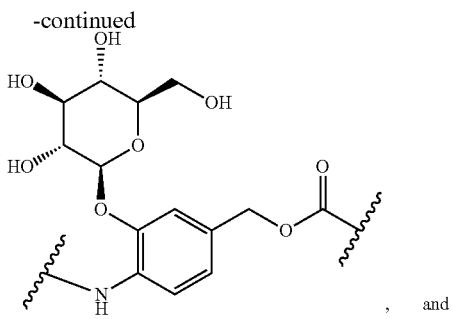
, and

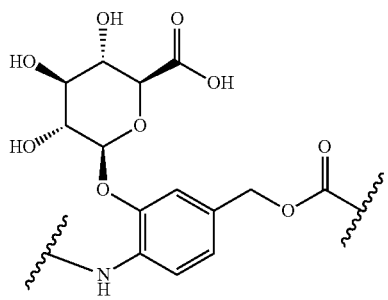

4. The compound of claim 2, wherein the compound has the structure of Formula (Ia), or a pharmaceutically acceptable salt thereof:

Formula (Ia)

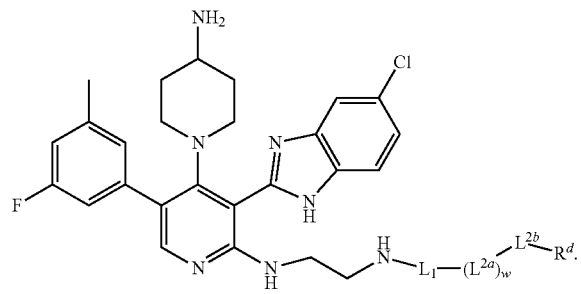

5. The compound of claim 2, or a pharmaceutically acceptable salt thereof, wherein each $L^{2a}$ is independently selected from the group consisting of natural and unnatural amino acids, wherein any free amine of an amino acid is optionally independently substituted with -CH3, wherein the natural or unnatural amino acid is selected from the group consisting of alanine (Ala), Ala (SO₃H), 3-(1-piperidinyl) alanine, cyclohexylalanine, arginine (Arg), asparagine (Asn), aspartate (Asp), cysteine (Cys), glutamine (Gln), glutamate (Glu), glycine (Gly), leucine (Leu), lysine (Lys), methionine (Met), phenylalanine (Phe), homophenylalanine, proline (Pro), serine (Ser), 3-homoserine, tyrosine (Tyr), Tyr (SO₃H), valine (Val), citrulline, β-alanine, β3-homoserine, β3-homolysine, and β3-homoglutamic acid.

6. The compound of claim 5, or a pharmaceutically acceptable salt thereof, wherein each $L^{2a}$ is independently selected from the group consisting of natural and unnatural amino acids, wherein any free amine of an amino acid is optionally independently substituted with —CH₃, and wherein the natural or unnatural amino acid is selected from alanine (Ala), Ala(SO₃H), arginine (Arg), asparagine (Asn), aspartate (Asp), cysteine (Cys), glutamine (Gln), glutamate (Glu), glycine (Gly), leucine (Leu), lysine (Lys), methionine (Met), phenylalanine (Phe), serine (Ser), valine (Val), and citrulline.

7. The compound of claim 6, or a pharmaceutically acceptable salt thereof, wherein $L^2$ is -$(L^{2a})_w$-$L^{2b}$-; and -$(L^{2a})_w$- is valine-citrulline, valine-alanine, methionine-valine-lysine, glycine-phenylalanine-glycine-glycine, tyrosine-arginine-valine, arginine-valine, or phenylalanine-lysine.

8. The compound of claim 1, or a pharmaceutically acceptable salt thereof, wherein $L^2$ is absent or is:

545
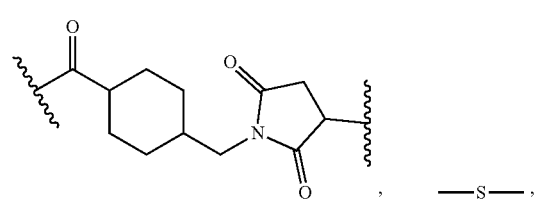
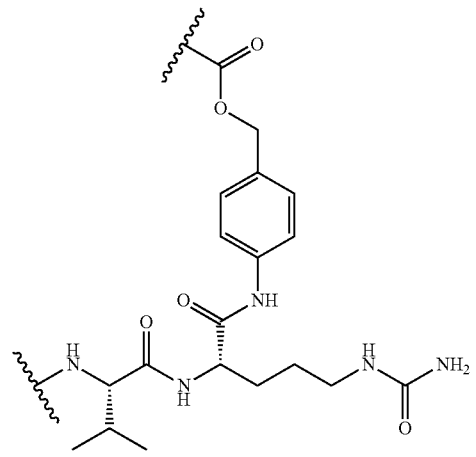
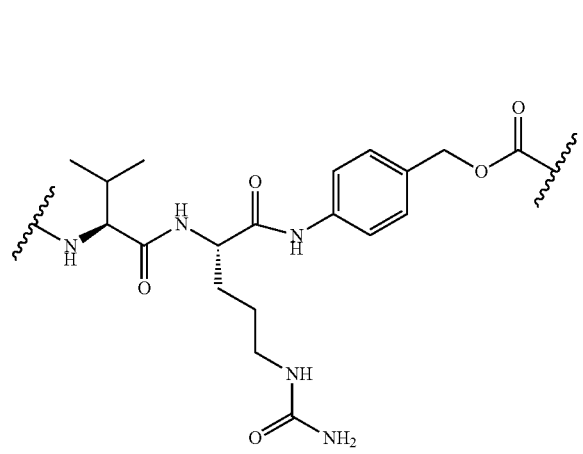
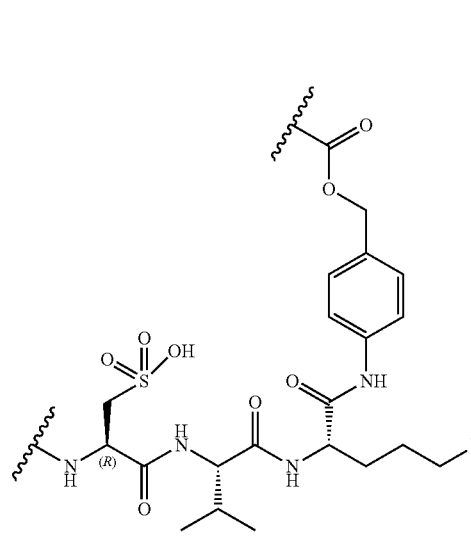
546
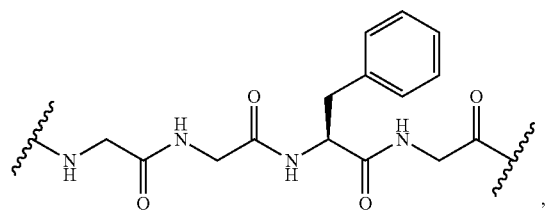, —S—,
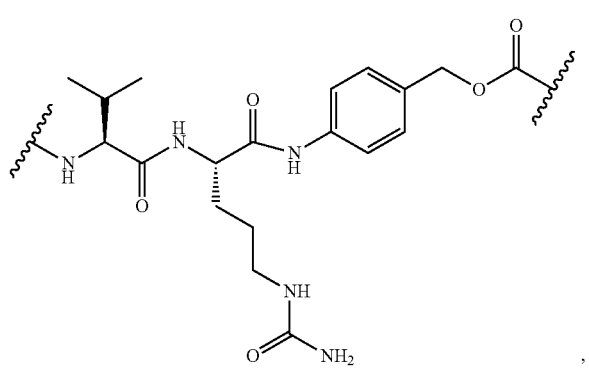
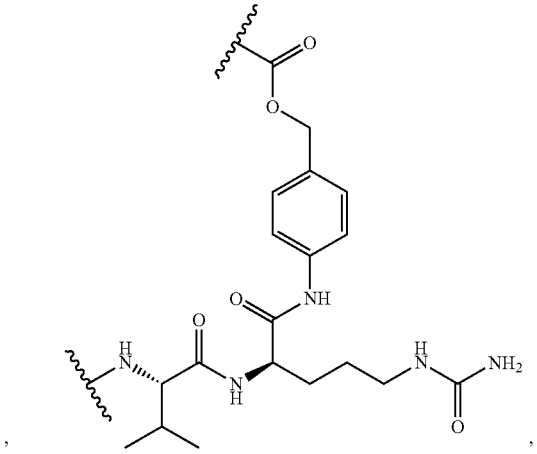
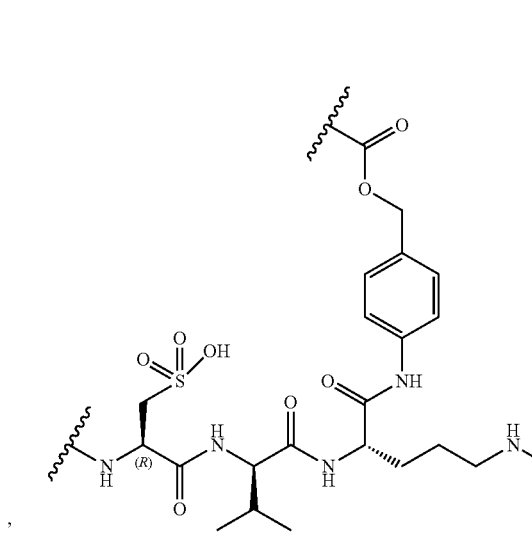

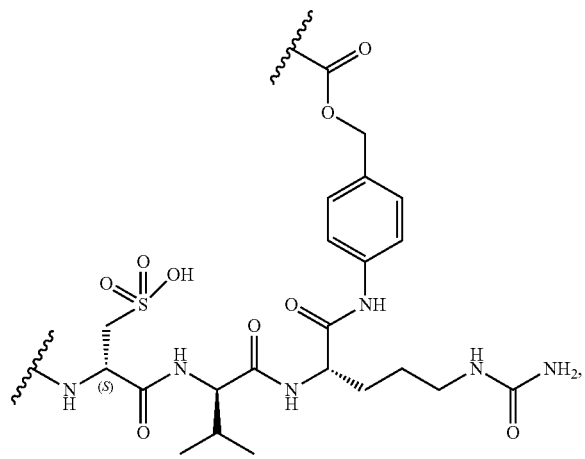
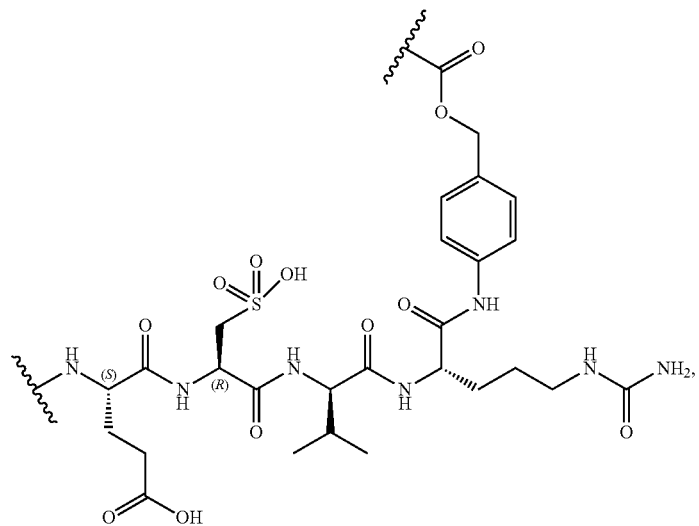
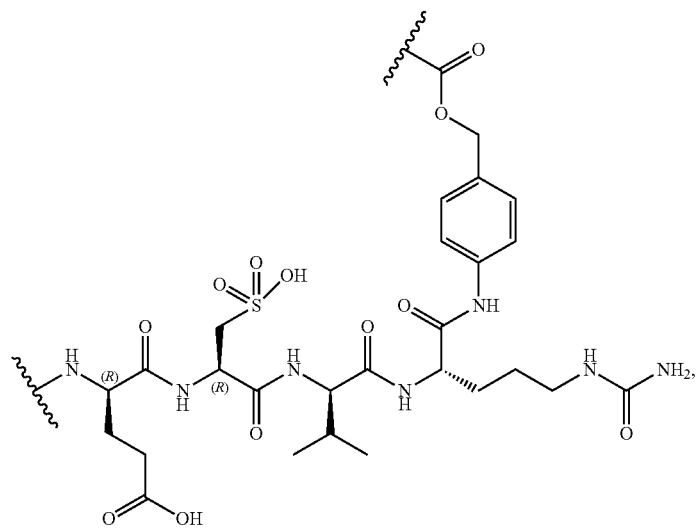

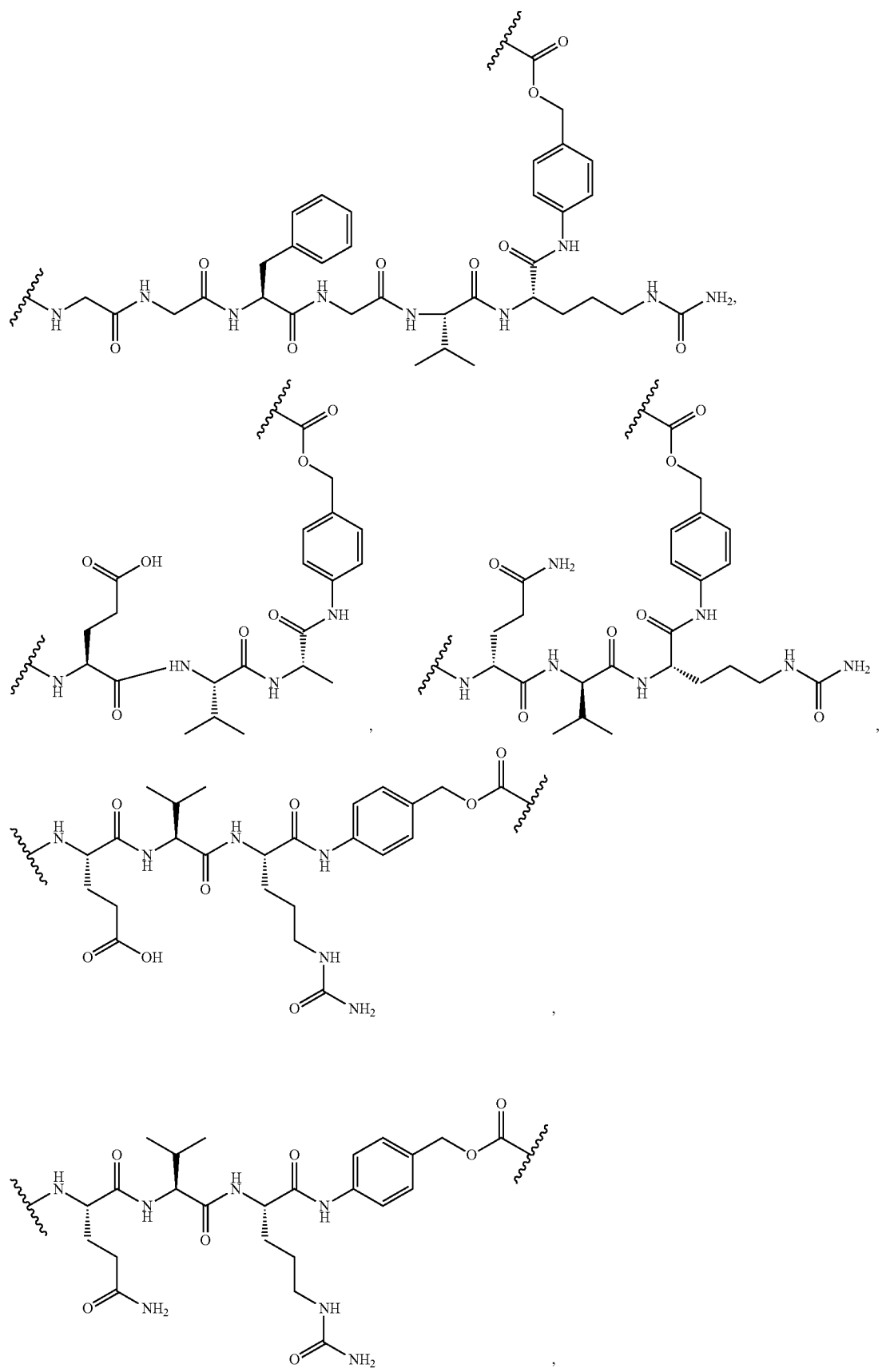

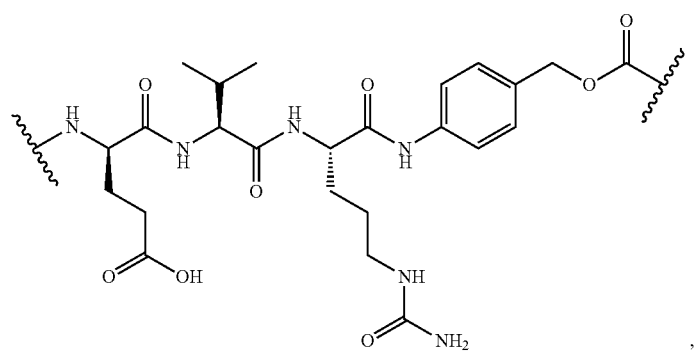
,
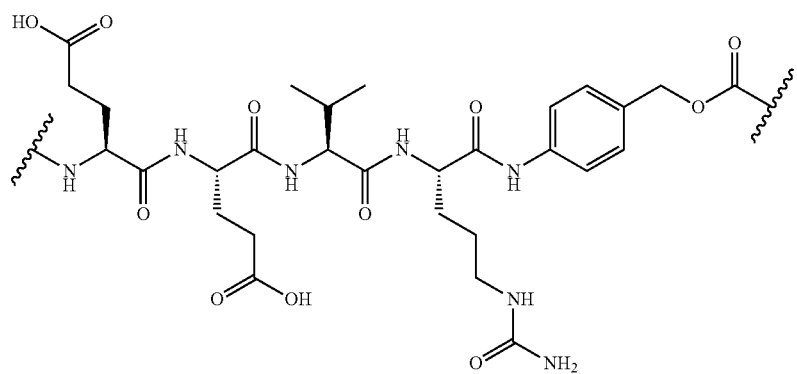
,
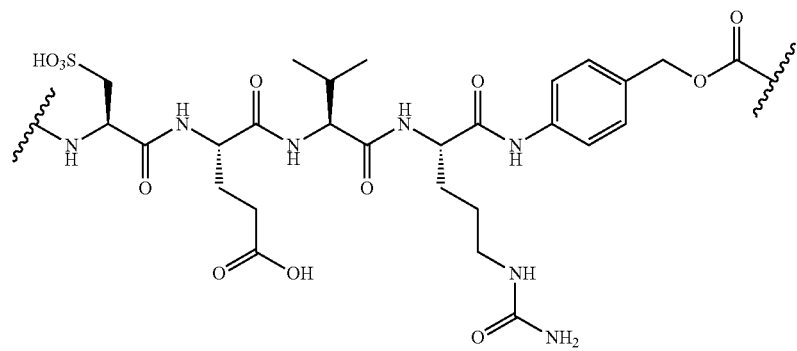
,
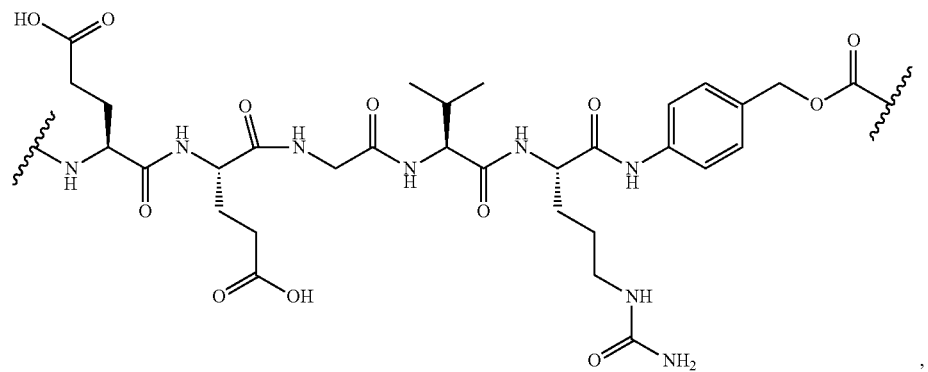
,

-continued
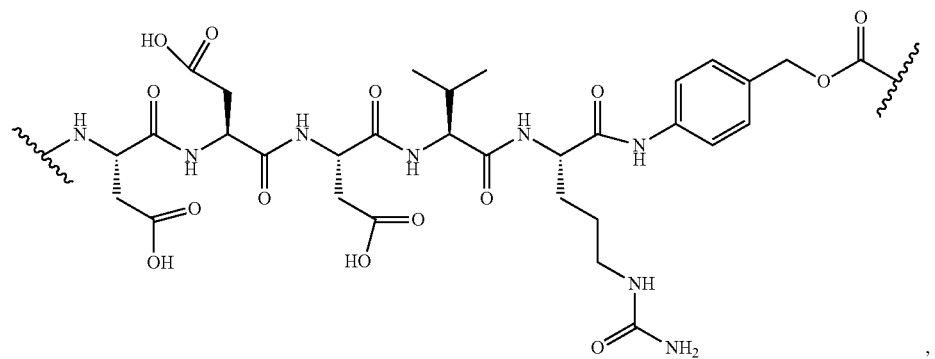
,
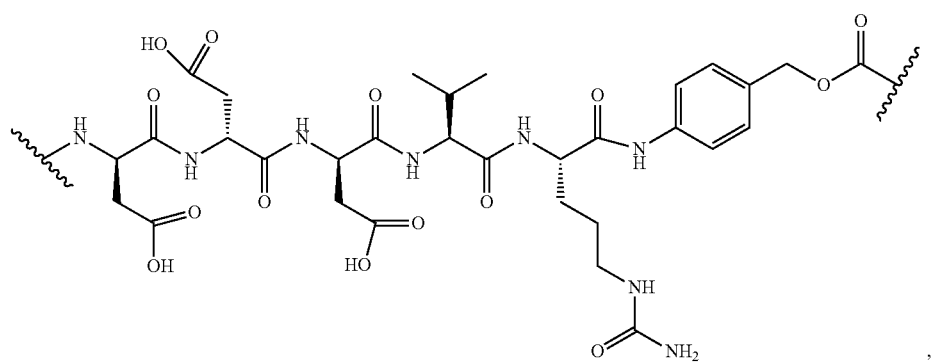
,
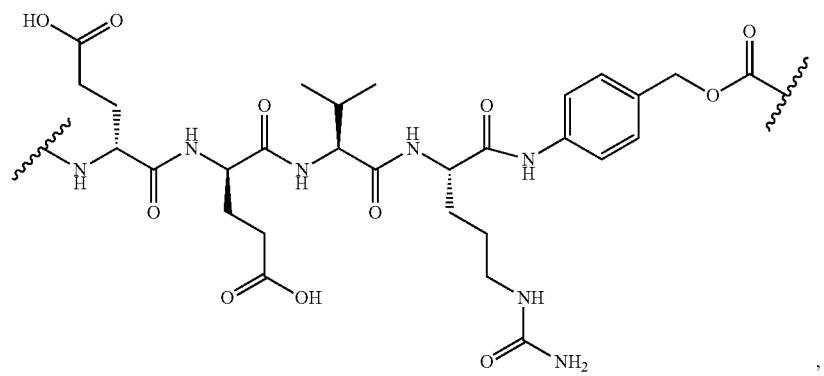
,
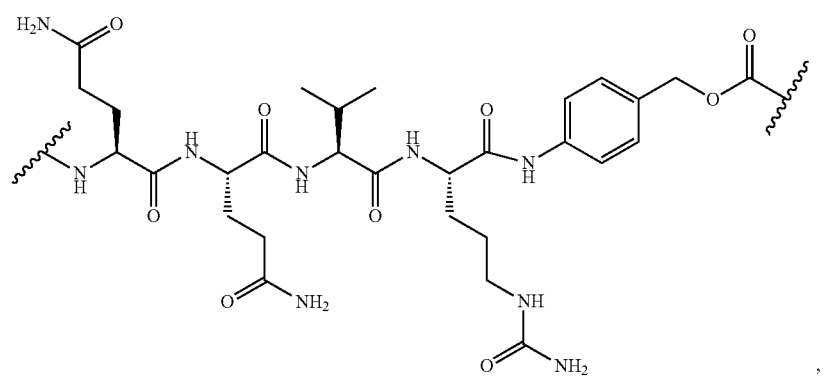
,

-continued
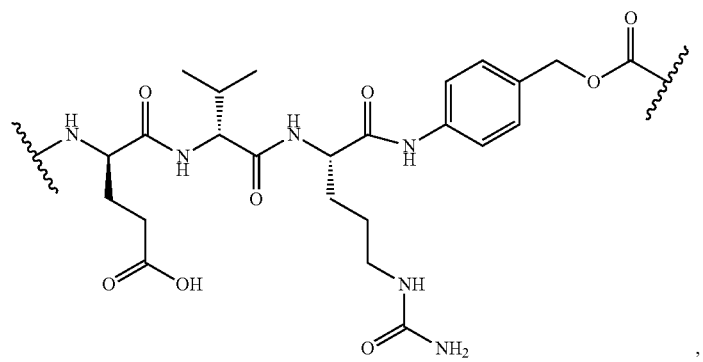
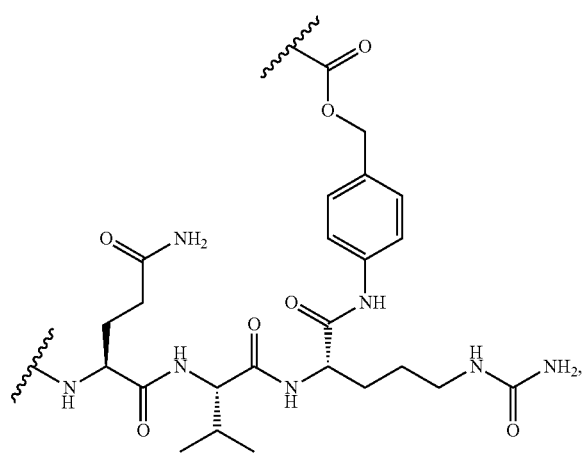
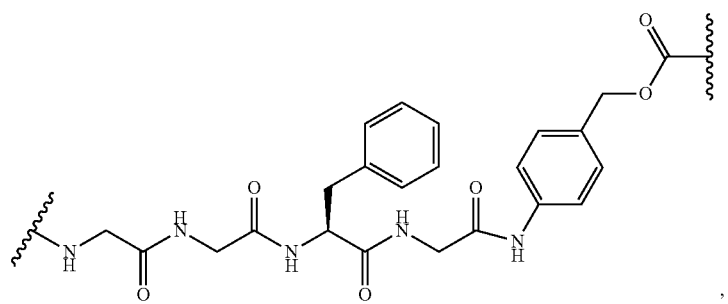
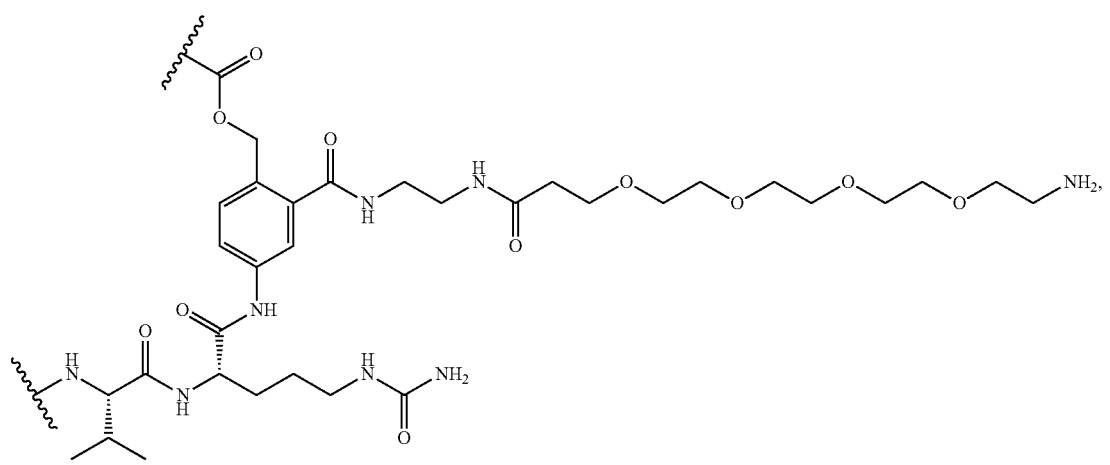

-continued
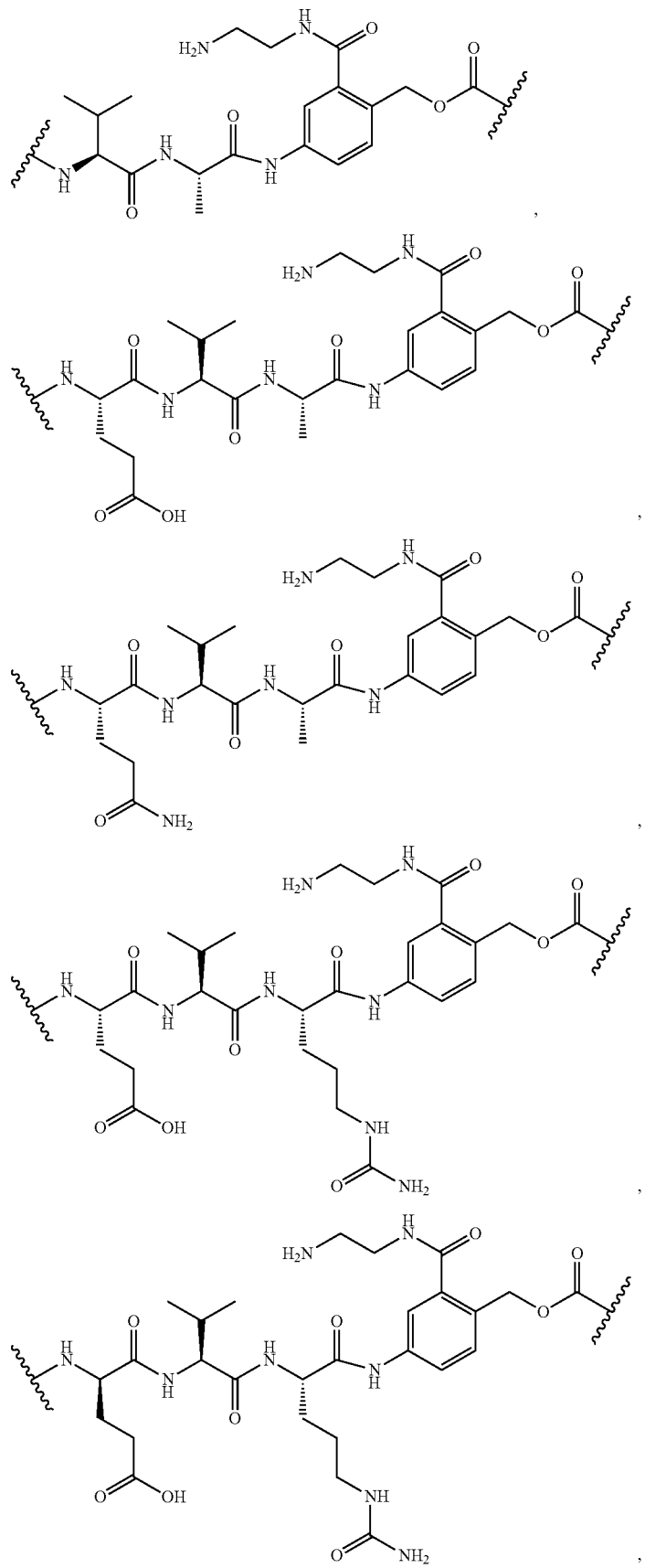

-continued
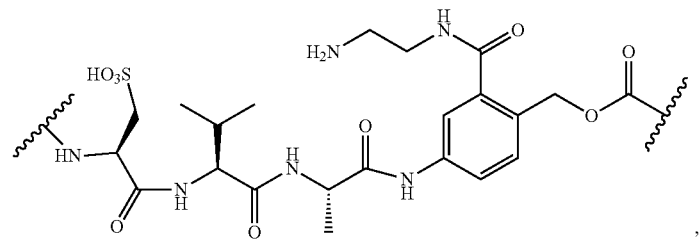
,
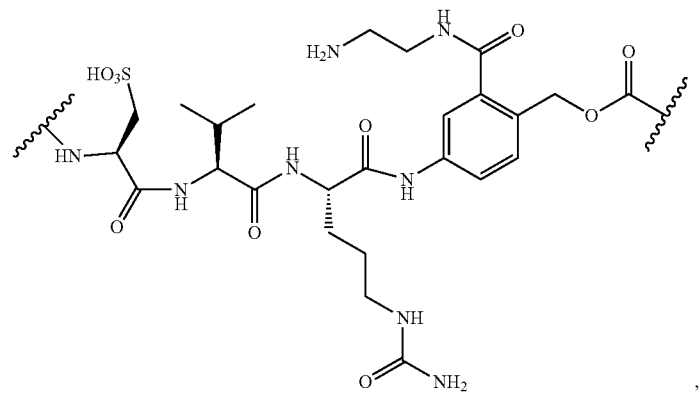
,
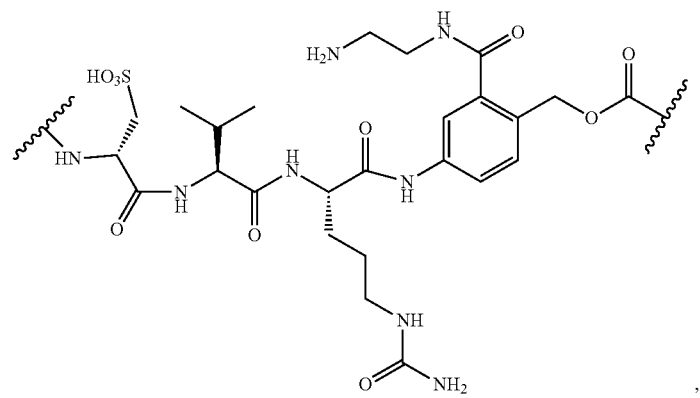
,
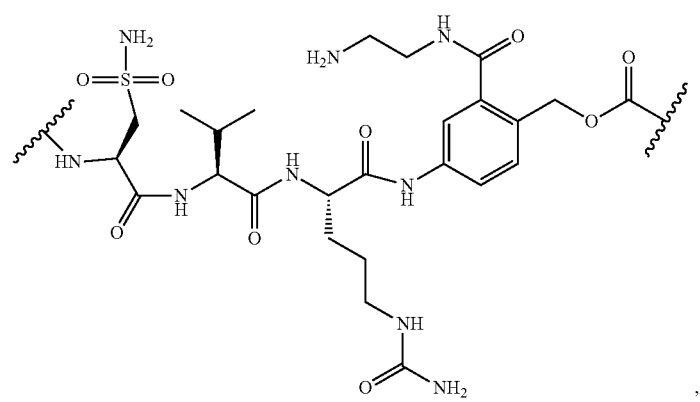
,

561  562
-continued
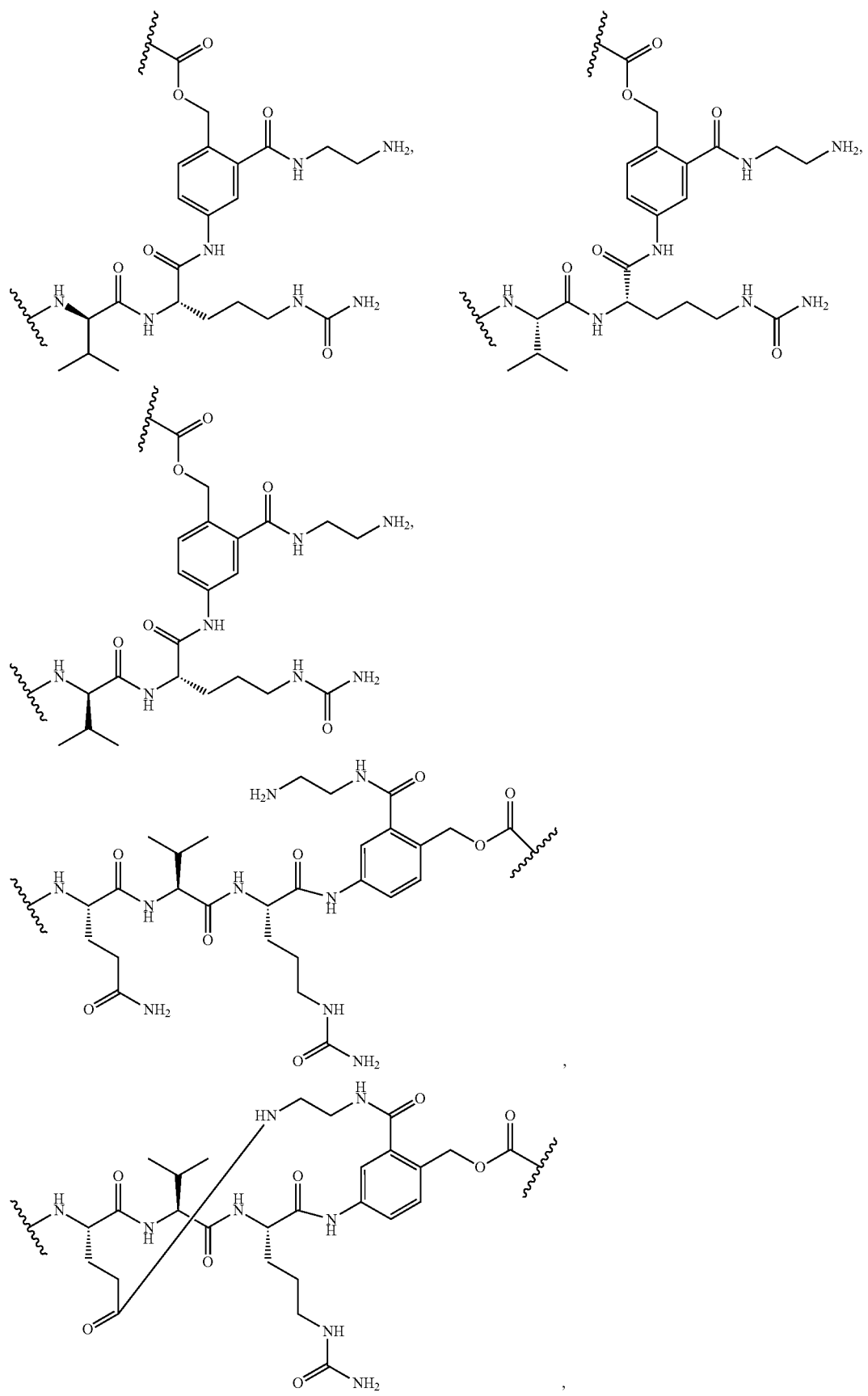

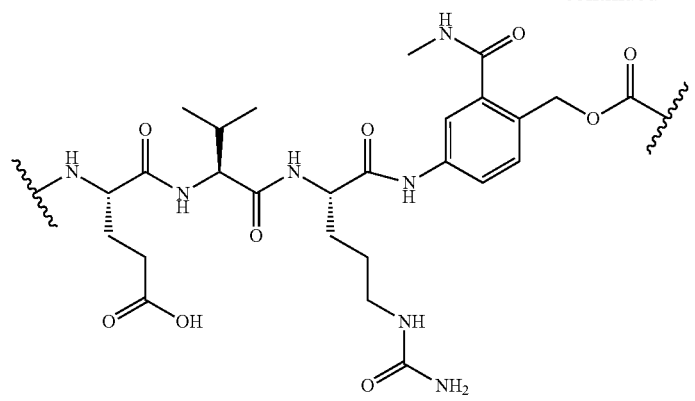,
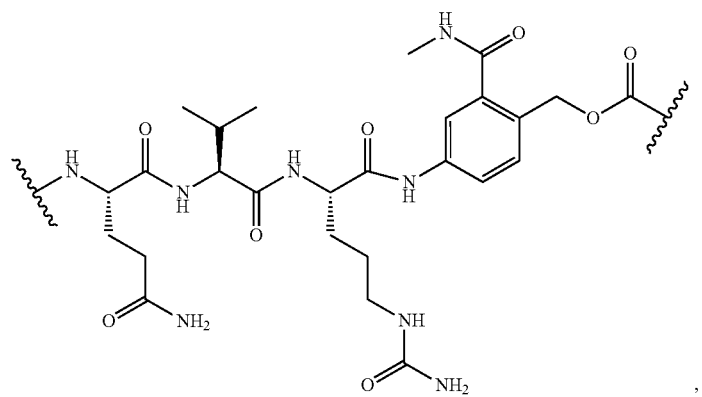,
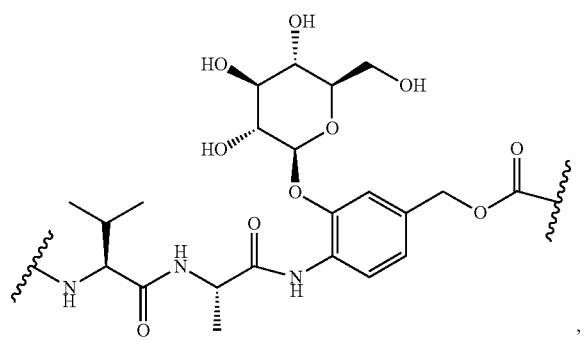,
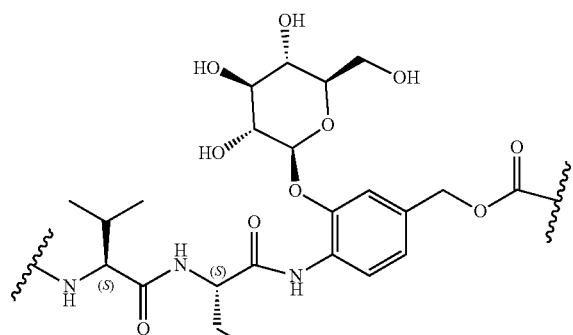,

565
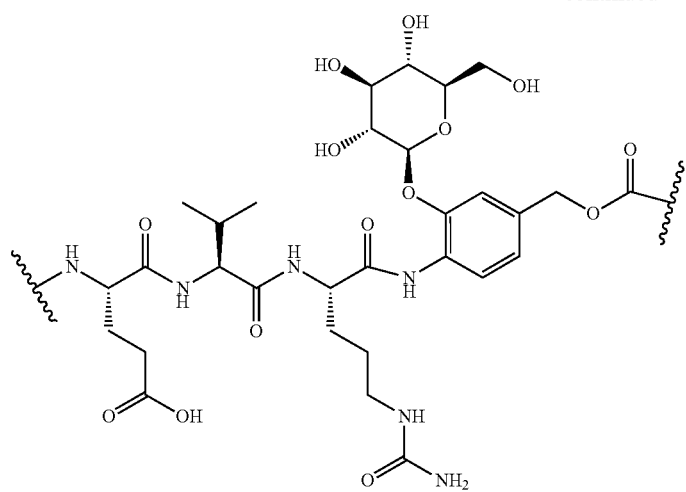
566
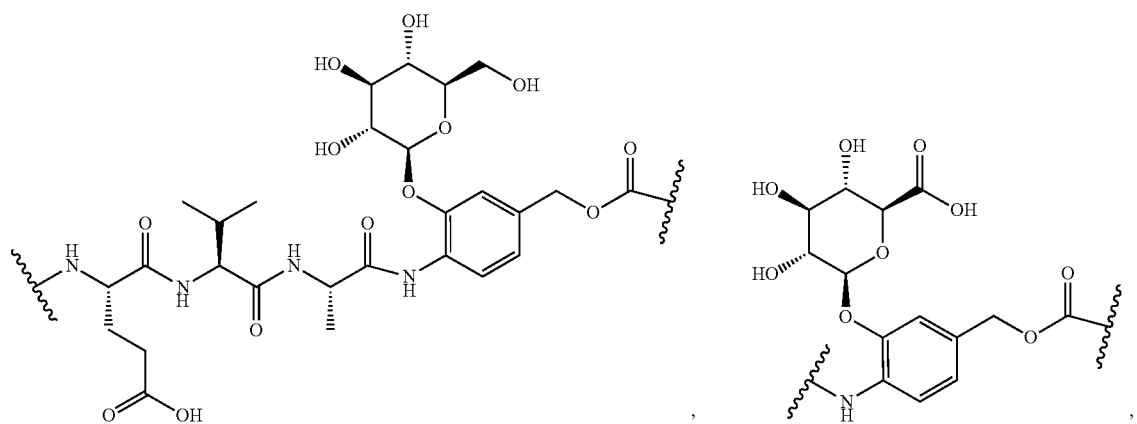
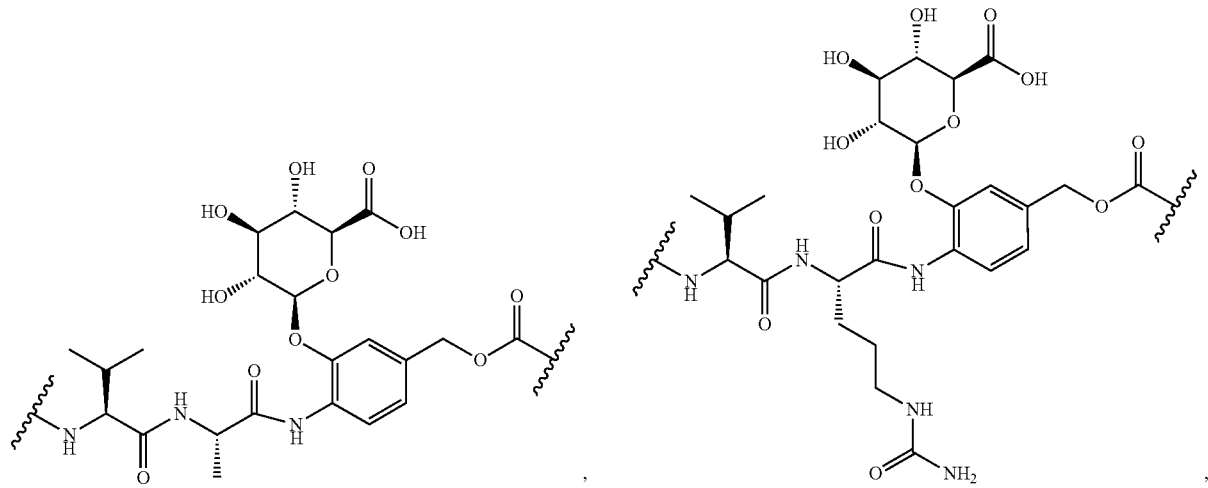

-continued
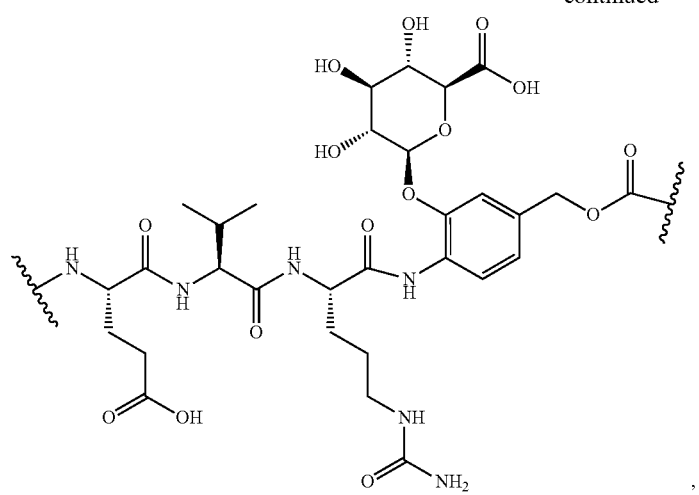
,
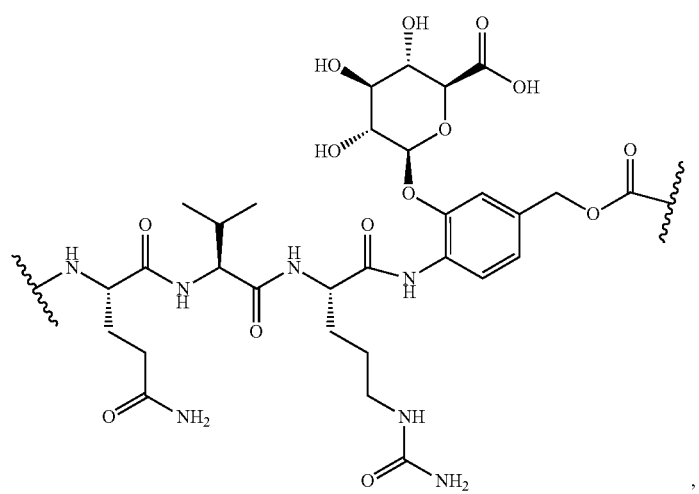
,
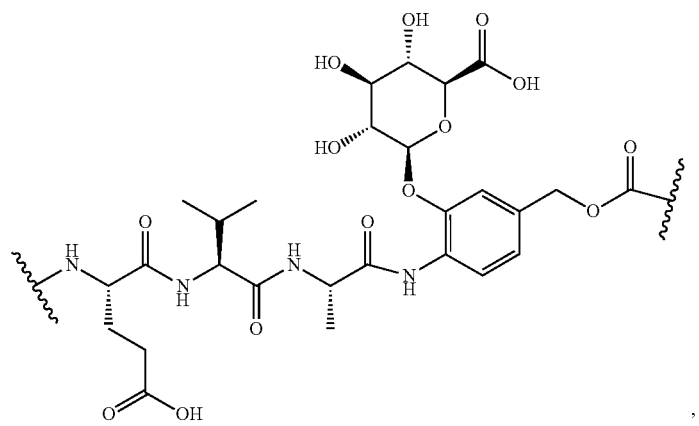
,

569
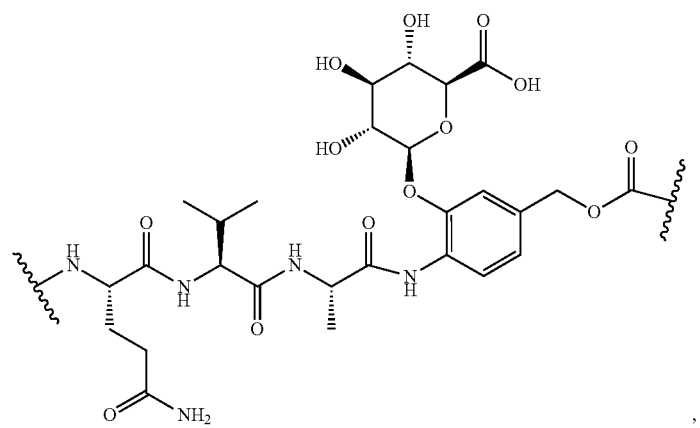
570
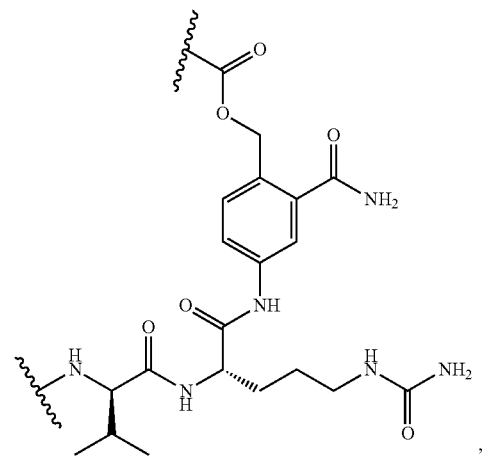
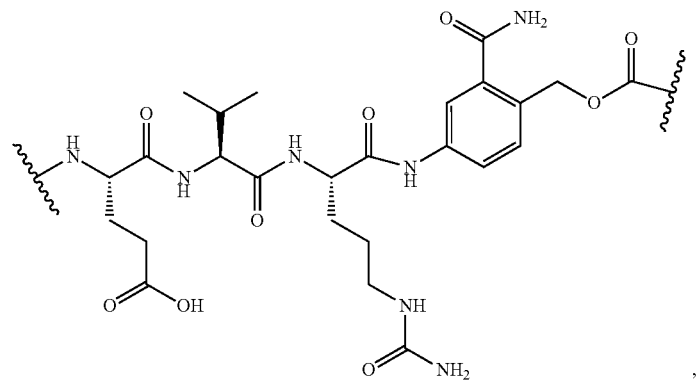
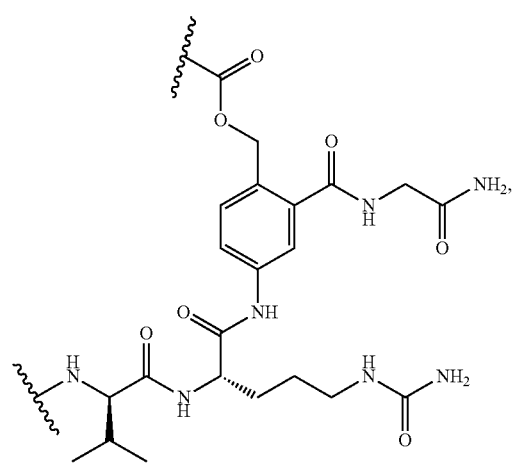
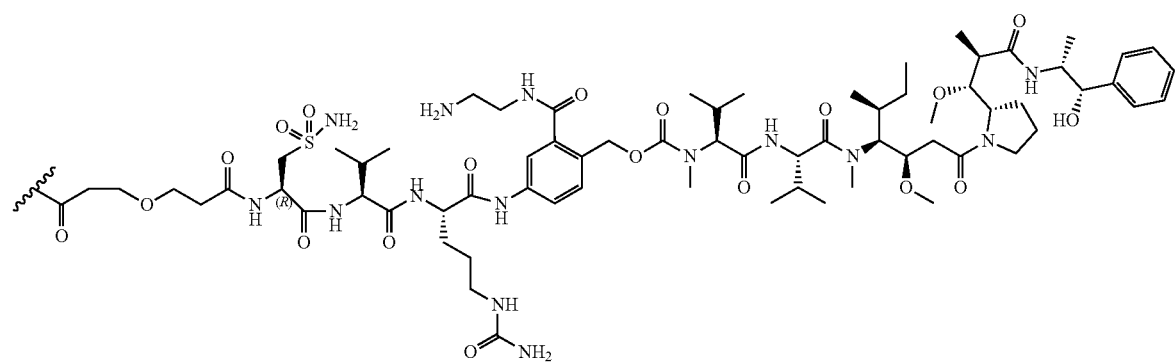

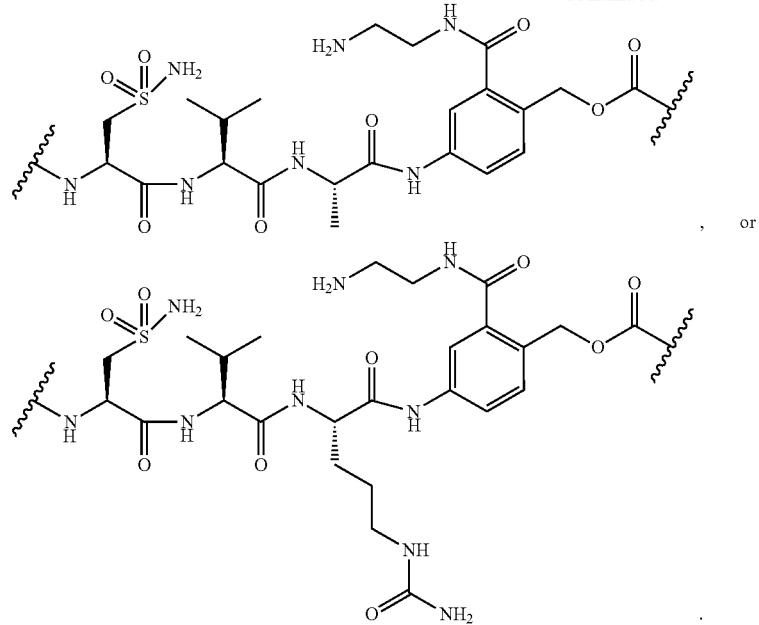

, or

9. The compound of claim 8, or a pharmaceutically acceptable salt thereof, wherein $L^2$ is absent or is:

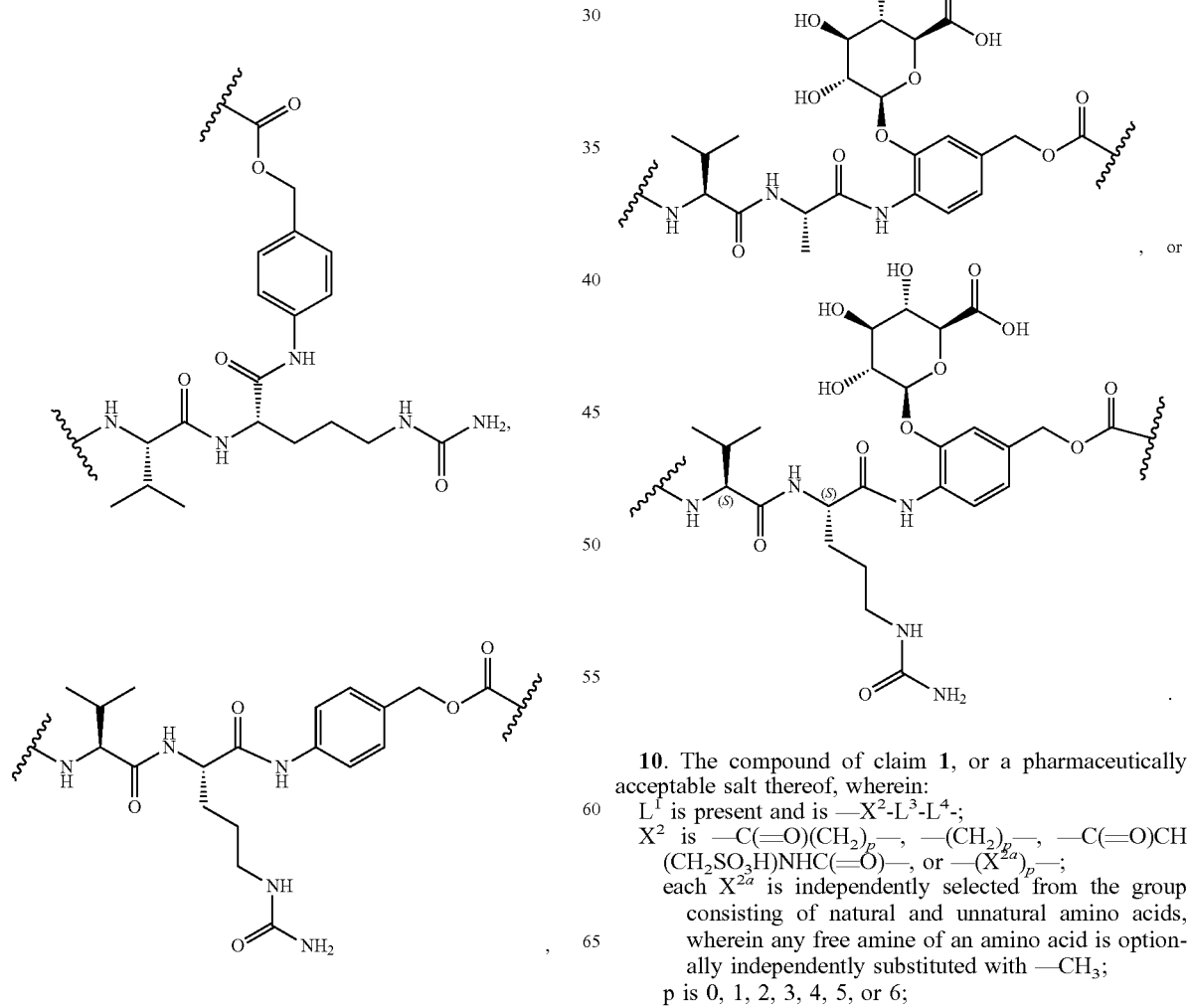

10. The compound of claim 1, or a pharmaceutically acceptable salt thereof, wherein:
$L^1$ is present and is —$X^2$-$L^3$-$L^4$-;
$X^2$ is —C(=O)(CH$_2$)$_p$—, —(CH$_2$)$_p$—, —C(=O)CH(CH$_2$SO$_3$H)NHC(=O)—, or —(X$^{2a}$)$_p$—;
each $X^{2a}$ is independently selected from the group consisting of natural and unnatural amino acids, wherein any free amine of an amino acid is optionally independently substituted with —CH$_3$;
p is 0, 1, 2, 3, 4, 5, or 6;

$L^3$ is absent, unsubstituted or substituted $C_1$-$C_{10}$alkylene, unsubstituted or substituted $C_1$-$C_{10}$heteroalkylene, $C_4$-$C_{20}$polyethylene glycol, or —$(X^3CH_2CH_2)_t$—;
each $X^3$ is independently selected from the group consisting of O and $NR^{10}$;
each t is independently 1, 2, 3, 4, 5, 6, 7, 8, 9, 10, 11, or 12;
$L^4$ is absent, or -$L^{4a}$-$(CH_2)_u$-$L^{4b}$-$(CH_2)_u$-$L^{4c}$-;
$L^{4a}$ is absent, —O—, —$NR^{10}$—, —$NR^{10}$(=O)—, —C(=O)$NR^{10}$—, or —C(=O)—;
$L^{4b}$ is absent, or unsubstituted or substituted N-containing 5 to 10 membered heterocycloalkylene; wherein any free amine of the N-containing 5 to 10 membered heterocycloalkylene is optionally independently substituted with-$CH_2CO_2H$;
$L^{4c}$ is absent, —O—, —$NR^{10}$—, —$NR^{10}$C(=O)—, —C(=O)$NR^{10}$—, —C(=O)$NR^{10}(CH_2)_uO(CH_2)_u$ C(=O)—, $CH(CH_2SO_3H)C(=O)NR^{10}(CH_2)_uO(CH_2)_uC(=O)$—, —C(=O)—, —CH(=N)—, —CH(=N—NH)—, —$CCH_3$(=N)—, —$CCH_3$(=N—NH)—, —C(=O)—($C_1$-$C_6$alkylene)-, —C(=O)$NR^{10}$—($C_1$-$C_6$alkylene)-, —$NR^{10}$C(=O)—($C_1$-$C_6$alkylene)-, —$NR^{10}$—($C_1$-$C_6$alkylene)- or $C_1$-$C_6$alkylene-;

each u is independently 0, 1, 2, 3, 4, 5, or 6; and each $R^{10}$ is independently selected from the group consisting of hydrogen, and $C_1$-$C_6$alkyl.

11. The compound of claim 10, or a pharmaceutically acceptable salt thereof, wherein:

$X^2$ is —C(=O)($CH_2$)$_p$—; p is 0, 1, 2, 3 or 4;

$L^3$ is unsubstituted or substituted $C_1$-$C_{10}$heteroalkylene, $C_4$-$C_{20}$polyethylene glycol, or —$(X^3CH_2CH_2)_t$—;

each $X^3$ is independently selected from the group consisting of O and $NR^{10}$; and each t is independently 1, 2, 3, 4, 5, 6, 7, 8, 9, 10, 11, or 12.

12. The compound of claim 10, or a pharmaceutically acceptable salt thereof, wherein:

$L^4$ is absent or -$L^{4a}$-; and $L^{4a}$ is —$NR^{10}$—, —$NR^{10}$C(=O)—, —C(=O)$NR^{10}$—, or —C(=O)—.

13. The compound of claim 1, or a pharmaceutically acceptable salt thereof, wherein $L^1$ is absent or is:

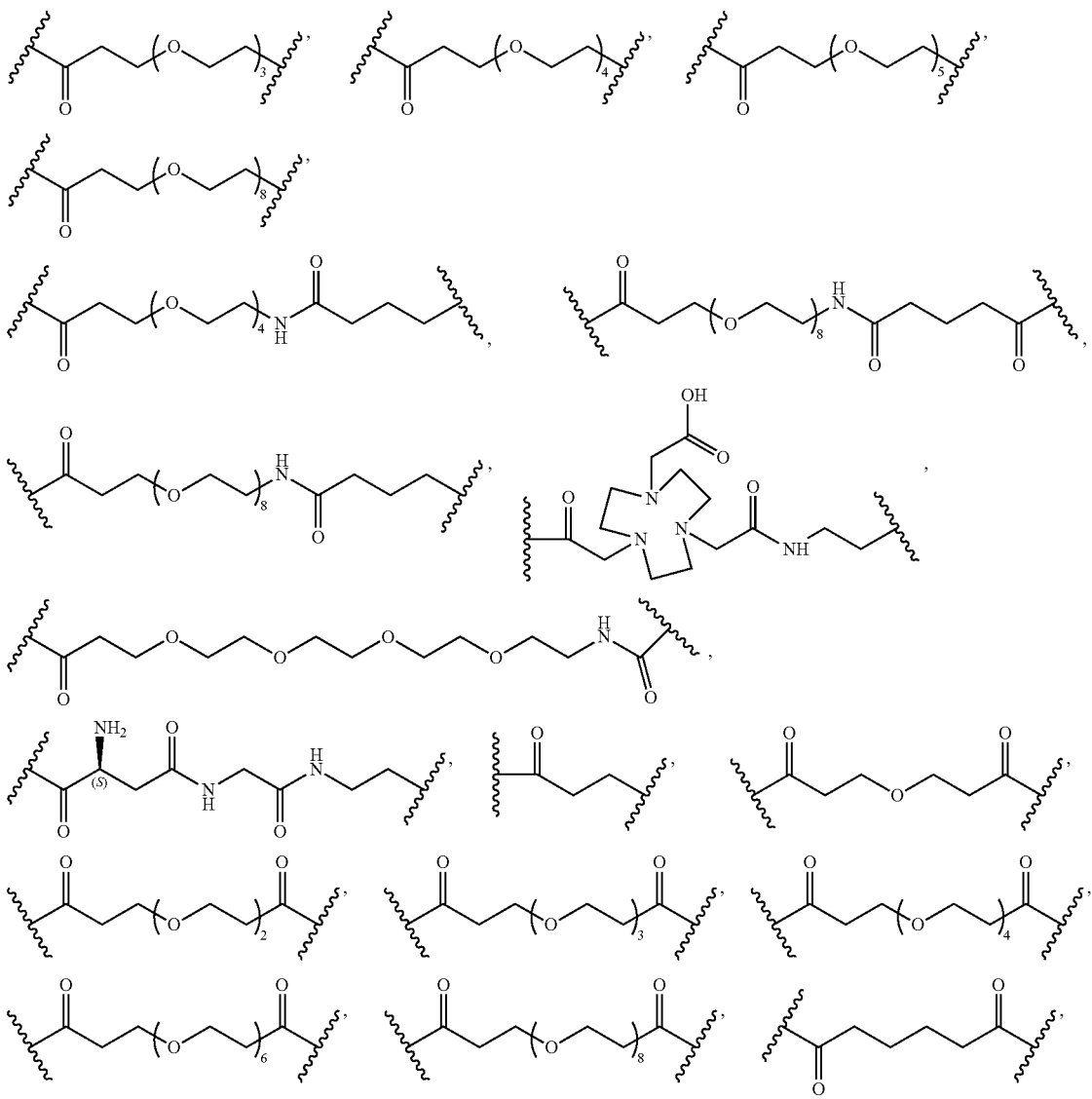

-continued
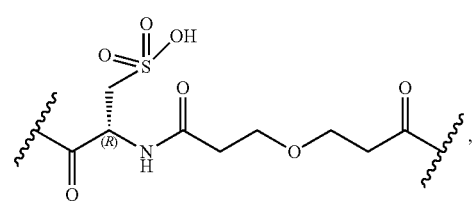
, 
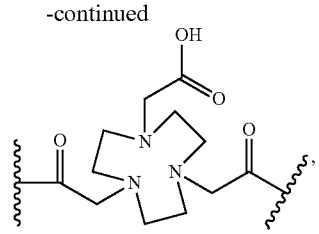
,
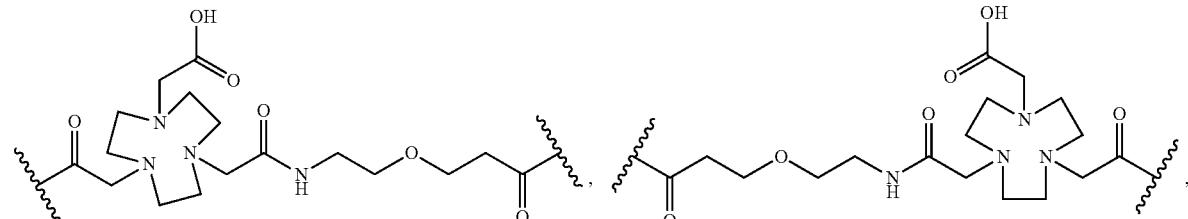
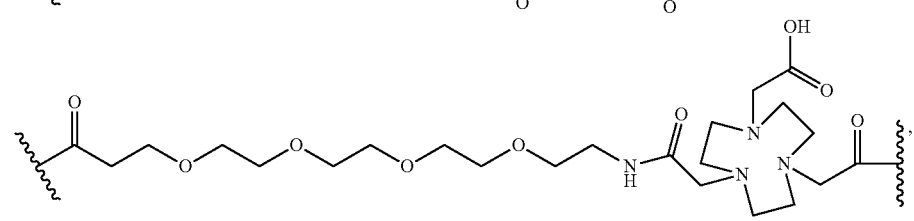
,
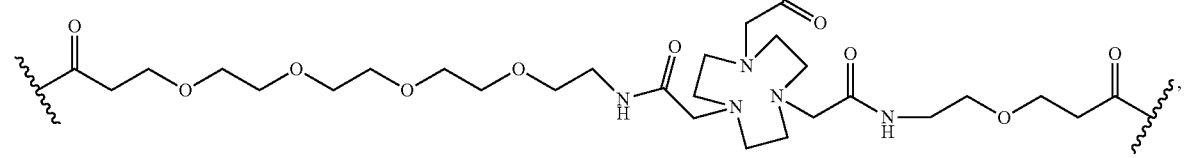
,
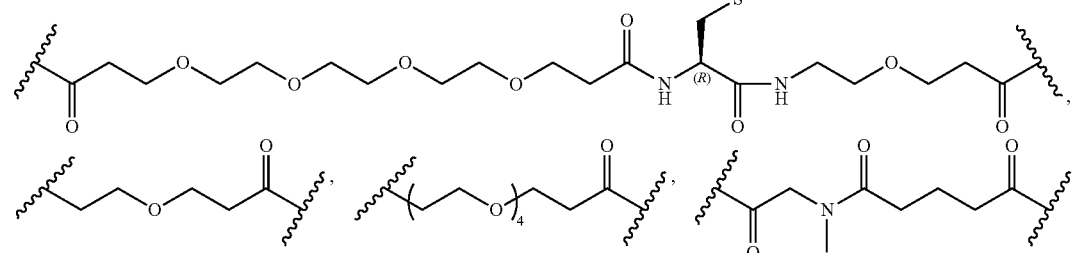
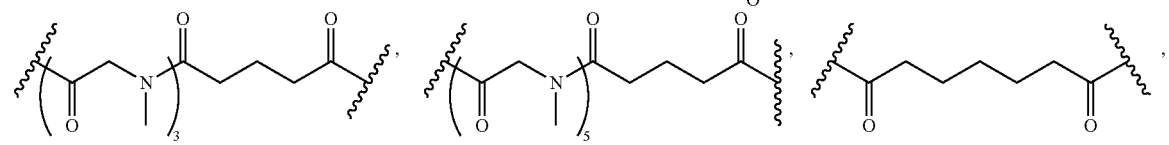
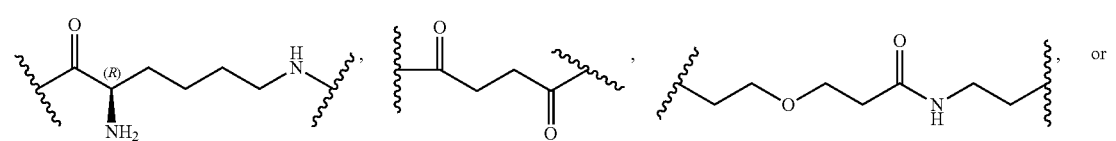
or
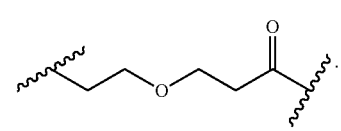
.

14. The compound of claim 13, or a pharmaceutically acceptable salt thereof, wherein $L^1$ is absent or is:
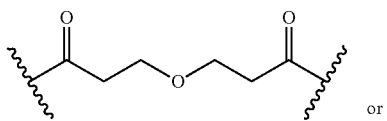 or
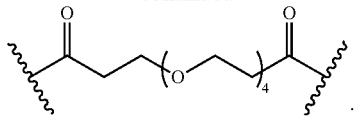
15. The compound of claim 1, or a pharmaceutically acceptable salt thereof, wherein L is:
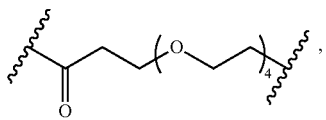, 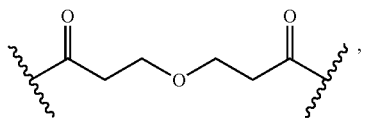,
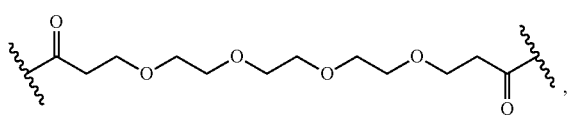 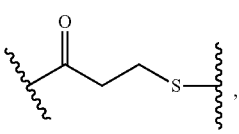,
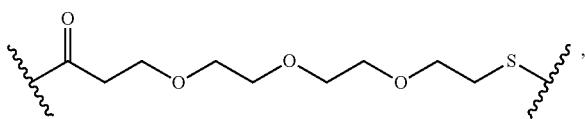, ,
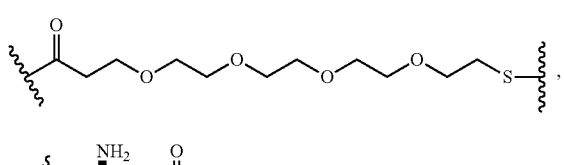 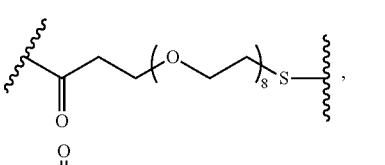,
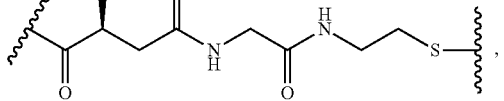 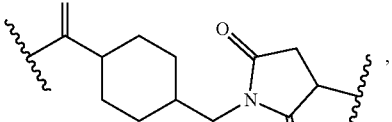
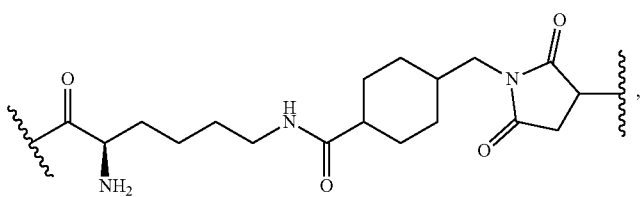
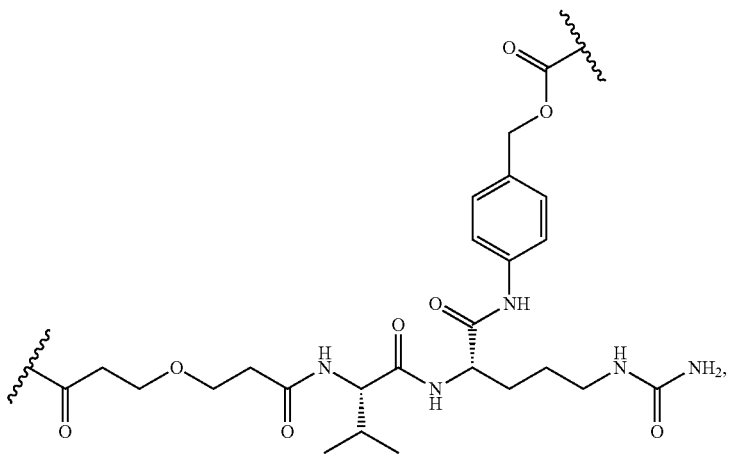

-continued
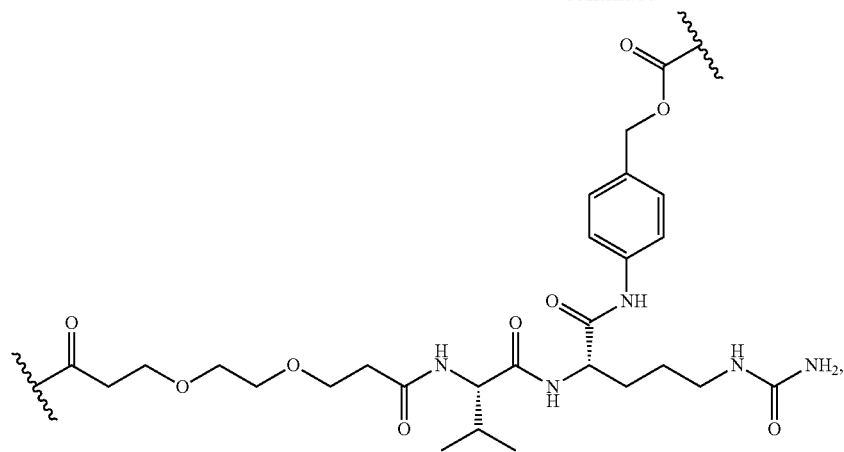
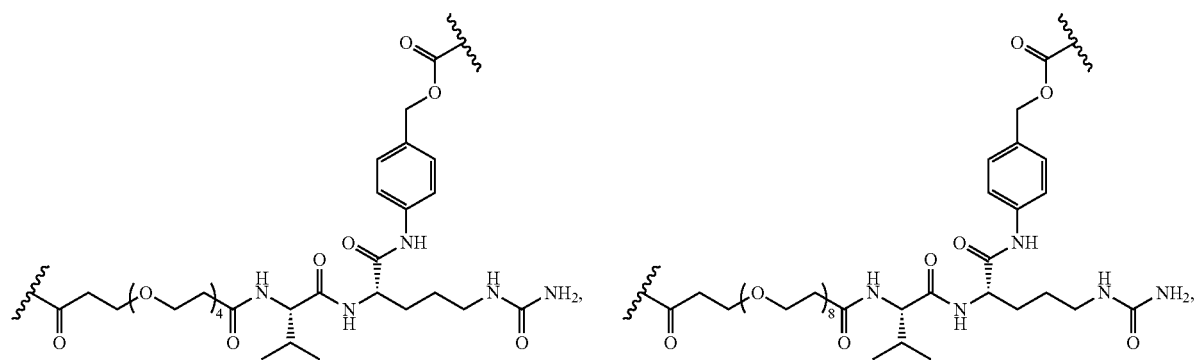
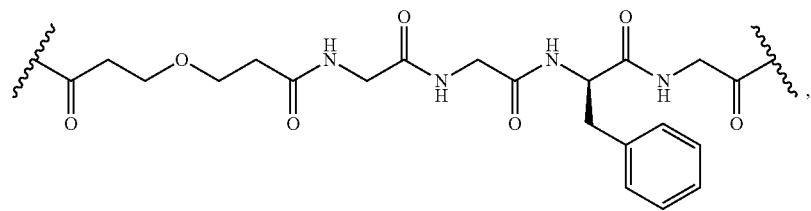
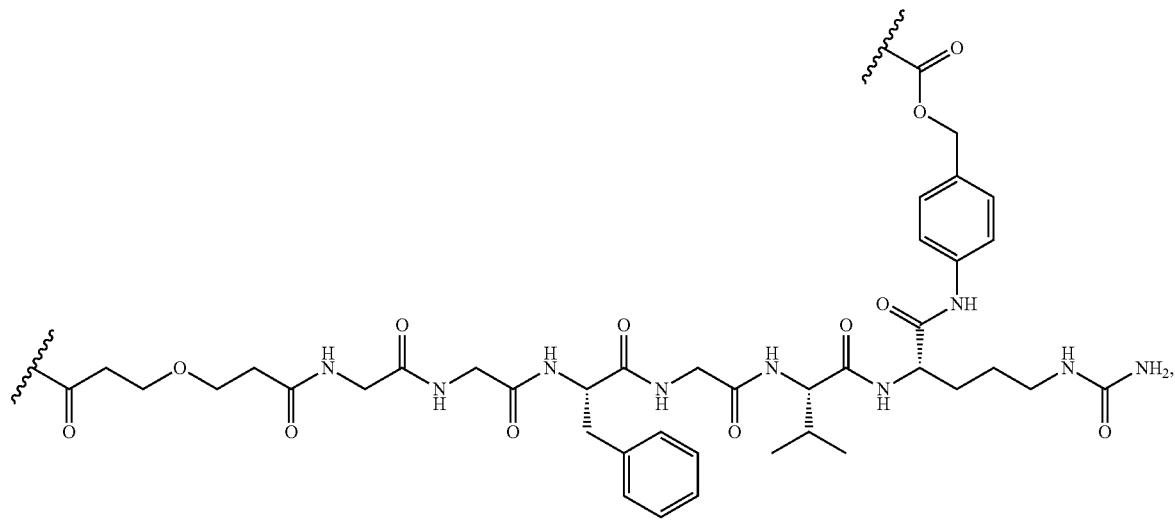

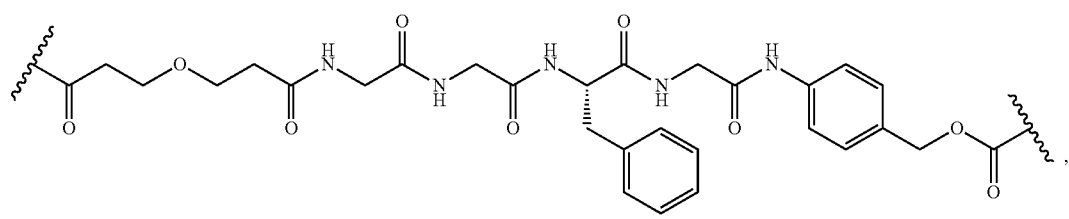
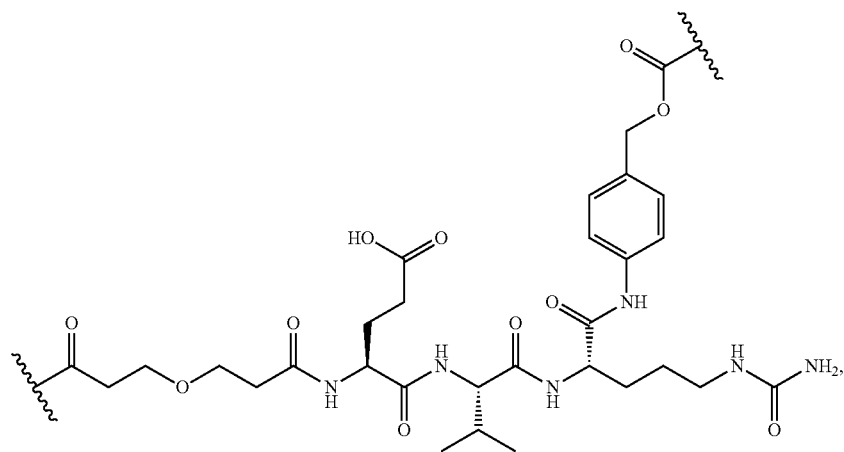
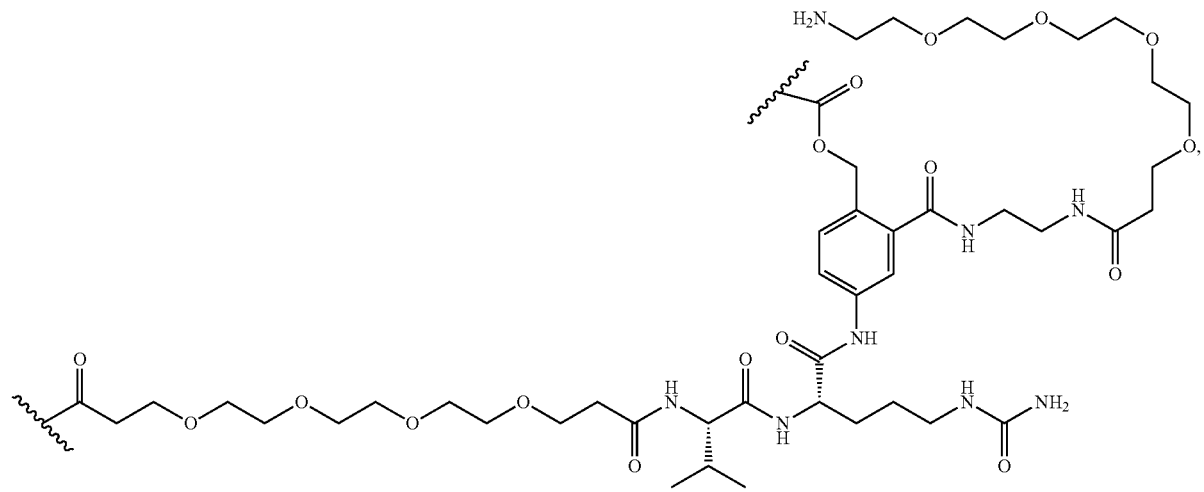
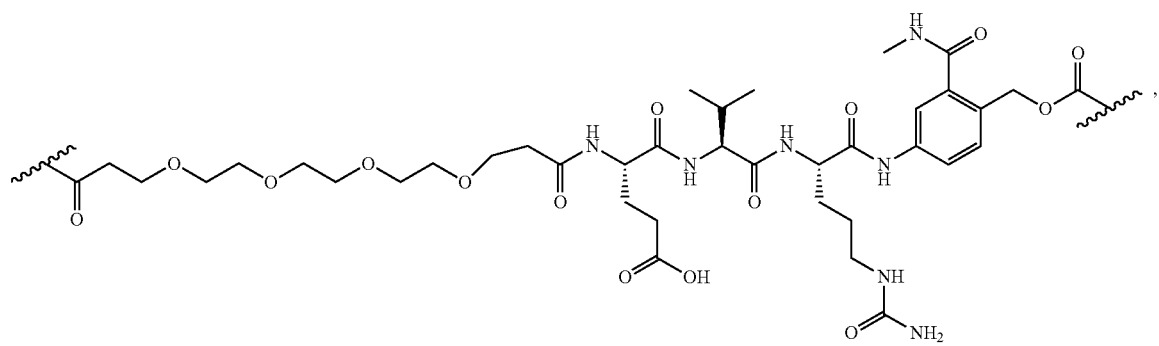

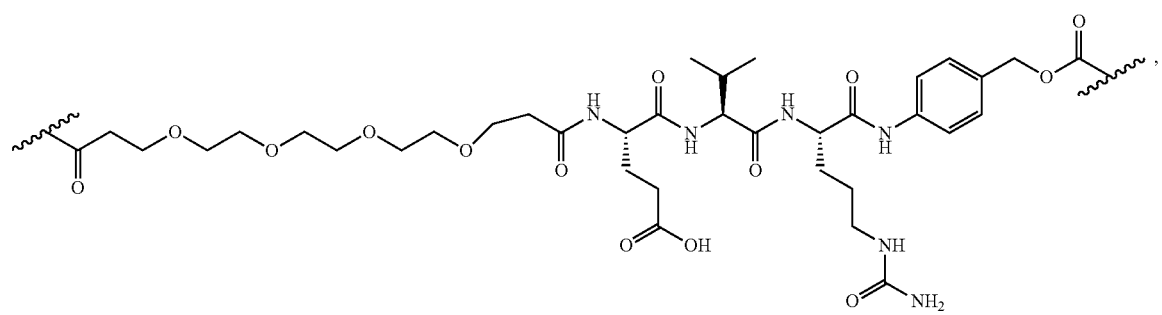
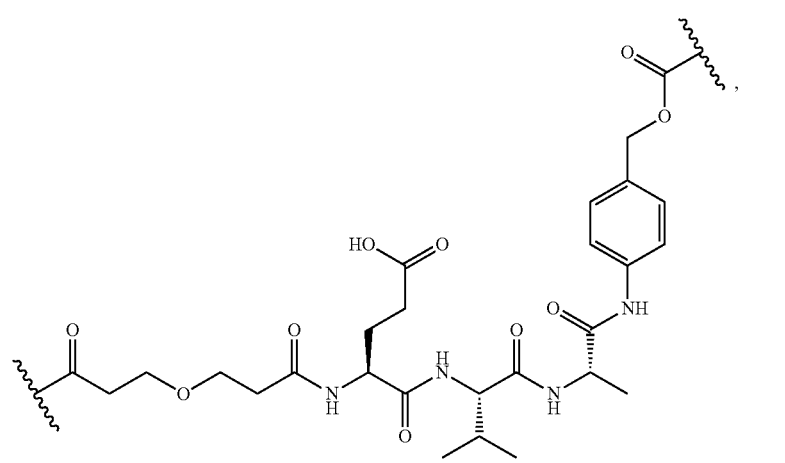
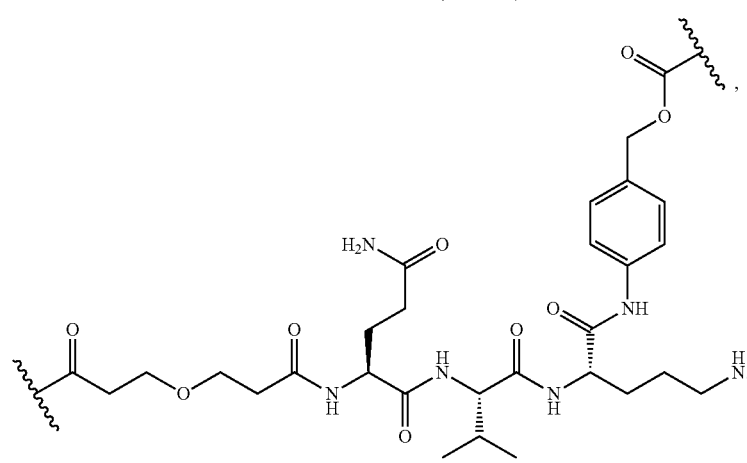
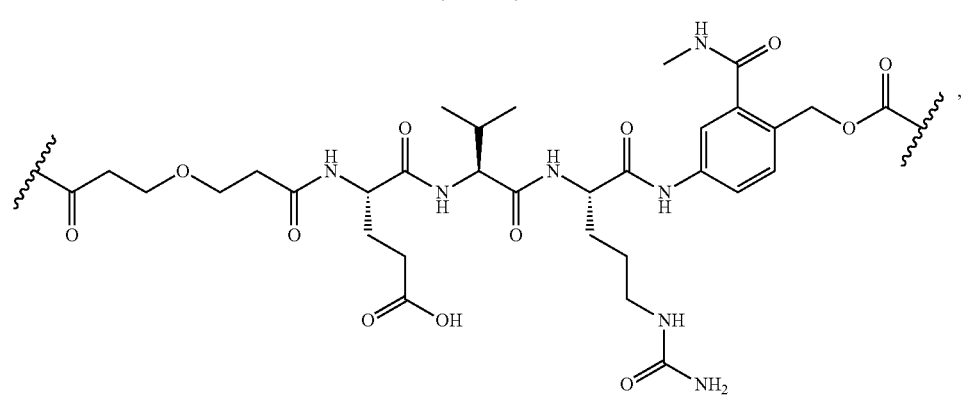

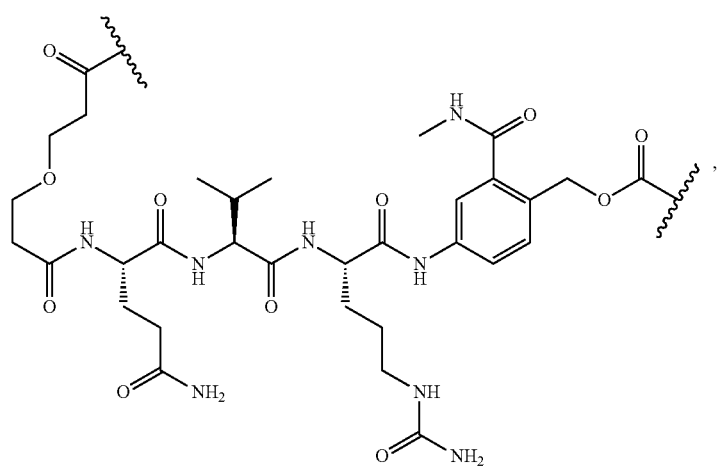
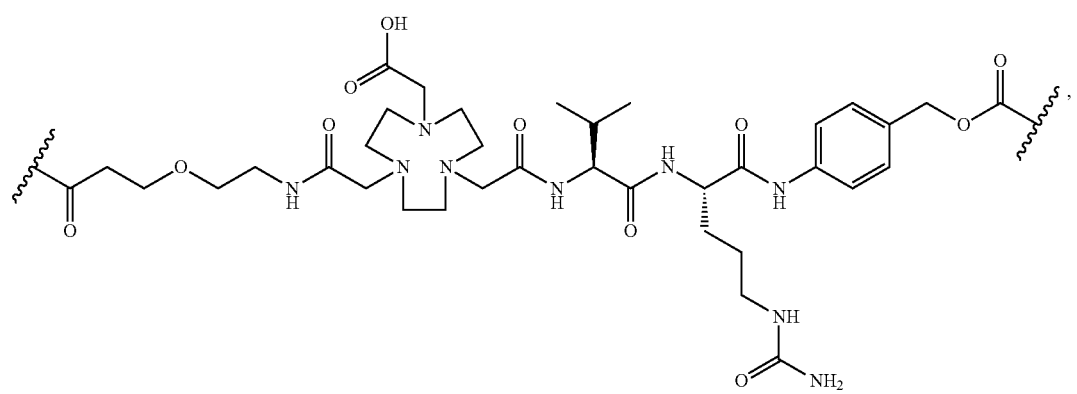
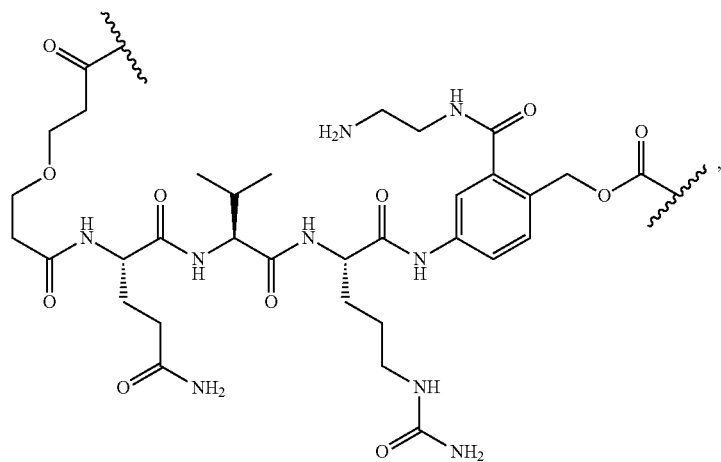

-continued
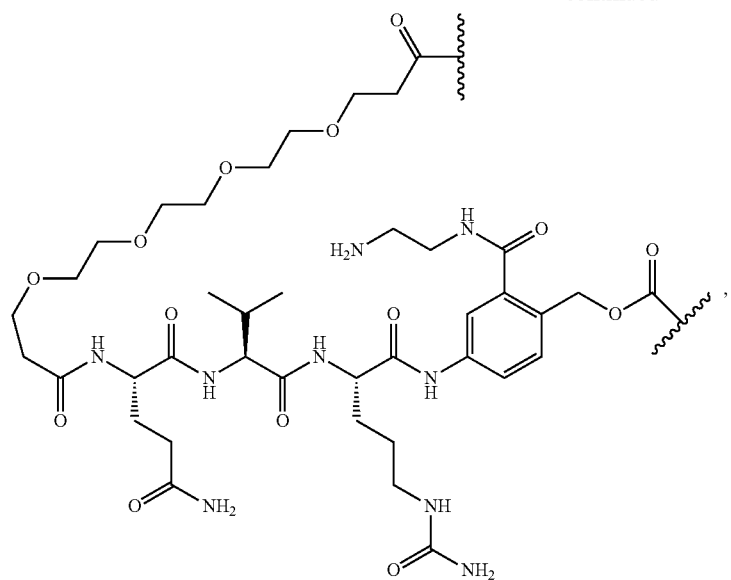
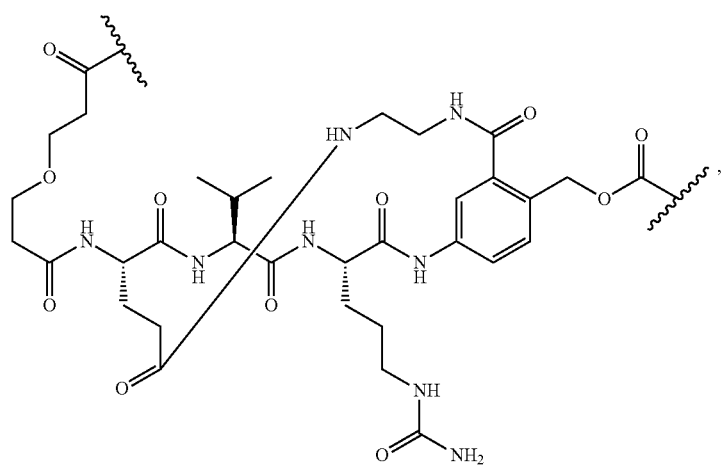
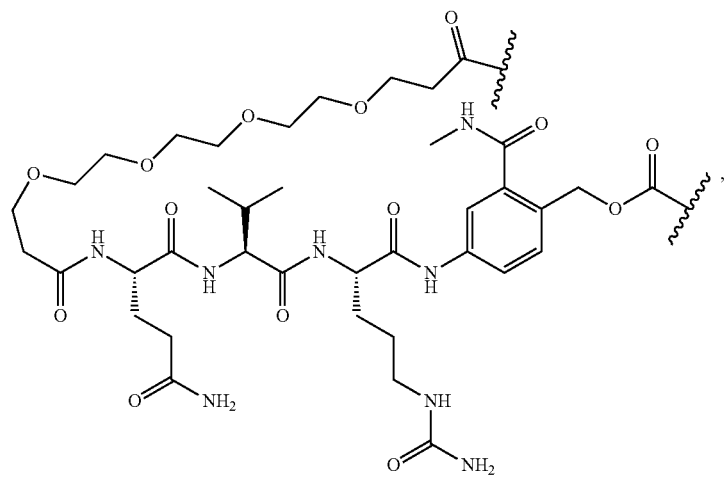

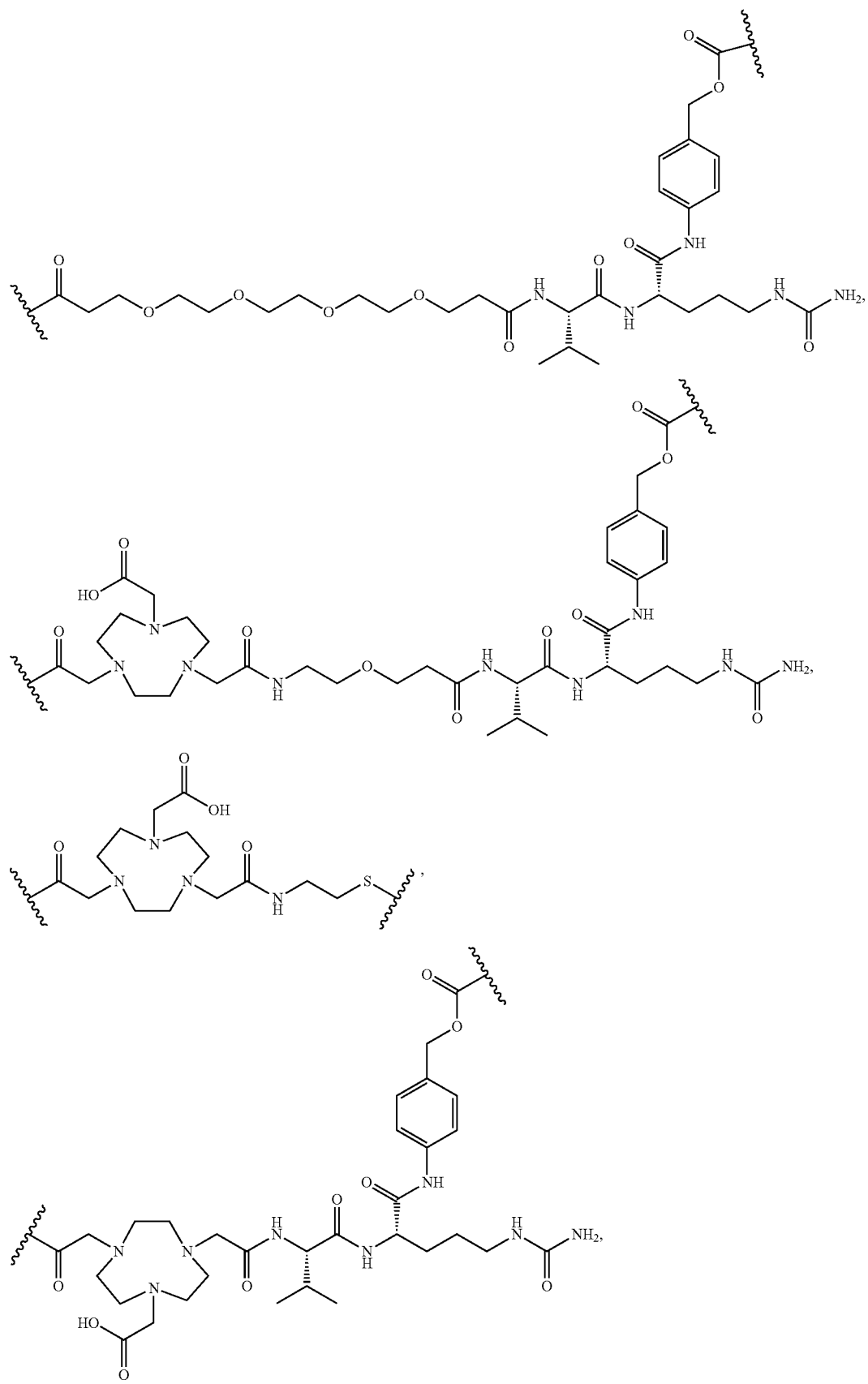

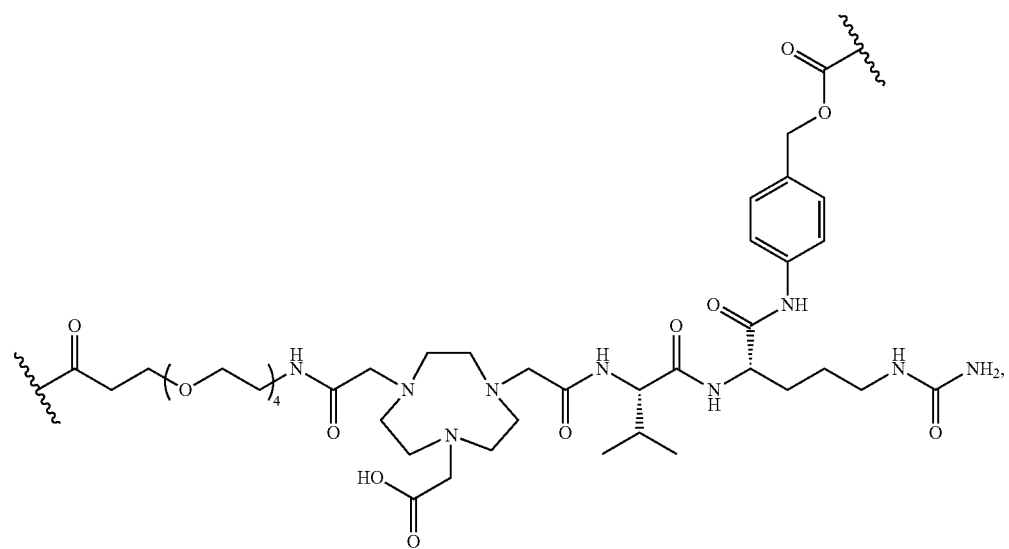
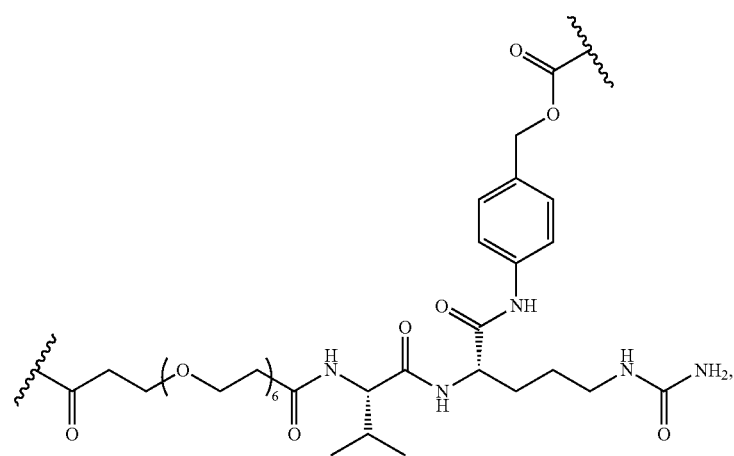
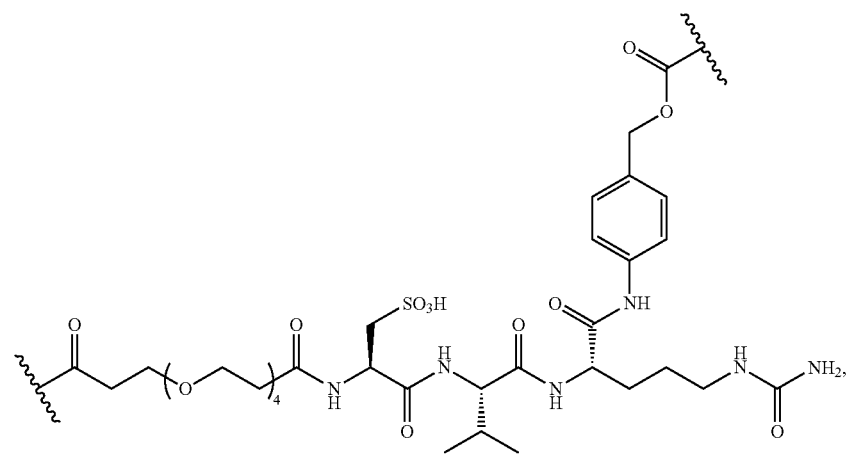

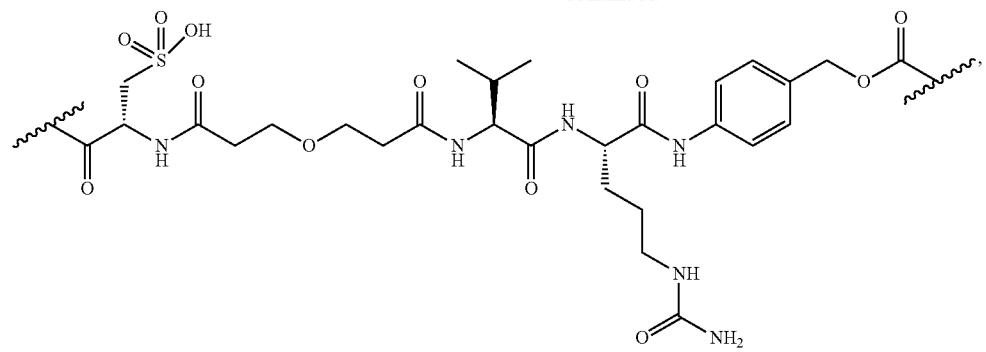
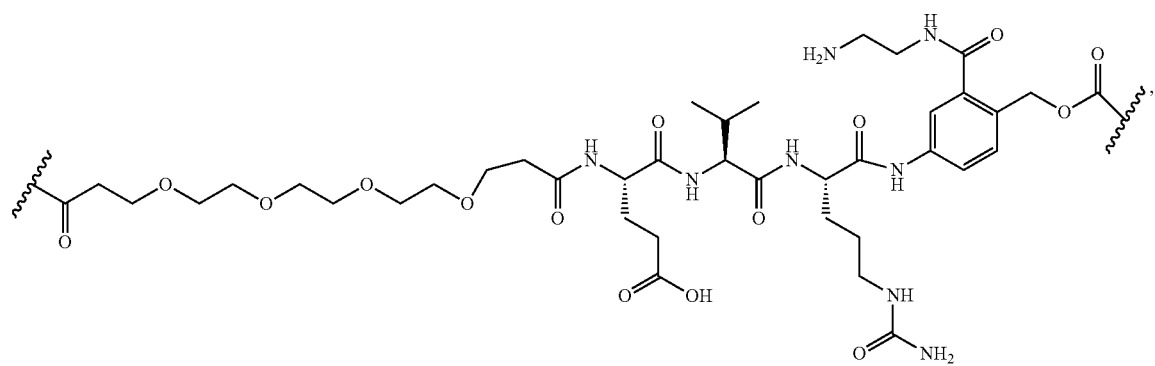
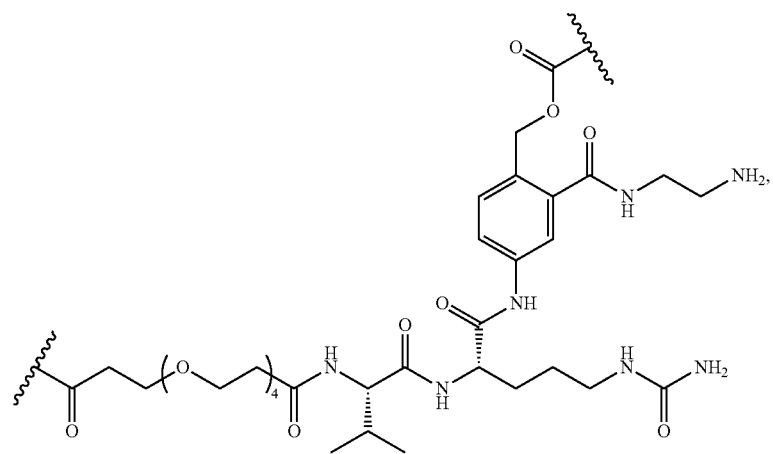
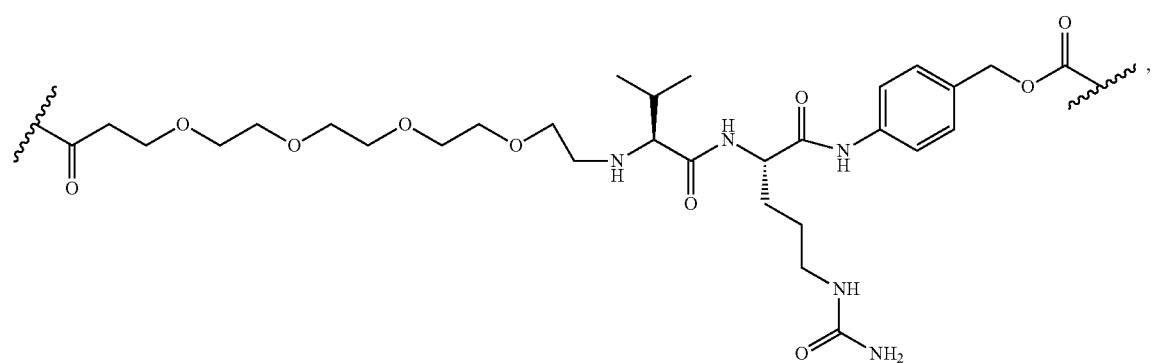

-continued
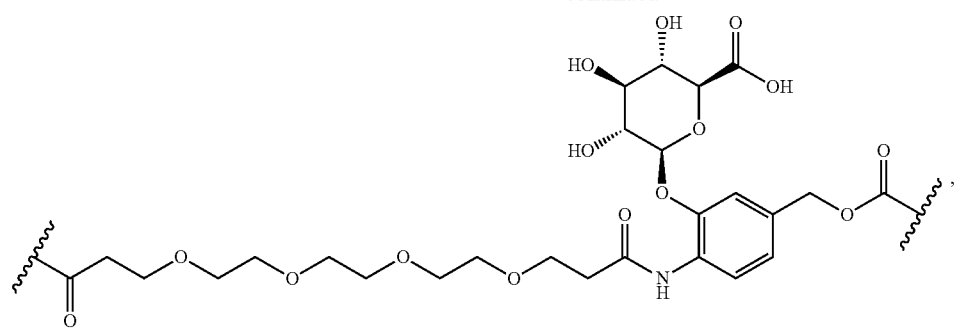
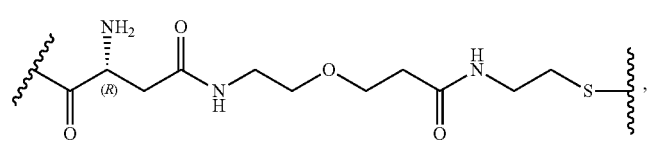
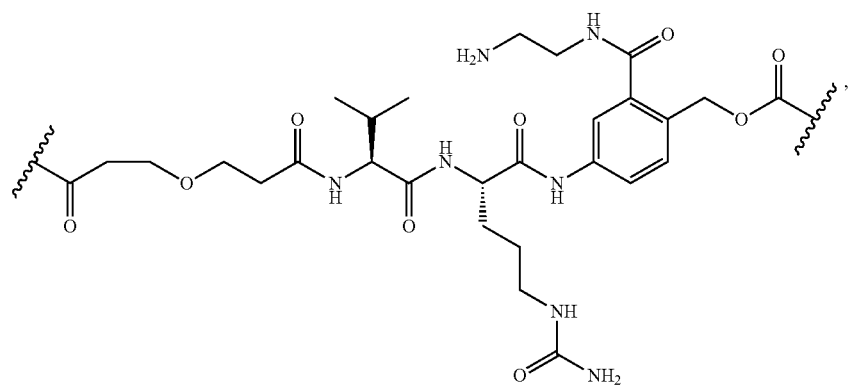
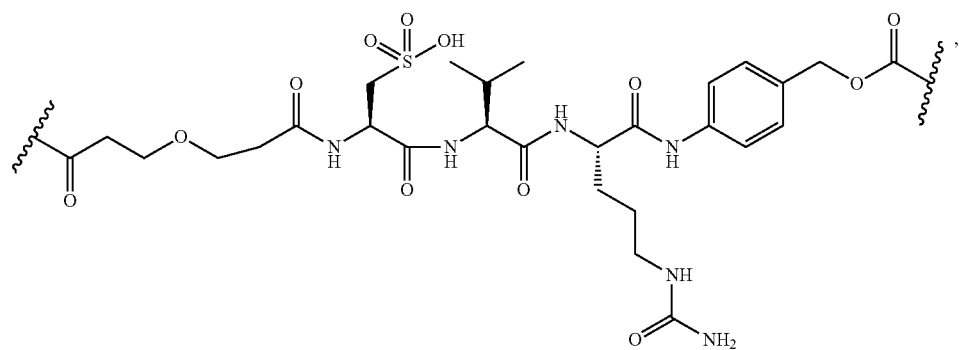
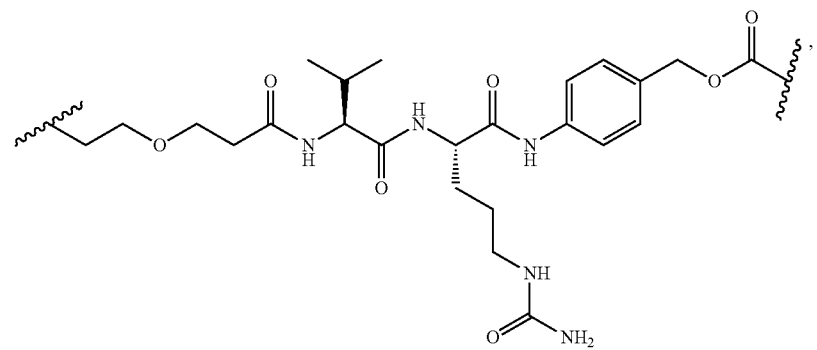

597
-continued
598
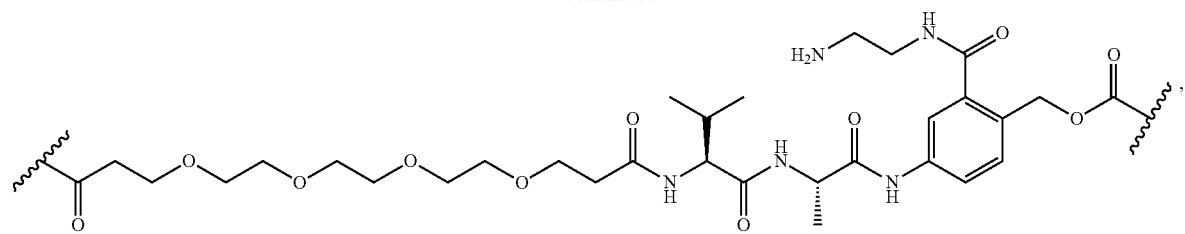
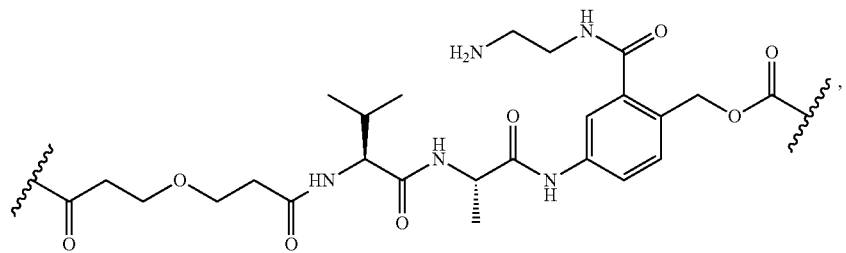
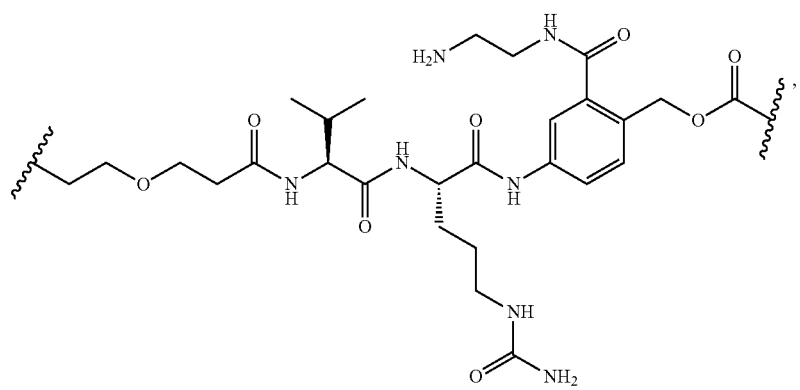
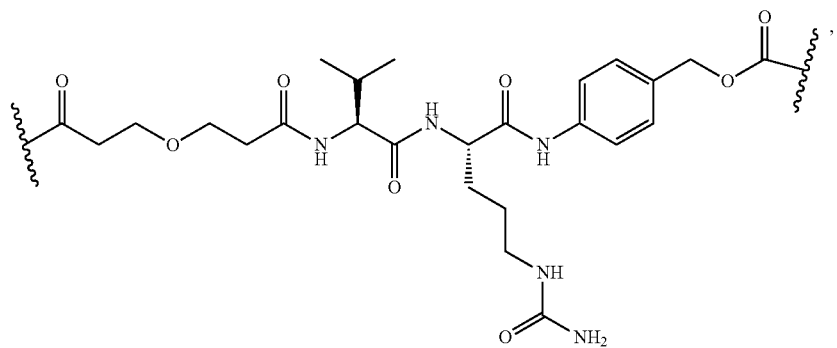
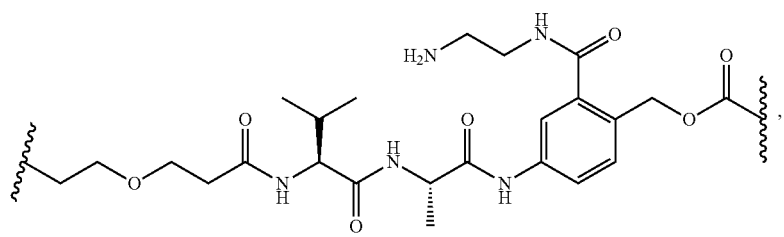

-continued
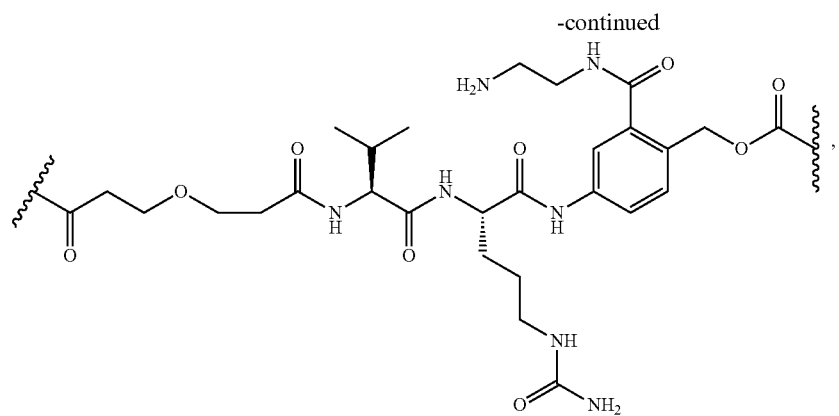
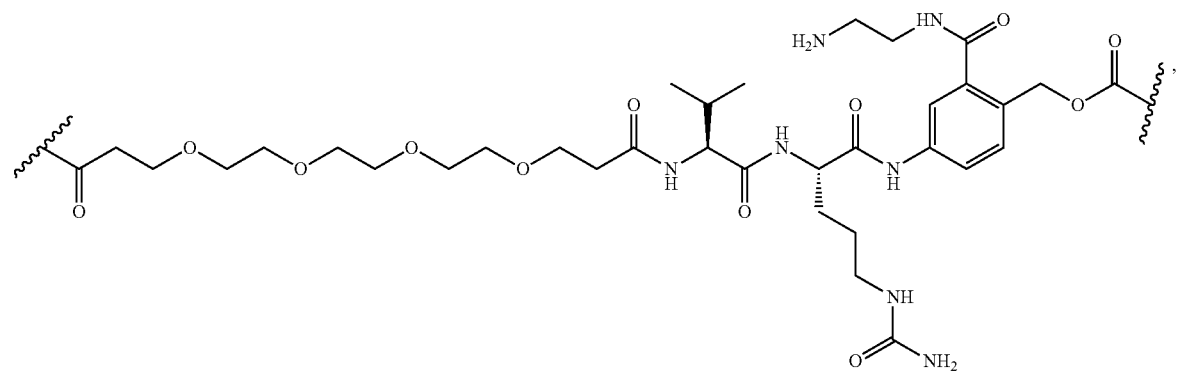
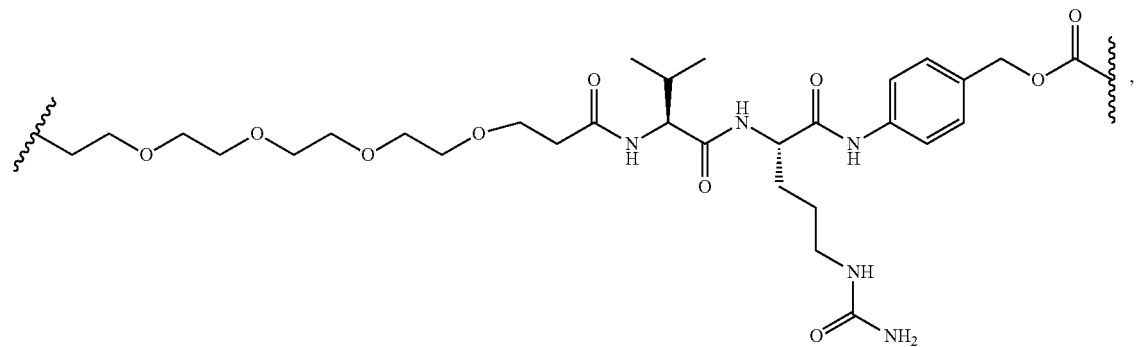
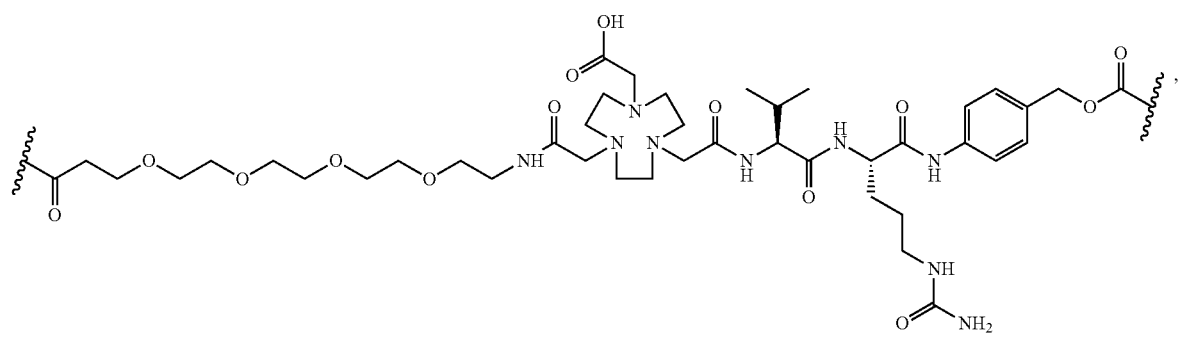

-continued
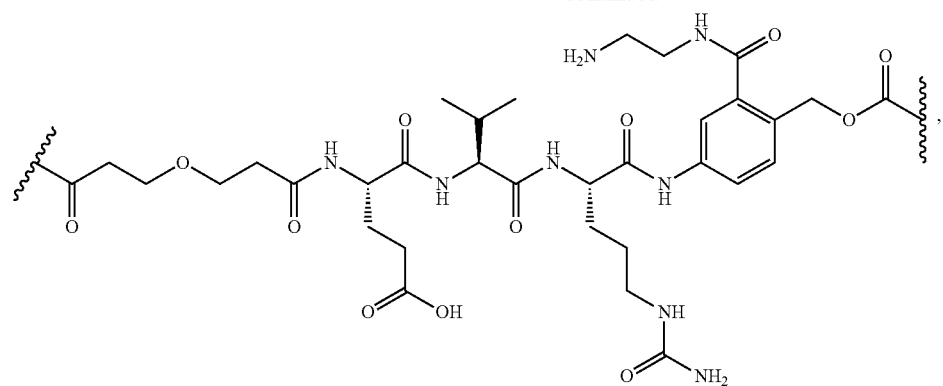
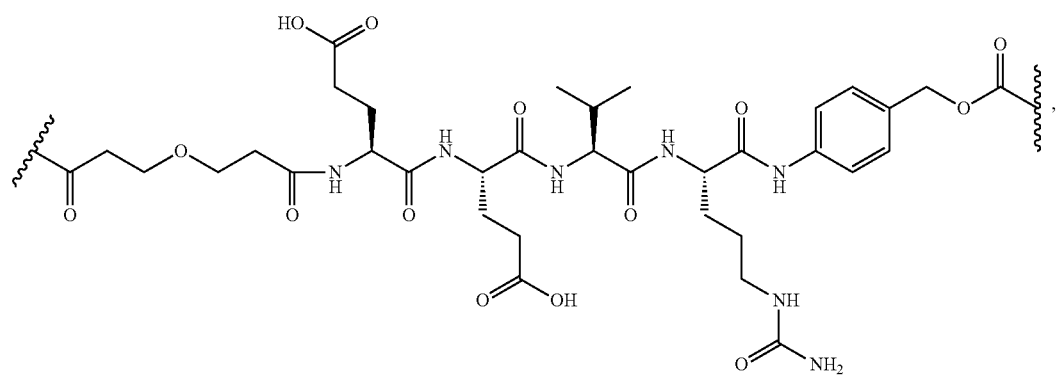
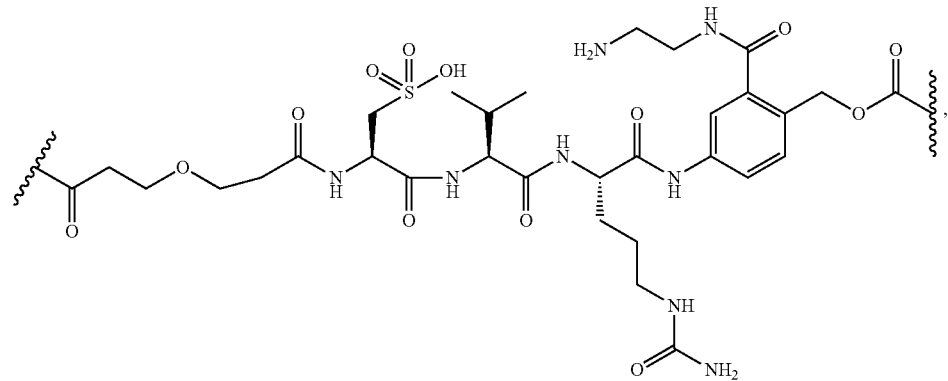
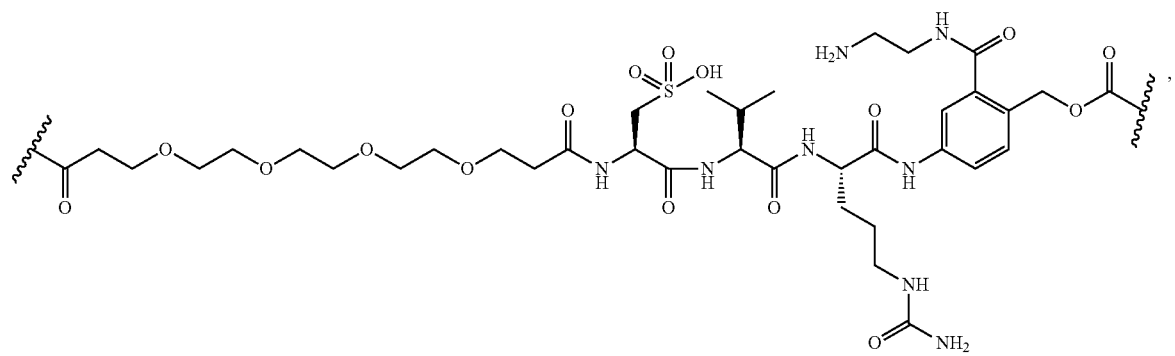

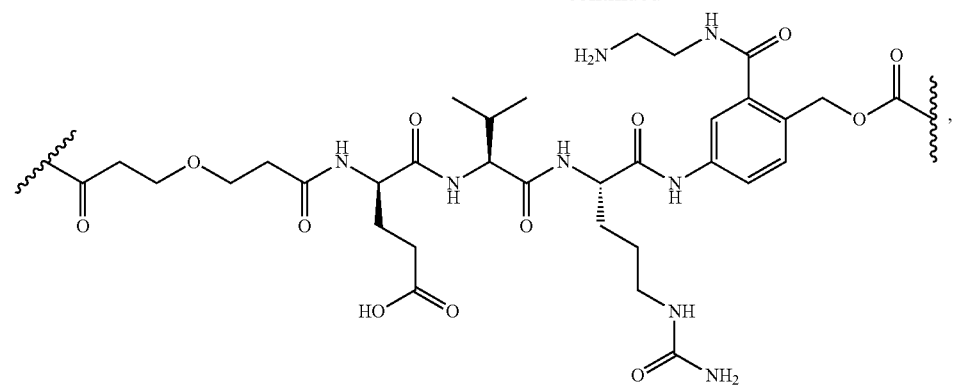
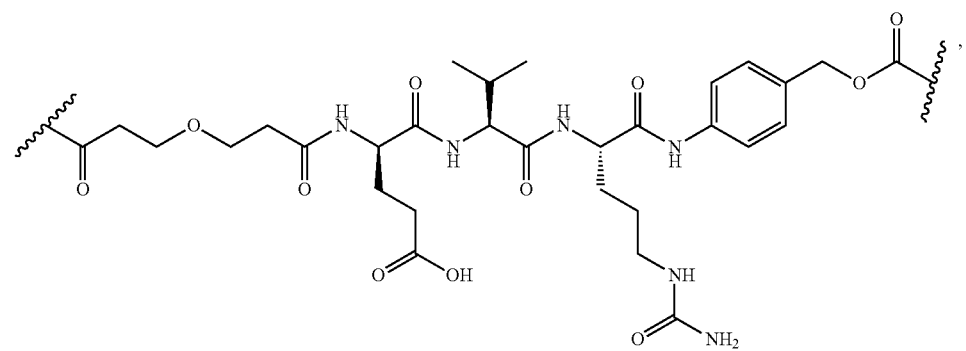
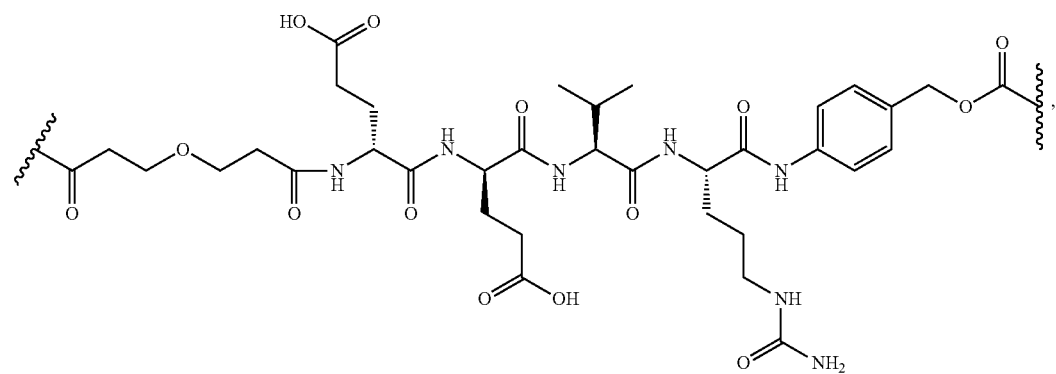
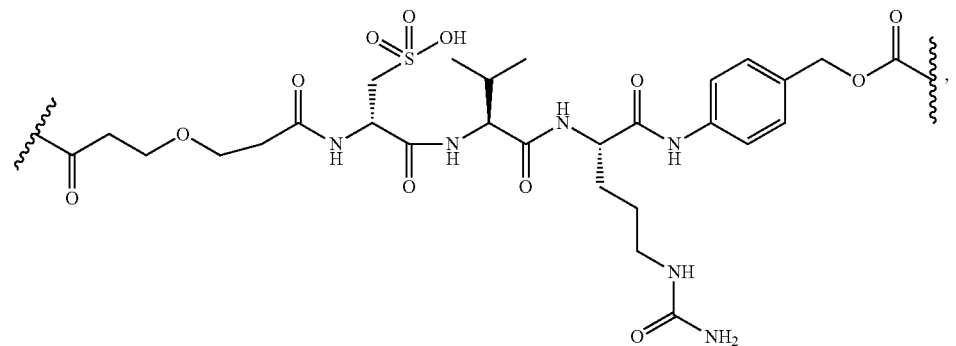

-continued
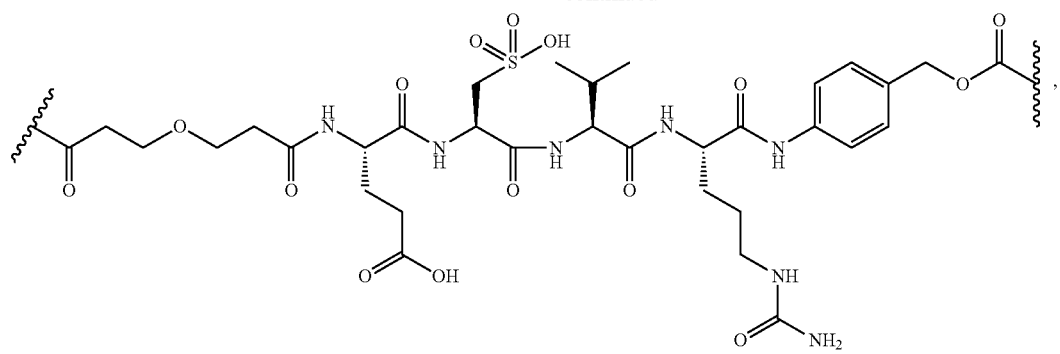
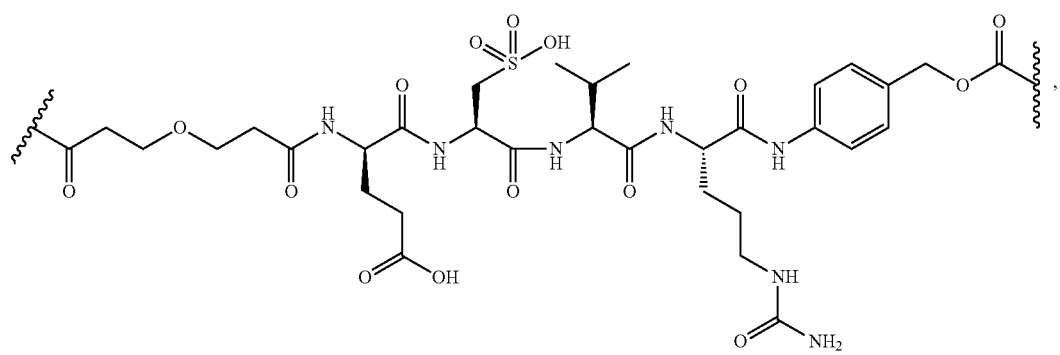
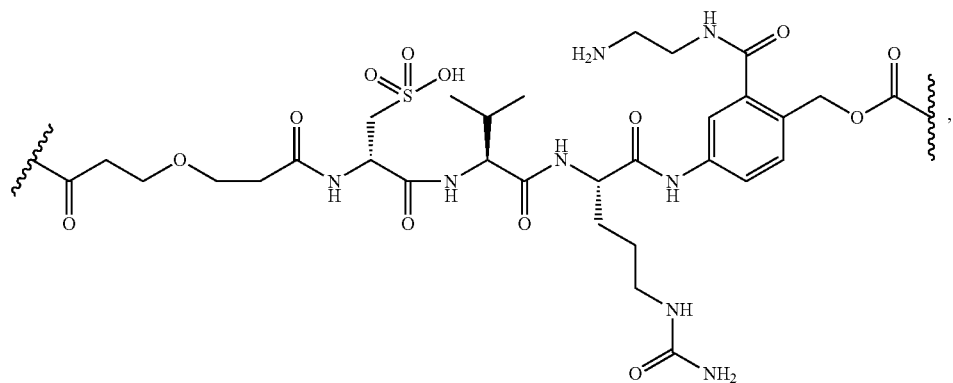
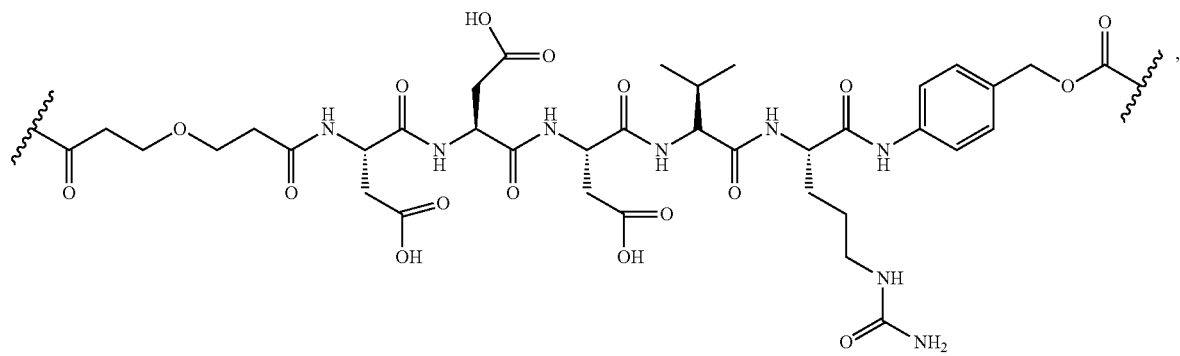

-continued
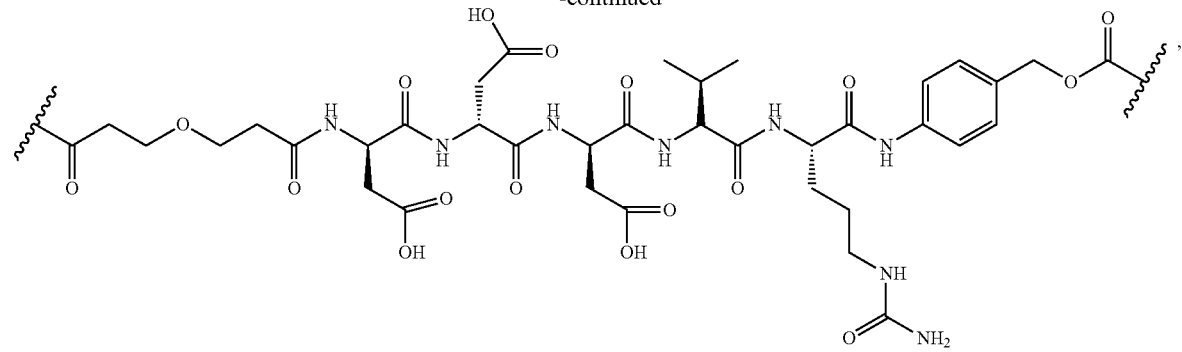
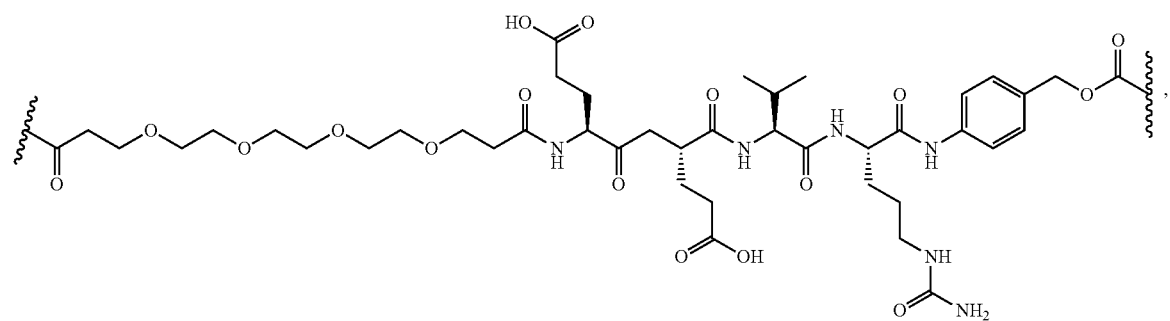 [SMILES: *C(=O)CCOCCOCCOCCOCCC(=O)N[C@@H](CCC(=O)O)C(=O)C[C@@H](CCC(=O)O)C(=O)N[C@H](C(=O)N[C@@H](CCCNC(N)=O)C(=O)Nc1ccc(COC(*)=O)cc1)C(C)C]
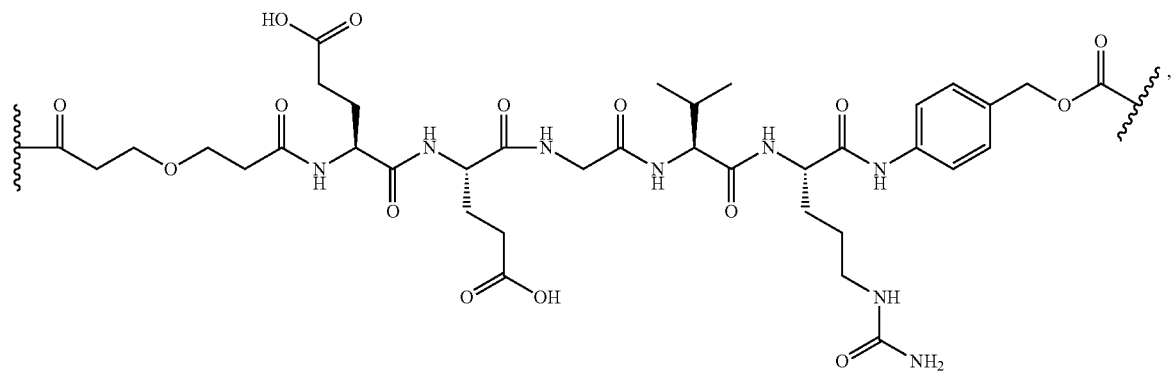
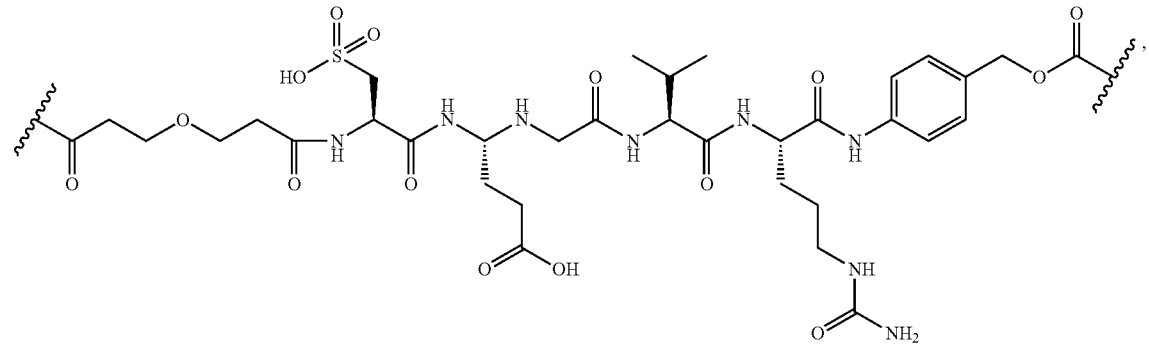

-continued
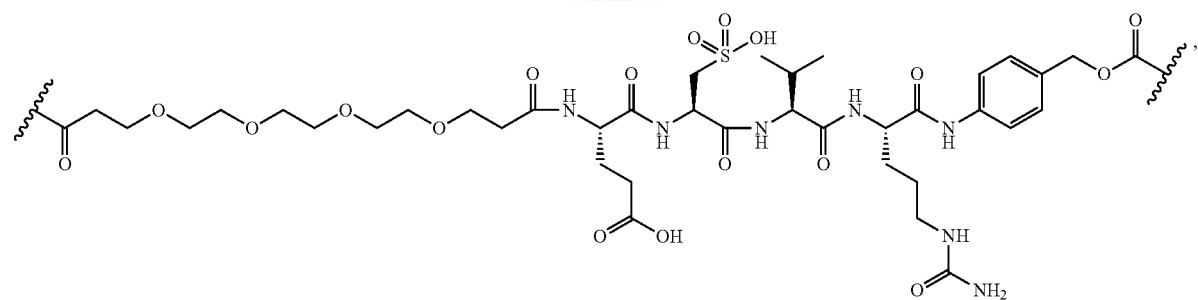
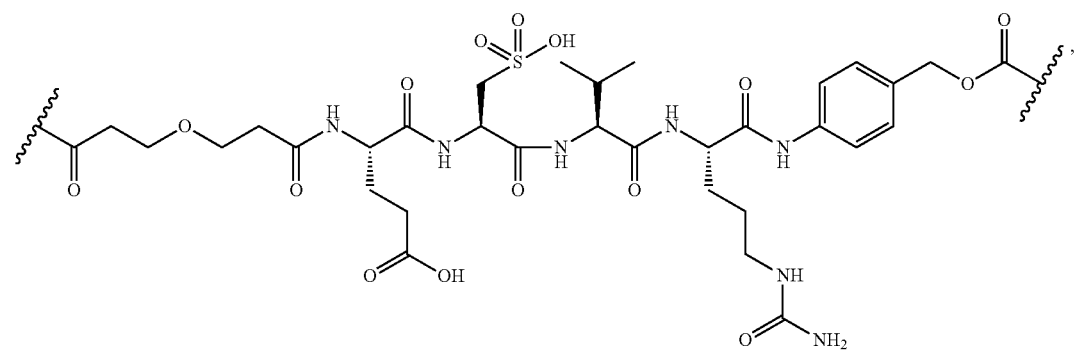
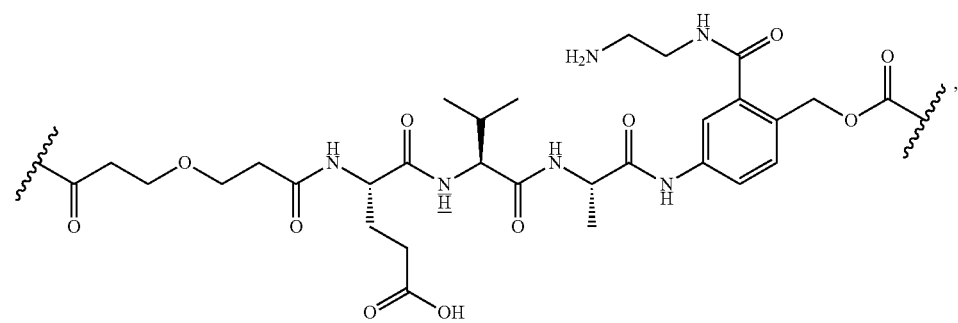
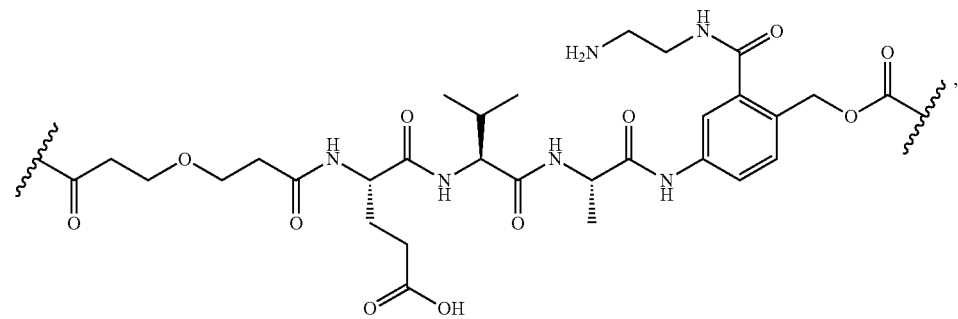
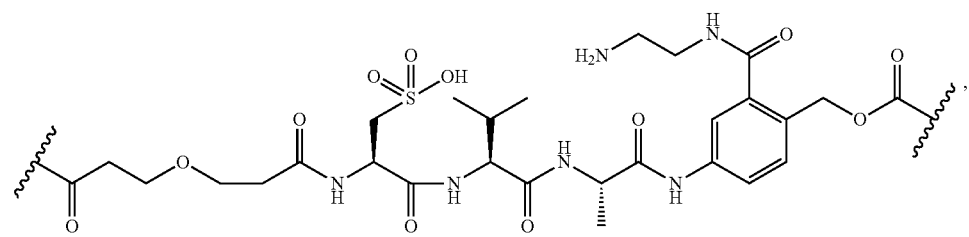

611 612
-continued
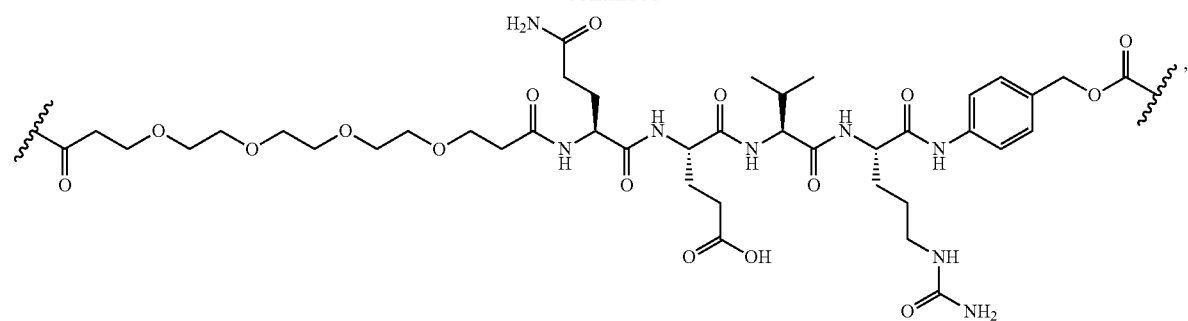
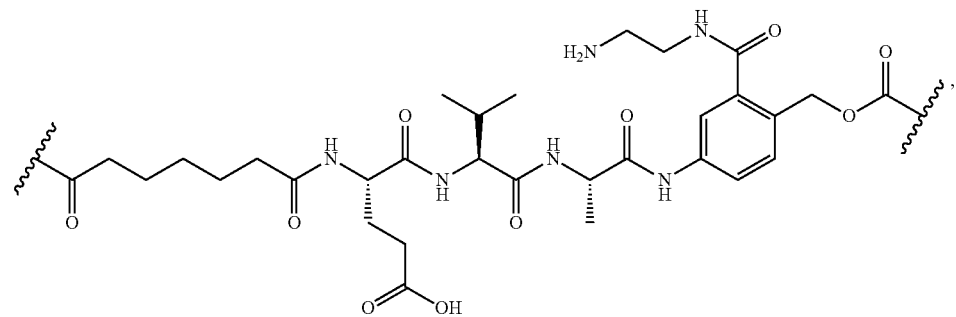
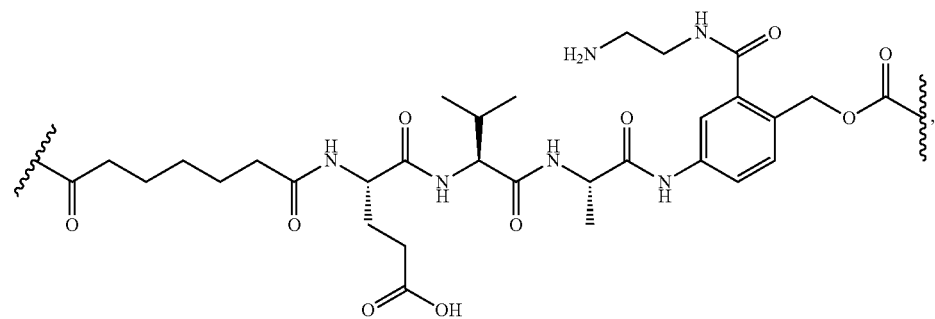
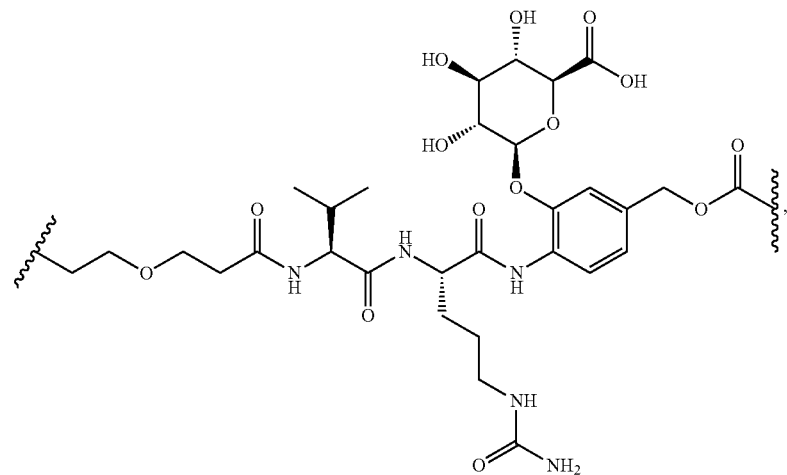

-continued
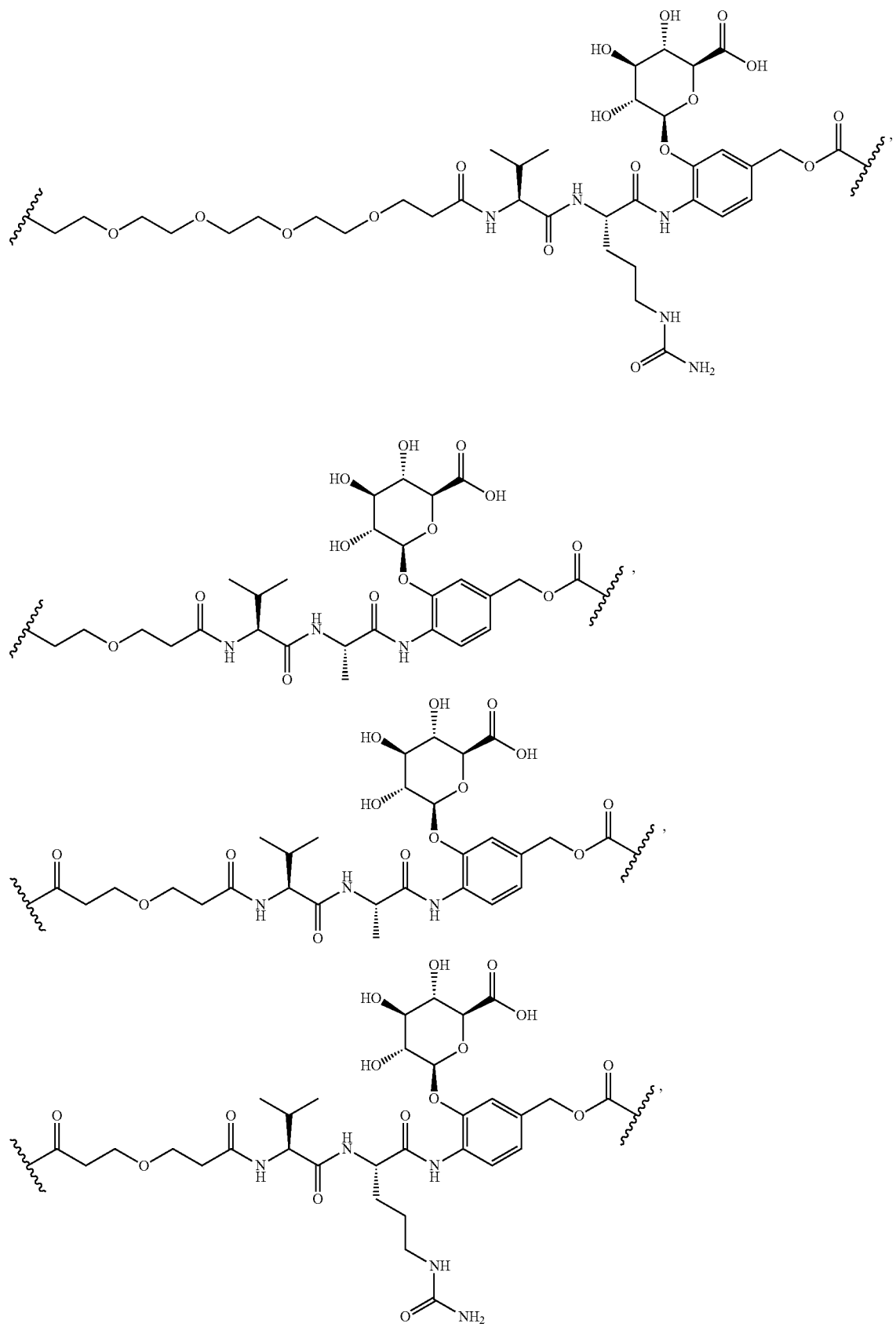

-continued
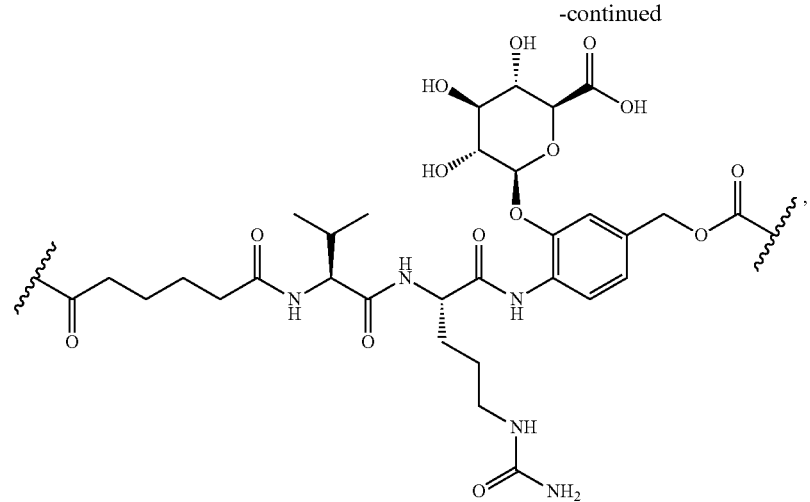
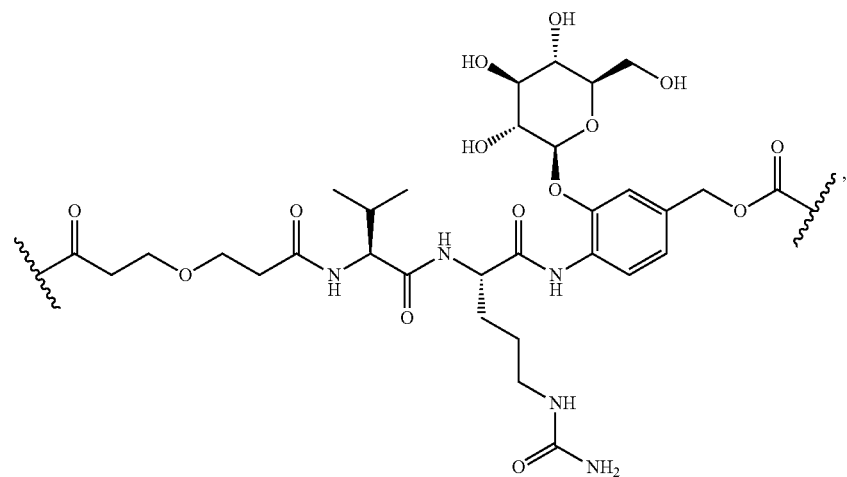
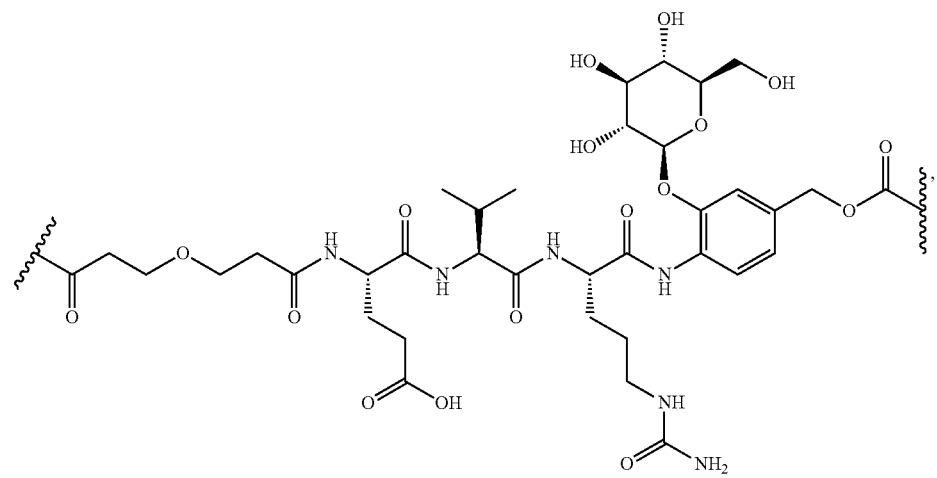

-continued
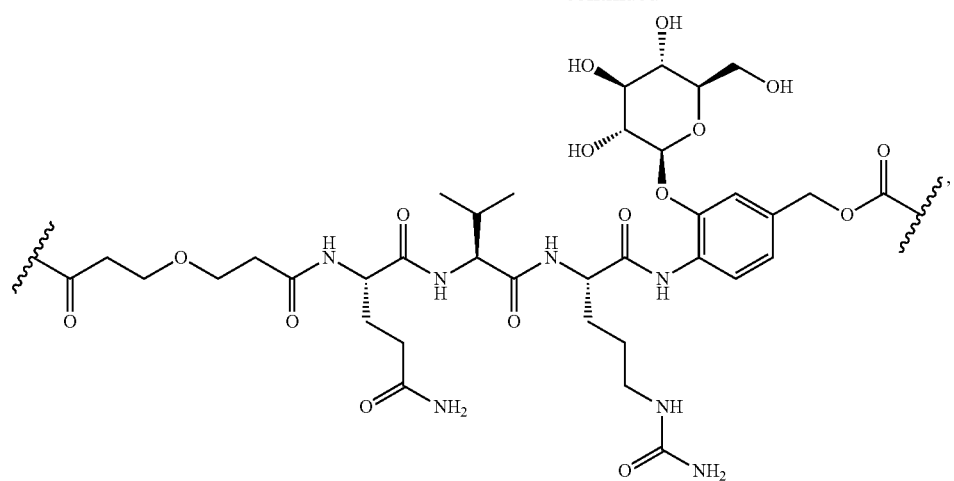
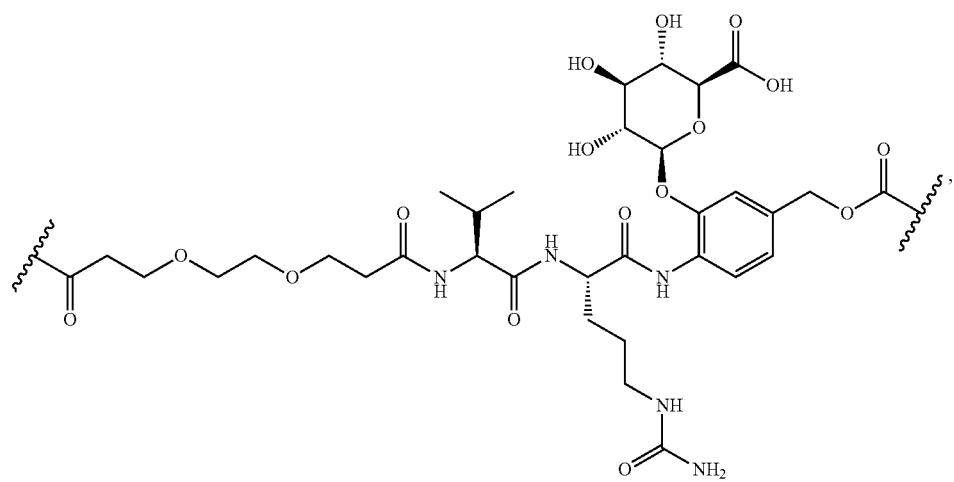
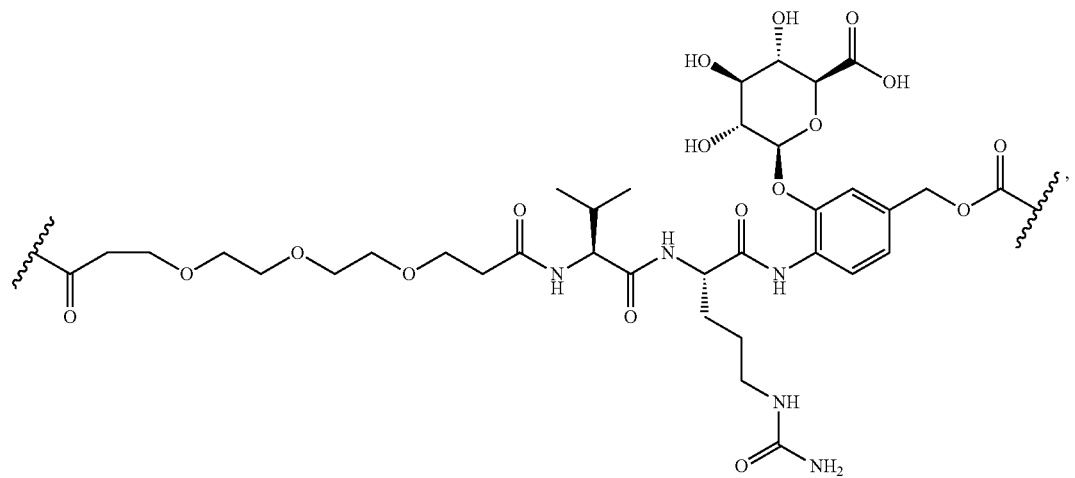

-continued
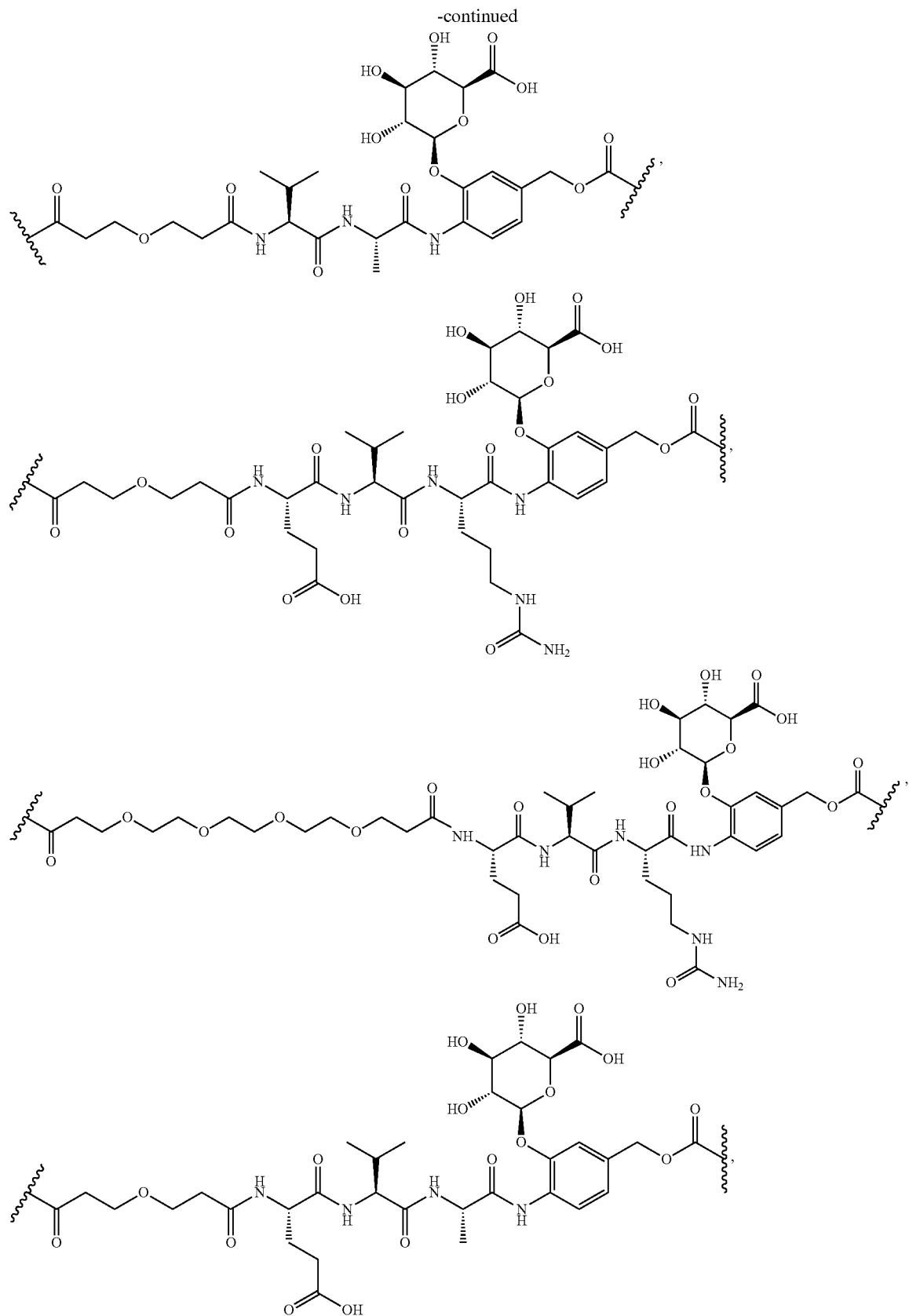

-continued
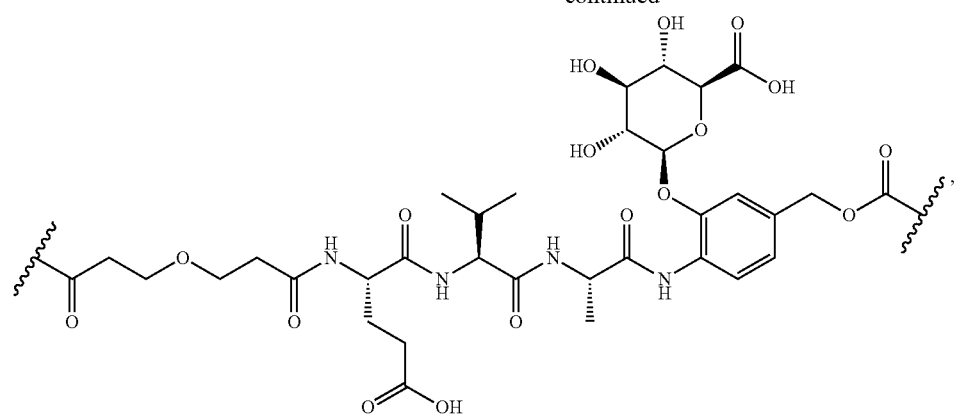
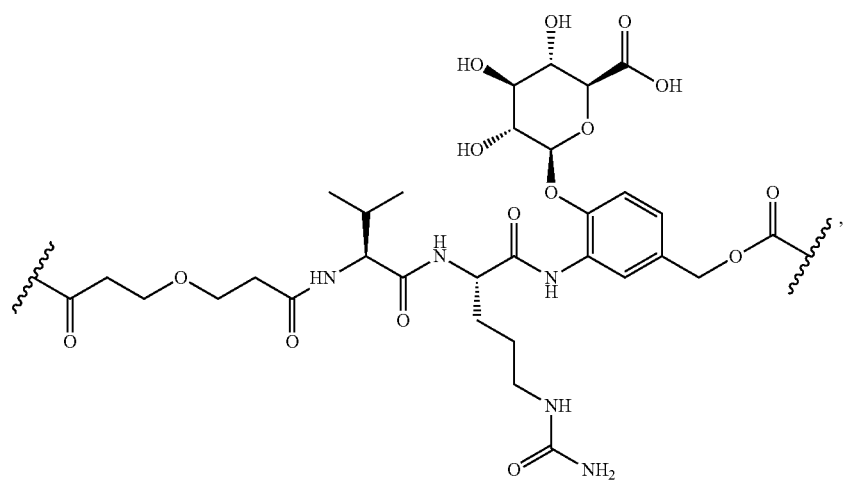
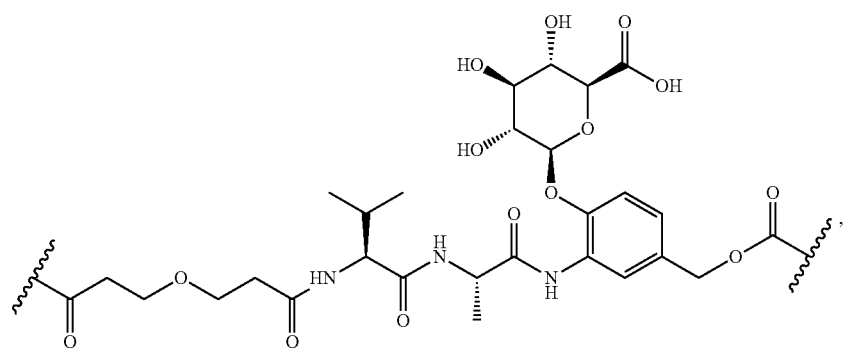
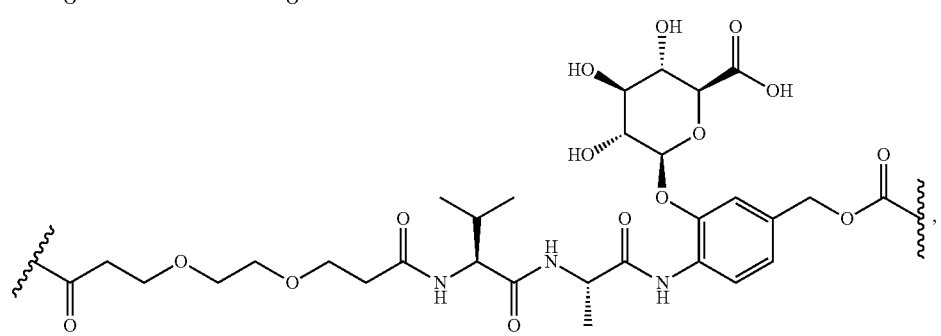

623 624
-continued
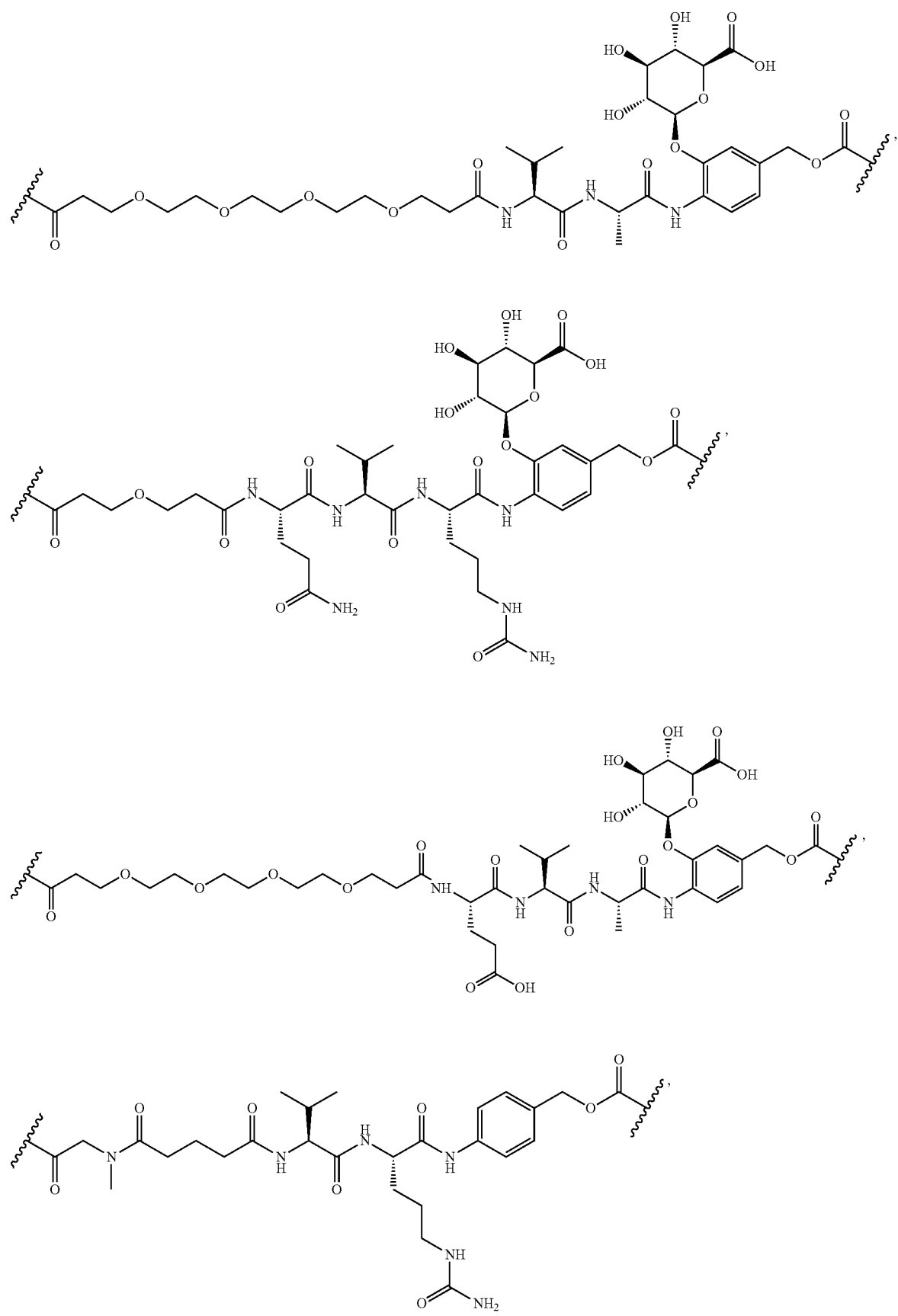

-continued
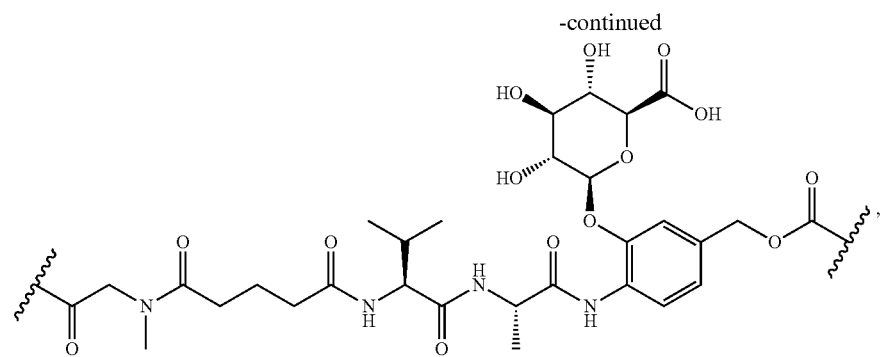
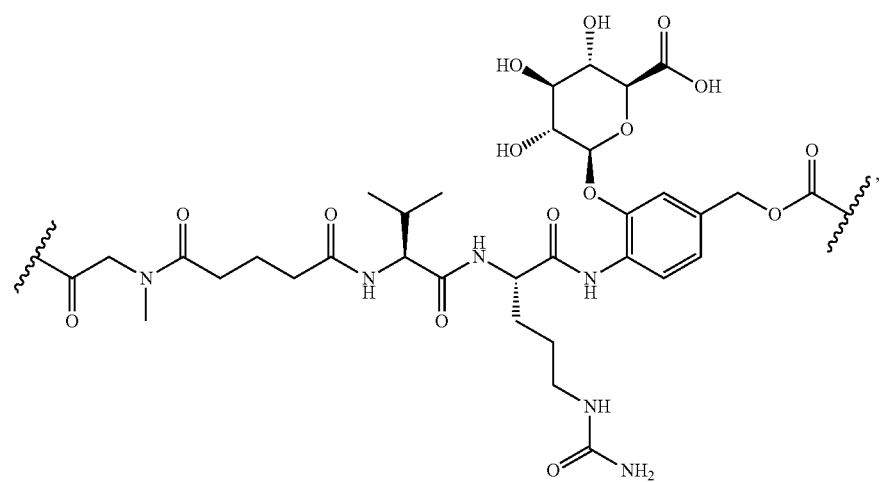
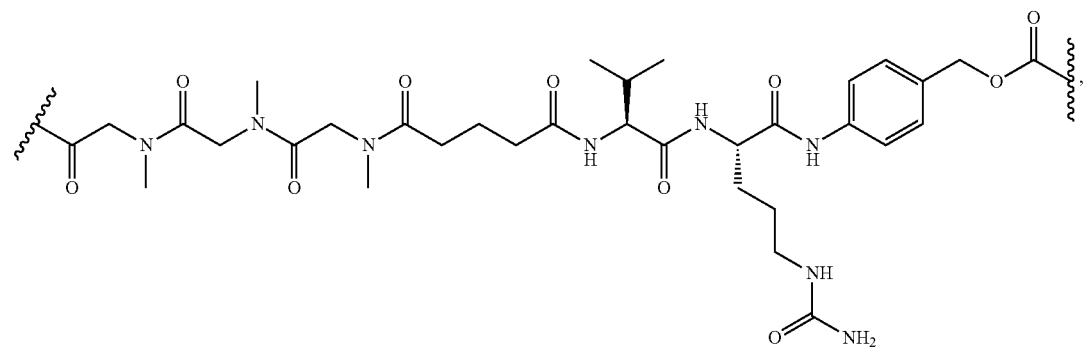
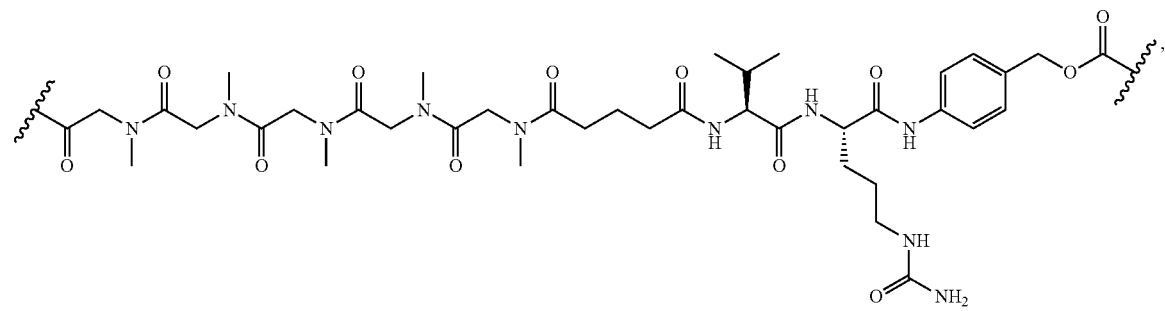

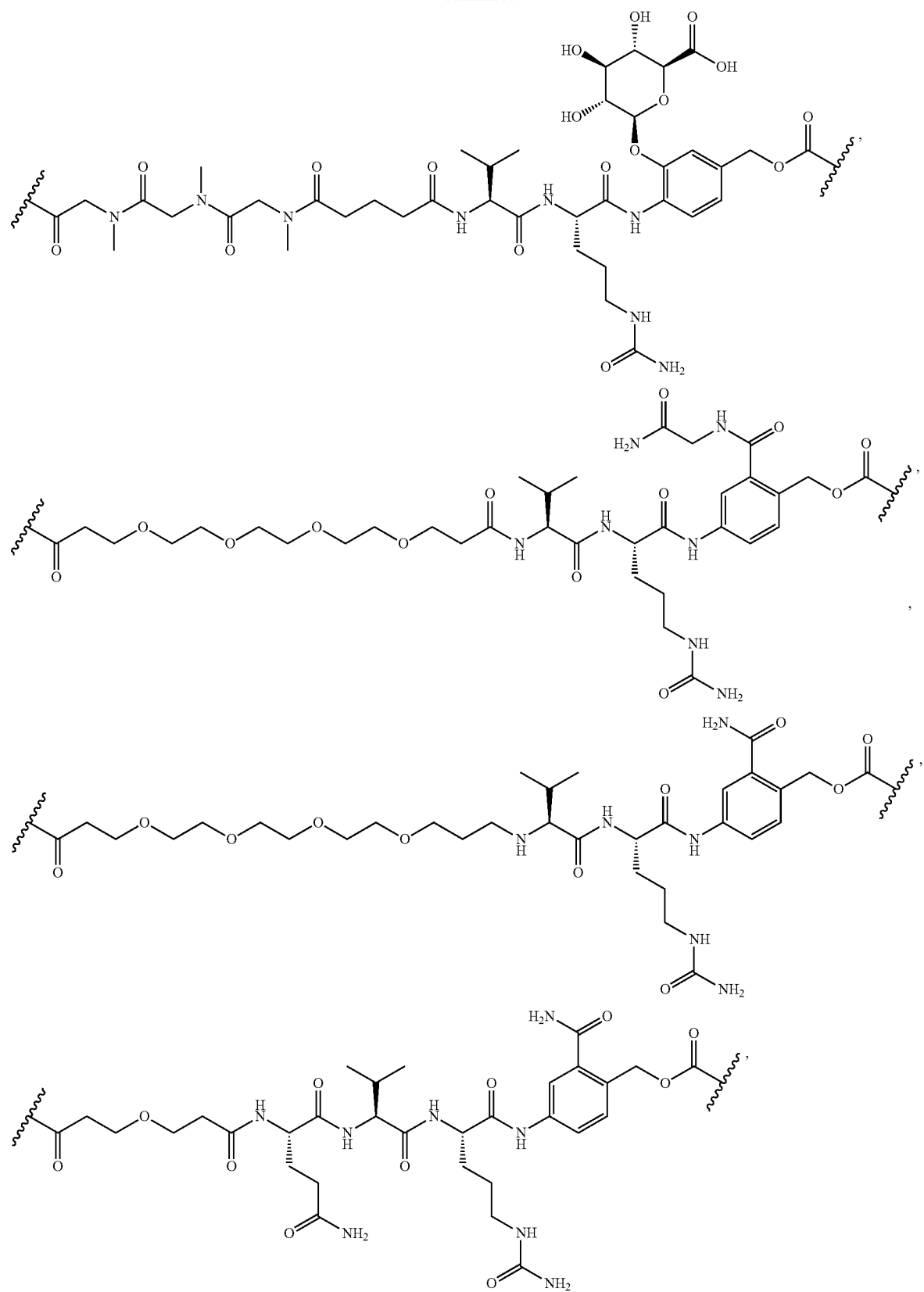

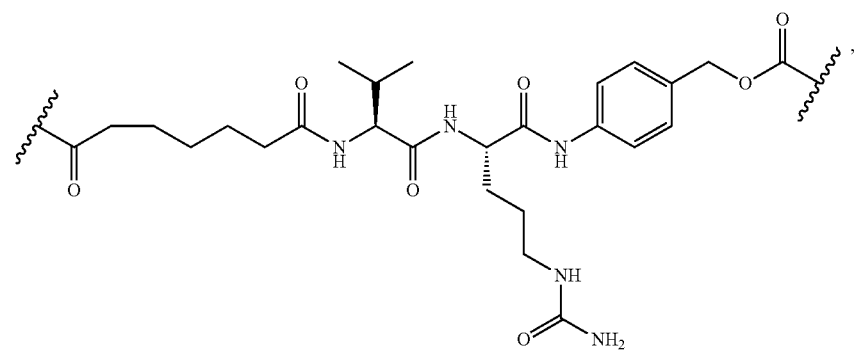
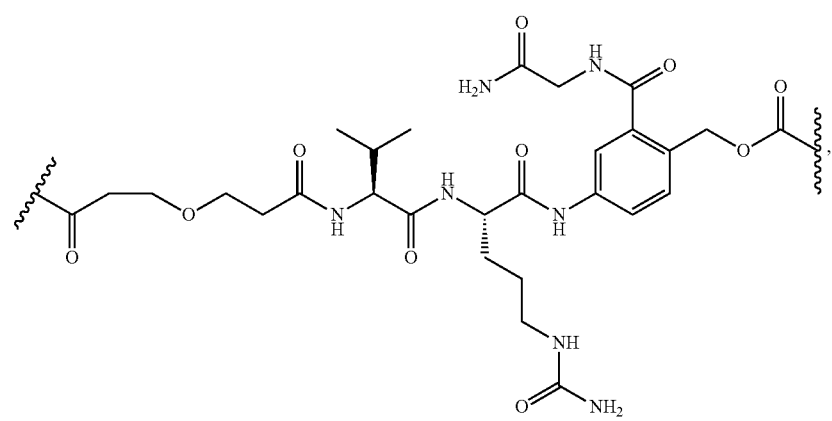
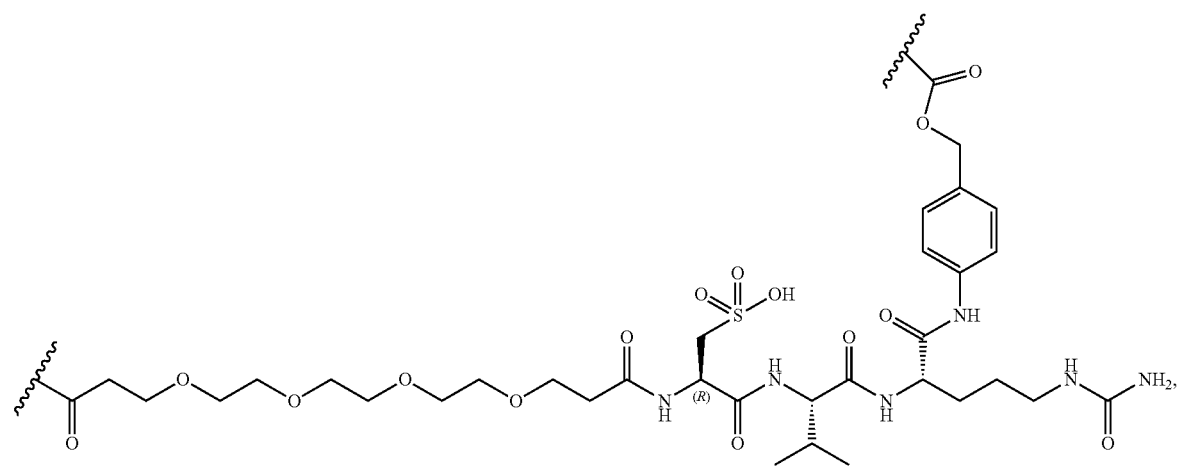
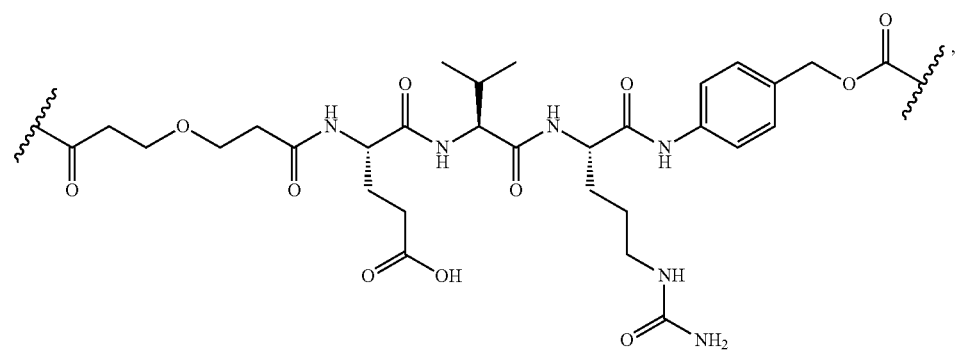

-continued
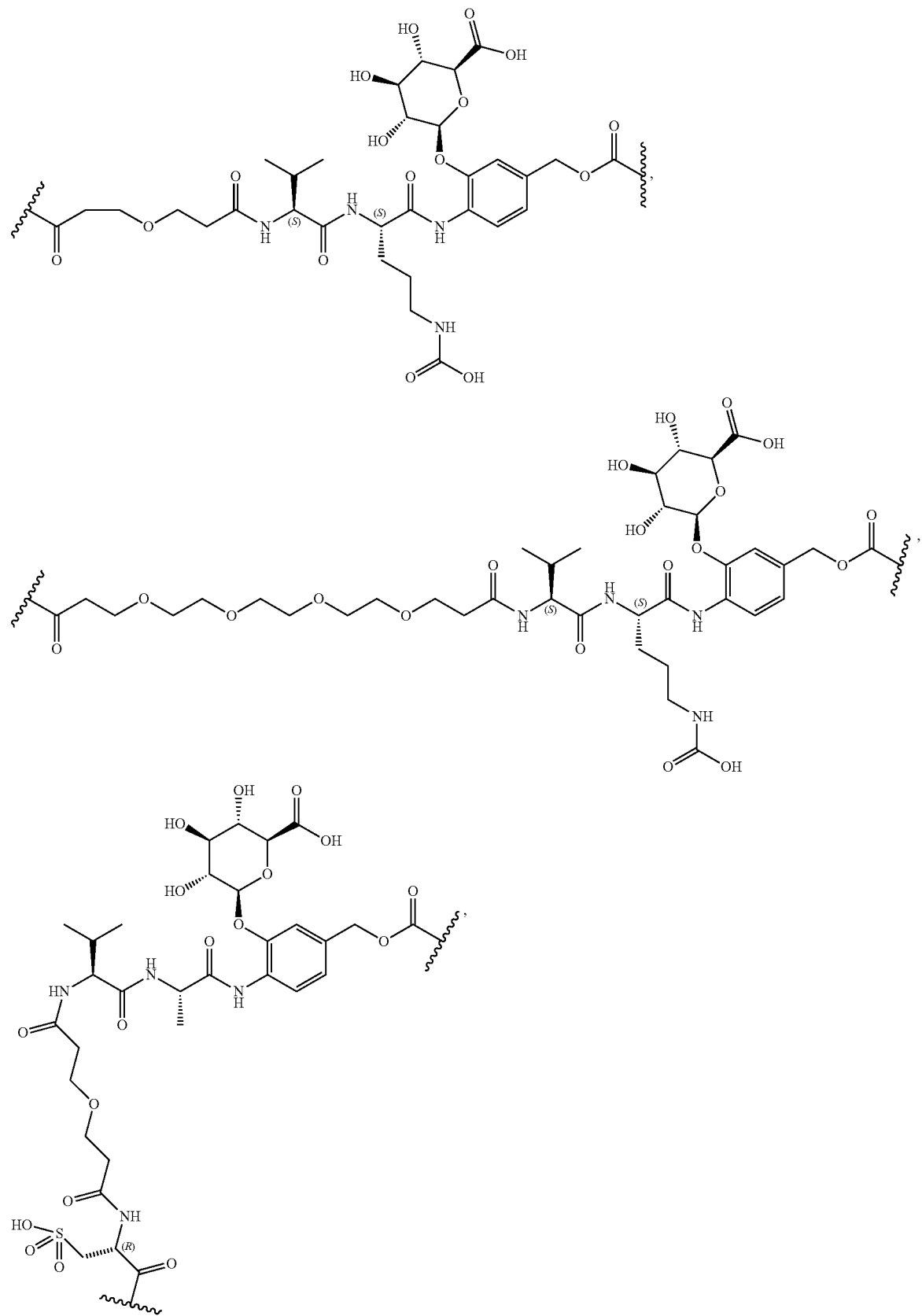

-continued
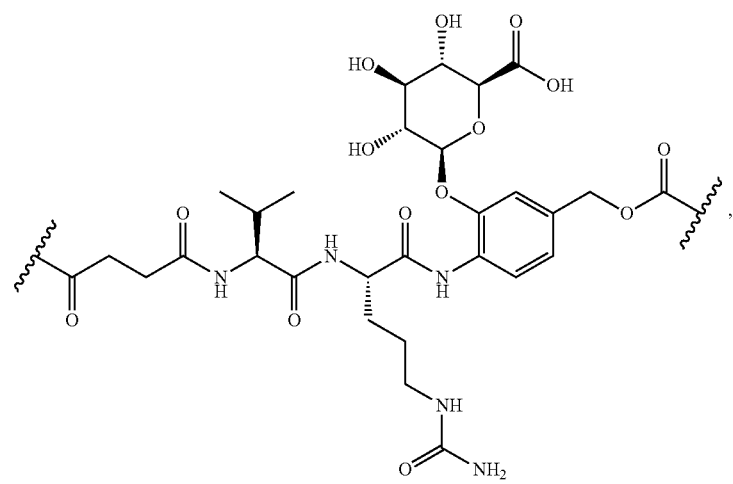
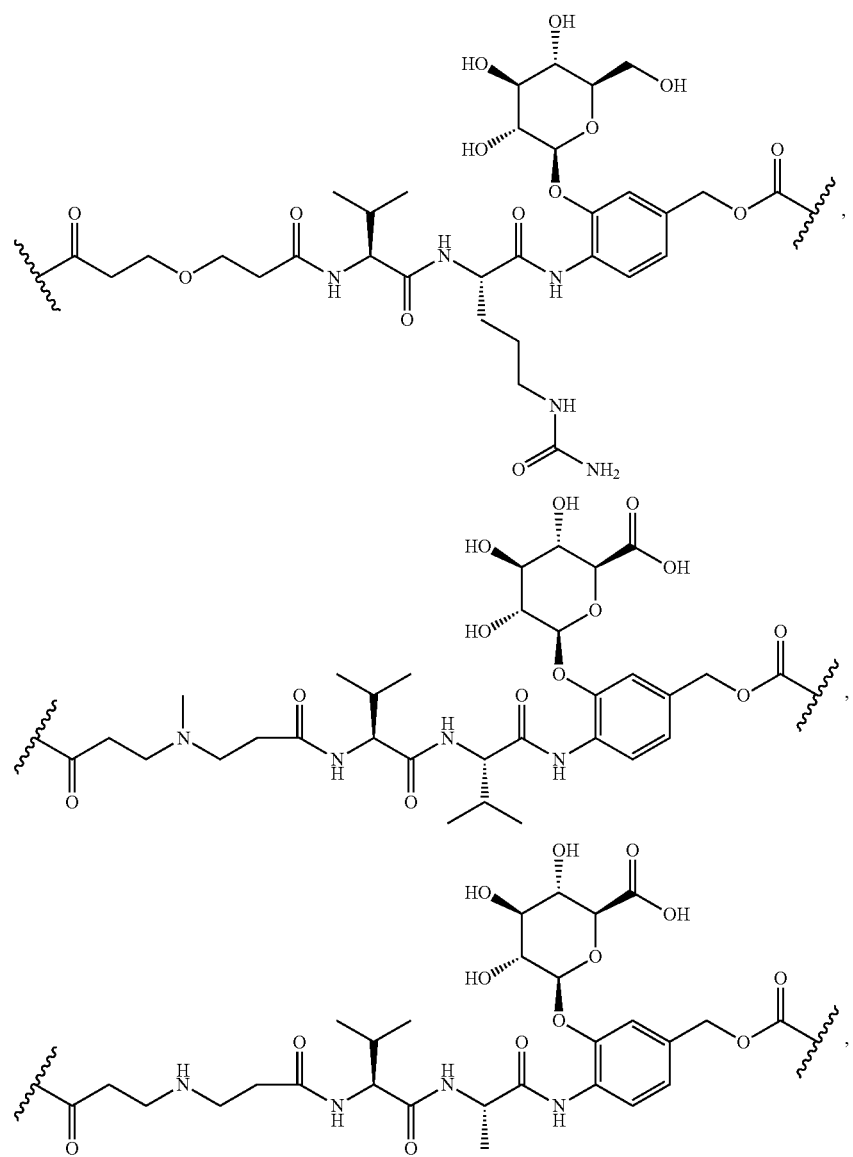

-continued
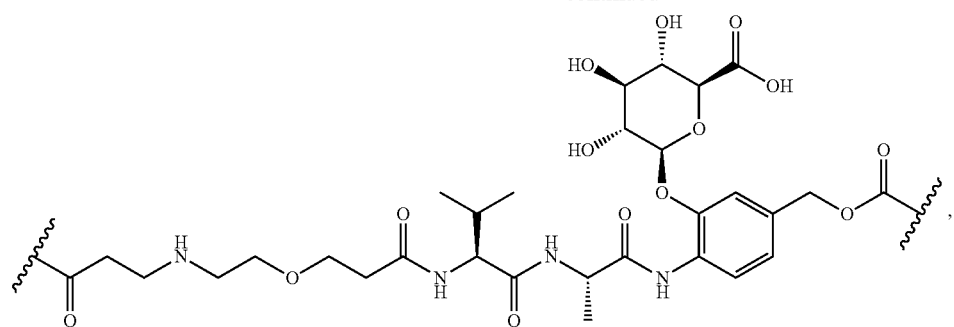
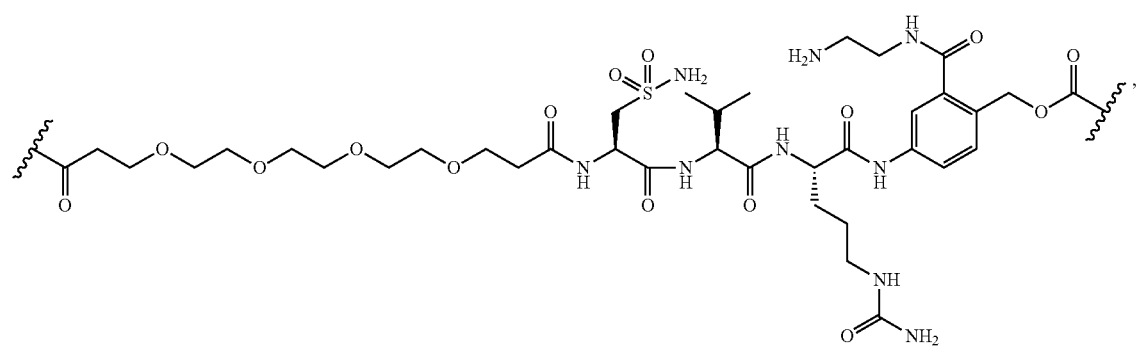
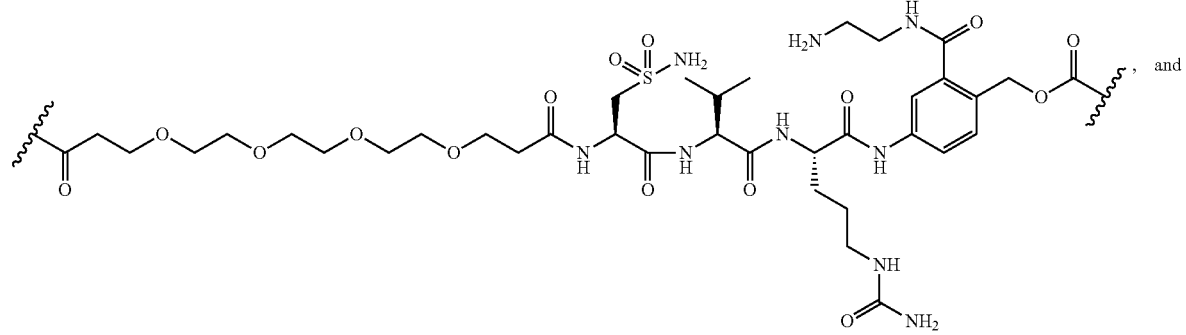, and
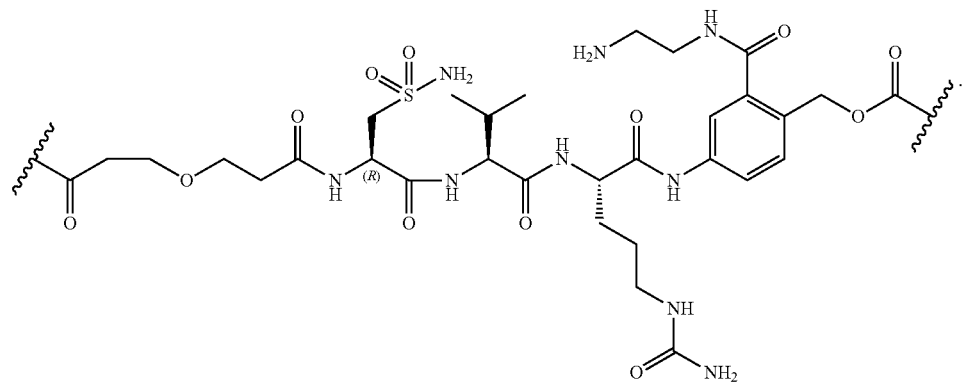

16. The compound of claim 1, or a pharmaceutically acceptable salt thereof, wherein, $R^d$ is:
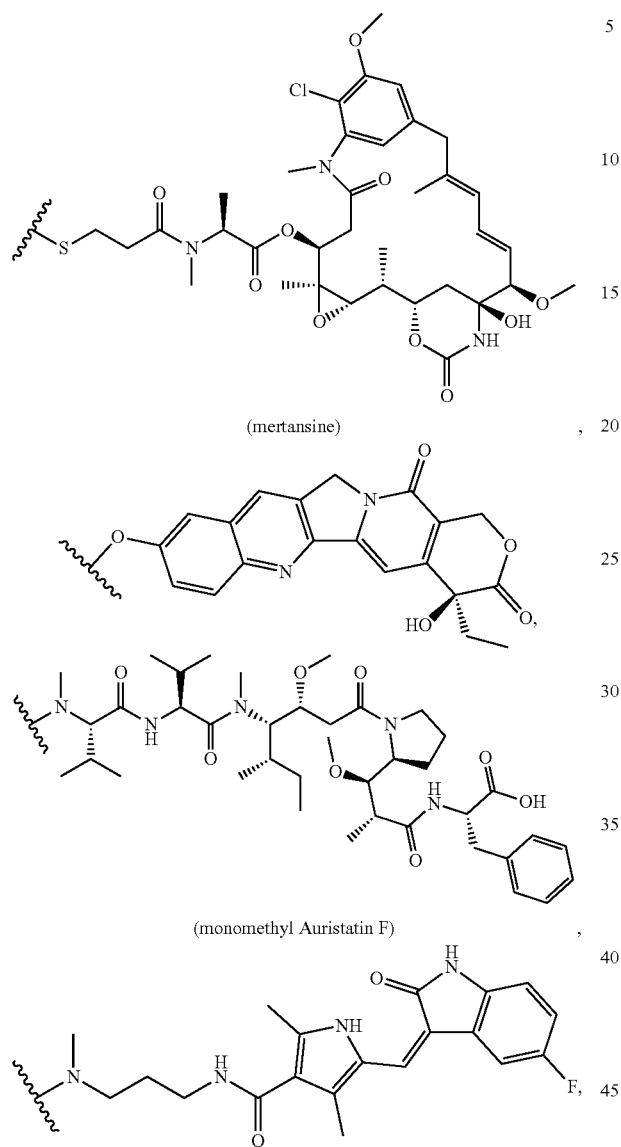
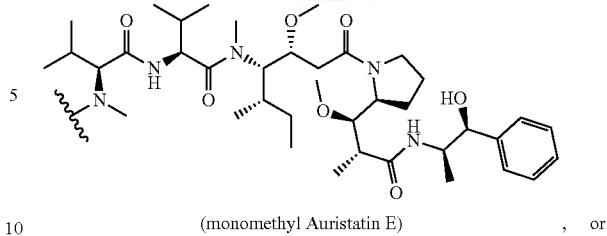
(monomethyl Auristatin E) , or
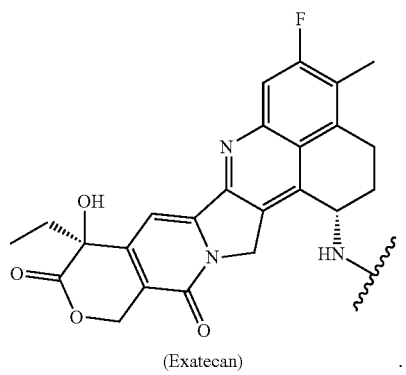
(Exatecan)
17. The compound of claim 16, or a pharmaceutically acceptable salt thereof, wherein, $R^d$ is:
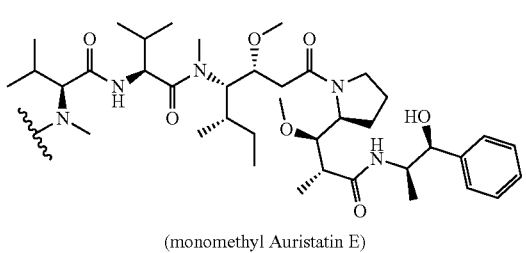
(monomethyl Auristatin E) .
18. The compound of claim 1, or a pharmaceutically acceptable salt thereof, wherein, -L-$R^d$ is:
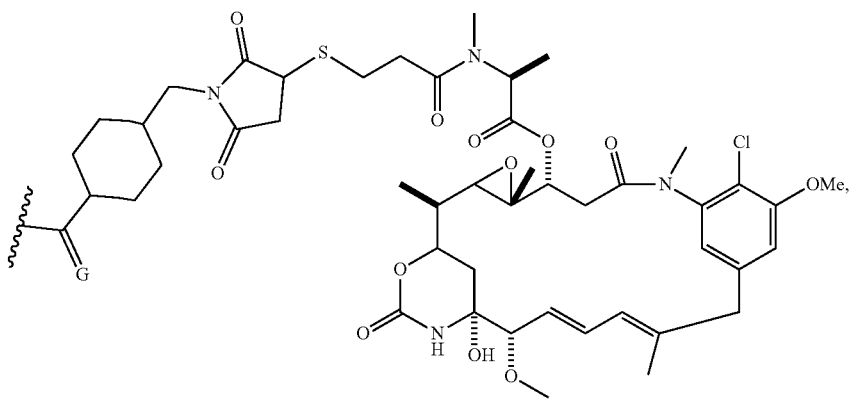

639
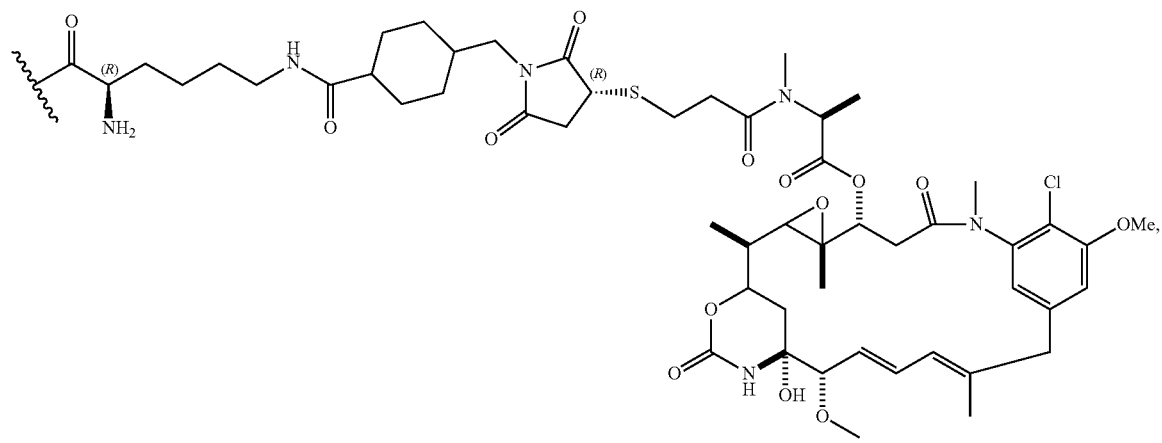
640
-continued
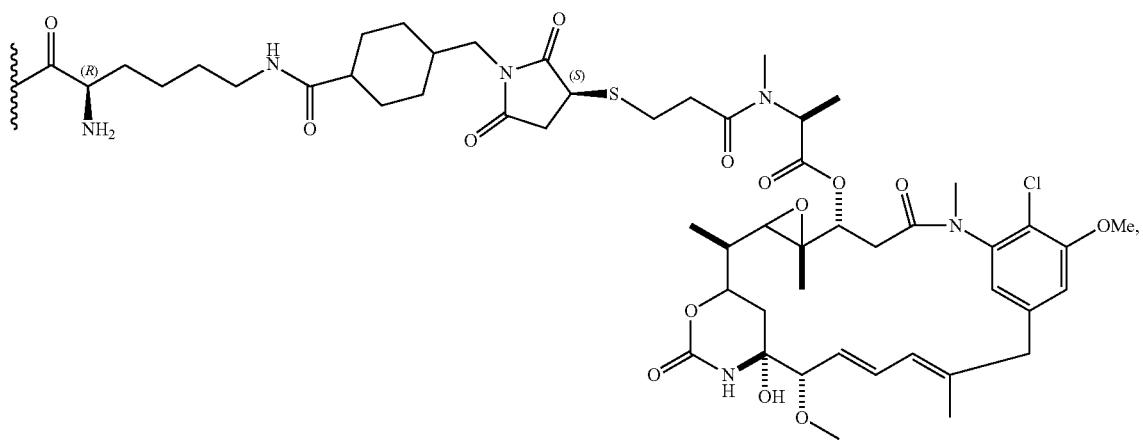
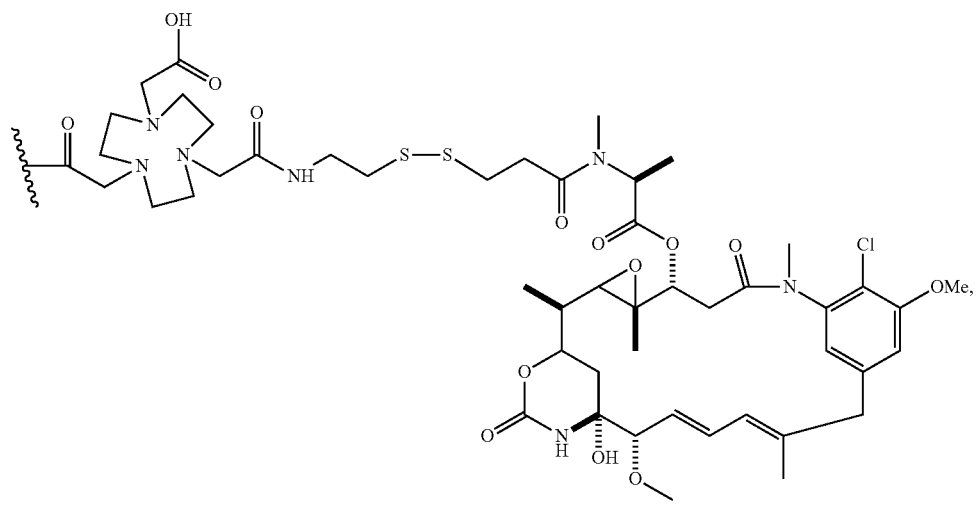
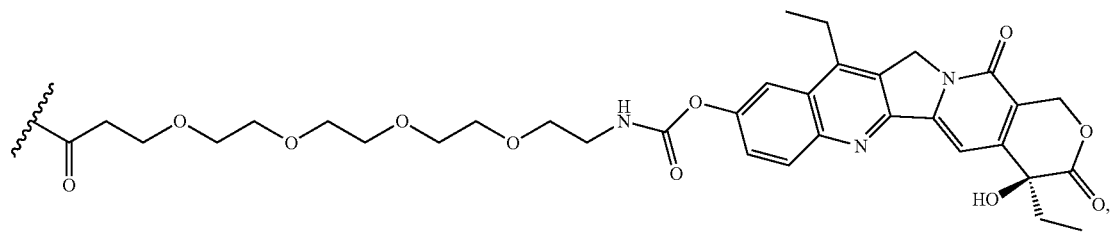

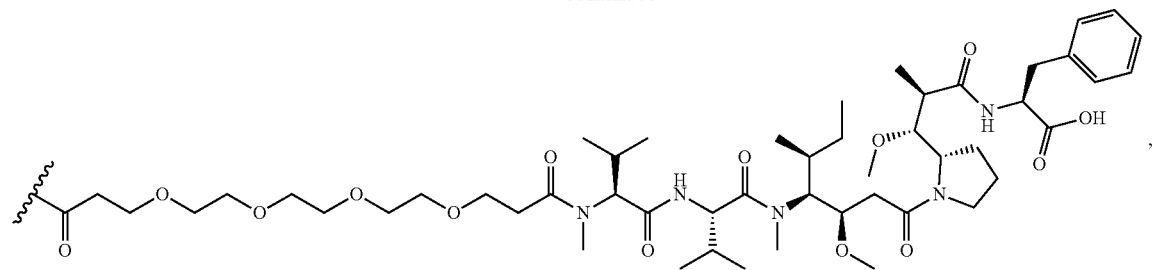
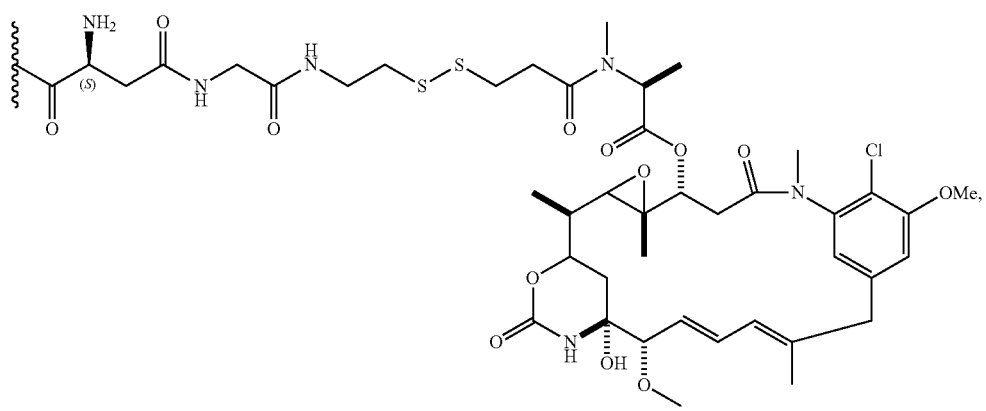
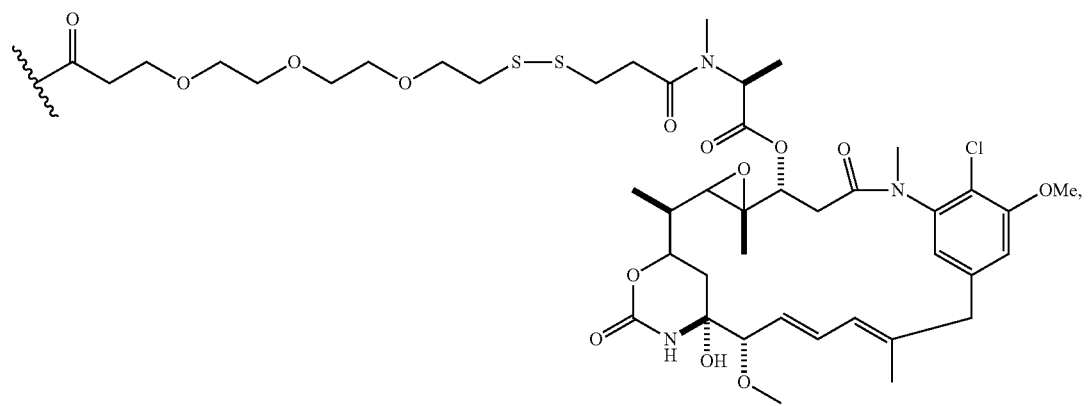
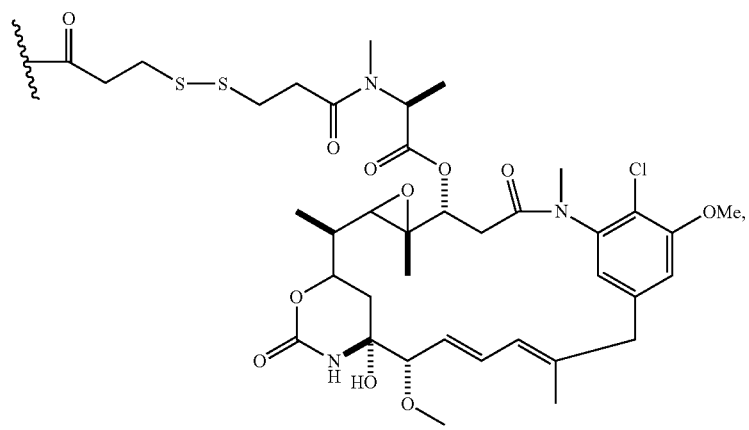

-continued
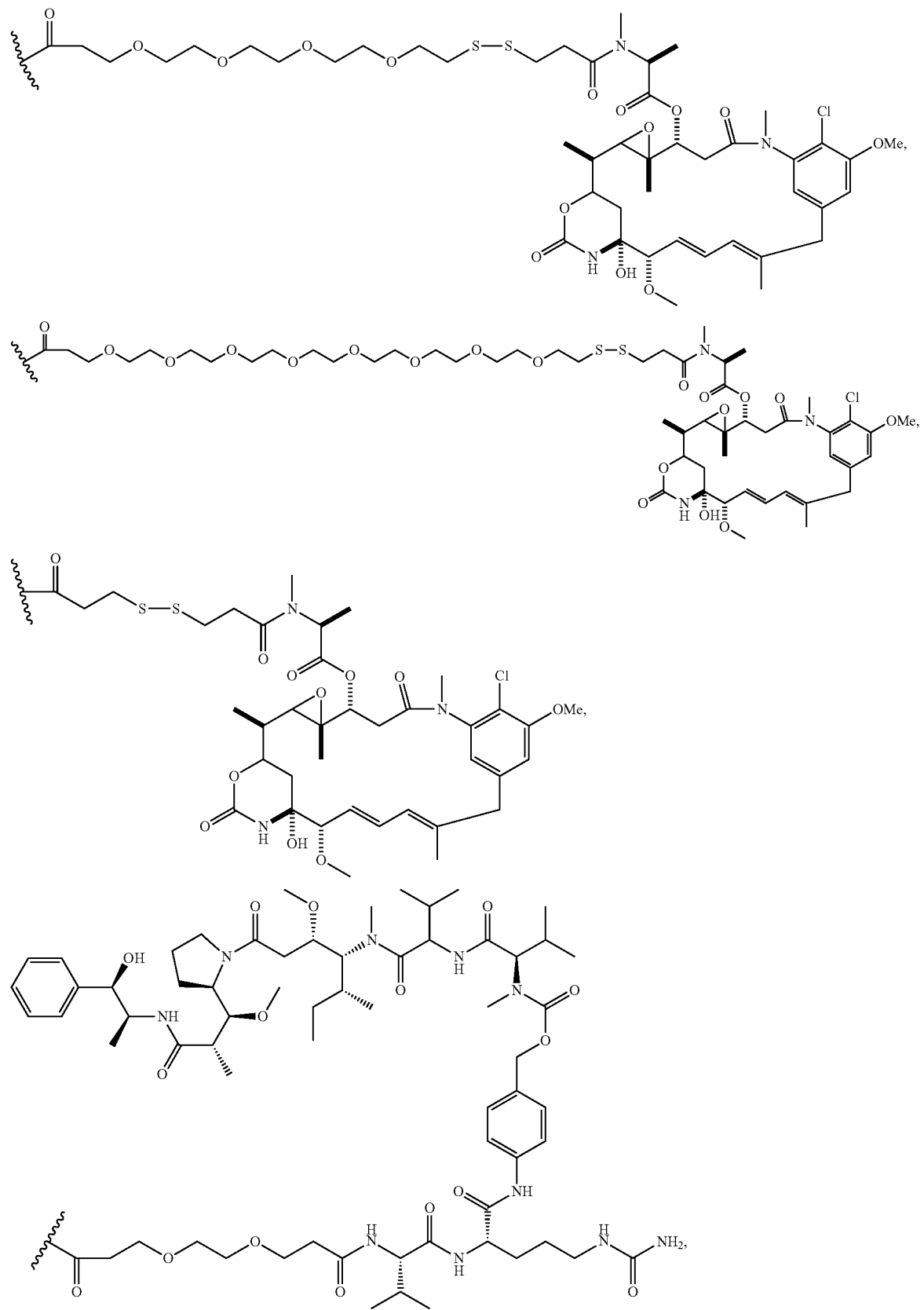

-continued
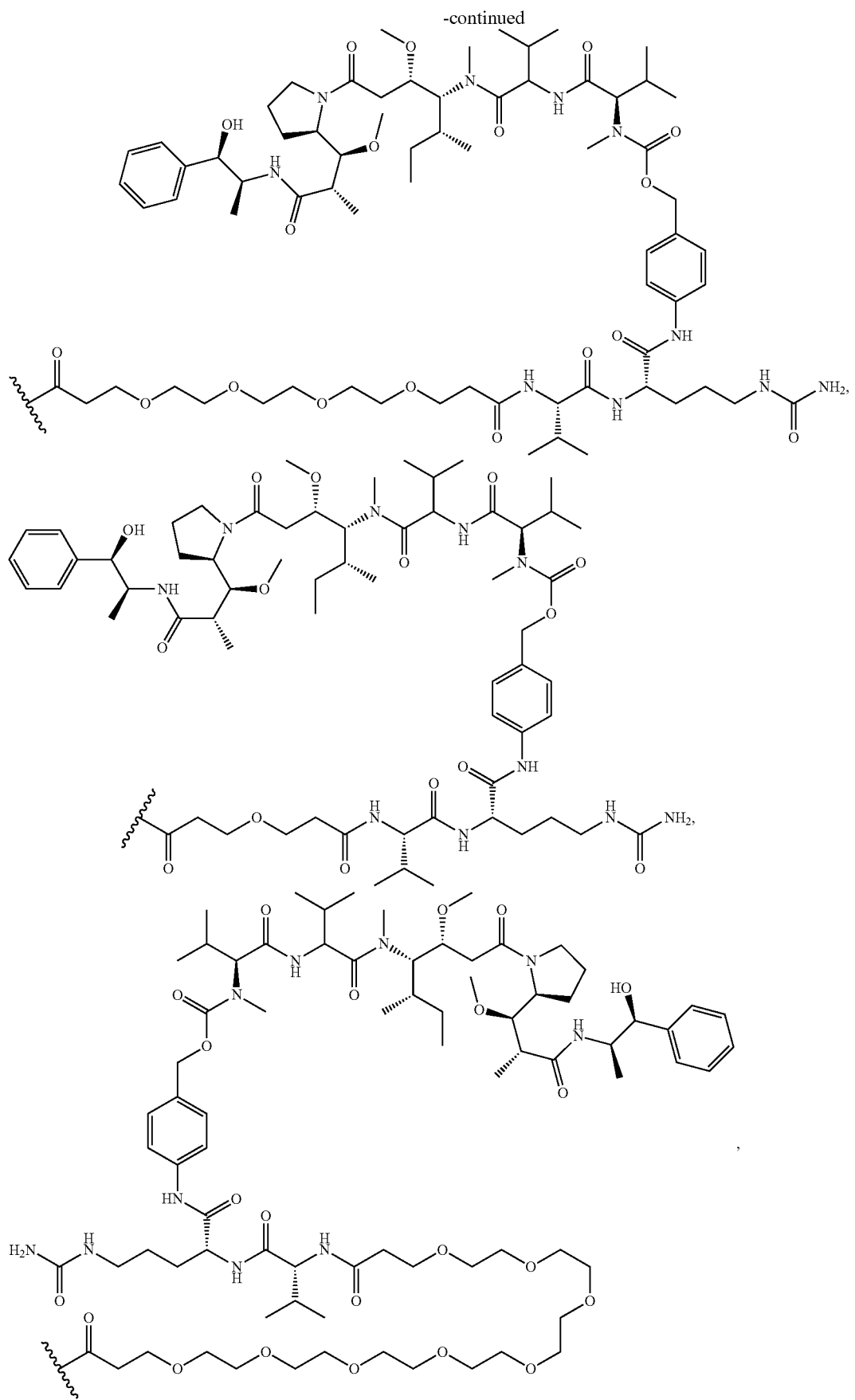

-continued
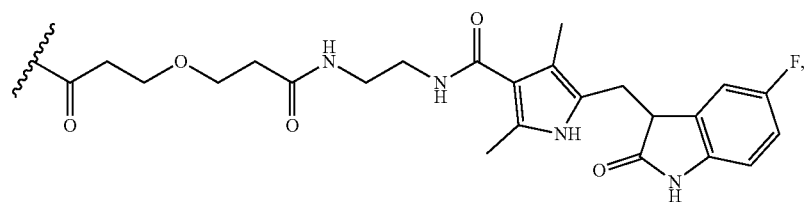
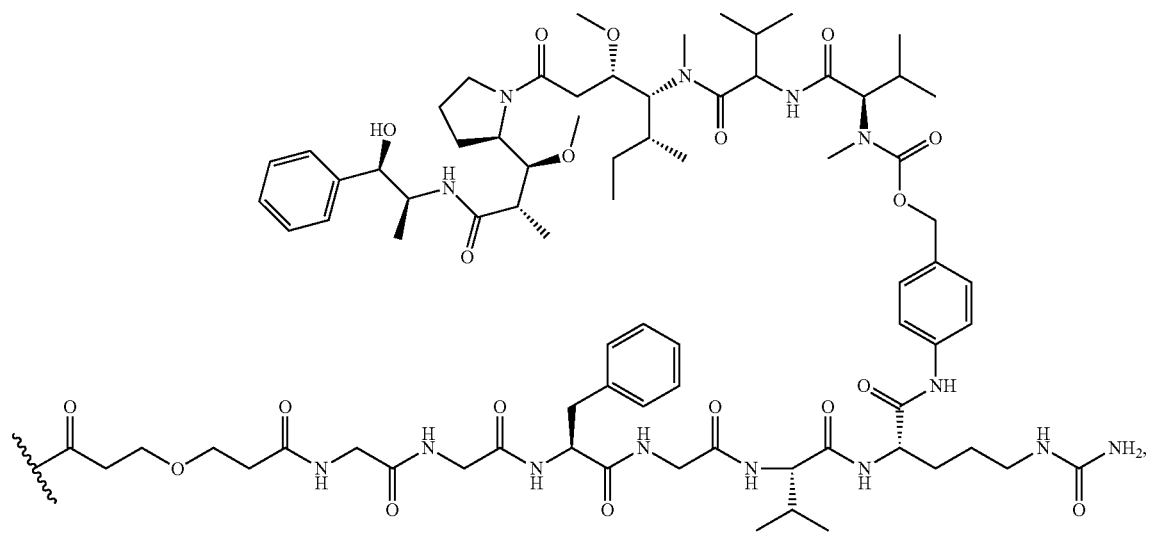
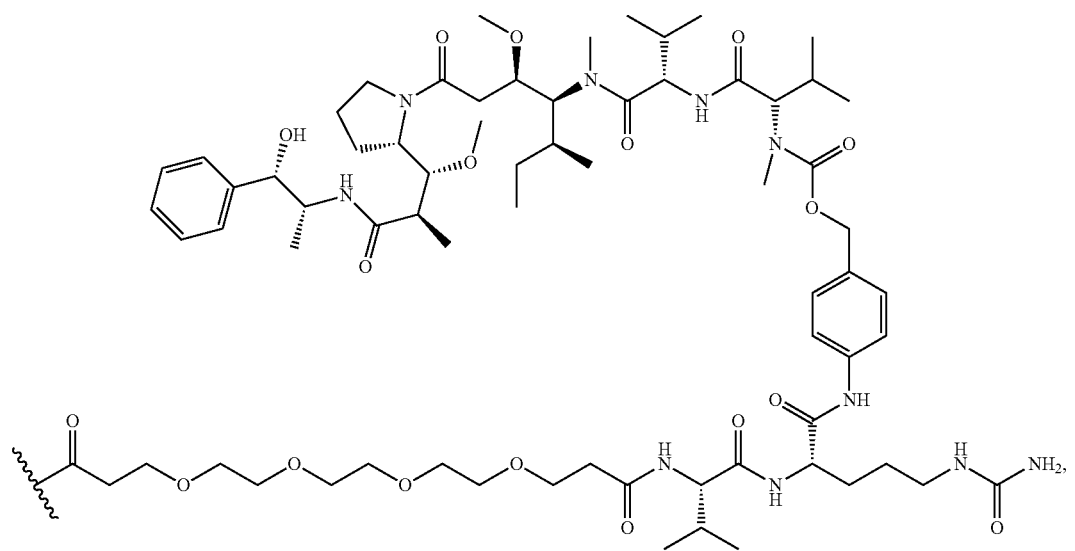

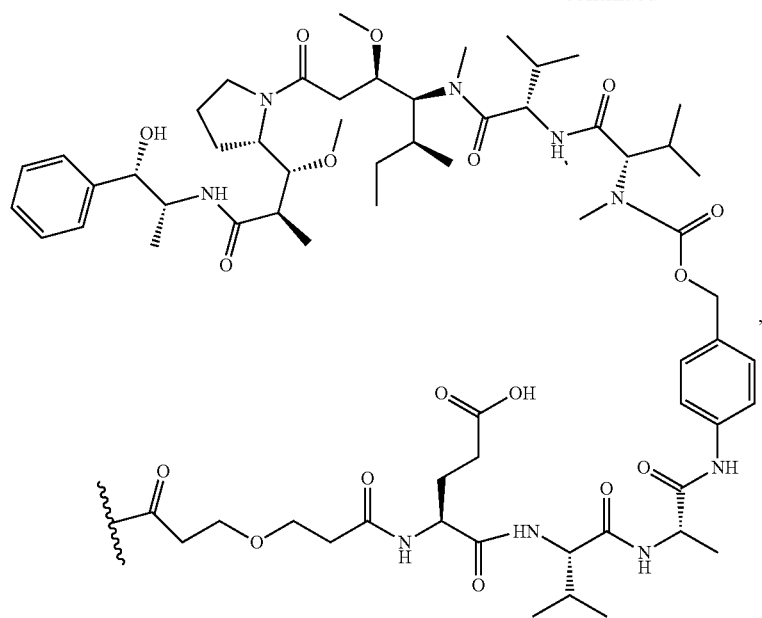
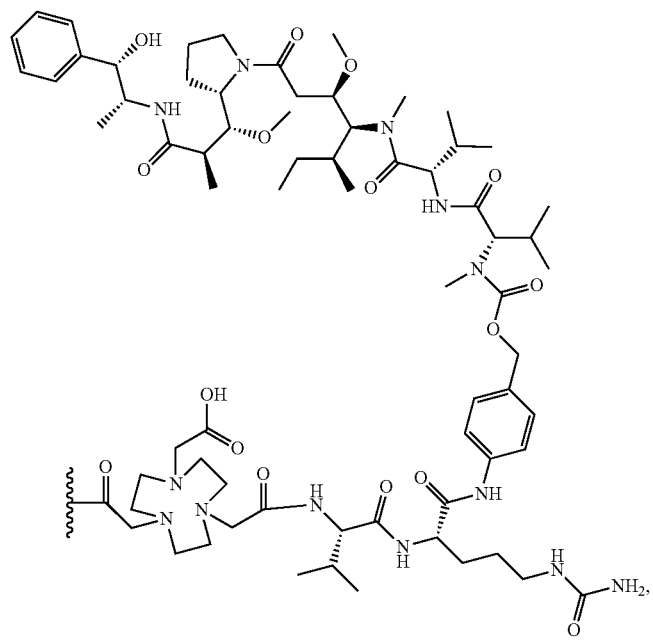
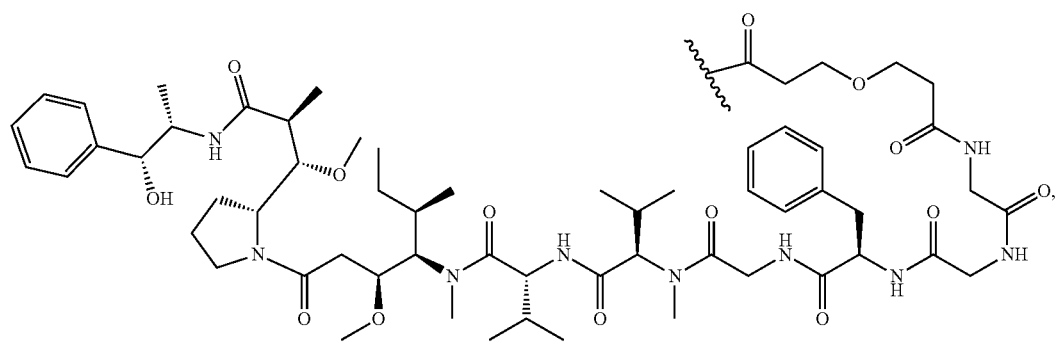

-continued
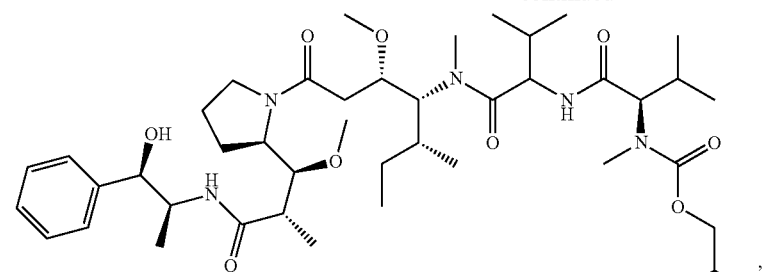
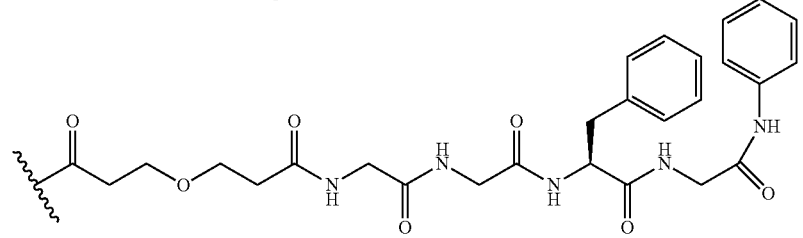
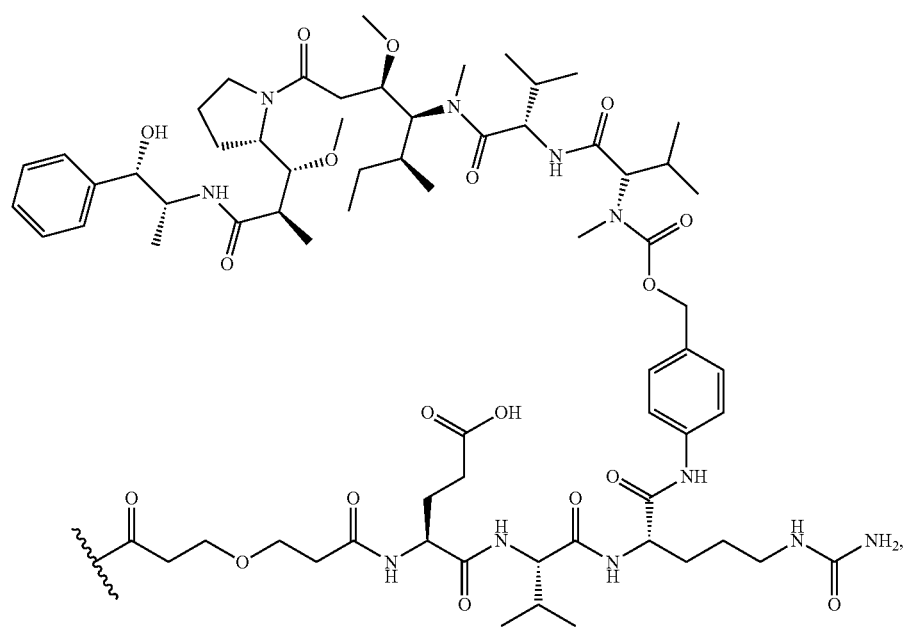

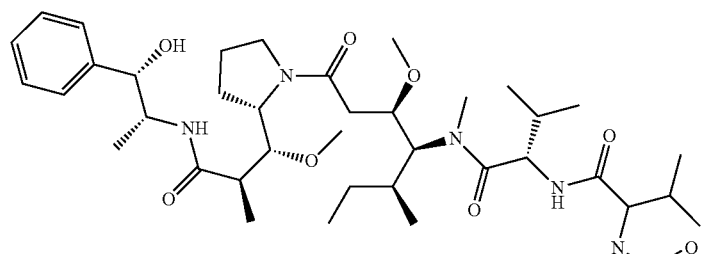
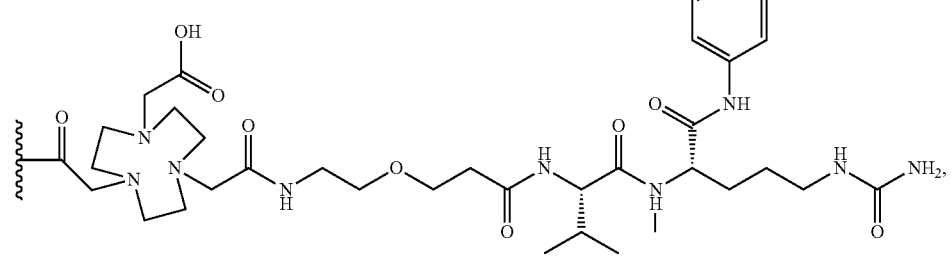
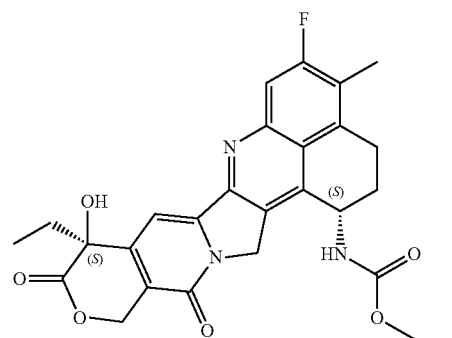
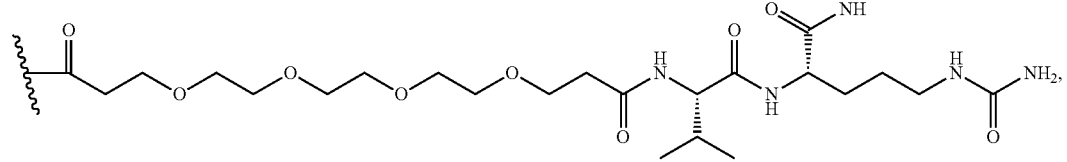

-continued
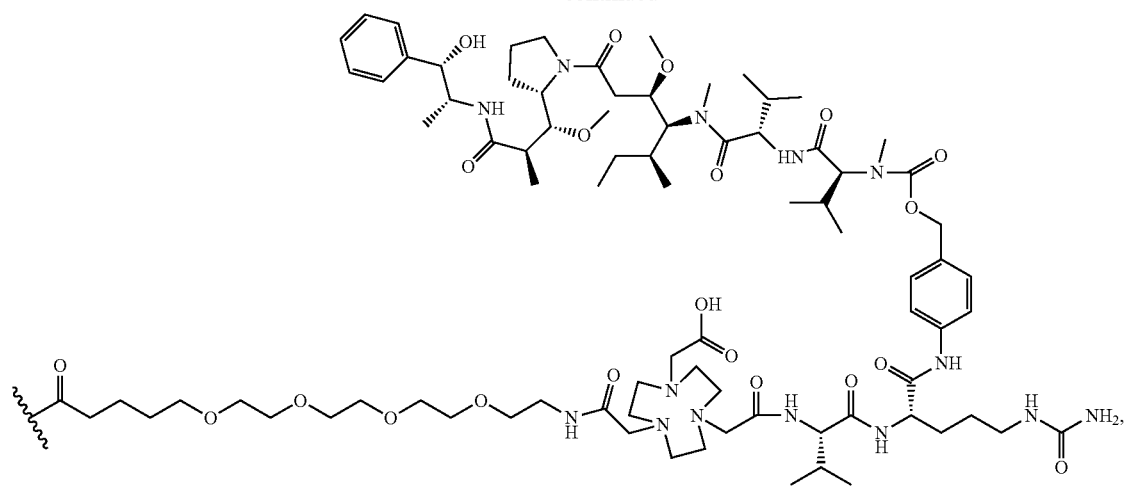
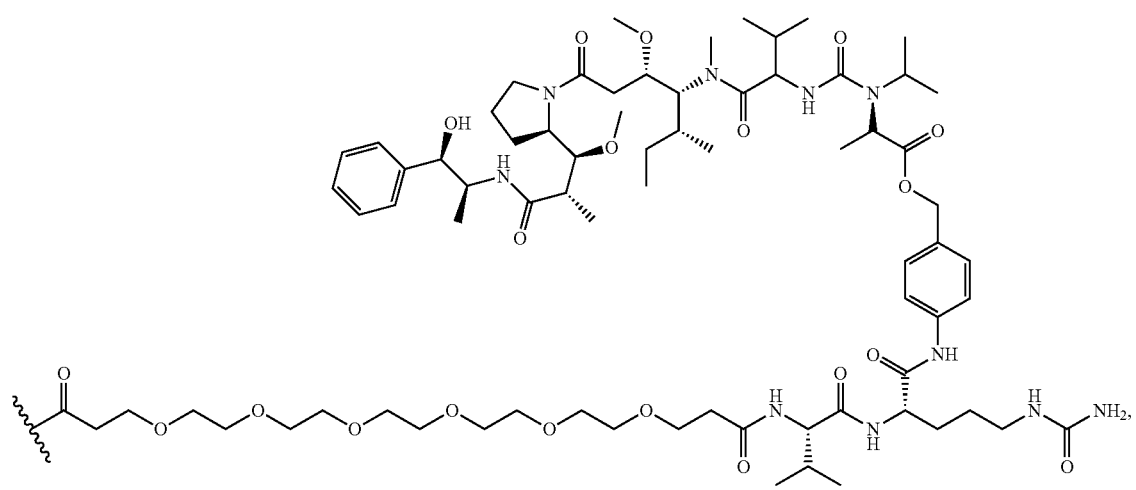
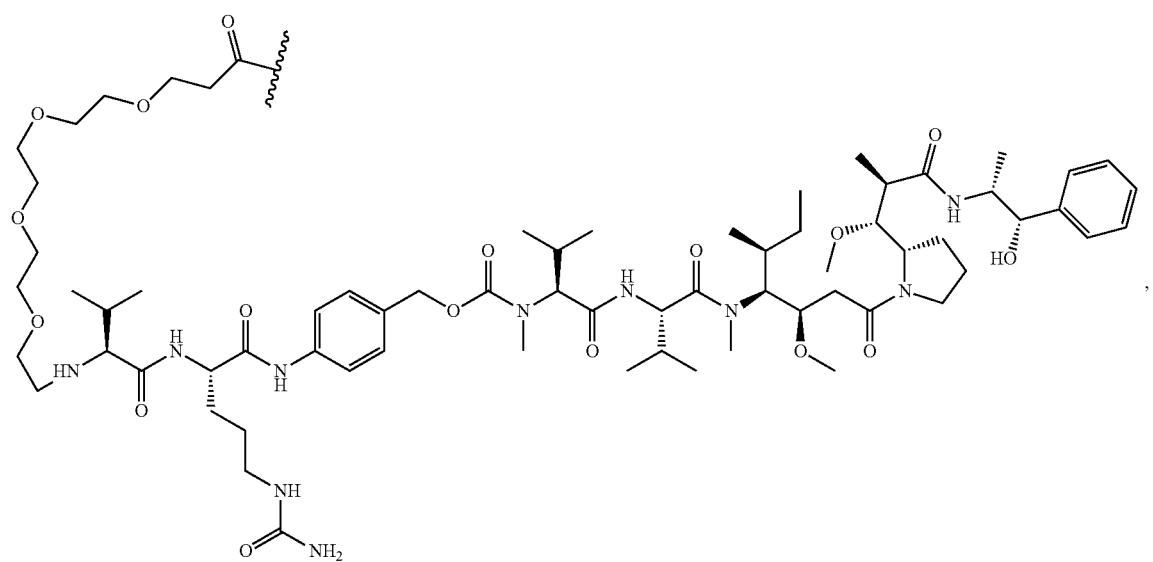

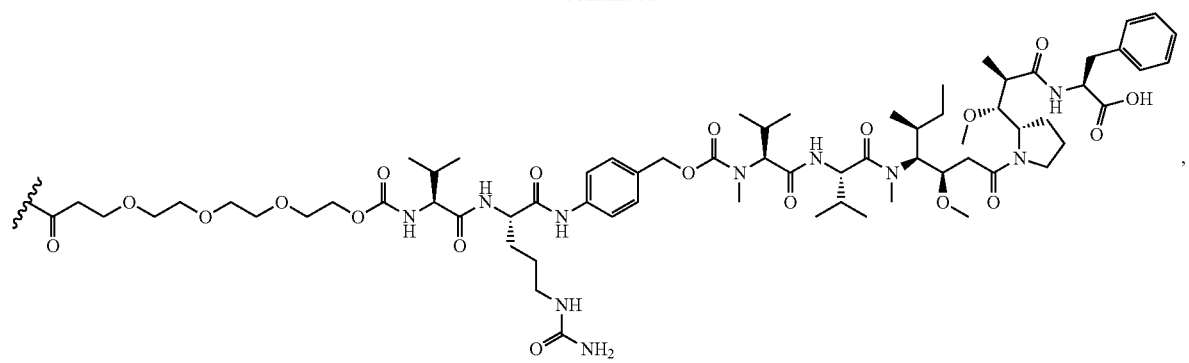
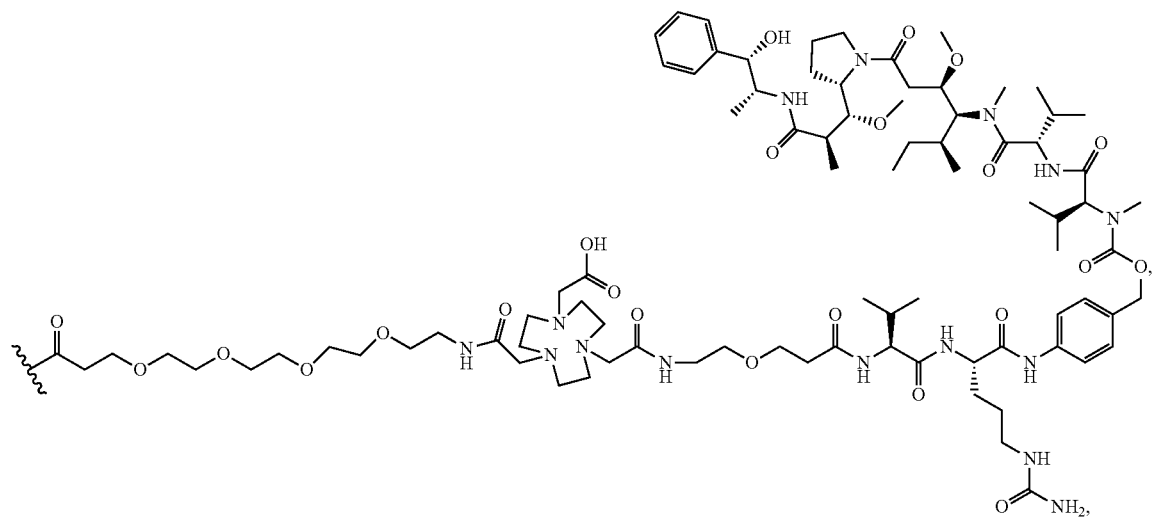
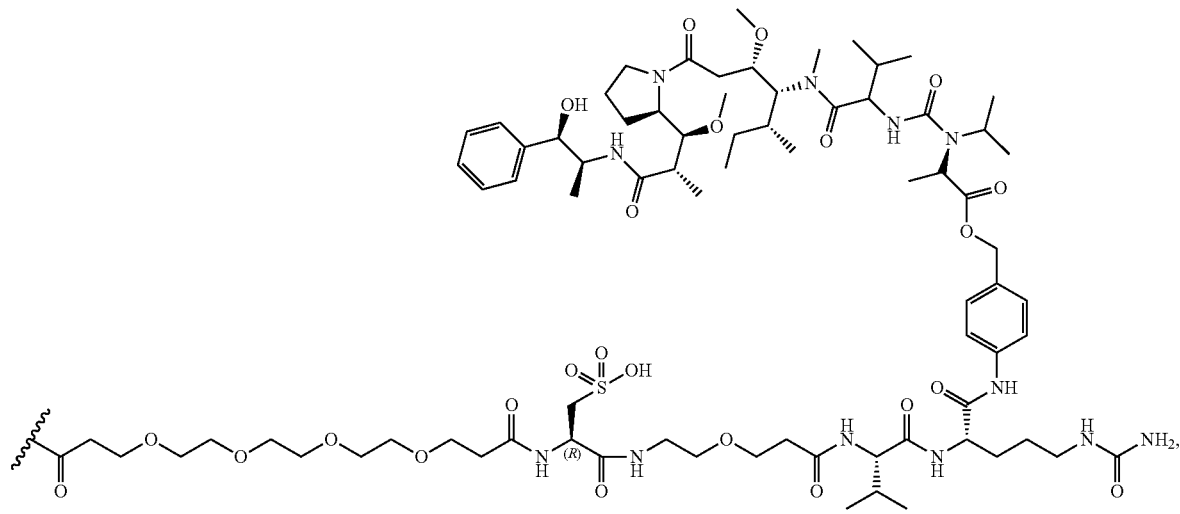

-continued
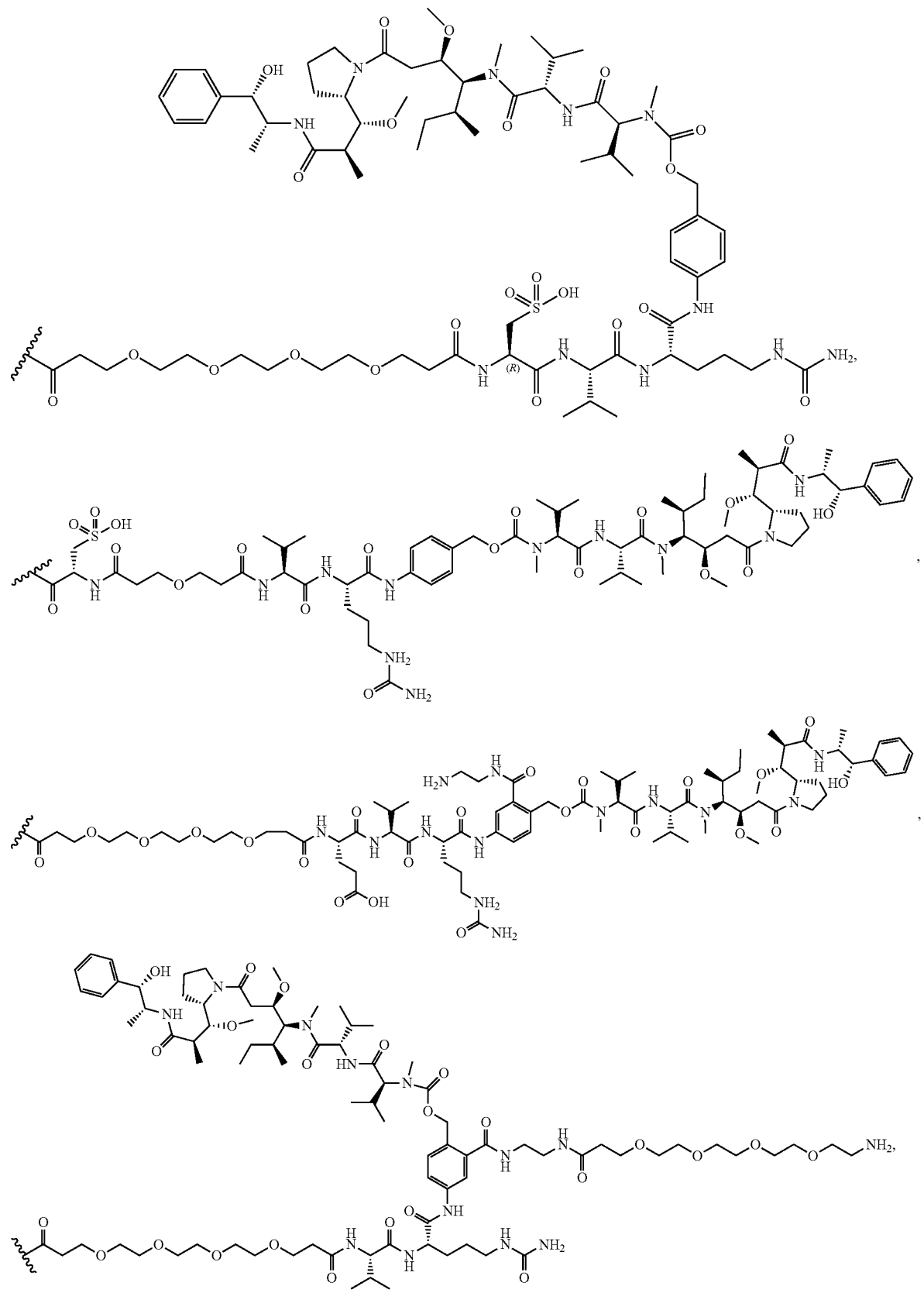

661
662
-continued
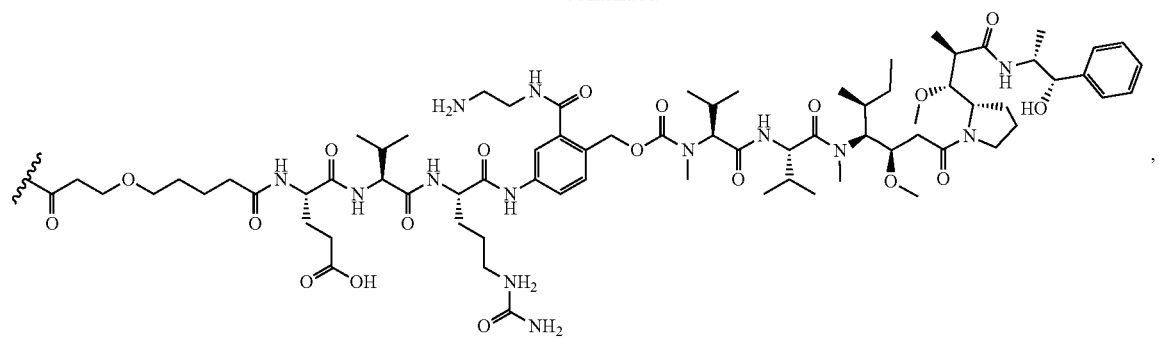
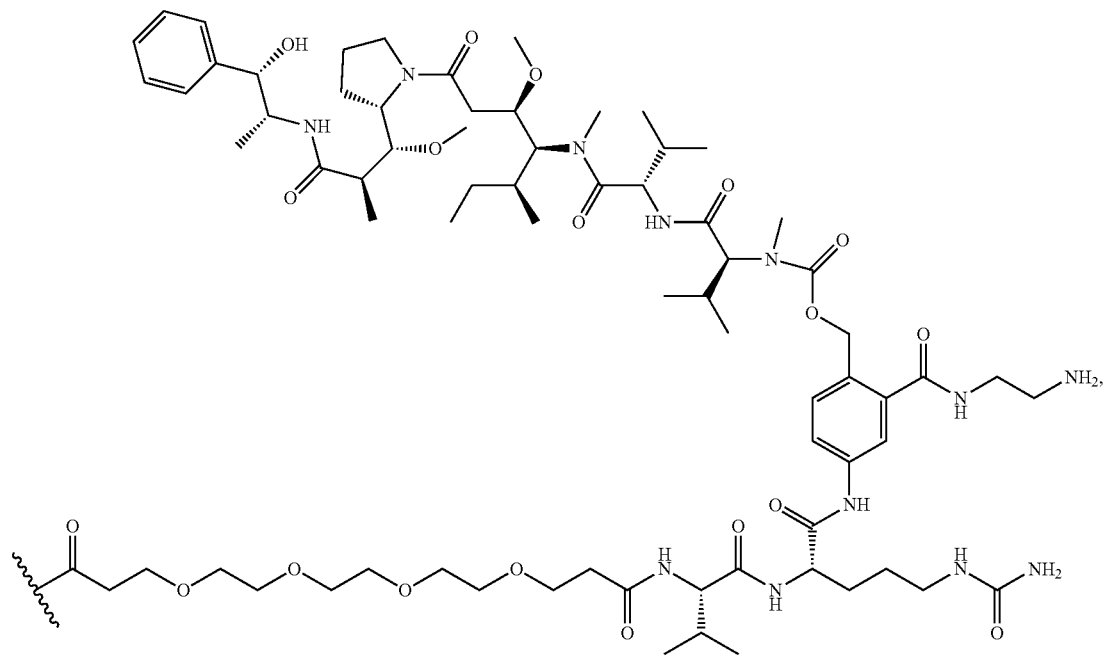
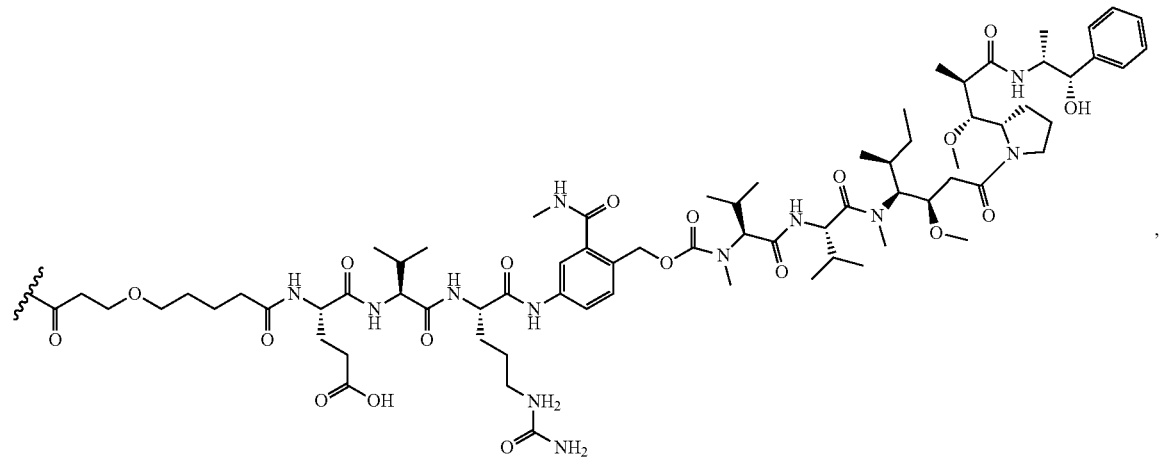

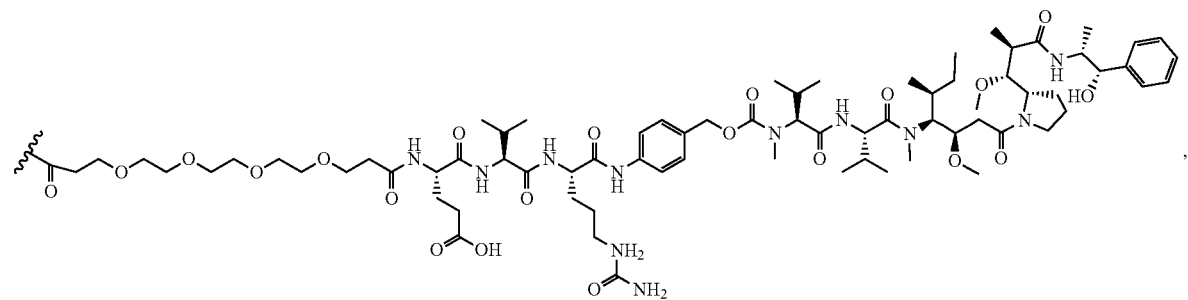
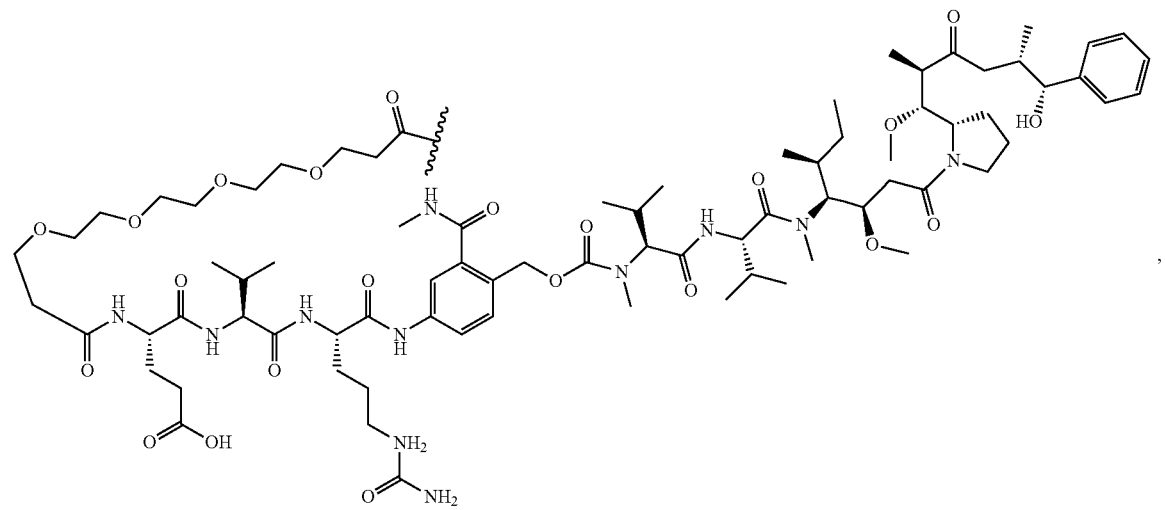
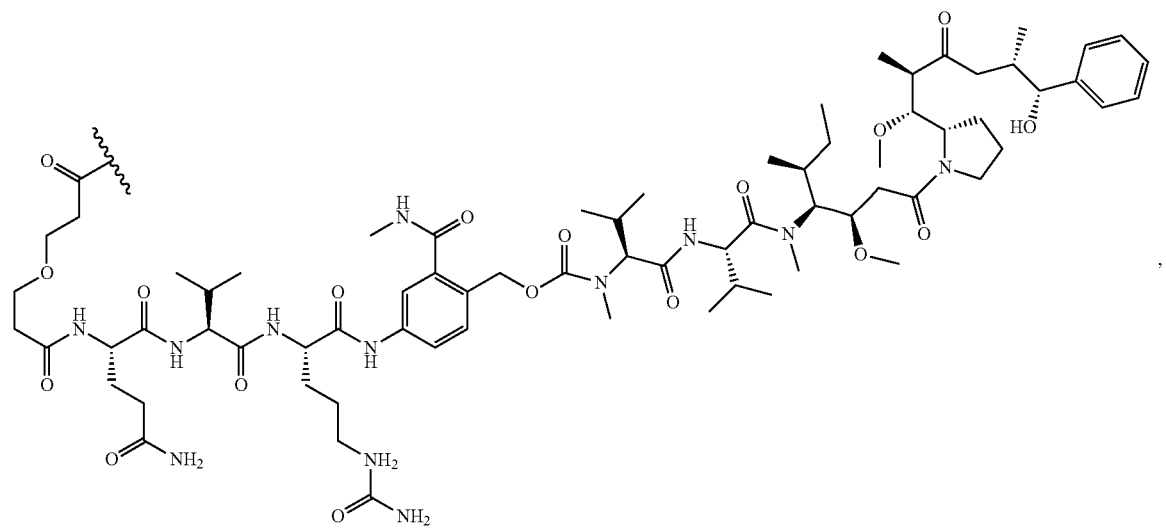
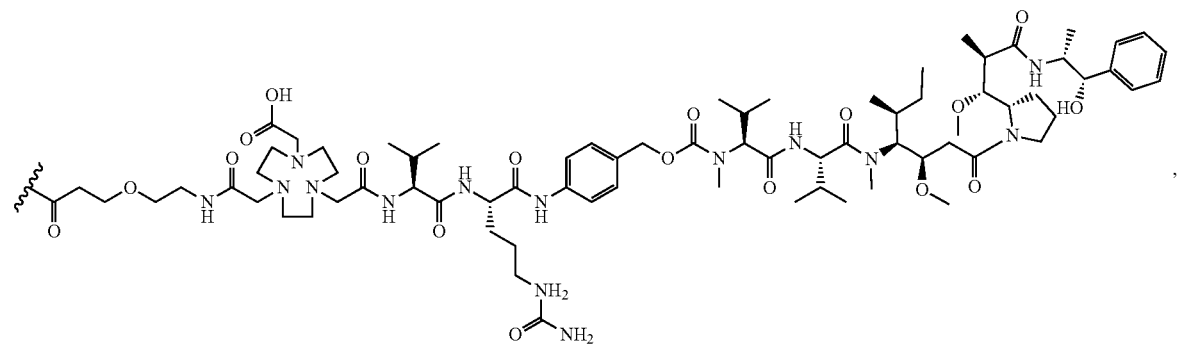

665
666
-continued
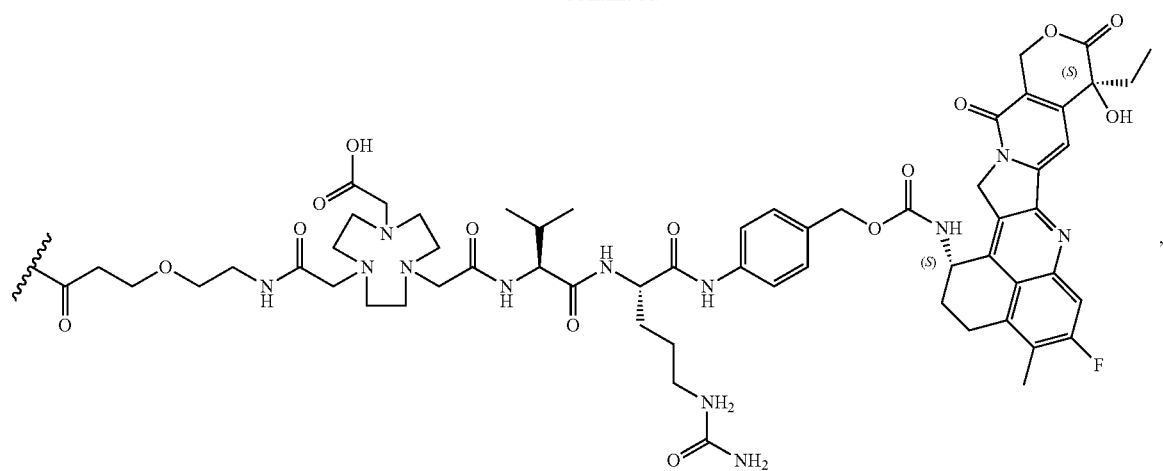
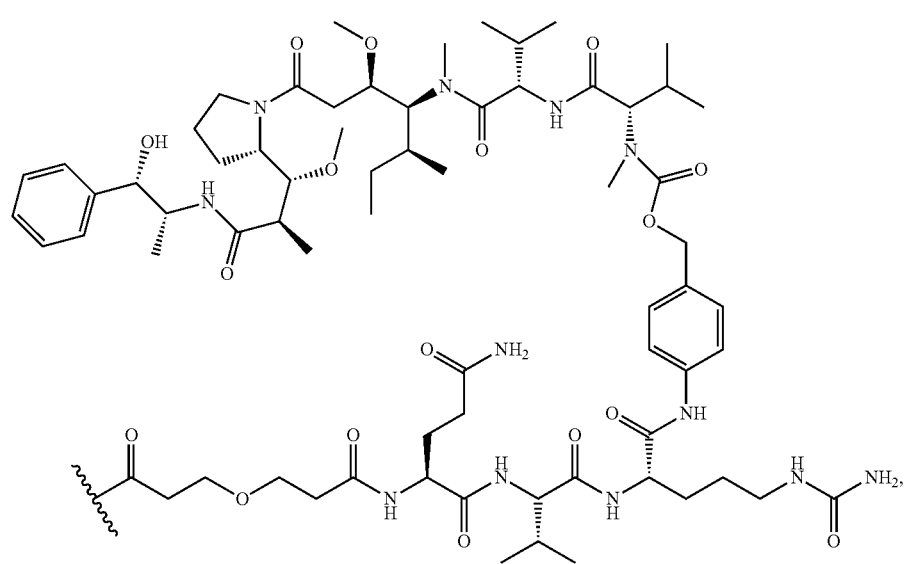
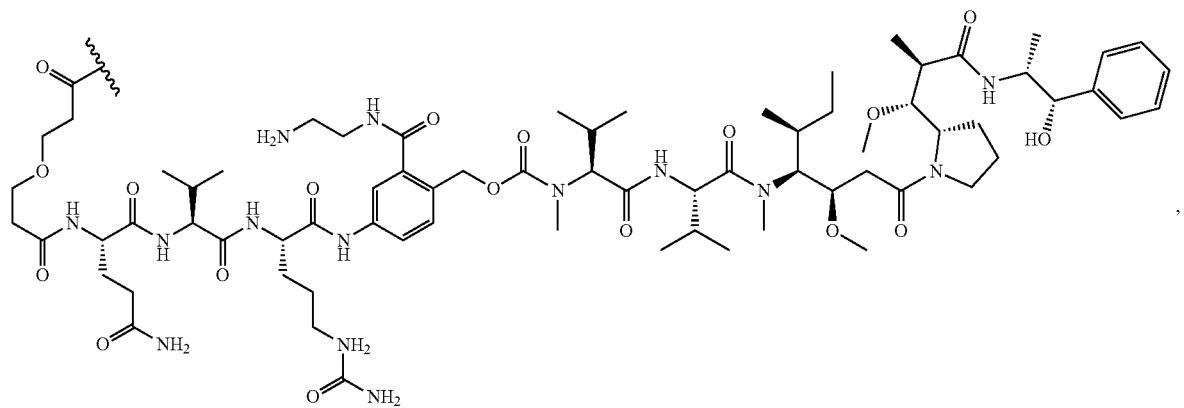

667
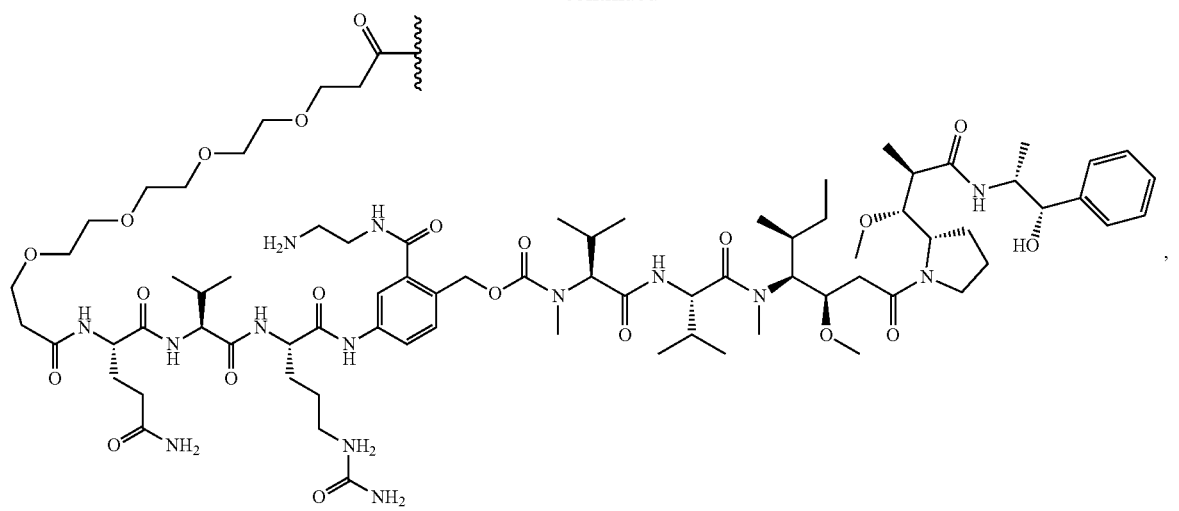
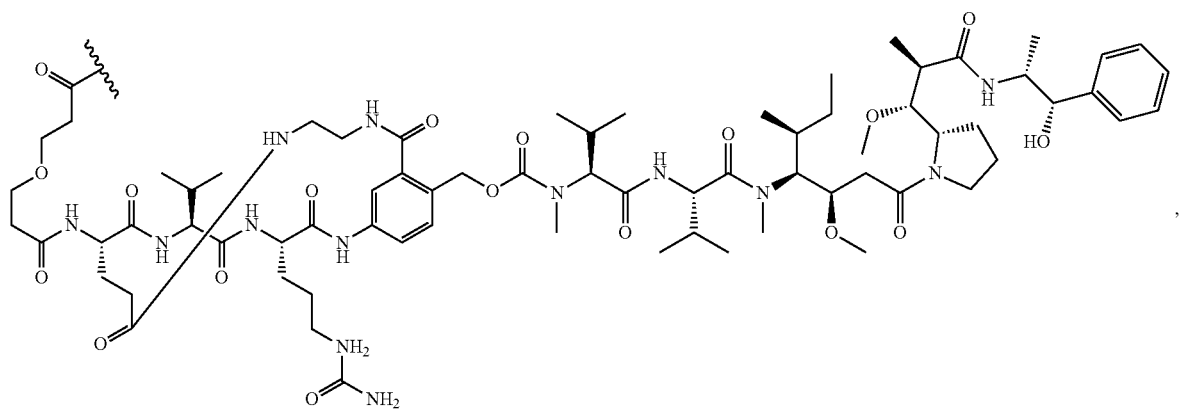
668
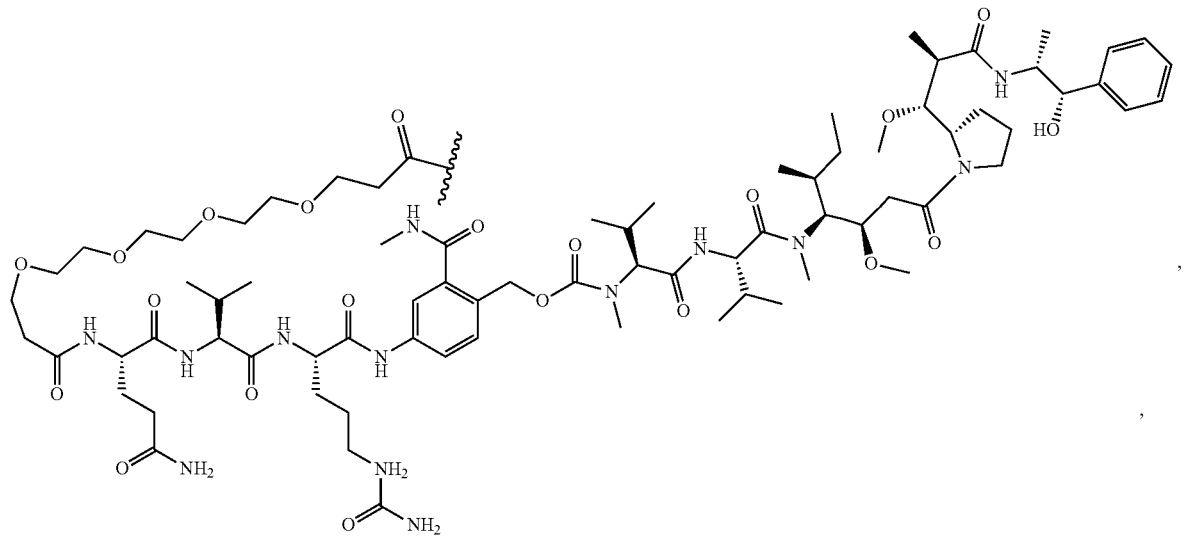

-continued
669
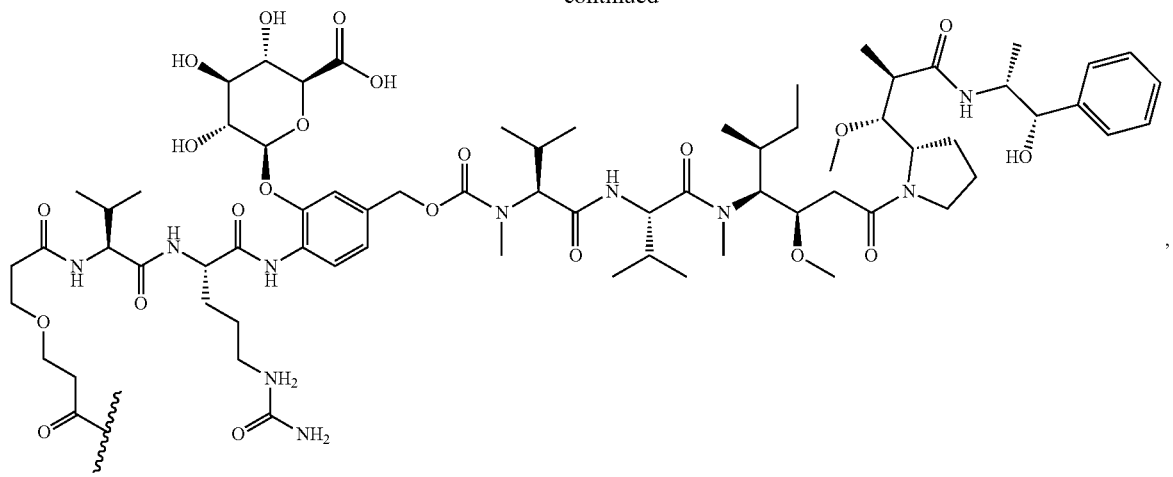
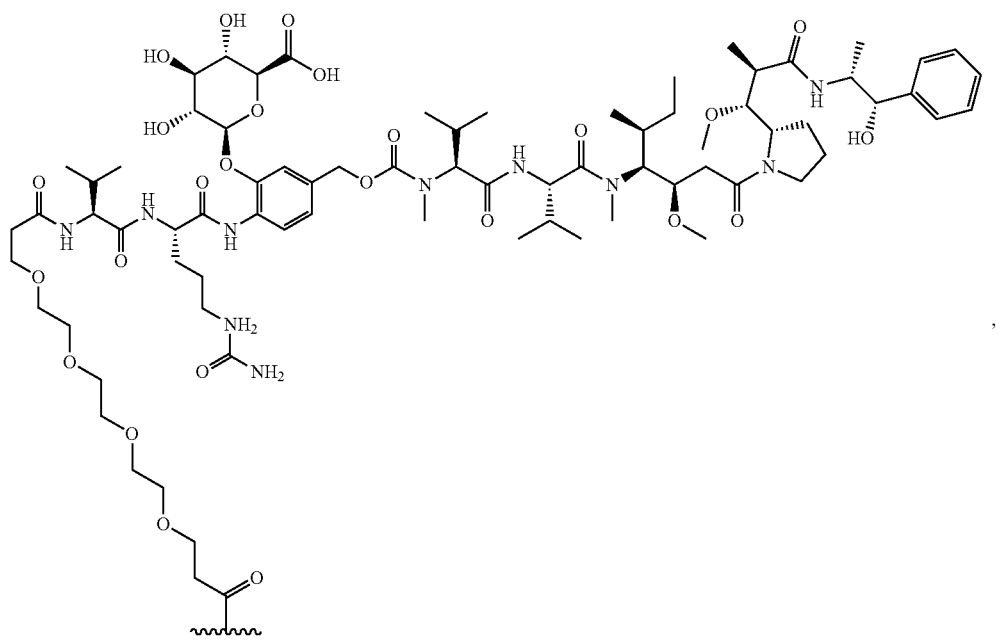
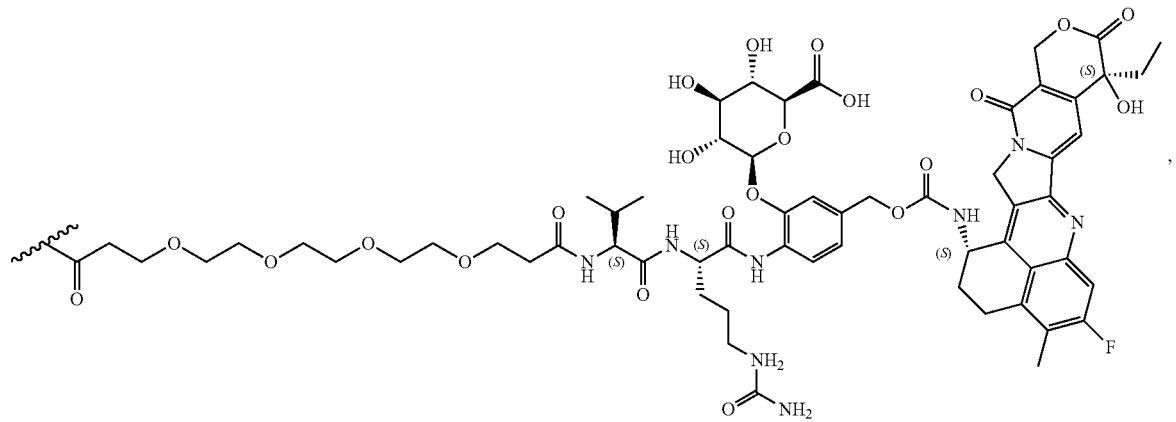
670

-continued
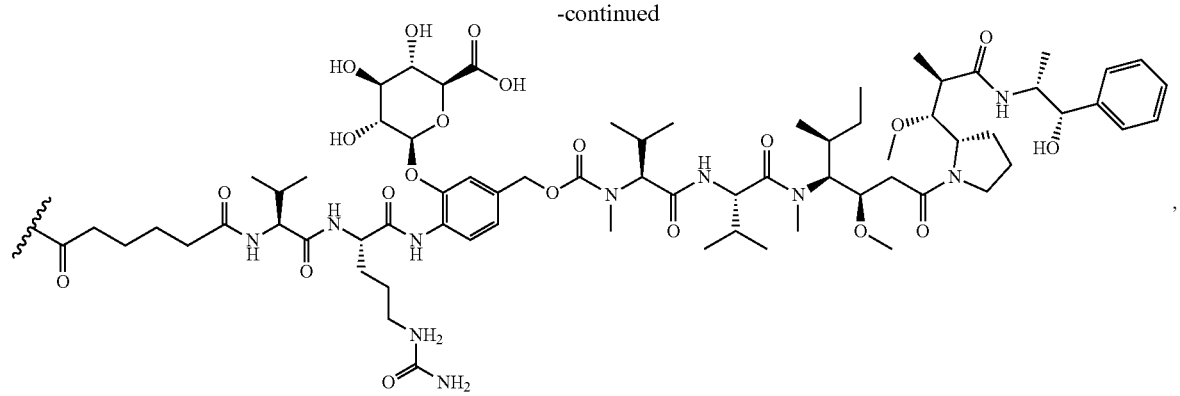
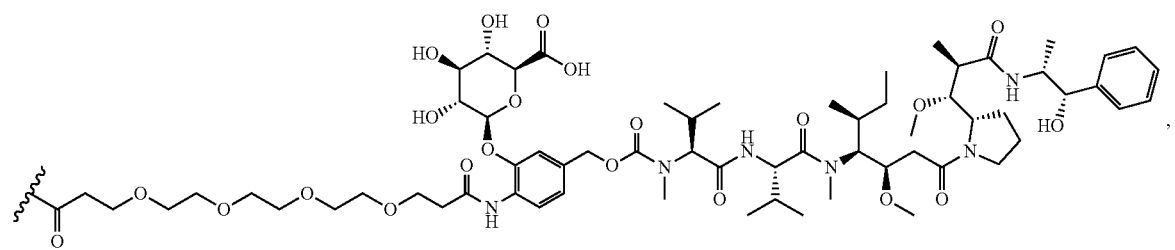
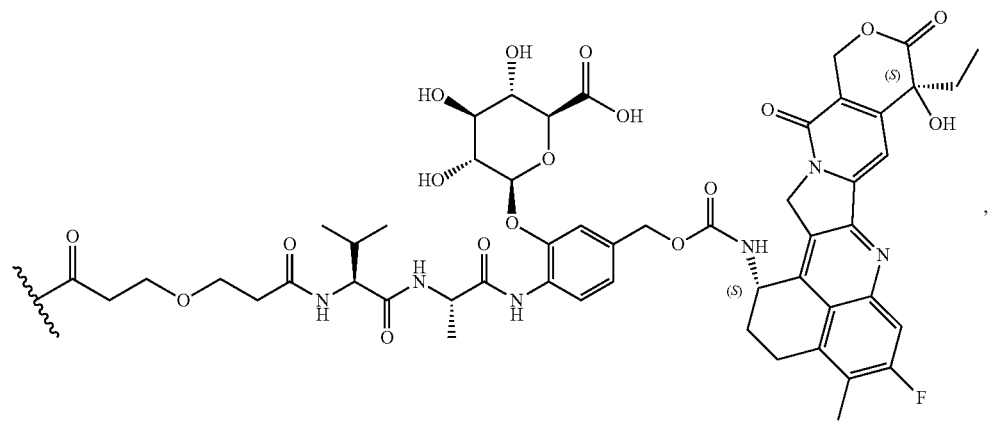
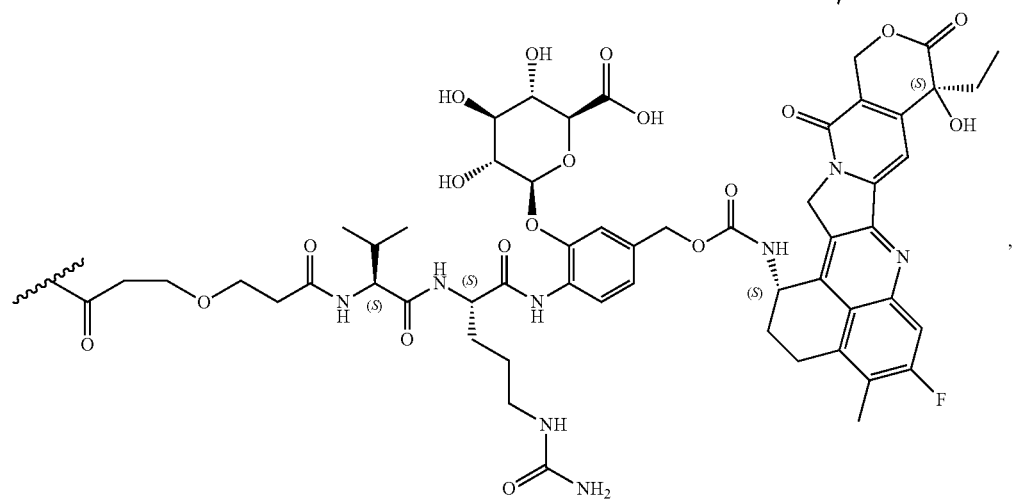

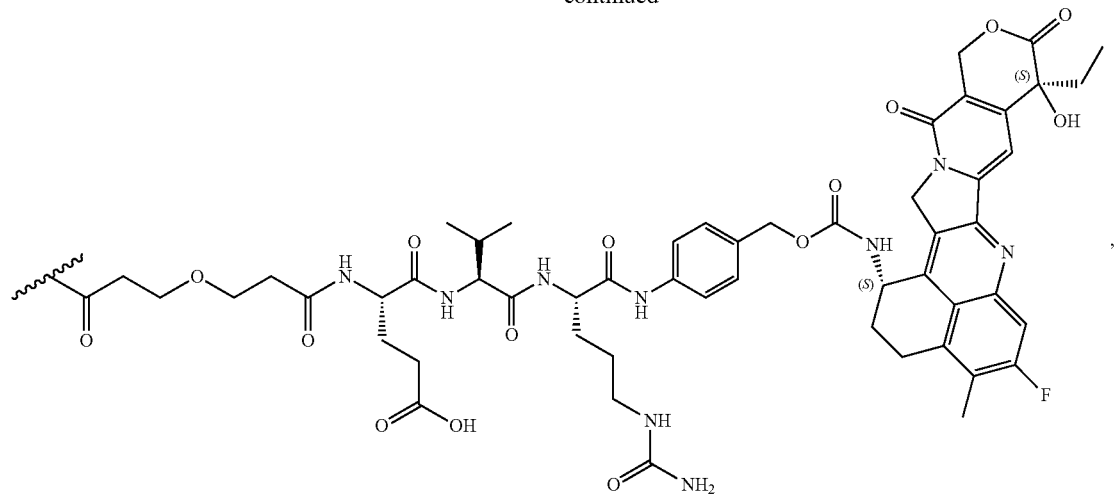
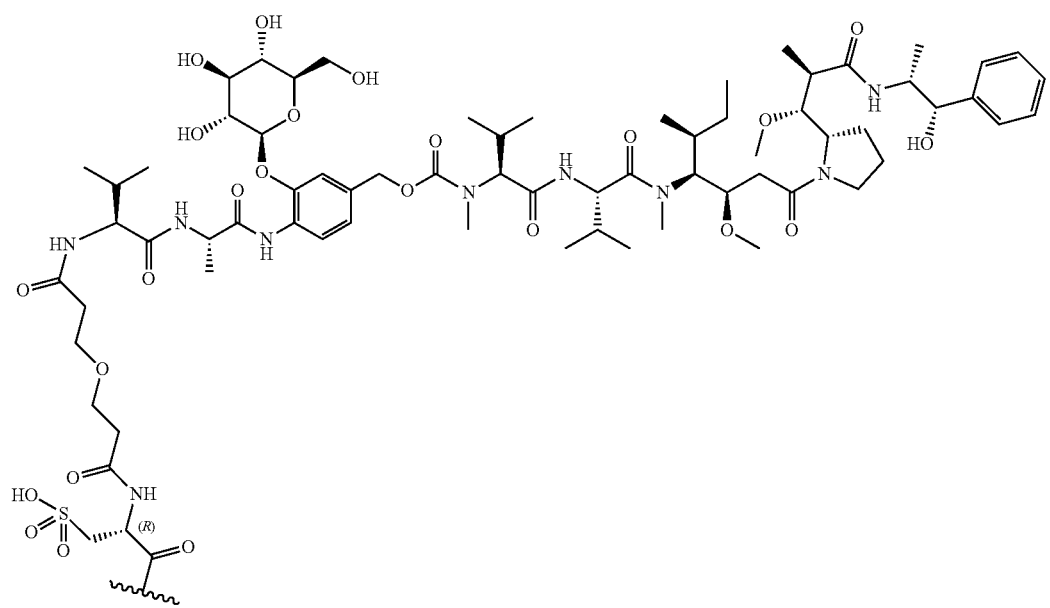
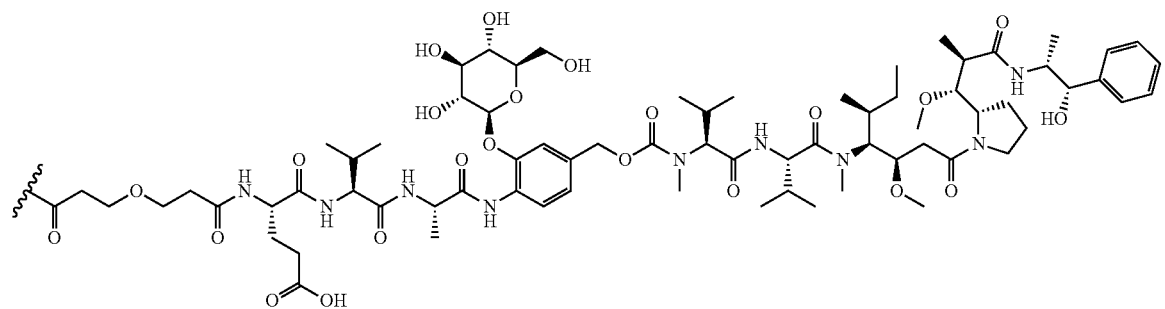

-continued
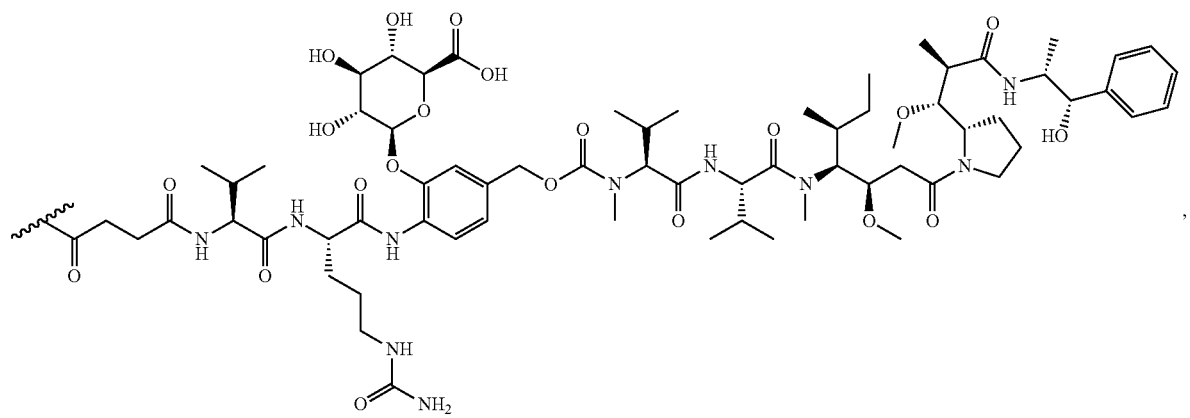
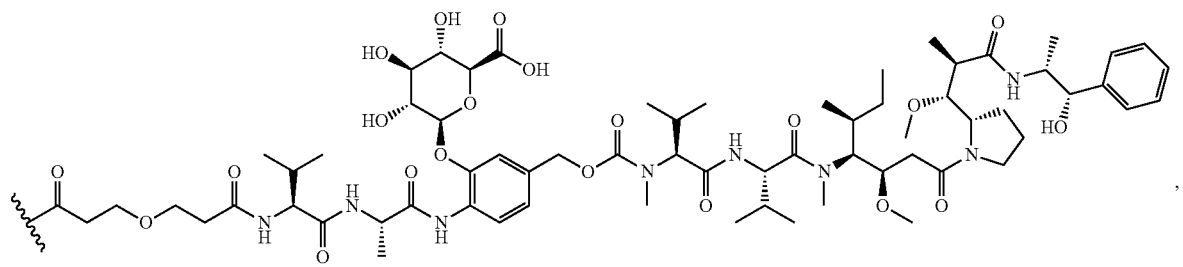
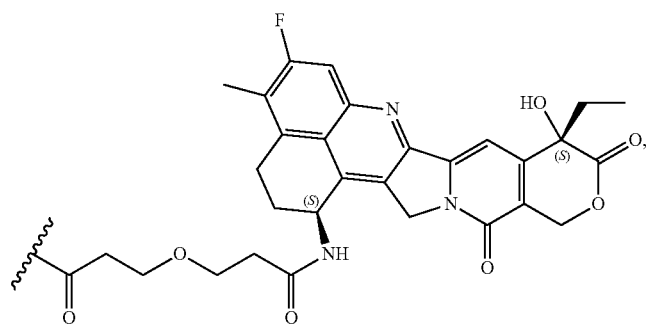
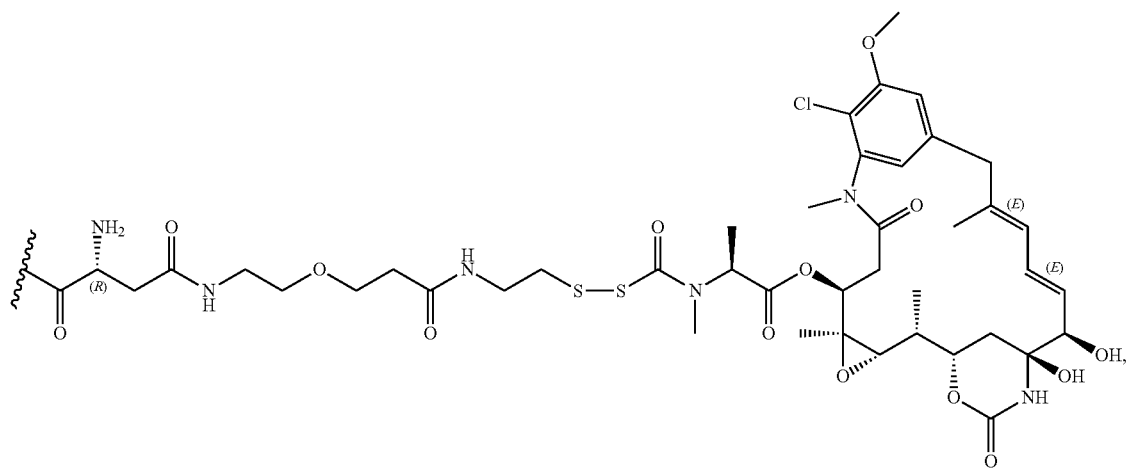

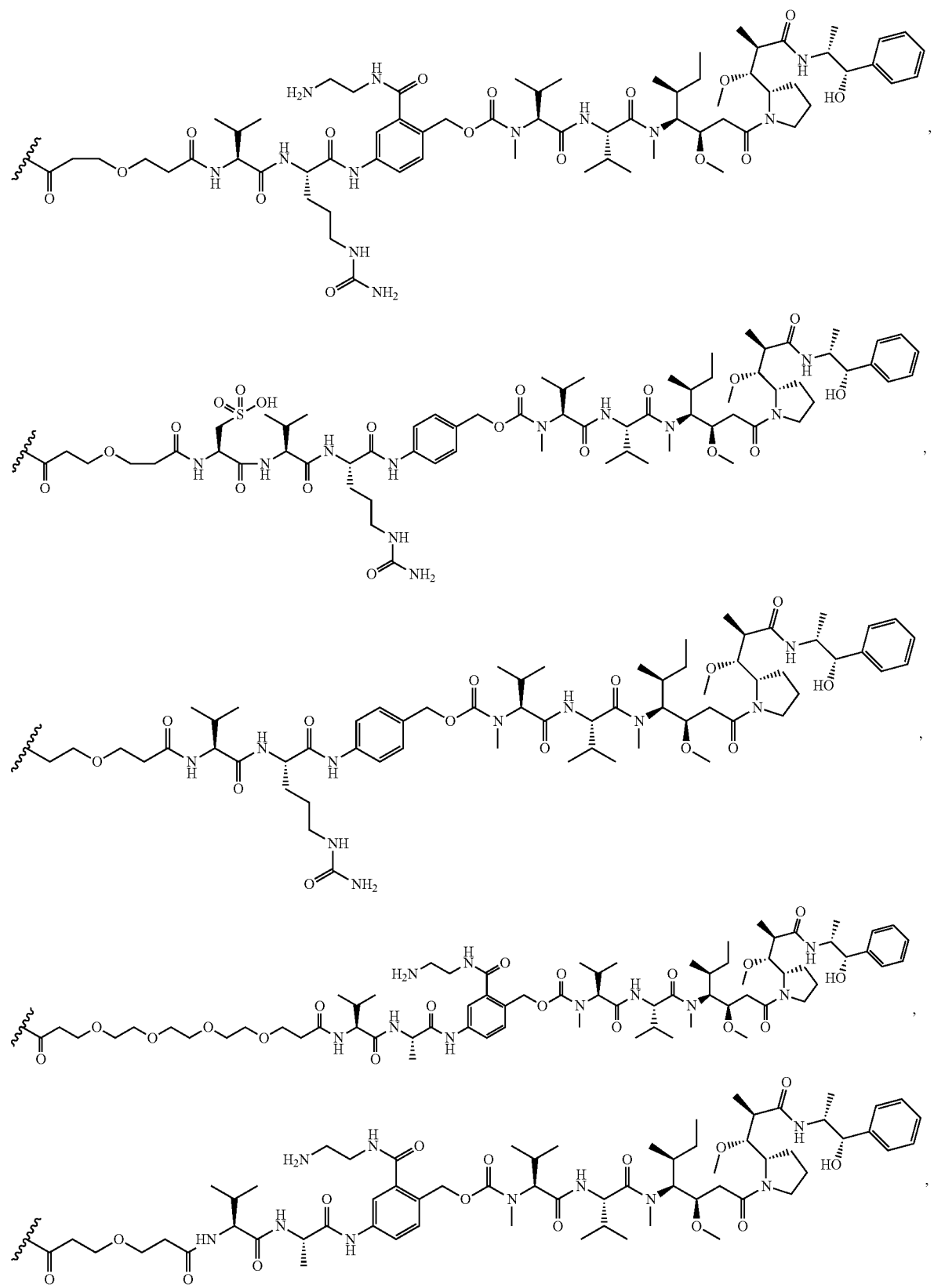

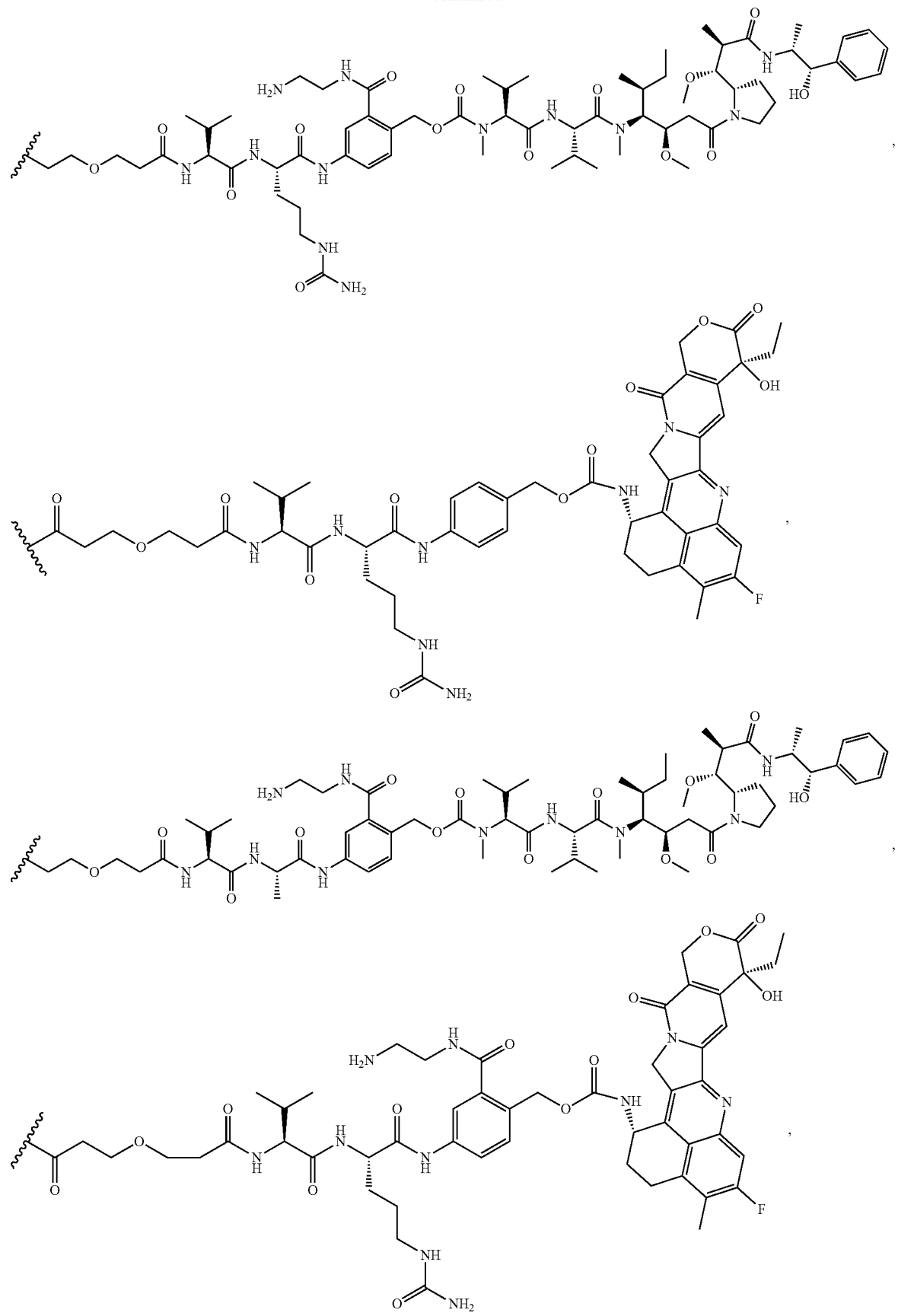

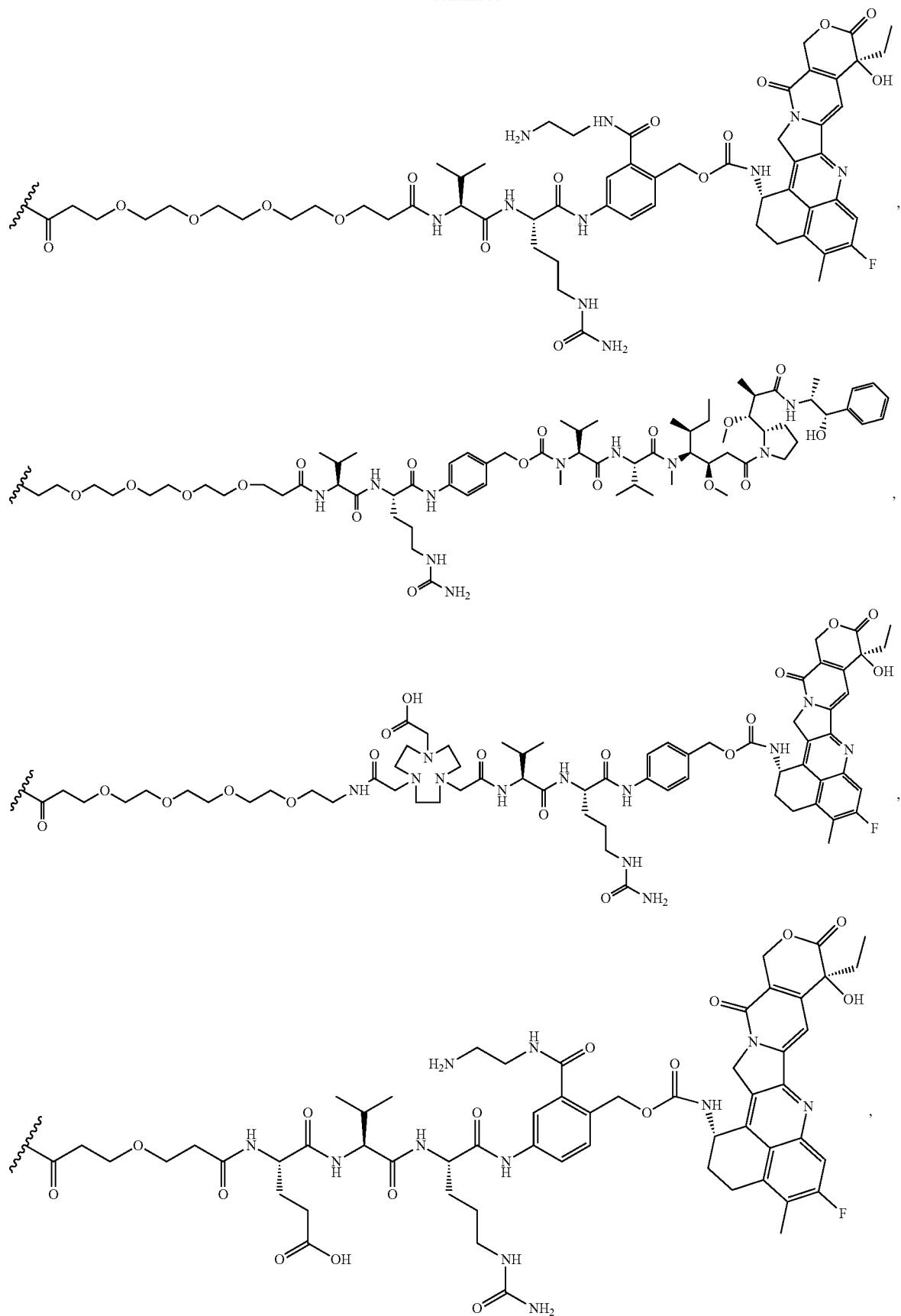

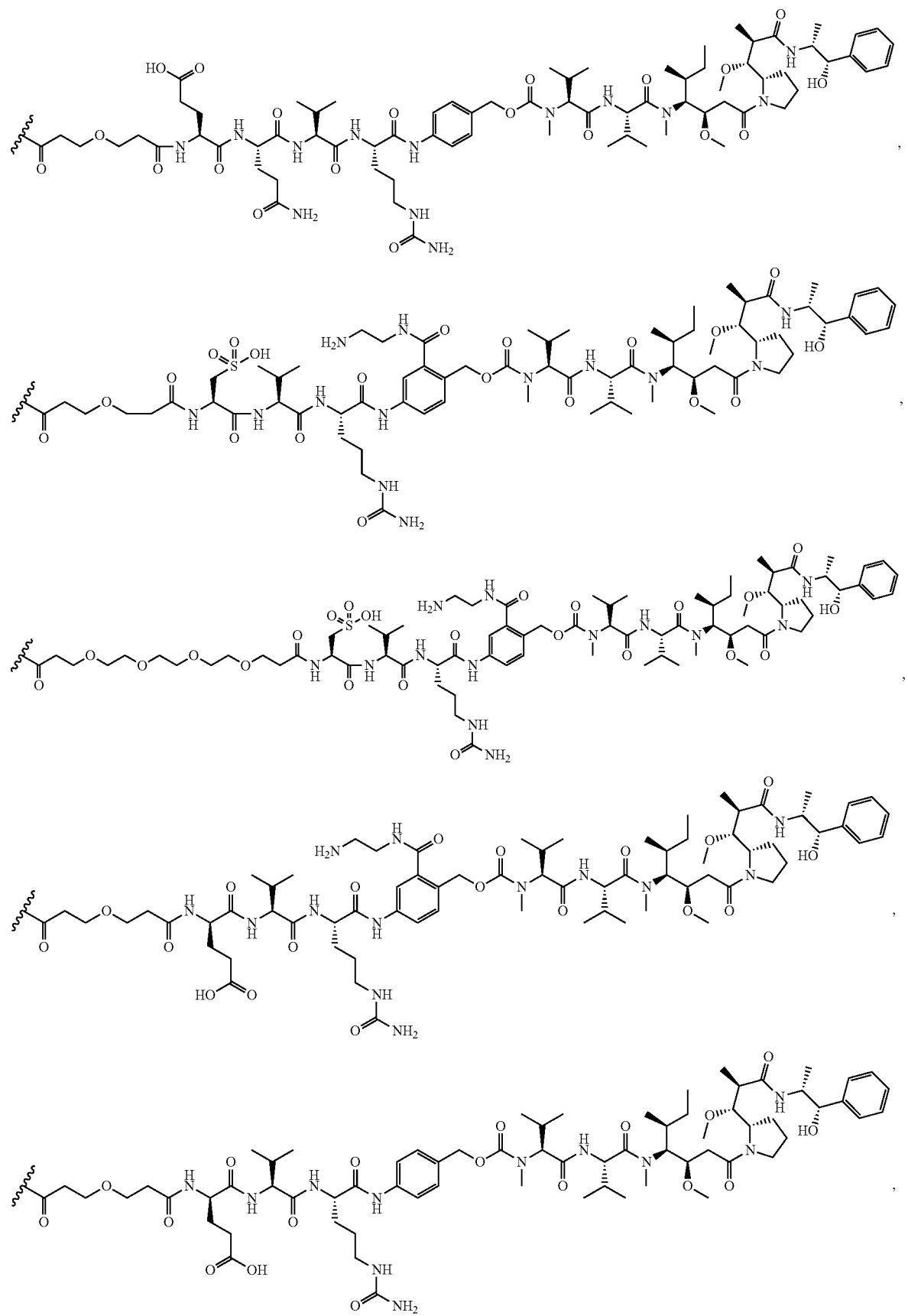

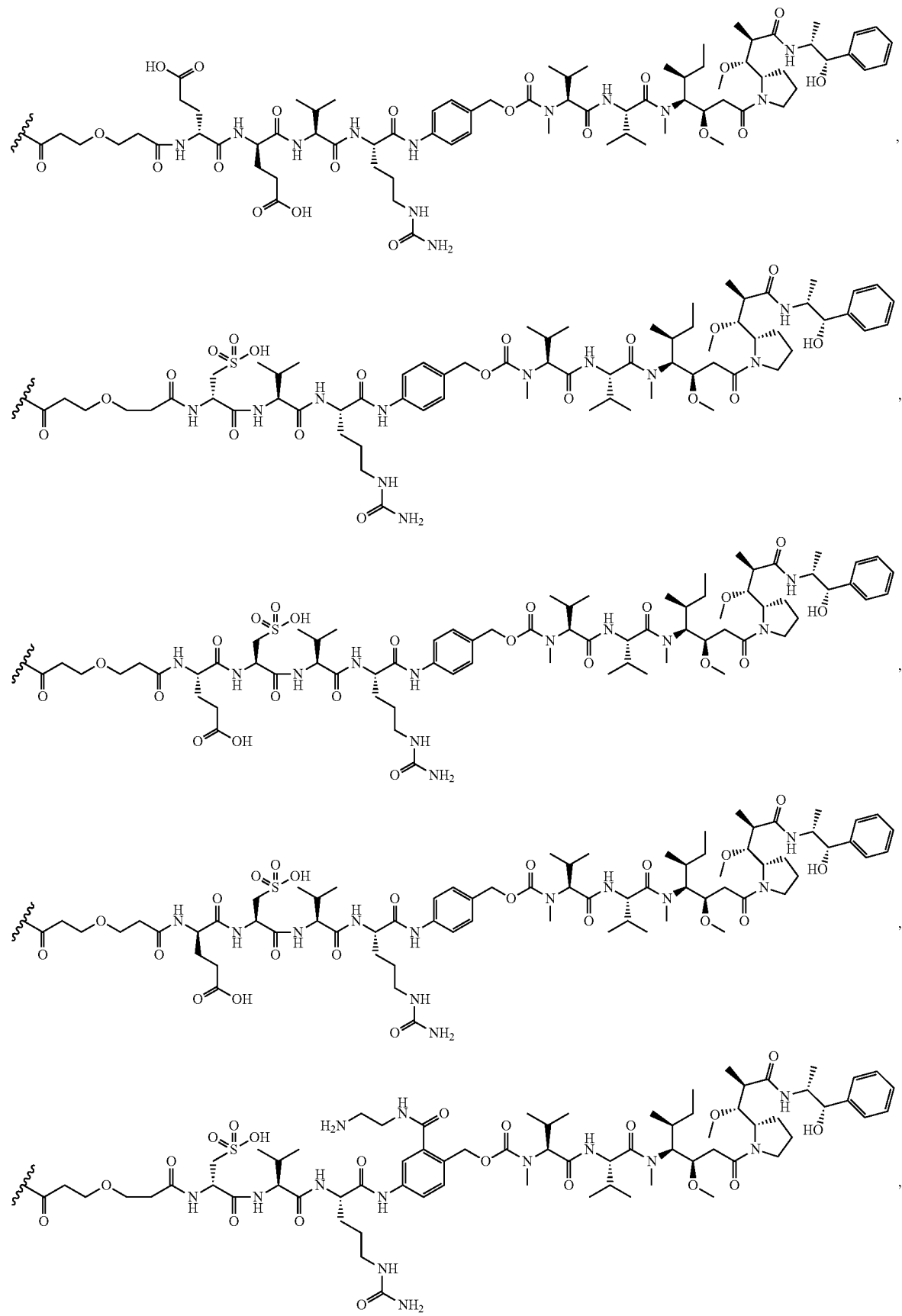

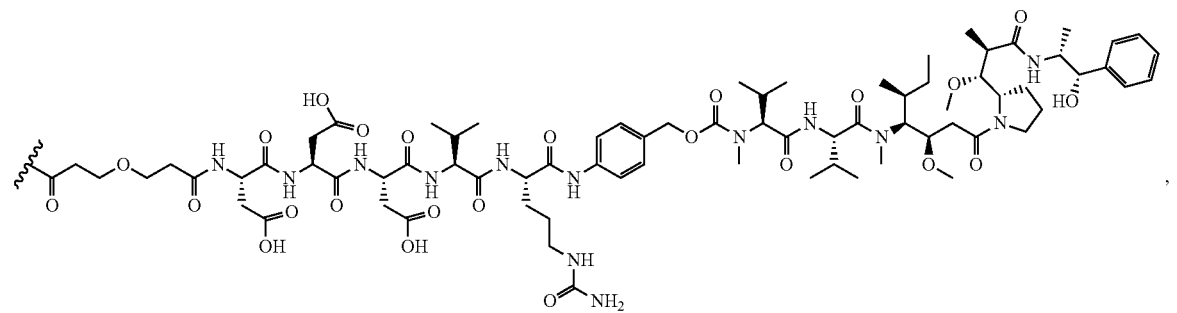
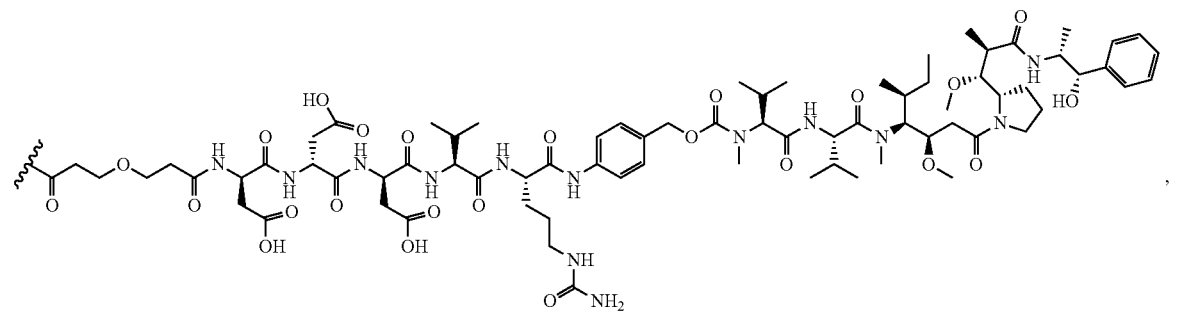
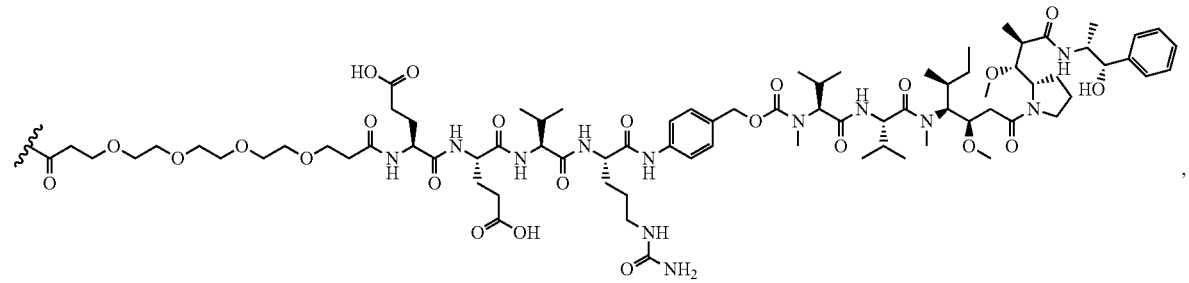
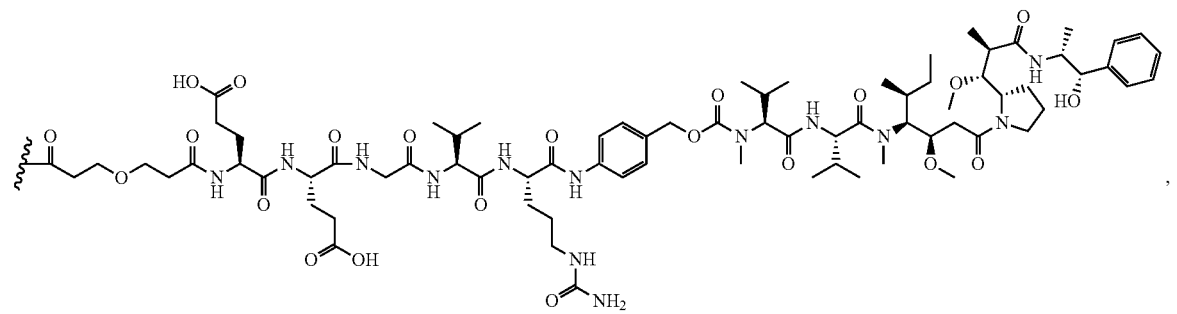
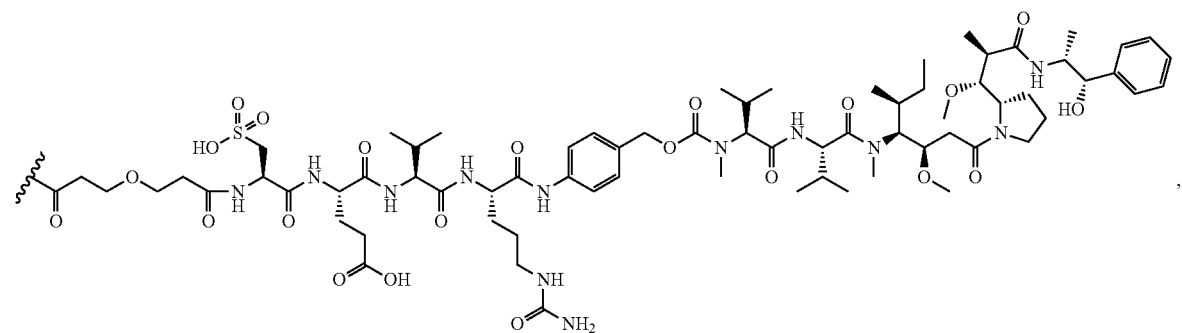

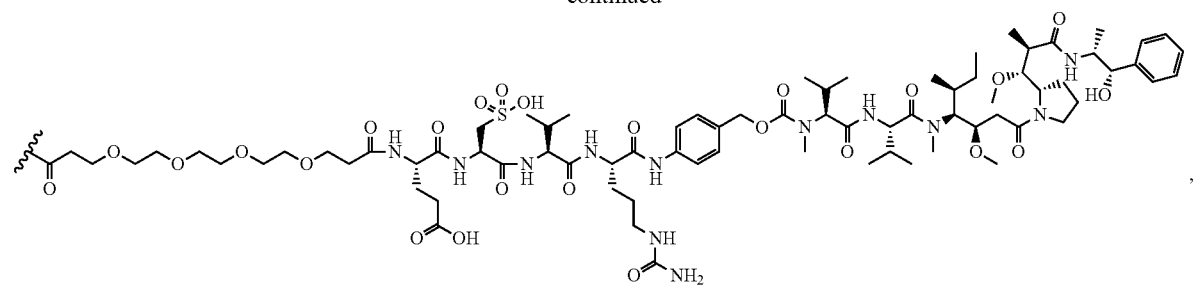
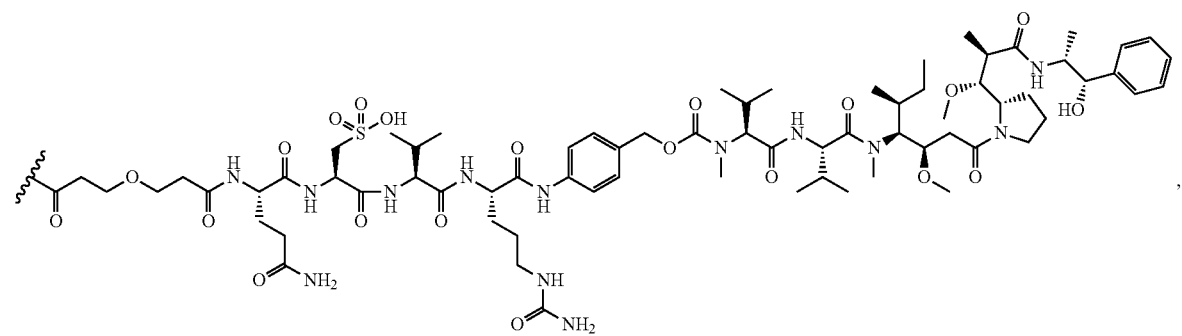
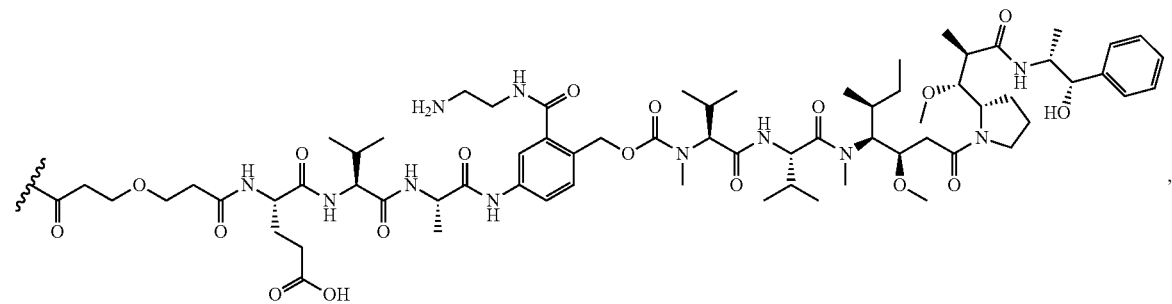
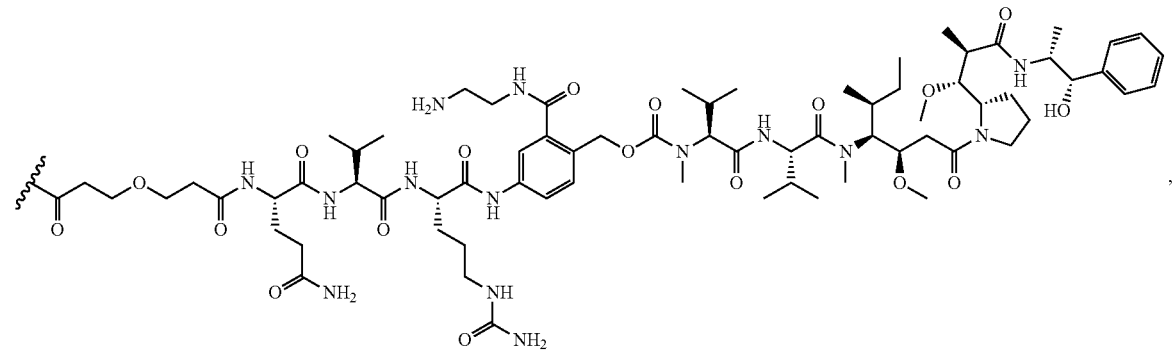
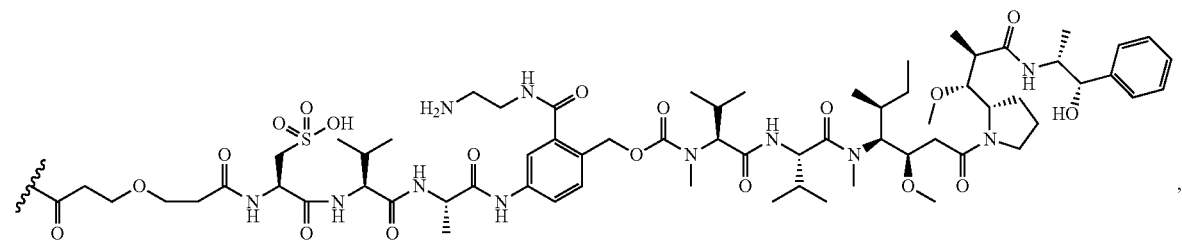

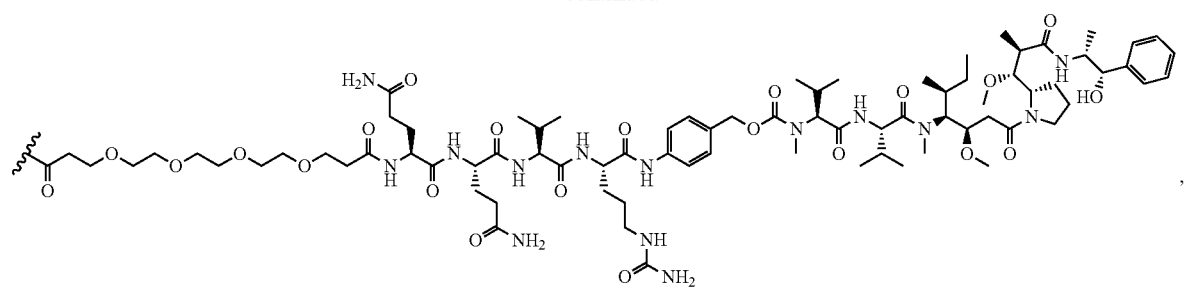
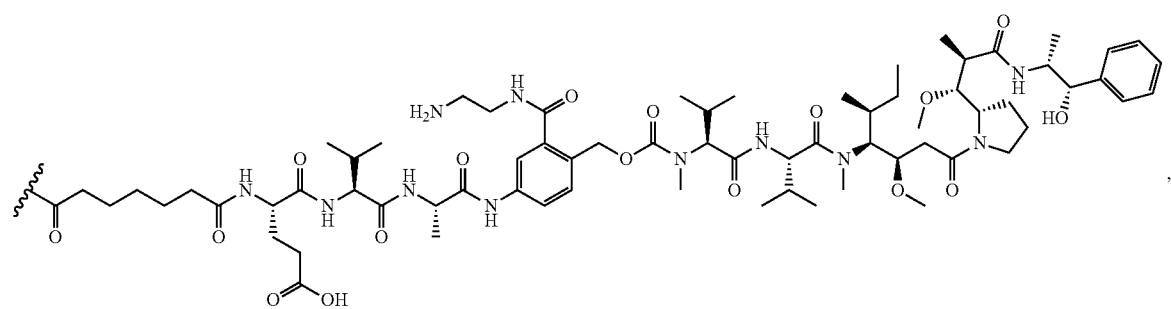
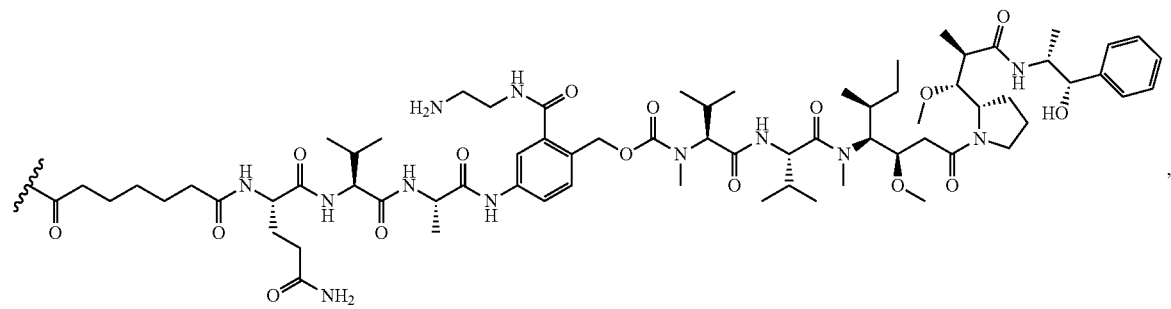
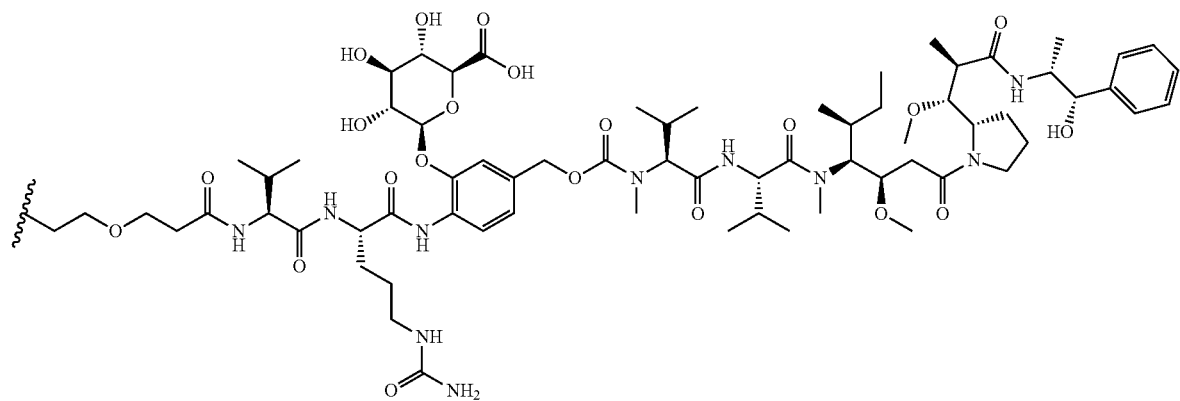
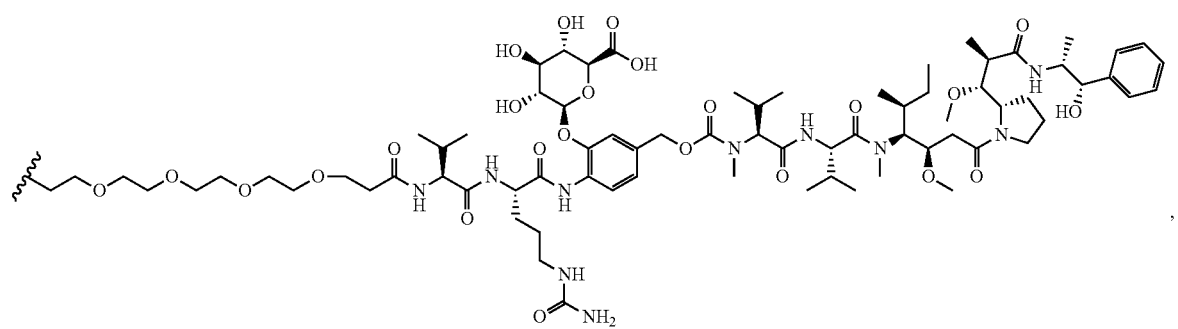

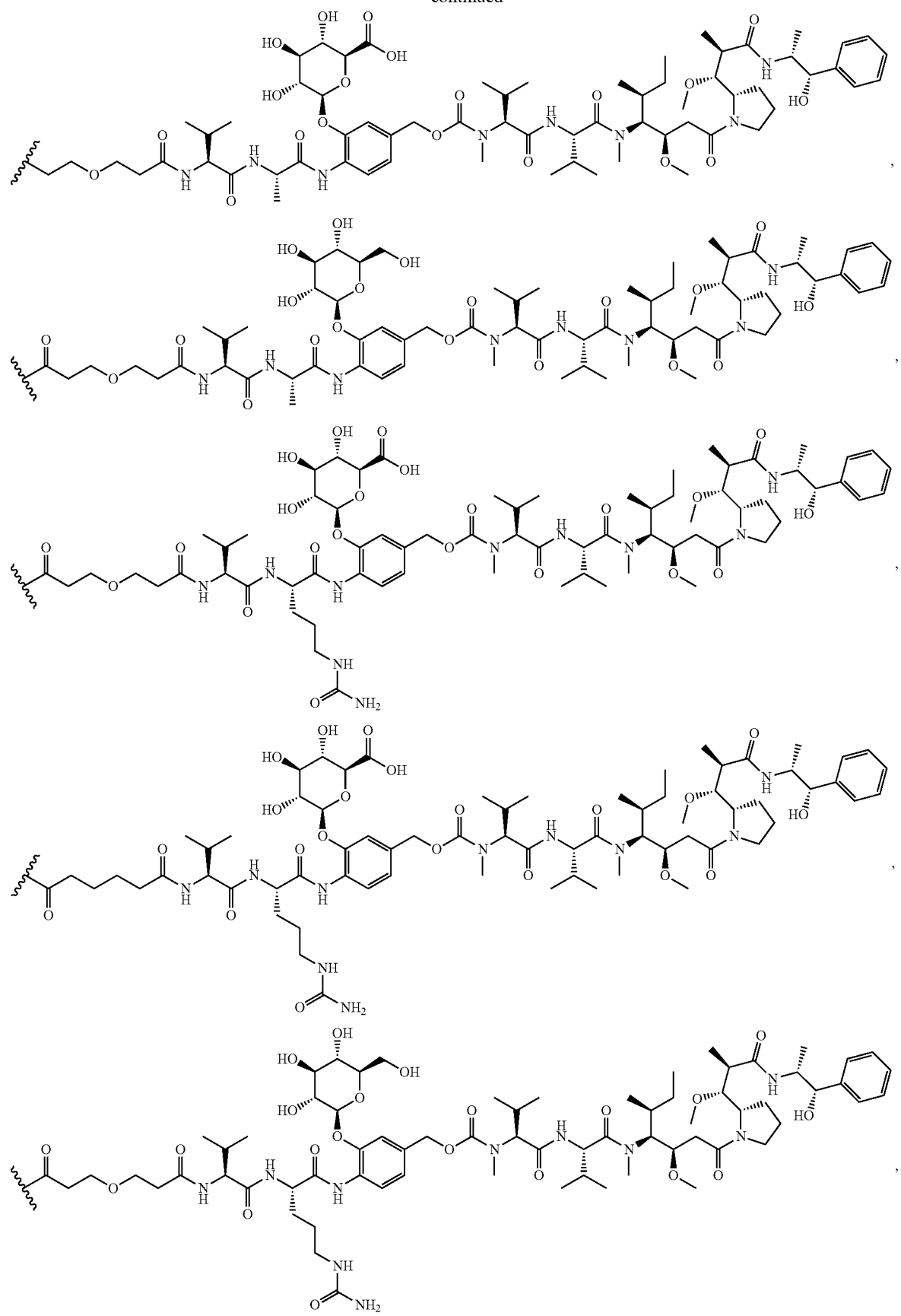

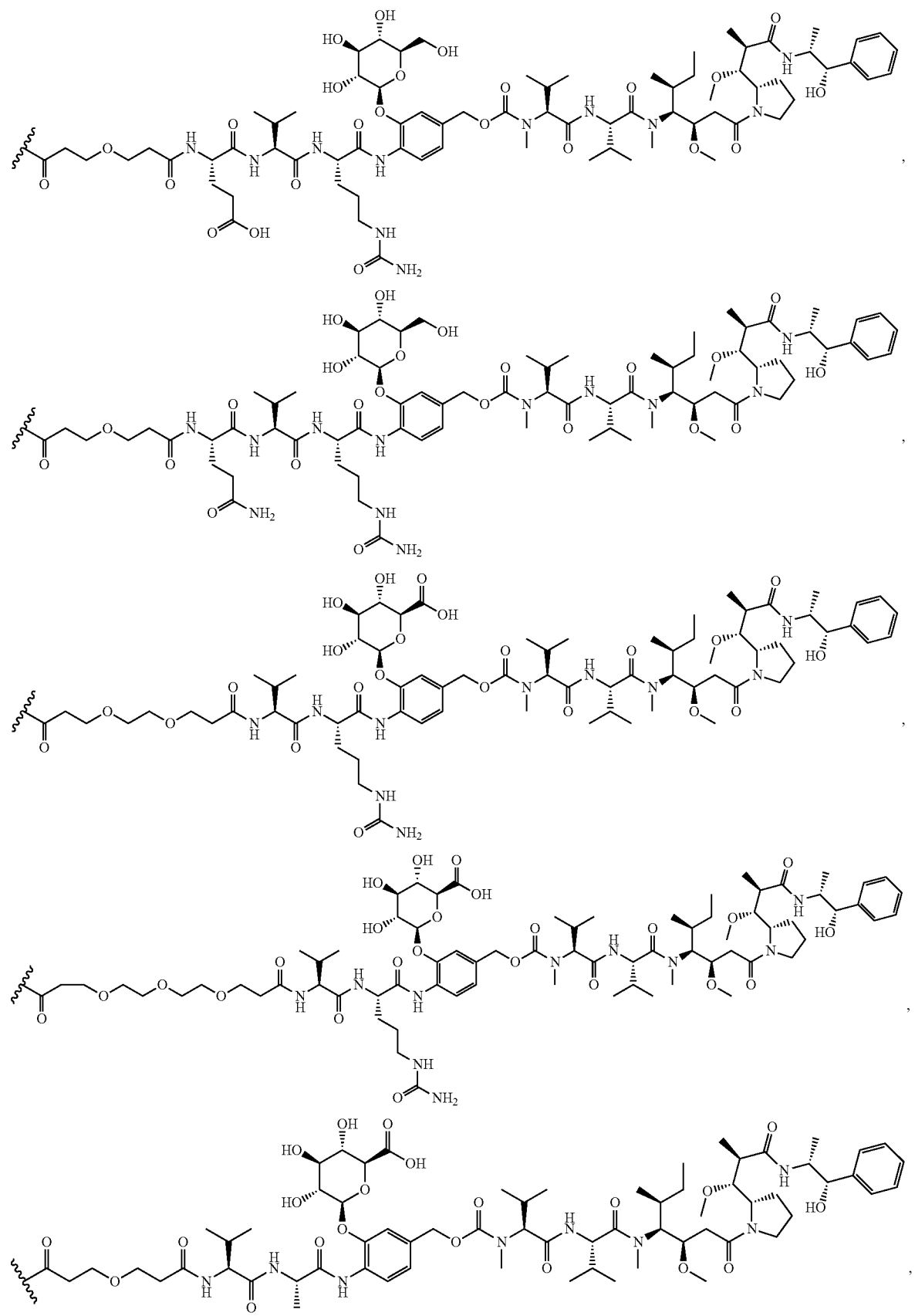

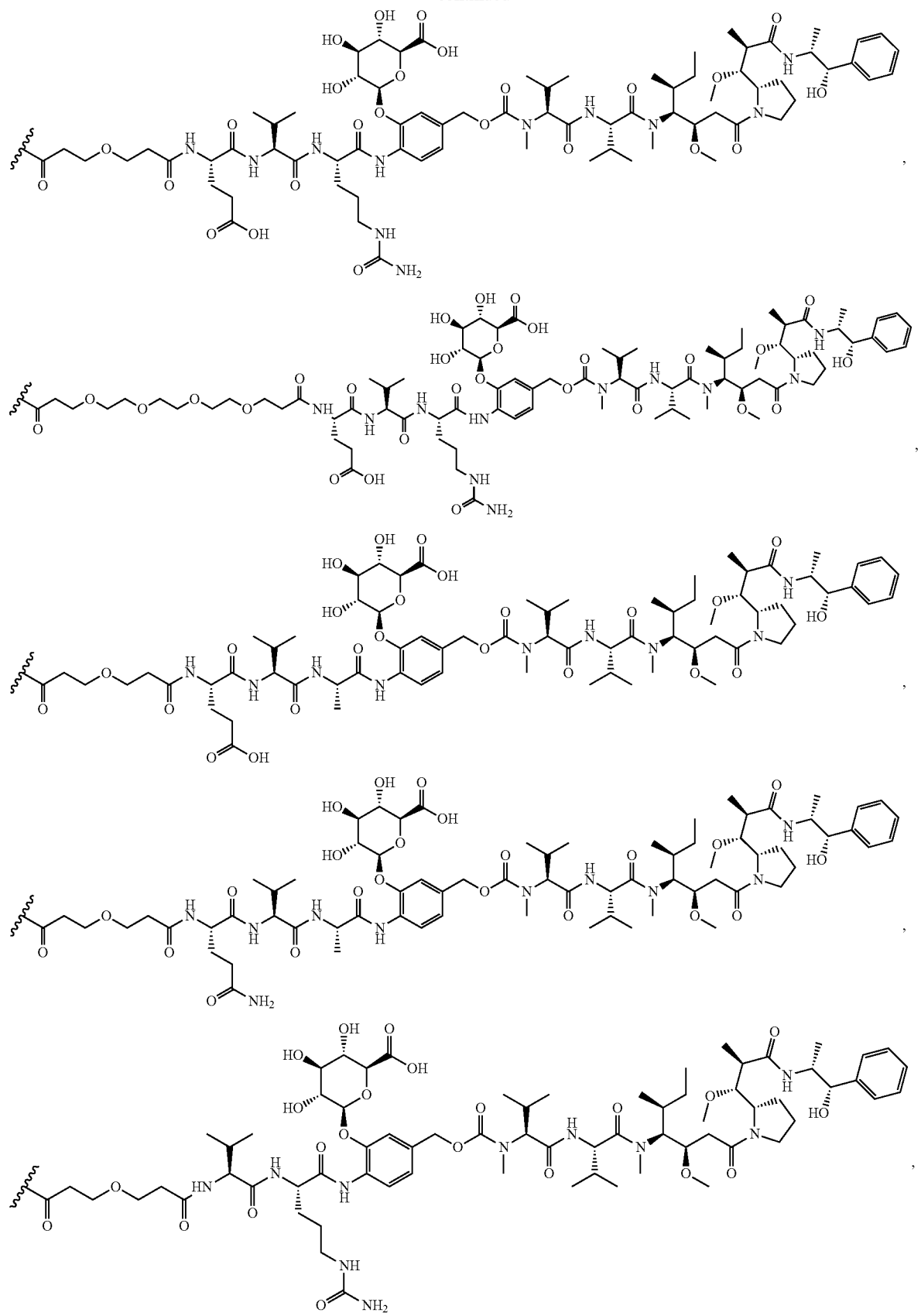

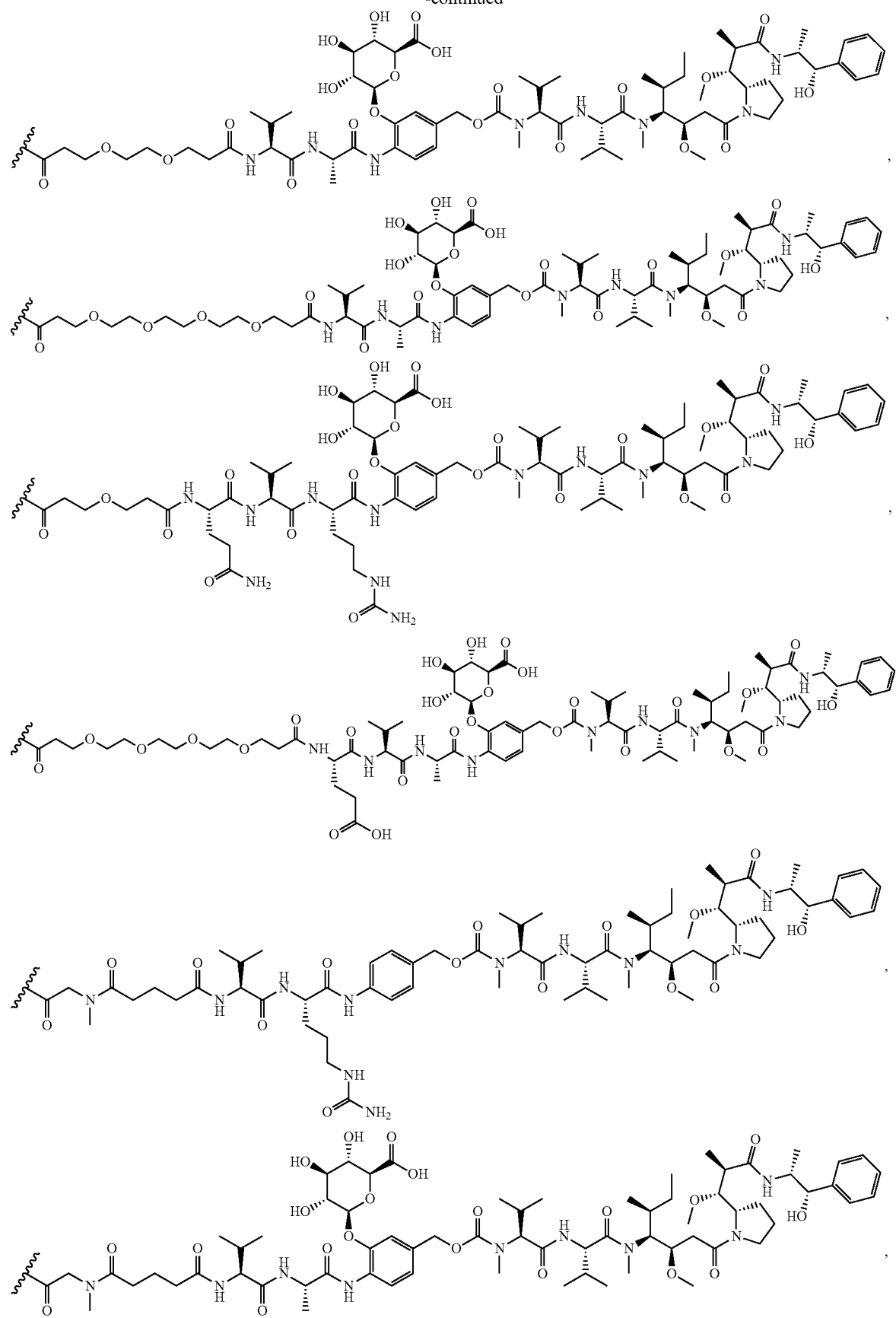

701 702
-continued
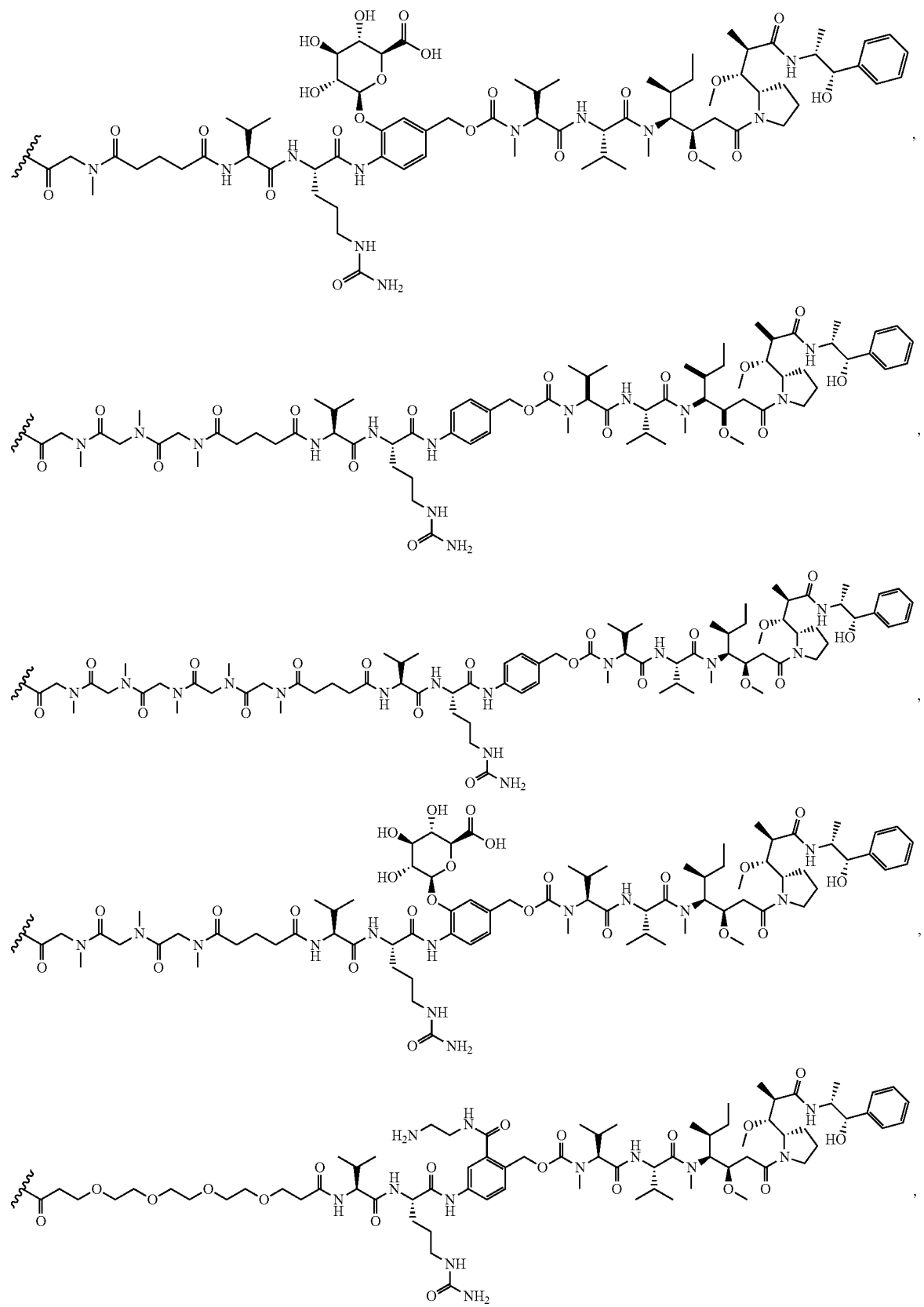

-continued
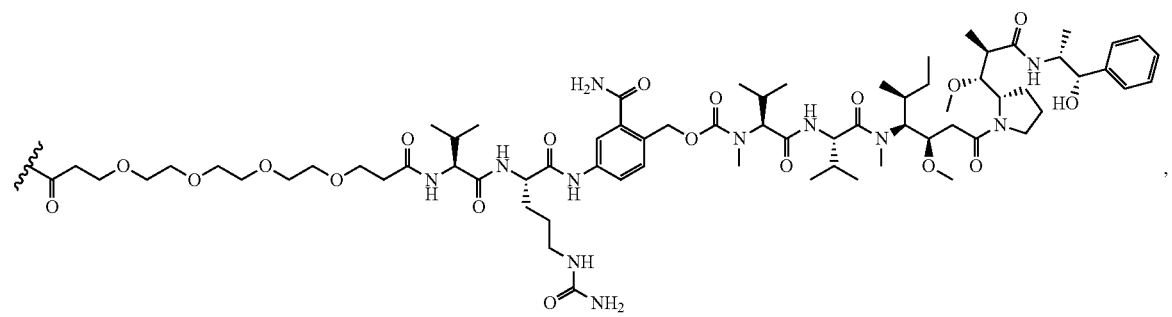
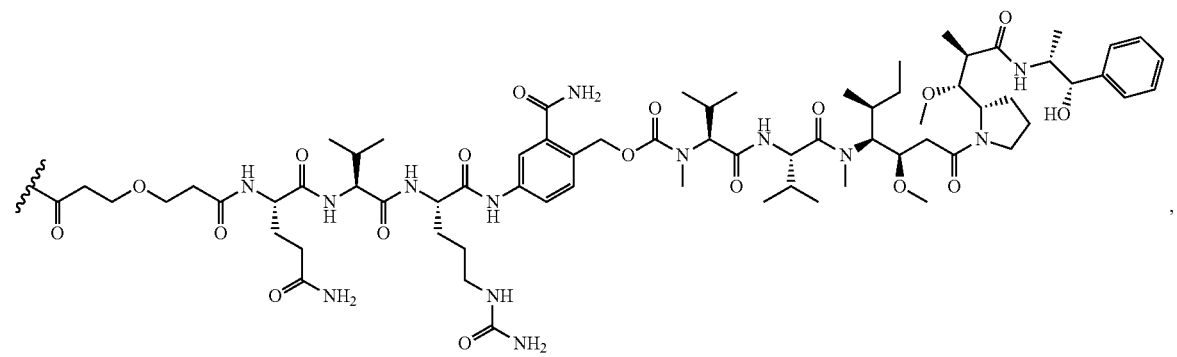
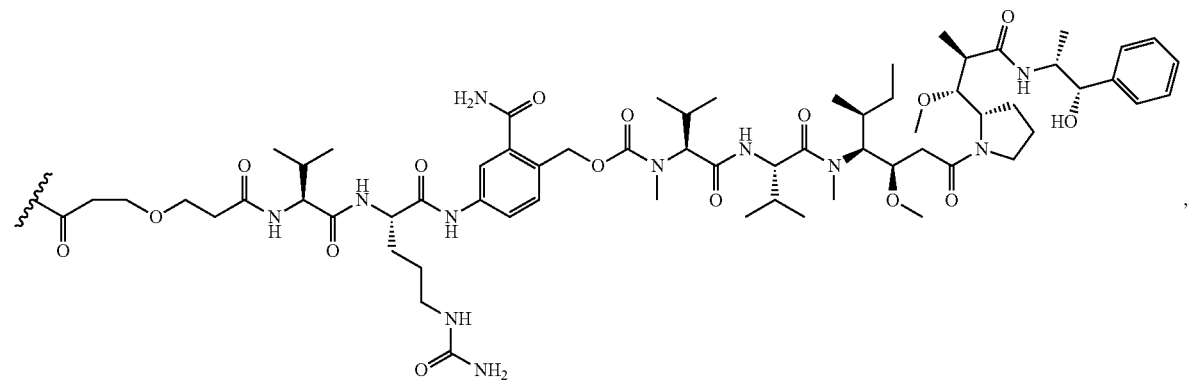
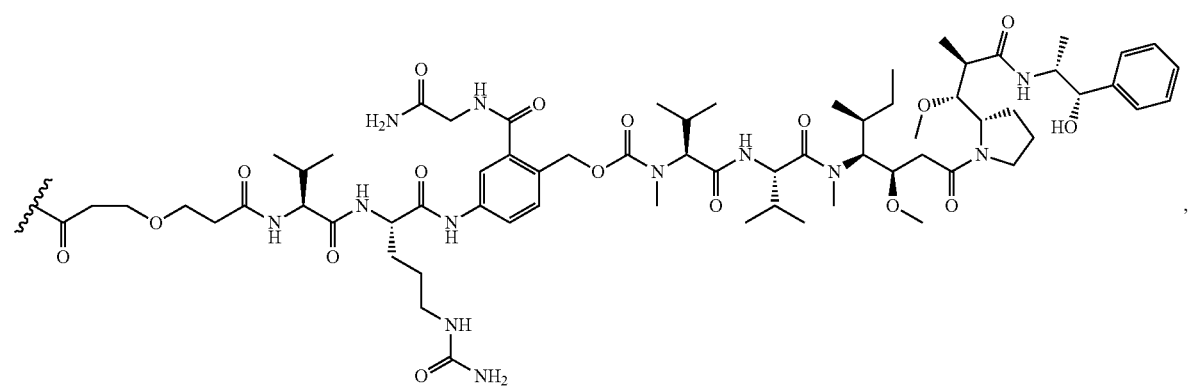

-continued
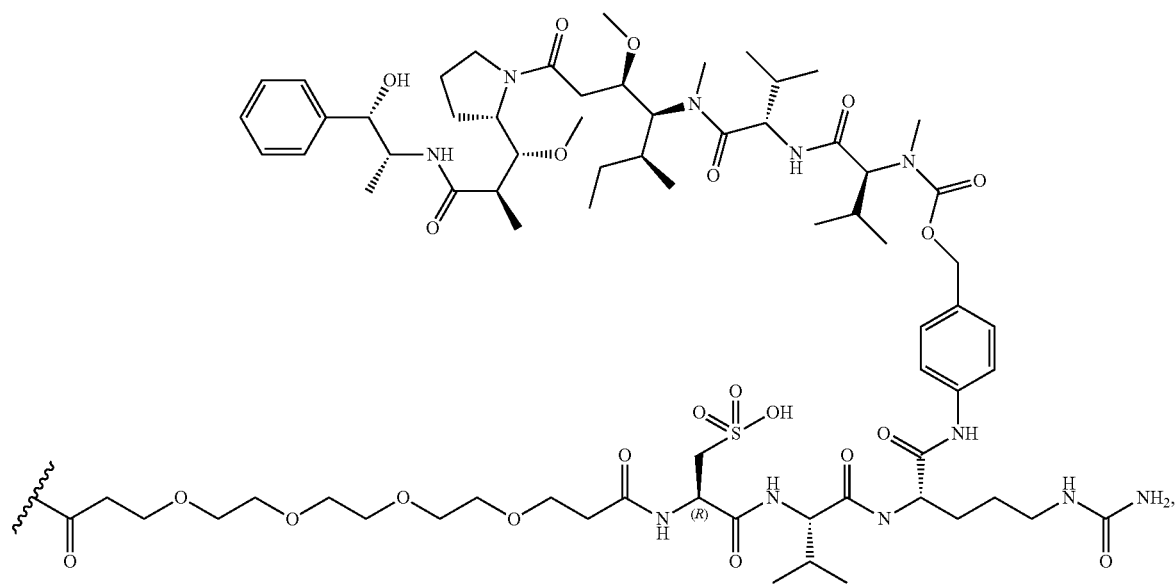
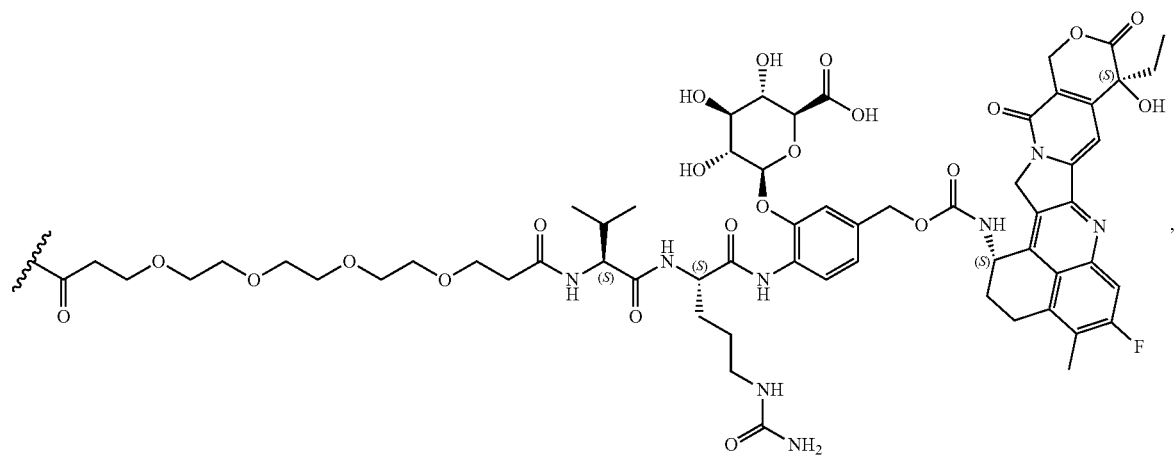
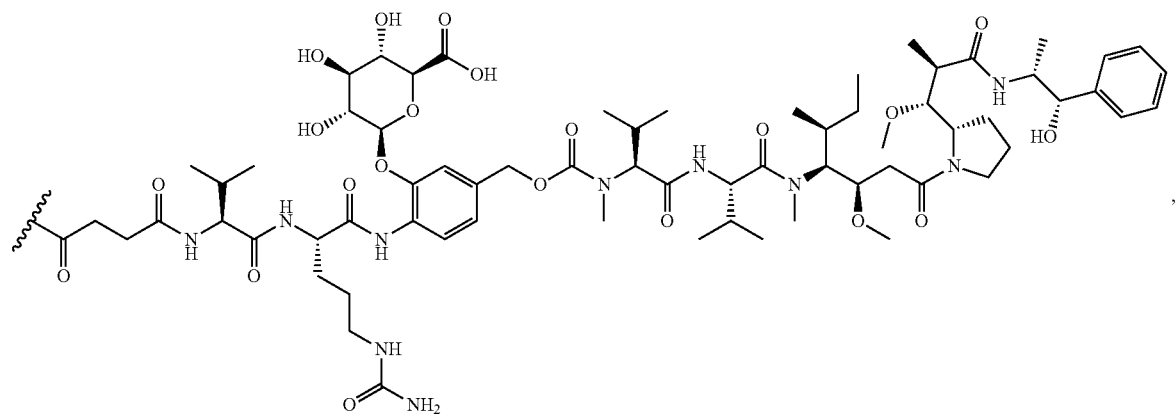

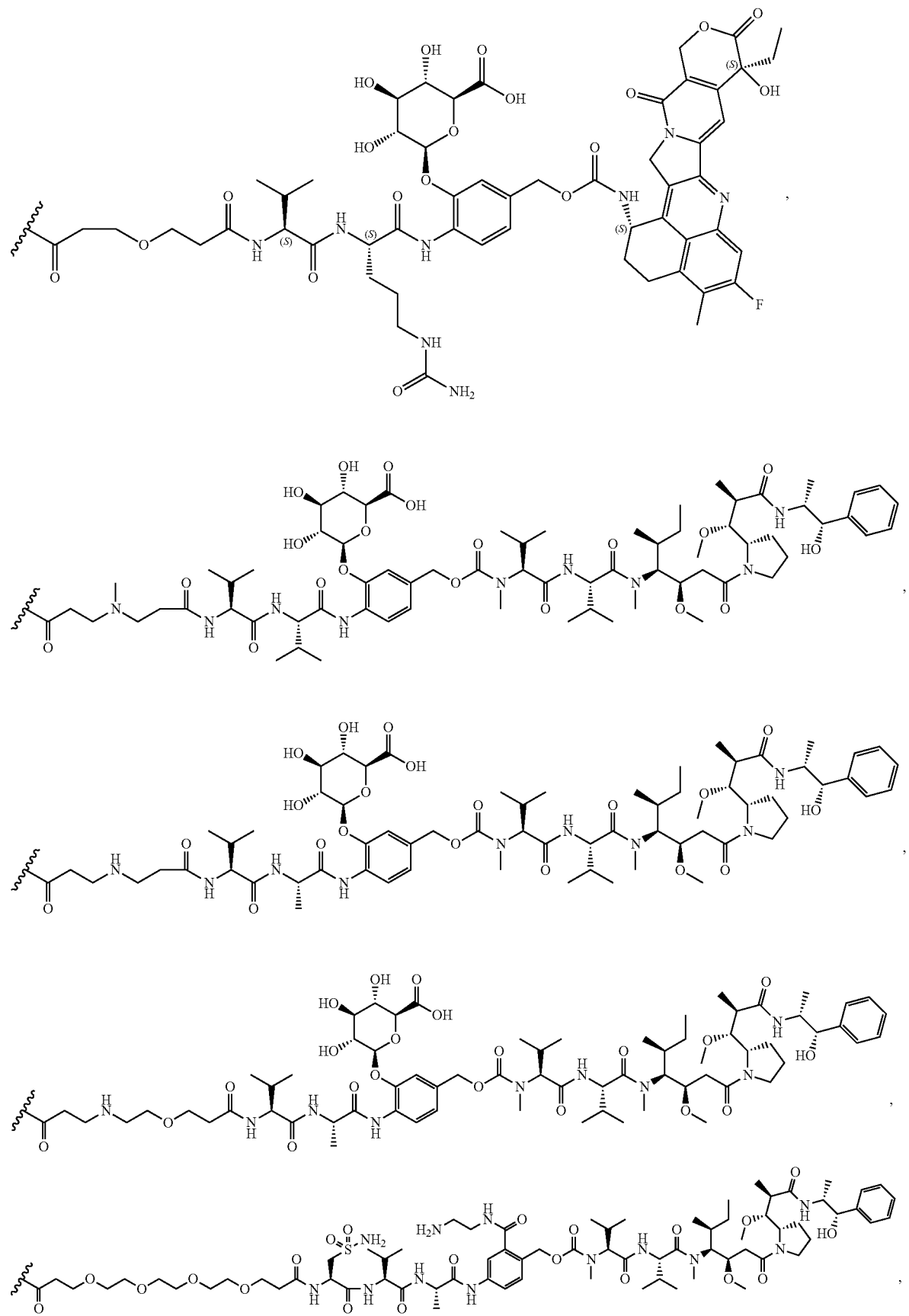

-continued
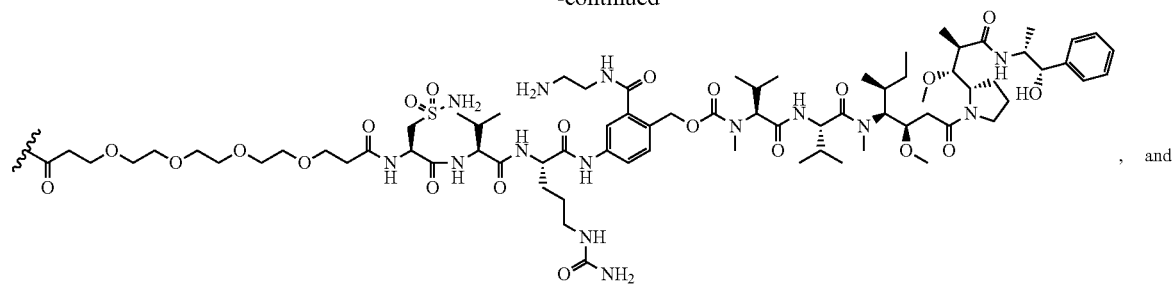
, and
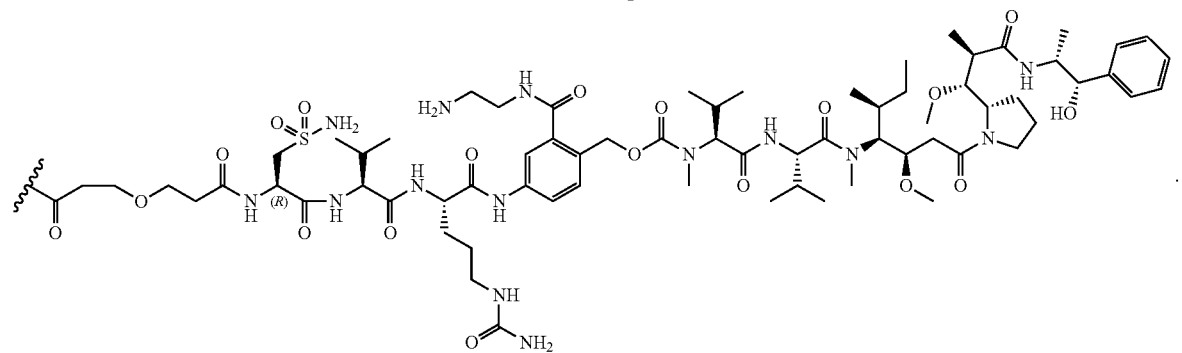
.
19. A compound, or pharmaceutically acceptable salt thereof, selected from the group consisting of:
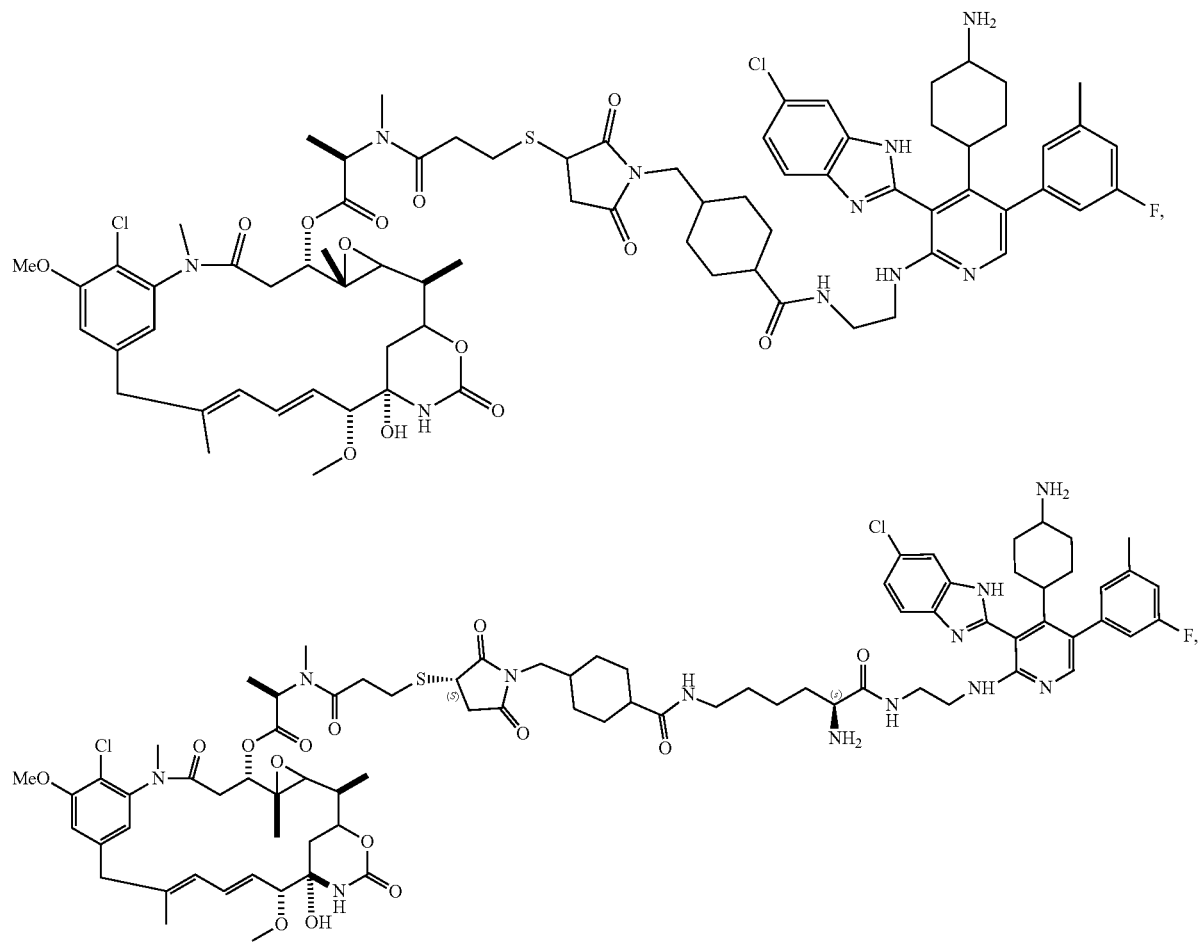

711 712
-continued
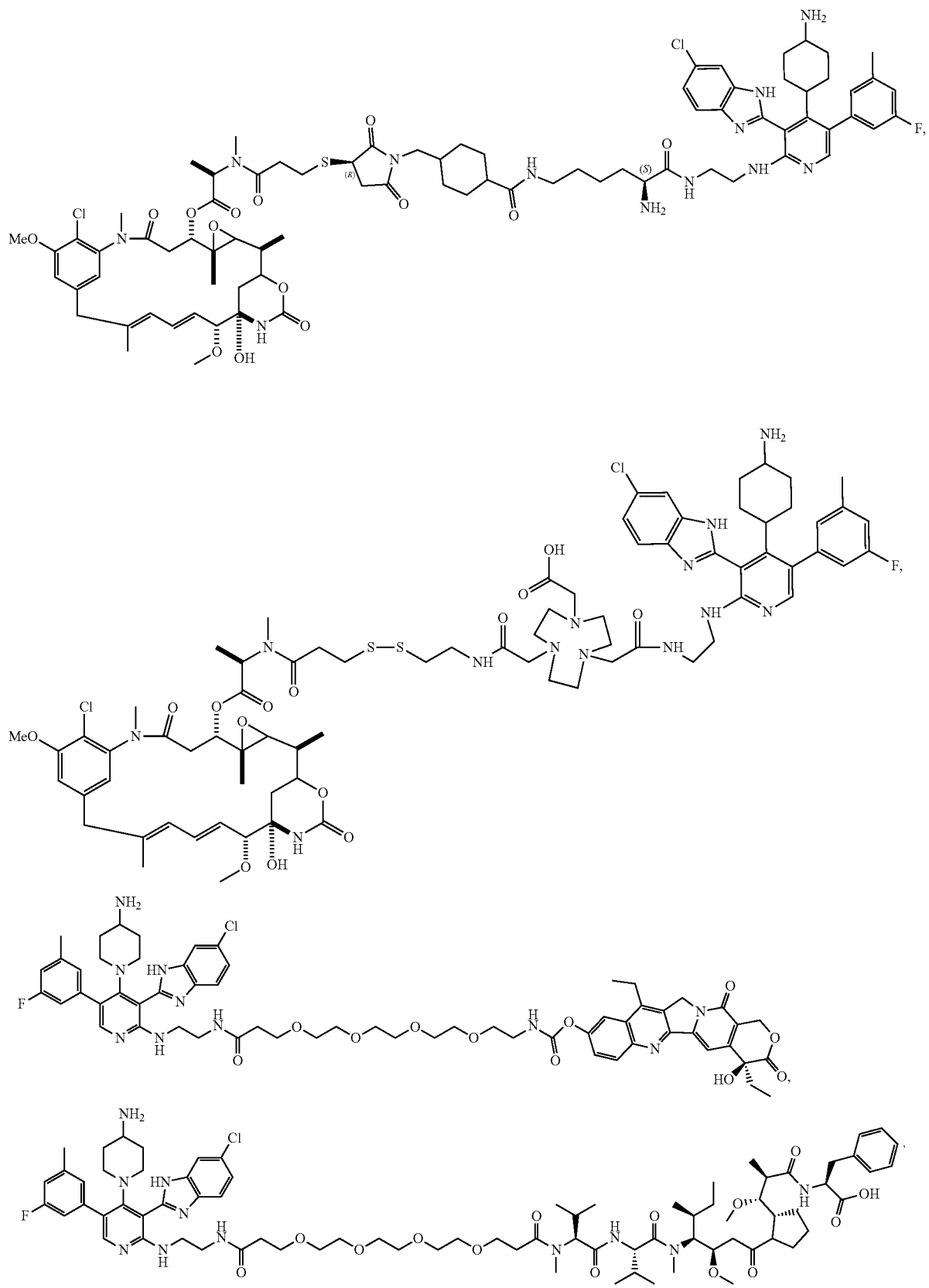

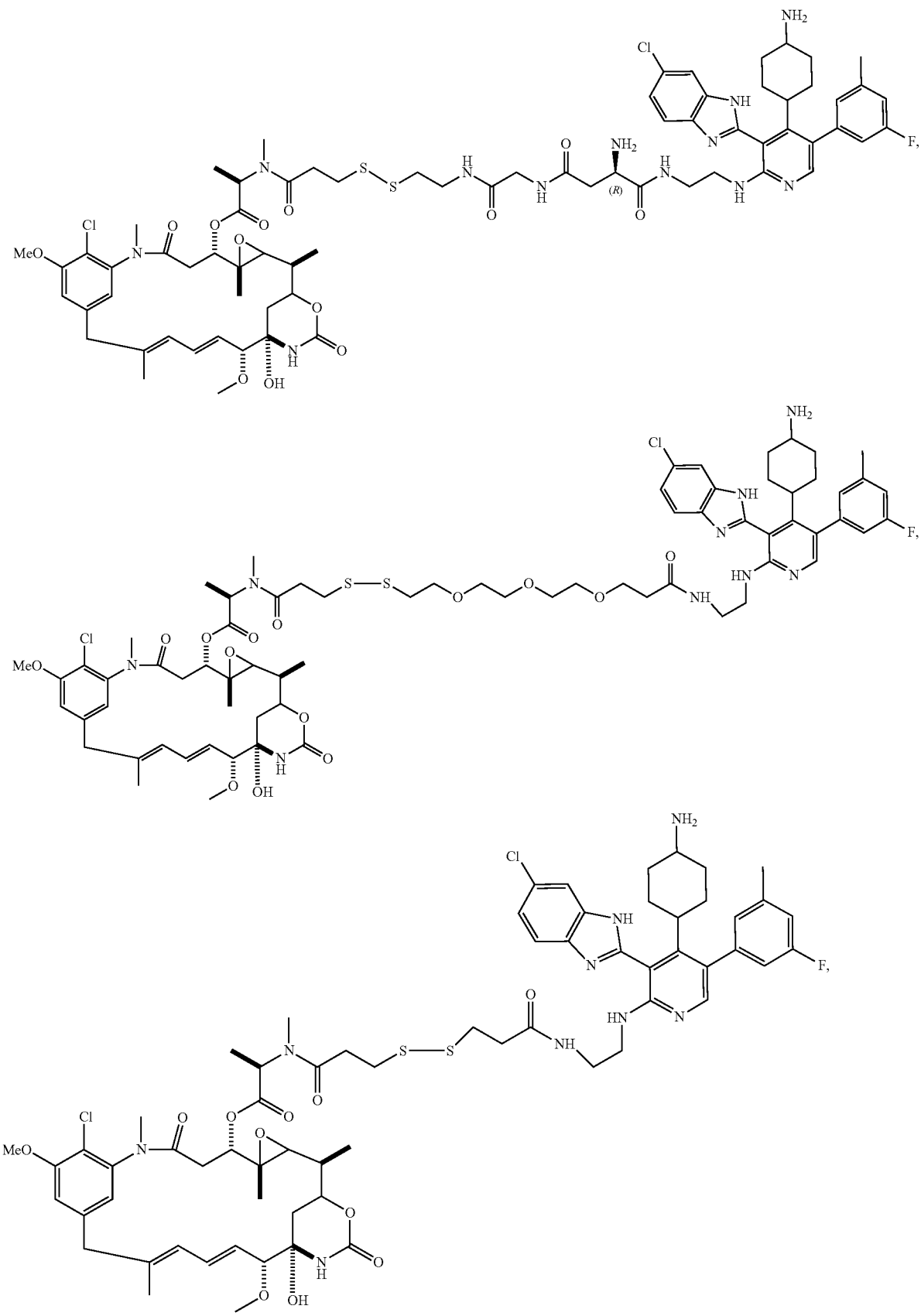

715
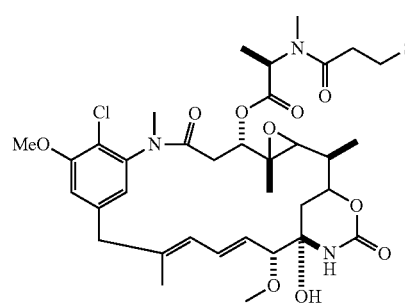
716
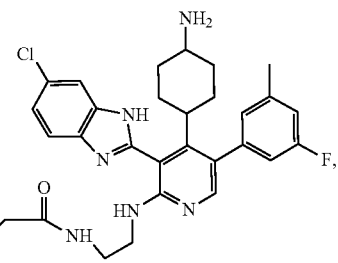
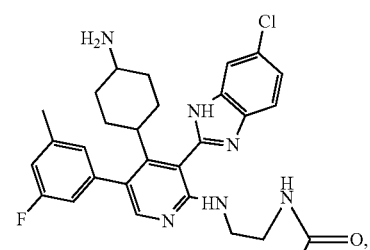
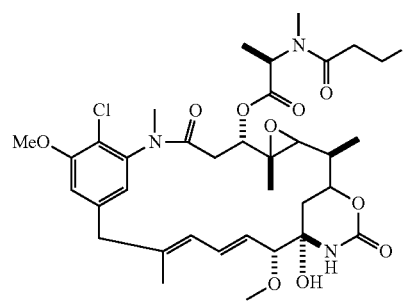
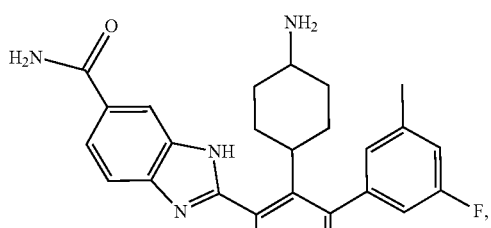
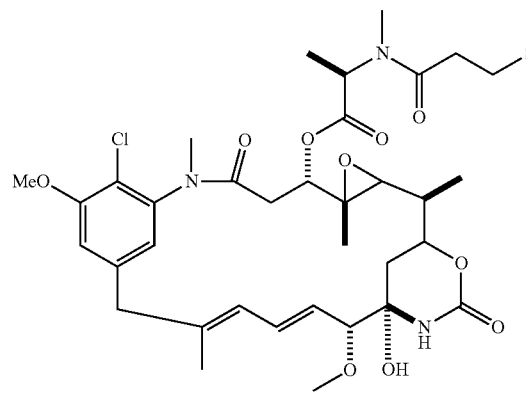

717
718
-continued
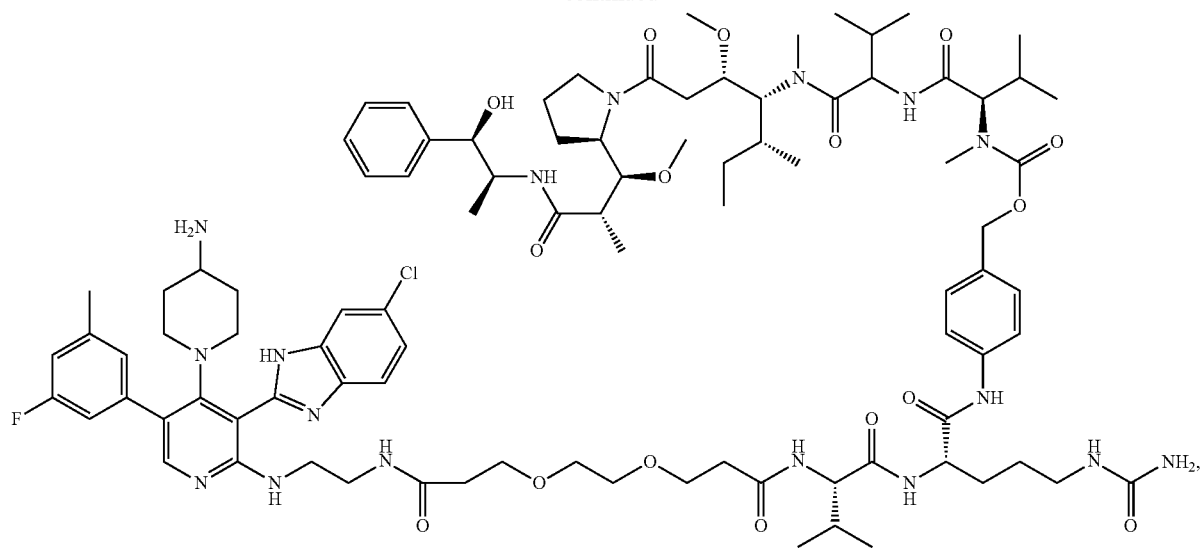
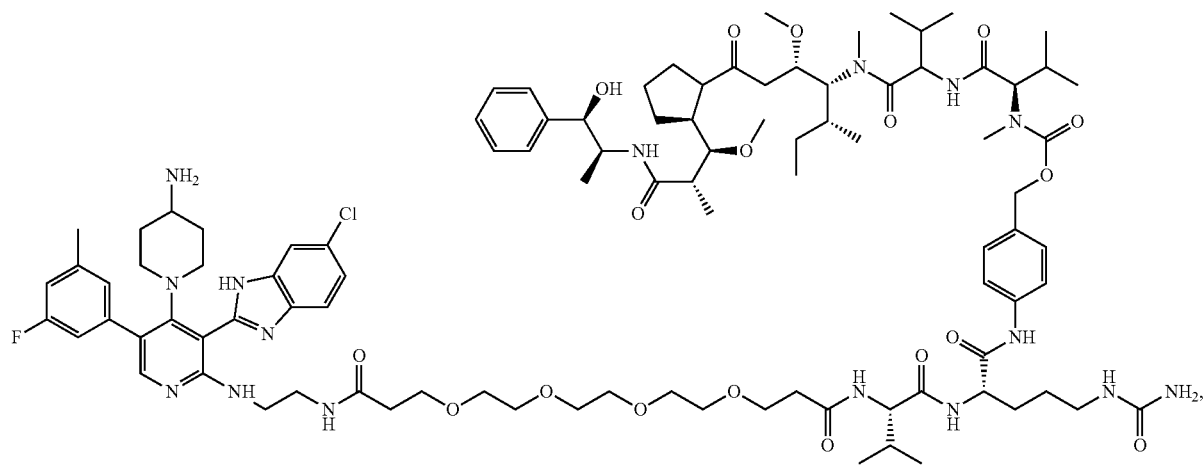
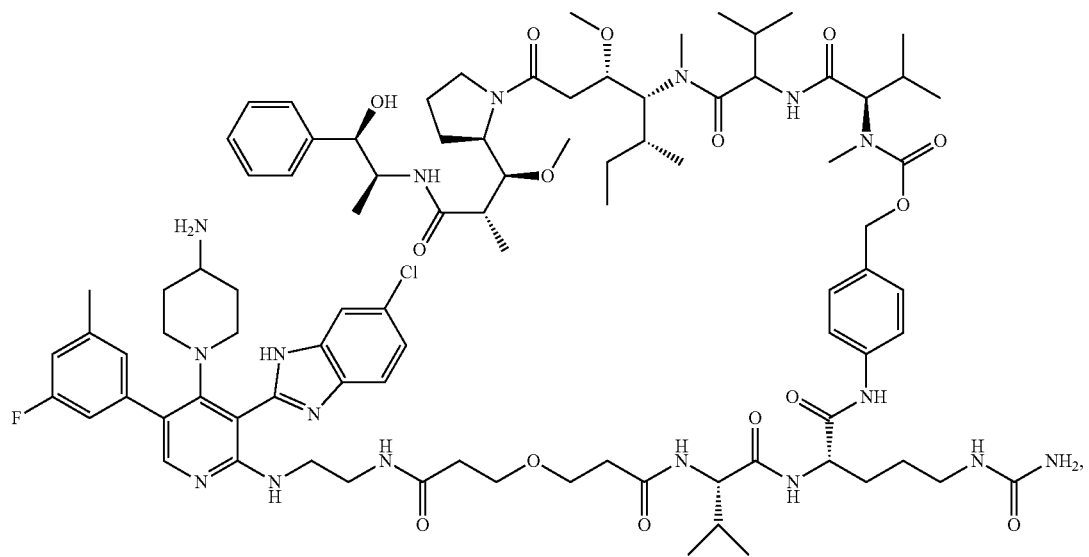

719
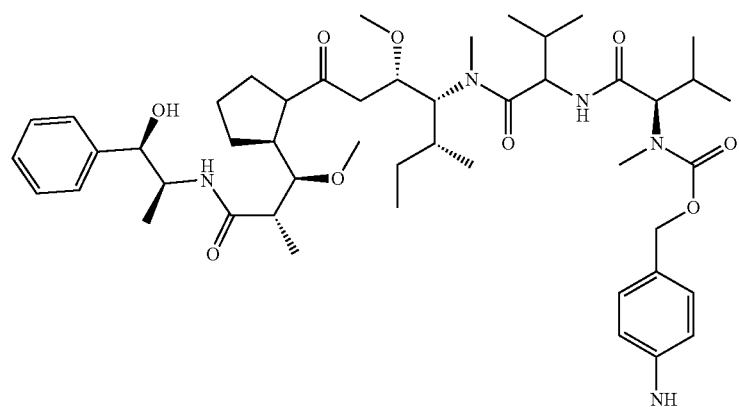
-continued
720
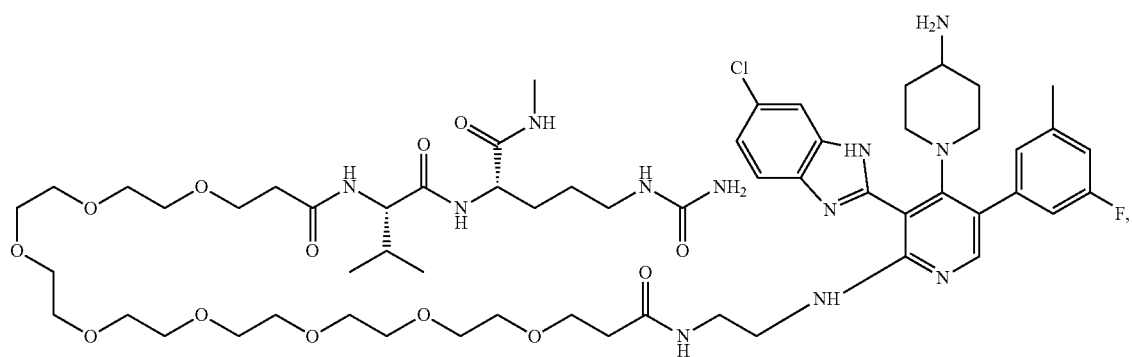
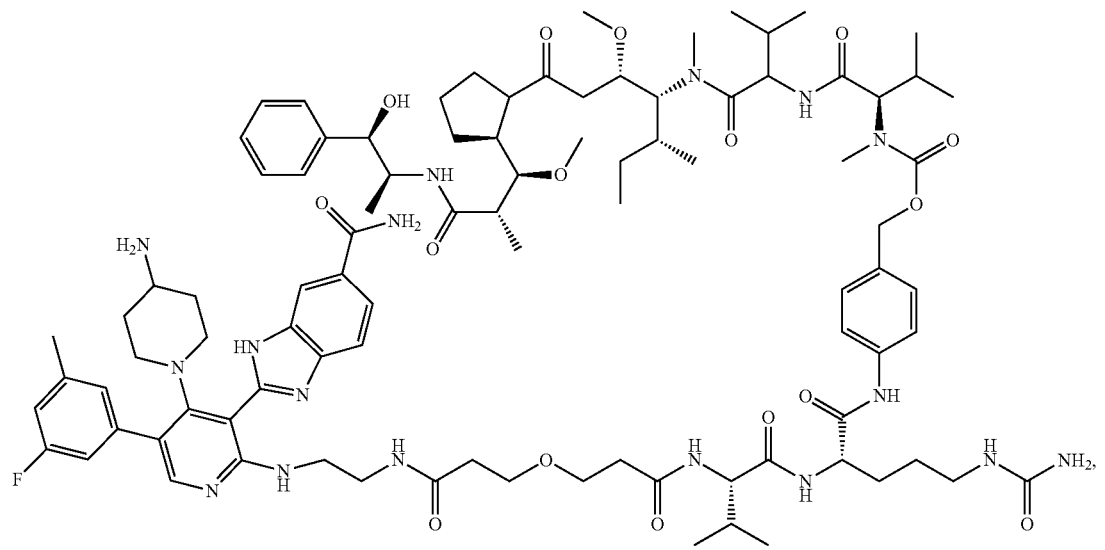

721 722
-continued
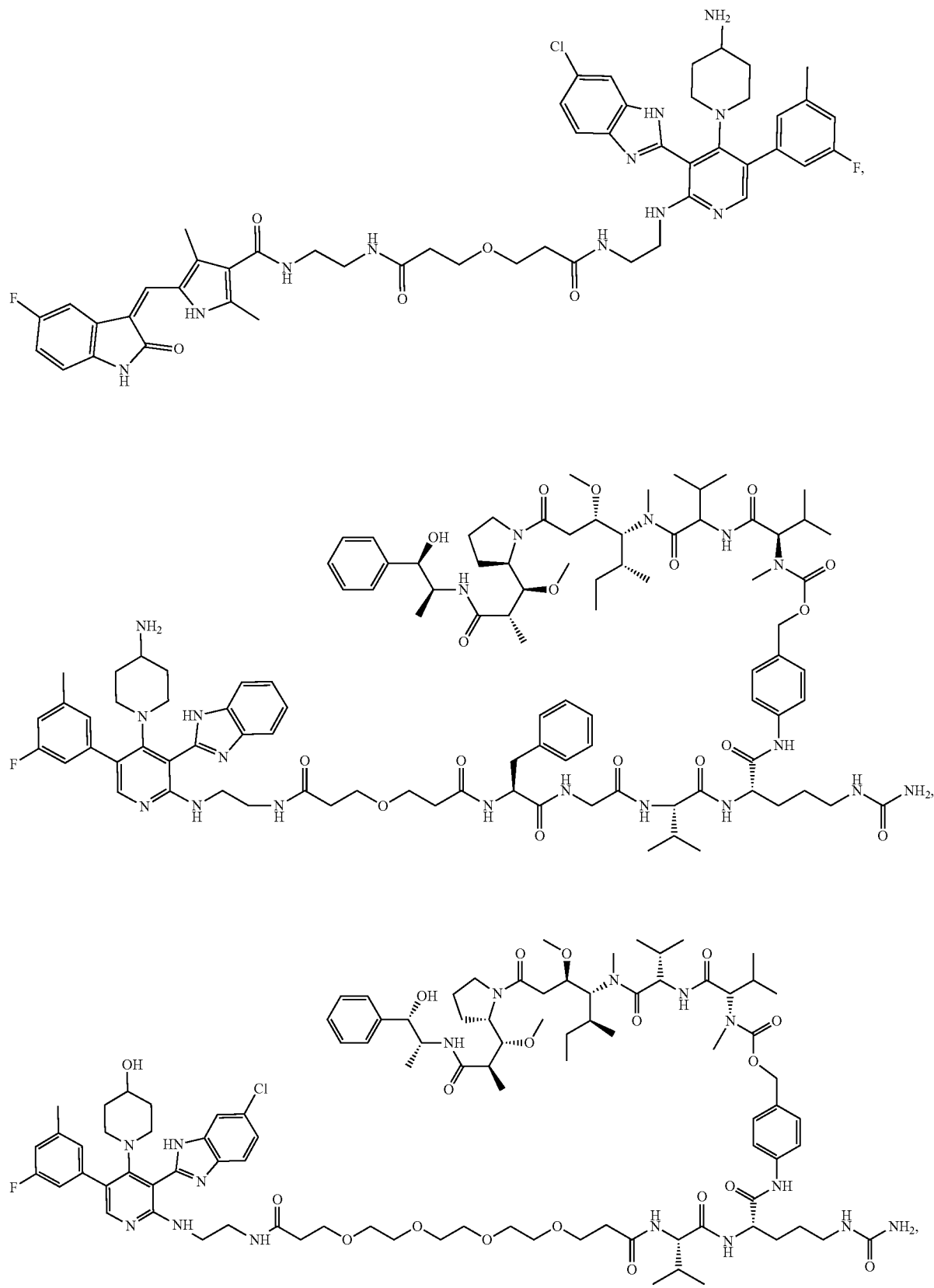

723
724
-continued
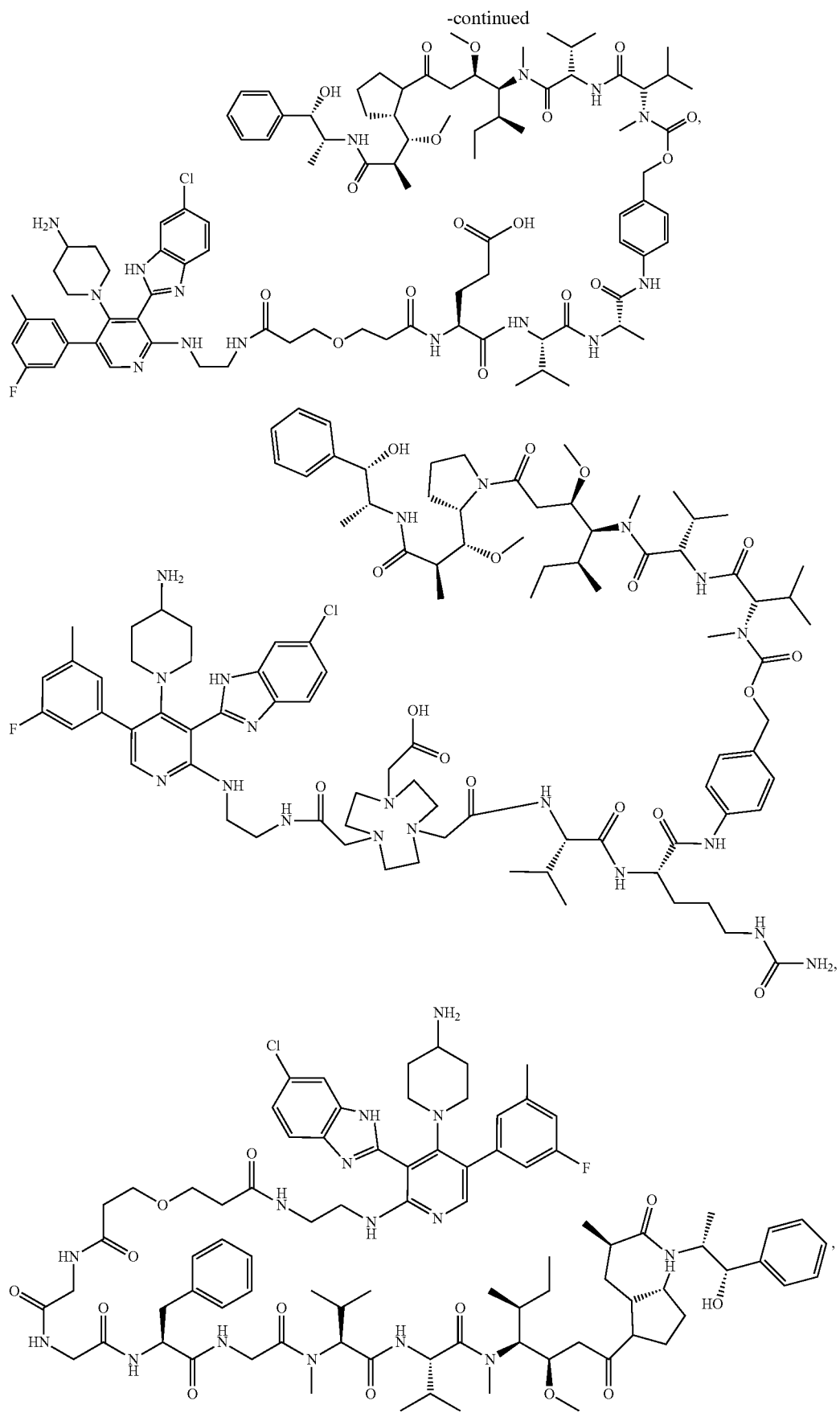

725
726
-continued
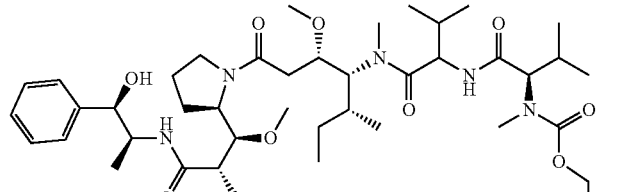
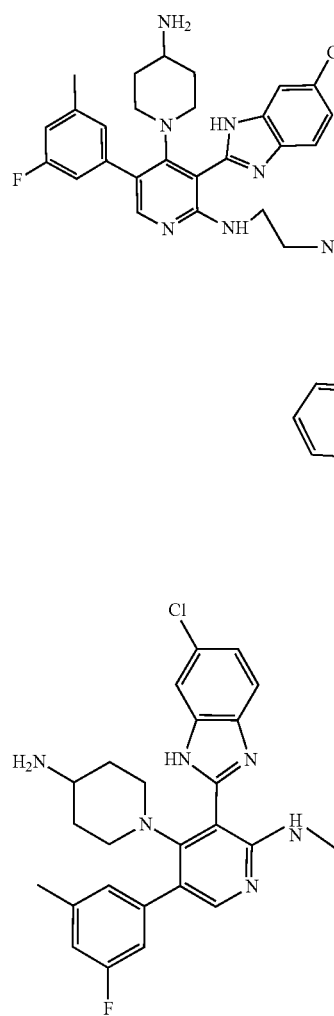
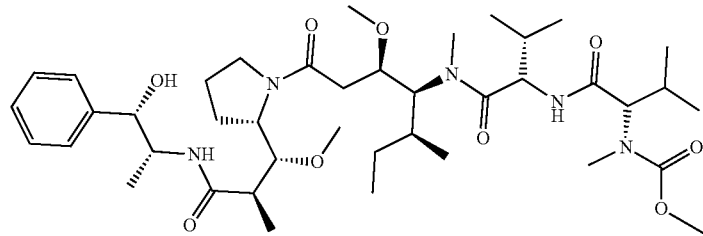
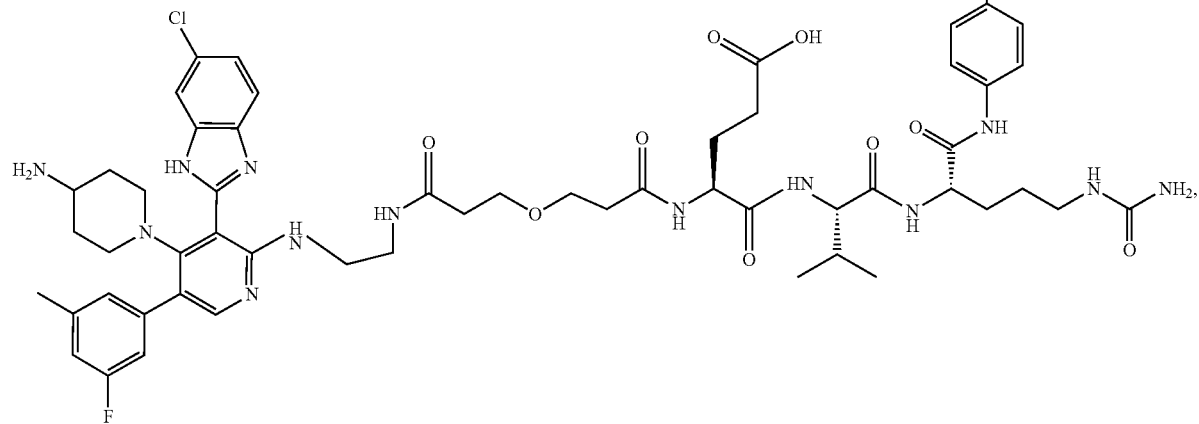
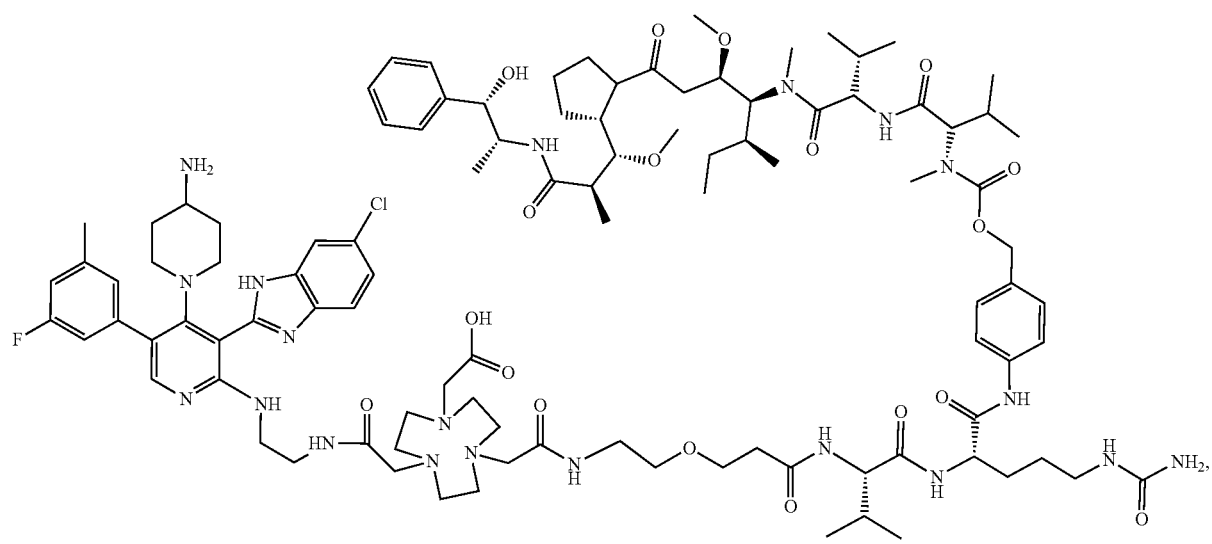

727
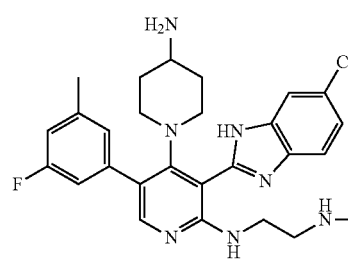
728
-continued
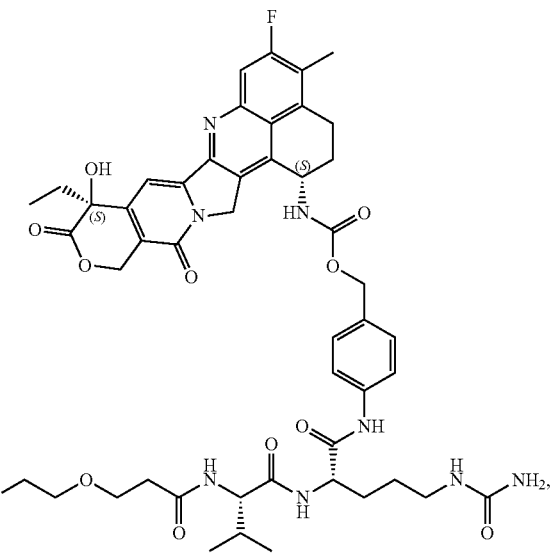
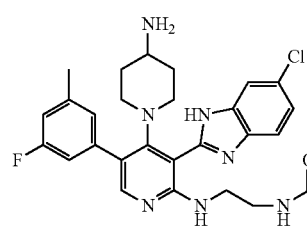
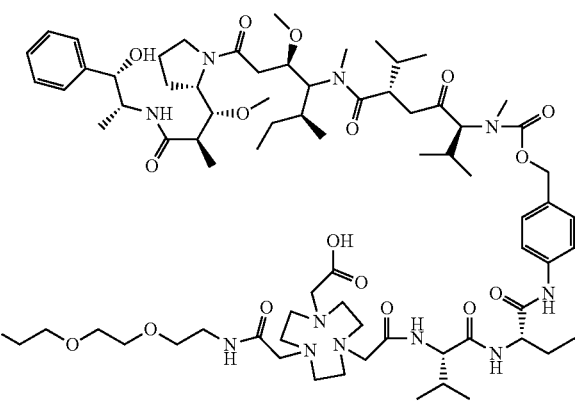
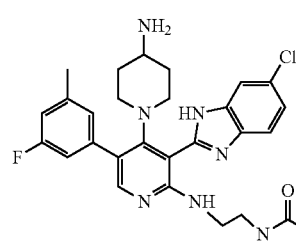
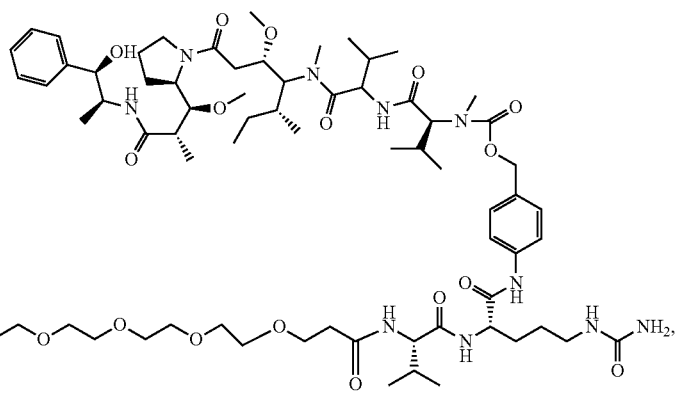

729 730
-continued
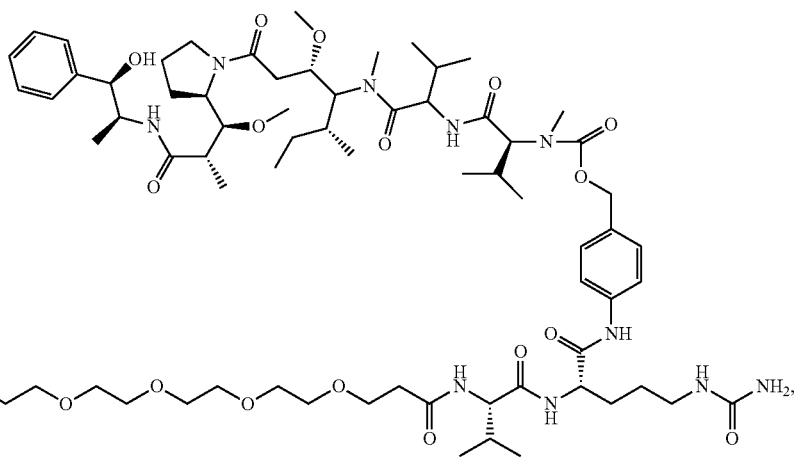
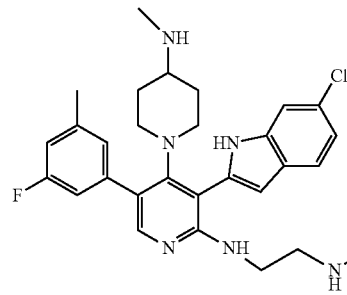
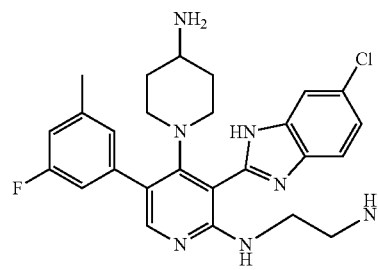
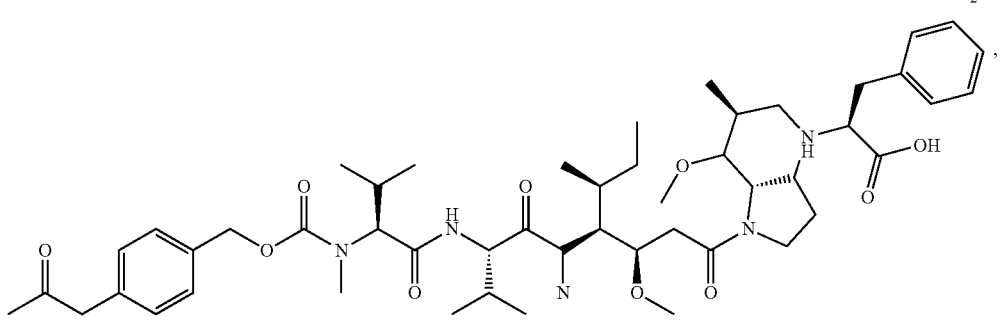
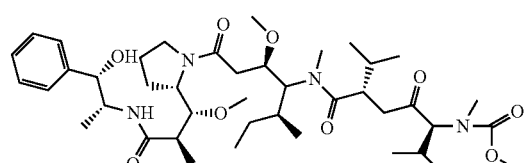
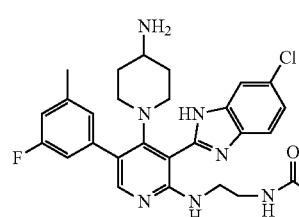
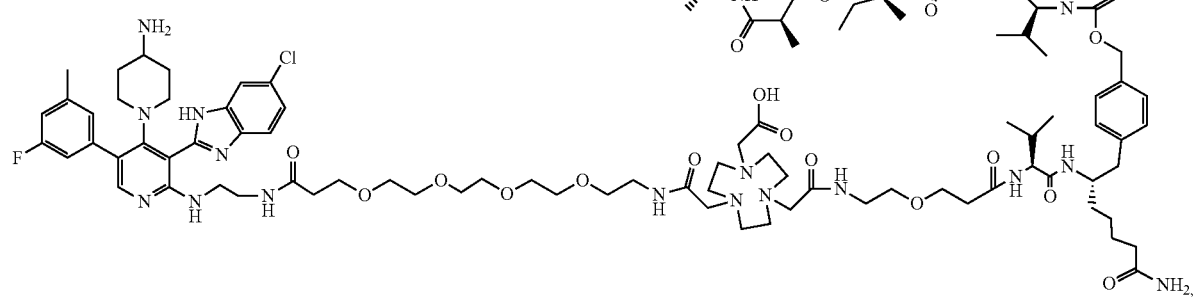

731
732
-continued
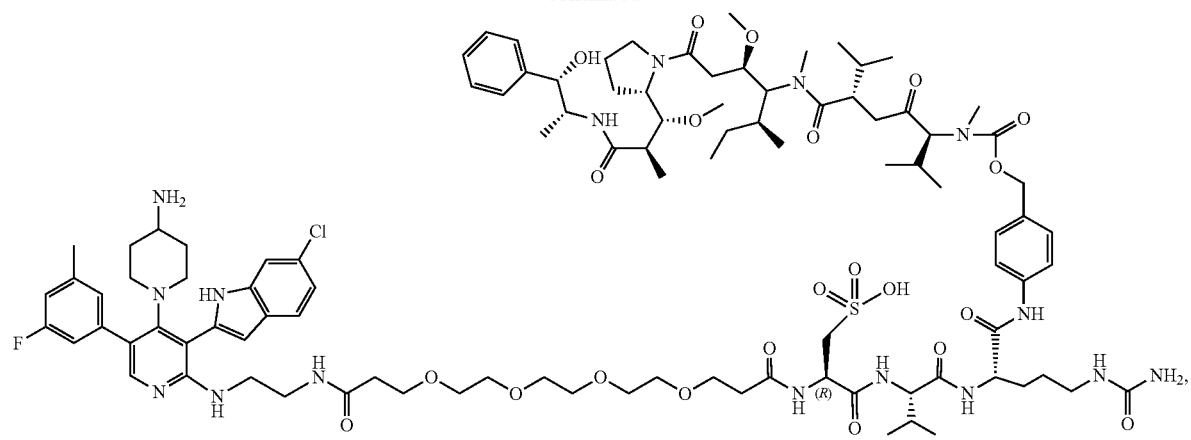
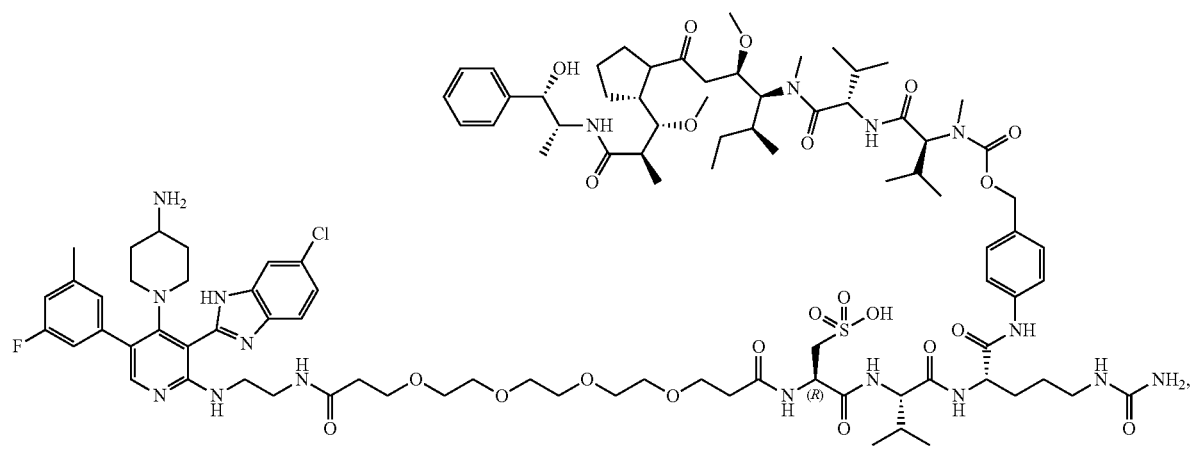
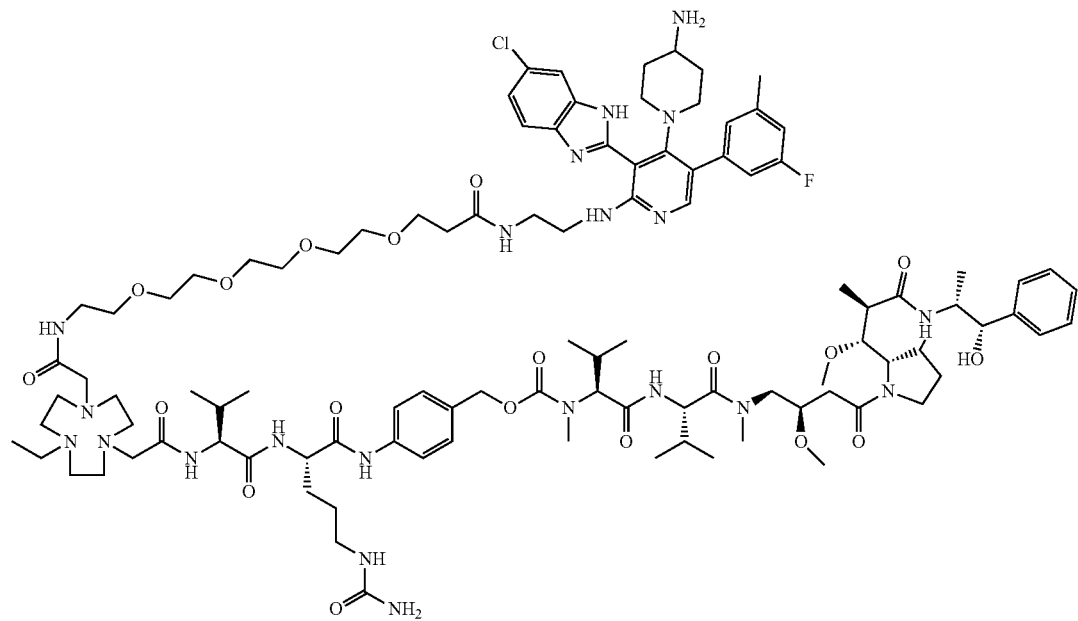

733 734
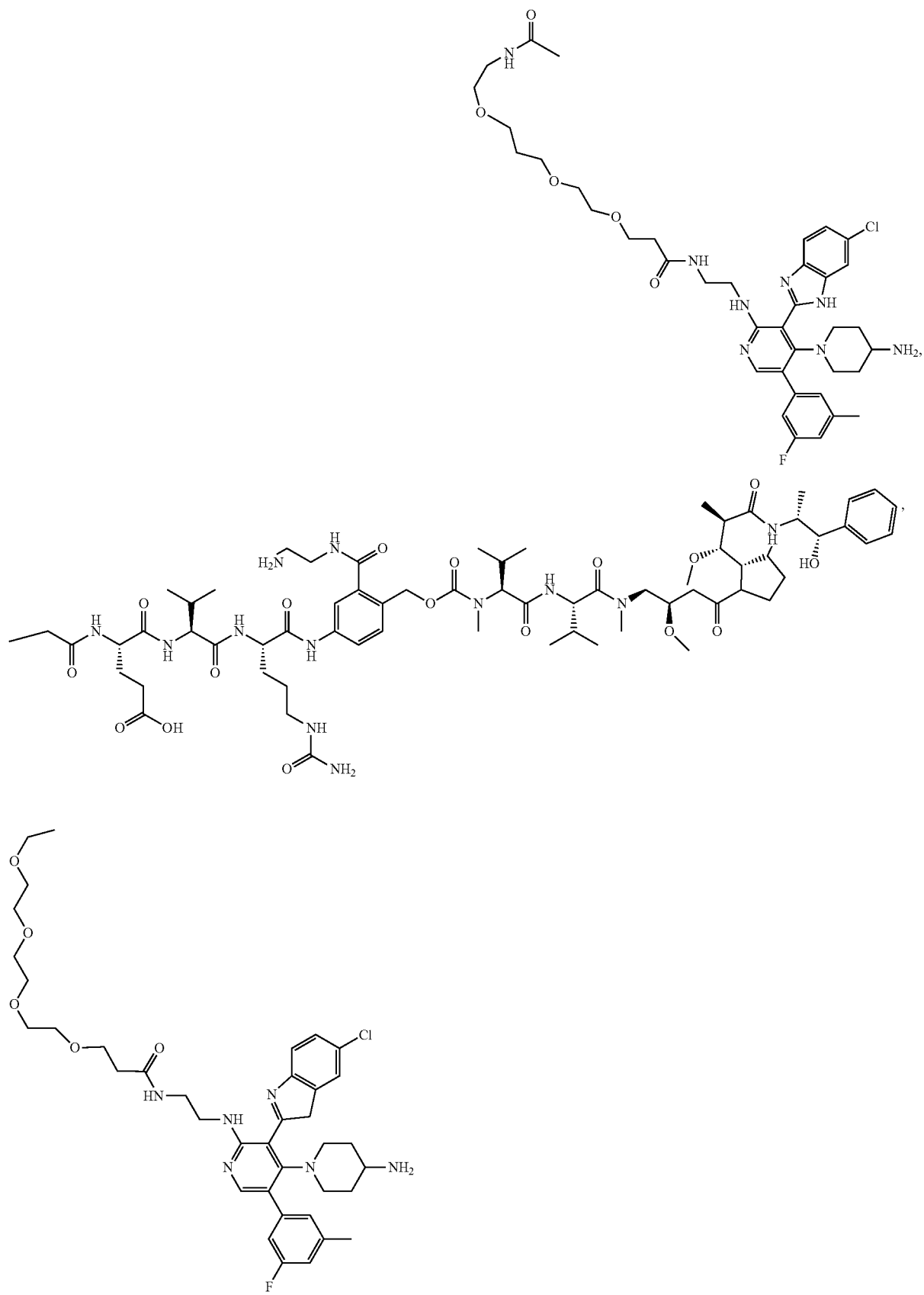

735 736
-continued
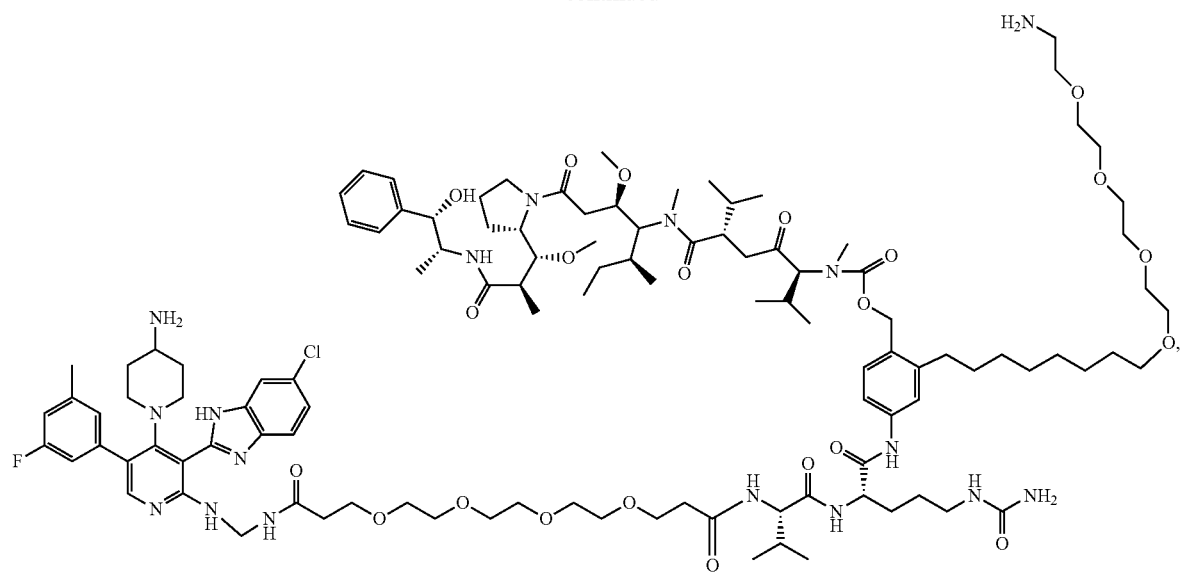
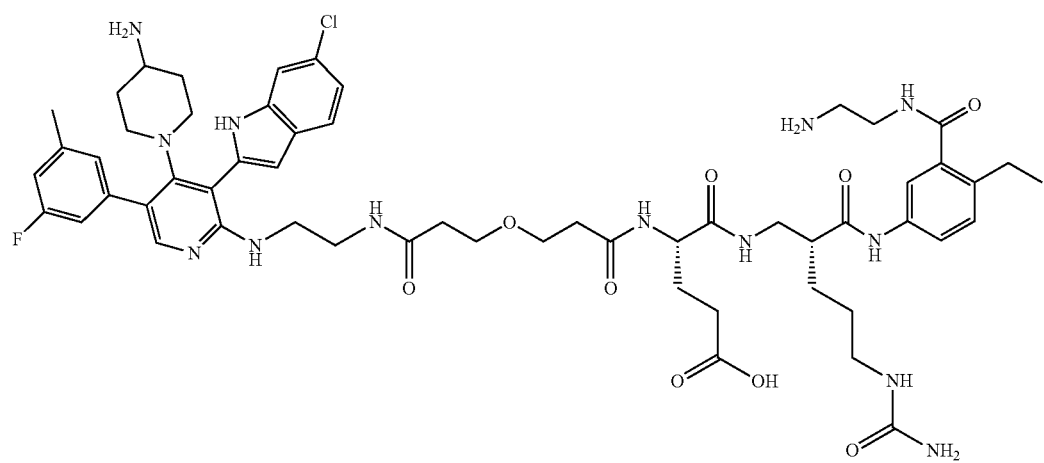
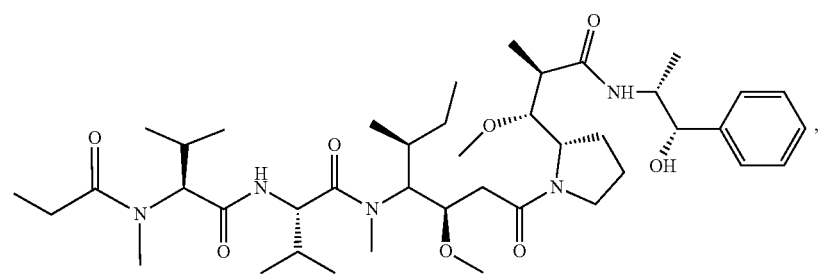

737 738
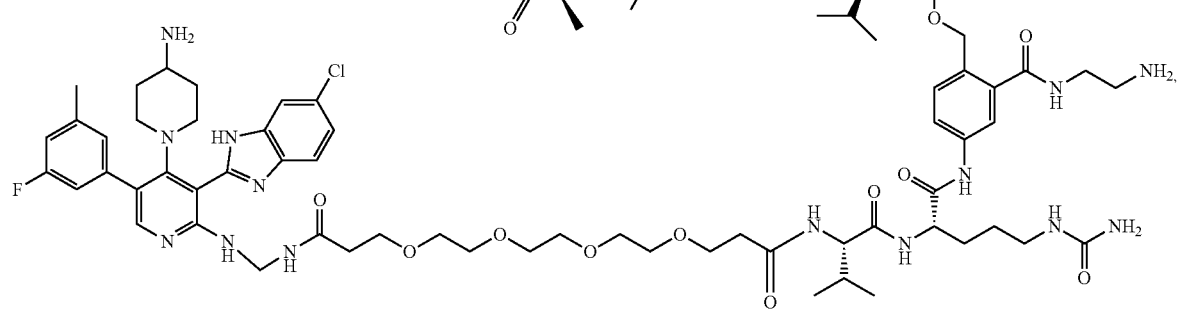
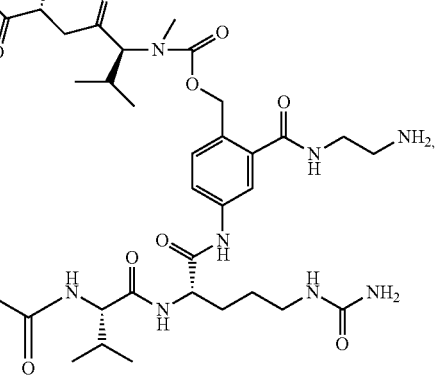
-continued
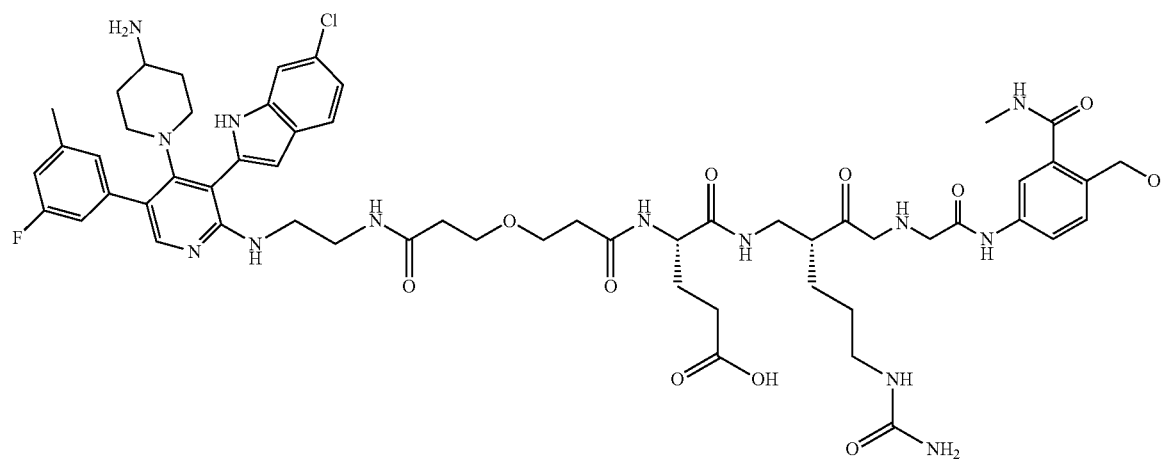
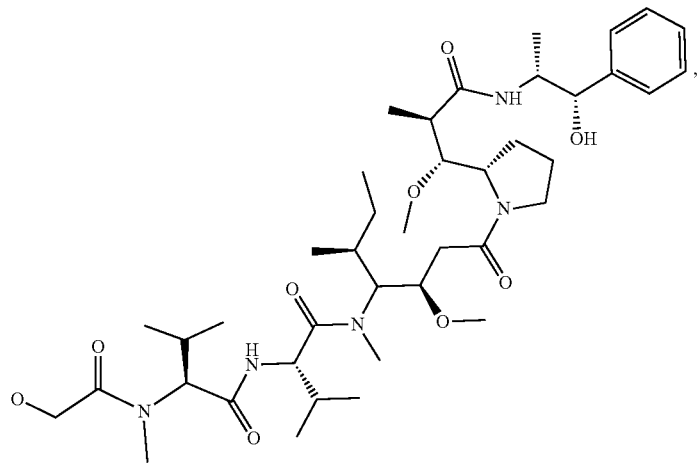

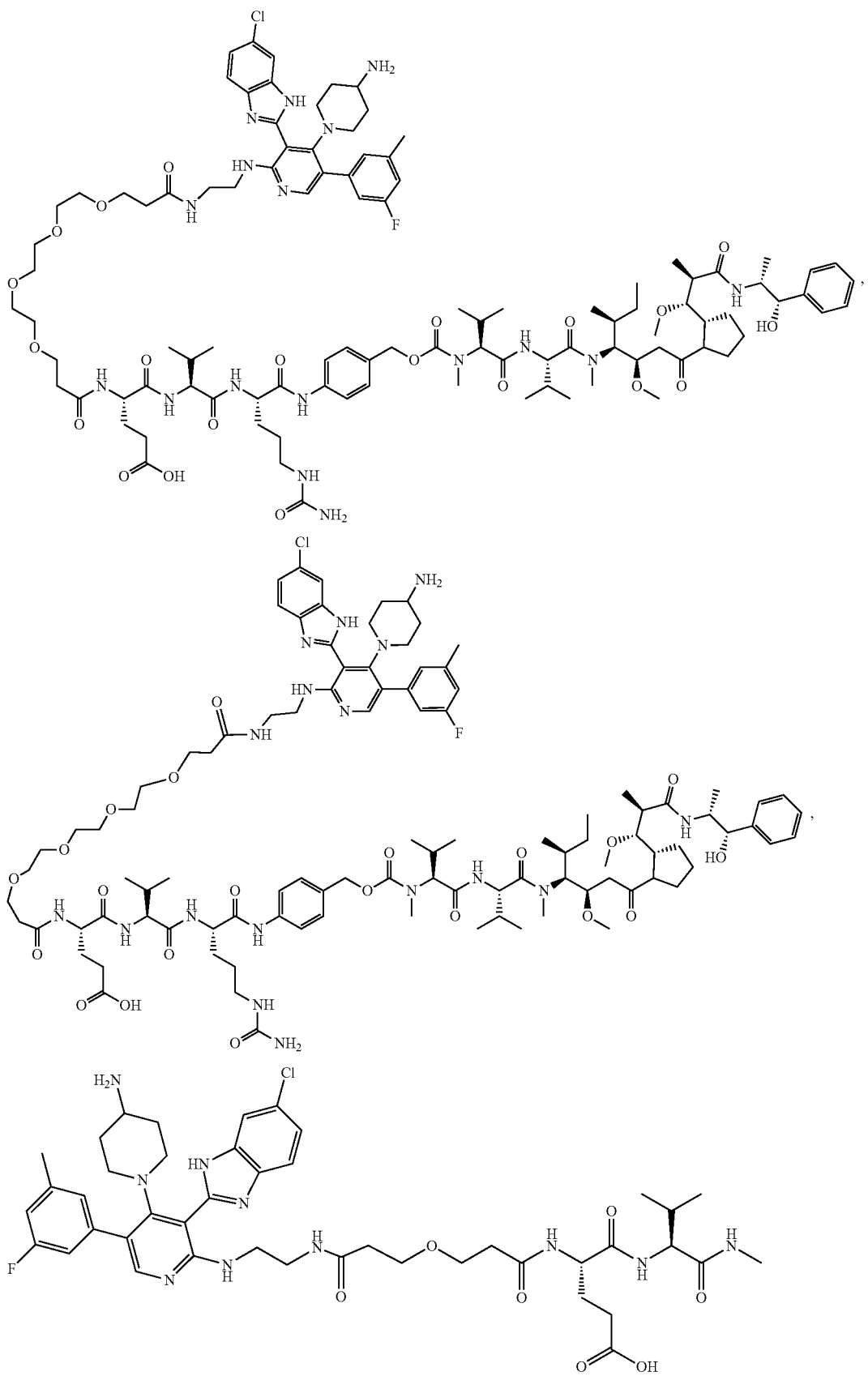

-continued
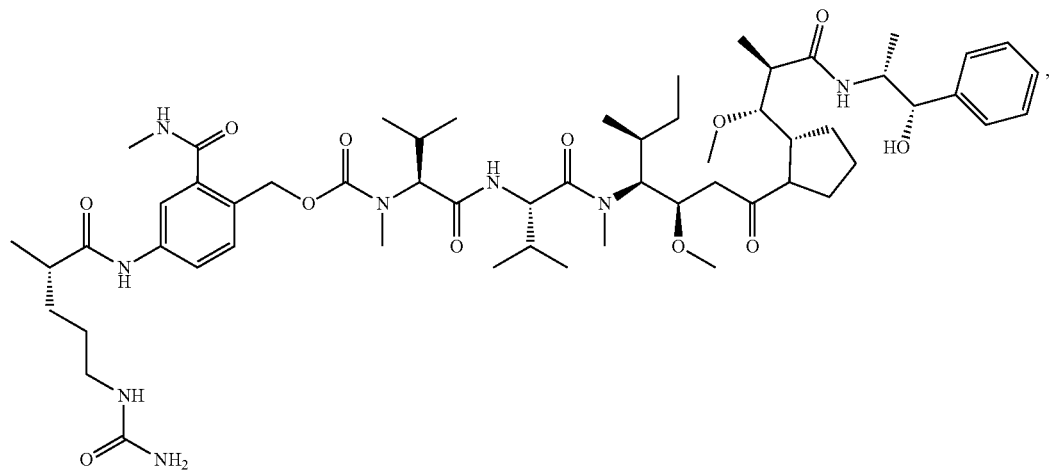
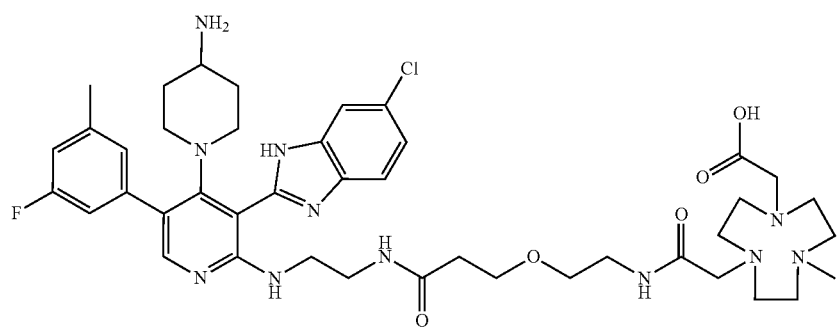
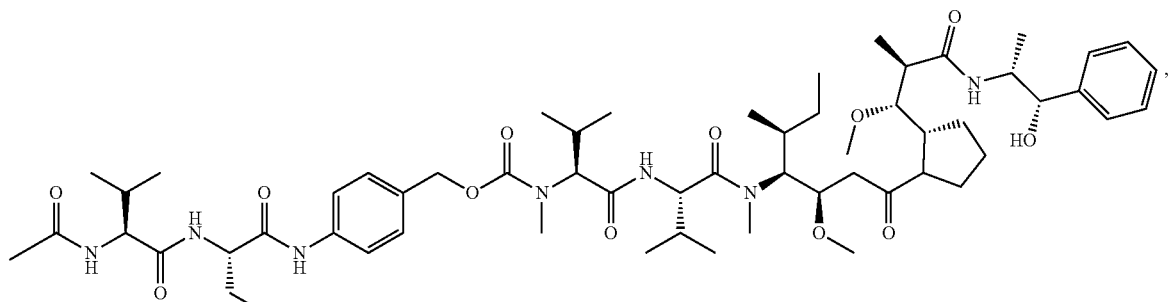
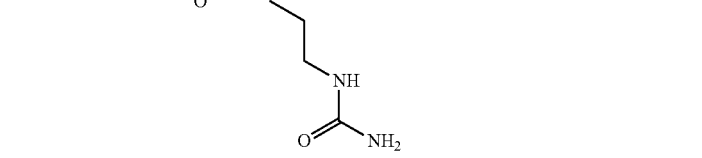
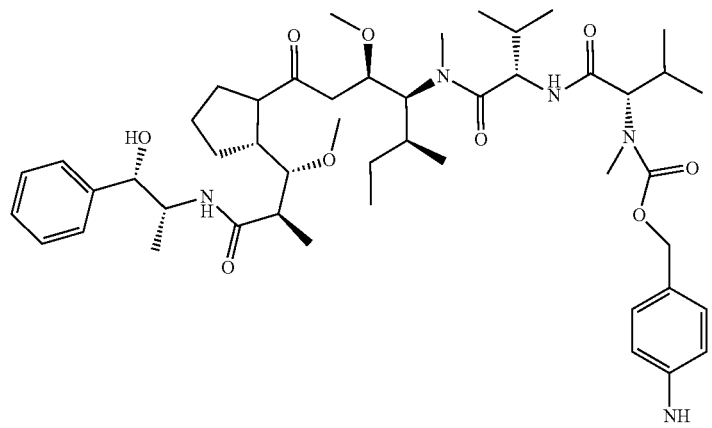

743
744
-continued
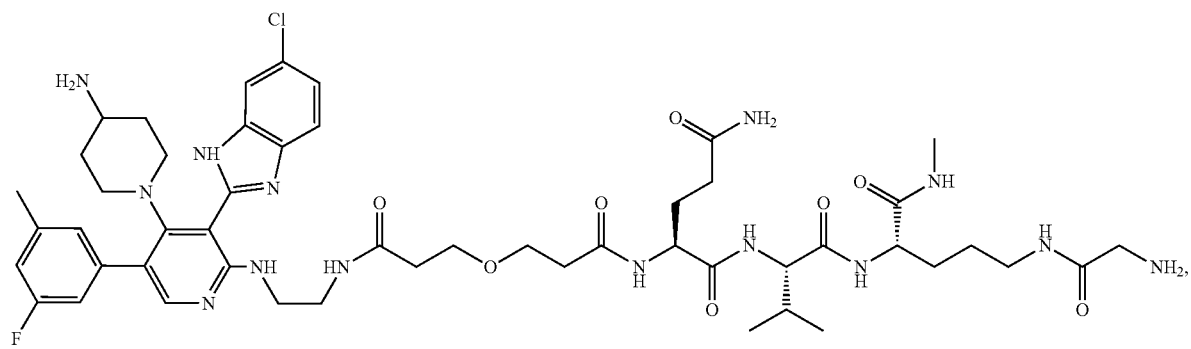
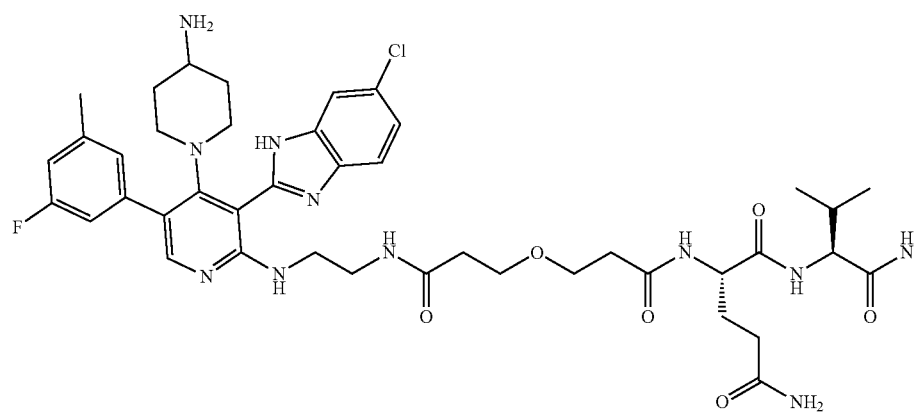
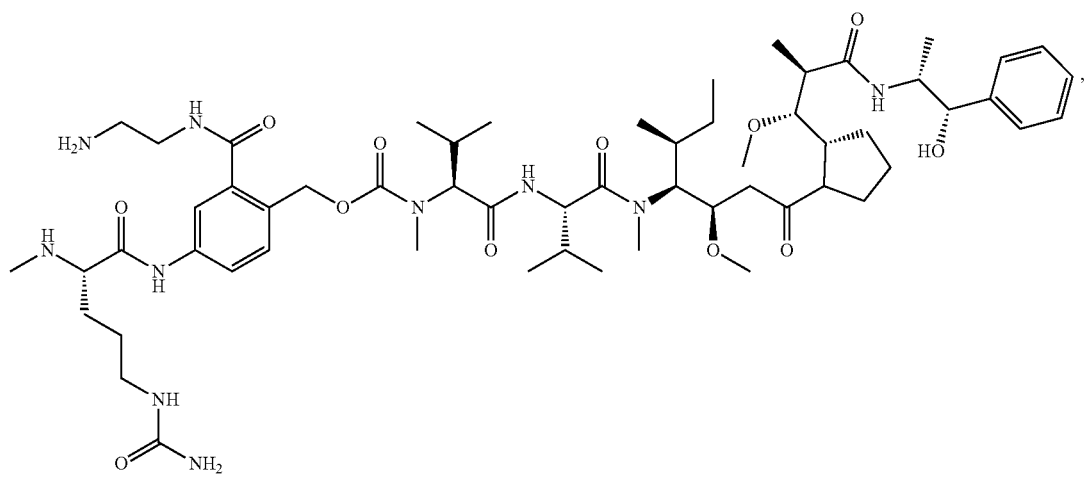

745
746
-continued
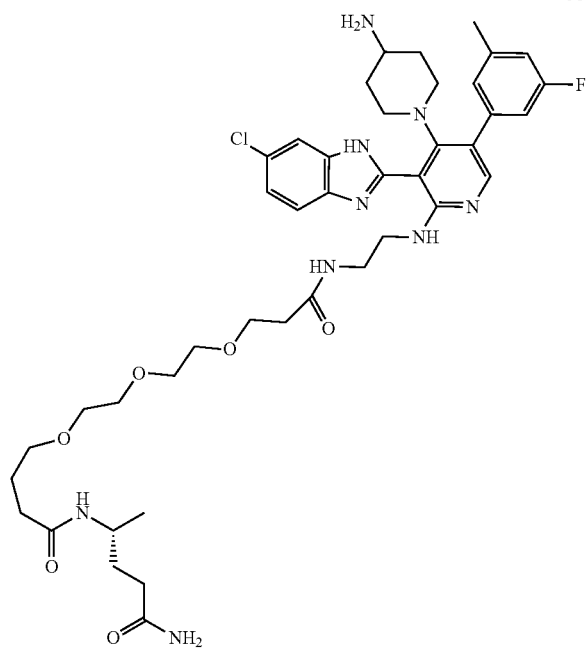
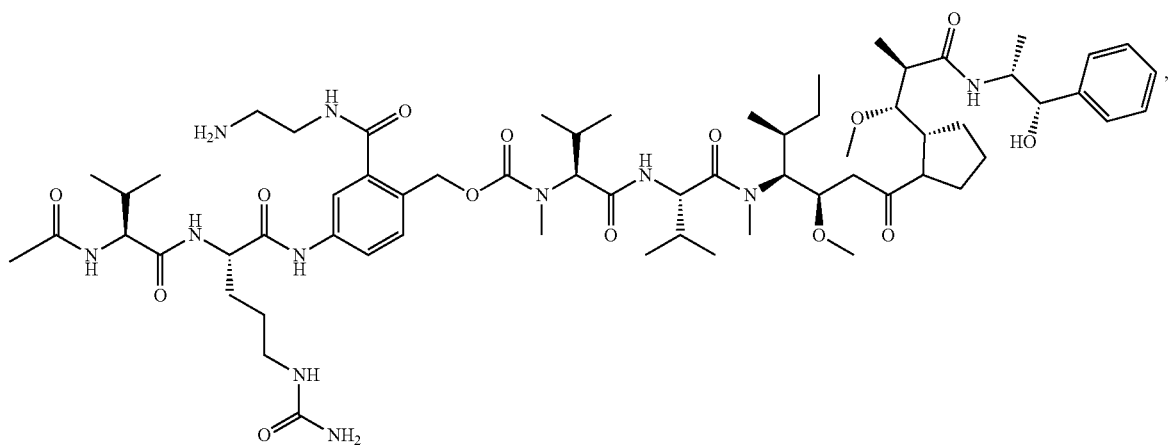
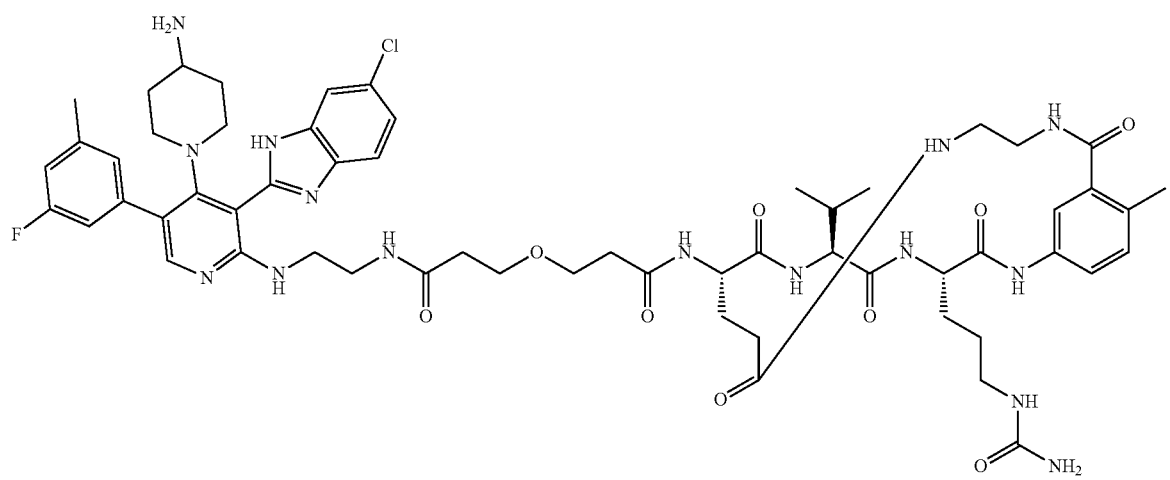

-continued
747
748
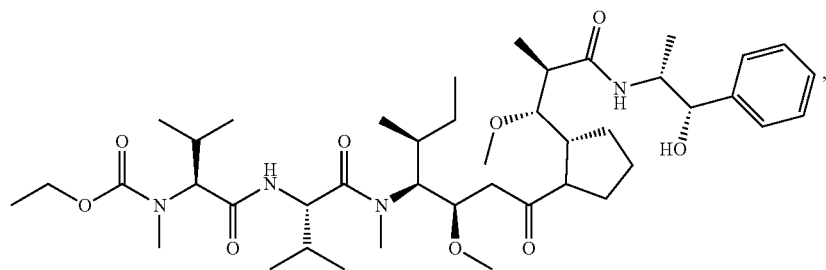
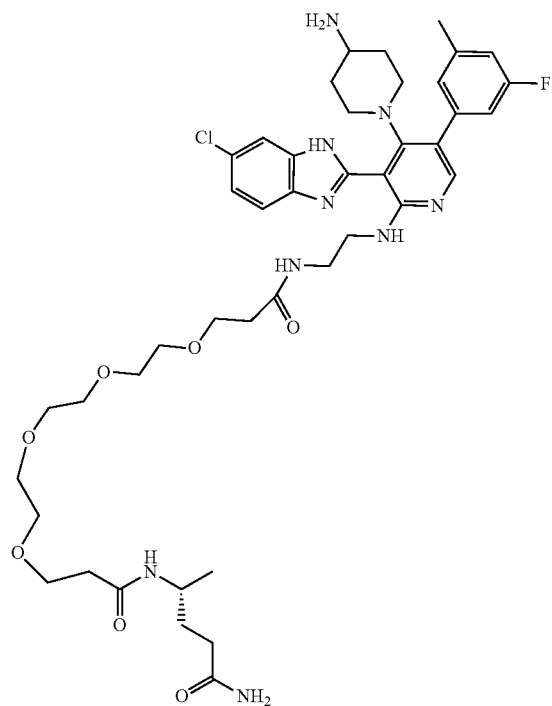
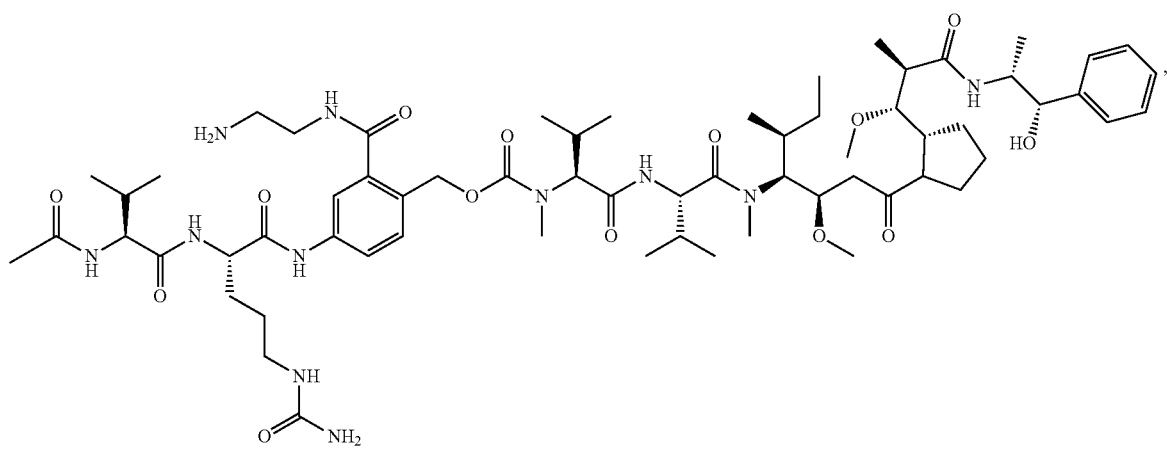

-continued
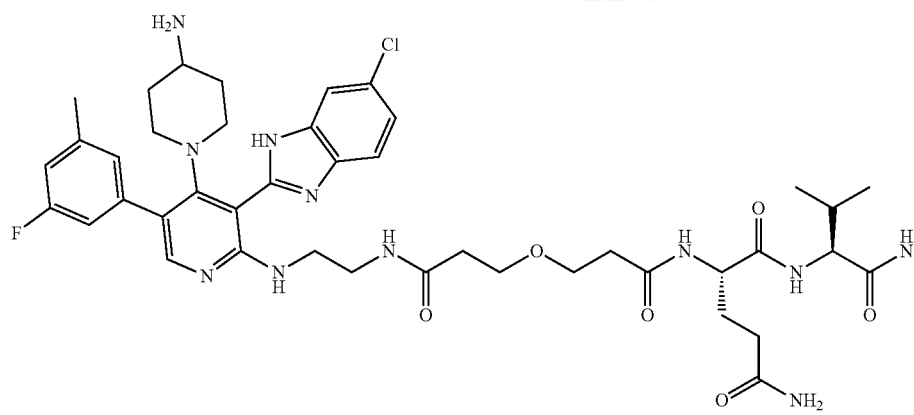
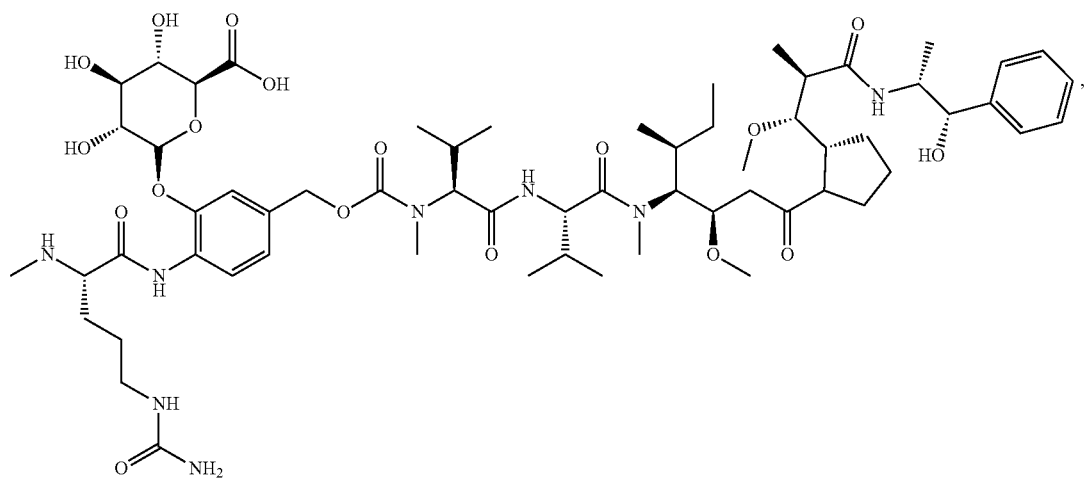
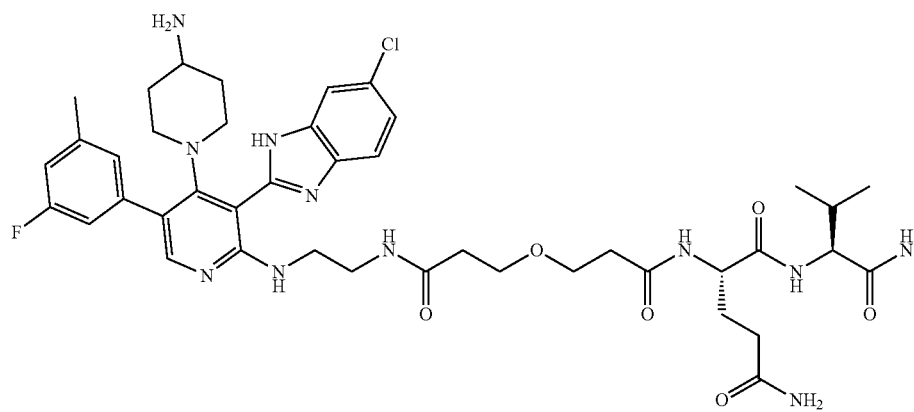

751 752
-continued
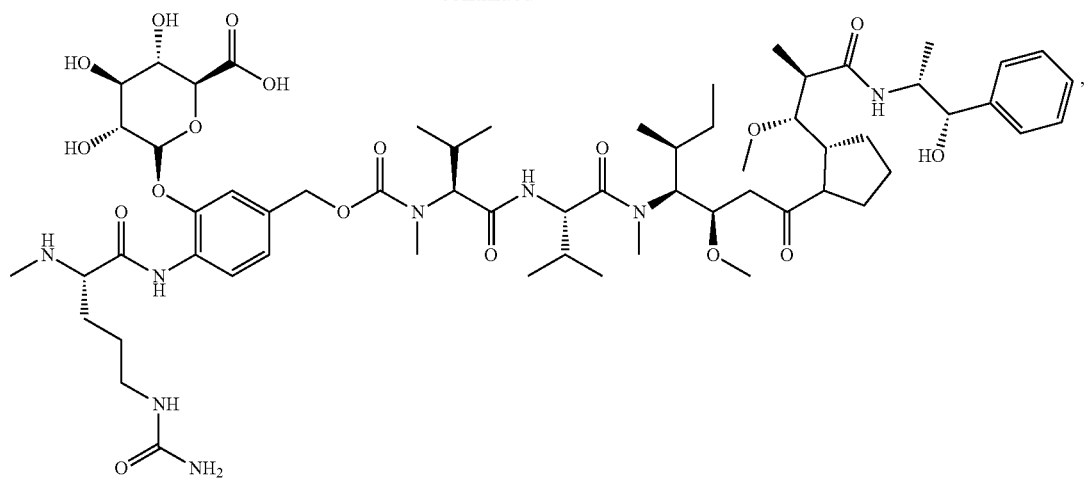
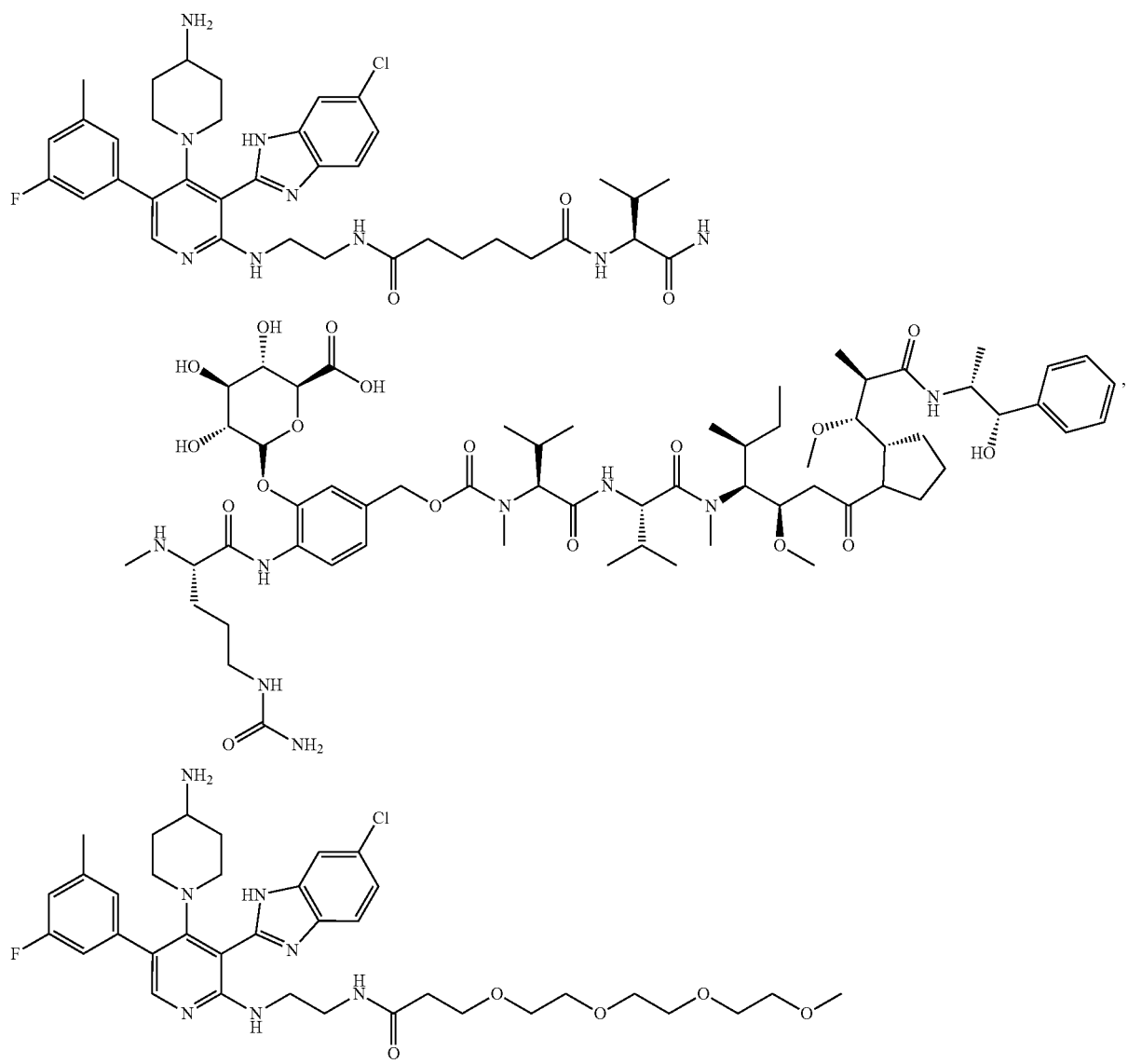

-continued
753
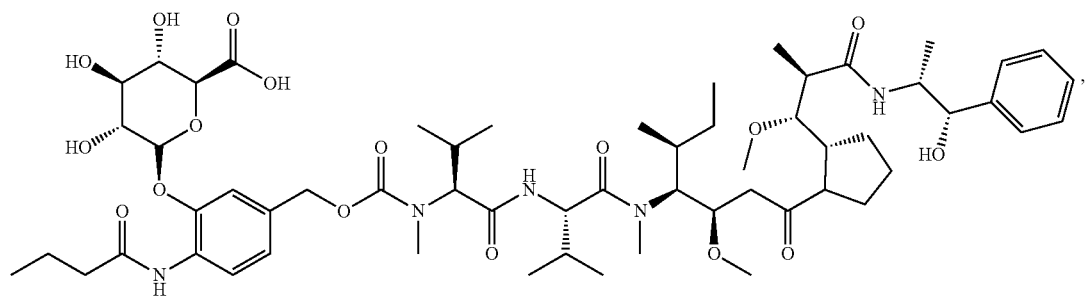
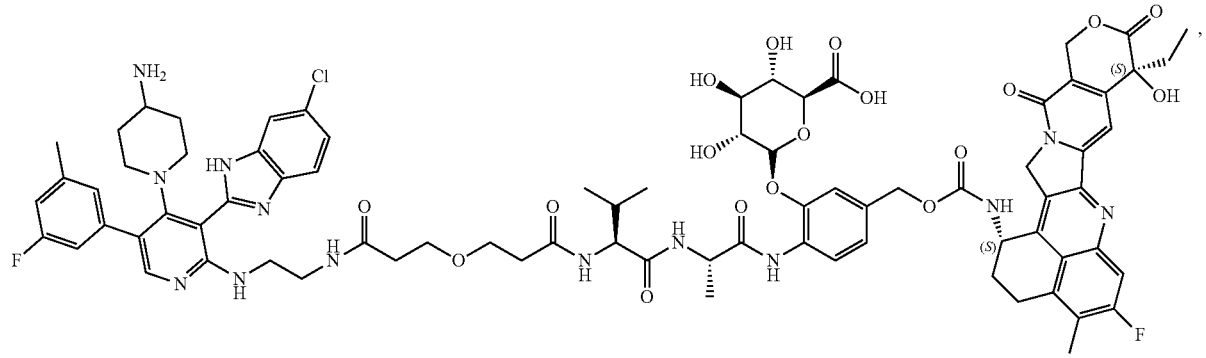
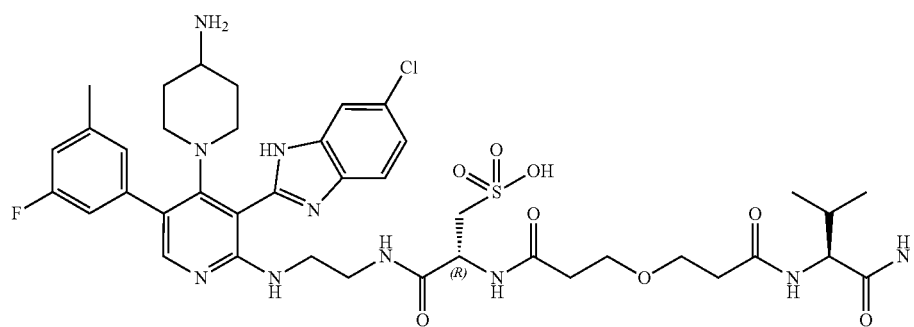
754
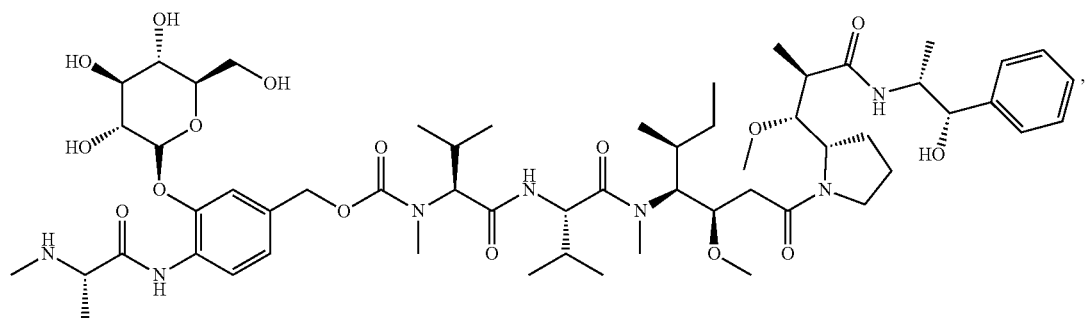
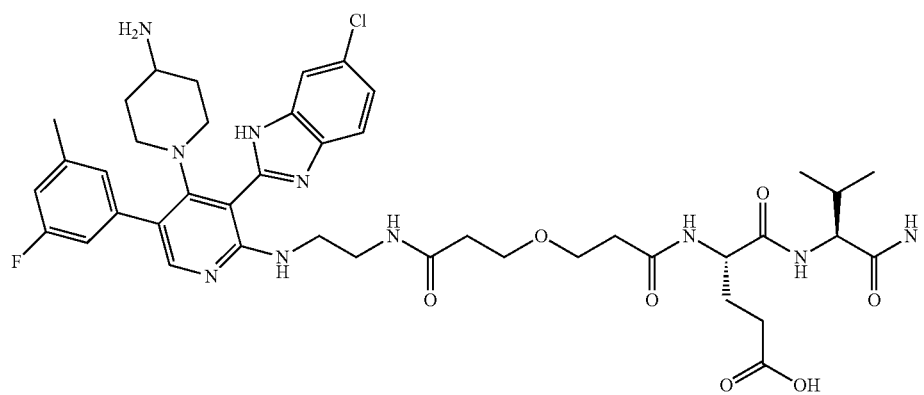

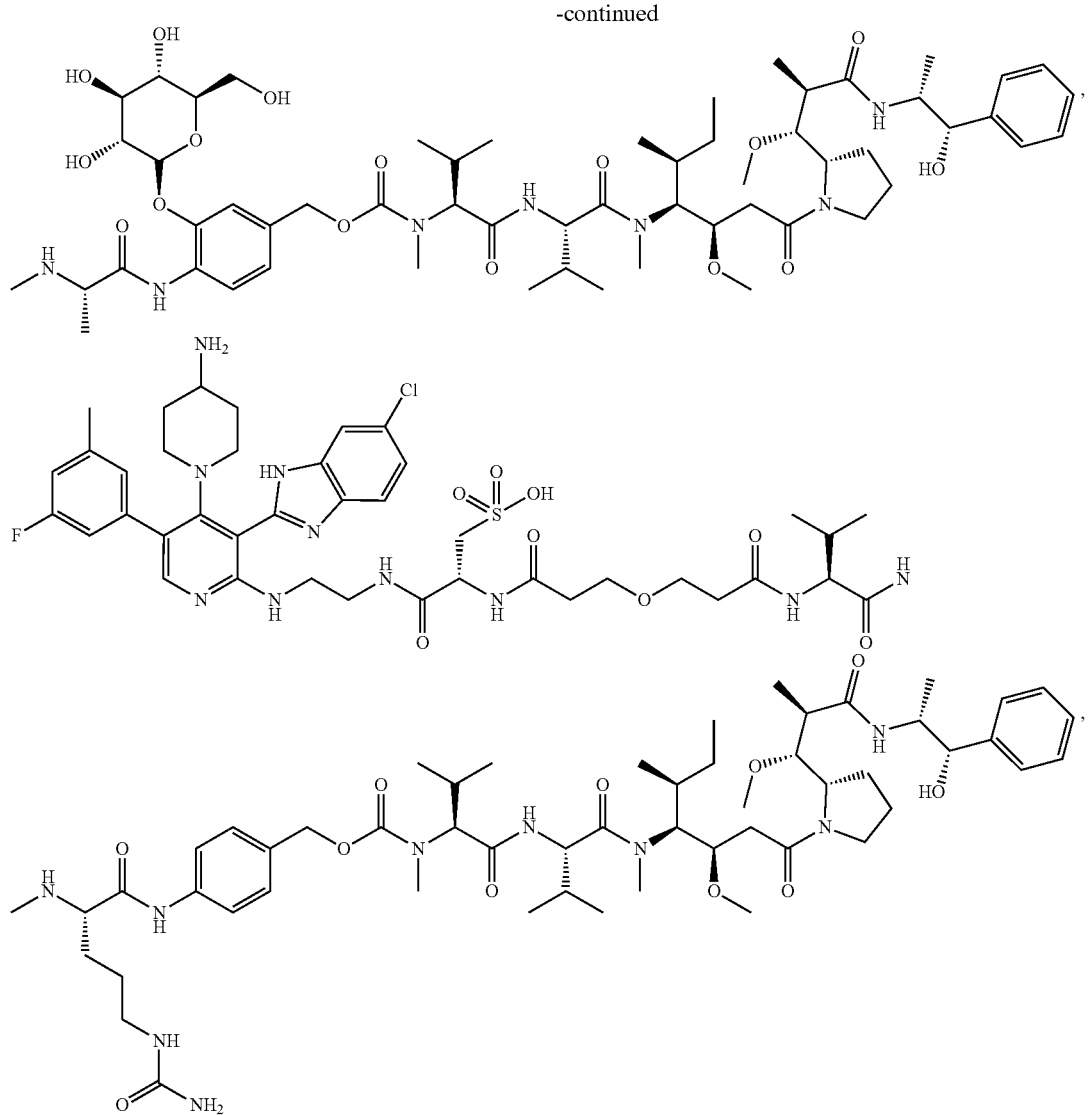

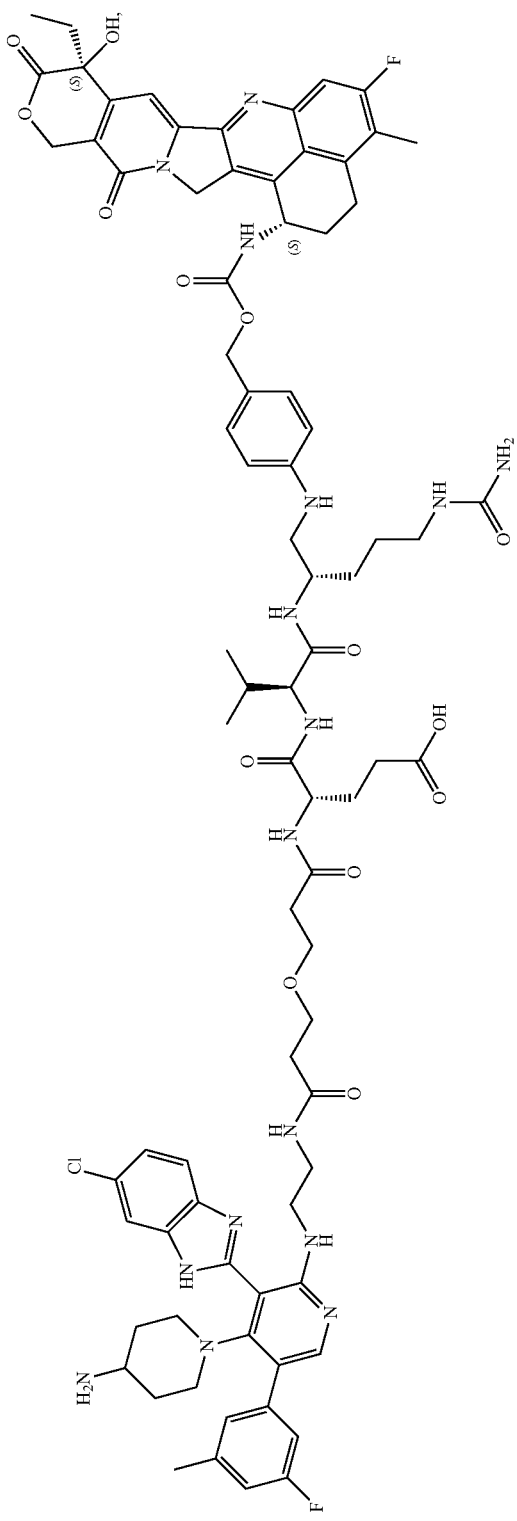
757
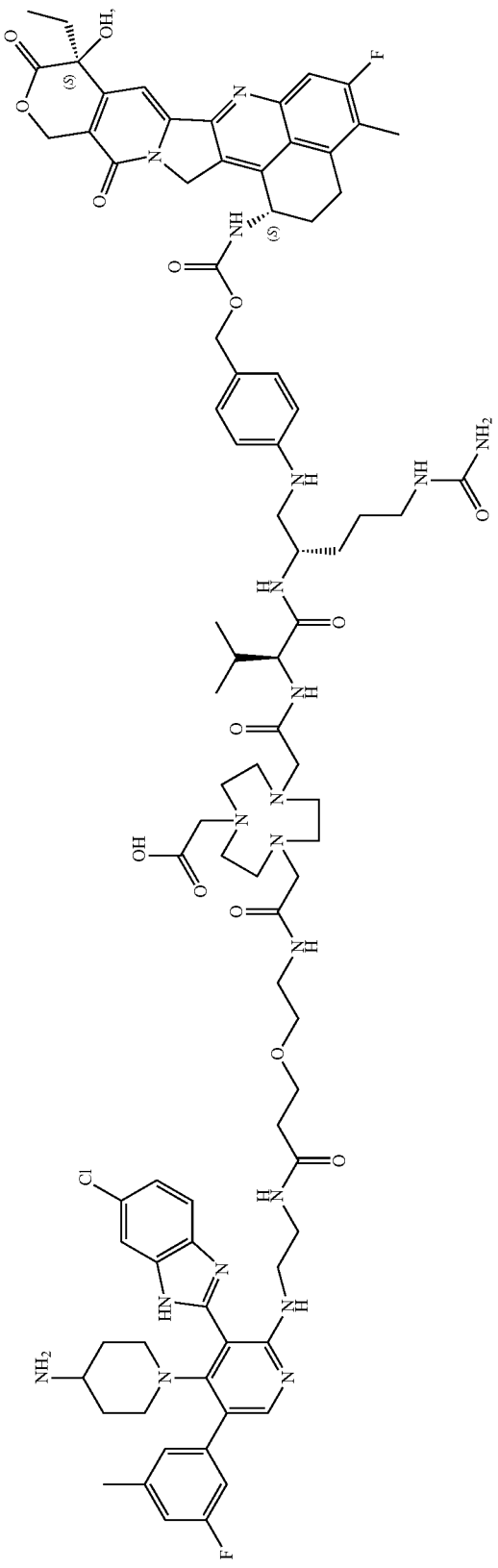
758

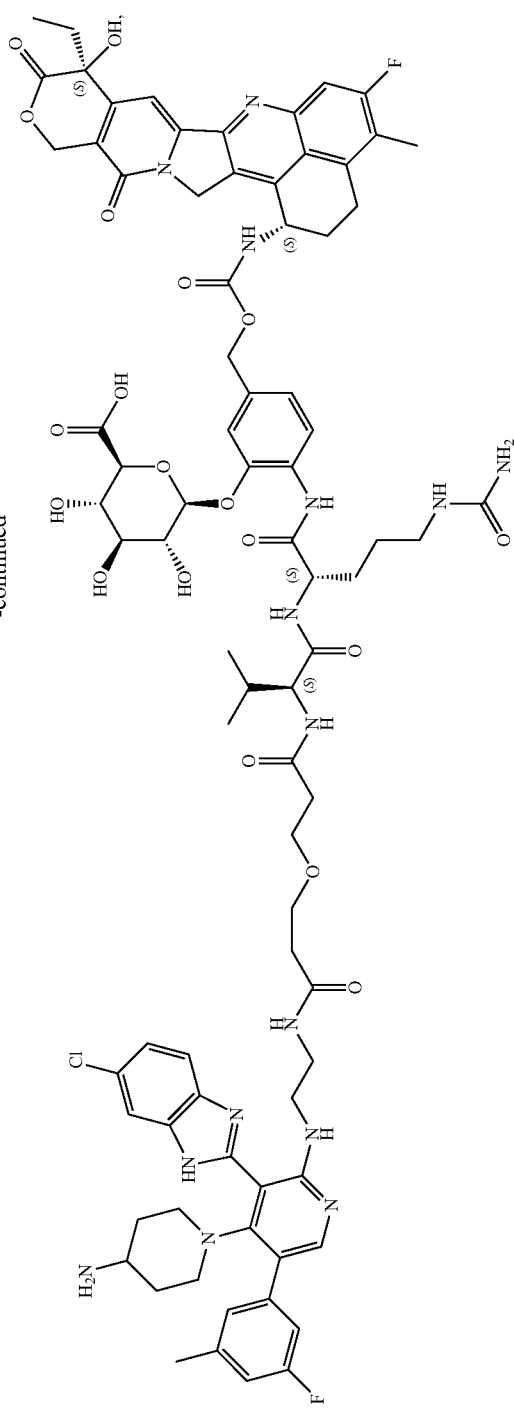
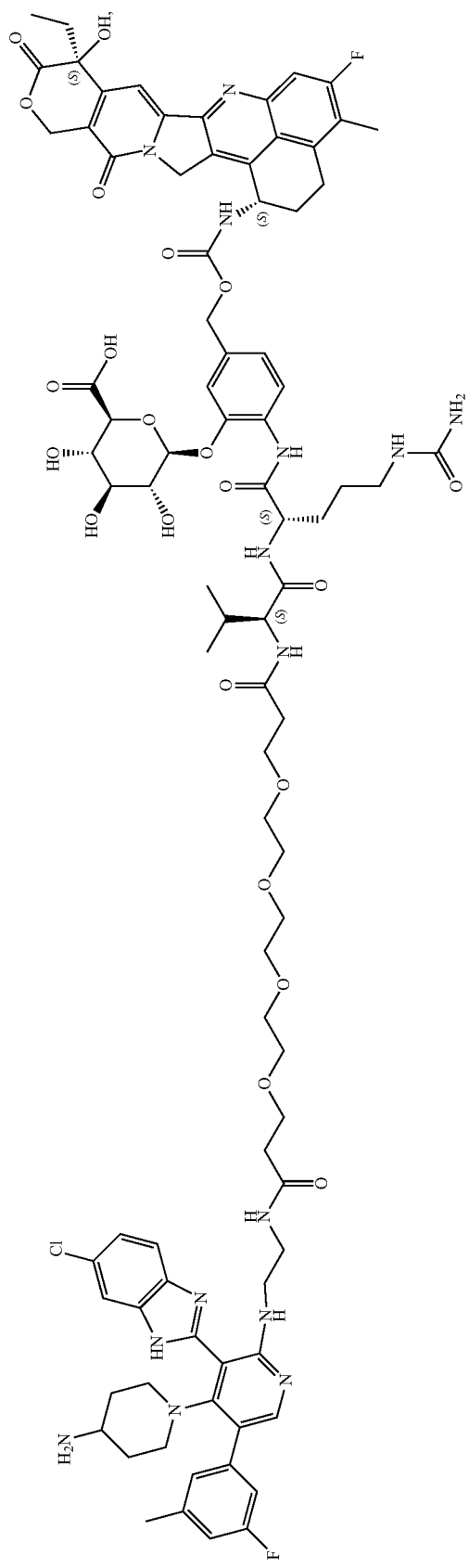

761
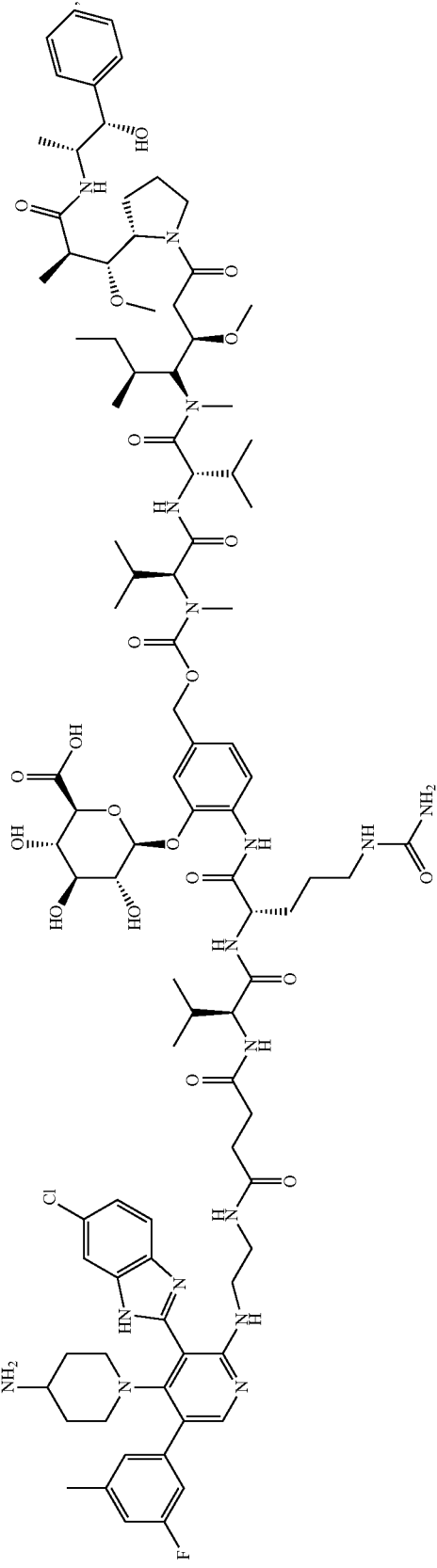
762
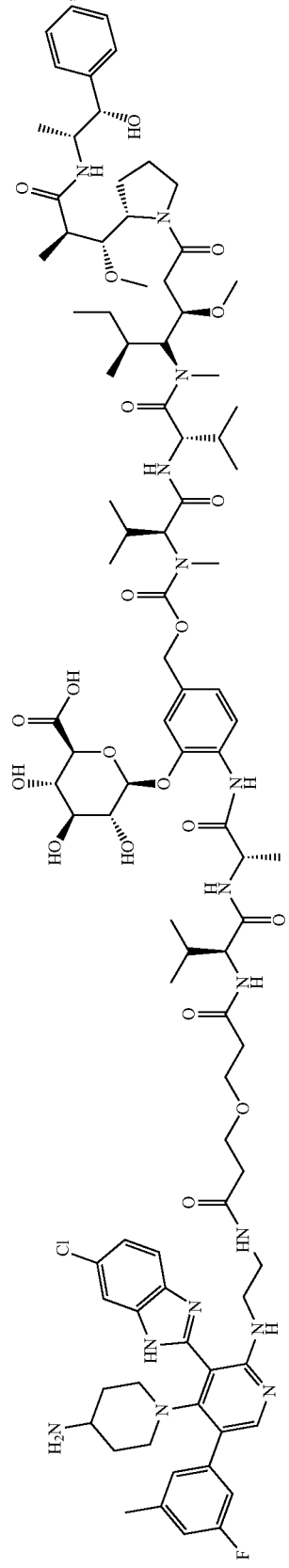

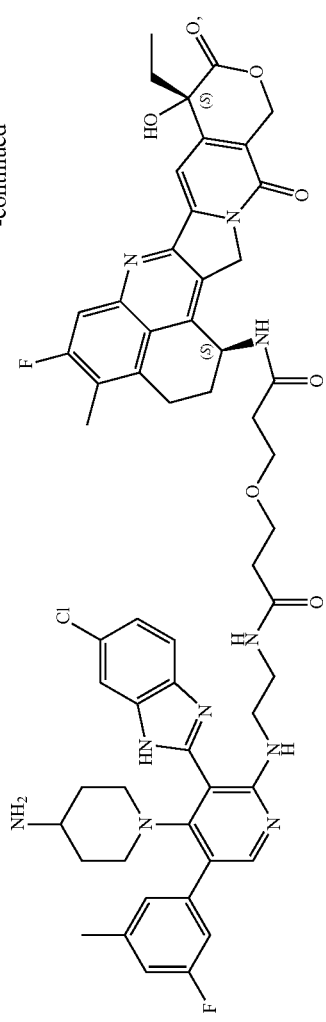
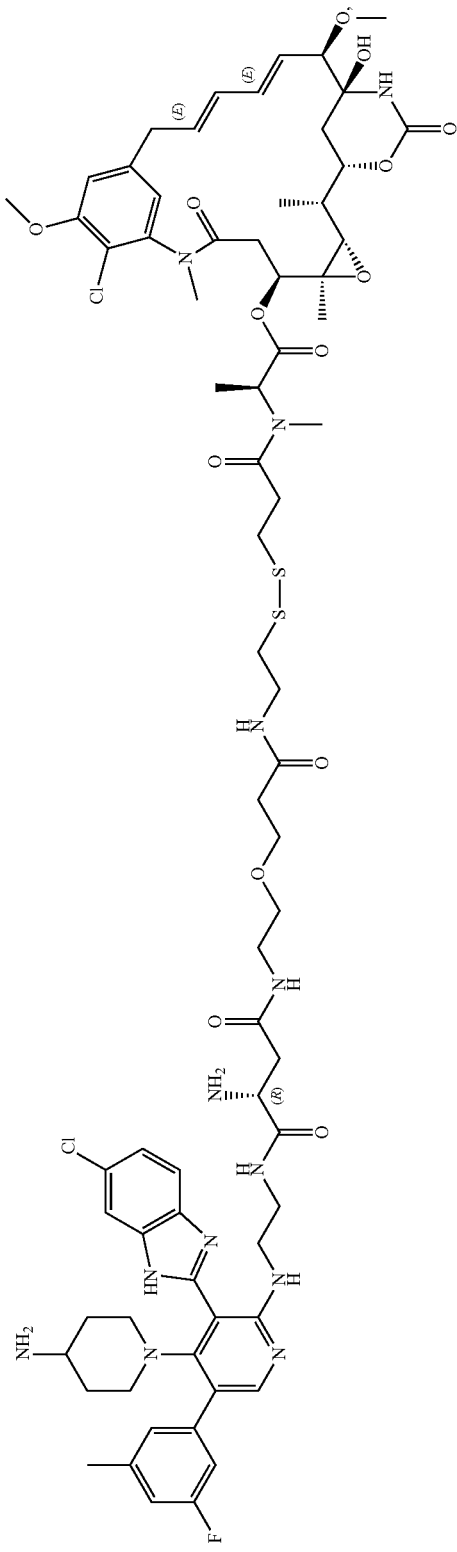

765
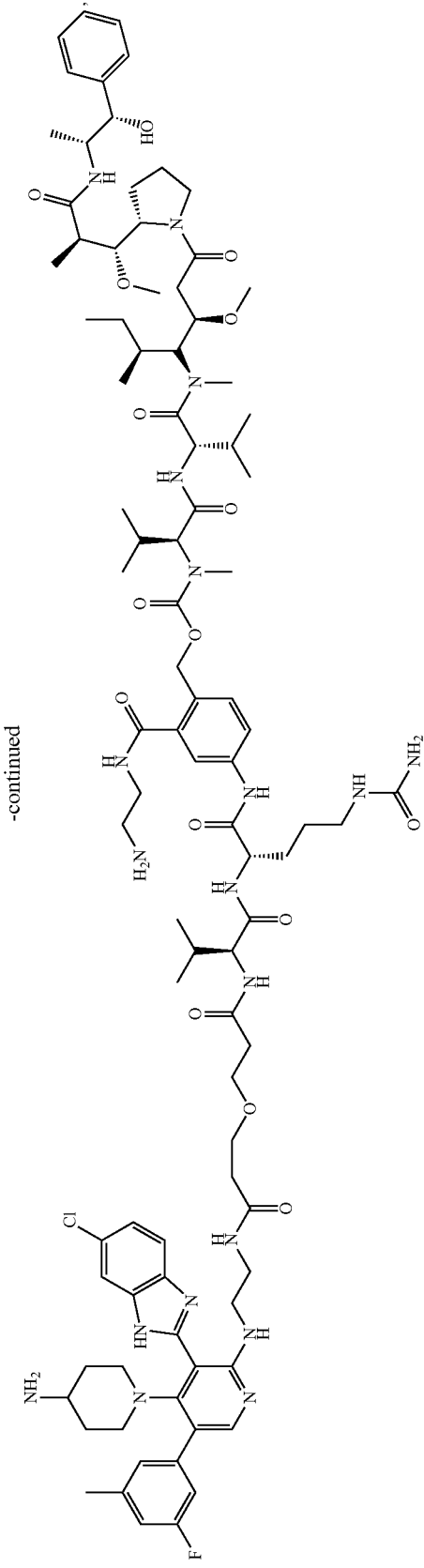
766
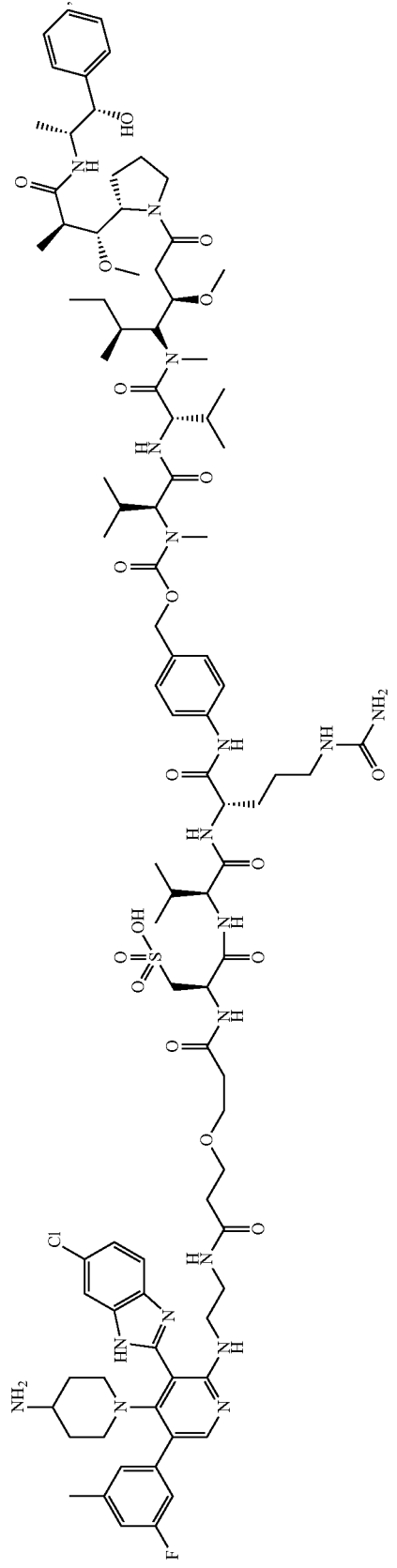

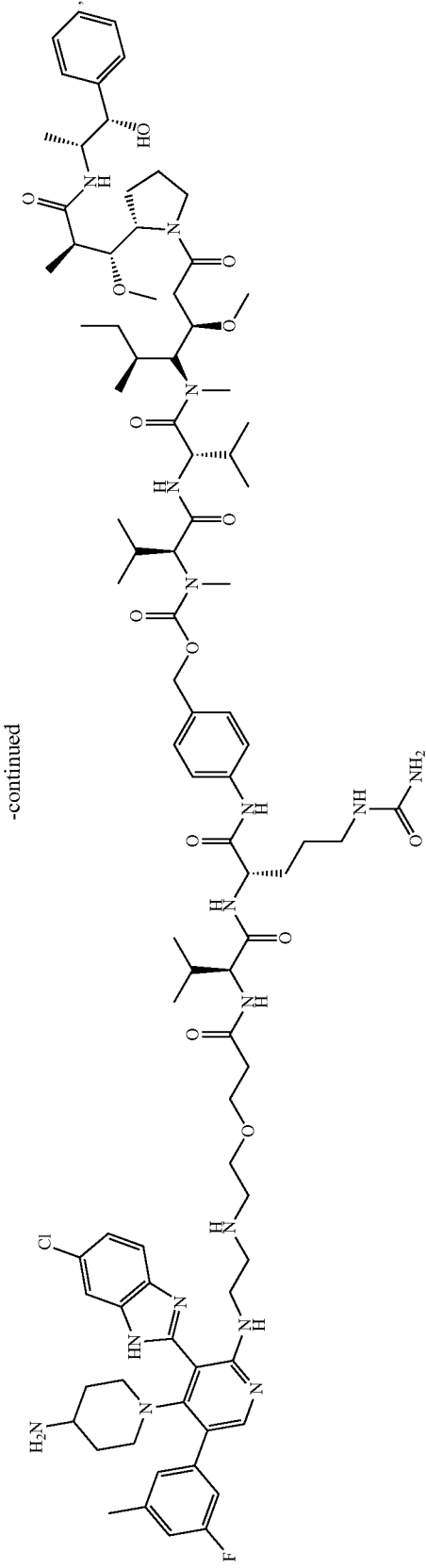
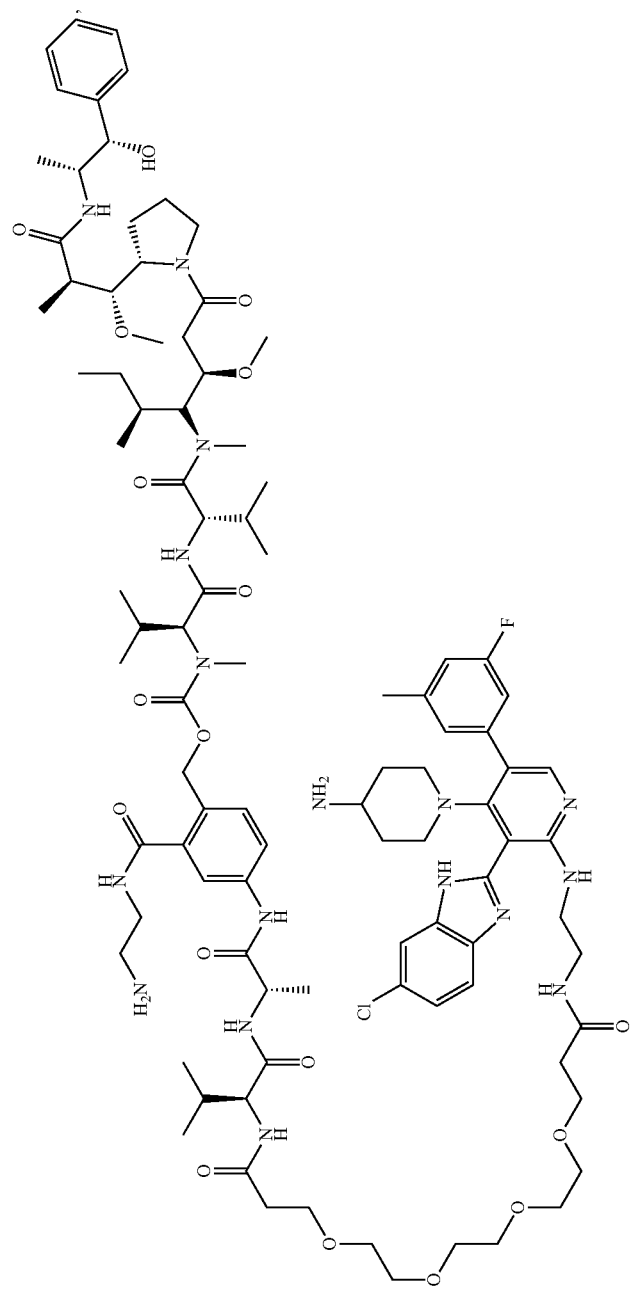

-continued
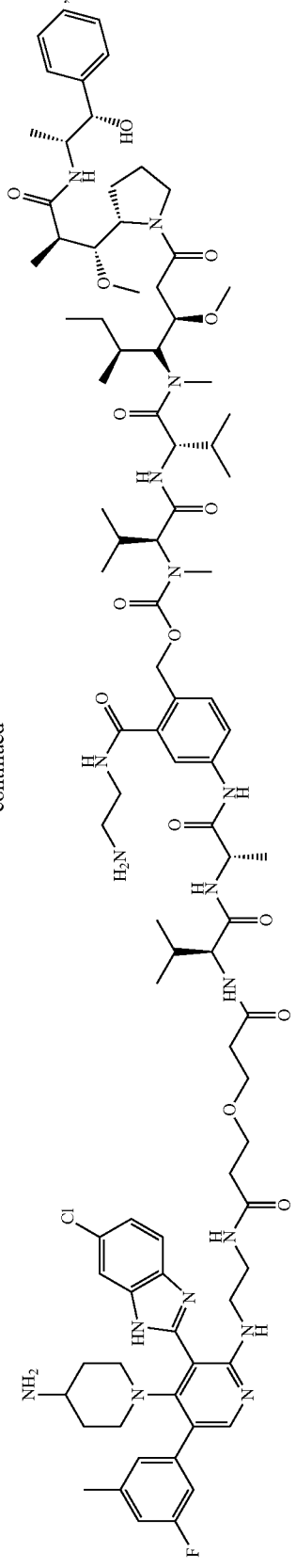
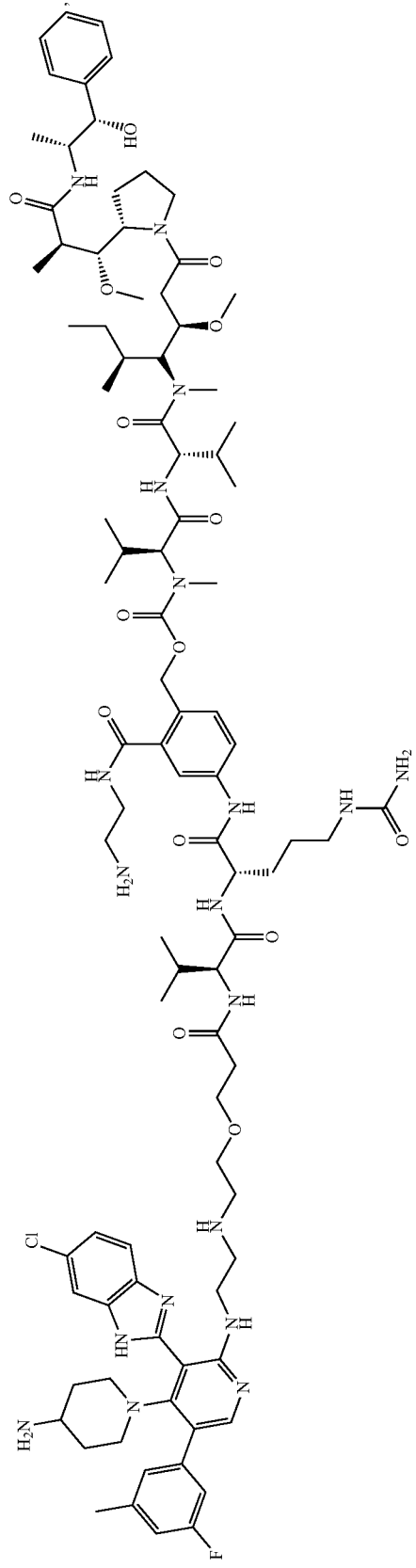

771
-continued
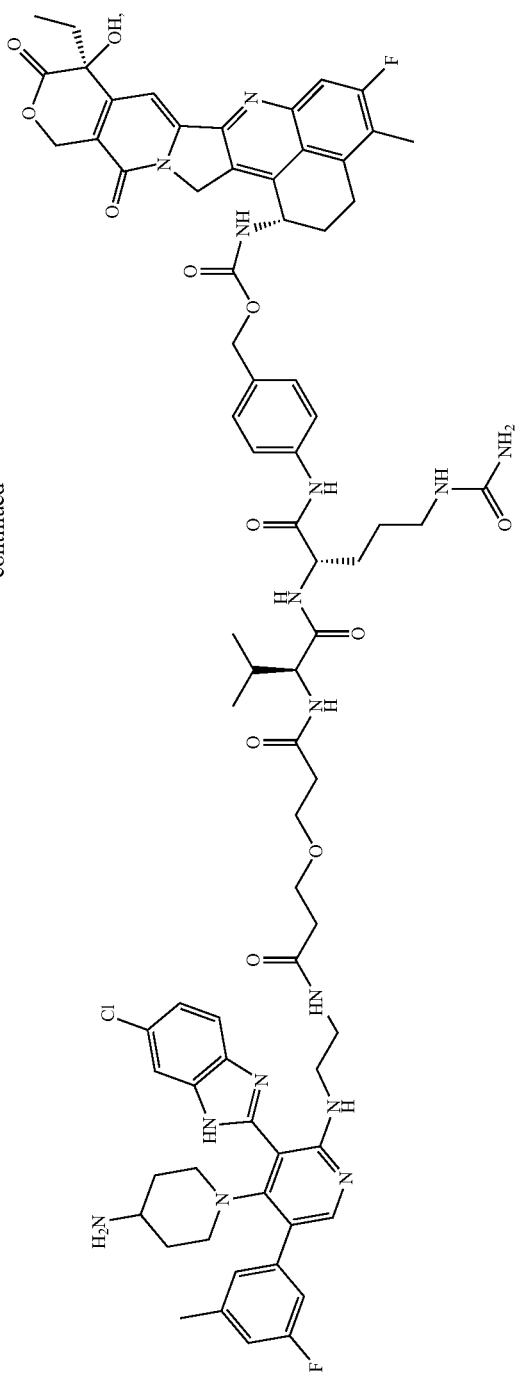
772
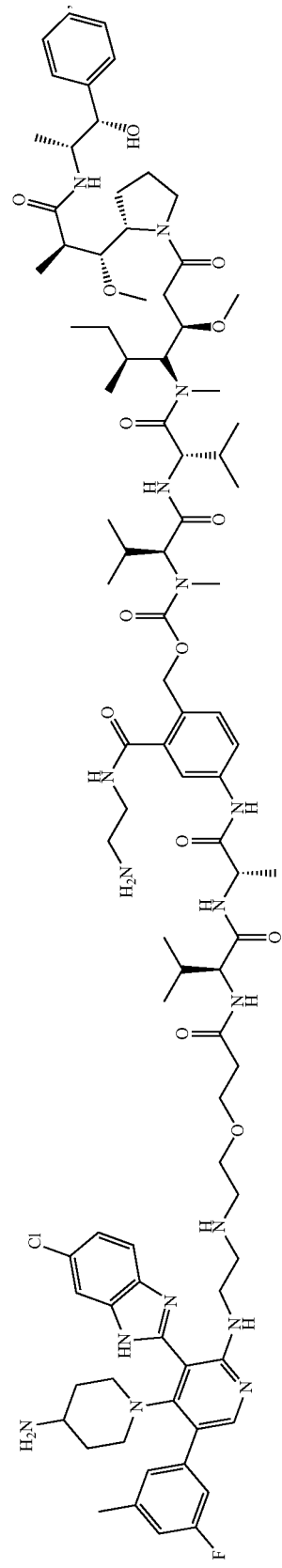

773
-continued
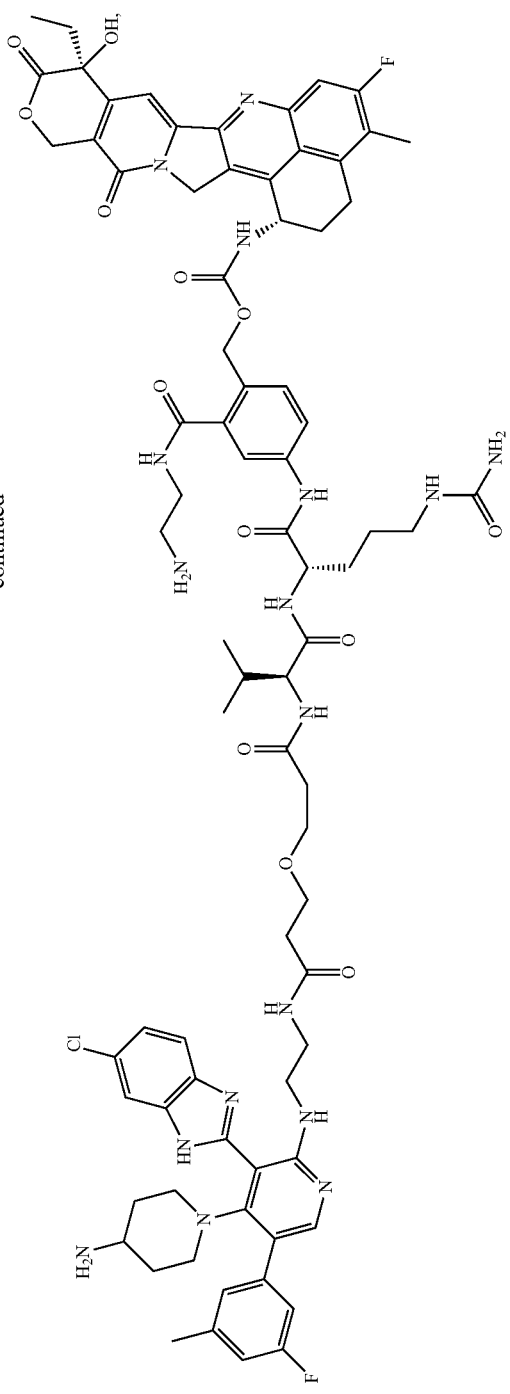
774
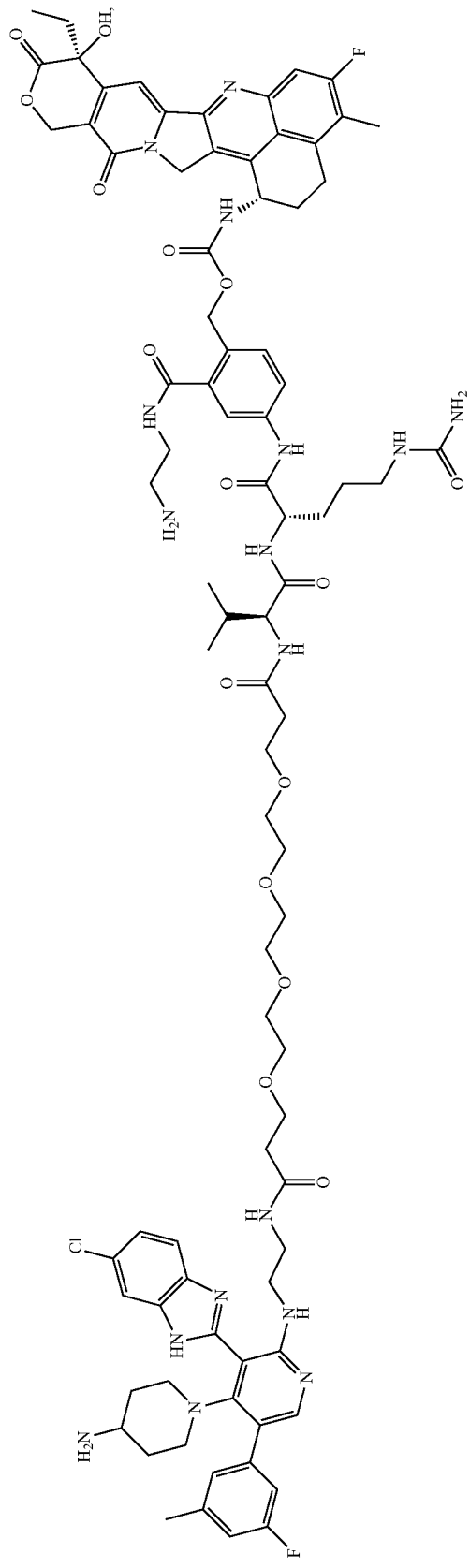

-continued
775
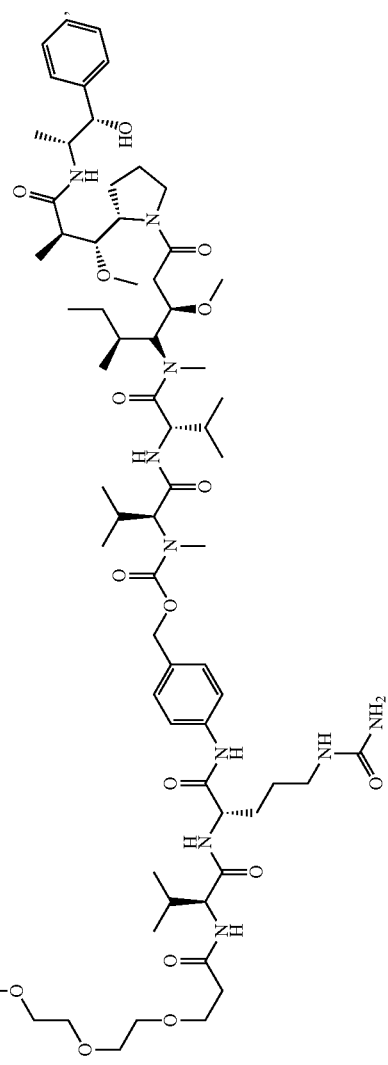
776
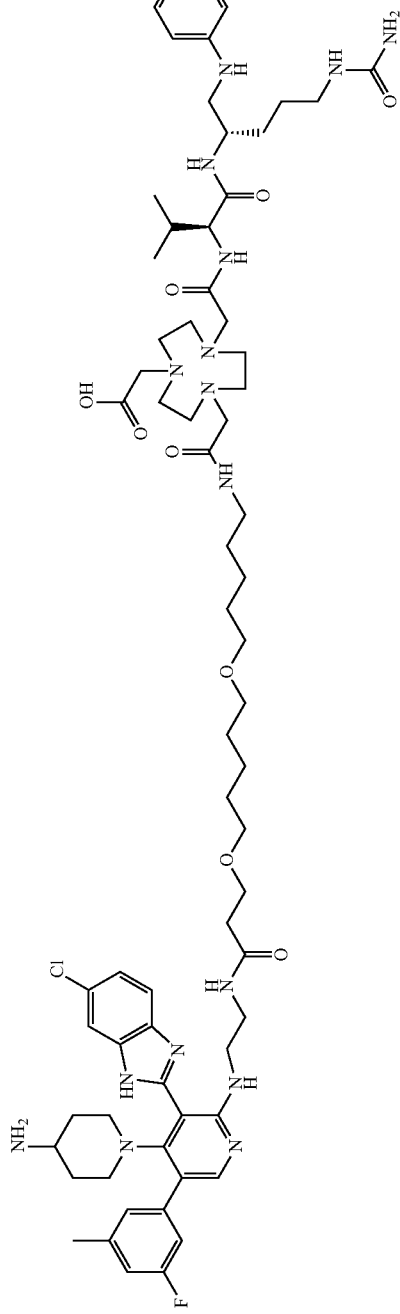

-continued
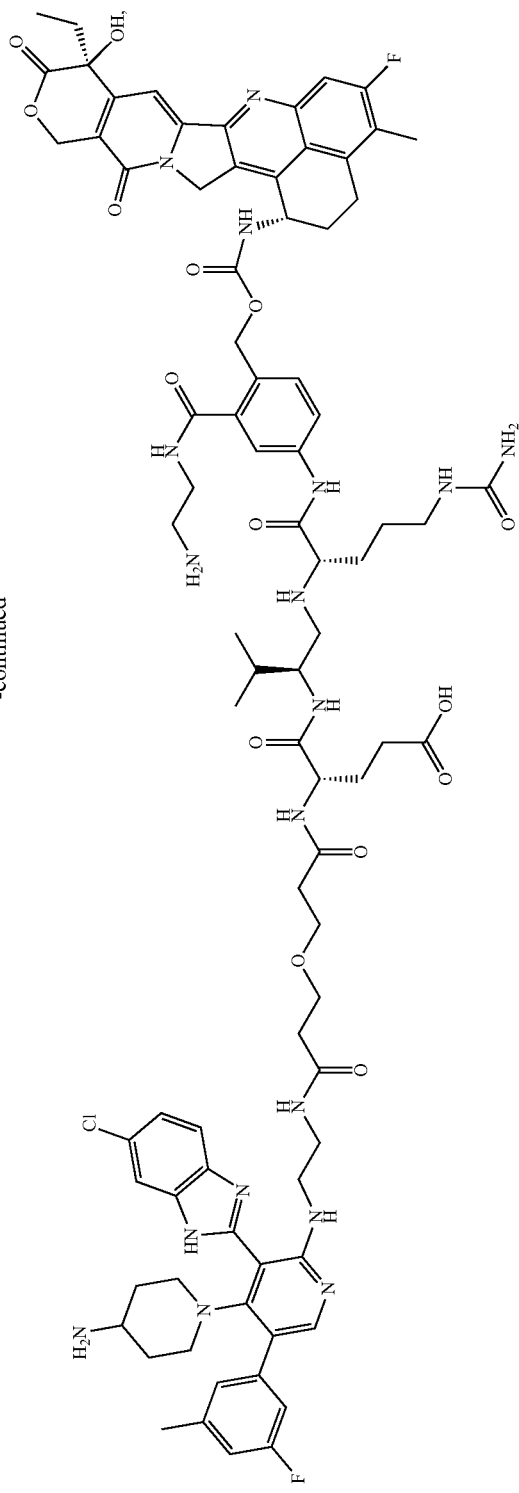
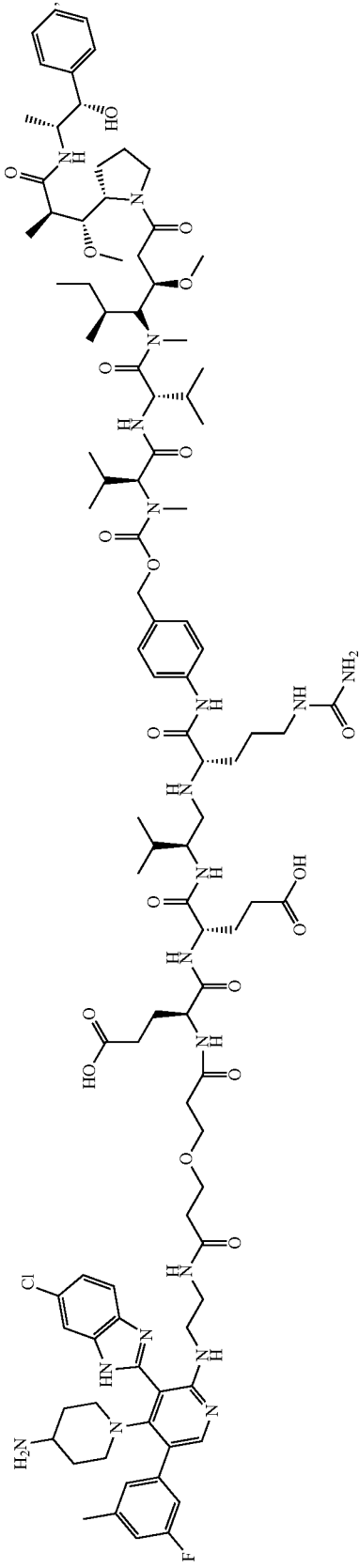

-continued
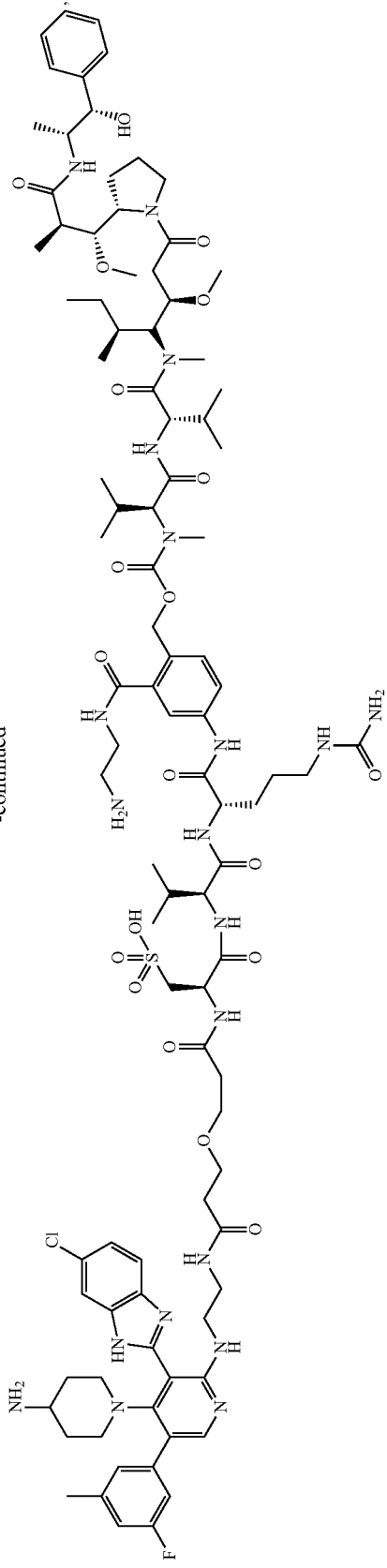
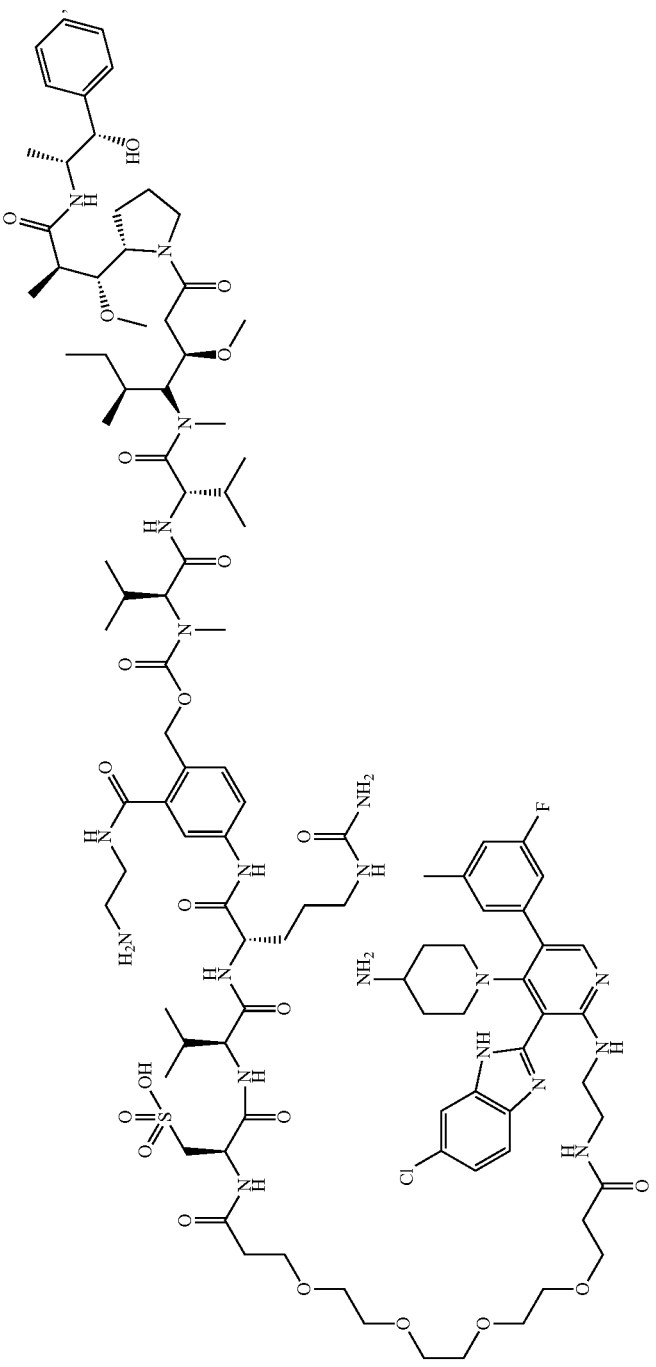

781
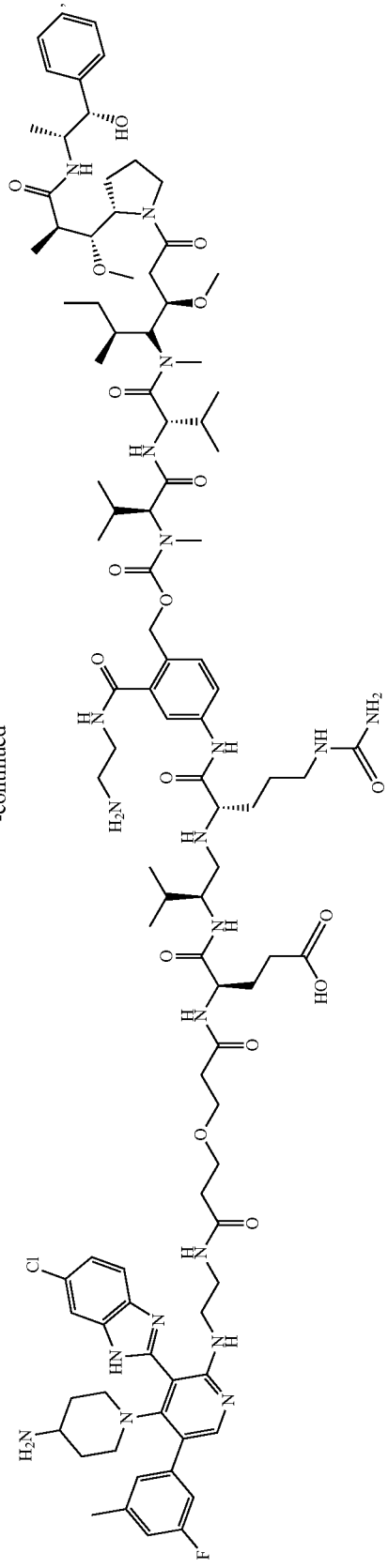
782
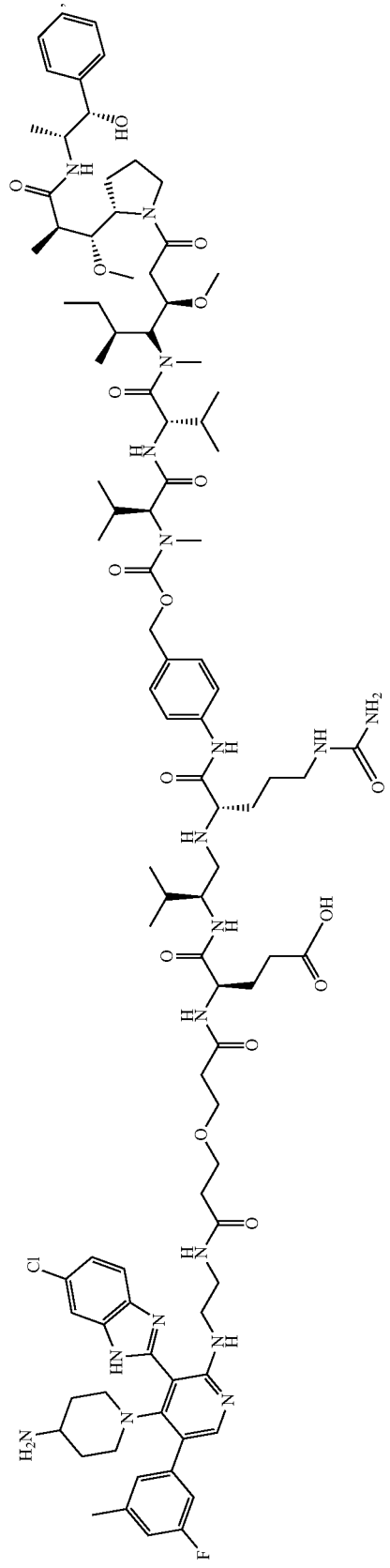

783
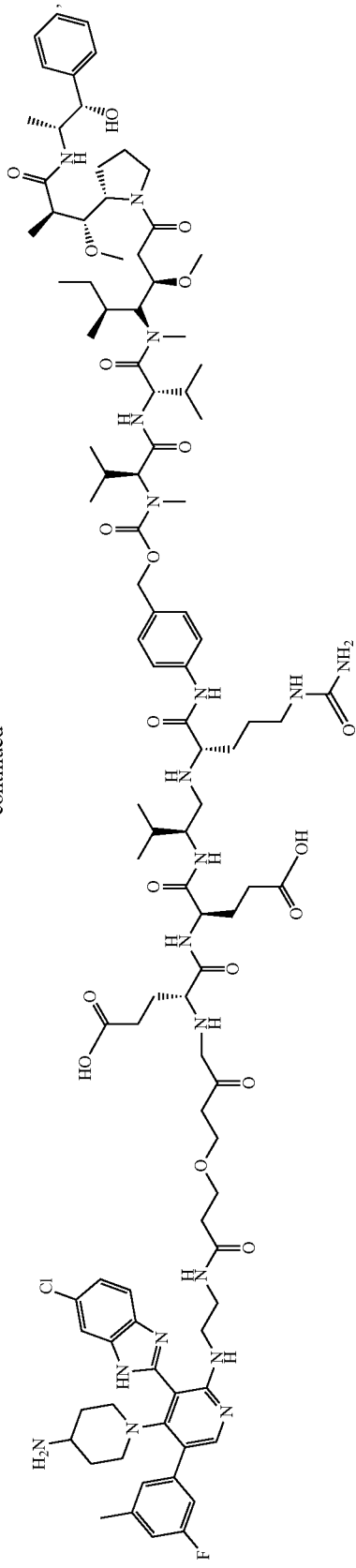
784
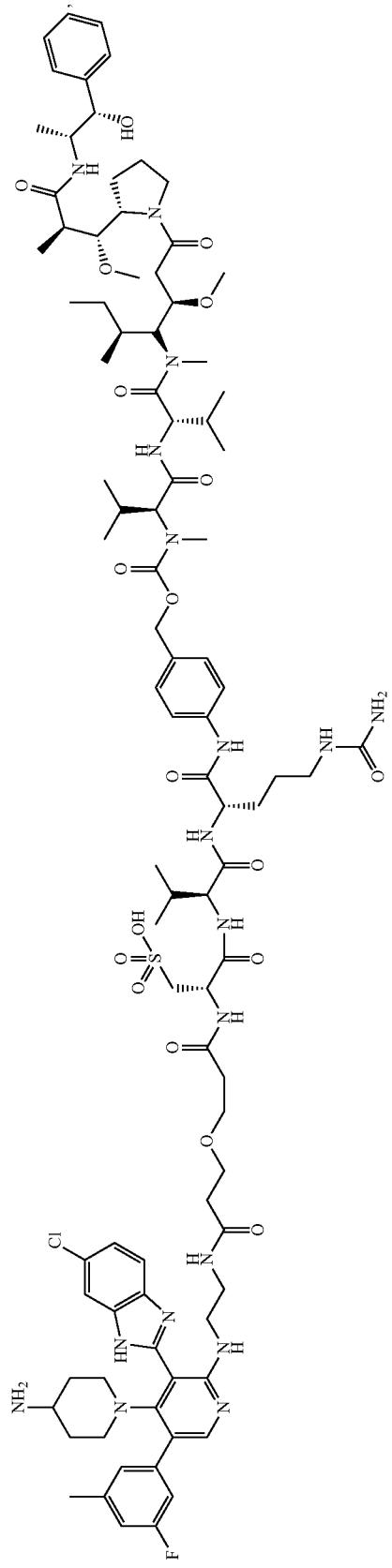

785
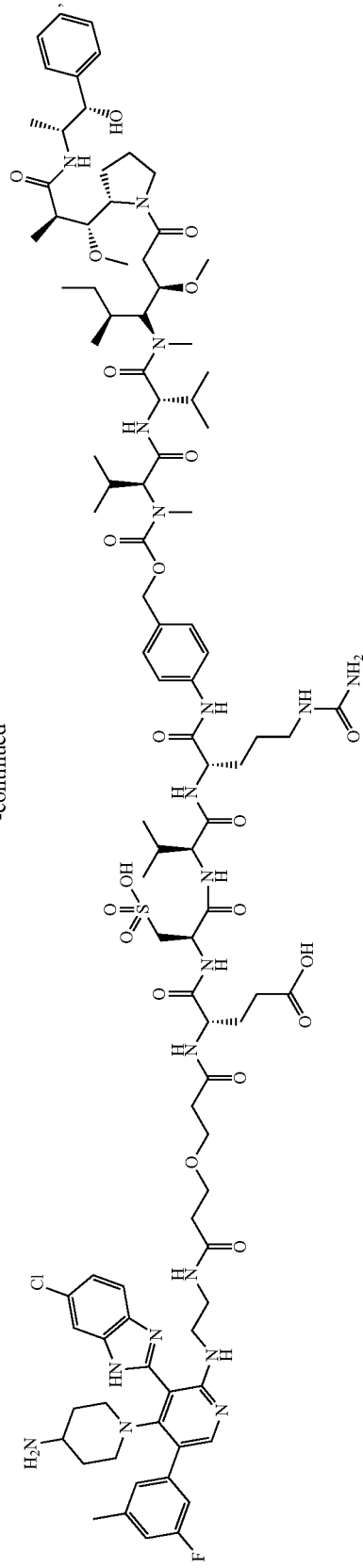
786
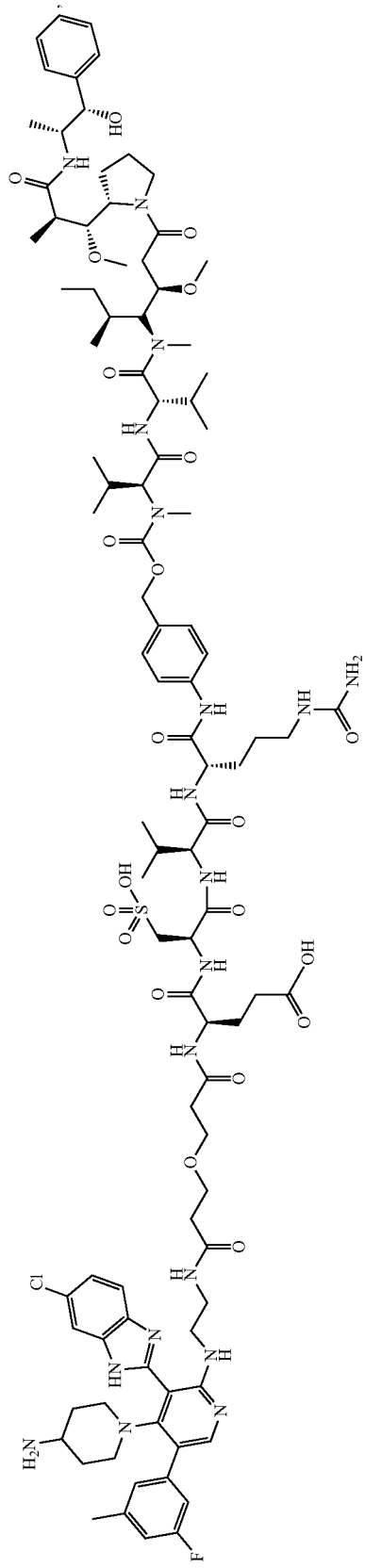

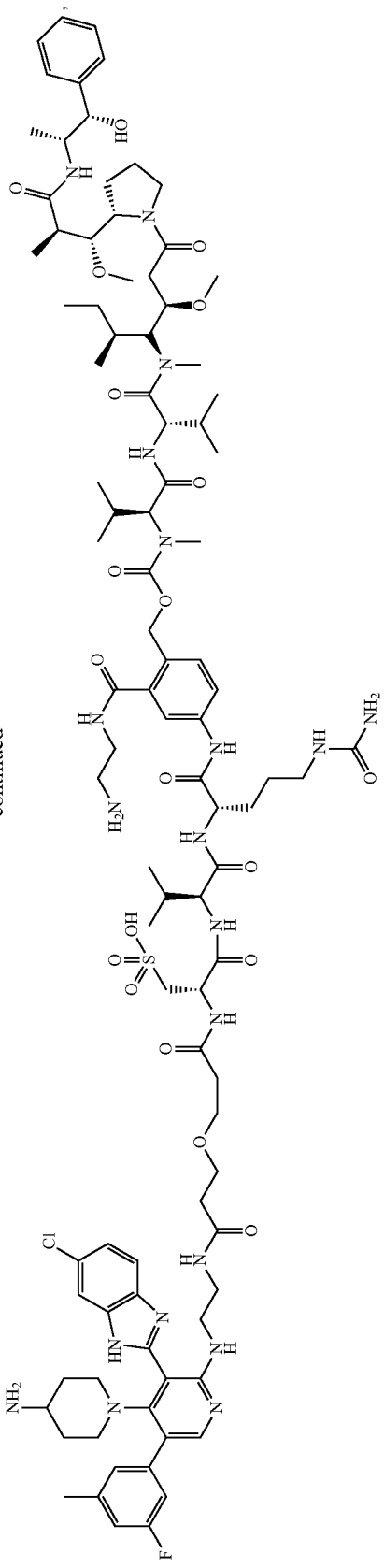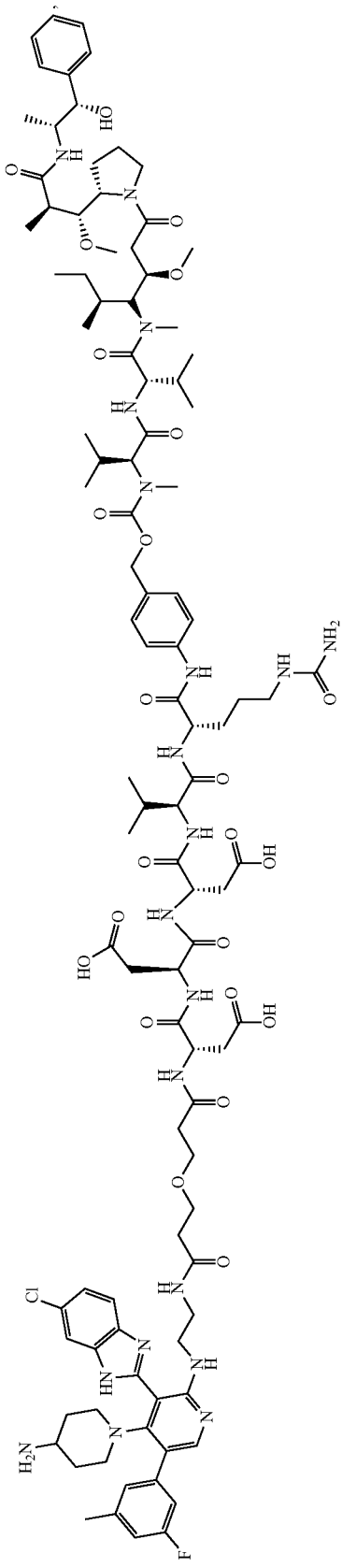

-continued
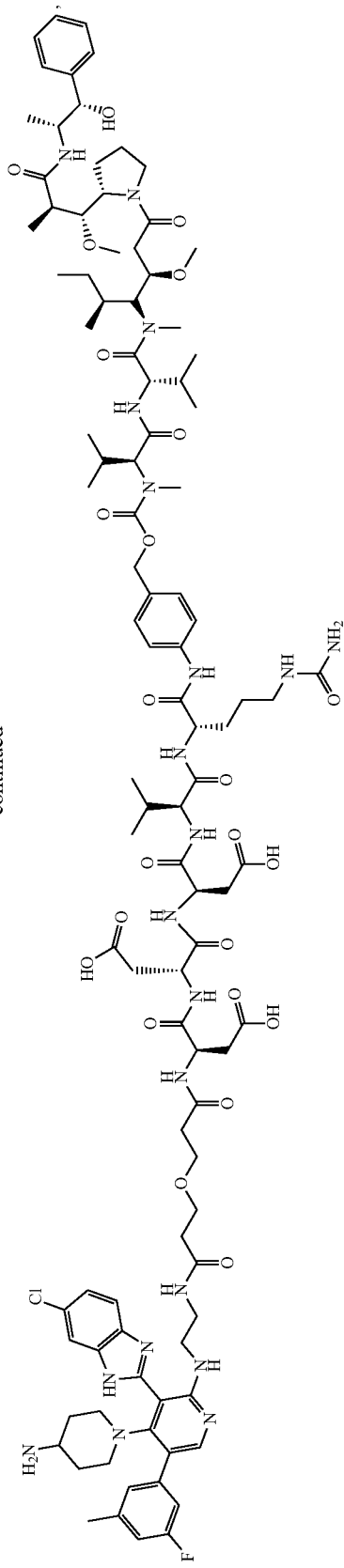
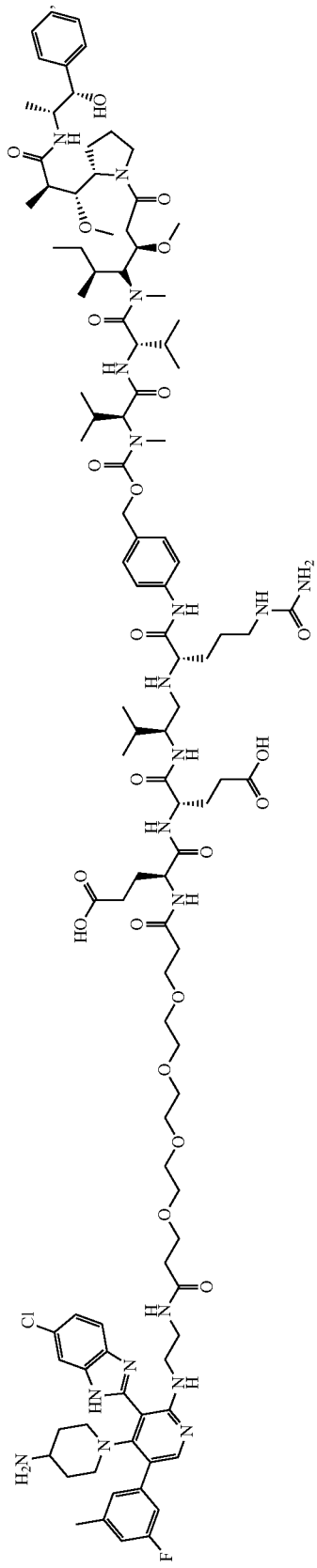

791
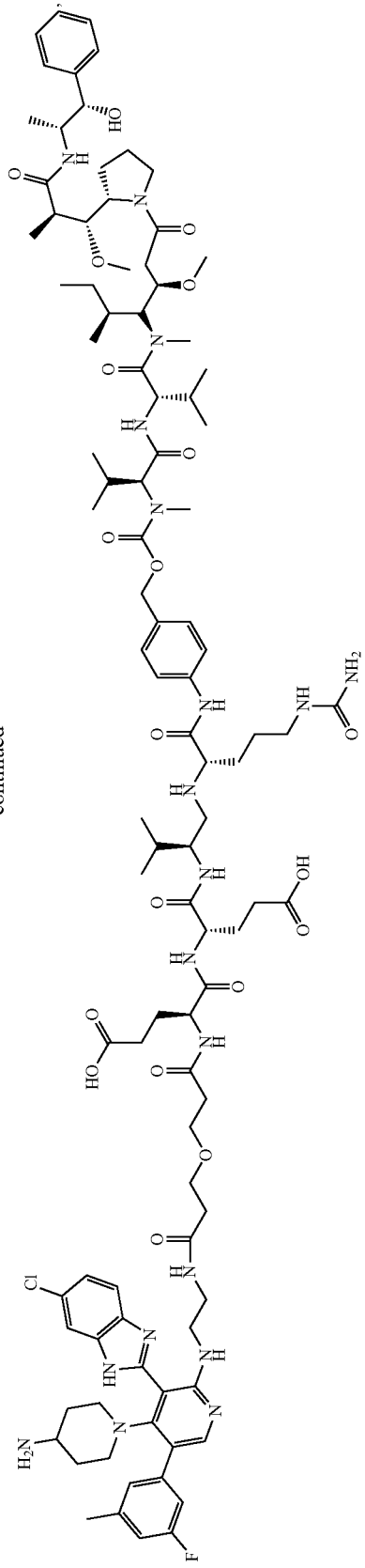
792
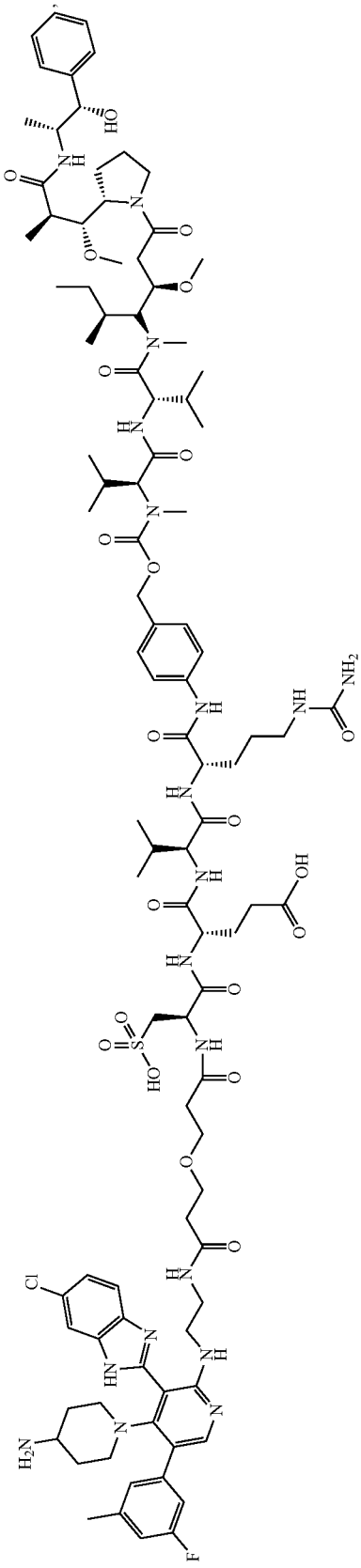

793
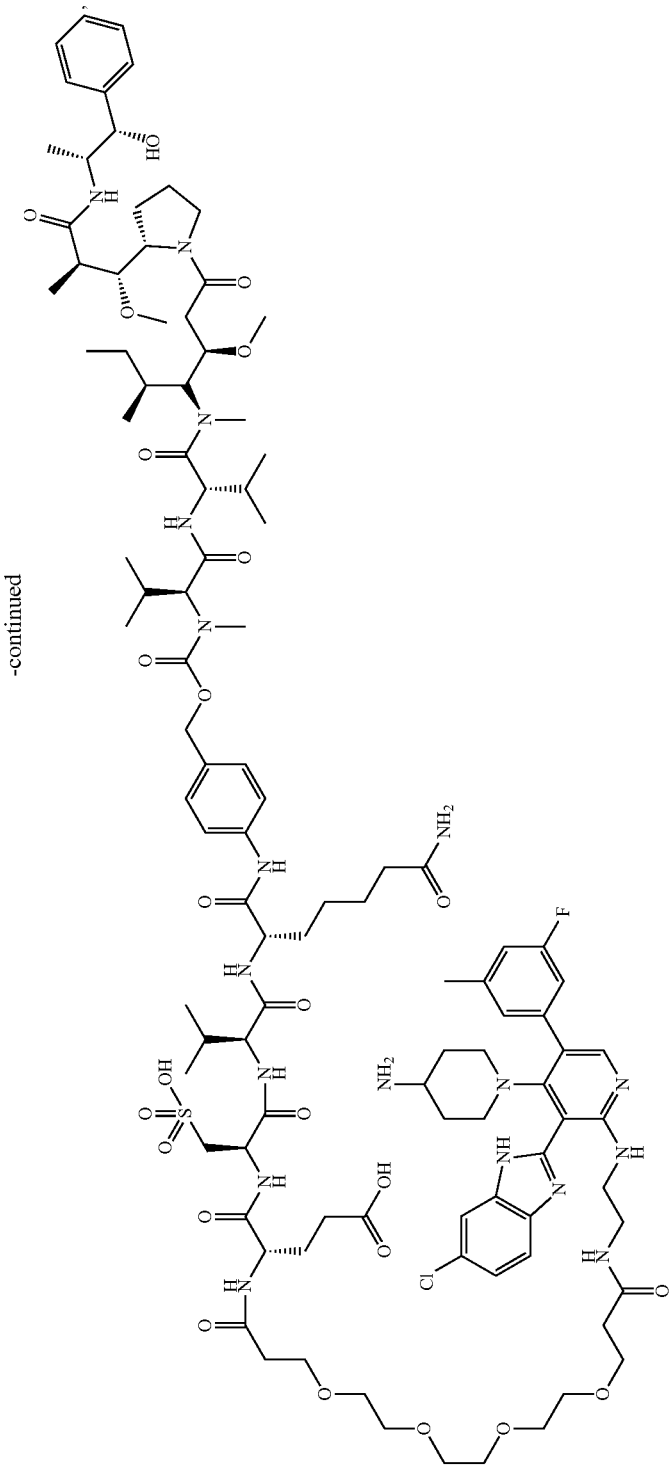
794
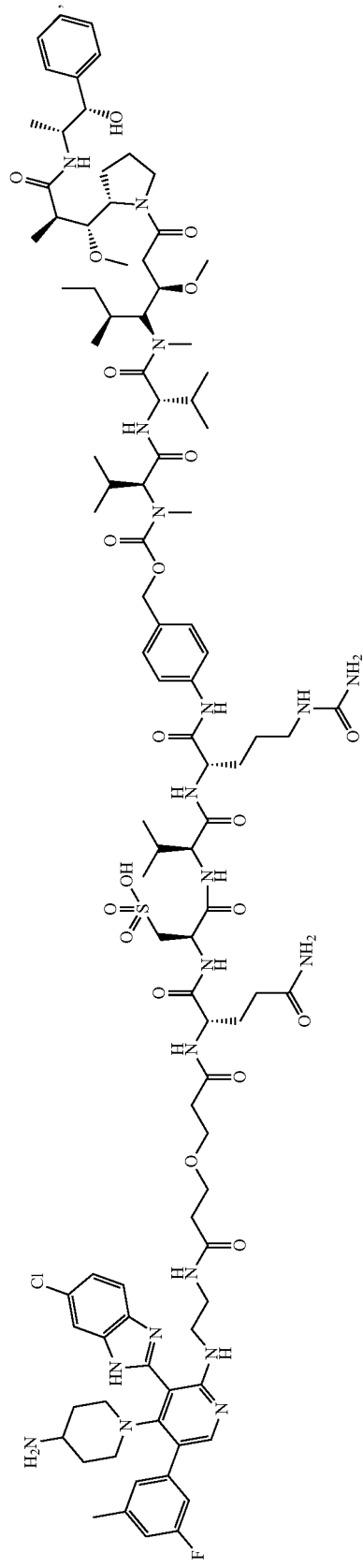

-continued
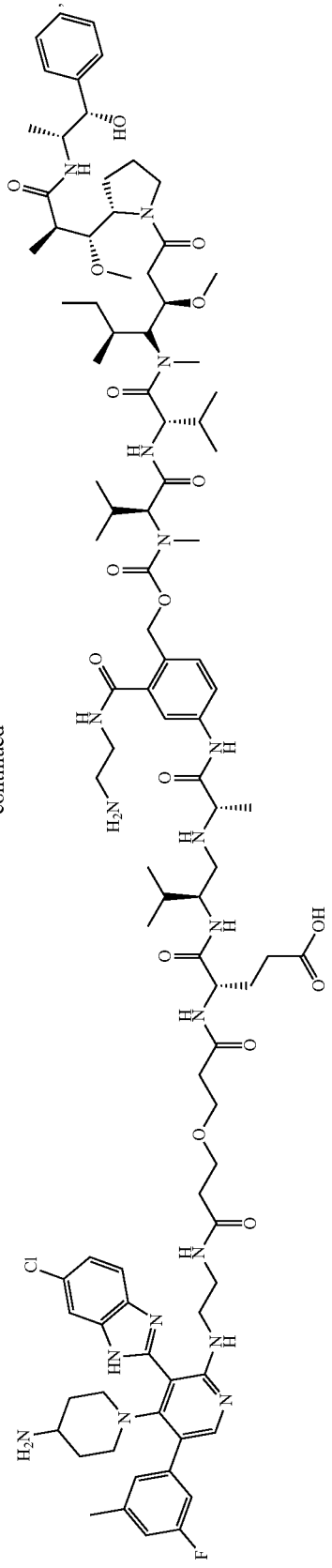
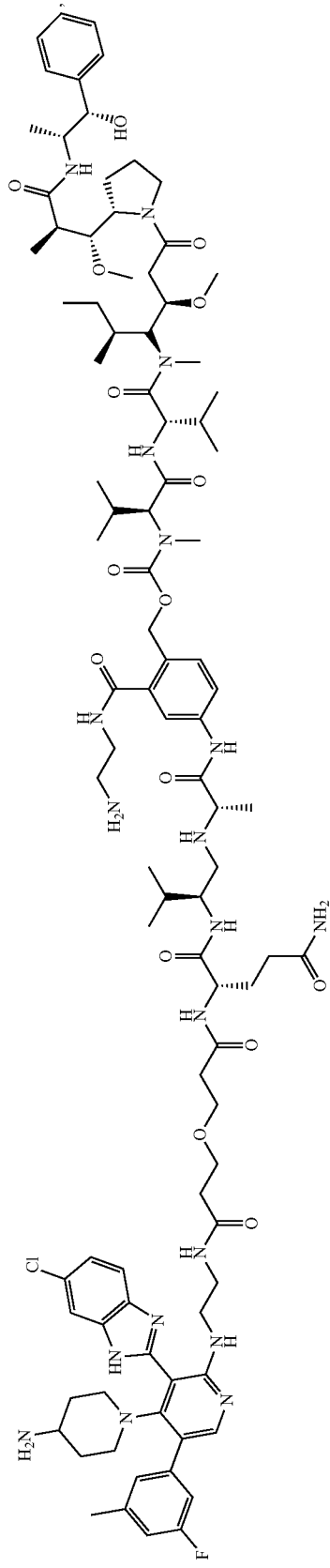

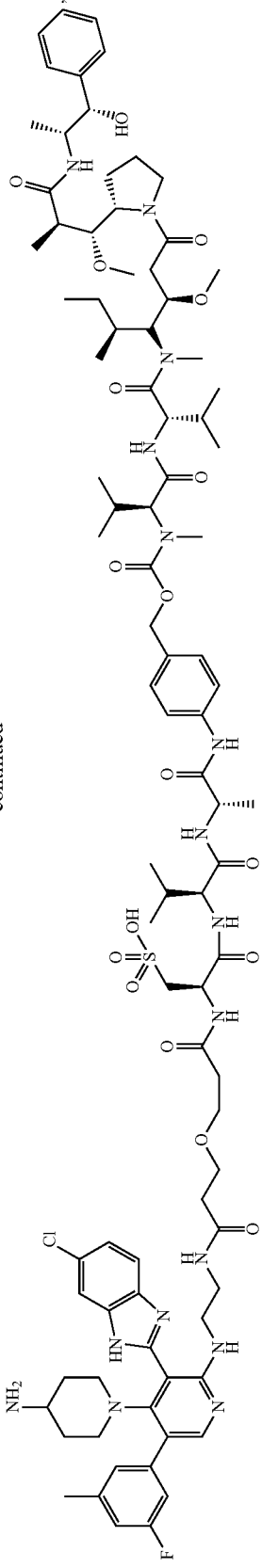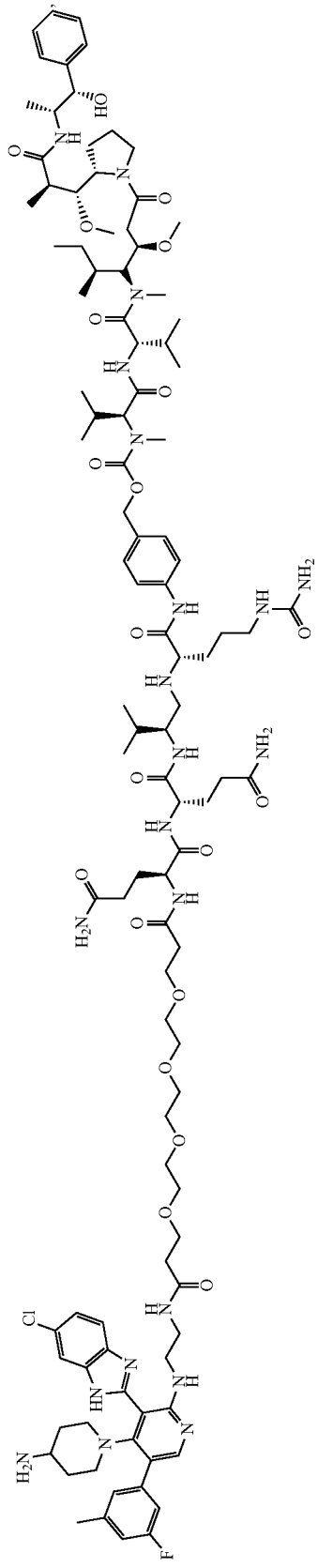

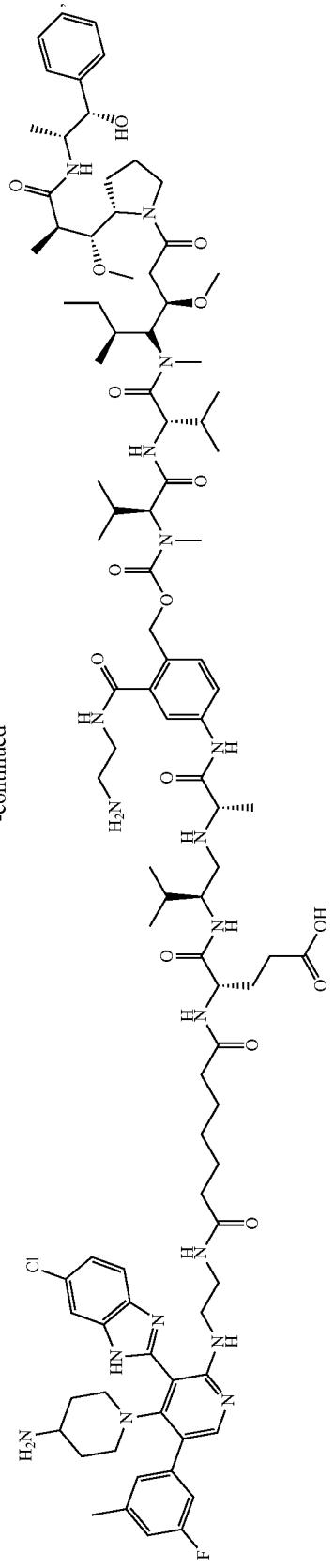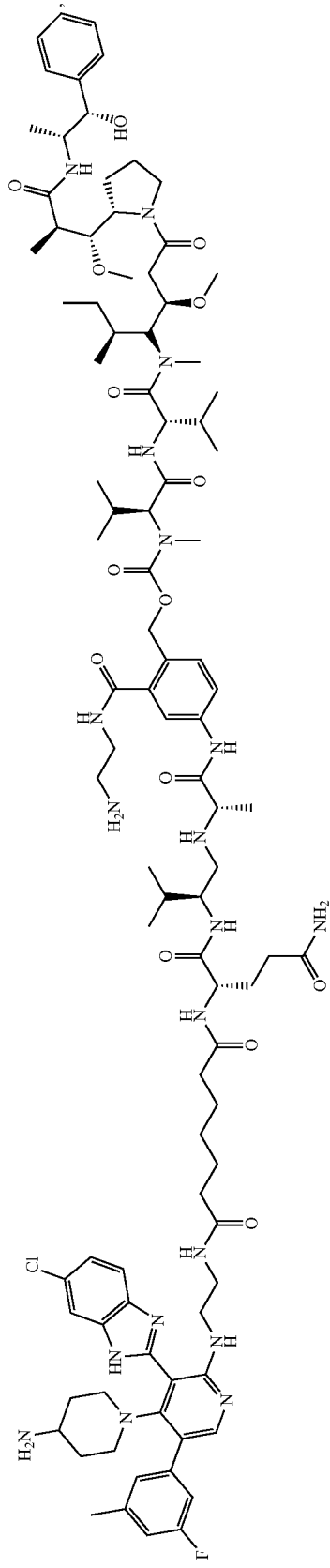

801
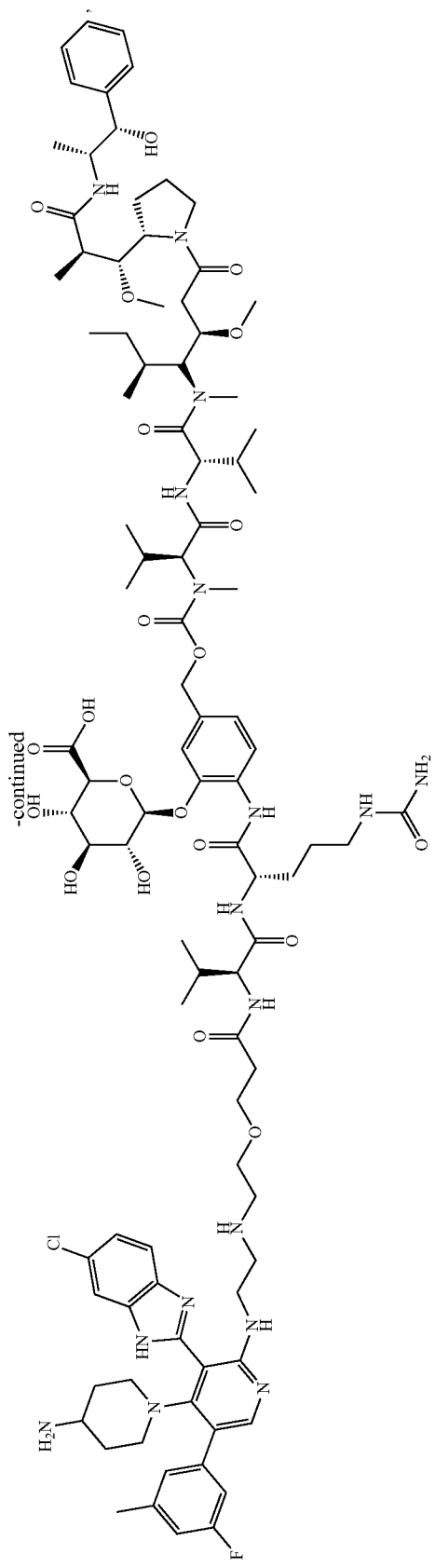
802
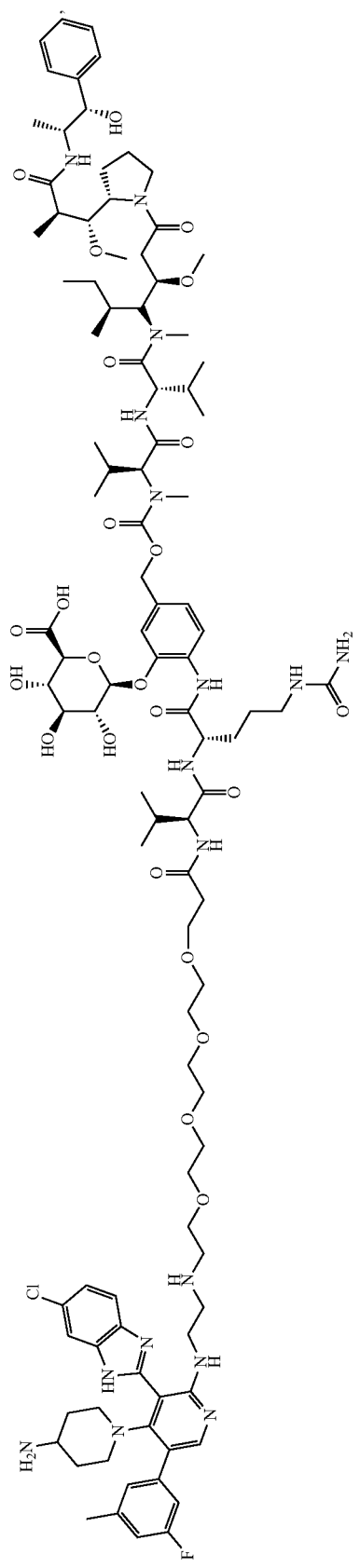

803
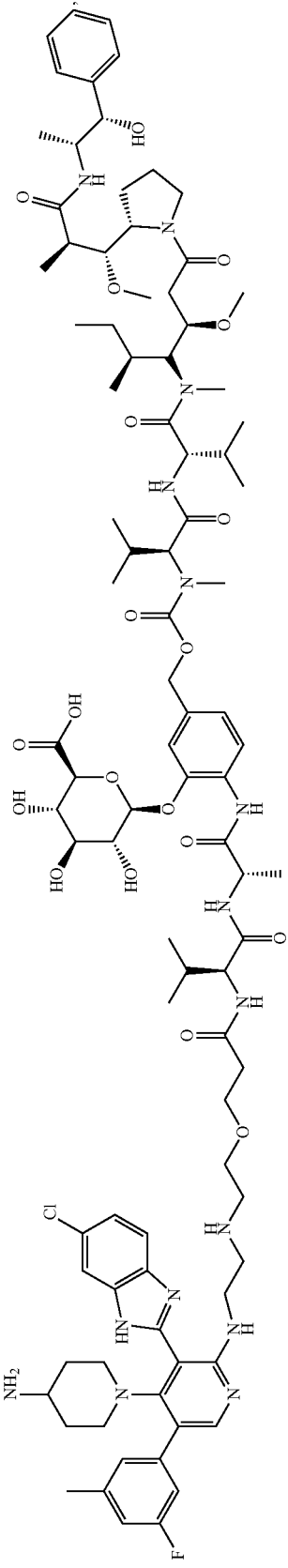
804
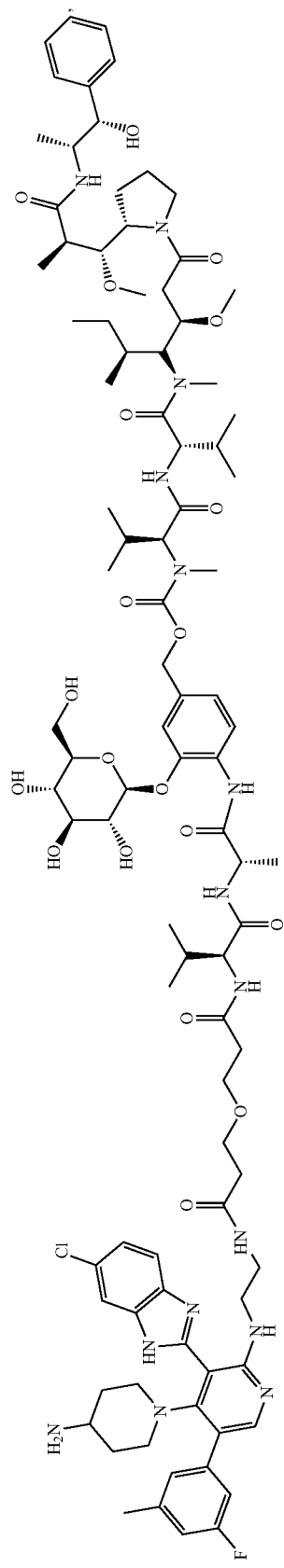

805
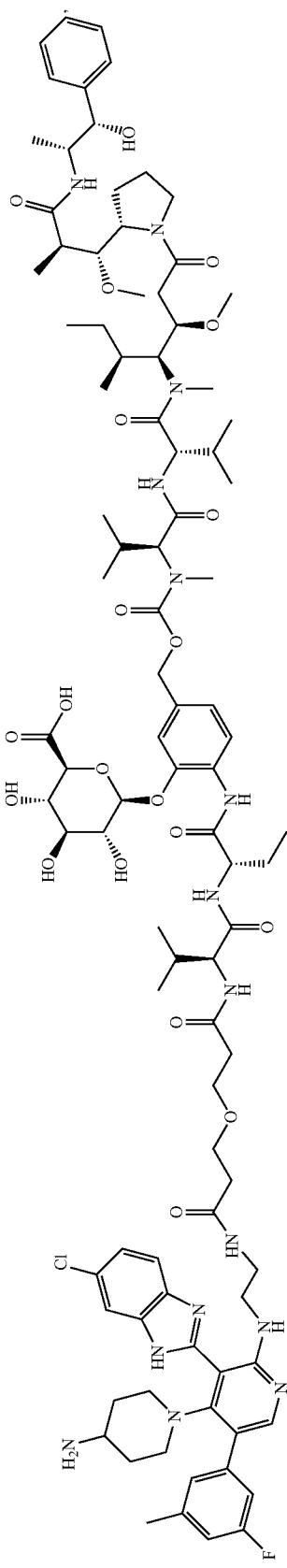
806
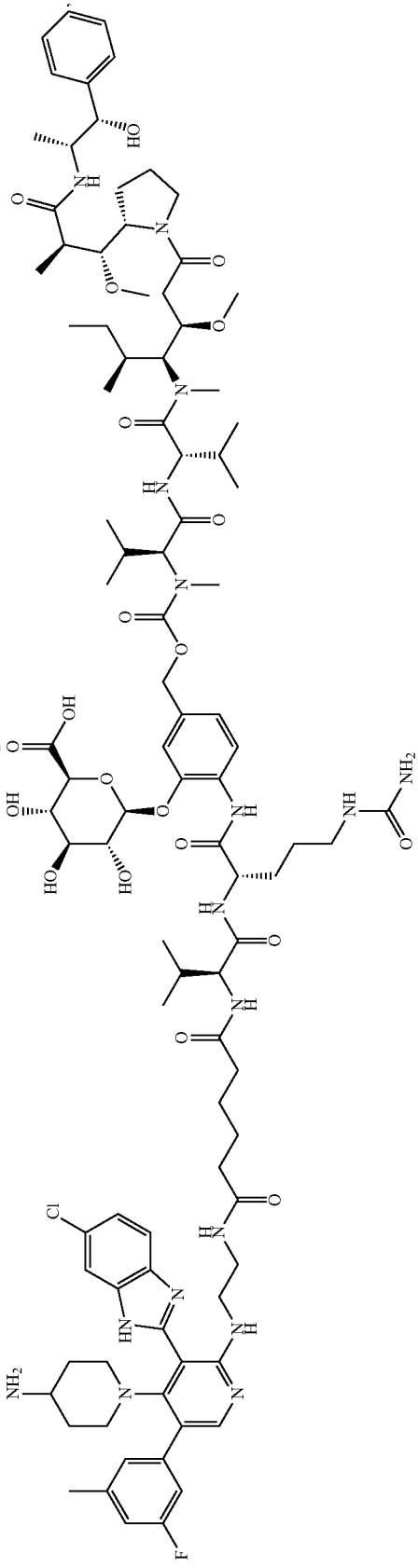

807
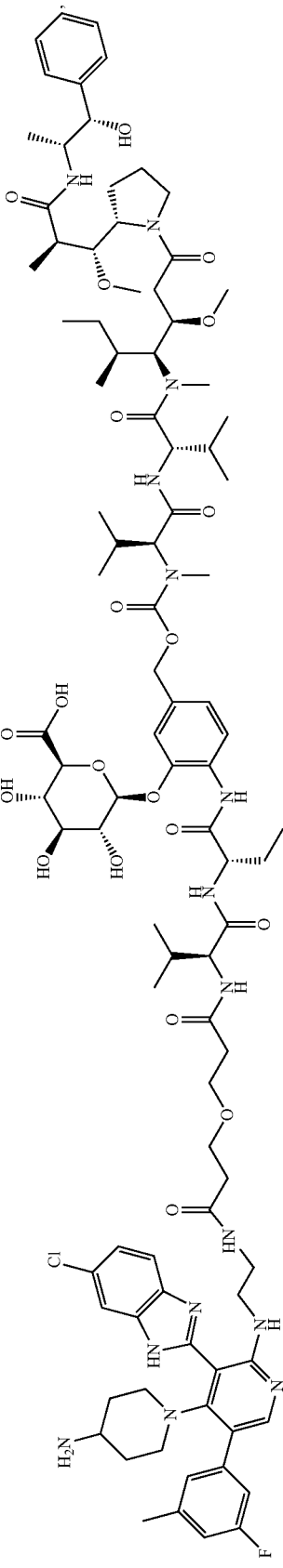
808
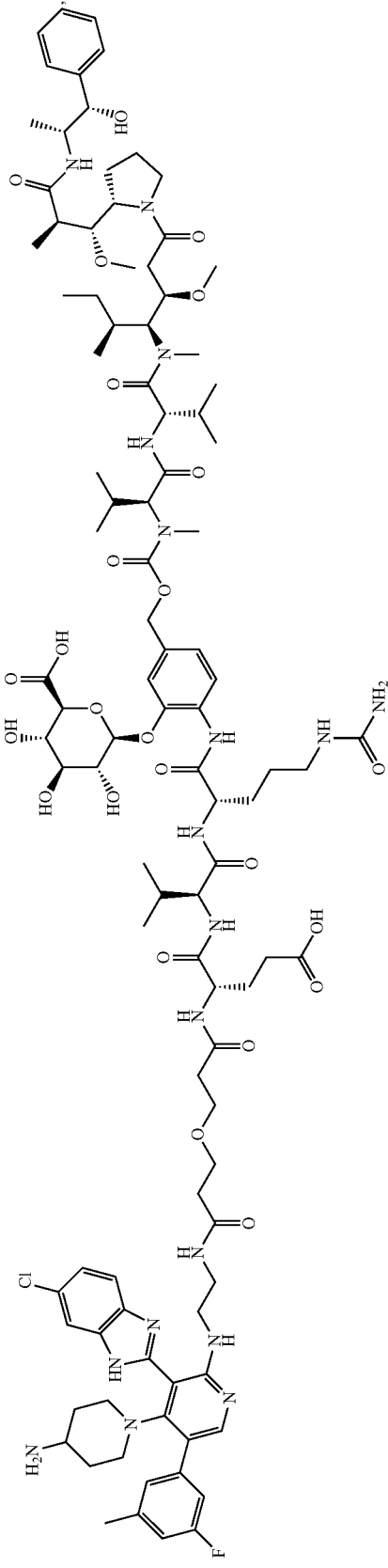

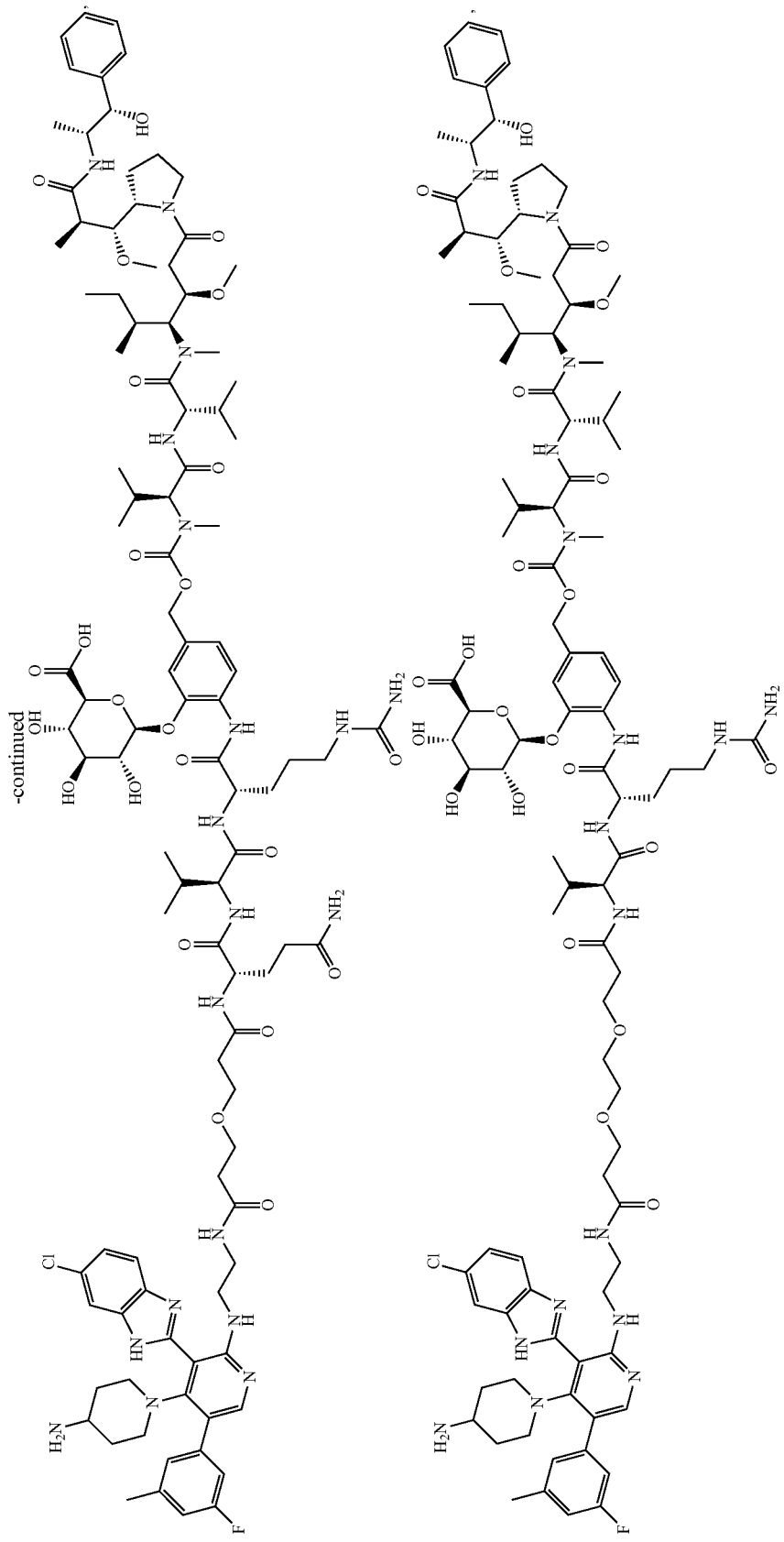

811 812
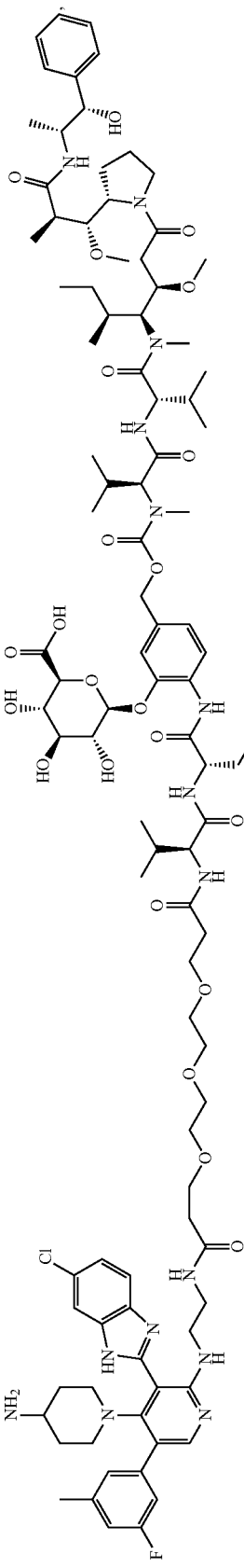
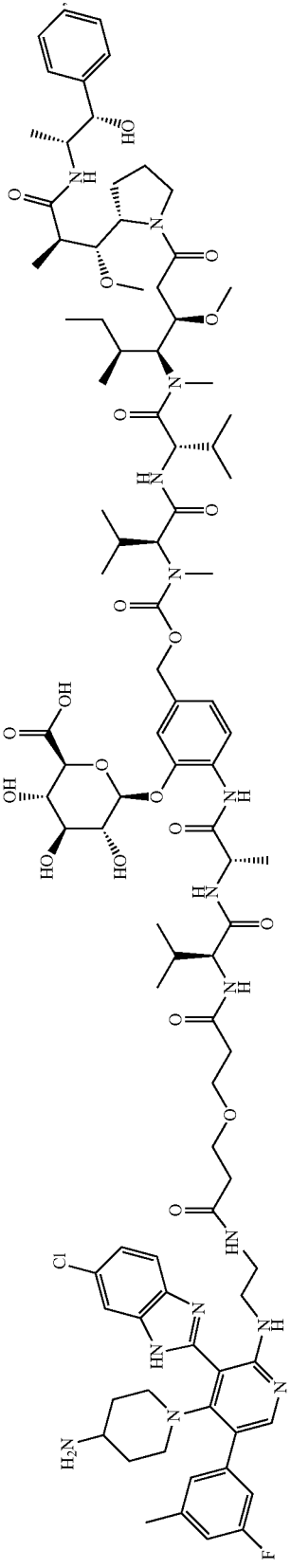
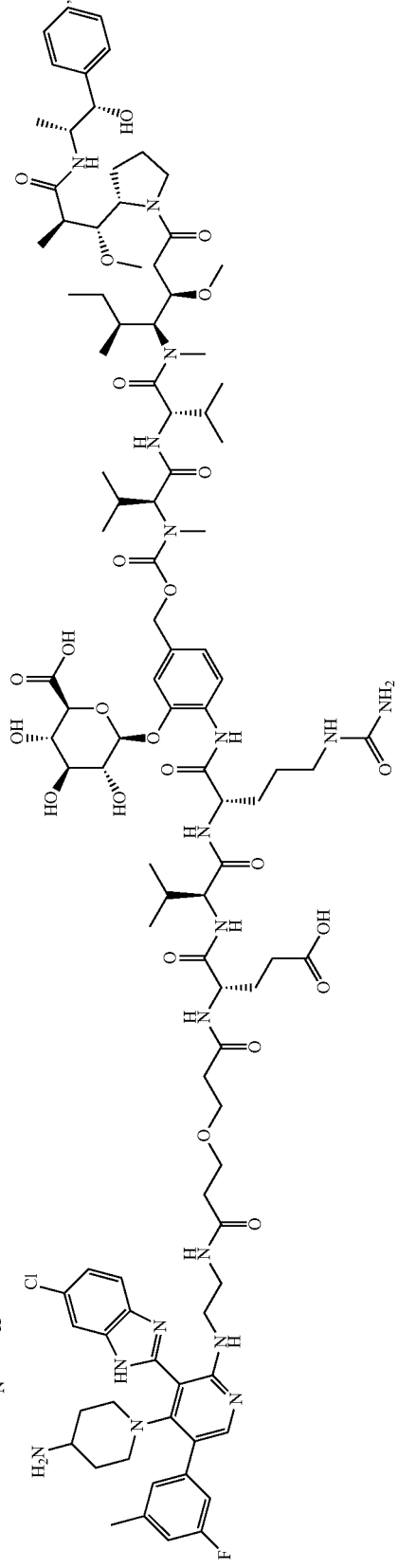

813
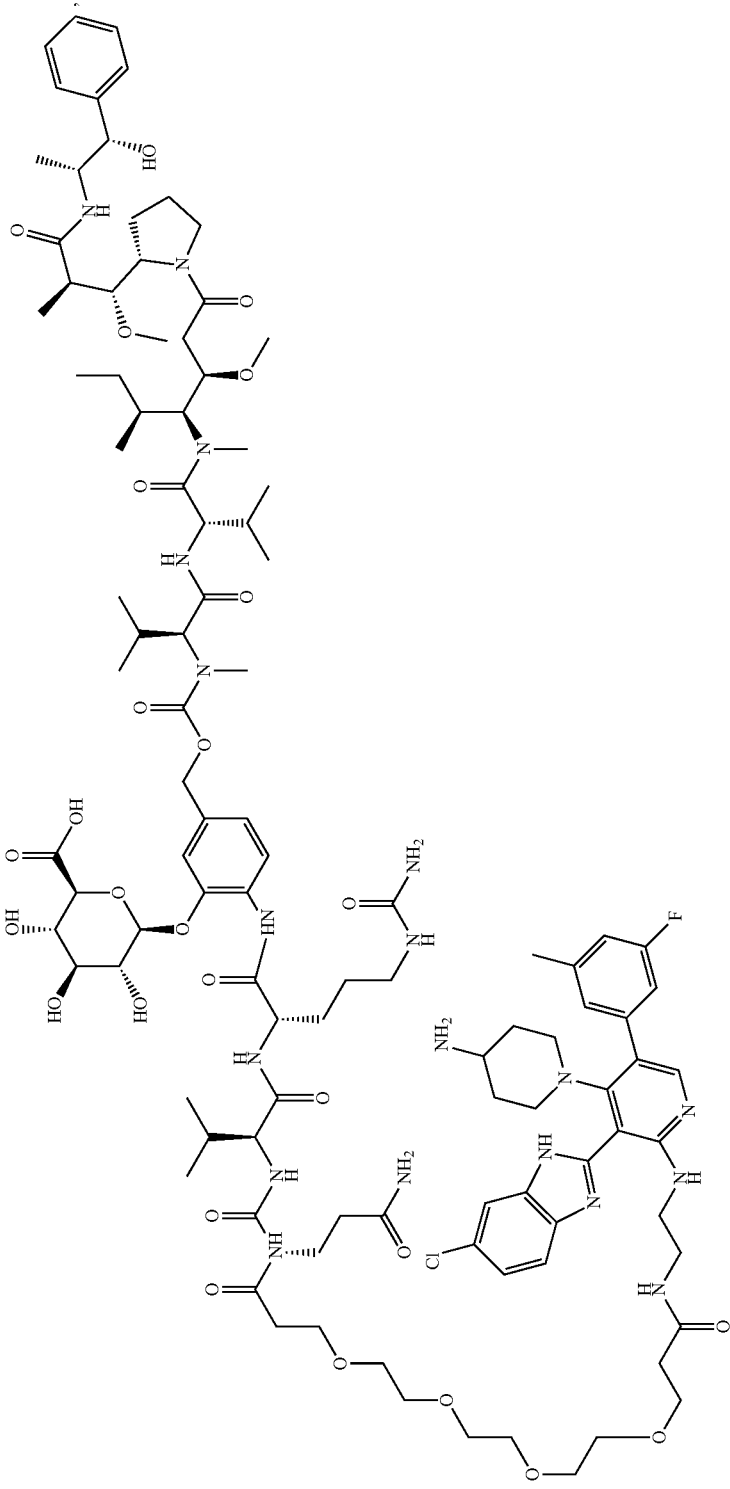
814
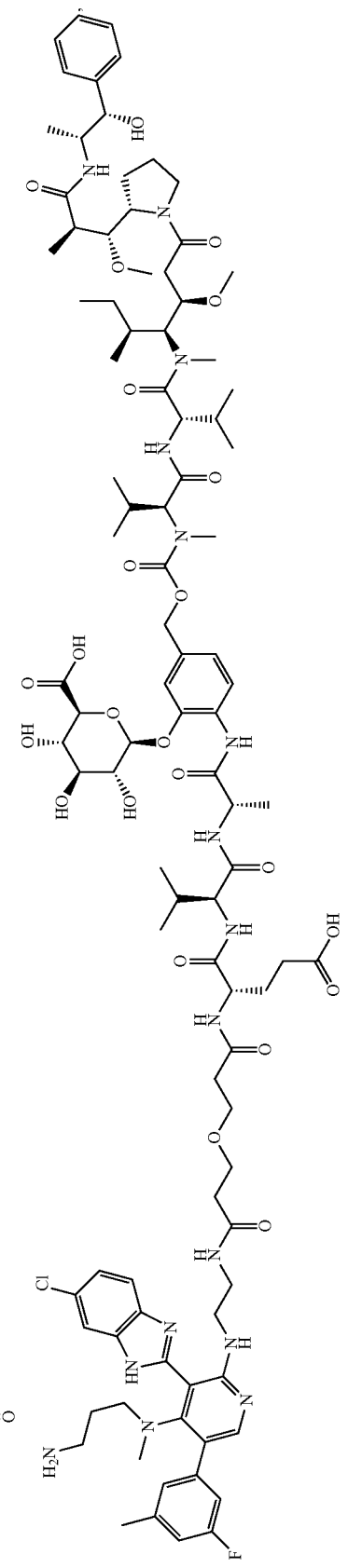

815
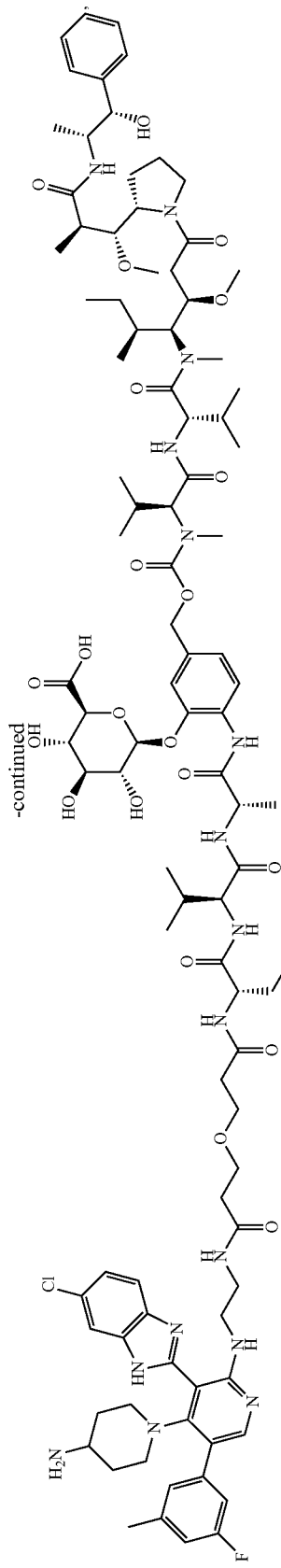
816
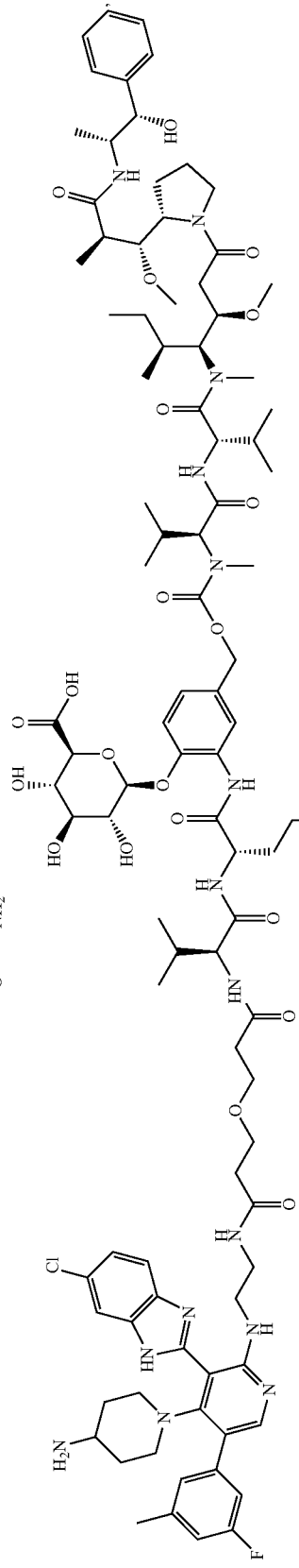
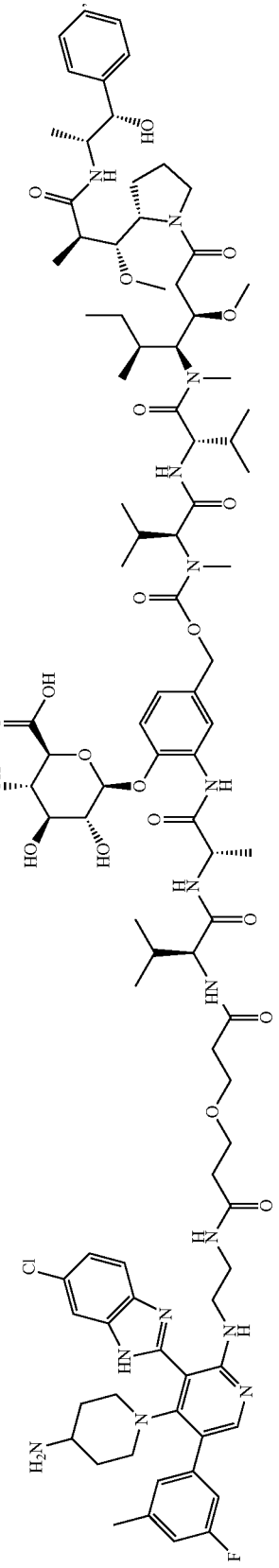

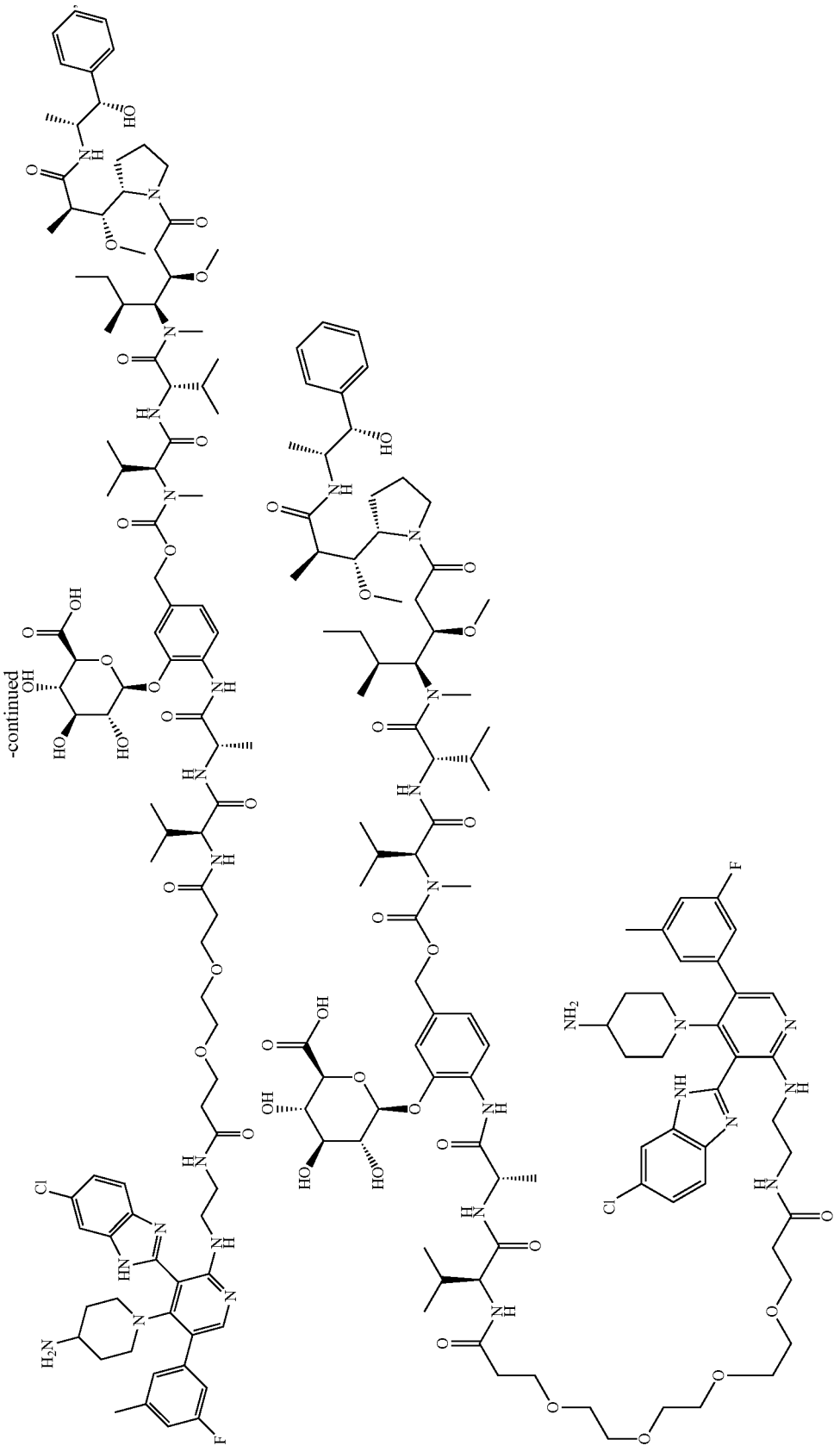

819 820
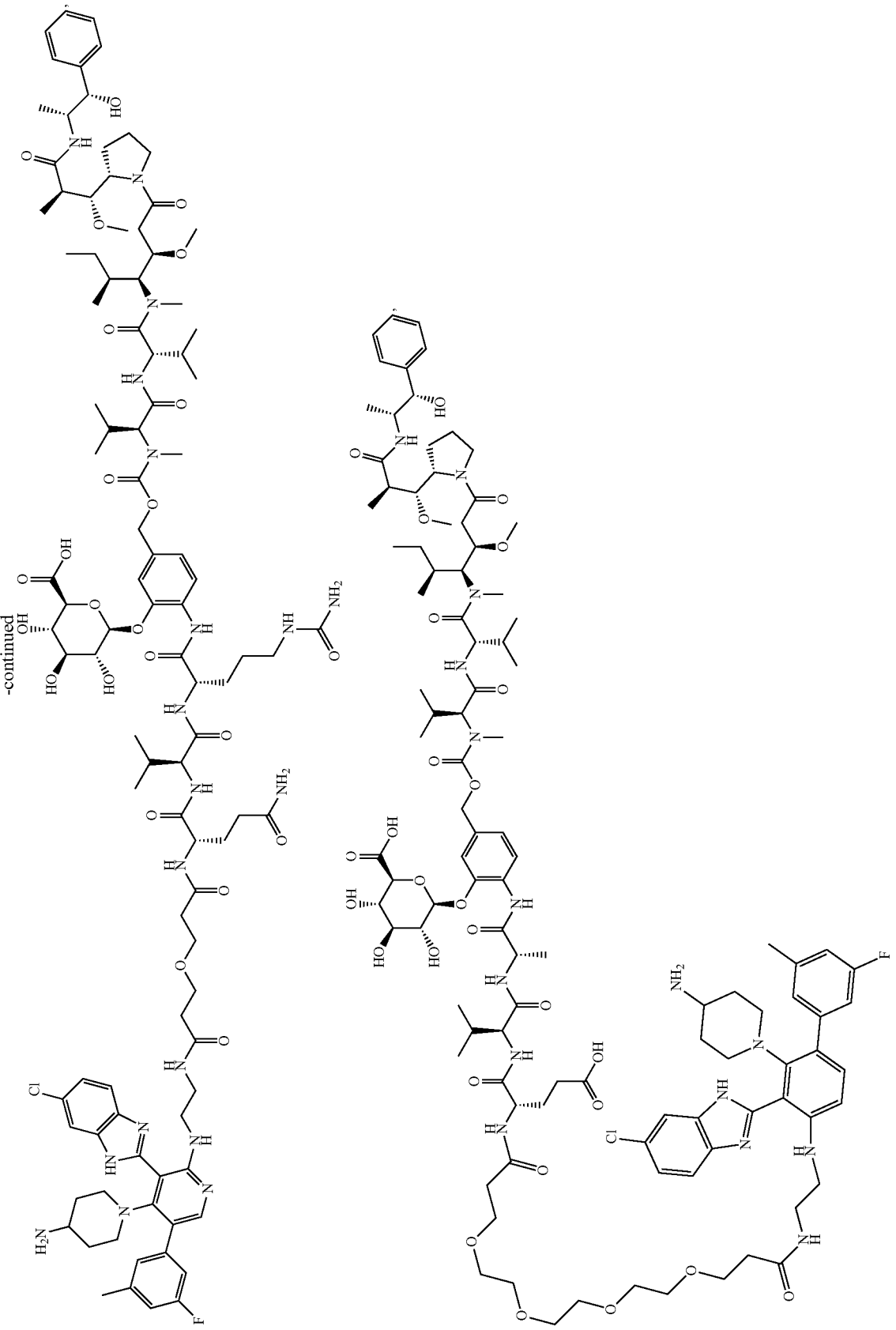

-continued
821
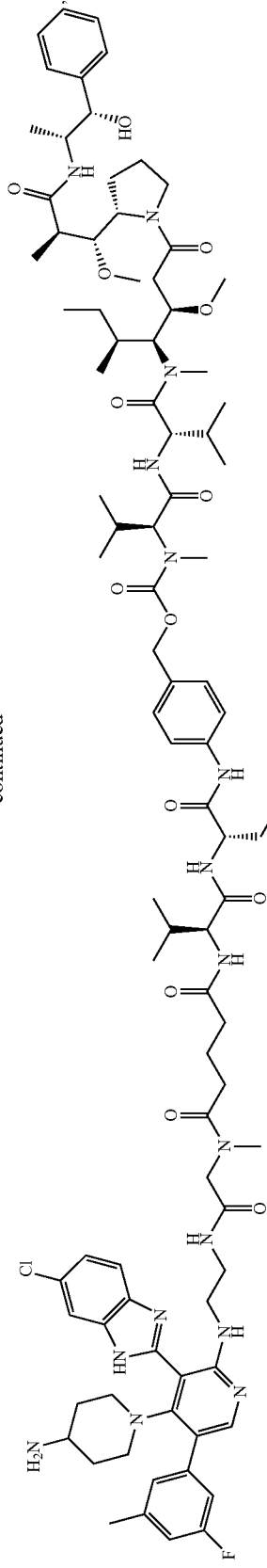
822
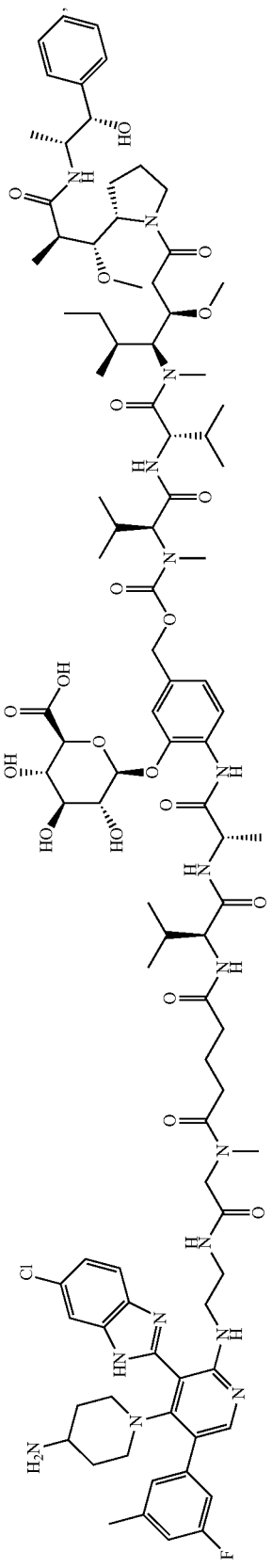
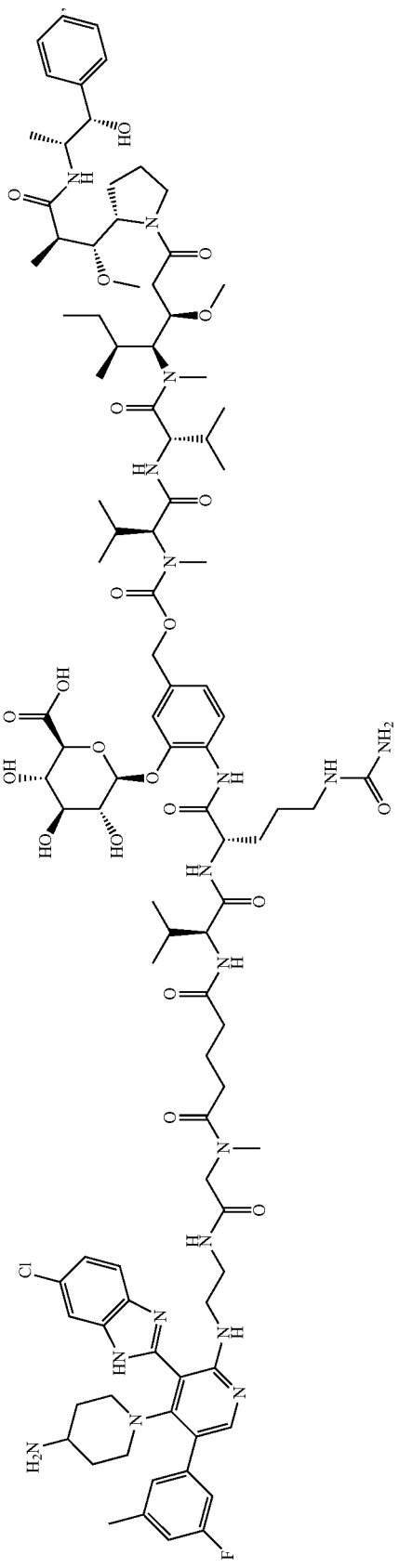

823
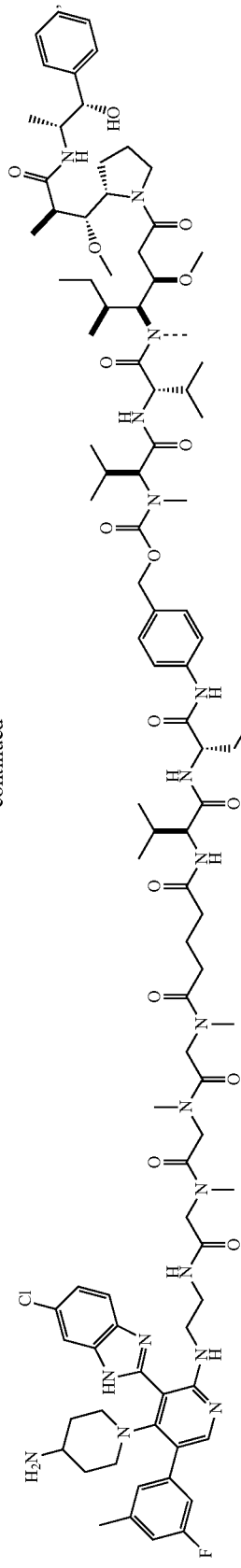
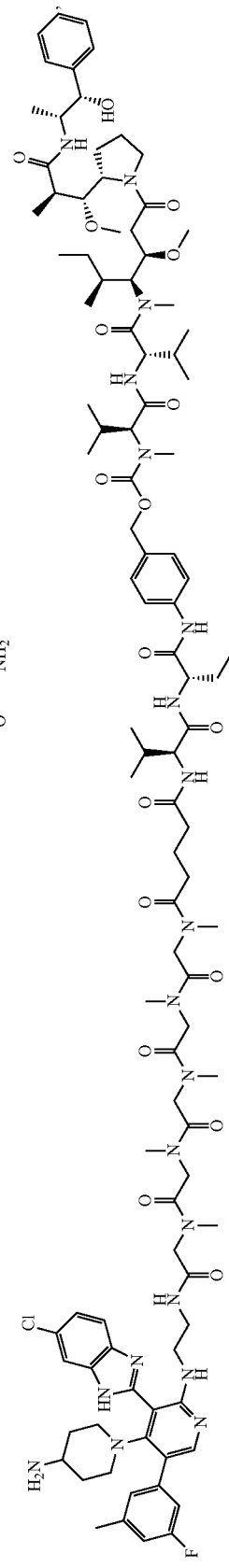
824
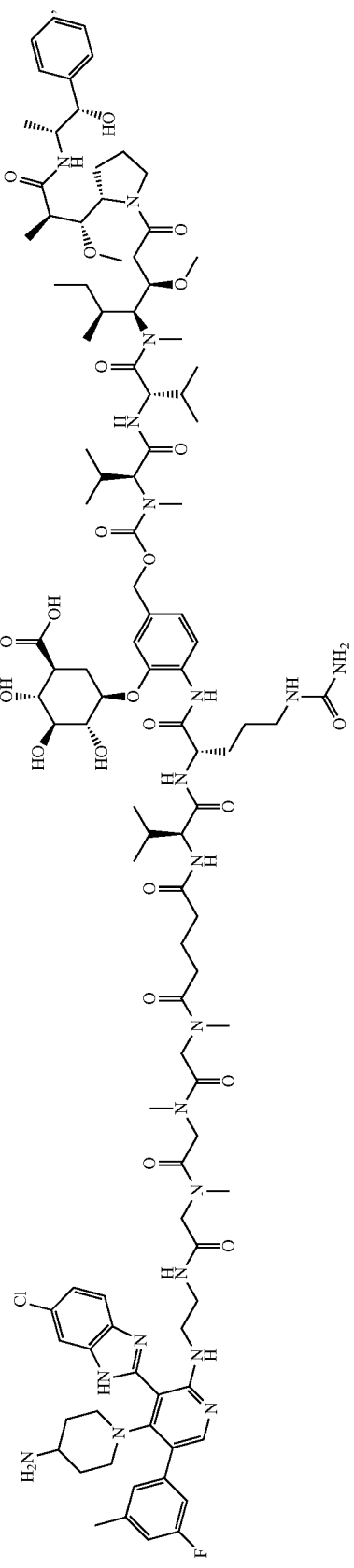

-continued
825
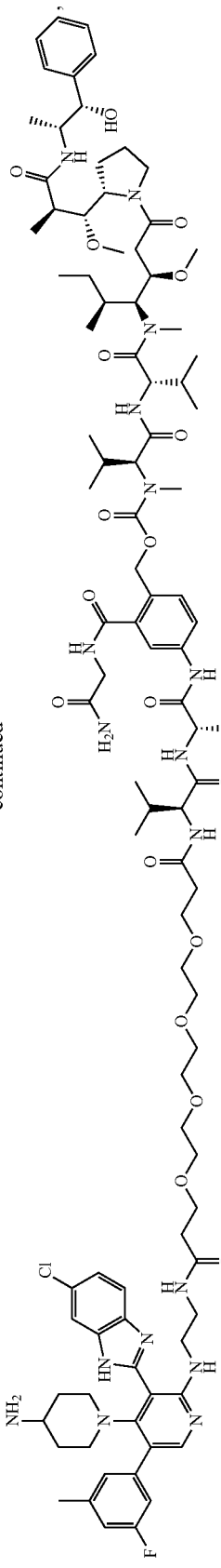
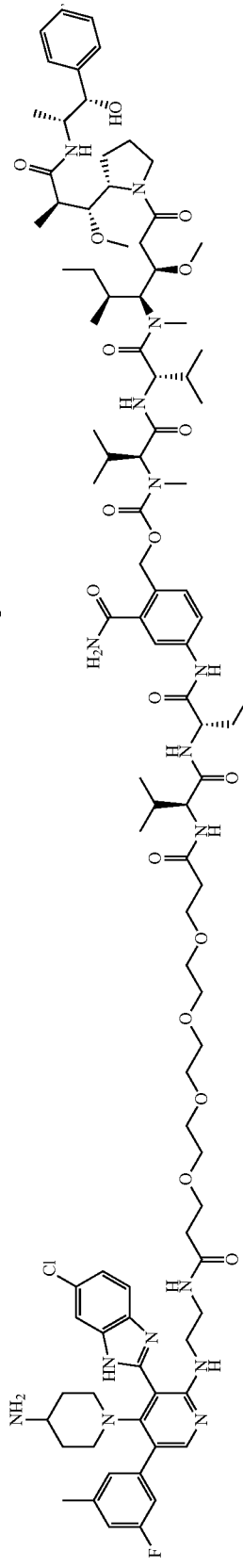
826
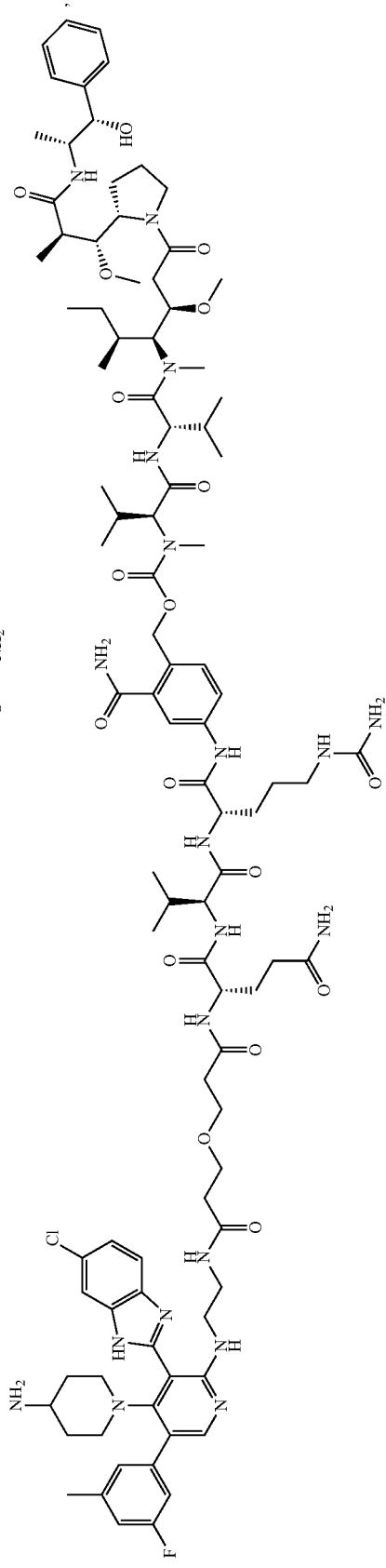

827
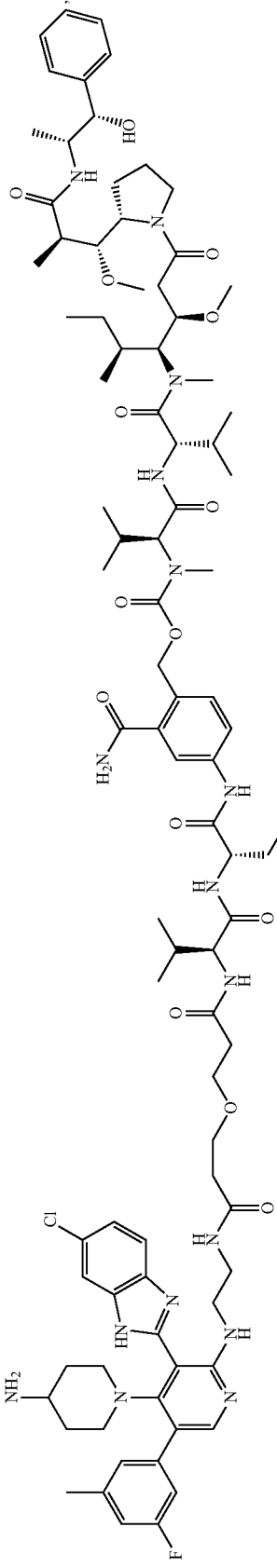
828
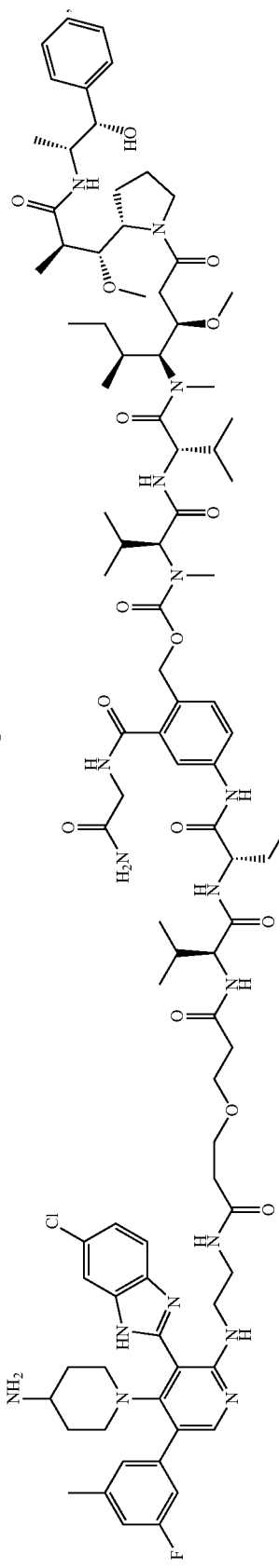

829 830
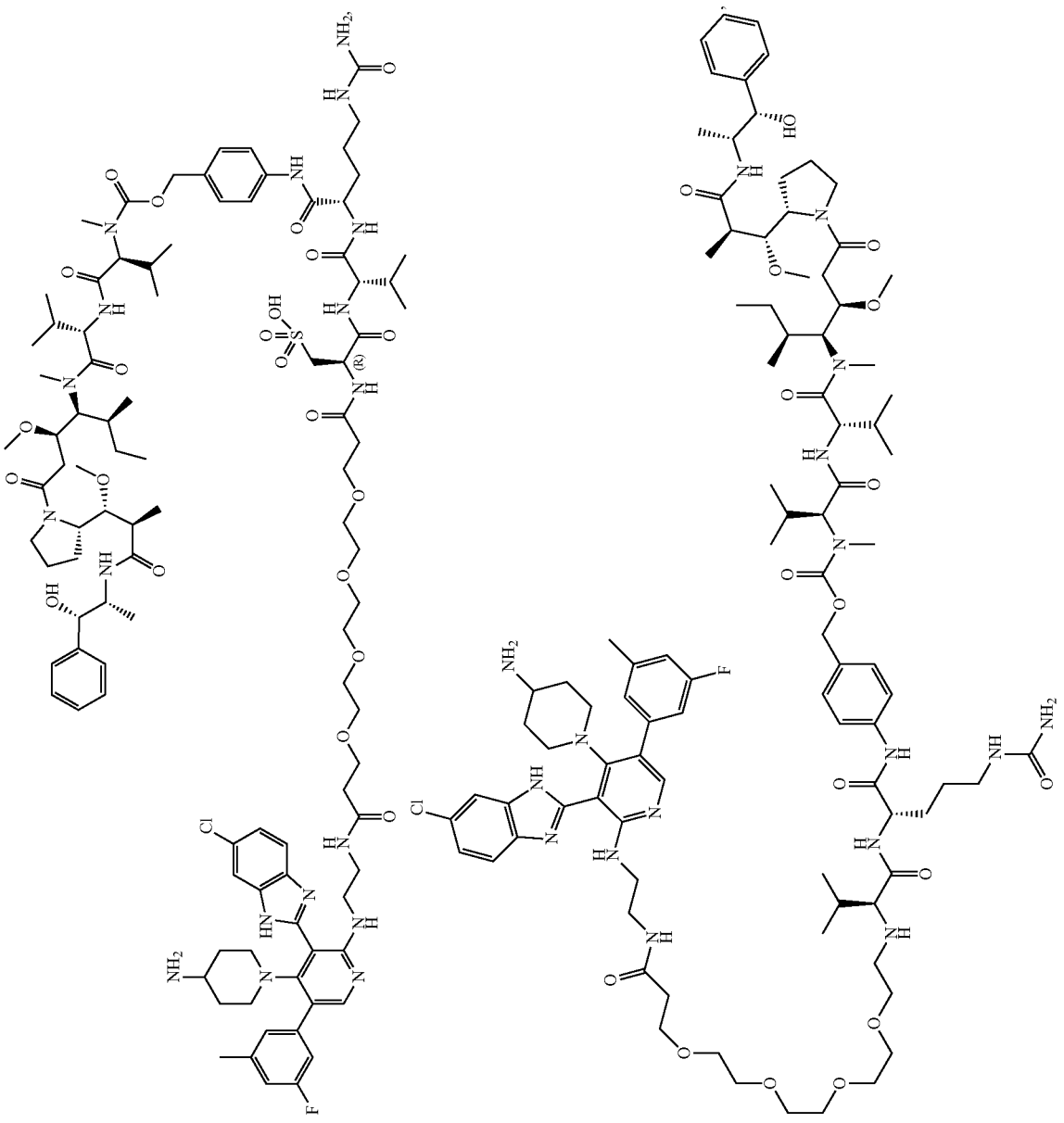
-continued

831
-continued
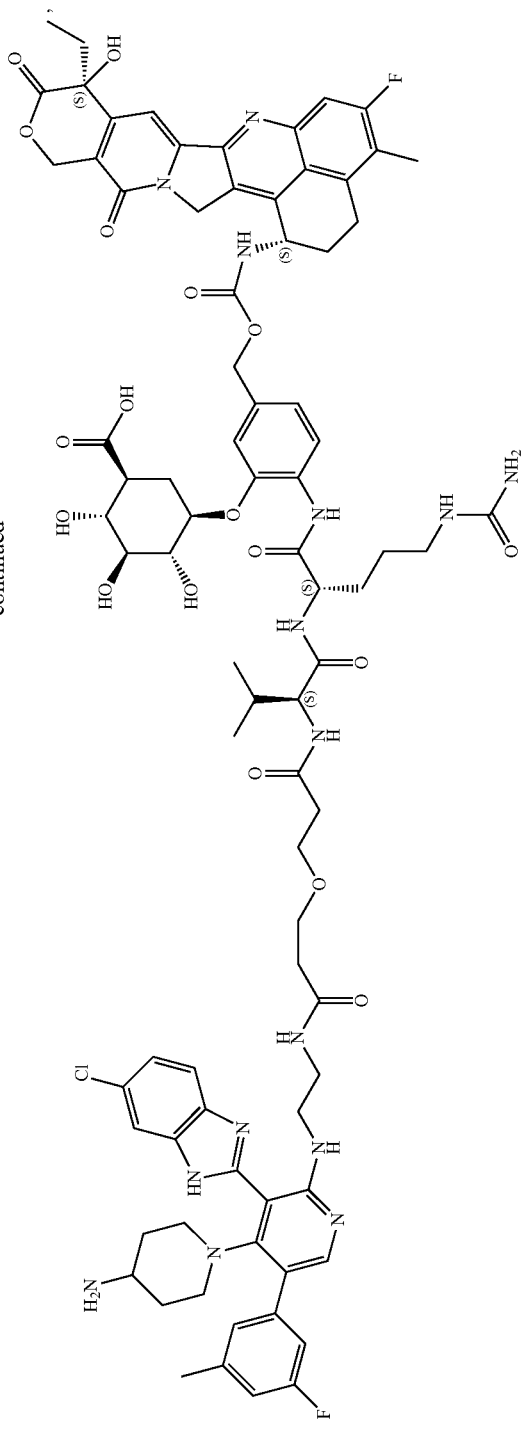
832
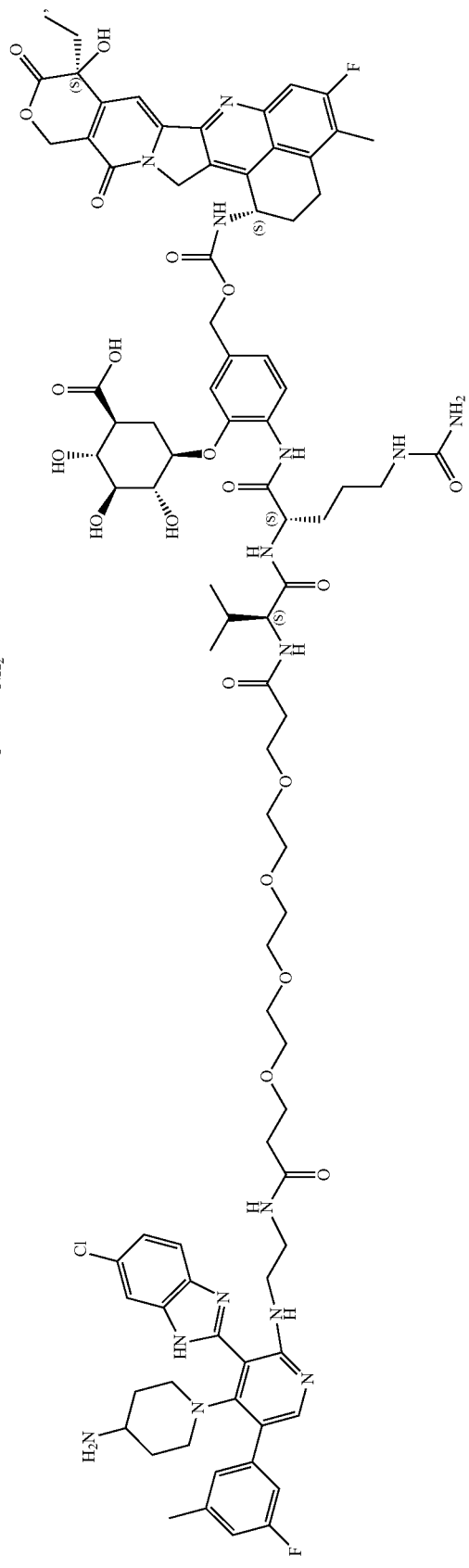

833 834
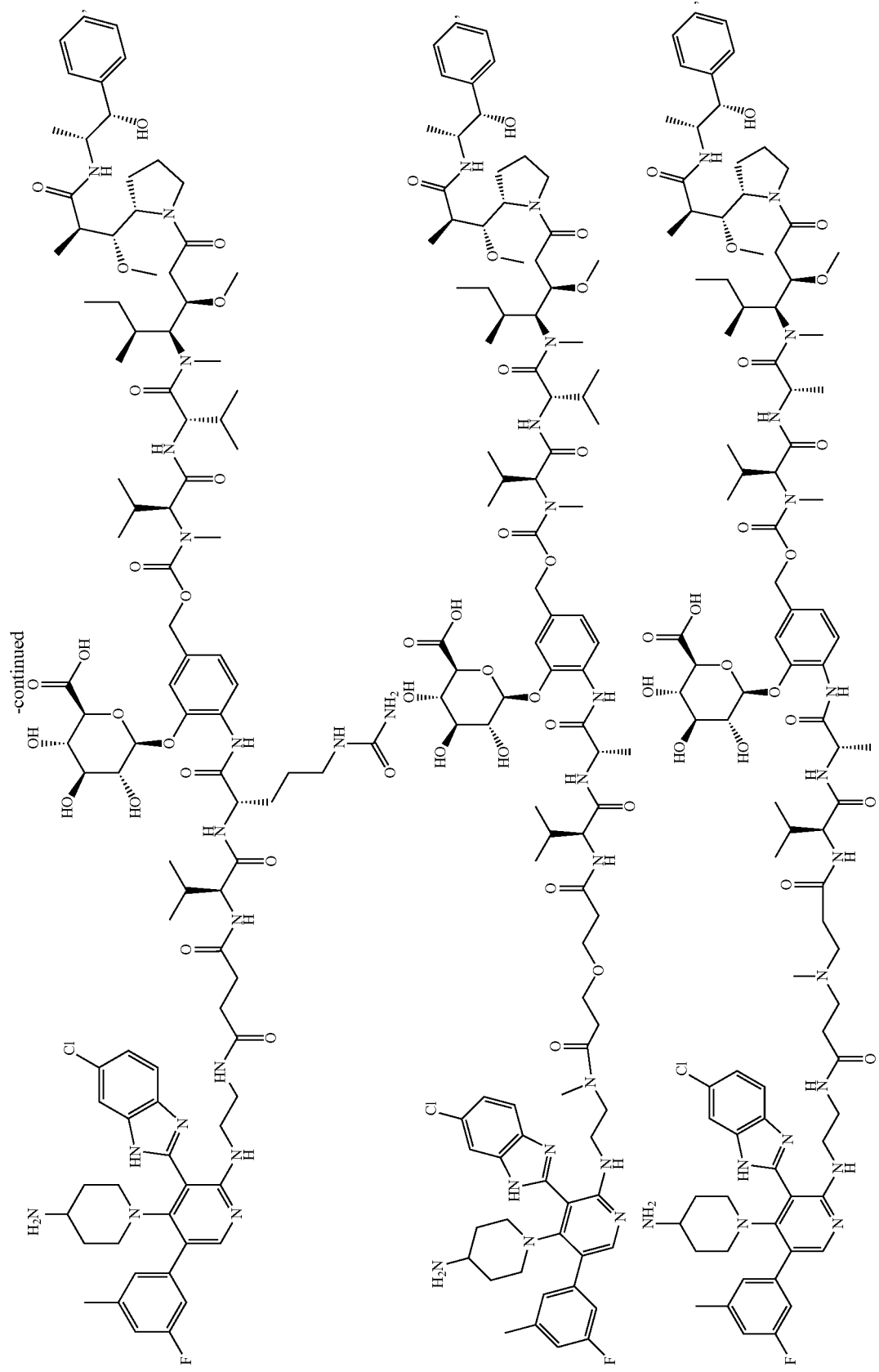

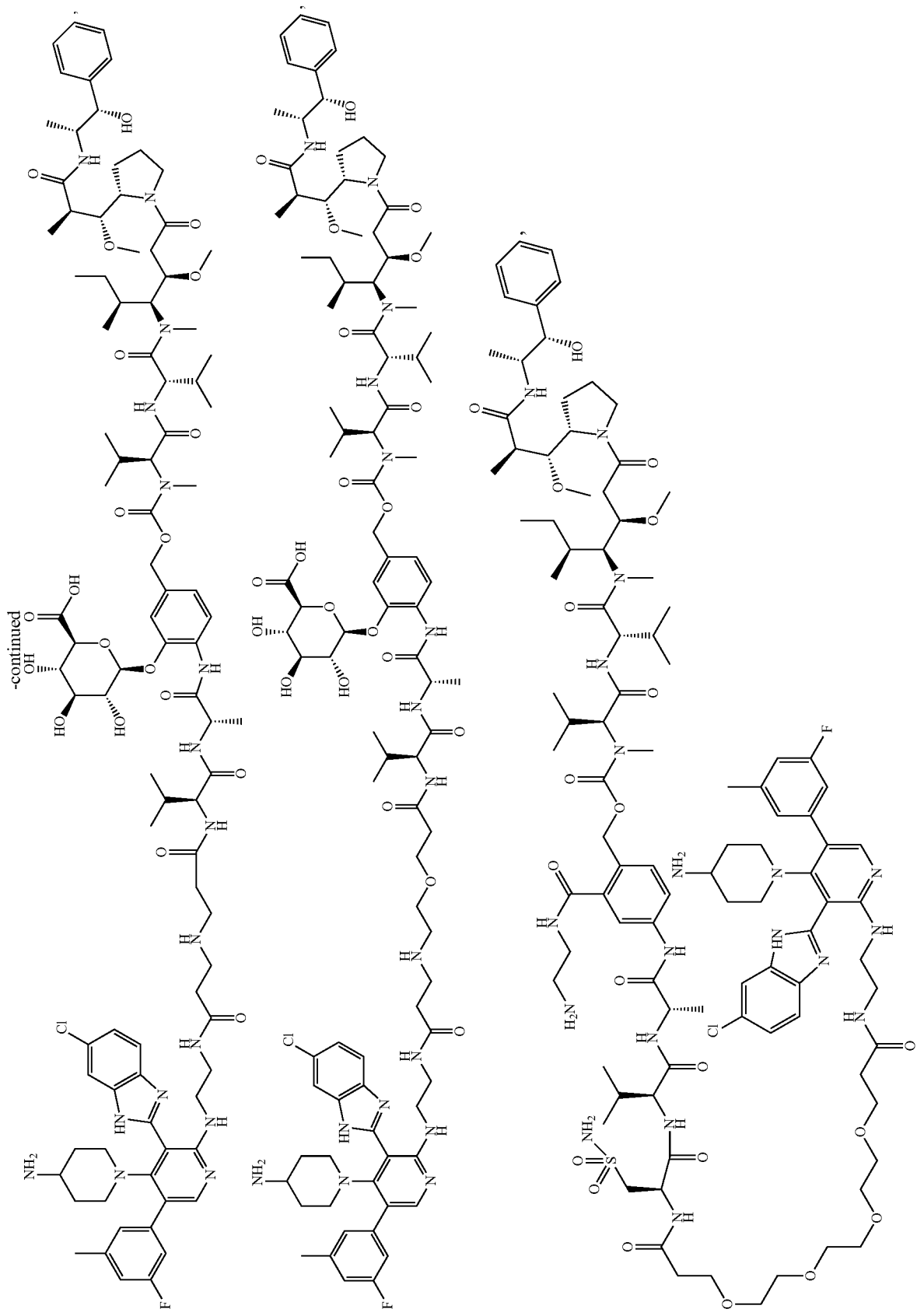

-continued
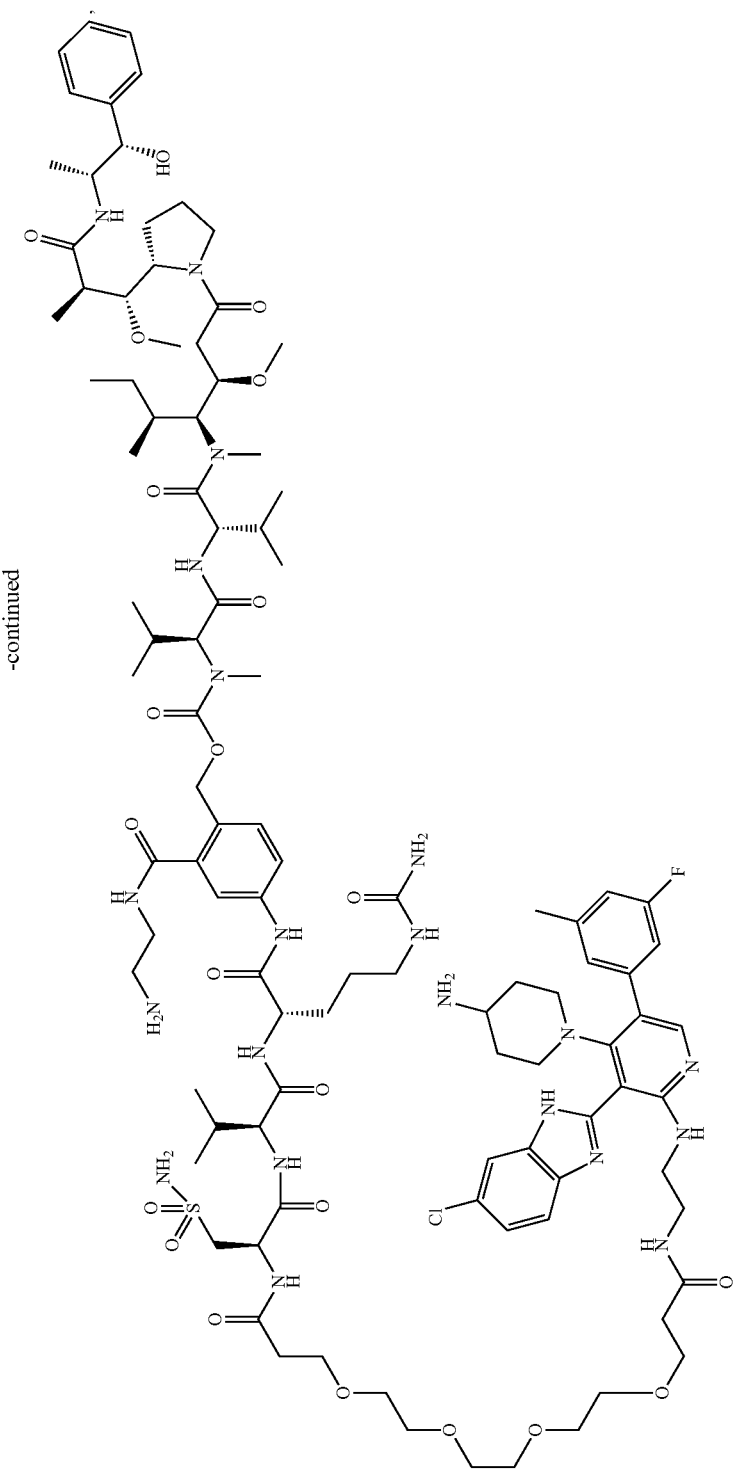
and

-continued
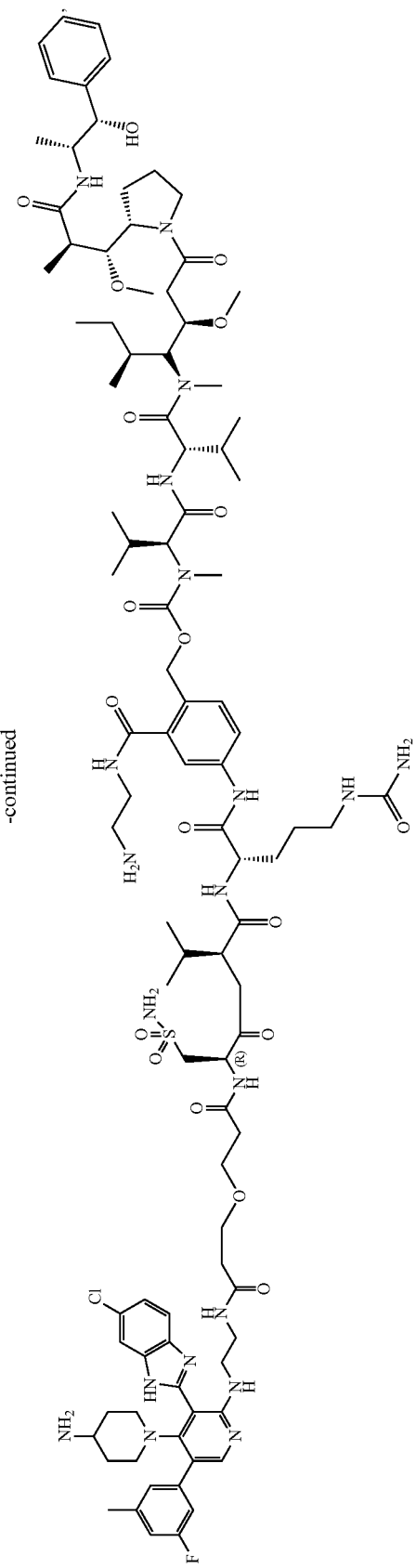

or a pharmaceutically acceptable salt thereof.

20. A compound, or pharmaceutically acceptable salt thereof, selected from the group consisting of:

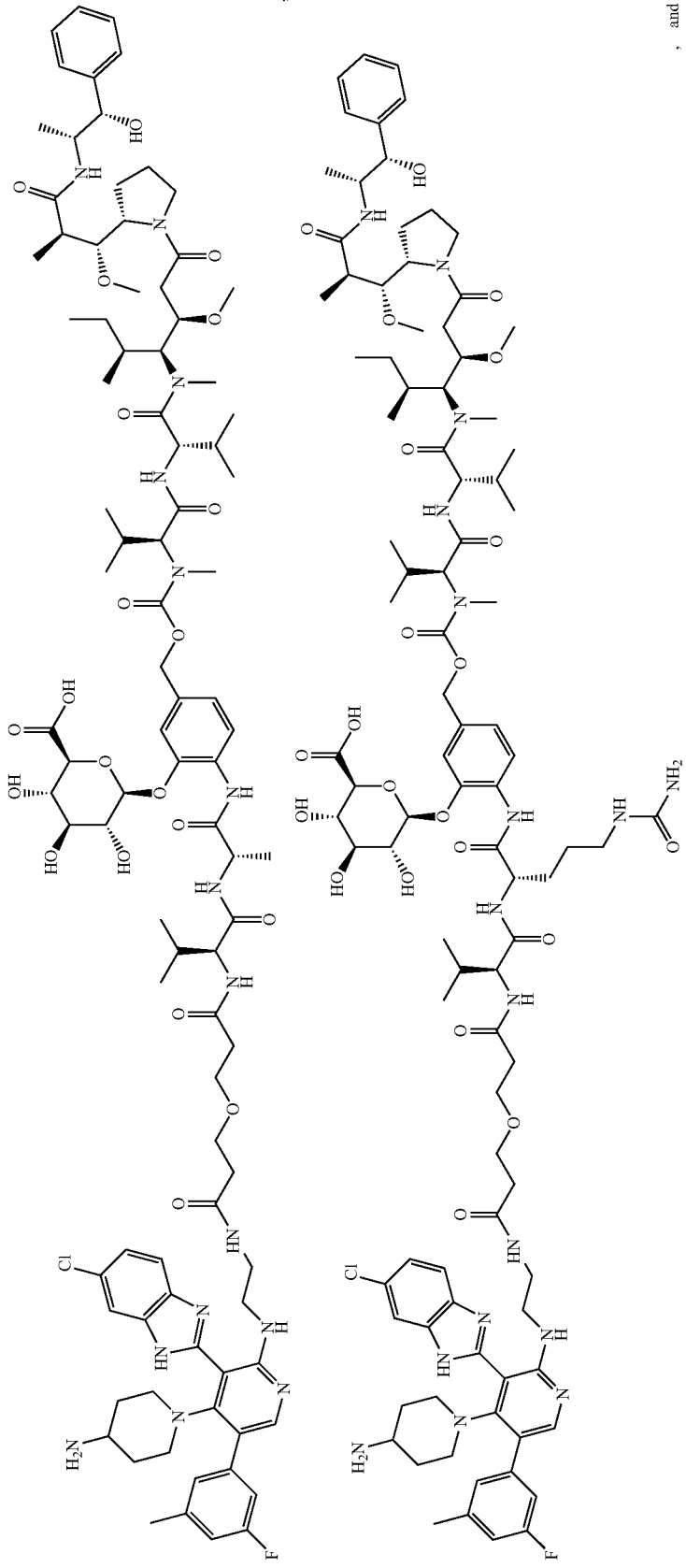
, and

-continued
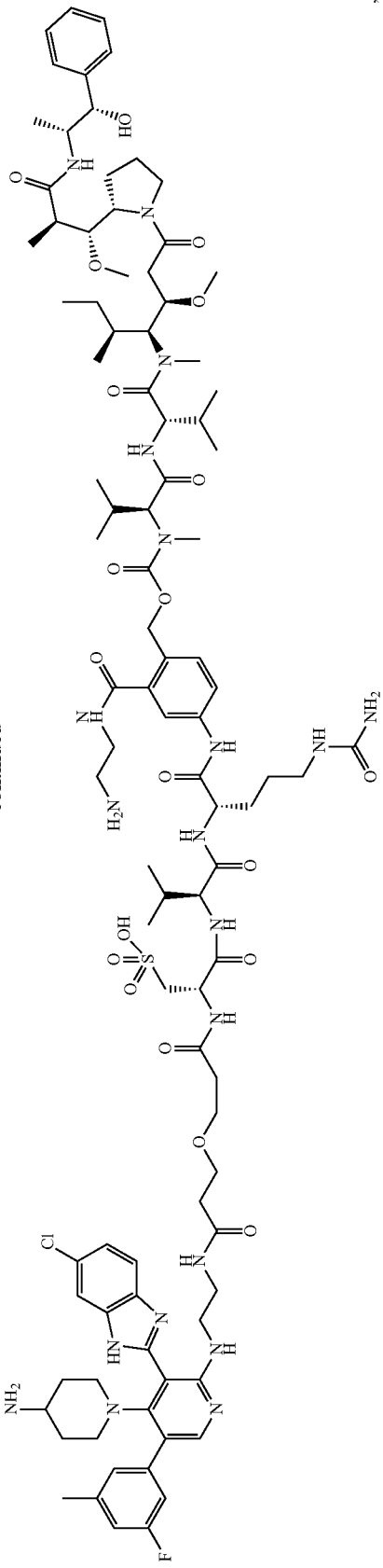

or a pharmaceutically acceptable salt thereof.

21. The compound of claim 20, wherein the compound is:

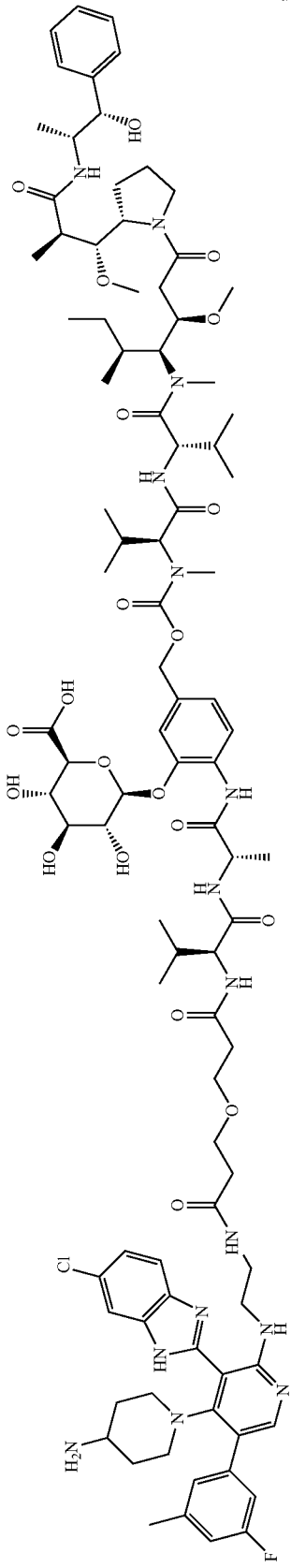

or a pharmaceutically acceptable salt thereof.

22. The compound of claim 20, wherein the compound is:

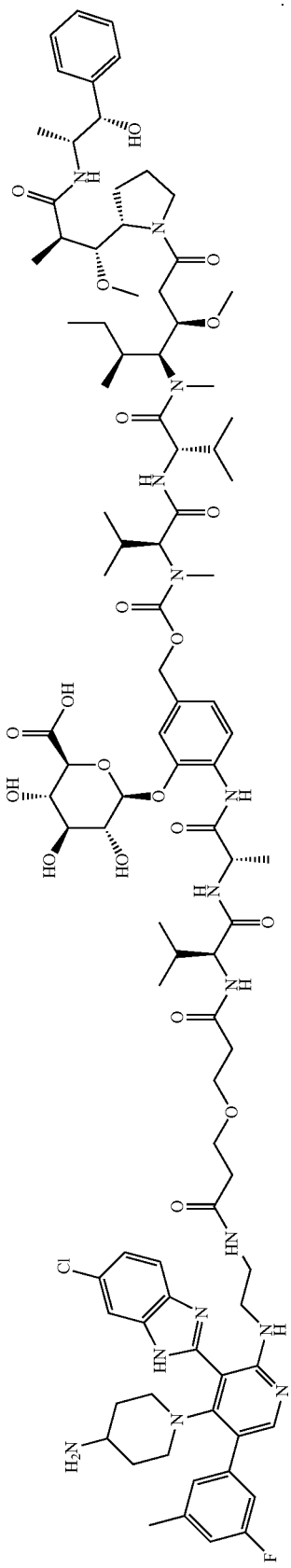

23. The compound of claim 20, wherein the compound is:

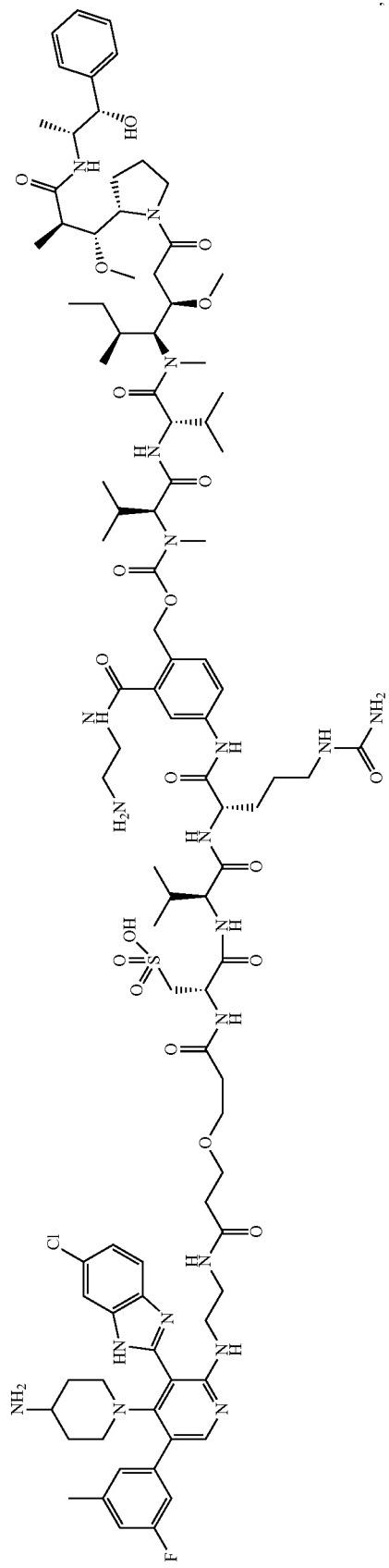

or pharmaceutically acceptable salt thereof.

24. The compound of claim 20, wherein the compound is:

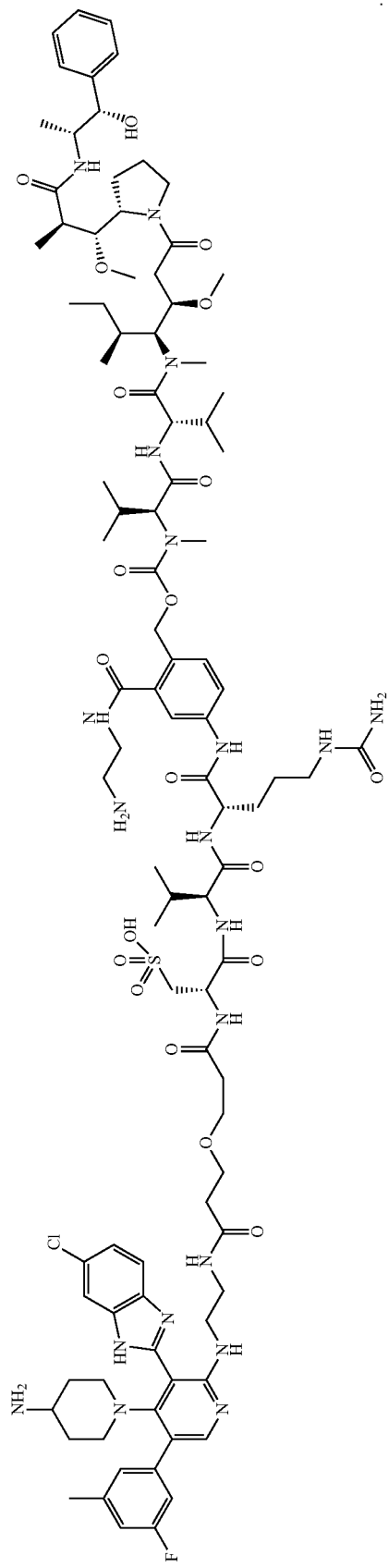

25. The compound of claim 20, wherein the compound is:

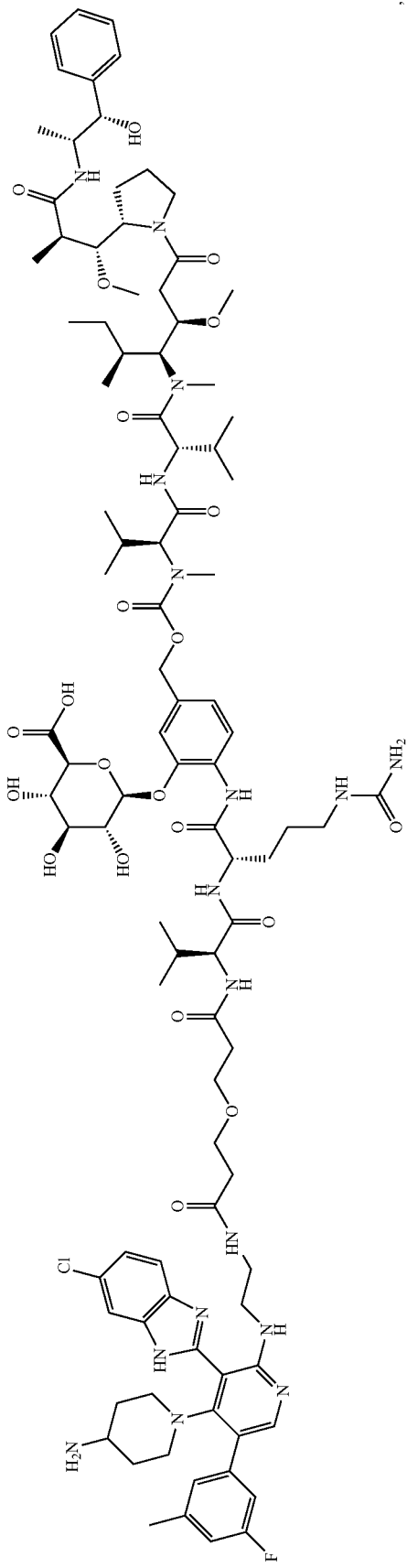

or a pharmaceutically acceptable salt thereof.

26. The compound of claim 19, wherein the compound is:

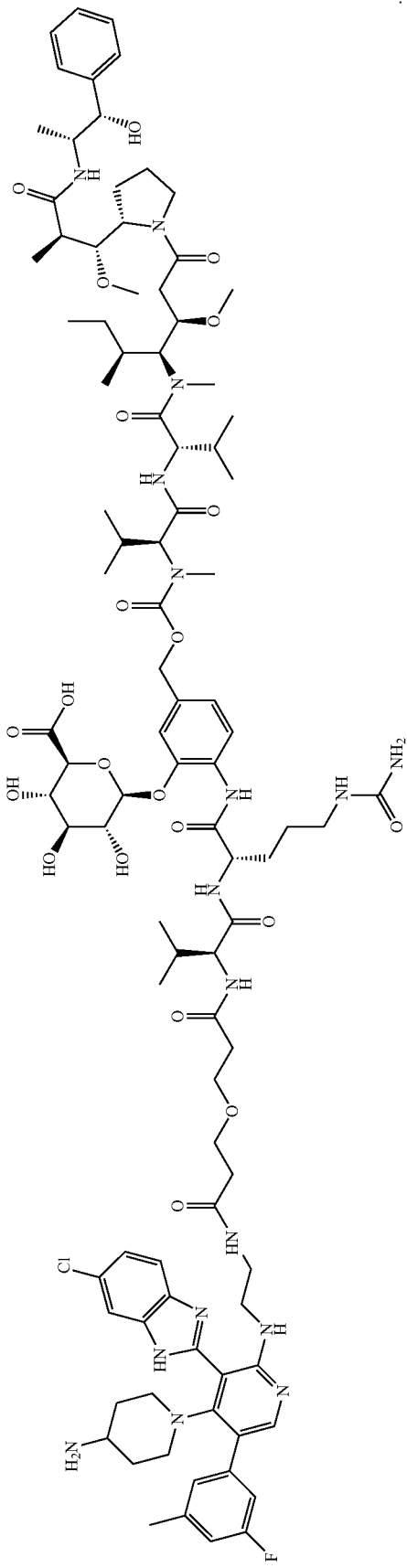

27. A method for the treatment of cancer comprising administering to a mammal with cancer an effective amount of a compound of claim 1, or a pharmaceutically acceptable salt thereof.

28. A method for the treatment of cancer comprising administering to a mammal with cancer an effective amount of a compound of claim 19, or a pharmaceutically acceptable salt thereof.

29. A method for the treatment of cancer comprising administering to a mammal with cancer an effective amount of a compound of claim 20, or a pharmaceutically acceptable salt thereof.

* * * * *